(12) United States Patent
Damschroder et al.

(10) Patent No.: US 8,883,992 B2
(45) Date of Patent: *Nov. 11, 2014

(54) HUMANIZED ANTI-CD19 ANTIBODIES

(71) Applicant: MedImmune, LLC, Gaithersburg, MD (US)

(72) Inventors: Melissa Damschroder, Germantown, MD (US); Peter Kiener, Potomac, MD (US); Herren Wu, Boyds, MD (US); William Dall'Acqua, Gaithersburg, MD (US); Ronald Herbst, Potomac, MD (US); Anthony Coyle, Boston, MA (US)

(73) Assignee: Medimmune, LLC, Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/661,138

(22) Filed: Oct. 26, 2012

(65) Prior Publication Data
US 2013/0115657 A1 May 9, 2013

Related U.S. Application Data

(63) Continuation of application No. 11/852,106, filed on Sep. 7, 2007, now Pat. No. 8,323,653.

(60) Provisional application No. 60/939,429, filed on May 22, 2007, provisional application No. 60/915,309, filed on May 1, 2007, provisional application No. 60/911,397, filed on Apr. 12, 2007, provisional application No. 60/866,917, filed on Nov. 22, 2006, provisional application No. 60/842,935, filed on Sep. 8, 2006.

(51) Int. Cl.
| | |
|---|---|
| C12N 15/13 | (2006.01) |
| C12N 5/10 | (2006.01) |
| C12N 15/63 | (2006.01) |
| C12N 15/79 | (2006.01) |
| C07K 16/28 | (2006.01) |
| A61K 39/00 | (2006.01) |

(52) U.S. Cl.
CPC ....... *C07K 16/2896* (2013.01); *C07K 2317/565* (2013.01); *C07K 2317/41* (2013.01); *C07K 2317/52* (2013.01); *A61K 2039/505* (2013.01); *C07K 2317/567* (2013.01); *C07K 2317/56* (2013.01); *C07K 2317/732* (2013.01); *C07K 16/2803* (2013.01); *C07K 2317/24* (2013.01); *C07K 2317/77* (2013.01); *C07K 2317/92* (2013.01); *C07K 2317/55* (2013.01)
USPC .............. 536/23.53; 435/69.6; 435/320.1; 435/328; 435/334; 435/343.1; 435/344.1; 436/548

(58) Field of Classification Search
None
See application file for complete search history.

(56) References Cited

U.S. PATENT DOCUMENTS

| | | |
|---|---|---|
| 5,417,972 A | 5/1995 | Bhat et al. |
| 5,530,101 A | 6/1996 | Queen et al. |
| 5,593,676 A | 1/1997 | Bhat et al. |
| 5,686,072 A | 11/1997 | Uhr et al. |
| 5,714,350 A | 2/1998 | Co et al. |
| 5,831,142 A | 11/1998 | Tedder et al. |
| 6,111,093 A | 8/2000 | Seed et al. |
| 6,134,982 A | 10/2000 | Takabatake |
| 6,306,393 B1 | 10/2001 | Goldenberg |
| 6,350,861 B1 | 2/2002 | Co et al. |
| 6,395,272 B1 | 5/2002 | Deo et al. |
| 6,528,624 B1 | 3/2003 | Idusogle et al. |
| 6,602,684 B1 | 8/2003 | Umana et al. |
| 6,896,885 B2 | 5/2005 | Hanna |
| 6,946,292 B2 | 9/2005 | Kanda et al. |
| 7,064,191 B2 | 6/2006 | Shinkawa et al. |
| 7,109,304 B2 | 9/2006 | Hansen et al. |
| 7,129,330 B1 | 10/2006 | Little et al. |
| 7,195,750 B2 | 3/2007 | Raestetter et al. |
| 7,214,775 B2 | 5/2007 | Hanai et al. |
| 2001/0036459 A1 | 11/2001 | Ravetch |
| 2002/0041847 A1 | 4/2002 | Goldenberg |
| 2002/0155604 A1 | 10/2002 | Ledbetter et al. |
| 2003/0003097 A1 | 1/2003 | Reff et al. |
| 2003/0048572 A1 | 3/2003 | Benson et al. |
| 2003/0115614 A1 | 6/2003 | Kanda et al. |
| 2003/0133930 A1 | 7/2003 | Goldenberg et al. |
| 2003/0148409 A1 | 8/2003 | Rossi et al. |
| 2003/0157108 A1 | 8/2003 | Presta |
| 2004/0126363 A1 | 7/2004 | Jensen et al. |
| 2004/0132101 A1 | 7/2004 | Lazar et al. |
| 2004/0185045 A1 | 9/2004 | Koenig et al. |
| 2004/0202658 A1 | 10/2004 | Benyunes |
| 2004/0228857 A1 | 11/2004 | Page et al. |
| 2005/0037000 A1 | 2/2005 | Stavenhagen et al. |

(Continued)

FOREIGN PATENT DOCUMENTS

| | | |
|---|---|---|
| EP | 0481790 B1 | 4/1992 |
| EP | 1229125 A1 | 8/2002 |

(Continued)

OTHER PUBLICATIONS

Cenry, RM et al., Immunother Emphasis Tumor Immunol., "Phase I trial of an anti-CD19 deglycosylated ricin A chain immunotoxin in non-Hodgkin's lymphoma: effect of an intensive schedule of administration", 18(4), 231-41 (1996).

De Gast, GC et al., J Hemathother, "Clinical experience with CD3 x CD19 bispecific antibodies in patients with B cell malignancies", 4(5), 433-7 (1995).

De Pascalis et al., "Grafting of "Abbreviated" Complementarily-Determining Regions Containing Specificity—Determining Residues Essential for Ligand Contact to Engineer a Less Immunogenic Humanized Monoclonal Antibody", The J. of Immunol., 169:3076-3084, 2002.

(Continued)

*Primary Examiner* — Ronald Schwadron

(57) ABSTRACT

Isolated nucleic acids encoding anti-CD19 mouse monoclonal antibodies are described herein. Also described are expression vectors, host cells and a method of producing anti-CD19 antibodies.

9 Claims, 68 Drawing Sheets

(56) References Cited

U.S. PATENT DOCUMENTS

Figure 2:
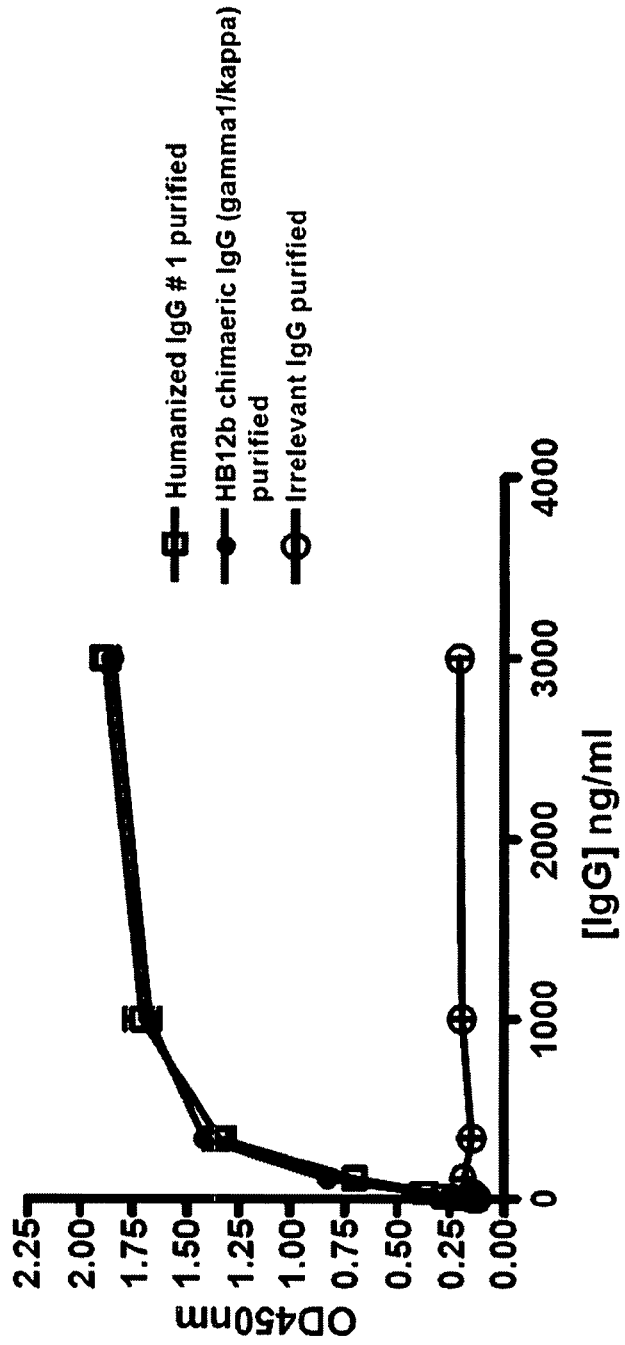

| | | |
|---|---|---|
| 2005/0054832 A1 | 3/2005 | Lazar et al. |
| 2005/0070693 A1 | 3/2005 | Hansen et al. |
| 2005/0089519 A1 | 4/2005 | Kipriyanov et al. |
| 2006/0057136 A1 | 3/2006 | Goldenberg |
| 2006/0099213 A9 | 5/2006 | Ghetie et al. |
| 2006/0233791 A1 | 10/2006 | Tedder et al. |
| 2006/0233814 A1 | 10/2006 | Goldmakher et al. |
| 2006/0240008 A1 | 10/2006 | Benyunes |
| 2006/0257398 A1 | 11/2006 | Hansen et al. |
| 2006/0263357 A1 | 11/2006 | Tedder et al. |
| 2006/0263367 A1 | 11/2006 | Fey et al. |
| 2006/0275284 A1 | 12/2006 | Hanna |
| 2006/0275308 A1 | 12/2006 | Warrell et al. |
| 2006/0280738 A1 | 12/2006 | Tedder |
| 2007/0003544 A1 | 1/2007 | Hanna |
| 2007/0009541 A1 | 1/2007 | Amphlett et al. |
| 2007/0031406 A1 | 2/2007 | Zand et al. |
| 2007/0071675 A1 | 3/2007 | Wu et al. |
| 2007/0087393 A1 | 4/2007 | Shults et al. |
| 2007/0123479 A1 | 5/2007 | Kufer et al. |
| 2007/0134312 A1 | 6/2007 | Hussein |
| 2007/0148686 A1 | 6/2007 | Kirszenbaum et al. |
| 2007/0166306 A1 | 7/2007 | Fey et al. |
| 2007/0178103 A1 | 8/2007 | Fey et al. |
| 2007/0196274 A1 | 8/2007 | Sun |
| 2007/0249529 A1 | 10/2007 | Hofmeister |
| 2007/0269370 A1 | 11/2007 | Davis et al. |

FOREIGN PATENT DOCUMENTS

| | | |
|---|---|---|
| EP | 1247865 B1 | 10/2002 |
| EP | 1266965 B1 | 12/2002 |
| EP | 1553832 B1 | 7/2005 |
| WO | WO-90/04413 A1 | 5/1990 |
| WO | WO-91/13974 A1 | 9/1991 |
| WO | WO-94/09363 A1 | 4/1994 |
| WO | WO-95/03770 A1 | 2/1995 |
| WO | WO-96/36360 A1 | 11/1996 |
| WO | WO 99/58572 A1 | 11/1999 |
| WO | WO-00/42072 A2 | 7/2000 |
| WO | WO-00/67796 A1 | 11/2000 |
| WO | WO-01/13945 A1 | 3/2001 |
| WO | WO 01/29246 A1 | 4/2001 |
| WO | WO-02/50118 A2 | 6/2002 |
| WO | WO-2005/012493 A2 | 2/2005 |
| WO | WO-2005/017148 A1 | 2/2005 |
| WO | WO 2006/089133 A2 | 8/2006 |
| WO | WO 2006/121852 A2 | 11/2006 |
| WO | WO 2006/133450 A2 | 12/2006 |
| WO | WO 2007/002223 A2 | 1/2007 |
| WO | WO 2007/076950 A1 | 7/2007 |
| WO | WO 2007/082715 A2 | 7/2007 |
| WO | WO 2007/085470 A2 | 8/2007 |

OTHER PUBLICATIONS

Dorken et al., "Production of Monoclonal Antibodies for the Diagnosis of Minimal Infiltration of Leukemic Cells into the Bone Marrow: B Cell Specific Antibodies, Verh. Dtsch. Ges. Path.," 67:65-69, (1983).

Grossbard, ML et al., Blood, "Adjuvant immunotoxin therapy with anti-B4-blocked ricin after autologous bone marow transplantation for patients with B-cell non-Hodgkin's lymphoma", 81(9), 2263-71, (1993).

Grossbard, ML et al., "Anti-B4-blocked ricin: a phase II trial of 7 day continuous infusinon in patients with multiple myeloma", British Journal of Hameatology, 102(2), 509-15 (1996).

Grossbard, ML et al., J Clin Oncol, "Anti-B4-blocked ricin: a phase I trial of 7-day continuous infusion in patients with B-cell neoplasms", 11(4), 726-37 (1993).

Groves et al., Fc dependent mechanisms are necessary for ADCC and effective depletion of murine B cells by humanized anti-CD19 mAb, Poster. Presented at 9th Annual Meeting, The American Association of Immunologists, 9th Annual Meeting, Miami, FL May 18-22, 2007.

Kanda et al., Comparison of biological activity among non-fucosylated therapeutic IgG1 antibodies . . . Glycobiology 17(1): 104-118 (2006).

Kiesel et al., "Removal of Cells From a Malignant B-Cell Line With Immunomagnetic Beads and With Complement and Immunoglobulin Switch Variant Mediated Cytolysis", Leukemia Research. vol. 11(12):1119-1125,(1987).

Krop, I. et al., "Eur J. Immunol.", "Self Renewal of B-1 Lymphocytes is Dependent on CD19", 26(1), 238-42 (1996).

MacCallum et al., "Antibody-antigen Interactions: Contact Analysis and Binding Site Topography", J. Mol. Biol., 262:732-745, 1996.

Manzke, O. et al., Int J Cancer, "Locoregional treatment of low-grade B-cell lymphoma with CD3xCD19 bispecific antibodies and CD28 costimulation I. Clinical phase I evaluation", 91(4), 508-15 (2001).

Manzke, O. et al., Int J Cancer, "Locoregional treatment of low-grade B-cell lymphoma with CD3xCD19 bispecific antibodies and CD28 costimulation II. Assessment of cellular immune responses", 91(4), 516-22 (2001).

Meeker, T et al., "A Unique Human B Lymphocyte Antigen Defined by a Monoclonal Antibody", Hybridoma, vol. 3(4):305-320 (1984).

Messman, RA et al., Clin Cancer Res., "A phase I study of combination therapy with immunotoxins IgG-HD37-deglycosylated ricin A chain (dgA) and IgG-RFB4-dgA (Combotox) in patients with refractory CD19(+), CD22(+) B cell lymphoma", 6(4), 1302-13 (2000).

Multani, PS et al., Clin Cancer Res. "Phase II clinical trial of bolus infusion anti-B4 blocked ricin immunoconjugate in patients with relapsed B-cell non-Hodgkin's lympohma.", 4(11),2599-604 (1998).

Pezzutto, A. et al., "CD19 Monoclonal Antibody HD37 Inhibits Anti-Immunoglobulin-induced B Cell Activation and Proliferation", The Journal of Immunology, 138(9):2793-2799, (1987).

Stone, MJ et al., Blood, "A phase I study of bolus versus continuous infusion of the anti-CD19 immunotoxin, IgG-HD37-dgA, in patients with B-cell lymphoma", 88(4), 1188-97 (1996).

Uckun, FM et al., "Detailed studies on expression and function of CD19 surface determinant using B43 monoclonal antibody", Blood 71:13 (1988).

Anderson et al., "Expression of human B cell-associated antigens on leukemias and lymphomas: a model of human B cell differentiation", blood, 53:1424-1433 (1964).

Anderson et al., "Targeting anti-cancer therapy using rituximab, a chimaeric anti-CD20 antibody (IDEC-C2B6) ini the treatment of non-Hodgkin's B-cell lymphoma", Biochem. Soc. Transc. 25:705-708 (1997).

Banfield et al., "A one-step large-scale method for T-and B-cell depletion of mobilized PBSC for allogenic transplantation", Cytotherapy, 6:1-6 (2004).

Becker et al., "Rituximab as Treatment for Refractory Kidney Transplant Rejection", American Journal of Transplantation, 4:996-1001 (2004).

De Vita et al., "Efficacy of Selective B Cell Blockade in the Treatment of Rheumatoid Arthritis", Arthritis & Rheumatism, 46(6):2029-2033 (2002).

Edwards et al. "Sustained improvement in rheumatoid arthritis following a protocol designed to deplete B lymphocytes", Rheumatology 40:205-211 (2001).

Grossbard et al., "Serotherapy of B-Cell Neoplasms With Anti-B4-Blocked Ricin: A Phase I Trial of Daily Bolus Infusion", Blood vol. 79(3):576-585 (1992).

Grossbard et al., "A Phase II Study of Adjuvant Therapy with Anti-B4-blocked Ricin after Autologous Bone Marrow Transplantation for Patients with Ralapsed B-Cell Non-Hodgkin'Lymphoma", Clinical Cancer Research, vol. 5:2392-2398 (1999).

Hekman et al., "Initial experience with treatment of human B cell lymphoma with anti-CD19 monoclonal antibody", Cancer Immunology Immunotheraphy 32:364-372.

Hooijberg et al., "Eradication of Large Human B Cell Tumors in Nude Mice with Unconjugated CD20 Monoclonal Antibodies and Interleukin 2[1]", Cancer Research, 55: 2627-2634 (1995).

Kaminski, et al. "Radioimmunotherapy of B-Cell Lymphoma With [$^{121}$I]Anti-B1 (Anti-CD-20) Antibody", New England Journal of Medicine 329(7):459-465 (1993).

(56) References Cited

OTHER PUBLICATIONS

Leandro et al., "Clinical Outcome in 22 patients with rheumatoid arthritis treated with B lymphocyte depletion", Annals of the Rheumatic Diseases 61:883-886 (2002).
Leandro et al. "An Open Study of B Lymphocyte Depletion in Systemic Lupus Erythematosus", Arthritis & Rheumatism, vol. 45(10):2673-2677 (2002).
LaVasseur et al., "Lymphocyte subsets may discern treatment effect in children and young adults with post-transplant lymphoproliferative disorder", Pediatri. Transplantation, 7:370-375 (2003).
Loken et al., "Flow cytometric analysis of human bone marrow. II. Normal B lymphocyte development", blood 70:1316-1324 (1987).
Maloney et al., "IDEC-C2B8 (Rituximab) Anti-CD20 Monoclonal Antibody Therapy in Patients With Relapsed Low-Grade Non-Hodgkin's Lymphoma", blood 90:2188-2195 (1997).
Maloney et al., "IDEC-CD2B8: Results of a Phase I Multiple-Dose Trial in Patients with Relapsed Non-Hodgkin's Lymphoma", Journal of Clinical Oncology 15(10):3266-3274 (1997).
McLaughlin et al., "Clinical Status and Optimal Use of Rituximab for B-Cell Lymphomas", Oncology, 12:1763-1769 (1998).
Nadler et al., "B4, A Huam B Lymphocyte-Assocated Antigen Expressed on Normal, Mitogen-Activated, and Malignant B Lymphocytes", The Journal of Immunology, 131(1):244-250(1983).
Onrust et al., "Rituximab", Drugs, 56:79-88 (1999).
Reff et al., "Depletion of B Cells in Vivo by a Chimeric Mouse Human Monoclonal Antibody to CD20", Blood, 83(2):435-445 (1994).
Riffle et al., "Donor-Specific Antibodies in Allograft Rejection: Clinical and Experimental Data", Transplantation, 79(3): S14-S18 (2005).
Schaar et al., "Successful Outcome With a "Quintuple Approach" of Posttransplant Lymphoproliferative Disorder", Transplantation, 71(1):47-52 (2001).
Scheuermann et al., "CD19 Antigen in Leukemia and Lymphoma Diagnosis and Immunotherapy", Leukemia and Lymphoma 18:385-397 (1995).
Silverman et al., "Rituximab Therapy and Autoimmune Disorders", Arthritis & Rheumatism, 48(6):1484-1492 (2003).
Sidner et al., "In vivo human B-cell subset recovery after in vivo depletion with rituximab, anti-human CD20 monoclonal antibody", Human Antibodies 13:55-62 (2004).
Smith, "Rituximab (monoclonal anti-CD20 antibody): mechanisms of action and resistance", Oncogene 22:7359-7368 (2003).
Snanoudj, et al., "Immunological Strategies Targeting B Cells in Organ Grafting", Transplantation, 79(3):533-535 (2005).
Sonnenday et al., "Plasmapheresis, CMV Hyperimmune Globulin, and Anti-CD20 Allow ABO-Incompatible Renal Transplantation Without Splenectomy", American Journal of Transplantation 4:1315-1322 (2004).
Tedder et al., "CD20: a regulator of cell-cycle progression of B lymphocytes", Immunology Today, 15(9):450-454 (1994).
Treon et al., "Expression of Serotherapy Target Antigens in Waldenstrom's Macroglobulinemia: Therapeutic Applications and Considerations", Seminars in Oncology, 30(2):248-252 (2003).
Tyden et al., "Successful Abo-Incompatible Kidney Transplantations Without Splenectomy Using Antigen-Specific Immunoadsorption and Rituximab", Transplantation, 76(4):730-743 (2003).
Vieira et al., "Rituximab for Reduction of Anti-HLA Antibodies in Patients Awaiting Renal Transplantation: 1, Safety, Pharmacodynamics, and Pharmacokinetics", Transplantation, 77(4):542-548 (2004).
Weiner, "Monoclonal Antibody Therapy of Cancer", Seminars in Oncology, 26(5)(14):43-51 (1999).
Nimmerjahn et al., "Antibodies, Fc Receptors and Cancer", Current Opinion in Immunology, 19:239-245 (2007).
Okazaki et al., "Fucose Depletion from Human IgG1 Oligosaccharide Enhances Binding Enthalpy and Association Rate Between IgG1 and FCγRIIIa", Journal of Molecular Biology 336:1239-1249 (2004).

Ghetie et al., "Anti-CD19 inhibits the Growth of Human B-Cell Tumor Lines In Vitro and of Daudi Cells in SCID Mice by inducing Cell Cycle Arrest", Blood, 83(5):1320-1336 (1994).
Shields et al., "Lack of Fucose on Human IgG1 N-Linked Oligosaccharide Improves Binding to Human FcγRIII and Antibody-dependent Cellular Toxicity", The Journal of Biological Chemistry 277(30):26733-26740 (2002).
Umana, et al., "Engineered glycoforms of an antineuroblastoma IgG1 with optimized antibody-dependent cellular cytotoxic activity", Nature Biotechnology, 17:176-180 (1999).
Bentley et al., "Human immunoglobulin variable region genes— DNA sequences of two $V_X$ genes and a pseudogene", Nature 288:730-733 (1980).
Tomlinson et al., "The Repertoire of Human Germline $V_H$ Sequences Reveals about Fifty Groups of $V_H$ Segments with Different Hypervariable Loops", Journal of Molecular Biology, 227:776-780 (1992).
Ravetch et al., "Structure of the Human Immunoglobulin α Locus: Characterization of Embryonic and Rearranged J and D Genes", Cell, 27:583-591 (1981).
Hiefer et al., "Evolution of Human Immunoglobulins, J Region Genes", The Journal of Biological Chemistry 257(3):1516-1522 (1962).
Alt et al., "Organization and Reorganization of Immunoglobulin Genes in A-MuLV-Transformed Cells: Rearrangement of Heavy but Not Light Chain Genes", Cell, 27:381-390 (1981).
Callard et al., "CD19 Regulation of Human B Cell Responses: B Cell Proliferation and Antibody Secretion are Inhibited or Enhanced by Ligation of the CD19 Surface Glycoprotein Depending on the Stimulating Signal Used", The Journal of Immunology, 148(10):2983-2987 (1992).
Zola et al., "Preparation and characterization to a chimeric CD19 monoclonal antibody", Immunology and Cell Biology 69:411-422 (1991).
Nicholson et al., "Construction and Characterization of a Functional CD19 Specific Single Chain $F_v$ Fragment for Immunotherapy of B Lineage Leukaemia and Lymphoma", Molecular Immunology 34(16-17):1157-1165 (1997).
Pietersz et al., "In vitro and in vivo antitumor activity of a chimeric anti-CD19 antibody", Cancer Immunol. Immunotherapy 41:53-60 (1995).
Flavell et al., "The anti-CD20 antibody rituximab augments the immunospecific therapeutic effectiveness of an anti-CD19 immunotoxin directed against human B-cell lymphoma", British Journal of Haematology, 134:157-170 (2006).
Vallera et al., "Radioimmunotherapy of CD22-Expressing Daudi Tumors in Nude Mice with a Y-Labeled Anti-CD22 Monocolonal Antibody", Clinical Cancer Research 11(21):7920-28 (2005).
Jacobson et al., "Short Analytical Review. Epidemiology and Estimated Population Burden of Selected Autoimmune Diseases in the United States", Clinical Immunology and Immunopathology, 84(3):223-243 (1997).
Mattila et al., "Extensive allelic sequence variation in the J region of the human immunoglobulin heavy chain gene locus", Eur. J. Immunol. 25:2578-2582 (1995).
Straubinger et al., "Two Unusual Human Immunoglobulin $V_x$ Genes", Biol. Chem. Hoppe-Seyler, 369:601-607 (1988).
Yazawa et al., "Immunotherapy using unconjugated CD19 monoclonal antibodies in animal models for B lymphocyte malignancies and autoimmune disease", Proc. Natl. Acad. Sci. USA, 102(42):15178-15183 (2005).
Davies et al., "Expression of GnTIII in a Recombinant Anti-CD20 CHO Production Cell Line: Expression of Antibodies with Altered Glycoforms Leads to an Increase in ADCC Through Higher Affinity for FCγRIII", Biotechol. Bioeng, 74:288-294 (2001).
Shinkawa et al., "The Absence of Fucose but Not the Presence of Galactose or Bisecting N-Acetylglucosamine of Human IgG1 Complex-type Oligosaccharades Shows the Critical Role of Enhancing Antibody-dependent Cellular Cytotoxicity", The Journal of Biological Chemistry, 278(5):3466-3473 (2003).

(56) References Cited

OTHER PUBLICATIONS

Tedder et al., "Fcγ receptor-dependent effector mechanisms regulate CD19 and CD20 antibody immunotherapies for B lymphocyte malignancies and autoimmunity", Springer Semin. Immun. 28:351-364 (2005).

Zhou et al. Tissue-specific expression of the human CD19 gene in transgenic mice inhibits antigen-independent B-lymphocyte development. Mol Cell Biol. 14(6):3884-94 (1994).

Lanzar, Greg A. et al., 2006, "Engineered antibody FC variants with enhanced effector function", PNAS, 103(11):4005-4010.

Zhukovsky, Eugene A. et al., "Fc Engineered Anti-CD19 Monoclonal Antibodies with Enhanced in Vitro Efficacy Against Multiple Lymphoma Cell Lines", Blood, 108(11), Part 2:270B, & 46th Annual Meeting of the American-Society of Hematology, Orlando, Florida, Dec. 9-12, 2006,Abstract 4747.

Bradbury et al., "The CD19/CD21 Signal Transducing Complex of Human B Lymphocytes Includes the Target of Antiproliferative Antibody-1 and Leu-13 Molecules, The Journal of Immunology", vol. 149(9), pp. 2841-2850 (1992).

Damchroder et al., International Search Report corresponding to PCT/US2007/077916 filed Sep. 7, 2007 for Humanized Anti-CD19 Antibodies and Their Use in Treatment of Oncology, Transplantation and Autoimmune Disease; mailed Aug. 13, 2008.

Monoclonal Antibody Therapy in Treating Patients with Lymphoma or Leukemia. ClinicalTrials.gov Identifier: NCT00003874. [retrieved on Feb. 27, 2008] Retrieved from the Internet: <URL:http://www.clinicaltrials.gov/ct/show/NCT00003874?order=1>; published on Nov. 1, 1999.

Phase I/II Study of Enriched CD34+ Cells with Depleted B-cells in Patients with B Lymphoid Malignancies. [retrieved on Feb. 27, 2008] Retrieved from the Internet: <URL:pubhttp://www.cancer.gov/search/viewclinicaltrials.aspx?cdrid=67039&version=healthprofessional&print=1> published on Jun. 1, 1999.

Tsimberidou AM, et al., Leuk Lymphoma, "Anti-B4-blocked ricin post chemotherapy in patients with chronic lymphocytic leukemia—long-term follow-up of a monoclonal antibody-based approach to residual disease", 44(10), 1719-25, (2003).

Hooijberg et al., "Enhanced Antitumor Effects of CD20 over CD19 Monoclonal Antibodies in a Nude Mouse Xenograft Model[1]", Cancer Research, 55:840-846 (1995).

Press et al., "Immunotherapy of Non-Hodgkin's Lymphomas", Hematology, vol. 2001, No. 1, 221-240 (2001).

Yanaba et al., "B Cell Depletion Delays Collagen—Induced Arthritis in Mice: Arthritis Induction Requires Synergy between Humoral and Cell-Mediated Immunity", J. Immunol. ;179(2):1369-80. (2007).

DiLillo et al. "Maintenance of Long-Lived Plasma Cells and Serological Memory Despite Mature and Memory B Cell Depletion during CD20 Immunotherapy in Mice", J Immunol. Jan. 1, 2008;180(1):361-71.

Roguska, Michael A. et al., 996, "A comparison of two murine monoclonal antibodies humanized by CDR-grafting and variable domain resurfacing", Protein Engineering, 9(10):895-904, 1996.

Damschroeder et al., Supplementary European Search Report corresponding to EP Application No. EP 07 84 2083, filed Sep. 7, 2007, "Humanized Anti-CD19 Antibodies and Their Use in Treatment of Tumors, Transplantation and Autoimmune Diseases".

A)

Light chain variable regions:

```
                     1          10         20         30         40         50
HB12B VK           DIVLTQSPTSLAVSLGQRATISCRASESVDTFGISFMNWFQQKPGQPPKLLIHHAASNQGS
HB12B-(A10/Jκ4)    EIVLTQSPDFQSVTPKEKVTITCRASESVDTFGISFMNWYQQKPDQSPKLLIKAASNQGS
HB12B-364987       EIVLTQSPDFQSVTPKEKVTITCRASESVDTFGISFMNWFQQKPDQSPKLLIHAASNQGS
HB12B-3649         EIVLTQSPDFQSVTPKEKVTITCRASESVDTFGISFMNWFQQKPDQSPKLLIHAASNQGS
HB12B-36           EIVLTQSPDFQSVTPKEKVTITCRASESVDTFGISFMNWFQQKPDQSPKLLIKAASNQGS 60         70         80         90        100
HB12B VK           GVPARFSGSGSGTDFSLNIHPMEEDDSAMYFCQQSKEVPFTFGSGTKLEIK
HB12B-(A10/Jκ4)    GVPSRFSGSGSGTDFTLTINSLEAEDAATYYCQQSKEVPFTFGGGTKVEIK
HB12B-364987       GVPSRFSGSGSGTDFTLTINSLEAEDAATYECQQSKEVPFTFGGGTKVEIK
HB12B-3649         GVPSRFSGSGSGTDFTLTINSLEAEDAATYYCQQSKEVPFTFGGGTKVEIK
HB12B-36           GVPSRFSGSGSGTDFTLTINSLEAEDAATYYCQQSKEVPFTFGGGTKVEIK
```

B)

Heavy chain variable regions:

```
                     1          10         20         30         40         50         60
HB12B VH           QVQLQQSGPELVKPGASVKMSCKASGYAFSSSWMNWVIQRPGQGLEWIGRIYPGDGDTNYNGKFKG
HB12B-(3-72/JH4)   EVQLVESGGGLVQPGGSLRLSCAASGFTFSSSWMNWVRQAPGKGLEWVGRIYPGDGDTNYNGKFKG
HB12B-9m           EVQLVESGGGLVQPGGSLRMSCAASGMAFSSSWMNWVHQAPGKGLEWMGRIYPGDGDTNYNGKFKG 70         80         90        100        110
HB12B VH           KATLTADKSSSTAYMQLSSLTSVDSAVYFCARSGFITTVLDFDYWGHGTTLTVSS
HB12B-(3-72/JH4)   RFTISRDDSKNSLYLQMNSLRAEDTAVYYCARSGFITTVLDFDYWGQGTLVTVSS
HB12B-9m           RATISRDDSKNSLYMQMNSLKTEDTAVYHCARSGFITTVLDFDYWGQGTLVTVSS
```

Fig. 1

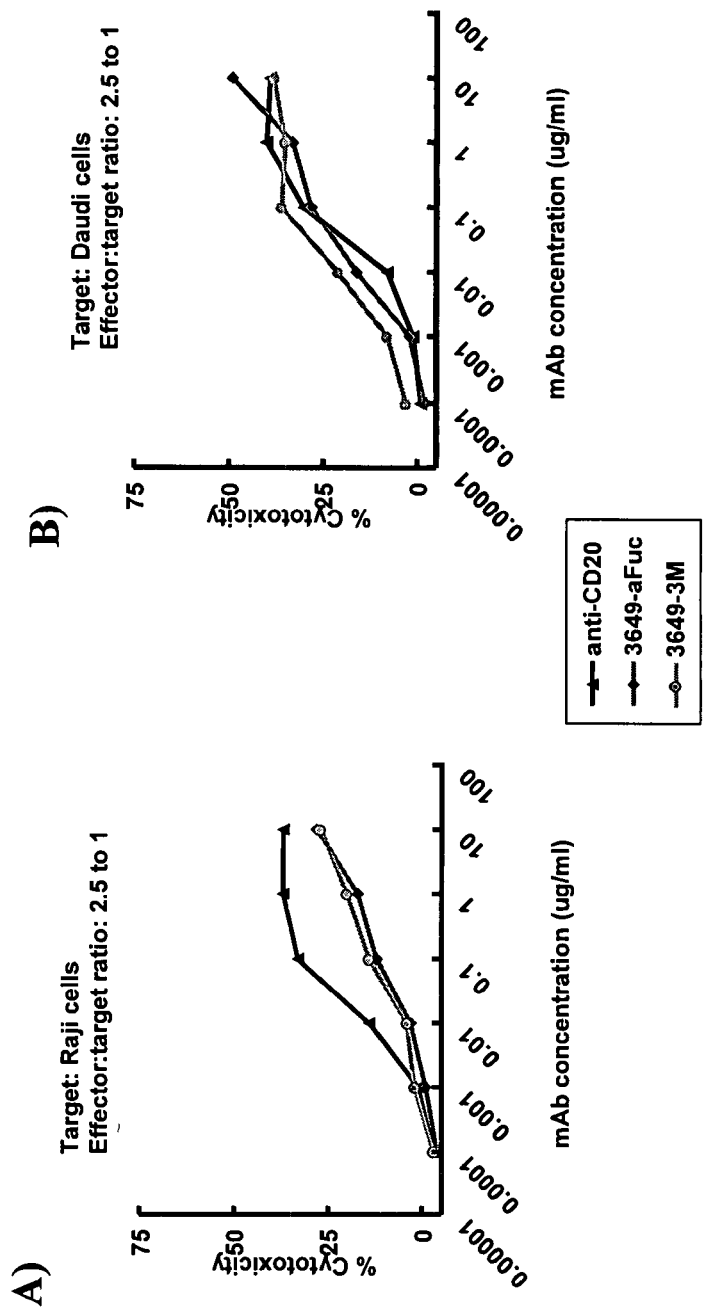
Fig. 8A/B

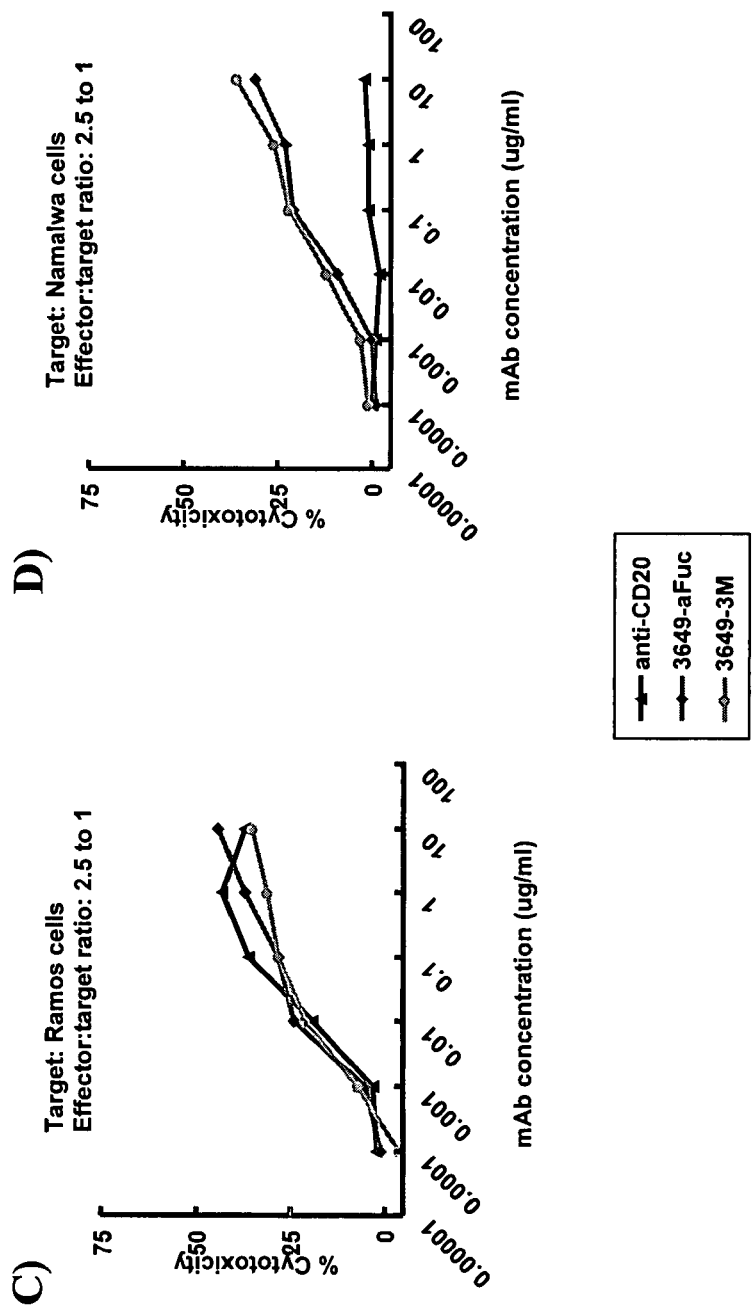
Fig. 8C/D

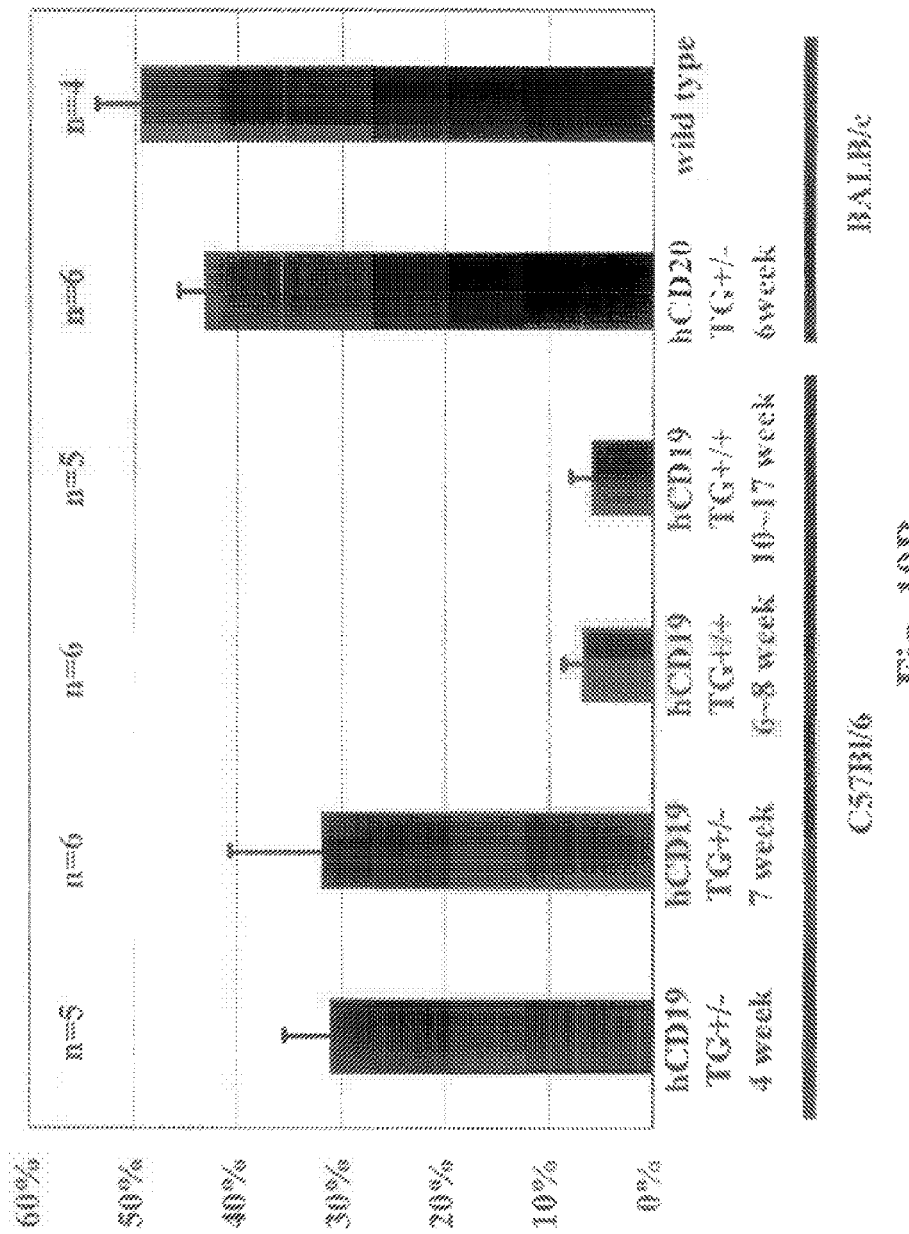

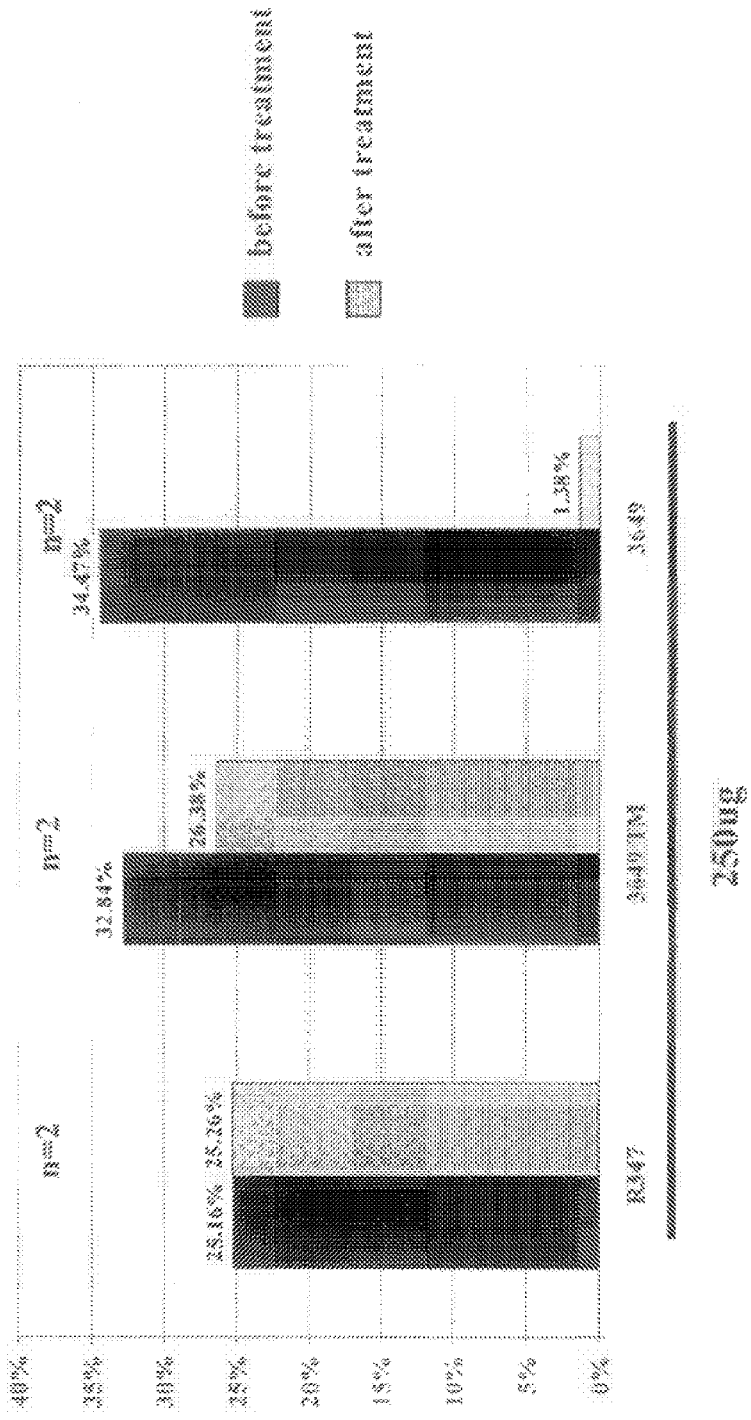

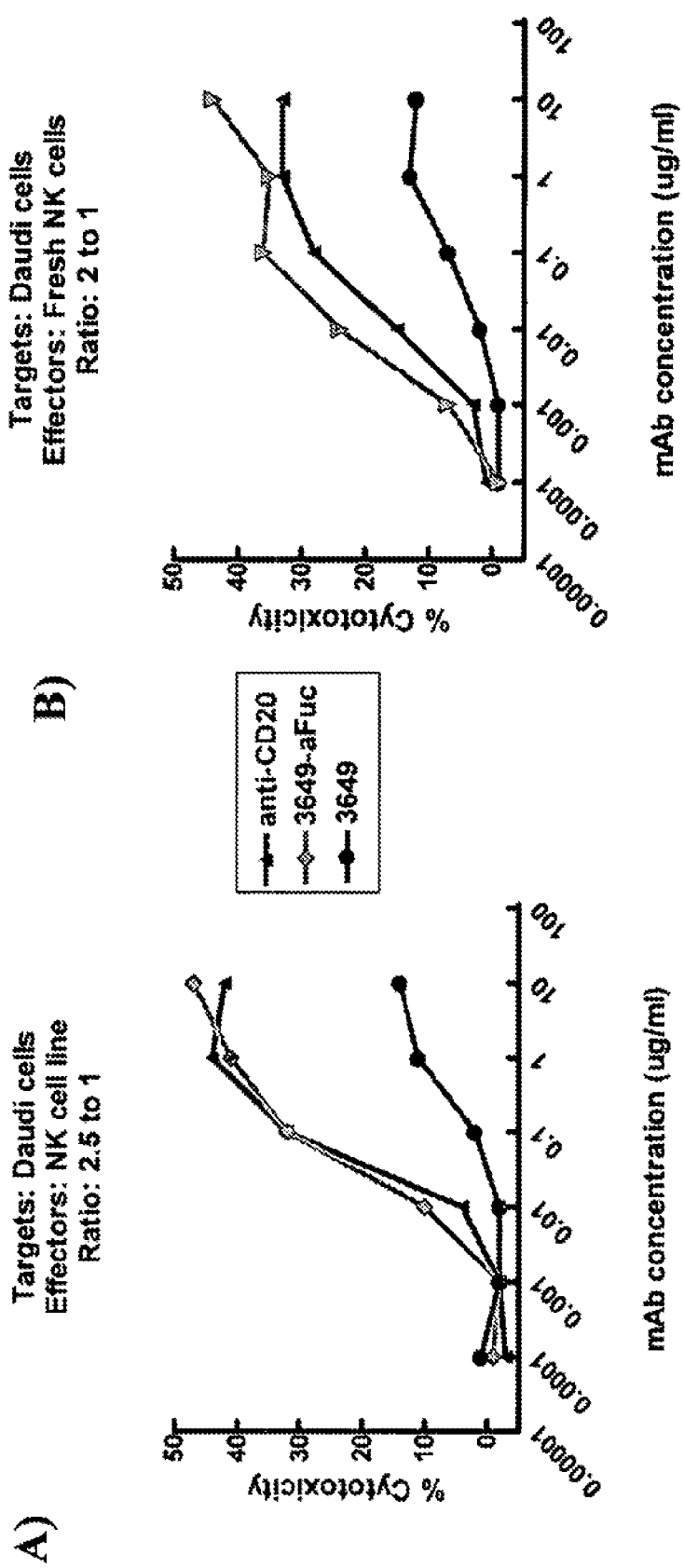
Fig. 16 A/B

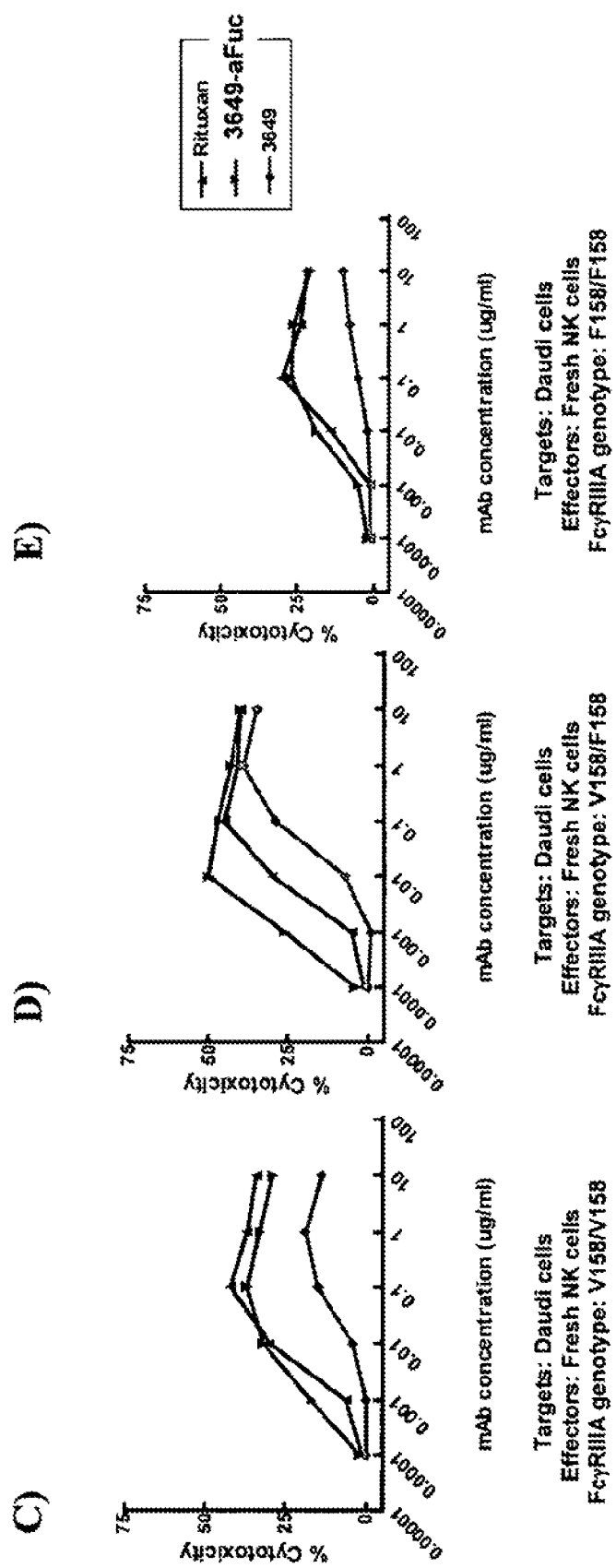
Fig. 16 C/D/E

Fig. 26A/B

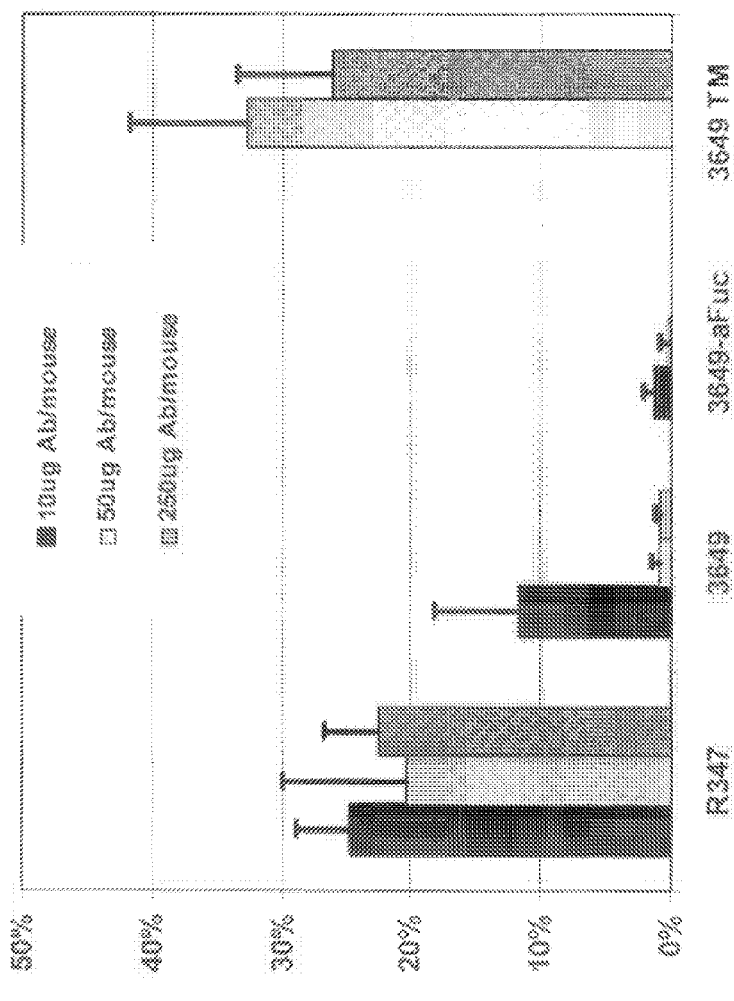

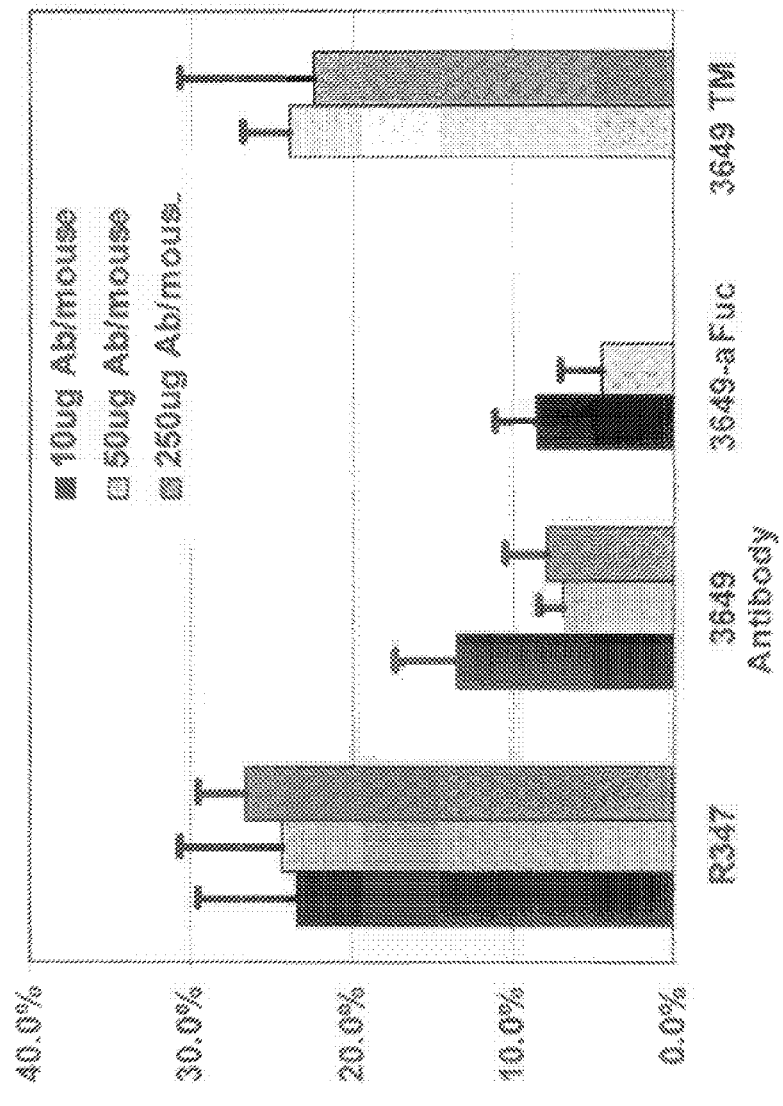

| | CDR1H | CDR2H | CDR3H | CDR1L | CDR2L | CDR3L |
|---|---|---|---|---|---|---|
| | SSWMN | RIYPGDGDTNYNVKFKG | SGFITTVRDFDY | RASESVDTFGISFMN | EASNQGS | QQSKEVPFT |
| 16C4 | ----- | ---------------- | ------------ | --------------- | ------- | --------- |
| 1A7 | -V--- | ---------------- | ------------ | ------H-------I | ---PY-- | -A-----I- |
| 3C3 | -V--- | ---------------- | ------------ | --------------- | ------- | -A------- |
| 3E5 | -V--- | ---------------- | ------------ | --------------- | ------- | -A---R--- |
| 3D4 | -V--- | ---------------- | ------------ | -------I------- | ------- | -A-----I- |
| 3F11 | -V--- | ---L------------ | ------------ | --------------- | ------- | -A-T-R--- |
| 5B5 | -V--- | ---------------- | ------------ | --------------- | ------- | -------I- |
| 6F7 | -V--- | ---------------- | ------------ | --------------I | ---PY-- | -A-T----- |
| 1C11 | ----- | ---------------- | ------------ | --------------- | ------- | --------- |
| 2B11 | -V--- | ---------------- | ------------ | -------I------- | ---TY-- | -A-T----- |
| 2D10 | -V--- | ---------------- | ------------ | --------------R | ------- | --------- |
| 3B4 | -T--- | ---------------- | ------------ | --------------- | ----P-- | -------I- |
| 5C11 | -V--- | ---L------------ | ------------ | --------------- | ----R-- | -A---R--- |
| 5D4 | ----- | ---------------- | ------------ | -----IH-------- | ------- | --------- |
| 6C2 | -V--- | ---------------- | ------------ | --------------- | ---PY-- | ---T-R--- |
| 6C11 | -V--- | ---------------- | ------------ | -------I---L--- | ------- | -A-----I- |
| 9G7 | -V--- | ---------------- | ------------ | -------I------I | ---PY-- | -A-T-R--- |
| 1H4 | -V--- | ---------------- | ------------ | --------------- | ------- | --------- |
| 5C4 | -V--- | ---------------- | ------------ | --------------- | ------- | --------- |

Fig. 33C

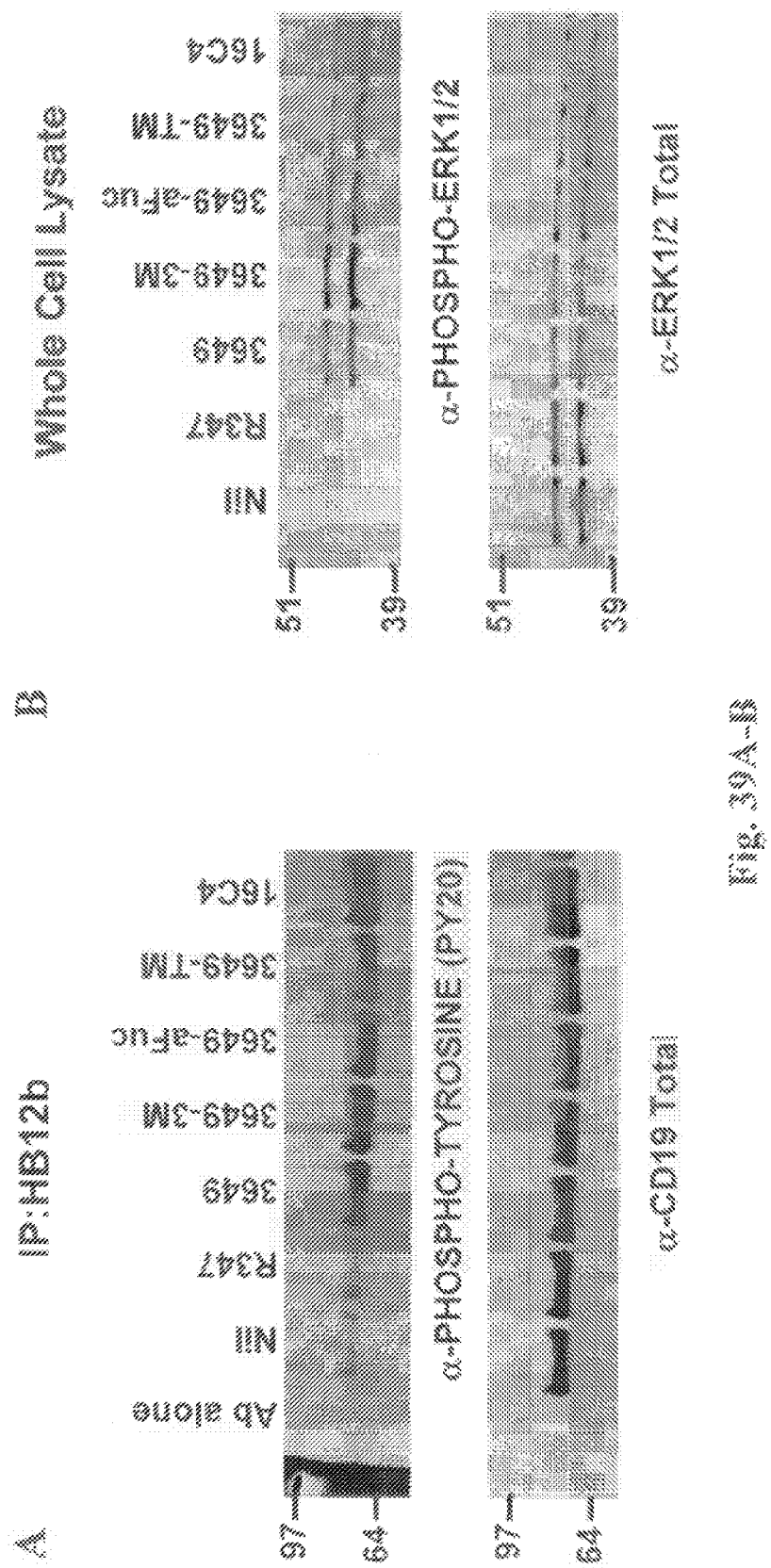
Fig. 39A-B

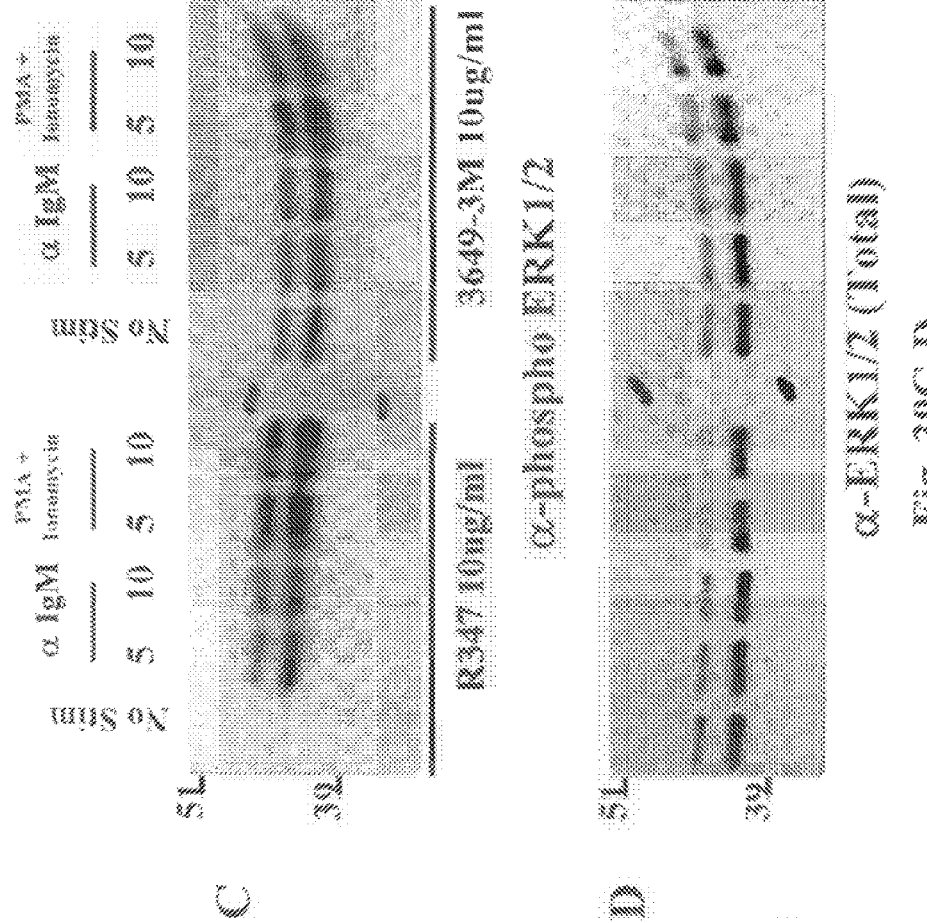
Fig. 39C-D

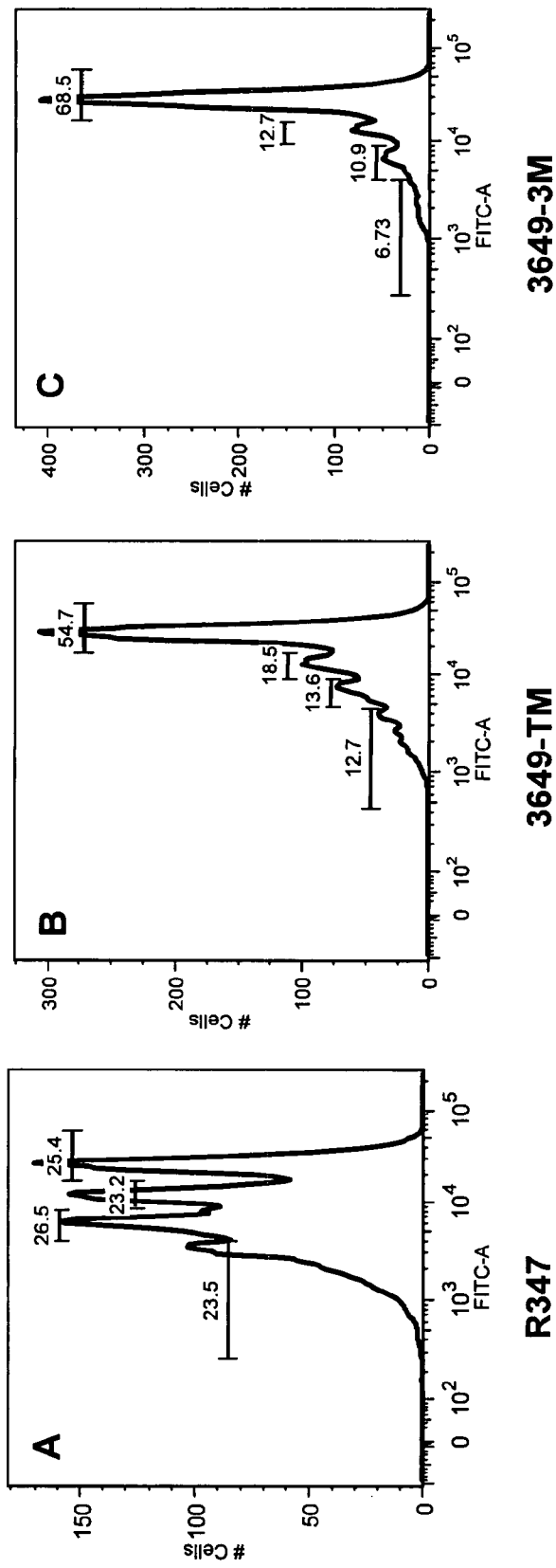
Fig. 42A-C

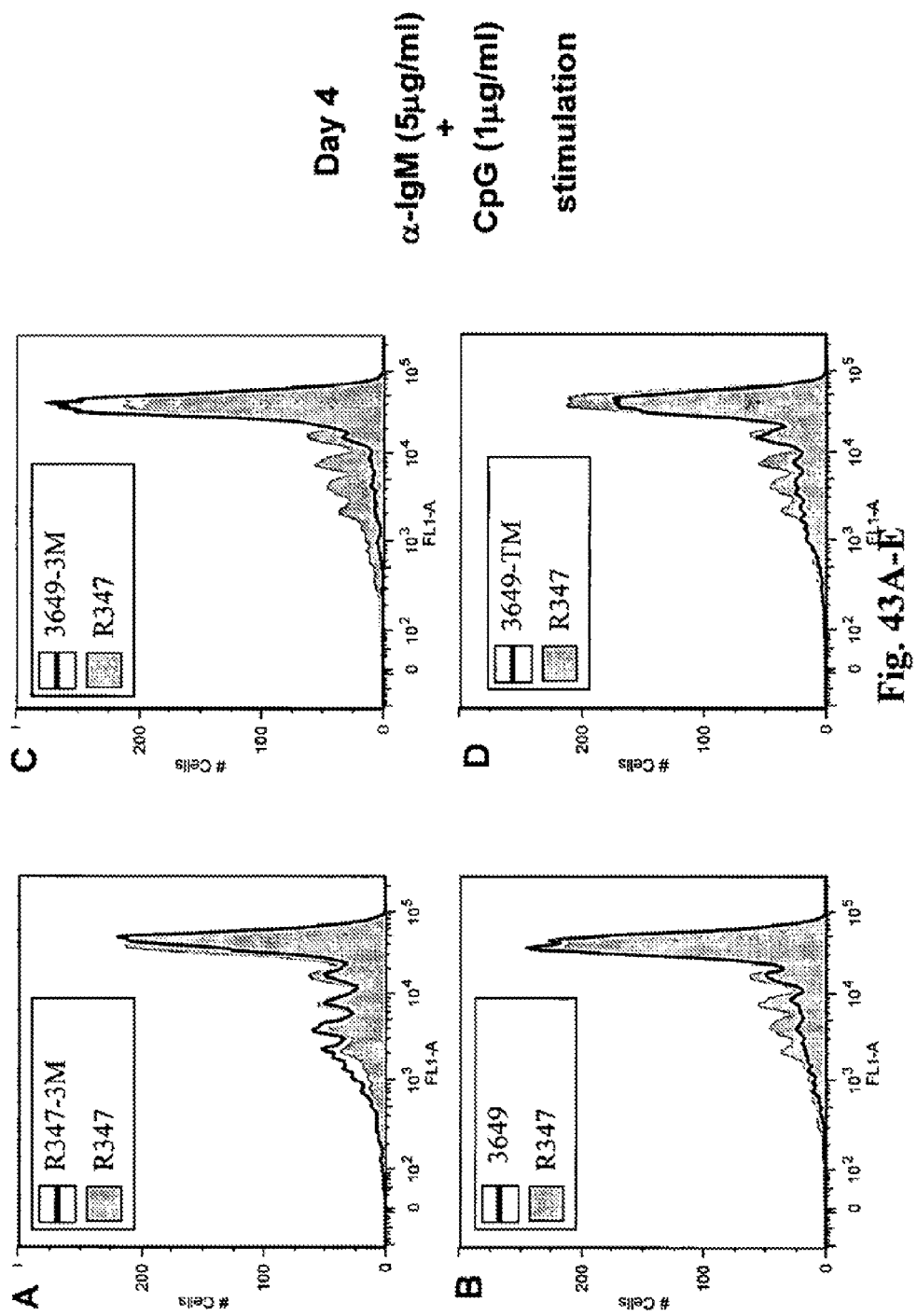
Fig. 43A-E

SEQUENCE LISTING

```
<160> NUMBER OF SEQ ID NOS: 239

<210> SEQ ID NO 1
<211> LENGTH: 367
<212> TYPE: DNA
<213> ORGANISM: Mus musculus

<400> SEQUENCE: 1
gaggtgcagc tgcaggagtc tggacctgag ctggtaaagc ctggggcttc agtgaagatg      60
tcctgcaagg cttctggata cacattcact agctatgtta tgcactgggt gaagcagaag     120
cctgggcagg gccttgagtg gattggatat tttaatcctt acaatgatgg tactgattac     180
tatgagaagt tcaaaggcaa ggccacactg acttcagaca aatcctccag cacagcctac     240
atggcgctca gcagcctgac ctctgaggac tctgcggtct attactgtgc aagagggacc     300
tattactacg gtagtagcta ccccttggac tactggggcc aaggcaccac tctcacagtc     360
tcctcag                                                                367

<210> SEQ ID NO 2
<211> LENGTH: 122
<212> TYPE: PRT
<213> ORGANISM: Mus musculus

<400> SEQUENCE: 2

Glu Val Gln Leu Gln Glu Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Phe Asn Pro Tyr Asn Asp Gly Thr Asp Tyr Tyr Glu Lys Phe
    50                  55                  60

Lys Gly Lys Ala Thr Leu Thr Ser Asp Lys Ser Ser Ser Thr Ala Tyr
65                  70                  75                  80

Met Ala Leu Ser Ser Leu Thr Ser Glu Asp Ser Ala Val Tyr Tyr Cys
                85                  90                  95

Ala Arg Gly Thr Tyr Tyr Tyr Gly Ser Ser Tyr Pro Phe Asp Tyr Trp
            100                 105                 110

Gly Gln Gly Thr Thr Leu Thr Val Ser Ser
        115                 120

<210> SEQ ID NO 3
<211> LENGTH: 333
<212> TYPE: DNA
<213> ORGANISM: Mus musculus

<400> SEQUENCE: 3
gatgttggga tgacccagac tccactcact ttgtcggtca ccattggaca accagcctct      60
ttctcttgca agtcaagtca gagcctctta tatagtaatg gaaaaaccta tttgaattgg     120
```

```
ttattacaga ggccaggcca gtctccaaag cgcctaatcc atctggtgtc taaactggac    180
tctgtccctg acaggttcac tggcagtgga tcaggaacag attttacact gaaaatcggc    240
agagtggagg ctgaggattt gggagtttat tactgcgtgc aaggtacaca ttttccgtac    300
acgttcggag gggggaccaa actagaaata aaa                                 333
```

<210> SEQ ID NO 4
<211> LENGTH: 111
<212> TYPE: PRT
<213> ORGANISM: Mus musculus

<400> SEQUENCE: 4

```
Asp Val Gly Met Thr Gln Thr Pro Leu Thr Leu Ser Val Thr Ile Gly
1               5                   10                  15

Gln Pro Ala Ser Phe Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile His Leu Val Ser Lys Leu Asp Ser Val Pro Asp
    50                  55                  60

Arg Phe Thr Gly Ser Gly Ser Gly Thr Asp Phe Thr Leu Lys Ile Gly
65                  70                  75                  80

Arg Val Glu Ala Glu Asp Leu Gly Val Tyr Tyr Cys Val Gln Gly Thr
                85                  90                  95

His Phe Pro Tyr Thr Phe Gly Gly Gly Thr Lys Leu Glu Ile Lys
            100                 105                 110
```

<210> SEQ ID NO 5
<211> LENGTH: 15
<212> TYPE: DNA
<213> ORGANISM: Mus musculus

<400> SEQUENCE: 5

```
agctatgtta tgcac                                                      15
```

<210> SEQ ID NO 6
<211> LENGTH: 5
<212> TYPE: PRT
<213> ORGANISM: Mus musculus

<400> SEQUENCE: 6

```
Ser Tyr Val Met His
1               5
```

<210> SEQ ID NO 7
<211> LENGTH: 51
<212> TYPE: DNA
<213> ORGANISM: Mus musculus

<400> SEQUENCE: 7

```
tattttaatc cttacaatga tggtactgat tactatgaga agttcaaagg c              51
```

<210> SEQ ID NO 8
<211> LENGTH: 17
<212> TYPE: PRT
<213> ORGANISM: Mus musculus

<400> SEQUENCE: 8

```
Tyr Phe Asn Pro Tyr Asn Asp Gly Thr Asp Tyr Tyr Glu Lys Phe Lys
1               5                   10                  15
```

Gly

<210> SEQ ID NO 9
<211> LENGTH: 39
<212> TYPE: DNA
<213> ORGANISM: Mus musculus

<400> SEQUENCE: 9
gggacctatt actacggtag tagctacccc tttgactac                    39

<210> SEQ ID NO 10
<211> LENGTH: 13
<212> TYPE: PRT
<213> ORGANISM: Mus musculus

<400> SEQUENCE: 10

Gly Thr Tyr Tyr Tyr Gly Ser Ser Tyr Pro Phe Asp Tyr
1               5                   10

<210> SEQ ID NO 11
<211> LENGTH: 48
<212> TYPE: DNA
<213> ORGANISM: Mus musculus

<400> SEQUENCE: 11
aagtcaagtc agagcctctt atatagtaat ggaaaaacct atttgaat          48

<210> SEQ ID NO 12
<211> LENGTH: 16
<212> TYPE: PRT
<213> ORGANISM: Mus musculus

<400> SEQUENCE: 12

Lys Ser Ser Gln Ser Leu Leu Tyr Ser Asn Gly Lys Thr Tyr Leu Asn
1               5                   10                  15

<210> SEQ ID NO 13
<211> LENGTH: 21
<212> TYPE: DNA
<213> ORGANISM: Mus musculus

<400> SEQUENCE: 13
ctggtgtcta aactggactc t                                       21

<210> SEQ ID NO 14
<211> LENGTH: 7
<212> TYPE: PRT
<213> ORGANISM: Mus musculus

<400> SEQUENCE: 14

Leu Val Ser Lys Leu Asp Ser
1               5

<210> SEQ ID NO 15
<211> LENGTH: 27
<212> TYPE: DNA
<213> ORGANISM: Mus musculus

<400> SEQUENCE: 15
gtgcaaggta cacattttcc gtacacg                                 27

<210> SEQ ID NO 16
<211> LENGTH: 9

```
<212> TYPE: PRT
<213> ORGANISM: Mus musculus

<400> SEQUENCE: 16

Val Gln Gly Thr His Phe Pro Tyr Thr
1               5

<210> SEQ ID NO 17
<211> LENGTH: 363
<212> TYPE: DNA
<213> ORGANISM: Mus musculus

<400> SEQUENCE: 17
caggtccagt tgcagcagtc tggacctgag ctggtgaagc ctggggcctc agtgaagatt    60
tcctgcaaag cttctggcta cgcattcagt agctcttgga tgaactgggt gatacagagg   120
cctggacagg gtcttgagtg gattggacgg atttatcctg agatggaga  tactaactac    180 aatggaagt tcaagggcaa ggccacactg actgcagaca atcctccag tacagcctac      240 atgcagctca gcagcctgac ctctgtggac tctgcggtct atttctgtgc aagatcagga    300
tttattacta cggttttaga ctttgactac tggggccacg gcaccactct cacagtctcc    360
tca                                                                  363

<210> SEQ ID NO 18
<211> LENGTH: 121
<212> TYPE: PRT
<213> ORGANISM: Mus musculus

<400> SEQUENCE: 18

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Ile Gln Arg Pro Gly Gln Gly Leu Glu Trp Ile
        35                  40                  45

Gly Arg Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Val Asp Ser Ala Val Tyr Phe Cys
                85                  90                  95

Ala Arg Ser Gly Phe Ile Thr Thr Val Leu Asp Phe Asp Tyr Trp Gly
            100                 105                 110

His Gly Thr Thr Leu Thr Val Ser Ser
        115                 120

<210> SEQ ID NO 19
<211> LENGTH: 333
<212> TYPE: DNA
<213> ORGANISM: Mus musculus

<400> SEQUENCE: 19
gacattgtgc tgacgcagtc tccaacctct ttggctgtgt ctctagggca gagggccacc    60
atctcctgca gagccagcga aagtgttgat acttttggca ttagttttat gaactggttc   120
caacagaaac caggacagcc acccaaactc ctcatccatg ctgcatccaa tcaaggatcc   180
ggggtccctg ccaggtttag tggtagtggg tctgggacgg acttcagcct caacatccat   240
cctatggagg aggatgatag tgcaatgtat ttctgtcagc aaagtaagga ggttccattc   300
```

```
acgttcggct cggggacaaa gttggaaata aaa                                   333
```

<210> SEQ ID NO 20
<211> LENGTH: 111
<212> TYPE: PRT
<213> ORGANISM: Mus musculus

<400> SEQUENCE: 20

```
Asp Ile Val Leu Thr Gln Ser Pro Thr Ser Leu Ala Val Ser Leu Gly
1               5                   10                  15

Gln Arg Ala Thr Ile Ser Cys Arg Ala Ser Glu Ser Val Asp Thr Phe
            20                  25                  30

Gly Ile Ser Phe Met Asn Trp Phe Gln Gln Lys Pro Gly Gln Pro Pro
        35                  40                  45

Lys Leu Leu Ile His Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Ser Ala Met Tyr Phe Cys Gln Gln Ser Lys
                85                  90                  95

Glu Val Pro Phe Thr Phe Gly Ser Gly Thr Lys Leu Glu Ile Lys
            100                 105                 110
```

<210> SEQ ID NO 21
<211> LENGTH: 15
<212> TYPE: DNA
<213> ORGANISM: Mus musculus

<400> SEQUENCE: 21

```
agctcttgga tgaac                                                       15
```

<210> SEQ ID NO 22
<211> LENGTH: 5
<212> TYPE: PRT
<213> ORGANISM: Mus musculus

<400> SEQUENCE: 22

```
Ser Ser Trp Met Asn
1               5
```

<210> SEQ ID NO 23
<211> LENGTH: 51
<212> TYPE: DNA
<213> ORGANISM: Mus musculus

<400> SEQUENCE: 23

```
cggatttatc ctggagatgg agatactaac tacaatggga agttcaaggg c               51
```

<210> SEQ ID NO 24
<211> LENGTH: 17
<212> TYPE: PRT
<213> ORGANISM: Mus musculus

<400> SEQUENCE: 24

```
Arg Ile Tyr Pro Gly Asp Gly Asp Thr Asn Tyr Asn Gly Lys Phe Lys
1               5                   10                  15

Gly
```

<210> SEQ ID NO 25
<211> LENGTH: 36

<212> TYPE: DNA
<213> ORGANISM: Mus musculus

<400> SEQUENCE: 25
tcaggattta ttactacggt tttagacttt gactac                          36

<210> SEQ ID NO 26
<211> LENGTH: 12
<212> TYPE: PRT
<213> ORGANISM: Mus musculus

<400> SEQUENCE: 26

Ser Gly Phe Ile Thr Thr Val Leu Asp Phe Asp Tyr
1               5                   10

<210> SEQ ID NO 27
<211> LENGTH: 45
<212> TYPE: DNA
<213> ORGANISM: Mus musculus

<400> SEQUENCE: 27
agagccagcg aaagtgttga tactttggc attagttttta tgaac               45

<210> SEQ ID NO 28
<211> LENGTH: 15
<212> TYPE: PRT
<213> ORGANISM: Mus musculus

<400> SEQUENCE: 28

Arg Ala Ser Glu Ser Val Asp Thr Phe Gly Ile Ser Phe Met Asn
1               5                   10                  15

<210> SEQ ID NO 29
<211> LENGTH: 21
<212> TYPE: DNA
<213> ORGANISM: Mus musculus

<400> SEQUENCE: 29
gctgcatcca atcaaggatc c                                         21

<210> SEQ ID NO 30
<211> LENGTH: 7
<212> TYPE: PRT
<213> ORGANISM: Mus musculus

<400> SEQUENCE: 30

Ala Ala Ser Asn Gln Gly Ser
1               5

<210> SEQ ID NO 31
<211> LENGTH: 27
<212> TYPE: DNA
<213> ORGANISM: Mus musculus

<400> SEQUENCE: 31
cagcaaagta aggaggttcc attcacg                                   27

<210> SEQ ID NO 32
<211> LENGTH: 9
<212> TYPE: PRT
<213> ORGANISM: Mus musculus

<400> SEQUENCE: 32

Gln Gln Ser Lys Glu Val Pro Phe Thr

<210> SEQ ID NO 33
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33

```
gaggtgcagc tggtggagtc tgggggaggc ttggtccagc ctggagggtc cctgagactc      60
tcctgtgcag cctctggatt caccttcagt agctcttgga tgaactgggt ccgccaggct     120
ccagggaagg ggctggagtg ggttggccgg atttatcctg agatggaga tactaactac      180
aatgggaagt tcaagggcag attcaccatc tcaagagatg attcaaagaa ctcactgtat     240
ctgcaaatga acagcctgaa aaccgaggac acggccgtgt attactgtgc tagatcagga     300
tttattacta cggttttaga ctttgactac tggggccaag gaaccctggt caccgtctcc     360
tca                                                                   363
```

<210> SEQ ID NO 34
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Ser
            20                  25                  30
Trp Met Asn Trp Val Arg Gln Ala Pro Gly Lys Gly Leu Glu Trp Val
        35                  40                  45
Gly Arg Ile Tyr Pro Gly Asp Gly Asp Thr Asn Tyr Asn Gly Lys Phe
    50                  55                  60
Lys Gly Arg Phe Thr Ile Ser Arg Asp Asp Ser Lys Asn Ser Leu Tyr
65                  70                  75                  80
Leu Gln Met Asn Ser Leu Lys Thr Glu Asp Thr Ala Val Tyr Tyr Cys
                85                  90                  95
Ala Arg Ser Gly Phe Ile Thr Thr Val Leu Asp Phe Asp Tyr Trp Gly
            100                 105                 110
Gln Gly Thr Leu Val Thr Val Ser Ser
        115                 120
```

<210> SEQ ID NO 35
<211> LENGTH: 90
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35

```
gaggtgcagc tggtggagtc tgggggaggc ttggtccagc ctggagggtc cctgagactc      60
tcctgtgcag cctctggatt caccttcagt                                       90
```

<210> SEQ ID NO 36

<210> SEQ ID NO 36
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser
            20                  25                  30
```

<210> SEQ ID NO 37
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

```
tgggtccgcc aggctccagg gaaggggctg gagtgggttg gc                    42
```

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Trp Val Arg Gln Ala Pro Gly Lys Gly Leu Glu Trp Val Gly
1               5                   10
```

<210> SEQ ID NO 39
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39

```
agattcacca tctcaagaga tgattcaaag aactcactgt atctgcaaat gaacagcctg    60
aaaaccgagg acacggccgt gtattactgt gctaga                              96
```

<210> SEQ ID NO 40
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Arg Phe Thr Ile Ser Arg Asp Asp Ser Lys Asn Ser Leu Tyr Leu Gln
1               5                   10                  15
Met Asn Ser Leu Lys Thr Glu Asp Thr Ala Val Tyr Tyr Cys Ala Arg
            20                  25                  30
```

<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 41
tggggccaag gaaccctggt caccgtctcc tca           33

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 42

Trp Gly Gln Gly Thr Leu Val Thr Val Ser Ser
1               5                   10

<210> SEQ ID NO 43
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 43
gaggtgcagc tggtggagtc tgggggaggc ttggtccagc ctggagggtc cctgagaatc     60
tcctgtgcag cctctggata cgccttcagt agctcttgga tgaactgggt catccaggct    120
ccagggaagg ggctggagtg gattggccgg atttatcctg agatggaga tactaactac     180 aatgggaagt tcaagggcag agccaccatc tcagcagatg attcaaagaa ctcactgtat    240
atgcaaatga acagcctgaa aaccgaggac acggccgtgt atatctgtgc tagatcagga    300
tttattacta cggttttaga ctttgactac tggggccaag gaaccctggt caccgtctcc    360
tca                                                                 363

<210> SEQ ID NO 44
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 44

Glu Val Gln Leu Val Glu Ser Gly Gly Gly Leu Val Gln Pro Gly Gly
1               5                   10                  15

Ser Leu Arg Ile Ser Cys Ala Ala Ser Gly Tyr Ala Phe Ser Ser Ser
            20                  25                  30

Trp Met Asn Trp Val Ile Gln Ala Pro Gly Lys Gly Leu Glu Trp Ile
        35                  40                  45

Gly Arg Ile Tyr Pro Gly Asp Gly Asp Thr Asn Tyr Asn Gly Lys Phe
    50                  55                  60

Lys Gly Arg Ala Thr Ile Ser Ala Asp Asp Ser Lys Asn Ser Leu Tyr
65                  70                  75                  80

Met Gln Met Asn Ser Leu Lys Thr Glu Asp Thr Ala Val Tyr Ile Cys
                85                  90                  95

Ala Arg Ser Gly Phe Ile Thr Thr Val Leu Asp Phe Asp Tyr Trp Gly
            100                 105                 110

Gln Gly Thr Leu Val Thr Val Ser Ser
        115                 120

<210> SEQ ID NO 45
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gaggtgcagc tggtggagtc tgggggaggc ttggtccagc ctggagggtc cctgagaatc    60
tcctgtgcag cctctggata cgccttcagt                                     90

<210> SEQ ID NO 46
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Val Glu Ser Gly Gly Gly Leu Val Gln Pro Gly Gly
1               5                   10                  15

Ser Leu Arg Ile Ser Cys Ala Ala Ser Gly Tyr Ala Phe Ser
            20                  25                  30

<210> SEQ ID NO 47
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tgggtcatcc aggctccagg gaaggggctg gagtggattg gc                        42

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Trp Val Ile Gln Ala Pro Gly Lys Gly Leu Glu Trp Ile Gly
1               5                   10

<210> SEQ ID NO 49
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
agagccacca tctcagcaga tgattcaaag aactcactgt atatgcaaat gaacagcctg    60
aaaaccgagg acacggccgt gtatatctgt gctaga                              96

<210> SEQ ID NO 50

<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Arg Ala Thr Ile Ser Ala Asp Asp Ser Lys Asn Ser Leu Tyr Met Gln
1               5                   10                  15

Met Asn Ser Leu Lys Thr Glu Asp Thr Ala Val Tyr Ile Cys Ala Arg
            20                  25                  30

<210> SEQ ID NO 51
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gaaattgtgc tgactcagtc tccagacttt cagtctgtga ctccaaagga gaaagtcacc      60
atcacctgca gagccagcga aagtgttgat acttttggca ttagtttat gaactggtac     120 cagcagaaac cagatcagtc tccaaagctc ctcatcaagg ctgcatccaa tcaaggatcc     180
ggggtcccct cgaggttcag tggcagtgga tctgggacag atttcaccct caccatcaat     240
agcctggaag ctgaagatgc tgcaacgtat tactgtcagc aaagtaagga ggttccattc     300
acgttcggcg agggaccaa ggtggagatc aaa                                   333

<210> SEQ ID NO 52
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Asp Thr Phe
            20                  25                  30

Gly Ile Ser Phe Met Asn Trp Tyr Gln Gln Lys Pro Asp Gln Ser Pro
        35                  40                  45

Lys Leu Leu Ile Lys Ala Ala Ser Asn Gln Gly Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Lys
                85                  90                  95

Glu Val Pro Phe Thr Phe Gly Gly Gly Thr Lys Val Glu Ile Lys
            100                 105                 110

<210> SEQ ID NO 53
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gaaattgtgc tgactcagtc tccagacttt cagtctgtga ctccaaagga gaaagtcacc    60
atcacctgc                                                             69

<210> SEQ ID NO 54
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 55
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tggtaccagc agaaaccaga tcagtctcca aagctcctca tcaag                     45

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Tyr Gln Gln Lys Pro Asp Gln Ser Pro Lys Leu Leu Ile Lys
1               5                   10                  15

<210> SEQ ID NO 57
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ggggtcccct cgaggttcag tggcagtgga tctgggacag atttcaccct caccatcaat    60
agcctggaag ctgaagatgc tgcaacgtat tactgt                               96

<210> SEQ ID NO 58
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gly Val Pro Ser Arg Phe Ser Gly Ser Gly Ser Gly Thr Asp Phe Thr
1               5                   10                  15

```
Leu Thr Ile Asn Ser Leu Glu Ala Glu Asp Ala Ala Thr Tyr Tyr Cys
            20                  25                  30

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ttcggcggag ggaccaaggt ggagatcaaa                                        30

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Phe Gly Gly Gly Thr Lys Val Glu Ile Lys
1               5                   10

<210> SEQ ID NO 61
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
gaaattgtgc tgactcagtc tccagacttt cagtctgtga ctccaaagga gaaagtcacc        60
atcacctgca gagccagcga aagtgttgat acttttggca ttagttttat gaactggttc       120
cagcagaaac cagatcagtc tccaaagctc ctcatccatg ctgcatccaa tcaaggatcc       180
ggggtcccct cgaggttcag tggcagtgga tctgggacag atttcaccct caccatcaat       240
agcctggaag ctgaagatgc tgcaacgtat ttctgtcagc aaagtaagga ggttccattc       300
acgttcggcg agggaccaa ggtggagatc aaa                                    333

<210> SEQ ID NO 62
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Asp Thr Phe
            20                  25                  30

Gly Ile Ser Phe Met Asn Trp Phe Gln Gln Lys Pro Asp Gln Ser Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Asn
65                  70                  75                  80
```

```
Ser Leu Glu Ala Glu Asp Ala Ala Thr Tyr Phe Cys Gln Gln Ser Lys
            85                  90                  95

Glu Val Pro Phe Thr Phe Gly Gly Gly Thr Lys Val Glu Ile Lys
        100                 105                 110
```

<210> SEQ ID NO 63
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tggttccagc agaaaccaga tcagtctcca aagctcctca tccat        45

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Trp Phe Gln Gln Lys Pro Asp Gln Ser Pro Lys Leu Leu Ile His
1               5                   10                  15
```

<210> SEQ ID NO 65
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ggggtcccct cgaggttcag tggcagtgga tctgggacag atttcaccct caccatcaat    60
agcctggaag ctgaagatgc tgcaacgtat ttctgt                              96

<210> SEQ ID NO 66
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

```
Gly Val Pro Ser Arg Phe Ser Gly Ser Gly Ser Gly Thr Asp Phe Thr
1               5                   10                  15

Leu Thr Ile Asn Ser Leu Glu Ala Glu Asp Ala Ala Thr Tyr Phe Cys
            20                  25                  30
```

<210> SEQ ID NO 67
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
gaaattgtgc tgactcagtc tccagacttt cagtctgtga ctccaaagga gaaagtcacc    60
atcacctgca gagccagcga agtgttgat acttttggca ttagttttat gaactggttc    120

```
cagcagaaac cagatcagtc tccaaagctc ctcatccatg ctgcatccaa tcaaggatcc      180
ggggtcccct cgaggttcag tggcagtgga tctgggacag atttcaccct caccatcaat      240
agcctggaag ctgaagatgc tgcaacgtat tactgtcagc aaagtaagga ggttccattc      300
acgttcggcg agggaccaa ggtggagatc aaa                                    333
```

<210> SEQ ID NO 68
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Asp Thr Phe
            20                  25                  30

Gly Ile Ser Phe Met Asn Trp Phe Gln Gln Lys Pro Asp Gln Ser Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Lys
                85                  90                  95

Glu Val Pro Phe Thr Phe Gly Gly Gly Thr Lys Val Glu Ile Lys
            100                 105                 110
```

<210> SEQ ID NO 69
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

```
gaaattgtgc tgactcagtc tccagacttt cagtctgtga ctccaaagga gaaagtcacc      60
atcacctgca gagccagcga aagtgttgat acttttggca ttagttttat gaactggttc      120
cagcagaaac cagatcagtc tccaaagctc ctcatcaagg ctgcatccaa tcaaggatcc      180
ggggtcccct cgaggttcag tggcagtgga tctgggacag atttcaccct caccatcaat      240
agcctggaag ctgaagatgc tgcaacgtat tactgtcagc aaagtaagga ggttccattc      300
acgttcggcg agggaccaa ggtggagatc aaa                                    333
```

<210> SEQ ID NO 70
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Asp Thr Phe
```

```
            20                  25                  30
Gly Ile Ser Phe Met Asn Trp Phe Gln Gln Lys Pro Asp Gln Ser Pro
        35                  40                  45

Lys Leu Leu Ile Lys Ala Ala Ser Asn Gln Gly Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Lys
                85                  90                  95

Glu Val Pro Phe Thr Phe Gly Gly Gly Thr Lys Val Glu Ile Lys
            100                 105                 110

<210> SEQ ID NO 71
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tggttccagc agaaaccaga tcagtctcca aagctcctca tcaag            45

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Trp Phe Gln Gln Lys Pro Asp Gln Ser Pro Lys Leu Leu Ile Lys
1               5                   10                  15

<210> SEQ ID NO 73
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
gaaattgtgc tgactcagtc tccagacttt cagtctgtga ctccaaagga gaaagtcacc    60
atcacctgca gagccagcga aagtgttgat acttttggca ttagttttat gaactggttc   120
cagcagaaac cagatcagtc tccaaagctc ctcatcaagg ctgcatccaa tcaaggatcc   180
ggggtcccct cgaggttcag tggcagtgga tctgggacag atttcaccct caccatcaat   240
agcctggaag ctgaagatgc tgcaacgtat ttctgtcagc aaagtaagga ggttccattc   300
acgttcggcg agggaccaa ggtggagatc aaa                                  333

<210> SEQ ID NO 74
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Ile Val Leu Thr Gln Ser Pro Asp Phe Gln Ser Val Thr Pro Lys
```

```
            1               5                   10                  15
Glu Lys Val Thr Ile Thr Cys Arg Ala Ser Glu Ser Val Asp Thr Phe
                20                  25                  30

Gly Ile Ser Phe Met Asn Trp Phe Gln Gln Lys Pro Asp Gln Ser Pro
            35                  40                  45

Lys Leu Leu Ile Lys Ala Ala Ser Asn Gln Gly Ser Gly Val Pro Ser
        50                  55                  60

Arg Phe Ser Gly Ser Gly Ser Gly Thr Asp Phe Thr Leu Thr Ile Asn
 65                 70                  75                  80

Ser Leu Glu Ala Glu Asp Ala Ala Thr Tyr Phe Cys Gln Gln Ser Lys
                85                  90                  95

Glu Val Pro Phe Thr Phe Gly Gly Gly Thr Lys Val Glu Ile Lys
            100                 105                 110
```

<210> SEQ ID NO 75
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 75

```
gaaattgtgc tgactcagtc tccagacttt cagtctgtga ctccaaagga gaaagtcacc    60
atcacctgca gagccagcga aagtgttgat acttttggca ttagttttat gaactggtac   120
cagcagaaac cagatcagtc tccaaagctc ctcatccatg ctgcatccaa tcaaggatcc   180
ggggtcccct cgaggttcag tggcagtgga tctgggacag atttcaccct caccatcaat   240
agcctggaag ctgaagatgc tgcaacgtat ttctgtcagc aaagtaagga ggttccattc   300
acgttcggcg gagggaccaa ggtggagatc aaa                                333
```

<210> SEQ ID NO 76
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

```
Glu Ile Val Leu Thr Gln Ser Pro Asp Phe Gln Ser Val Thr Pro Lys
 1               5                   10                  15

Glu Lys Val Thr Ile Thr Cys Arg Ala Ser Glu Ser Val Asp Thr Phe
                20                  25                  30

Gly Ile Ser Phe Met Asn Trp Tyr Gln Gln Lys Pro Asp Gln Ser Pro
            35                  40                  45

Lys Leu Leu Ile His Ala Ala Ser Asn Gln Gly Ser Gly Val Pro Ser
        50                  55                  60

Arg Phe Ser Gly Ser Gly Ser Gly Thr Asp Phe Thr Leu Thr Ile Asn
 65                 70                  75                  80

Ser Leu Glu Ala Glu Asp Ala Ala Thr Tyr Phe Cys Gln Gln Ser Lys
                85                  90                  95

Glu Val Pro Phe Thr Phe Gly Gly Gly Thr Lys Val Glu Ile Lys
            100                 105                 110
```

<210> SEQ ID NO 77
<211> LENGTH: 333
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 77

```
gaaattgtgc tgactcagtc tccagacttt cagtctgtga ctccaaagga gaaagtcacc    60
atcacctgca gagccagcga aagtgttgat acttttggca ttagtttat gaactggtac   120
cagcagaaac cagatcagtc tccaaagctc ctcatcaagg ctgcatccaa tcaaggatcc   180
ggggtcccct cgaggttcag tggcagtgga tctgggacag atttcaccct caccatcaat   240
agcctggaag ctgaagatgc tgcaacgtat ttctgtcagc aaagtaagga ggttccattc   300
acgttcggcg agggaccaa ggtggagatc aaa                                 333
```

<210> SEQ ID NO 78
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 78

```
Glu Ile Val Leu Thr Gln Ser Pro Asp Phe Gln Ser Val Thr Pro Lys
1               5                   10                  15
Glu Lys Val Thr Ile Thr Cys Arg Ala Ser Glu Ser Val Asp Thr Phe
            20                  25                  30
Gly Ile Ser Phe Met Asn Trp Tyr Gln Gln Lys Pro Asp Gln Ser Pro
        35                  40                  45
Lys Leu Leu Ile Lys Ala Ala Ser Asn Gln Gly Ser Gly Val Pro Ser
    50                  55                  60
Arg Phe Ser Gly Ser Gly Ser Gly Thr Asp Phe Thr Leu Thr Ile Asn
65                  70                  75                  80
Ser Leu Glu Ala Glu Asp Ala Ala Thr Tyr Phe Cys Gln Gln Ser Lys
                85                  90                  95
Glu Val Pro Phe Thr Phe Gly Gly Gly Thr Lys Val Glu Ile Lys
            100                 105                 110
```

<210> SEQ ID NO 79
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79

```
gaaattgtgc tgactcagtc tccagacttt cagtctgtga ctccaaagga gaaagtcacc    60
atcacctgca gagccagcga aagtgttgat acttttggca ttagtttat gaactggtac   120
cagcagaaac cagatcagtc tccaaagctc ctcatccatg ctgcatccaa tcaaggatcc   180
ggggtcccct cgaggttcag tggcagtgga tctgggacag atttcaccct caccatcaat   240
agcctggaag ctgaagatgc tgcaacgtat tactgtcagc aaagtaagga ggttccattc   300
acgttcggcg agggaccaa ggtggagatc aaa                                 333
```

<210> SEQ ID NO 80
<211> LENGTH: 111
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 80

Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Asp Thr Phe
            20                  25                  30

Gly Ile Ser Phe Met Asn Trp Tyr Gln Gln Lys Pro Asp Gln Ser Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Asn
65              70                  75                  80

Ser Leu Glu Ala Glu Asp Ala Ala Thr Tyr Tyr Cys Gln Gln Ser Lys
                85                  90                  95

Glu Val Pro Phe Thr Phe Gly Gly Gly Thr Lys Val Glu Ile Lys
            100                 105                 110

<210> SEQ ID NO 81
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tggtaccagc agaaaccaga tcagtctcca aagctcctca tccat             45

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Trp Tyr Gln Gln Lys Pro Asp Gln Ser Pro Lys Leu Leu Ile His
1               5                   10                  15

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic
      humanized VH leader peptide

<400> SEQUENCE: 83

Met Gly Asp Asn Asp Ile His Phe Ala Phe Leu Ser Thr Gly Val His
1               5                   10                  15

Ser

<210> SEQ ID NO 84
<211> LENGTH: 22
<212> TYPE: PRT
<213> ORGANISM: Artificial Sequence
<220> FEATURE:
<223> OTHER INFORMATION: Description of Artificial Sequence: Synthetic
      humanized VKI-L12 leader peptide
```

<400> SEQUENCE: 84

Met Asp Met Arg Val Pro Ala Gln Leu Leu Gly Leu Leu Leu Leu Trp
1               5                   10                  15

Leu Pro Gly Ala Lys Cys
            20

<210> SEQ ID NO 85
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tatatatatc tagacatata tatgggtgac aatgacatcc actttgcctt tctctcc    57

<210> SEQ ID NO 86
<211> LENGTH: 89
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tccactttgc ctttctctcc acaggtgtcc actccgaggt gcagctggtg gagtctgggg    60
gaggcttggt ccagcctgga gggtccctg                                       89

<210> SEQ ID NO 87
<211> LENGTH: 67
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gttcatccaa gagctactga aggtgaatcc agaggctgca caggagagtc tcagggaccc    60
tccaggc                                                              67

<210> SEQ ID NO 88
<211> LENGTH: 73
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
agctcttgga tgaactgggt ccgccaggct ccagggaagg ggctggagtg ggttggccgg    60
atttatcctg gag                                                       73

<210> SEQ ID NO 89
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gcccttgaac ttcccattgt agttagtatc tccatctcca ggataaatcc ggccaaccca    60
ctcca 65

<210> SEQ ID NO 90
<211> LENGTH: 70
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 90
ggaagttcaa gggcagattc accatctcaa gagatgattc aaagaactca ctgtatctgc    60
aaatgaacag    70

<210> SEQ ID NO 91
<211> LENGTH: 68
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 91
aatcctgatc tagcacagta atacacggcc gtgtcctcgg ttttcaggct gttcatttgc    60
agatacag    68

<210> SEQ ID NO 92
<211> LENGTH: 58
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 92
gtgtattact gtgctagatc aggatttatt actacggttt tagactttga ctactggg    58

<210> SEQ ID NO 93
<211> LENGTH: 74
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 93
tatatatagg gcccttggtg gaggctgagg agacggtgac cagggttcct tggccccagt    60
agtcaaagtc taaa    74

<210> SEQ ID NO 94
<211> LENGTH: 63
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 94
tatatatacc ccggggccaa atgtgaaatt gtgctgactc agtctccaga ctttcagtct    60
gtg    63

<210> SEQ ID NO 95
<211> LENGTH: 67
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 95
caacactttc gctggctctg caggtgatgg tgactttctc ctttggagtc acagactgaa      60
agtctgg                                                               67

<210> SEQ ID NO 96
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gccagcgaaa gtgttgatac ttttggcatt agttttatga actggttcca gcagaaacca      60
gatcagtc                                                              68

<210> SEQ ID NO 97
<211> LENGTH: 67
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
cgaggggacc ccggatcctt gattggatgc agcatggatg aggagctttg gagactgatc      60
tggtttc                                                               67

<210> SEQ ID NO 98
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
gatccggggt cccctcgagg ttcagtggca gtggatctgg gacagatttc accctcacca      60
tcaatagc                                                              68

<210> SEQ ID NO 99
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
gaacctcctt actttgctga cagaaatacg ttgcagcatc ttcagcttcc aggctattga      60
tggtgagg                                                              68

<210> SEQ ID NO 100
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 100
gcaaagtaag gaggttccat tcacgttcgg cggagggacc aaggtggaga tcaaa        55

<210> SEQ ID NO 101
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tatatatacg tacgtttgat ctccaccttg gtccctccgc cga                    43

<210> SEQ ID NO 102
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Thr
            20                  25                  30

Trp Met Asn Trp Val Arg Gln Ala Pro Gly Lys Gly Leu Glu Trp Val
        35                  40                  45

Gly Arg Ile Tyr Pro Gly Asp Gly Asp Thr Asn Tyr Asn Gly Lys Phe
    50                  55                  60

Lys Gly Arg Phe Thr Ile Ser Arg Asp Asp Ser Lys Asn Ser Leu Tyr
65                  70                  75                  80

Leu Gln Met Asn Ser Leu Lys Thr Glu Asp Thr Ala Val Tyr Tyr Cys
                85                  90                  95

Ala Arg Ser Gly Phe Ile Thr Thr Val Tyr Asp Phe Asp Tyr Trp Gly
            100                 105                 110

Gln Gly Thr Leu Val Thr Val Ser Ser
        115                 120

<210> SEQ ID NO 103
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Trp Met Asn Trp Val Arg Gln Ala Pro Gly Lys Gly Leu Glu Trp Val
        35                  40                  45

Gly Arg Ile Tyr Pro Gly Asp Gly Asp Thr Asn Tyr Asn Gly Lys Phe
    50                  55                  60

Lys Gly Arg Phe Thr Ile Ser Arg Asp Asp Ser Lys Asn Ser Leu Tyr
65                  70                  75                  80

```
Leu Gln Met Asn Ser Leu Lys Thr Glu Asp Thr Ala Val Tyr Tyr Cys
                85                  90                  95

Ala Arg Ser Gly Phe Ile Thr Thr Val Arg Asp Phe Asp Tyr Trp Gly
            100                 105                 110

Gln Gly Thr Leu Val Thr Val Ser Ser
        115                 120

<210> SEQ ID NO 104
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Trp Met Asn Trp Val Arg Gln Ala Pro Gly Lys Gly Leu Glu Trp Val
        35                  40                  45

Gly Arg Ile Tyr Pro Gly Asp Gly Asp Thr Asn Tyr Asn Ala Lys Phe
    50                  55                  60

Lys Gly Arg Phe Thr Ile Ser Arg Asp Asp Ser Lys Asn Ser Leu Tyr
65                  70                  75                  80

Leu Gln Met Asn Ser Leu Lys Thr Glu Asp Thr Ala Val Tyr Tyr Cys
                85                  90                  95

Ala Arg Ser Gly Phe Ile Thr Thr Val Arg Asp Phe Asp Tyr Trp Gly
            100                 105                 110

Gln Gly Thr Leu Val Thr Val Ser Ser
        115                 120

<210> SEQ ID NO 105
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Trp Met Asn Trp Val Arg Gln Ala Pro Gly Lys Gly Leu Glu Trp Val
        35                  40                  45

Gly Arg Ile Tyr Pro Gly Asp Gly Asp Thr Asn Tyr Asn Gly Lys Phe
    50                  55                  60

Lys Gly Arg Phe Thr Ile Ser Arg Asp Asp Ser Lys Asn Ser Leu Tyr
65                  70                  75                  80

Leu Gln Met Asn Ser Leu Lys Thr Glu Asp Thr Ala Val Tyr Tyr Cys
                85                  90                  95

Ala Arg Ser Gly Phe Ile Thr Thr Val His Asp Phe Asp Tyr Trp Gly
            100                 105                 110

Gln Gly Thr Leu Val Thr Val Ser Ser
        115                 120
```

<210> SEQ ID NO 106
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Trp Met Asn Trp Val Arg Gln Ala Pro Gly Lys Gly Leu Glu Trp Val
        35                  40                  45

Gly Arg Ile Tyr Pro Gly Asp Gly Asp Thr Asn Tyr Asn Val Lys Phe
    50                  55                  60

Lys Gly Arg Phe Thr Ile Ser Arg Asp Asp Ser Lys Asn Ser Leu Tyr
65                  70                  75                  80

Leu Gln Met Asn Ser Leu Lys Thr Glu Asp Thr Ala Val Tyr Tyr Cys
                85                  90                  95

Ala Arg Ser Gly Phe Ile Thr Thr Val Arg Asp Phe Asp Tyr Trp Gly
            100                 105                 110

Gln Gly Thr Leu Val Thr Val Ser Ser
        115                 120
```

<210> SEQ ID NO 107
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 107

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Trp Met Asn Trp Val Arg Gln Ala Pro Gly Lys Gly Leu Glu Trp Val
        35                  40                  45

Gly Arg Ile Tyr Pro Gly Asp Gly Asp Thr Asn Tyr Tyr Gly Lys Phe
    50                  55                  60

Lys Gly Arg Phe Thr Ile Ser Arg Asp Asp Ser Lys Asn Ser Leu Tyr
65                  70                  75                  80

Leu Gln Met Asn Ser Leu Lys Thr Glu Asp Thr Ala Val Tyr Tyr Cys
                85                  90                  95

Ala Arg Ser Gly Phe Ile Thr Thr Val Arg Asp Phe Asp Tyr Trp Gly
            100                 105                 110

Gln Gly Thr Leu Val Thr Val Ser Ser
        115                 120
```

<210> SEQ ID NO 108
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Trp Met Asn Trp Val Arg Gln Ala Pro Gly Lys Gly Leu Glu Trp Val
        35                  40                  45

Gly Arg Ile Tyr Pro Gly Asp Gly Asp Thr Asn Tyr Asp Gly Lys Phe
    50                  55                  60

Lys Gly Arg Phe Thr Ile Ser Arg Asp Asp Ser Lys Asn Ser Leu Tyr
65                  70                  75                  80

Leu Gln Met Asn Ser Leu Lys Thr Glu Asp Thr Ala Val Tyr Tyr Cys
                85                  90                  95

Ala Arg Ser Gly Phe Ile Thr Thr Val Arg Asp Phe Asp Tyr Trp Gly
            100                 105                 110

Gln Gly Thr Leu Val Thr Val Ser Ser
        115                 120

<210> SEQ ID NO 109
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Trp Met Asn Trp Val Arg Gln Ala Pro Gly Lys Gly Leu Glu Trp Val
        35                  40                  45

Gly Arg Ile Tyr Pro Gly Asp Gly Asp Thr Asn Tyr Leu Gly Lys Phe
    50                  55                  60

Lys Gly Arg Phe Thr Ile Ser Arg Asp Asp Ser Lys Asn Ser Leu Tyr
65                  70                  75                  80

Leu Gln Met Asn Ser Leu Lys Thr Glu Asp Thr Ala Val Tyr Tyr Cys
                85                  90                  95

Ala Arg Ser Gly Phe Ile Thr Thr Val Arg Asp Phe Asp Tyr Trp Gly
            100                 105                 110

Gln Gly Thr Leu Val Thr Val Ser Ser
        115                 120

<210> SEQ ID NO 110
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Asp Thr Phe
            20                  25                  30

Gly Ile Ser Phe Ile Asn Trp Phe Gln Gln Lys Pro Asp Gln Ser Pro

```
                35                  40                  45
Lys Leu Leu Ile His Glu Ala Ser Asn Gln Gly Ser Gly Val Pro Ser
         50                  55                  60
Arg Phe Ser Gly Ser Gly Ser Gly Thr Asp Phe Thr Leu Thr Ile Asn
 65                  70                  75                  80
Ser Leu Glu Ala Glu Asp Ala Ala Thr Tyr Tyr Cys Gln Gln Thr Lys
                 85                  90                  95
Glu Val Pro Phe Thr Phe Gly Gly Gly Thr Lys Val Glu Ile Lys
            100                 105                 110

<210> SEQ ID NO 111
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Glu Ile Val Leu Thr Gln Ser Pro Asp Phe Gln Ser Val Thr Pro Lys
 1               5                  10                  15
Glu Lys Val Thr Ile Thr Cys Arg Ala Ser Glu Ser Val Asp Thr Phe
                20                  25                  30
Gly Ile Ser Phe Met Asn Trp Phe Gln Gln Lys Pro Asp Gln Ser Pro
            35                  40                  45
Lys Leu Leu Ile His Glu Ala Ser Asn Gln Gly Ser Gly Val Pro Ser
         50                  55                  60
Arg Phe Ser Gly Ser Gly Ser Gly Thr Asp Phe Thr Leu Thr Ile Asn
 65                  70                  75                  80
Ser Leu Glu Ala Glu Asp Ala Ala Thr Tyr Tyr Cys Gln Gln Ser Lys
                 85                  90                  95
Glu Val Pro Phe Thr Phe Gly Gly Gly Thr Lys Val Glu Ile Lys
            100                 105                 110

<210> SEQ ID NO 112
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Glu Ile Val Leu Thr Gln Ser Pro Asp Phe Gln Ser Val Thr Pro Lys
 1               5                  10                  15
Glu Lys Val Thr Ile Thr Cys Arg Ala Ser Glu Ser Val Asp His Phe
                20                  25                  30
Gly Ile Ser Phe Met Asn Trp Phe Gln Gln Lys Pro Asp Gln Ser Pro
            35                  40                  45
Lys Leu Leu Ile His Glu Ala Ser Asn Gln Gly Ser Gly Val Pro Ser
         50                  55                  60
Arg Phe Ser Gly Ser Gly Ser Gly Thr Asp Phe Thr Leu Thr Ile Asn
 65                  70                  75                  80
Ser Leu Glu Ala Glu Asp Ala Ala Thr Tyr Tyr Cys Gln Gln Ser Lys
                 85                  90                  95
Glu Val Pro Ile Thr Phe Gly Gly Gly Thr Lys Val Glu Ile Lys
            100                 105                 110
```

<210> SEQ ID NO 113
<211> LENGTH: 111
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 113

Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Asp Thr Phe
            20                  25                  30

Gly Ile Ser Phe Met Asn Trp Phe Gln Gln Lys Pro Asp Gln Ser Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Lys
                85                  90                  95

Glu Val Pro Ile Thr Phe Gly Gly Gly Thr Lys Val Glu Ile Lys
            100                 105                 110

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 114

Ser Thr Trp Met Asn
1               5

<210> SEQ ID NO 115
<211> LENGTH: 17
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 115

Arg Ile Tyr Pro Gly Asp Gly Asp Thr Asn Tyr Asn Ala Lys Phe Lys
1               5                   10                  15

Gly

<210> SEQ ID NO 116
<211> LENGTH: 17
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 116

Arg Ile Tyr Pro Gly Asp Gly Asp Thr Asn Tyr Asn Val Lys Phe Lys
1               5                   10                  15

Gly

<210> SEQ ID NO 117

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Arg Ile Tyr Pro Gly Asp Gly Asp Thr Asn Tyr Tyr Gly Lys Phe Lys
1               5                   10                  15

Gly

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Arg Ile Tyr Pro Gly Asp Gly Asp Thr Asn Tyr Asp Gly Lys Phe Lys
1               5                   10                  15

Gly

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Arg Ile Tyr Pro Gly Asp Gly Asp Thr Asn Tyr Leu Gly Lys Phe Lys
1               5                   10                  15

Gly

<210> SEQ ID NO 120
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ser Gly Phe Ile Thr Thr Val Tyr Asp Phe Asp Tyr
1               5                   10

<210> SEQ ID NO 121
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ser Gly Phe Ile Thr Thr Val Arg Asp Phe Asp Tyr
1               5                   10

<210> SEQ ID NO 122
<211> LENGTH: 12
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 122

Ser Gly Phe Ile Thr Thr Val His Asp Phe Asp Tyr
1               5                   10

<210> SEQ ID NO 123
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Arg Ala Ser Glu Ser Val Asp Thr Phe Gly Ile Ser Phe Ile Asn
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Arg Ala Ser Glu Ser Val Asp His Phe Gly Ile Ser Phe Met Asn
1               5                   10                  15

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Glu Ala Ser Asn Gln Gly Ser
1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gln Gln Thr Lys Glu Val Pro Phe Thr
1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gln Gln Ser Lys Glu Val Pro Ile Thr
1               5

<210> SEQ ID NO 128
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
gctggtggtg ccgttctata gccatagcga ggtgcagctg gtggagtctg g            51

<210> SEQ ID NO 129
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
ggaagaccga tgggcccttg gtggaggctg aggagacggt gaccagggtt ccttg        55

<210> SEQ ID NO 130
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
ggtcgttcca ttttactccc actccgaaat tgtgctgact cagtctccag actttcag    58

<210> SEQ ID NO 131
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
gatgaagaca gatggtgcag ccacagtacg tttgatctcc accttggtcc ctccgccgaa  60
cg                                                                 62

<210> SEQ ID NO 132
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: a, c, t or g

<400> SEQUENCE: 132
gcctggcgga cccassncat ccaagagcta ctgaaggtga atccag                 46

<210> SEQ ID NO 133
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (20)..(20)
<223> OTHER INFORMATION: a, c, t or g

<400> SEQUENCE: 133
gcctggcgga cccagttssn ccaagagcta ctgaaggtga atccag            46

<210> SEQ ID NO 134
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: a, c, t or g

<400> SEQUENCE: 134
gcctggcgga cccagttcat ssnagagcta ctgaaggtga atccag            46

<210> SEQ ID NO 135
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(26)
<223> OTHER INFORMATION: a, c, t or g

<400> SEQUENCE: 135
gcctggcgga cccagttcat ccassngcta ctgaaggtga atccag            46

<210> SEQ ID NO 136
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(29)
<223> OTHER INFORMATION: a, c, t or g

<400> SEQUENCE: 136
gcctggcgga cccagttcat ccaagassna ctgaaggtga atccag            46

<210> SEQ ID NO 137
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: a, c, t or g

<400> SEQUENCE: 137
gcctggcgga cccawsncat ccaagagcta ctgaaggtga atccag            46

<210> SEQ ID NO 138
```

```
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: a, c, t or g

<400> SEQUENCE: 138
gcctggcgga cccagttwsn ccaagagcta ctgaaggtga atccag              46

<210> SEQ ID NO 139
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: a, c, t or g

<400> SEQUENCE: 139
gcctggcgga cccagttcat wsnagagcta ctgaaggtga atccag              46

<210> SEQ ID NO 140
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(26)
<223> OTHER INFORMATION: a, c, t or g

<400> SEQUENCE: 140
gcctggcgga cccagttcat ccawsngcta ctgaaggtga atccag              46

<210> SEQ ID NO 141
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(29)
<223> OTHER INFORMATION: a, c, t or g

<400> SEQUENCE: 141
gcctggcgga cccagttcat ccaagawsna ctgaaggtga atccag              46

<210> SEQ ID NO 142
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
ctggcggacc cagthcatcm aagwgctact gaaggtgaat cc                  42
```

<210> SEQ ID NO 143
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 143
ctggcggacc cagthcatct cagwgctact gaaggtgaat cc                          42

<210> SEQ ID NO 144
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 144
ctggcggacc cagagcatcm aagwgctact gaaggtgaat cc                          42

<210> SEQ ID NO 145
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 145
ctggcggacc cagagcatct cagwgctact gaaggtgaat cc                          42

<210> SEQ ID NO 146
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 146
ctgcccttga acttcscatw gtagttagda tctccatctc cag                         43

<210> SEQ ID NO 147
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 147
ctgcccttga acttcscatw gtagttatta tctccatctc cag                         43

<210> SEQ ID NO 148
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 148
ctgcccttga acttcscaag gtagttagda tctccatctc cag                         43

<210> SEQ ID NO 149
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ctgcccttga acttcscaag gtagttatta tctccatctc cag                                43

<210> SEQ ID NO 150
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
cccagtagtc aaagtcgtra accgtagkaa taaatcctga tctagc                             46

<210> SEQ ID NO 151
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
cccagtagtc aaagtcsaaa accgtagkaa taaatcctga tctagc                             46

<210> SEQ ID NO 152
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
cccagtagtc aaagtctcga accgtagkaa taaatcctga tctagc                             46

<210> SEQ ID NO 153
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
ctgctggaac cagttyvtaa aactaakgcc aaaatgaata cactttcgc tggc                     54

<210> SEQ ID NO 154
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
ctgctggaac cagttyvtaa aactaakgcc aaaatgatca cactttcgc tggc                     54

<210> SEQ ID NO 155

<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
ctgctggaac cagttyvtaa aactaakgcc aaaagtaata acactttcgc tggc    54

<210> SEQ ID NO 156
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
ctgctggaac cagttyvtaa aactaakgcc aaaagtatca acactttcgc tggc    54

<210> SEQ ID NO 157
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ggggaccccg gatccttgat tggatgcata atggatgagg agctttgg    48

<210> SEQ ID NO 158
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ggggaccccg gagtattgat tggatgcata atggatgagg agctttgg    48

<210> SEQ ID NO 159
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
ggggaccccg gatcctgkat tggatgcata atggatgagg agctttgg    48

<210> SEQ ID NO 160
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
ggggaccccg gatccttgat tggatgcckc atggatgagg agctttgg    48

<210> SEQ ID NO 161
<211> LENGTH: 48

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ggggaccccg gagtattgat tggatgcckc atggatgagg agctttgg            48

<210> SEQ ID NO 162
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
ggggaccccg gatcctgkat tggatgcckc atggatgagg agctttgg            48

<210> SEQ ID NO 163
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ctccgccgaa cgtgawtgga acctccttag wttgctgaca gtaatacg            48

<210> SEQ ID NO 164
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ctccgccgaa cgtgtttgga acctccttag wttgctgaca gtaatacg            48

<210> SEQ ID NO 165
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
aactaatgcc aaaagtaata acactttcgc tggctctg                       38

<210> SEQ ID NO 166
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
cataaaacta atgccaaaat gaataacact ttcgctggct ctgcagg             47

<210> SEQ ID NO 167
<211> LENGTH: 47
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 167
ccagttcata aaactaatgc caaaatgatc aacactttcg ctggctc                    47

<210> SEQ ID NO 168
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
ggatccttga ttggatgcct catggatgag gagctttgg                             39

<210> SEQ ID NO 169
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
gtccctccgc cgaacgtgwt tggaacctcc ttactttgc                             39

<210> SEQ ID NO 170
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
cctggcggac ccagttcatc tcagagctac tgaaggtgaa tcc                        43

<210> SEQ ID NO 171
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
cctggcggac ccagtacatc tcagagctac tgaaggtgaa tcc                        43

<210> SEQ ID NO 172
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
cctggcggac ccagtacatc caagagctac tgaaggtgaa tcc                        43

<210> SEQ ID NO 173
<211> LENGTH: 42
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 173
gaatctgccc ttgaacttcg cattgtagtt agtatctcca tc                        42

<210> SEQ ID NO 174
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
cttggcccca gtagtcaaag tctcgaaccg tagtaataaa tcctg                     45

<210> SEQ ID NO 175
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
cttggcccca gtagtcaaag tcgygaaccg tagtaataaa tcctg                     45

<210> SEQ ID NO 176
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
ggaccccgga tcctstattg gatgcctcat gg                                   32

<210> SEQ ID NO 177
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
cctcgagggg accccggagt atstattgga tgcctcatgg atg                       43

<210> SEQ ID NO 178
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
ggaccccgga tcctgsattg gatgcctcat gg                                   32

<210> SEQ ID NO 179
<211> LENGTH: 43
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 179
cctcgagggg accccggagt atgsattgga tgcctcatgg atg                        43

<210> SEQ ID NO 180
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
ctccgccgaa cgtgwttgga acctccttag wttgctgaca gtaatacg                   48

<210> SEQ ID NO 181
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
cgccgaacgt gaatggaacc cgcttagwtt gcgcacagta atacgttgca gc              52

<210> SEQ ID NO 182
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
cgccgaacgt gaatggaacc cgcttagwtt gctgacagta atacgttg                   48

<210> SEQ ID NO 183
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ctccgccgaa cgtgwttgga acctccttag wttgcgcaca gtaatacgtt gc              52

<210> SEQ ID NO 184
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
cctggcggac ccagttcatc caaacgctac tgaaggtgaa tcc                        43

<210> SEQ ID NO 185
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 185
gcctggcgga cccagtwcat cmaaacgcta ctgaaggtga atc        43

<210> SEQ ID NO 186
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
gagcctggcg gacccagagc atcmaaacgc tactgaaggt gaatc      45

<210> SEQ ID NO 187
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
cttgaacttc acatwgtagt taktatctcc atctccarga taaatccggc ca    52

<210> SEQ ID NO 188
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
cttgaacttc acattgtagt taktatctcc atctccarga taaatccggc ca    52

<210> SEQ ID NO 189
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
cttgaacttc acatwgtagt tagtatctcc atctccarga taaatccggc ca    52

<210> SEQ ID NO 190
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
gtcaaagtcg cgaaccgtag kaataaatcc tgatctagc             39

<210> SEQ ID NO 191
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Val
            20                  25                  30

Trp Met Asn Trp Val Arg Gln Ala Pro Gly Lys Gly Leu Glu Trp Val
        35                  40                  45

Gly Arg Ile Tyr Pro Gly Asp Gly Asp Thr Asn Tyr Asn Val Lys Phe
    50                  55                  60

Lys Gly Arg Phe Thr Ile Ser Arg Asp Asp Ser Lys Asn Ser Leu Tyr
65                  70                  75                  80

Leu Gln Met Asn Ser Leu Lys Thr Glu Asp Thr Ala Val Tyr Tyr Cys
                85                  90                  95

Ala Arg Ser Gly Phe Ile Thr Thr Val Arg Asp Phe Asp Tyr Trp Gly
            100                 105                 110

Gln Gly Thr Leu Val Thr Val Ser Ser
        115                 120

<210> SEQ ID NO 192
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Val
            20                  25                  30

Trp Met Asn Trp Val Arg Gln Ala Pro Gly Lys Gly Leu Glu Trp Val
        35                  40                  45

Gly Arg Ile Tyr Leu Gly Asp Gly Asp Thr Asn Tyr Asn Val Lys Phe
    50                  55                  60

Lys Gly Arg Phe Thr Ile Ser Arg Asp Asp Ser Lys Asn Ser Leu Tyr
65                  70                  75                  80

Leu Gln Met Asn Ser Leu Lys Thr Glu Asp Thr Ala Val Tyr Tyr Cys
                85                  90                  95

Ala Arg Ser Gly Phe Ile Thr Thr Val Arg Asp Phe Asp Tyr Trp Gly
            100                 105                 110

Gln Gly Thr Leu Val Thr Val Ser Ser
        115                 120

<210> SEQ ID NO 193
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Asp His Phe
            20                  25                  30

```
Gly Ile Ser Phe Ile Asn Trp Phe Gln Gln Lys Pro Asp Gln Ser Pro
            35                  40                  45

Lys Leu Leu Ile His Glu Ala Ser Asn Pro Tyr Ser Gly Val Pro Ser
 50                      55                  60

Arg Phe Ser Gly Ser Gly Ser Gly Thr Asp Phe Thr Leu Thr Ile Asn
 65                  70                  75                  80

Ser Leu Glu Ala Glu Asp Ala Ala Thr Tyr Tyr Cys Ala Gln Ser Lys
                 85                  90                  95

Glu Val Pro Ile Thr Phe Gly Gly Gly Thr Lys Val Glu Ile Lys
             100                 105                 110

<210> SEQ ID NO 194
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Glu Ile Val Leu Thr Gln Ser Pro Asp Phe Gln Ser Val Thr Pro Lys
 1               5                  10                  15

Glu Lys Val Thr Ile Thr Cys Arg Ala Ser Glu Ser Val Asp Thr Phe
             20                  25                  30

Gly Ile Ser Phe Met Asn Trp Phe Gln Gln Lys Pro Asp Gln Ser Pro
            35                  40                  45

Lys Leu Leu Ile His Glu Ala Ser Asn Gln Gly Ser Gly Val Pro Ser
 50                      55                  60

Arg Phe Ser Gly Ser Gly Ser Gly Thr Asp Phe Thr Leu Thr Ile Asn
 65                  70                  75                  80

Ser Leu Glu Ala Glu Asp Ala Ala Thr Tyr Tyr Cys Ala Gln Ser Lys
                 85                  90                  95

Glu Val Pro Phe Thr Phe Gly Gly Gly Thr Lys Val Glu Ile Lys
             100                 105                 110

<210> SEQ ID NO 195
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Glu Ile Val Leu Thr Gln Ser Pro Asp Phe Gln Ser Val Thr Pro Lys
 1               5                  10                  15

Glu Lys Val Thr Ile Thr Cys Arg Ala Ser Glu Ser Val Asp Thr Phe
             20                  25                  30

Gly Ile Ser Phe Met Asn Trp Phe Gln Gln Lys Pro Asp Gln Ser Pro
            35                  40                  45

Lys Leu Leu Ile His Glu Ala Ser Asn Gln Gly Ser Gly Val Pro Ser
 50                      55                  60

Arg Phe Ser Gly Ser Gly Ser Gly Thr Asp Phe Thr Leu Thr Ile Asn
 65                  70                  75                  80

Ser Leu Glu Ala Glu Asp Ala Ala Thr Tyr Tyr Cys Ala Gln Ser Lys
                 85                  90                  95

Arg Val Pro Phe Thr Phe Gly Gly Gly Thr Lys Val Glu Ile Lys
             100                 105                 110
```

```
<210> SEQ ID NO 196
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Ile Thr Phe
            20                  25                  30

Gly Ile Ser Phe Met Asn Trp Phe Gln Gln Lys Pro Asp Gln Ser Pro
        35                  40                  45

Lys Leu Leu Ile His Glu Ala Ser Asn Gln Gly Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Lys
                85                  90                  95

Glu Val Pro Phe Thr Phe Gly Gly Gly Thr Lys Val Glu Ile Lys
            100                 105                 110

<210> SEQ ID NO 197
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Asp Thr Phe
            20                  25                  30

Gly Ile Ser Phe Met Asn Trp Phe Gln Gln Lys Pro Asp Gln Ser Pro
        35                  40                  45

Lys Leu Leu Ile His Glu Ala Ser Asn Gln Gly Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Ala Gln Thr Lys
                85                  90                  95

Arg Val Pro Phe Thr Phe Gly Gly Gly Thr Lys Val Glu Ile Lys
            100                 105                 110

<210> SEQ ID NO 198
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Asp Thr Phe
```

```
            20                  25                  30

Gly Ile Ser Phe Met Asn Trp Phe Gln Gln Lys Pro Asp Gln Ser Pro
            35                  40                  45

Lys Leu Leu Ile His Glu Ala Ser Asn Gln Gly Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Lys
                85                  90                  95

Glu Val Pro Ile Thr Phe Gly Gly Gly Thr Lys Val Glu Ile Lys
                100                 105                 110

<210> SEQ ID NO 199
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Asp Thr Phe
                20                  25                  30

Gly Ile Ser Phe Ile Asn Trp Phe Gln Gln Lys Pro Asp Gln Ser Pro
            35                  40                  45

Lys Leu Leu Ile His Glu Ala Ser Asn Pro Tyr Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Lys
                85                  90                  95

Glu Val Pro Phe Thr Phe Gly Gly Gly Thr Lys Val Glu Ile Lys
                100                 105                 110

<210> SEQ ID NO 200
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Asp Thr Phe
                20                  25                  30

Gly Ile Ser Phe Met Asn Trp Phe Gln Gln Lys Pro Asp Gln Ser Pro
            35                  40                  45

Lys Leu Leu Ile His Glu Ala Ser Asn Gln Gly Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Ala Gln Thr Lys
                85                  90                  95

Glu Val Pro Phe Thr Phe Gly Gly Gly Thr Lys Val Glu Ile Lys
```

<210> SEQ ID NO 201
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Asp Thr Phe
            20                  25                  30

Gly Ile Ser Phe Met Asn Trp Phe Gln Gln Lys Pro Asp Gln Ser Pro
        35                  40                  45

Lys Leu Leu Ile His Glu Ala Ser Asn Gln Gly Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Ala Gln Thr Lys
                85                  90                  95

Glu Val Pro Asn Thr Phe Gly Gly Gly Thr Lys Val Glu Ile Lys
            100                 105                 110
```

<210> SEQ ID NO 202
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Ile Thr Phe
            20                  25                  30

Gly Ile Ser Phe Met Asn Trp Phe Gln Gln Lys Pro Asp Gln Ser Pro
        35                  40                  45

Lys Leu Leu Ile His Glu Ala Ser Asn Thr Tyr Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Ala Gln Ser Lys
                85                  90                  95

Arg Val Pro Phe Thr Phe Gly Gly Gly Thr Lys Val Glu Ile Lys
            100                 105                 110
```

<210> SEQ ID NO 203
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

```
Glu Ile Val Leu Thr Gln Ser Pro Asp Phe Gln Ser Val Thr Pro Lys
1               5                   10                  15
```

Glu Lys Val Thr Ile Thr Cys Arg Ala Ser Glu Ser Val Asp Thr Phe
            20                  25                  30

Gly Ile Ser Phe Arg Asn Trp Phe Gln Gln Lys Pro Asp Gln Ser Pro
        35                  40                  45

Lys Leu Leu Ile His Glu Ala Ser Asn Gln Gly Ser Gly Val Pro Ser
 50                  55                  60

Arg Phe Ser Gly Ser Gly Ser Gly Thr Asp Phe Thr Leu Thr Ile Asn
 65                  70                  75                  80

Ser Leu Glu Ala Glu Asp Ala Ala Thr Tyr Tyr Cys Gln Gln Ser Lys
                85                  90                  95

Glu Val Pro Phe Thr Phe Gly Gly Gly Thr Lys Val Glu Ile Lys
            100                 105                 110

<210> SEQ ID NO 204
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Asp Thr Phe
            20                  25                  30

Gly Ile Ser Phe Met Asn Trp Phe Gln Gln Lys Pro Asp Gln Ser Pro
        35                  40                  45

Lys Leu Leu Ile His Glu Ala Ser Asn Pro Gly Ser Gly Val Pro Ser
 50                  55                  60

Arg Phe Ser Gly Ser Gly Ser Gly Thr Asp Phe Thr Leu Thr Ile Asn
 65                  70                  75                  80

Ser Leu Glu Ala Glu Asp Ala Ala Thr Tyr Tyr Cys Gln Gln Thr Lys
                85                  90                  95

Arg Val Pro Phe Thr Phe Gly Gly Gly Thr Lys Val Glu Ile Lys
            100                 105                 110

<210> SEQ ID NO 205
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Ile His Phe
            20                  25                  30

Gly Ile Ser Phe Met Asn Trp Phe Gln Gln Lys Pro Asp Gln Ser Pro
        35                  40                  45

Lys Leu Leu Ile His Glu Ala Ser Asn Arg Gly Ser Gly Val Pro Ser
 50                  55                  60

Arg Phe Ser Gly Ser Gly Ser Gly Thr Asp Phe Thr Leu Thr Ile Asn
 65                  70                  75                  80

Ser Leu Glu Ala Glu Asp Ala Ala Thr Tyr Tyr Cys Ala Gln Ser Lys
                85                  90                  95

```
Glu Val Pro Ile Thr Phe Gly Gly Gly Thr Lys Val Glu Ile Lys
                100                 105                 110

<210> SEQ ID NO 206
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Asp Thr Phe
            20                  25                  30

Gly Leu Ser Phe Met Asn Trp Phe Gln Gln Lys Pro Asp Gln Ser Pro
        35                  40                  45

Lys Leu Leu Ile His Glu Ala Ser Asn Pro Tyr Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Lys
                85                  90                  95

Glu Val Pro Phe Thr Phe Gly Gly Gly Thr Lys Val Glu Ile Lys
                100                 105                 110

<210> SEQ ID NO 207
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Ile Thr Phe
            20                  25                  30

Gly Ile Ser Phe Ile Asn Trp Phe Gln Gln Lys Pro Asp Gln Ser Pro
        35                  40                  45

Lys Leu Leu Ile His Glu Ala Ser Asn Pro Tyr Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Ala Gln Thr Lys
                85                  90                  95

Arg Val Pro Phe Thr Phe Gly Gly Gly Thr Lys Val Glu Ile Lys
                100                 105                 110

<210> SEQ ID NO 208
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208
```

```
Ser Val Trp Met Asn
1               5

<210> SEQ ID NO 209
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ser Thr Trp Met Asn
1               5

<210> SEQ ID NO 210
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Arg Ile Tyr Leu Gly Asp Gly Asp Thr Asn Tyr Asn Val Lys Phe Lys
1               5                   10                  15

Gly

<210> SEQ ID NO 211
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Arg Ala Ser Glu Ser Val Asp His Phe Gly Ile Ser Phe Ile Asn
1               5                   10                  15

<210> SEQ ID NO 212
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Arg Ala Ser Glu Ser Val Ile Thr Phe Gly Ile Ser Phe Met Asn
1               5                   10                  15

<210> SEQ ID NO 213
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Arg Ala Ser Glu Ser Val Asp Thr Phe Gly Ile Ser Phe Ile Asn
1               5                   10                  15

<210> SEQ ID NO 214
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 214

Arg Ala Ser Glu Ser Val Asp Thr Phe Gly Ile Ser Phe Arg Asn
1               5                   10                  15

<210> SEQ ID NO 215
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Arg Ala Ser Glu Ser Val Ile His Phe Gly Ile Ser Phe Met Asn
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Arg Ala Ser Glu Ser Val Asp Thr Phe Gly Leu Ser Phe Met Asn
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Arg Ala Ser Glu Ser Val Ile Thr Phe Gly Ile Ser Phe Ile Asn
1               5                   10                  15

<210> SEQ ID NO 218
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Glu Ala Ser Asn Pro Tyr Ser
1               5

<210> SEQ ID NO 219
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Glu Ala Ser Asn Thr Tyr Ser
1               5
```

<210> SEQ ID NO 220
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Glu Ala Ser Asn Pro Gly Ser
1               5

<210> SEQ ID NO 221
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Glu Ala Ser Asn Arg Gly Ser
1               5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ala Gln Ser Lys Glu Val Pro Ile Thr
1               5

<210> SEQ ID NO 223
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Ala Gln Ser Lys Glu Val Pro Phe Thr
1               5

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ala Gln Ser Lys Arg Val Pro Phe Thr
1               5

<210> SEQ ID NO 225
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ala Gln Thr Lys Arg Val Pro Phe Thr
1               5

<210> SEQ ID NO 226
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gln Gln Ser Lys Glu Val Pro Ile Thr
1               5

<210> SEQ ID NO 227
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ala Gln Thr Lys Glu Val Pro Phe Thr
1               5

<210> SEQ ID NO 228
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ala Gln Thr Lys Glu Val Pro Asn Thr
1               5

<210> SEQ ID NO 229
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Gln Gln Thr Lys Arg Val Pro Phe Thr
1               5

<210> SEQ ID NO 230
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser, Thr or Val

<400> SEQUENCE: 230

Ser Xaa Trp Met Asn
1               5

```
<210> SEQ ID NO 231
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pro or Leu
<220> FEATURE:
<221> NAME/KEY: MOD_RES
<222> LOCATION: (12)..(12)
<223> OTHER INFORMATION: Asn, Tyr, Asp or Leu
<220> FEATURE:
<221> NAME/KEY: MOD_RES
<222> LOCATION: (13)..(13)
<223> OTHER INFORMATION: Gly, Ala or Val

<400> SEQUENCE: 231

Arg Ile Tyr Xaa Gly Asp Gly Asp Thr Asn Tyr Xaa Xaa Lys Phe Lys
1               5                   10                  15

Gly

<210> SEQ ID NO 232
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Arg, Leu, Tyr or His

<400> SEQUENCE: 232

Ser Gly Phe Ile Thr Thr Val Xaa Asp Phe Asp Tyr
1               5                   10

<210> SEQ ID NO 233
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ile or Asp
<220> FEATURE:
<221> NAME/KEY: MOD_RES
<222> LOCATION: (8)..(8)
<223> OTHER INFORMATION: Thr or His
<220> FEATURE:
<221> NAME/KEY: MOD_RES
<222> LOCATION: (11)..(11)
<223> OTHER INFORMATION: Ile or Leu
<220> FEATURE:
<221> NAME/KEY: MOD_RES
<222> LOCATION: (14)..(14)
<223> OTHER INFORMATION: Ile, Met or Arg

<400> SEQUENCE: 233

Arg Ala Ser Glu Ser Val Xaa Xaa Phe Gly Xaa Ser Phe Xaa Asn
1               5                   10                  15

<210> SEQ ID NO 234
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or Ala
<220> FEATURE:
<221> NAME/KEY: MOD_RES
<222> LOCATION: (5)..(5)
<223> OTHER INFORMATION: Pro, Gln or Thr
<220> FEATURE:
<221> NAME/KEY: MOD_RES
<222> LOCATION: (6)..(6)
<223> OTHER INFORMATION: Tyr or Gly

<400> SEQUENCE: 234

Xaa Ala Ser Asn Xaa Xaa Ser
1               5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Ala
<220> FEATURE:
<221> NAME/KEY: MOD_RES
<222> LOCATION: (3)..(3)
<223> OTHER INFORMATION: Ser ot Thr
<220> FEATURE:
<221> NAME/KEY: MOD_RES
<222> LOCATION: (5)..(5)
<223> OTHER INFORMATION: Glu or Arg
<220> FEATURE:
<221> NAME/KEY: MOD_RES
<222> LOCATION: (8)..(8)
<223> OTHER INFORMATION: Phe, Ile or Asn

<400> SEQUENCE: 235

Xaa Gln Xaa Lys Xaa Val Pro Xaa Thr
1               5

<210> SEQ ID NO 236
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Thr
            20                  25                  30

Trp Met Asn Trp Val Arg Gln Ala Pro Gly Lys Gly Leu Glu Trp Val
        35                  40                  45

Gly Arg Ile Tyr Pro Gly Asp Gly Asp Thr Asn Tyr Asn Val Lys Phe
    50                  55                  60

Lys Gly Arg Phe Thr Ile Ser Arg Asp Asp Ser Lys Asn Ser Leu Tyr
65                  70                  75                  80
```

```
Leu Gln Met Asn Ser Leu Lys Thr Glu Asp Thr Ala Val Tyr Tyr Cys
                85                  90                  95

Ala Arg Ser Gly Phe Ile Thr Thr Val Arg Asp Phe Asp Tyr Trp Gly
            100                 105                 110

Gln Gly Thr Leu Val Thr Val Ser Ser
        115                 120

<210> SEQ ID NO 237
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Leu or Ile
<220> FEATURE:
<221> NAME/KEY: MOD_RES
<222> LOCATION: (27)..(27)
<223> OTHER INFORMATION: Phe or Tyr
<220> FEATURE:
<221> NAME/KEY: MOD_RES
<222> LOCATION: (28)..(28)
<223> OTHER INFORMATION: Thr or Ala
<220> FEATURE:
<221> NAME/KEY: MOD_RES
<222> LOCATION: (32)..(32)
<223> OTHER INFORMATION: Ser, Thr or Val
<220> FEATURE:
<221> NAME/KEY: MOD_RES
<222> LOCATION: (38)..(38)
<223> OTHER INFORMATION: Arg or Ile
<220> FEATURE:
<221> NAME/KEY: MOD_RES
<222> LOCATION: (48)..(48)
<223> OTHER INFORMATION: Val or Ile
<220> FEATURE:
<221> NAME/KEY: MOD_RES
<222> LOCATION: (53)..(53)
<223> OTHER INFORMATION: Leu or Pro
<220> FEATURE:
<221> NAME/KEY: MOD_RES
<222> LOCATION: (61)..(61)
<223> OTHER INFORMATION: Asn, Tyr, Asp or Leu
<220> FEATURE:
<221> NAME/KEY: MOD_RES
<222> LOCATION: (62)..(62)
<223> OTHER INFORMATION: Gly, Ala or Val
<220> FEATURE:
<221> NAME/KEY: MOD_RES
<222> LOCATION: (68)..(68)
<223> OTHER INFORMATION: Phe or Ala
<220> FEATURE:
<221> NAME/KEY: MOD_RES
<222> LOCATION: (72)..(72)
<223> OTHER INFORMATION: Arg or Ala
<220> FEATURE:
<221> NAME/KEY: MOD_RES
<222> LOCATION: (81)..(81)
<223> OTHER INFORMATION: Leu or Met
<220> FEATURE:
<221> NAME/KEY: MOD_RES
<222> LOCATION: (95)..(95)
<223> OTHER INFORMATION: Tyr or Ile
<220> FEATURE:
<221> NAME/KEY: MOD_RES
<222> LOCATION: (106)..(106)
<223> OTHER INFORMATION: Leu, Arg, Tyr or His

<400> SEQUENCE: 237

Glu Val Gln Leu Val Glu Ser Gly Gly Gly Leu Val Gln Pro Gly Gly
1               5                   10                  15
```

```
Ser Leu Arg Xaa Ser Cys Ala Ala Ser Gly Xaa Xaa Phe Ser Ser Xaa
            20                  25                  30

Trp Met Asn Trp Val Xaa Gln Ala Pro Gly Lys Gly Leu Glu Trp Xaa
        35                  40                  45

Gly Arg Ile Tyr Xaa Gly Asp Gly Asp Thr Asn Tyr Xaa Xaa Lys Phe
 50                  55                  60

Lys Gly Arg Xaa Thr Ile Ser Xaa Asp Asp Ser Lys Asn Ser Leu Tyr
 65                  70                  75                  80

Xaa Gln Met Asn Ser Leu Lys Thr Glu Asp Thr Ala Val Tyr Xaa Cys
                85                  90                  95

Ala Arg Ser Gly Phe Ile Thr Thr Val Xaa Asp Phe Asp Tyr Trp Gly
            100                 105                 110

Gln Gly Thr Leu Val Thr Val Ser Ser
        115                 120

<210> SEQ ID NO 238
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Asp or Ile
<220> FEATURE:
<221> NAME/KEY: MOD_RES
<222> LOCATION: (31)..(31)
<223> OTHER INFORMATION: Thr or His
<220> FEATURE:
<221> NAME/KEY: MOD_RES
<222> LOCATION: (34)..(34)
<223> OTHER INFORMATION: Ile or Leu
<220> FEATURE:
<221> NAME/KEY: MOD_RES
<222> LOCATION: (37)..(37)
<223> OTHER INFORMATION: Met, Ile or Arg
<220> FEATURE:
<221> NAME/KEY: MOD_RES
<222> LOCATION: (40)..(40)
<223> OTHER INFORMATION: Phe or Tyr
<220> FEATURE:
<221> NAME/KEY: MOD_RES
<222> LOCATION: (53)..(53)
<223> OTHER INFORMATION: Lys or His
<220> FEATURE:
<221> NAME/KEY: MOD_RES
<222> LOCATION: (54)..(54)
<223> OTHER INFORMATION: Ala or Glu
<220> FEATURE:
<221> NAME/KEY: MOD_RES
<222> LOCATION: (58)..(58)
<223> OTHER INFORMATION: Gln, Pro or Thr
<220> FEATURE:
<221> NAME/KEY: MOD_RES
<222> LOCATION: (59)..(59)
<223> OTHER INFORMATION: Gly or Tyr
<220> FEATURE:
<221> NAME/KEY: MOD_RES
<222> LOCATION: (91)..(91)
<223> OTHER INFORMATION: Tyr or Phe
<220> FEATURE:
<221> NAME/KEY: MOD_RES
<222> LOCATION: (93)..(93)
<223> OTHER INFORMATION: Gln or Ala
<220> FEATURE:
<221> NAME/KEY: MOD_RES
<222> LOCATION: (95)..(95)
<223> OTHER INFORMATION: Ser or Thr
<220> FEATURE:
```

```
<221> NAME/KEY: MOD_RES
<222> LOCATION: (97)..(97)
<223> OTHER INFORMATION: Glu or Arg
<220> FEATURE:
<221> NAME/KEY: MOD_RES
<222> LOCATION: (100)..(100)
<223> OTHER INFORMATION: Phe, Ile or Asn

<400> SEQUENCE: 238

Glu Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Xaa Xaa Phe
            20                  25                  30

Gly Xaa Ser Phe Xaa Asn Trp Xaa Gln Gln Lys Pro Asp Gln Ser Pro
        35              40                  45

Lys Leu Leu Ile Xaa Xaa Ala Ser Asn Xaa Xaa Ser Gly Val Pro Ser
    50              55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Xaa Cys Xaa Gln Xaa Lys
                85                  90                  95

Xaa Val Pro Xaa Thr Phe Gly Gly Thr Lys Val Glu Ile Lys
                100                 105                 110

<210> SEQ ID NO 239
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Arg Ala Ser Glu Ser Val Ile Thr Phe Gly Leu Ser Phe Met Asn
1               5                   10                  15
```

HUMANIZED ANTI-CD19 ANTIBODIES

This application is a divisional of U.S. application Ser. No. 11/852,106 filed on Sep. 7, 2007, now U.S. Pat. No. 8,323,653, said application Ser. No. 11/852,106 claims benefit under 35 U.S.C. §119(e) of the following U.S. Provisional Application Nos. 60/842,935 filed Sep. 8, 2006, 60/866,917 filed on Nov. 22, 2006, 60/911,397 filed on Apr. 12, 2007, 60/915,309 filed on May 1, 2007 and 60/939,429 filed on May 22, 2007. Each of the above listed applications is incorporated by reference herein in its entirety for all purposes.

REFERENCE TO THE SEQUENCE LISTING

This application incorporates by reference a Sequence Listing submitted with this application as text file entitled MED053US.txt created on Oct. 9, 2012 and having a size of 105 kilobytes.

1. INTRODUCTION

The present invention relates to human, humanized, or chimeric anti-CD19 antibodies that bind to the human CD19 antigen. The present invention is also directed to compositions comprising human, humanized, or chimeric anti-CD19 antibodies that may mediate one or more of the following: complement-dependent cell-mediated cytotoxicity (CDC), antigen-dependent cell-mediated-cytotoxicity (ADCC), and programmed cell death (apoptosis). The present invention is further directed to compositions comprising human, humanized, or chimeric anti-CD19 antibodies of the IgG1 and/or IgG3 human isotype, as well as to compositions comprising human, humanized, or chimeric anti-CD19 antibodies of the IgG2 and/or IgG4 human isotype that may mediate human ADCC, CDC, or apoptosis. The present invention is further directed to methods for the treatment of B cell disorders or diseases in human subjects, including B cell malignancies, using the therapeutic human, humanized, or chimeric anti-CD19 antibodies that bind to the human CD19 antigen. The present invention is directed to methods for the treatment and prevention of autoimmune disease as well as the treatment and prevention of graft-versus-host disease (GVHD), humoral rejection, and post-transplantation lymphoproliferative disorder in human transplant recipients using therapeutic human, humanized, or chimeric anti-CD19 antibodies that bind to the human CD19 antigen.

2. BACKGROUND

B cells express a wide array of cell surface molecules during their differentiation and proliferation. Examples include the CD10, CD19, CD20, CD21, CD22, CD23, CD24, CD37, CD53, CD72, CD74, CD75, CD77, CD79a, CD79b, CD80, CD81, CD82, CD83, CD84, CD85, and CD86 leukocyte surface markers. These markers have been generally suggested as therapeutic targets for the treatment of B cell disorders or diseases such as B cell malignancies, autoimmune diseases, and transplant rejection. Antibodies that specifically bind them have been developed, and some have been tested as therapeutic agent for the treatment of diseases and disorders.

For example, chimeric or radiolabeled monoclonal antibody (mAb)-based therapies directed against the CD20 cell surface molecule specific for mature B cells and their malignant counterparts have been shown to be an effective in vivo treatment for non-Hodgkin's lymphoma (Tedder et al., Immunol. Today 15:450-454 (1994); Press et al., Hematology:221-240 (2001); Kaminski et al., N. Engl. J. Med. 329:459-465 (1993); Weiner, Semin. Oncol. 26:43-51 (1999); Onrust et al., Drugs 58:79-88 (1999); McLaughlin et al., Oncology 12:1763-1769 (1998); Reff et al., Blood 83:435-445 (1994); Maloney et al., Blood 90:2188-2195 (1997); Malone et al., J. Clin. Oncol. 15:3266-3274 (1997); Anderson et al., Biochem. Soc. Transac. 25:705-708 (1997)). Anti-CD20 monoclonal antibody therapy has also been found to be partially effective in attenuating the manifestations of rheumatoid arthritis, systemic lupus erythematosus, idiopathic thrombocytopenic purpura and hemolytic anemia, as well as other immune-mediated diseases (Silverman et al., Arthritis Rheum. 48:1484-1492 (2002); Edwards et al., Rheumatology 40:1-7 (2001); De Vita et al., Arthritis Rheumatism 46:2029-2033 (2002); Leandro et al., Ann. Rheum. Dis. 61:883-888 (2002); Leandro et al., Arthritis Rheum. 46:2673-2677 (2001)). The anti-CD20 (IgG1) antibody, RITUXAN™ (rituximab), has successfully been used in the treatment of certain diseases such as adult immune thrombocytopenic purpura, rheumatoid arthritis, and autoimmune hemolytic anemia (Cured et al., WO 00/67796). Despite the effectiveness of these therapies, B cell depletion is less effective where B cells do not express or express CD20 at low levels, (e.g., on pre-B cells or immature B cells) or have lost CD20 expression following CD20 immunotherapy (Smith et al., Oncogene 22:7359-7368 (2003)).

Murine monoclonal anti-CD19 antibodies have been described in the art, for example, HD37 (IgG1, kappa) (DAKO North America, Inc, Carpinteria, Calif.), BU12 (Callard et al., J. Immunology, 148(10):2983-7 (1992)), 4G7 (IgG1) (Meeker et al., Hybridoma, 3(4):305-20 (1984 Winter)), J4.119 (Beckman Coulter, Krefeld, Germany), B43 (PharMingen, San Diego, Calif.), SJ25C1 (BD PharMingen, San Diego, Calif.), FMC63 (IgG2a) (Zola et al., Immunol. Cell. Biol. 69(PT6): 411-22 (1991); Nicholson et al., Mol. Immunol., 34:1157-1165 (1997); Pietersz et al., Cancer Immunol. Immunotherapy, 41:53-60 (1995)), 89B(B4) (IgG1) (Beckman Coulter, Miami, Fla.; Nadler et al., J. Immunol., 131:244-250 (1983)), and/or HD237 (IgG2b) (Fourth International Workshop on Human Leukocyte Differentiation Antigens, Vienna, Austria, 1989; and Pezzutto et al., J. Immunol., 138(9):2793-2799 (1987)). Anti-CD19 antibodies or conjugates thereof have also shown therapeutic potential in various animal models of B cell disorders and diseases (Falvell et al., Br. J. Hematol. 134(2):157-70 (2006); Vallera et al., Clin. Cancer Res. 11(21):7920-8 (2005); Yazawa et al., Proc. Natl. Acad. Sci. USA 102(42):15178-83 (2005)).

In particular, the use of humanized CD19 antibodies has been described for the treatment of B-cell disease such as lymphoma, leukemia, or autoimmune disease (see, Hansen U.S. Patent Application Publication No. US2005/0070693; U.S. Pat. No. 7,109,304).

Despite recent advances in cancer therapy, B cell malignancies, such as the B cell subtypes of non-Hodgkin's lymphomas, and chronic lymphocytic leukemia, are major contributors of cancer-related deaths. Accordingly, there is a great need for further, improved therapeutic regimens for the treatment of B cell malignancies.

Both cellular (T cell-mediated) and humoral (antibody, B cell-mediated) immunity are now known to play significant roles in graft rejection. While the importance of T cell-mediated immunity in graft rejection is well established, the critical role of humoral immunity in acute and chronic rejection has only recently become evident. Consequently, most of the advances in the treatment and prevention of graft rejection have developed from therapeutic agents that target T cell activation. The first therapeutic monoclonal antibody that was FDA approved for the treatment of graft rejection was the murine monoclonal antibody ORTHOCLONE-OKT3™ (muromonab-CD3), directed against the CD3 receptor of T cells. OKT3 has been joined by a number of other anti-lymphocyte directed antibodies, including the monoclonal anti-CD52 CAMPATH™ antibodies, CAMPATH™-1G, CAMPATH™-1H (alemtuzumab), and CAMPATH™-1M), and polyclonal anti-thymocyte antibody preparations (referred to as anti-thymocyte globulin, or "ATG," also called "thymoglobin" or "thymoglobulin"). Other T cell antibodies approved for the prevention of transplant rejection include the chimeric monoclonal antibody SIMULECT™ (basiliximab) and the humanized monoclonal antibody ZENAPAX™ (daclizumab), both of which target the high-affinity IL-2 receptor of activated T cells.

The importance of humoral immunity in graft rejection was initially thought to be limited to hyperacute rejection, in which the graft recipient possesses anti-donor HLA antibodies prior to transplantation, resulting in rapid destruction of the graft in the absence of an effective therapeutic regimen of antibody suppression. Recently, it has become evident that humoral immunity is also an important factor mediating both acute and chronic rejection. For example, clinical observations demonstrated that graft survival in patients capable of developing class I or class IT anti-HLA alloantibodies (also referred to as "anti-MHC alloantibodies") was reduced compared to graft survival in patients that could not develop such antibodies. Clinical and experimental data also indicate that other donor-specific alloantibodies and autoantibodies are critical mediators of rejection. For a current review of the evidence supporting a role for donor-specific antibodies in allograft rejection, see Rifle et al., Transplantation, 79:S14-S18 (2005). Thus, due to the relatively recent appreciation of the role of humoral immunity in acute and chronic graft rejection, current therapeutic agents and strategies for targeting humoral immunity are less well developed than those for targeting cellular immunity. Accordingly, there is a need in the art for improved reagents and methods for treating and preventing graft rejection, i.e. graft-versus-host disease (GVHD), humoral rejection, and post-transplantation lymphoproliferative disorder in human transplant recipients.

Autoimmune diseases as a whole cause significant morbidity and disability. Based on incidence data collected from 1965 to 1995, it has been estimated that approximately 1.2 million persons will develop a new autoimmune disease over the next five years. Jacobsen et al. (Clin Immunol. Immunopathol. 84:223 (1997)) evaluated over 130 published studies and estimated that in 1996, 8.5 million people in the United States (3.2% of the population) had at least one of the 24 autoimmune diseases examined in these studies. Considering the major impact of autoimmune diseases on public health, effective and safe treatments are needed to address the burden of these disorders. Thus, there is a need in the art for improved reagents and methods for treating autoimmune disease.

3. SUMMARY

The present invention relates to human, humanized, or chimeric anti-CD19 antibodies that bind to the human CD19 antigen, as well as to compositions comprising those antibodies. In one embodiment, the present invention provides chimeric and humanized versions of anti-CD19 mouse monoclonal antibodies, HB12A and HB12B.

In another embodiment, anti-CD19 antibodies of the invention comprise one, two, three, four, five, or all six of the CDRs of HB12A (clone B410F12-2-A6-C2 was deposited with the American Type Culture Collection ("ATCC") on Feb. 11, 2005, ATCC Patent Deposit Designation: PTA-6580) or HB12B (clone B43H12-3-B2-B6 was deposited with the American Type Culture Collection ("ATCC") on Feb. 11, 2005, ATCC Patent Deposit Designation: PTA-6581).

The amino acid sequences for CDR1, CDR2, and CDR3 of the heavy chain variable region of HB12A defined according to Kabat are identified as SEQ ID NO:6, SEQ ID NO:8, and SEQ ID NO:10, respectively. The amino acid sequences for CDR1, CDR2 and CDR3 of the light chain variable region of HB12A defined according to Kabat are identified as SEQ ID NO:12, SEQ ID NO:14, and SEQ ID NO:16, respectively.

The amino acid sequences for CDR1, CDR2, and CDR3 of the heavy chain variable region of HB12B defined according to Kabat are identified as SEQ ID NO:22, SEQ ID NO:24, and SEQ ID NO:26, respectively. The amino acid sequences for CDR1, CDR2 and CDR3 of the light chain variable region of HB12B defined according to Kabat are identified as SEQ ID NO:28, SEQ ID NO:30, and SEQ TD NO:32, respectively.

In one embodiment, an anti-CD19 antibody of the invention comprises one, two, three, four, five, or six CDRs having the amino acid sequence of a CDR listed in Table 1, infra.

TABLE 1

Residues that are different from the amino acid sequence of the corresponding HB12B parental CDR appear in bold, underlined. Amino acid residues corresponding to a given variable position within the consensus CDR sequences (SEQ ID NO.: 230-235) are listed in parenthesis. In specific embodiments, a CDR of the invention may comprise any permutation of the individual amino acid residues corresponding to variable positions within the CDR.

| Antibody Name | VH Domain | VH CDR1 | VH CDR2 | VH CDR3 | VK Domain | VK CDR1 | VK CDR2 | VK CDR3 |
|---|---|---|---|---|---|---|---|---|
| HB12A | SEQ. ID NO.: 2 | SYVMH (SEQ. ID NO.: 6) | YFNPYNDGT DYYEKFKG (SEQ. ID NO.: 8) | GTYYYGSSY PFDY (SEQ. ID NO.: 10) | SEQ. ID NO.: 4 | KSSQSLLYSN GKTYLN (SEQ. ID NO.: 12) | LVSKLDS (SEQ. ID NO.: 14) | VQGTHFPYT (SEQ. ID NO.: 16) |
| HB12B | SEQ. ID NO.: 18 | SSWMN (SEQ. ID NO.: 22) | RIYPGDGDT NYNGKFKG (SEQ. ID NO.: 24) | SGFITTVLDF DY (SEQ. ID NO.: 26) | SEQ. ID NO.: 20 | RASESVDTFG ISFMN (SEQ. ID NO.: 28) | AASNQGS (SEQ. ID NO.: 30) | QQSKEVPFT (SEQ. ID NO.: 32) |
| 3649 | SEQ. ID NO.: 34 | SSWMN (SEQ. ID NO.: 22) | RIYPGDGDT NYNGKFKG (SEQ. ID NO.: 24) | SGFITTVLDF DY (SEQ. ID NO.: 26) | SEQ. ID NO.: 68 | RASESVDTFG ISFMN (SEQ. ID NO.: 28) | AASNQGS (SEQ. ID NO.: 30) | QQSKEVPFT (SEQ. ID NO.: 32) |

TABLE 1-continued

Residues that are different from the amino acid sequence of the corresponding HB12B parental CDR appear in bold, underlined. Amino acid residues corresponding to a given variable position within the consensus CDR sequences (SEQ ID NO.: 230-235) are listed in parenthesis. In specific embodiments, a CDR of the invention may comprise any permutation of the individual amino acid residues corresponding to variable positions within the CDR.

| Antibody Name | VH Domain | VH CDR1 | VH CDR2 | VH CDR3 | VK Domain | VK CDR1 | VK CDR2 | VK CDR3 |
|---|---|---|---|---|---|---|---|---|
| 7E12 | SEQ. ID NO.: 102 | STWMN (SEQ. ID NO.: 114) | RIYPGDGDT NYNGKFKG (SEQ. ID NO.: 24) | SGFITTVYDF DY (SEQ. ID NO.: 120) | SEQ. ID NO.: 110 | RASESVDTFG ISFIN (SEQ. ID NO.: 123) | EASNQGS (SEQ. ID NO.: 125) | QQTKEVPFT (SEQ. ID NO.: 126) |
| 14H5 | SEQ. ID NO.: 103 | SSWMN (SEQ. ID NO.: 22) | RIYPGDGDT NYNGKFKG (SEQ. ID NO.: 24) | SGFITTVRDF DY (SEQ. ID NO.: 121) | SEQ. ID NO.: 111 | RASESVDTFG ISFMN (SEQ. ID NO.: 28) | EASNQGS (SEQ. ID NO.: 125) | QQSKEVPFT (SEQ. ID NO.: 32) |
| 16C9 | SEQ. ID NO.: 103 | SSWMN (SEQ. ID NO.: 22) | RIYPGDGDT NYNGKFKG (SEQ. ID NO.: 24) | SGFITTVRDF DY (SEQ. ID NO.: 121) | SEQ. ID NO.: 113 | RASESVDTFG ISFMN (SEQ. ID NO.: 28) | AASNQGS (SEQ. ID NO.: 30) | QQSKEVPIT (SEQ. ID NO.: 127) |
| 15D1 | SEQ. ID NO.: 104 | SSWMN (SEQ. ID NO.: 22) | RIYPGDGDT NYNAKFKG (SEQ. ID NO.: 115) | SGFITTVRDF DY (SEQ. ID NO.: 121) | SEQ. ID NO.: 112 | RASESVDHF GISFMN (SEQ. ID NO.: 124) | EASNQGS (SEQ. ID NO.: 125) | QQSKEVPIT (SEQ. ID NO.: 127) |
| 15D7 | SEQ. ID NO.: 105 | SSWMN (SEQ. ID NO.: 22) | RIYPGDGDT NYNGKFKG (SEQ. ID NO.: 24) | SGFITTVHDF DY (SEQ. ID NO.: 122) | SEQ. ID NO.: 111 | RASESVDTFG ISFMN (SEQ. ID NO.: 28) | EASNQGS (SEQ. ID NO.: 125) | QQSKEVPFT (SEQ. ID NO.: 32) |
| 16C4 | SEQ. ID NO.: 106 | SSWMN (SEQ. ID NO.: 22) | RIYPGDGDT NYNNVKFKG (SEQ. ID NO.: 116) | SGFITTVRDF DY (SEQ. ID NO.: 121) | SEQ. ID NO.: 111 | RASESVDTFG ISFMN (SEQ. ID NO.: 28) | EASNQGS (SEQ. ID NO.: 125) | QQSKEVPFT (SEQ. ID NO.: 32) |
| 14H5-YG | SEQ. ID NO.: 107 | SSWMN (SEQ. ID NO.: 22) | RIYPGDGDT NYYGKFKG (SEQ. ID NO.: 117) | SGFITTVRDF DY (SEQ. ID NO.: 121) | SEQ. ID NO.: 111 | RASESVDTFG ISFMN (SEQ. ID NO.: 28) | EASNQGS (SEQ. ID NO.: 125) | QQSKEVPFT (SEQ. ID NO.: 32) |
| 14H5-DG | SEQ. ID NO.: 108 | SSWMN (SEQ. ID NO.: 22) | RIYPGDGDT NYDGKFKG (SEQ. ID NO.: 118) | SGFITTVRDF DY (SEQ. ID NO.: 121) | SEQ. ID NO.: 111 | RASESVDTFG ISFMN (SEQ. ID NO.: 28) | EASNQGS (SEQ. ID NO.: 125) | QQSKEVPFT (SEQ. ID NO.: 32) |
| 14H5-LG | SEQ. ID NO.: 109 | SSWMN (SEQ. ID NO.: 22) | RIYPGDGDT NYLGKFKG (SEQ. ID NO.: 119) | SGFITTVRDF DY (SEQ. ID NO.: 121) | SEQ. ID NO.: 111 | RASESVDTFG ISFMN (SEQ. ID NO.: 28) | EASNQGS (SEQ. ID NO.: 125) | QQSKEVPFT (SEQ. ID NO.: 32) |
| 1A7 | SEQ. ID NO.: 191 | SVWMN (SEQ. ID NO.: 208) | RIYPGDGDT NYNVKFKG (SEQ. ID NO.: 116) | SGFITTVRDF DY (SEQ. ID NO.: 121) | SEQ. ID NO.: 111 | RASESVDTFG ISFMN (SEQ. ID NO.: 28) | EASNQGS (SEQ. ID NO.: 125) | QQSKEVPFT (SEQ. ID NO.: 32) |
| 3C3 | SEQ. ID NO.: 191 | SVWMN (SEQ. ID NO.: 208) | RIYPGDGDT NYNVKFKG (SEQ. ID NO.: 116) | SGFITTVRDF DY (SEQ. ID NO.: 121) | SEQ. ID NO.: 193 | RASESVDHF GISFIN (SEQ. ID NO.: 211) | EASNPYS (SEQ. ID NO.: 218) | AQSKEVPIT (SEQ. ID NO.: 222) |
| 3E5 | SEQ. ID NO.: 191 | SVWMN (SEQ. ID NO.: 208) | RIYPGDGDT NYNVKFKG (SEQ. ID NO.: 116) | SGFITTVRDF DY (SEQ. ID NO.: 121) | SEQ. ID NO.: 194 | RASESVDTFG ISFMN (SEQ. ID NO.: 28) | EASNQGS (SEQ. ID NO.: 125) | AQSKEVPFT (SEQ. ID NO.: 223) |
| 3D4 | SEQ. ID NO.: 191 | SVWMN (SEQ. ID NO.: 208) | RIYPGDGDT NYNVKFKG (SEQ. ID NO.: 116) | SGFITTVRDF DY (SEQ. ID NO.: 121) | SEQ. ID NO.: 195 | RASESVDTFG ISFMN (SEQ. ID NO.: 28) | EASNQGS (SEQ. ID NO.: 125) | AQSKRVPFT (SEQ. ID NO.: 224) |
| 3F11 | SEQ. ID NO.: 192 | SVWMN (SEQ. ID NO.: 208) | RIYLGDGDT NYNVKFKG (SEQ. ID NO.: 210) | SGFITTVRDF DY (SEQ. ID NO.: 121) | SEQ. ID NO.: 196 | RASESVITFGI SFMN (SEQ. ID NO.: 212) | EASNQGS (SEQ. ID NO.: 125) | QQSKEVPFT (SEQ ID NO: 32) |

TABLE 1-continued

Residues that are different from the amino acid sequence of the corresponding HB12B parental CDR appear in bold, underlined. Amino acid residues corresponding to a given variable position within the consensus CDR sequences (SEQ ID NO.: 230-235) are listed in parenthesis. In specific embodiments, a CDR of the invention may comprise any permutation of the individual amino acid residues corresponding to variable positions within the CDR.

| Antibody Name | VH Domain | VH CDR1 | VH CDR2 | VH CDR3 | VK Domain | VK CDR1 | VK CDR2 | VK CDR3 |
|---|---|---|---|---|---|---|---|---|
| 5B5 | SEQ. ID NO.: 191 | SVWMN (SEQ. ID NO.: 208) | RIYPGDGDT NYNVKFKG (SEQ. ID NO.: 116) | SGFITTVRDF DY (SEQ. ID NO.: 121) | SEQ. ID NO.: 197 | RASESVDTFG ISFMN (SEQ. ID NO.: 28) | EASNQGS (SEQ. ID NO.: 125) | AQTKRVPFT (SEQ. ID NO.: 225) |
| 6F7 | SEQ. ID NO.: 191 | SVWMN (SEQ. ID NO.: 208) | RIYPGDGDT NYNVKFKG (SEQ. ID NO.: 116) | SGFITTVRDF DY (SEQ. ID NO.: 121) | SEQ. ID NO.: 198 | RASESVDTFG ISFMN (SEQ. ID NO.: 28) | EASNQGS (SEQ. ID NO.: 125) | QQSKEVPIT (SEQ. ID NO.: 226) |
| 1C11 | SEQ. ID NO.: 106 | SSWMN (SEQ. ID NO.: 22) | RIYPGDGDT NYNVKFKG (SEQ. ID NO.: 116) | SGFITTVRDF DY (SEQ. ID NO.: 121) | SEQ. ID NO.: 199 | RASESVDTFG ISFIN (SEQ. ID NO.: 213) | EASNPYS (SEQ. ID NO.: 218) | QQSKEVPFT (SEQ. ID NO.: 32) |
| 2B11 | SEQ. ID NO.: 106 | SSWMN (SEQ. ID NO.: 22) | RIYPGDGDT NYNVKFKG (SEQ. ID NO.: 116) | SGFITTVRDF DY (SEQ. ID NO.: 121) | SEQ. ID NO.: 200 | RASESVDTFG ISFMN (SEQ. ID NO.: 28) | EASNQGS (SEQ. ID NO.: 125) | AQTKEVPFT (SEQ. ID NO.: 227) |
| 2D10 | SEQ. ID NO.: 191 | SVWMN (SEQ. ID NO.: 208) | RIYPGDGDT NYNVKFKG (SEQ. ID NO.: 116) | SGFITTVRDF DY (SEQ. ID NO.: 121) | SEQ. ID NO.: 201 | RASESVDTFG ISFMN (SEQ. ID NO.: 28) | EASNQGS (SEQ. ID NO.: 125) | AQTKEVPNT (SEQ. ID NO.: 228) |
| 3B4 | SEQ. ID NO.: 236 | STWMN (SEQ. ID NO.: 209) | RIYPGDGDT NYNVKFKG (SEQ. ID NO.: 116) | SGFITTVRDF DY (SEQ. ID NO.: 121) | SEQ. ID NO.: 111 | RASESVDTFG ISFMN (SEQ. ID NO.: 28) | EASNQGS (SEQ. ID NO.: 125) | QQSKEVPFT (SEQ. ID NO.: 32) |
| 5C11 | SEQ. ID NO.: 191 | SVWMN (SEQ. ID NO.: 208) | RIYPGDGDT NYNVKFKG (SEQ. ID NO.: 116) | SGFITTVRDF DY (SEQ. ID NO.: 121) | SEQ. ID NO.: 202 | RASESVITFGI SFMN (SEQ. ID NO.: 212) | EASNTYS (SEQ. ID NO.: 219) | AQSKRVPFT (SEQ. ID NO.: 224) |
| 5D4 | SEQ. ID NO.: 106 | SSWMN (SEQ. ID NO.: 22) | RIYPGDGDT NYNVKFKG (SEQ. ID NO.: 116) | SGFITTVRDF DY (SEQ. ID NO.: 121) | SEQ. ID NO.: 203 | RASESVDTFG ISFRN (SEQ. ID NO.: 214) | EASNQGS (SEQ. ID NO.: 125) | QQSKEVPFT (SEQ. ID NO.: 32) |
| 6C2 | SEQ. ID NO.: 106 | SSWMN (SEQ. ID NO.: 22) | RIYPGDGDT NYNVKFKG (SEQ. ID NO.: 116) | SGFITTVRDF DY (SEQ. ID NO.: 121) | SEQ. ID NO.: 198 | RASESVDTFG ISFMN (SEQ. ID NO.: 28) | EASNQGS (SEQ. ID NO.: 125) | QQSKEVPIT (SEQ. ID NO.: 226) |
| 6C11 | SEQ. ID NO.: 192 | SVWMN (SEQ. ID NO.: 208) | RIYLGDGDT NYNVKFKG (SEQ. ID NO.: 210) | SGFITTVRDF DY (SEQ. ID NO.: 121) | SEQ. ID NO.: 204 | RASESVDTFG ISFMN (SEQ. ID NO.: 28) | EASNPGS (SEQ. ID NO.: 220) | QQTKRVPFT (SEQ. ID NO.: 229) |
| 9G7 | SEQ. ID NO.: 191 | SVWMN (SEQ. ID NO.: 208) | RIYPGDGDT NYNVKFKG (SEQ. ID NO.: 116) | SGFITTVRDF DY (SEQ. ID NO.: 121) | SEQ. ID NO.: 205 | RASESVIHFG ISFMN (SEQ. ID NO.: 215) | EASNRGS (SEQ. ID NO.: 221) | AQSKEVPIT (SEQ. ID NO.: 222) |
| 1H4 | SEQ. ID NO.: 191 | SVWMN (SEQ. ID NO.: 208) | RIYPGDGDT NYNVKFKG (SEQ. ID NO.: 116) | SGFITTVRDF DY (SEQ. ID NO.: 121) | SEQ. ID NO.: 206 | LSFMN (SEQ. ID NO.: 216) | EASNPYS (SEQ. ID NO.: 218) | QQSKEVPFT (SEQ. ID NO.: 32) |
| 3C6 | SEQ. ID NO.: 191 | SVWMN (SEQ. ID NO.: 208) | RIYPGDGDT NYNVKFKG (SEQ. ID NO.: 116) | SGFITTVRDF DY (SEQ ID NO.: 121) | SEQ. ID NO.: 197 | RASESVDTFG ISFMN (SEQ. ID NO.: 28) | EASNQGS (SEQ. ID NO.: 125) | AQTKRVPFT (SEQ. ID NO.: 225) |
| 5C4 | SEQ. ID NO.: 191 | SVWMN (SEQ. ID NO.: 208) | RIYPGDGDT NYNVKFKG (SEQ. ID NO.: 116) | SGFITTVRDF DY (SEQ. ID NO.: 121) | SEQ. ID NO.: 207 | RASESVITFGI SFIN (SEQ. ID NO.: 217) | EASNPYS (SEQ. ID NO.: 218) | AQTKRVPFT (SEQ. ID NO.: 225) |

TABLE 1-continued

Residues that are different from the amino acid sequence of the corresponding HB12B parental CDR appear in bold, underlined. Amino acid residues corresponding to a given variable position within the consensus CDR sequences (SEQ ID NO.: 230-235) are listed in parenthesis. In specific embodiments, a CDR of the invention may comprise any permutation of the individual amino acid residues corresponding to variable positions within the CDR.

| Antibody Name | VH Domain | VH CDR1 | VH CDR2 | VH CDR3 | VK Domain | VK CDR1 | VK CDR2 | VK CDR3 |
|---|---|---|---|---|---|---|---|---|
| Consensus | SEQ ID NO.: 237 | S(S/T/V)WMN (SEQ. ID NO.: 230) | RIY(P/L)GDG DTNY(N/Y/D/L)(G/A/V)KFK G (SEQ. ID NO.: 231) | SGFITIV(R/L/Y/H)DFDY (SEQ. ID NO.: 232) | SEQ ID NO.: 238 | RASESV(I/D)(T/H)FG(I/L)SF(I/M/R)N (SEQ. ID NO.: 233) | (E/A)ASN(P/Q/T)(Y/G)S (SEQ. ID NO.: 234) | (Q/A)Q(S/T)K(E/R)VP(F/I/N)T (SEQ. ID NO.: 235) |

In one embodiment, an anti-CD19 antibody of the invention may comprise one or more framework regions of HB12A or HB12B. In one embodiment, an antibody of the invention may further comprise heavy and/or light chain framework (FW) regions from a human antibody (e.g., from a human germline antibody sequence such as VH3-72, JH4, VkA10, or Jk4), wherein said human framework regions may comprise one or more mutations in which a human FW residue is exchanged for the corresponding residue present in the parental mouse (e.g., HB12A or HB12B) heavy or light chain.

In one embodiment, an anti-CD19 antibody of the invention may comprise one or more CDRs having the amino acid sequence of a CDR listed in Table 1. supra and may further comprise one or more heavy chain framework (FW) regions of the VH region designated HB12B-(3-72/JH4) (SEQ ID NO:34). In another embodiment, an anti-CD19 antibody of the invention comprises one or more CDRs having the amino acid sequence of a CDR listed in Table 1. supra and further comprises one or more heavy chain framework (FW) regions of the VH region designated HB12B-(3-72/JH4) (SEQ ID NO:34). In one embodiment, an anti-CD19 antibody of the invention may comprise one or more CDRs having the amino acid sequence of a CDR listed in Table 1. supra and may further comprise one or more light chain framework (FW) regions of the VK region designated HB12B-(A10-Jk4) (SEQ ID NO:52). In one embodiment, an anti-CD19 antibody of the invention comprises one or more CDRs having the amino acid sequence of a CDR listed in Table 1. supra and further comprises one or more light chain framework (FW) regions of the VK region designated HB12B-(A10-Jk4) (SEQ ID NO:52). In another embodiment, an anti-CD19 antibody described herein may comprise one or more CDRs having the amino acid sequence of a CDR listed in Table 1. supra, one or more light chain framework regions of the VK region designated HB12B-(A10-Jk4), and one or more heavy chain framework regions of the VH region designated HB12B-(3-72/JH4). In a further embodiment, an anti-CD19 antibody described herein comprises one or more CDRs having the amino acid sequence of a CDR listed in Table 1. supra, one or more light chain framework regions of the VK region designated HB12B-(A10-Jk4), and one or more heavy chain framework regions of the VH region designated HB12B-(3-72/JH4).

For instance, in one embodiment a humanized anti-CD19 antibody of the invention may comprise a heavy chain variable region which comprises four framework regions, FW1, FW2, FW3, and FW4, wherein FW1 comprises the amino acid sequence of SEQ ID NO:36, FW2 comprises the amino acid sequence of SEQ ID NO:38, FW3 comprises the amino acid sequence of SEQ ID NO:40, and FW4 comprises the amino acid sequence of SEQ ID NO:42. In one embodiment, a humanized anti-CD19 antibody of the invention comprises a heavy chain variable region which comprises four framework regions, FW1, FW2, FW3, and FW4, wherein FW1 comprises the amino acid sequence of SEQ ID NO:36, FW2 comprises the amino acid sequence of SEQ ID NO:38, FW3 comprises the amino acid sequence of SEQ ID NO:40, and FW4 comprises the amino acid sequence of SEQ ID NO:42.

In addition, a humanized anti-CD19 monoclonal antibody of the invention may comprise a light chain variable region comprising four framework regions, FW1, FW2, FW3, and FW4, wherein FW1 comprises the amino acid sequence of SEQ ID NO:54; those in which FW2 comprises an amino acid sequence selected from the group consisting of SEQ ID NO:56, SEQ ID NO:64, and SEQ ID NO:72; those in which FW3 comprises an amino acid sequence selected from the group consisting of SEQ ID NO:58, and SEQ ID NO:66; and those in which FW4 comprises the amino acid sequence of SEQ ID NO:60. In one embodiment, a humanized anti-CD19 monoclonal antibody of the invention comprises a light chain variable region comprising four framework regions, FW1, FW2, FW3, and FW4, wherein FW1 comprises the amino acid sequence of SEQ ID NO:54; those in which FW2 comprises an amino acid sequence selected from the group consisting of SEQ ID NO:56, SEQ ID NO:64, and SEQ ID NO:72; those in which FW3 comprises an amino acid sequence selected from the group consisting of SEQ ID NO:58, and SEQ ID NO:66; and those in which FW4 comprises the amino acid sequence of SEQ ID NO:60.

In one embodiment, an anti-CD19 antibody of the invention may comprise a VH comprising the amino acid sequence of SEQ ID NO.:237 or a VL comprising the amino acid sequence of SEQ ID NO.:238, wherein said antibody binds a human CD19 antigen. In another embodiment, an anti-CD19 antibody of the invention comprises a VH comprising the amino acid sequence of SEQ ID NO.:237 and a VL comprising the amino acid sequence of SEQ ID NO.:238.

In particular embodiments, an anti-CD19 antibody of the invention may comprise a light chain variable region selected from the group consisting of HB12B VK (SEQ ID NO:20), HB12B-(A10-Jk4) (SEQ ID NO:52), HB12B-364987 (SEQ ID NO:62), HB12B-3649 (SEQ ID NO:68), HB12B-36 (SEQ ID NO:70), HB12A VK (SEQ ID NO:4), 7E12 VK (SEQ ID NO:110), 14H5 VK (SEQ ID NO:111), 15D1 VK (SEQ ID NO:112), 16C9 VK (SEQ ID NO:113), 3C3 VK (SEQ ID NO:193), 3E5 VK (SEQ ID NO:194), 3D4 VK (SEQ ID NO:195), 3F1 VK (SEQ ID NO:196), 5B5 VK (SEQ ID NO:197), 6F7 VK (SEQ ID NO:198), 1C11 VK (SEQ ID NO:199), 2B11 VK (SEQ ID NO:200), 2D10 VK (SEQ ID NO:201), 5C11 VK (SEQ ID NO:202), 5D4 VK (SEQ ID NO:203), 6C11 VK (SEQ ID NO:204), 9G7 VK (SEQ ID NO:205), 1H4 VK (SEQ ID NO:206), and 5C4 VK (SEQ ID NO:207).

In specific embodiments, the present invention further relates to an anti-CD19 antibody comprising a heavy chain variable region selected from the group consisting of HB12B VH (SEQ ID NO:18), HB12B-(3-72/JH4) (SEQ ID NO:34), HB12A VH (SEQ ID NO:2), 7E12 VH (SEQ ID NO:102), 14H5 VH (SEQ ID NO:103), 15D1 VH (SEQ ID NO:104), 15D7 VH (SEQ ID NO:105), 16C4 VH (SEQ ID NO:106), 14H5-YG (SEQ ID NO:107), 14H5-DG (SEQ ID NO:108), 14H5-LG (SEQ ID NO:109), 1A7 VH (SEQ ID NO:191), 3C3 VH (SEQ ID NO:191), 6C11 VH (SEQ ID NO:191), 9G7 (SEQ ID NO:191), 3B4 VH (SEQ ID NO:236), and 3F11 VH (SEQ ID NO:192).

In a particular embodiment, an anti-CD19 antibody of the invention comprises the HB12B-3649 (SEQ ID NO:68) light chain variable region and the HB12B-(3-72/JH4) (SEQ ID NO:34) heavy chain variable region. A DNA clone comprising the humanized anti-hCD19 VH HB12B-(3-72/JH4) was deposited with the American Type Culture Collection ("ATCC") on Oct. 26, 2006. A DNA clone comprising the humanized anti-hCD19 VK HB12B-3649 was deposited with the American Type Culture Collection ("ATCC") on Oct. 26, 2006.

In one embodiment, a humanized anti-CD19 antibody of the invention may bind to human CD19 with an affinity comparable to that of the mouse monoclonal antibodies HB12A and/or HB12B, or with an affinity comparable to that of the chHB12B antibody comprising HB12B VH (SEQ ID NO:18) and HB12B VK (SEQ ID NO:20).

The invention further provides polynucleotides comprising a nucleotide sequence encoding a human, humanized, or chimeric anti-CD19 antibody of the invention or fragments thereof. The invention also encompasses polynucleotides that hybridize under stringent or lower stringency hybridization conditions, as defined herein, to polynucleotides that encode a human, humanized, or chimeric antibody that specifically binds to human CD19.

Another embodiment of the invention is a vector comprising one or more nucleotide sequences encoding a human, humanized, or chimeric anti-CD19 antibody described herein or fragments thereof.

The present invention further relates to an isolated cell comprising a vector wherein said vector comprises one or more nucleotide sequences encoding a human, humanized, or chimeric anti-CD19 antibody of the invention or fragments thereof.

Chimeric, human, and humanized anti-CD19 monoclonal antibodies described herein include those of the IgG1, IgG2, IgG3, or IgG4 human isotype.

In one embodiment, a humanized anti-CD19 antibody described herein mediates antibody-dependent cellular cytotoxicity (ADCC), complement-dependent cell-mediated cytotoxicity (CDC), and/or apoptosis.

In a further embodiment, a humanized anti-CD19 antibody described herein inhibits anti-IgM/CpG stimulated B cell proliferation.

The present invention further relates to pharmaceutical compositions comprising a chimeric, human, and humanized anti-CD19 antibody.

In still another aspect, the present invention is directed toward a method of treating a B cell malignancy in a human, comprising administering to a human in need thereof a therapeutically-effective amount of a chimeric, human, or humanized anti-CD19 monoclonal antibody.

In a further aspect, the present invention relates to a method of treating an autoimmune disease or disorder in a human, comprising administering to a human in need thereof a therapeutically-effective amount of a chimeric, human, or humanized anti-CD19 monoclonal antibody.

The present invention further relates to a method of treating or preventing humoral rejection in a human transplant patient, comprising administering to a human in need thereof a therapeutically-effective amount of a chimeric, human, or humanized anti-CD19 monoclonal antibody.

3.1. Definitions

As used herein, the terms "antibody" and "antibodies" (immunoglobulins) encompass monoclonal antibodies (including full-length monoclonal antibodies), polyclonal antibodies, multispecific antibodies (e.g., bispecific antibodies) formed from at least two intact antibodies, human antibodies, humanized antibodies, camelised antibodies, chimeric antibodies, single-chain Fvs (scFv), single-chain antibodies, single domain antibodies, domain antibodies, Fab fragments, F(ab')2 fragments, antibody fragments that exhibit the desired biological activity, disulfide-linked Fvs (sdFv), and anti-idiotypic (anti-Id) antibodies (including, e.g., anti-Id antibodies to antibodies of the invention), intrabodies, and epitope-binding fragments of any of the above. In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Light chains are classified as either lambda chains or kappa chains based on the amino acid sequence of the light chain constant region. The variable domain of a kappa light chain may also be denoted herein as VK. The term "variable region" may also be used to describe the variable domain of a heavy chain or light chain. Particular amino acid residues are believed to form an interface between the light and heavy chain variable domains. Such antibodies may be derived from any mammal, including, but not limited to, humans, monkeys, pigs, horses, rabbits, dogs, cats, mice, etc.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in segments called Complementarity Determining Regions (CDRs) both in the light chain and the heavy chain variable domains. The more highly conserved portions of the variable domains are called the framework regions (FW). The variable domains of native heavy and light chains each comprise four FW regions, largely adopting a β-sheet configuration, connected by three CDRs, which form loops connecting, and in some cases forming part of, the β-sheet structure. The CDRs in each chain are held together in close proximity by the FW regions and, with the CDRs from the other chain, contribute to the formation of the antigen-binding site of antibodies (see, Kabat et al., Sequences of Proteins of Immunological Interest, 5th Ed. Public Health Service, National Institutes of Health, Bethesda, Md. (1991)). The constant domains are generally not involved directly in antigen binding, but may influence antigen binding affinity and may exhibit various effector functions, such as participation of the antibody in ADCC, CDC, and/or apoptosis.

The term "hypervariable region" when used herein refers to the amino acid residues of an antibody which are associated with its binding to antigen. The hypervariable regions encompass the amino acid residues of the "complementarity determining regions" or "CDRs" (e.g., residues 24-34 (L1), 50-56 (L2) and 89-97 (L3) of the light chain variable domain and residues 31-35 (H1), 50-65 (H2) and 95-102 (H3) of the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, J. Mol. Biol., 196:901-917 (1987)). "Framework" or "FW" residues are those variable domain residues flanking the CDRs. FW residues are present in chimeric, humanized, human, domain antibodies, diabodies, vaccibodies, linear antibodies, and bispecific antibodies.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, monoclonal antibodies are advantageous in that they can be synthesized by hybridoma cells that are uncontaminated by other immunoglobulin producing cells. Alternative production methods are known to those trained in the art, for example, a monoclonal antibody may be produced by cells stably or transiently transfected with the heavy and light chain genes encoding the monoclonal antibody.

The modifier "monoclonal" indicates the character of the antibody as being obtained from a substantially homogeneous population of antibodies, and is not to be construed as requiring engineering of the antibody by any particular method. The term "monoclonal" is used herein to refer to an antibody that is derived from a clonal population of cells, including any eukaryotic, prokaryotic, or phage clone, and not the method by which the antibody was engineered. For example, the monoclonal antibodies to be used in accordance with the present invention may be made by the hybridoma method first described by Kohler et al., Nature, 256:495 (1975), or may be made by any recombinant DNA method (see, e.g., U.S. Pat. No. 4,816,567), including isolation from phage antibody libraries using the techniques described in Clackson et al., Nature, 352:624-628 (1991) and Marks et al., J. Mol. Biol., 222:581-597 (1991), for example. These methods can be used to produce monoclonal mammalian, chimeric, humanized, human, domain antibodies, diabodies, vaccibodies, linear antibodies, and bispecific antibodies.

The term "chimeric" antibodies includes antibodies in which at least one portion of the heavy and/or light chain is identical with or homologous to corresponding sequences in antibodies derived from a particular species or belonging to a particular antibody class or subclass, and at least one other portion of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)). Chimeric antibodies of interest herein include "primatized" antibodies comprising variable domain antigen-binding sequences derived from a nonhuman primate (e.g., Old World Monkey, such as baboon, rhesus or cynomolgus monkey) and human constant region sequences (U.S. Pat. No. 5,693,780).

"Humanized" forms of nonhuman (e.g., murine) antibodies are chimeric antibodies that contain minimal sequence derived from nonhuman immunoglobulin. For the most part, humanized antibodies are human immunoglobulins (recipient antibody) in which the native CDR residues are replaced by residues from the corresponding CDR of a nonhuman species (donor antibody) such as mouse, rat, rabbit or nonhuman primate having the desired specificity, affinity, and capacity. In some instances, FW region residues of the human immunoglobulin are replaced by corresponding nonhuman residues. Furthermore, humanized antibodies may comprise residues that are not found in the recipient antibody or in the donor antibody. These modifications are made to further refine antibody performance. In general, a humanized antibody heavy or light chain will comprise substantially all of at least one or more variable domains, in which all or substantially all of the CDRs correspond to those of a nonhuman immunoglobulin and all or substantially all of the FWs are those of a human immunoglobulin sequence. In certain embodiments, the humanized antibody will comprise at least a portion of an immunoglobulin constant region (Fc), typically that of a human immunoglobulin. For further details, see, Jones et al., Nature, 321:522-525 (1986); Riechmann et al., Nature, 332:323-329 (1988); and Presta, Curr. Op. Struct. Biol., 2:593-596 (1992).

A "human antibody" can be an antibody derived from a human or an antibody obtained from a transgenic organism that has been "engineered" to produce specific human antibodies in response to antigenic challenge and can be produced by any method known in the art. In certain techniques, elements of the human heavy and light chain loci are introduced into strains of the organism derived from embryonic stem cell lines that contain targeted disruptions of the endogenous heavy chain and light chain loci. The transgenic organism can synthesize human antibodies specific for human antigens, and the organism can be used to produce human antibody-secreting hybridomas. A human antibody can also be an antibody wherein the heavy and light chains are encoded by a nucleotide sequence derived from one or more sources of human DNA. A fully human antibody also can be constructed by genetic or chromosomal transfection methods, as well as phage display technology, or in vitro activated B cells, all of which are known in the art.

"Antibody-dependent cell-mediated cytotoxicity" and "ADCC" refer to a cell-mediated reaction in which non-specific cytotoxic cells (e.g., Natural Killer (NK) cells, neutrophils, and macrophages) recognize bound antibody on a target cell and subsequently cause lysis of the target cell. In one embodiment, such cells are human cells. While not wishing to be limited to any particular mechanism of action, these cytotoxic cells that mediate ADCC generally express Fc receptors (FcRs). The primary cells for mediating ADCC, NK cells, express FcγRIII, whereas monocytes express FcγRI, FcγRII, FcγRIII and/or FcγRIV. FcR expression on hematopoietic cells is summarized in Ravetch and Kinet, Annu Rev. Immunol., 9:457-92 (1991). To assess ADCC activity of a molecule, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecules of interest may be assessed in vivo, e.g., in an animal model such as that disclosed in Clynes et al., Proc. Natl. Acad. Sci. (USA), 95:652-656 (1998).

"Complement dependent cytotoxicity" or "CDC" refers to the ability of a molecule to initiate complement activation and lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santaro et al., J. Immunol. Methods, 202:163 (1996), may be performed.

"Effector cells" are leukocytes which express one or more FcRs and perform effector functions. The cells express at least FcγRI, FCγRII, FcγRII and/or FcγRIV and carry out ADCC effector function. Examples of human leukocytes which mediate ADCC include peripheral blood mononuclear cells (PBMC), natural killer (NK) cells, monocytes, cytotoxic T cells and neutrophils.

The terms "Fc receptor" or "FcR" are used to describe a receptor that binds to the Fc region of an antibody. In one embodiment, the FcR is a native sequence human FcR. Moreover, in certain embodiments, the FcR is one which binds an IgG antibody (a gamma receptor) and includes receptors of the FcγRI, FcγRII, FcγRII, and FcγRIV subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See, Daëron, Annu. Rev. Immunol., 15:203-234 (1997)). FcRs are reviewed in Ravetch and Kinet, Annu. Rev. Immunol., 9:457-92 (1991); Capel et al., Immunomethods, 4:25-34 (1994); and de Haas et al., J. Lab. Clin. Med., 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., Immunol., 117:587 (1976) and Kim et al., J. Immunol., 24:249 (1994)).

"Fv" is the minimum antibody fragment which contains a complete antigen-recognition and binding site. This region consists of a dimer of one heavy and one light chain variable domain in tight, non-covalent or covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

"Affinity" of an antibody for an epitope to be used in the treatment(s) described herein is a term well understood in the art and means the extent, or strength, of binding of antibody to epitope. Affinity may be measured and/or expressed in a number of ways known in the art, including, but not limited to, equilibrium dissociation constant (KD or Kd), apparent equilibrium dissociation constant (KD' or Kd'), and IC50 (amount needed to effect 50% inhibition in a competition assay). It is understood that, for purposes of this invention, an affinity is an average affinity for a given population of antibodies which bind to an epitope. Values of KD' reported herein in terms of mg IgG per mL or mg/mL indicate mg Ig per mL of serum, although plasma can be used. When antibody affinity is used as a basis for administration of the treatment methods described herein, or selection for the treatment methods described herein, antibody affinity can be measured before and/or during treatment, and the values obtained can be used by a clinician in assessing whether a human patient is an appropriate candidate for treatment.

As used herein, the term "avidity" is a measure of the overall binding strength (i.e., both antibody arms) with which an antibody binds an antigen. Antibody avidity can be determined by measuring the dissociation of the antigen-antibody bond in antigen excess using any means known in the art, such as, but not limited to, by the modification of indirect fluorescent antibody as described by Gray et al., J. Virol. Meth., 44:11-24. (1993)

An "epitope" is a term well understood in the art and means any chemical moiety that exhibits specific binding to an antibody. An "antigen" is a moiety or molecule that contains an epitope, and, as such, also specifically binds to antibody.

A "B cell surface marker" as used herein is an antigen expressed on the surface of a B cell which can be targeted with an agent which binds thereto. B cell surface markers include the CD10, CD19, CD20, CD21, CD22, CD23, CD24, CD25, CD37, CD53, CD72, CD73, CD74, CD75, CD77, CD79a, CD79b, CD80, CD81, CD82, CD83, CD84, CD85, and CD86 leukocyte surface markers. A B cell surface marker of particular interest is preferentially expressed on B cells compared to other non-B cell tissues of a mammal and may be expressed on both precursor B cells and mature B-lineage cells. In one embodiment, the marker is CD19, which is found on B cells at various stages of differentiation.

The term "antibody half-life" as used herein means a pharmacokinetic property of an antibody that is a measure of the mean survival time of antibody molecules following their administration. Antibody half-life can be expressed as the time required to eliminate 50 percent of a known quantity of immunoglobulin from the patient's body or a specific compartment thereof, for example, as measured in serum or plasma, i.e., circulating half-life, or in other tissues. Half-life may vary from one immunoglobulin or class of immunoglobulin to another. In general, an increase in antibody half-life results in an increase in mean residence time (MRT) in circulation for the antibody administered.

The term "isotype" refers to the classification of an antibody's heavy or light chain constant region. The constant domains of antibodies are not involved in binding to antigen, but exhibit various effector functions. Depending on the amino acid sequence of the heavy chain constant region, a given human antibody or immunoglobulin can be assigned to one of five major classes of immunoglobulins: IgA, IgD, IgE, IgG, and IgM. Several of these classes may be further divided into subclasses (isotypes), e.g., IgG1 (gamma 1), IgG2

(gamma 2), IgG3 (gamma 3), and IgG4 (gamma 4), and IgA1 and IgA2. The heavy chain constant regions that correspond to the different classes of immunoglobulins are called α, δ, ε, γ, and μ, respectively. The structures and three-dimensional configurations of different classes of immunoglobulins are well-known. Of the various human immunoglobulin classes, only human IgG1, IgG2, IgG3, IgG4, and IgM are known to activate complement. Human IgG1 and IgG3 are known to mediate ADCC in humans. Human light chain constant regions may be classified into two major classes, kappa and lambda As used herein, the term "immunogenicity" means that a compound is capable of provoking an immune response (stimulating production of specific antibodies and/or proliferation of specific T cells).

As used herein, the term "antigenicity" means that a compound is recognized by an antibody or may bind to an antibody and induce an immune response.

By the terms "treat," "treating" or "treatment of" (or grammatically equivalent terms) it is meant that the severity of the subject's condition is reduced or at least partially improved or ameliorated and/or that some alleviation, mitigation or decrease in at least one clinical symptom is achieved and/or there is an inhibition or delay in the progression of the condition and/or prevention or delay of the onset of a disease or illness. Thus, the terms "treat," "treating" or "treatment of" (or grammatically equivalent terms) refer to both prophylactic and therapeutic treatment regimes.

As used herein, a "sufficient amount" or "an amount sufficient to" achieve a particular result refers to an amount of an antibody or composition of the invention that is effective to produce a desired effect, which is optionally a therapeutic effect (i.e., by administration of a therapeutically effective amount). For example, a "sufficient amount" or "an amount sufficient to" can be an amount that is effective to deplete B cells.

A "therapeutically effective" amount as used herein is an amount that provides some improvement or benefit to the subject. Stated in another way, a "therapeutically effective" amount is an amount that provides some alleviation, mitigation, and/or decrease in at least one clinical symptom. Clinical symptoms associated with the disorders that can be treated by the methods of the invention are well-known to those skilled in the art. Further, those skilled in the art will appreciate that the therapeutic effects need not be complete or curative, as long as some benefit is provided to the subject.

4. BRIEF DESCRIPTION OF THE DRAWINGS

FIG. 1A-B: (A) Amino acid sequence alignment of the HB12B VK (SEQ ID NO:20), HB12B-(A10-Jk4) (SEQ ID NO:52), HB12B-364987 (SEQ ID NO:62), HB12B-3649 (SEQ ID NO:68), and HB12B-36 (SEQ ID NO:70) light chains variable regions. Sequence residues are numbered according to Kabat. CDR residues, defined according to Kabat, are boxed. Vernier, Interchain, and Canonical residues of HB12B VK (SEQ ID NO:20) are highlighted in light gray. Amino acid substitutions of HB12B-364987 (SEQ ID NO:62) (Y40F, K53H, Y91F), HB12B-3649 (SEQ ID NO:68) (Y40F, K53H), and HB12B-36 (SEQ ID NO:70) (Y40F) relative to the grafted antibody HB12B-(A10-Jk4) (SEQ ID NO:52) variable domain are highlighted in dark gray. (B) Amino acid sequence alignment of the HB12B VH (SEQ ID NO:18), HB12B-(3-72/JH4) (SEQ ID NO:34), and HB12B-9m (SEQ ID NO:44) heavy chain variable regions. Sequence residues are numbered according to Kabat. CDR residues, defined according to Kabat, are boxed. Vernier, Interchain, and Canonical residues of HB12B VH are highlighted in light gray. Amino acid substitutions of HB12B-9m (SEQ ID NO:44) (L20I, F27Y, T28A, R38I, V49I, F67A, R71A, L80M, I91Y) relative to the grafted antibody HB12B-(3-72/JH4) (SEQ ID NO:34) variable domain are highlighted in dark gray.

FIG. 2. Binding profile of humanized anti-CD19 antibody #1, comprising HB12B-(3-72/JH4) VH (SEQ ID NO:34) and HB12B-364987 VK (SEQ ID NO:62), to recombinant human CD19 expressing 300B4 cells in a cell based ELISA assay. OD450 readings for humanized anti-CD19 antibody #1 are marked with an open square. Chimeric HB12B antibody comprising HB12B VH (SEQ ID NO:18) and HB12B VK (SEQ ID NO:20) was used as a reference standard (closed circle). A human IgG1 antibody of irrelevant specificity was included in the assay as a negative control (open circle). The binding profile of humanized anti-CD19 antibody #1 closely matches that of the chimeric anti-CD19 antibody.

Figure 3:
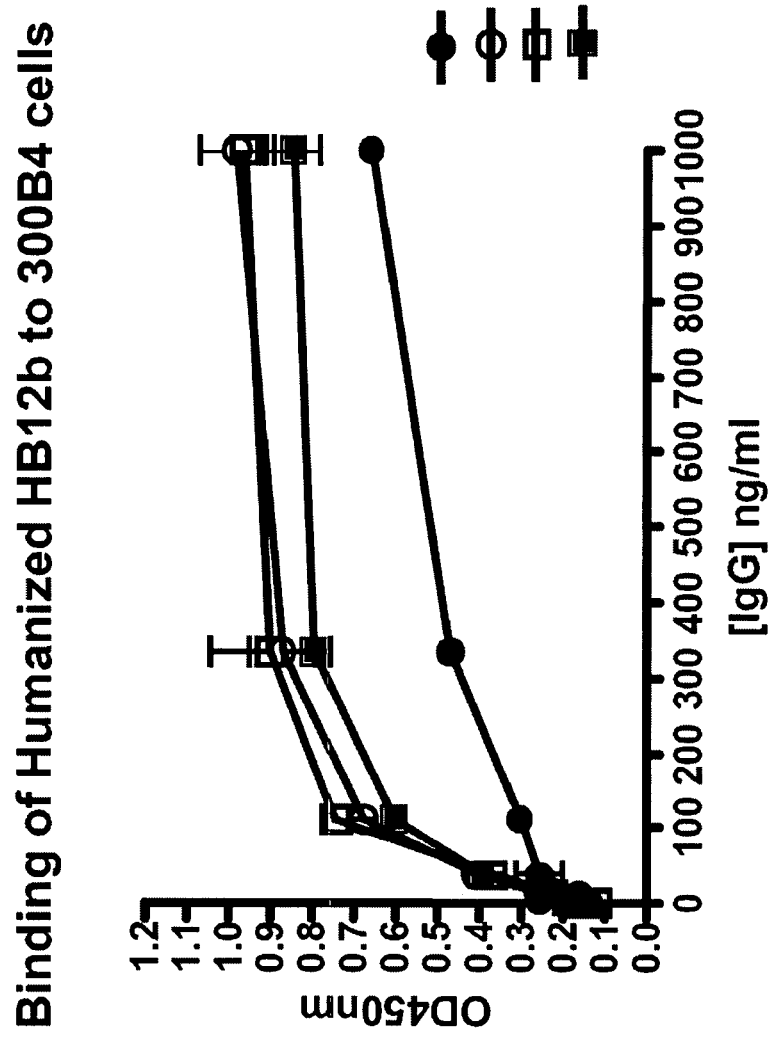

FIG. 3. Binding profile of humanized anti-CD19 antibody #1, #2, and #3 to recombinant human CD19 expressing 300B4 cells in a cell based ELISA assay. Humanized anti-CD19 antibody #1 comprises HB12B-(3-72/JH4) VH (SEQ ID NO:34) and HB12B-364987 VK (SEQ ID NO:62). Humanized anti-CD19 antibody #2 comprises HB12B-(3-72/JH4) VH (SEQ ID NO:34) and HB12B-3649 VK (SEQ ID NO:68). Humanized anti-CD19 antibody #3 comprises HB12B-(3-72/JH4) VH (SEQ ID NO:34) and HB12B-36 VK (SEQ ID NO:70). The binding profile of humanized anti-CD19 antibody #1, #2, and #3 is marked with open squares, open circles, and closed circles, respectively. Chimeric HB12B antibody comprising HB12B VH (SEQ ID NO:18) and HB12B VK (SEQ ID NO:20) was used as reference standard (closed square). The binding profile of humanized anti-CD19 antibody #1 and #2 closely matches that of the chimeric anti-CD19 antibody. The binding of humanized anti-CD19 antibody #3 to recombinant human CD19 expressing 300B4 cells is significantly weaker than that of the chimeric HB12B antibody.

Figure 4:
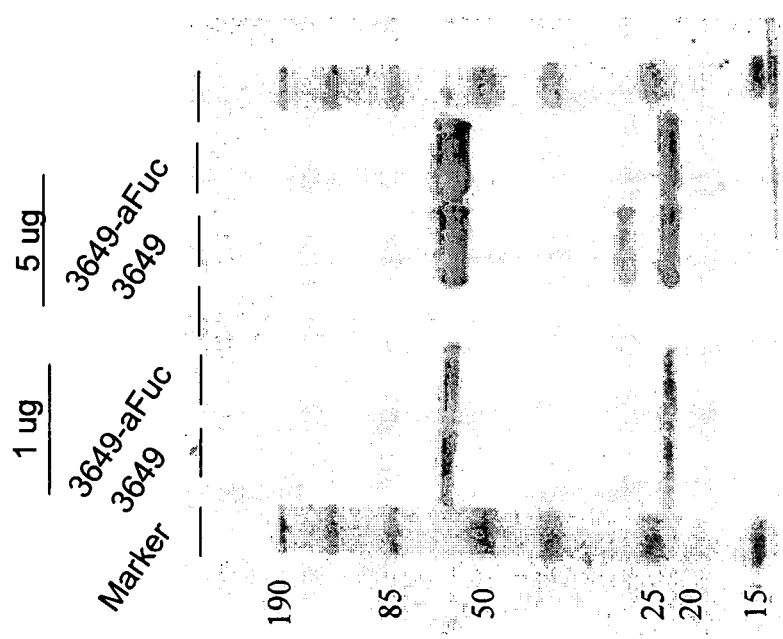

FIG. 4. Coomassie stained SDS/PAGE of purified anti-hCD19 antibodies. 1 and 5 micrograms of fucosylated (3649) and afucosylated (3649-aFuc) purified humanized anti-CD19 antibody #2 was analyzed by SDS/PAGE. The purified preparations are substantially free from contaminating proteins.

Figure 5:
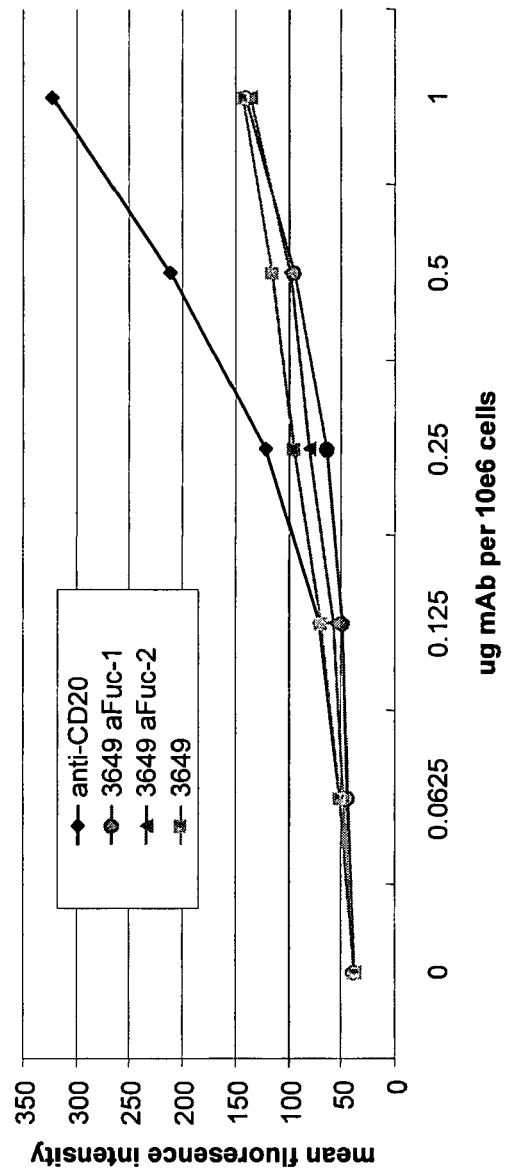
Figure 5:
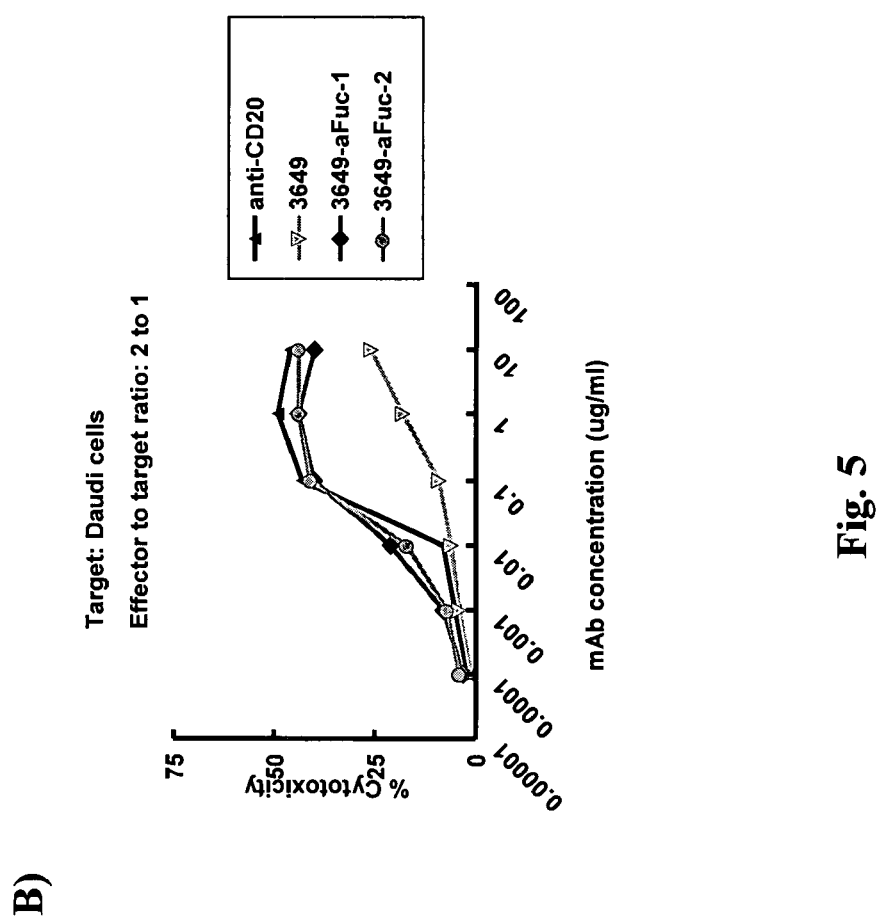

FIG. 5. (A) Mean fluorescence intensity of immunostained Daudi cells incubated with different concentrations of humanized anti-CD19 antibody #2. Daudi cells were incubated with different concentrations of fucosylated (3649) or afucosylated (3649 aFuc-1 and 3649 aFuc-2) anti-CD19 antibody #2. Cells were subsequently stained with RPE conjugated goat anti-human IgG F(ab)'2 and analyzed on a flow cytometer following standard protocols. Daudi cells incubated with an anti-CD20 antibody were included as positive control. The fucosylated and afucosylated preparations of humanized anti-CD19 antibody #2 display overlapping staining profiles. Mean fluorescence intensity of anti-CD19 stained cells is lower than that of anti-CD20 stained cells at all antibody concentrations tested. (B) In vitro ADCC activity of humanized anti-CD19 antibodies. In vitro ADCC activity of fucosylated (3649) and afucosylated (3649-aFuc1 and 3649-aFuc2) preparations of humanized anti-CD19 antibody #2 was assayed using the CytoTox 96™ kit (Promega) following the manufacturer's instructions. Daudi cells were used as targets. The assay was also performed using a positive control anti-CD20 antibody. Both afucosylated preparations of humanized anti-CD19 antibody #2, as well as the positive control anti-CD20 antibody displayed similar, robust ADCC activity. The ADCC activity of the fucosylated anti-CD19 antibody #2 is lower under the conditions used.

Figure 6:
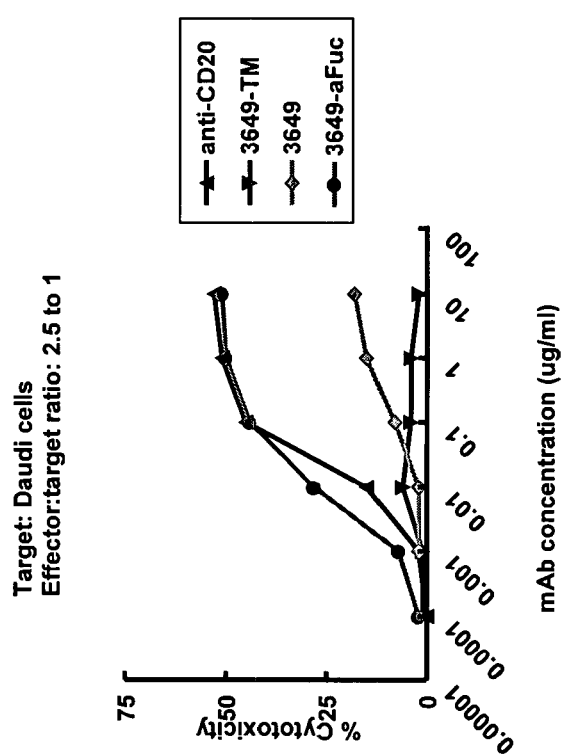

FIG. 6. In vitro ADCC activity of humanized anti-CD19 antibodies. In vitro ADCC activity of fucosylated (3649) and afucosylated (3649-aFuc) humanized anti-CD19 antibody #2 was assayed using the CytoTox 96™ kit (Promega) following the manufacturer's instructions. Daudi cells served as targets. An anti-CD20 antibody was used as positive control. An Fc variant of the anti-CD19 antibody #2 (3649-TM) with abolished ADCC was used as negative control. The afucosylated humanized anti-CD19 antibody #2 (3649-aFuc) and the positive control anti-CD20 antibody displayed similar, robust ADCC activity. The ADCC activity of the fucosylated humanized anti-CD19 antibody #2 (3649) is lower under the conditions used. The negative control Fc variant anti-CD19 antibody #2 showed no ADCC activity under the conditions used.

Figure 7:
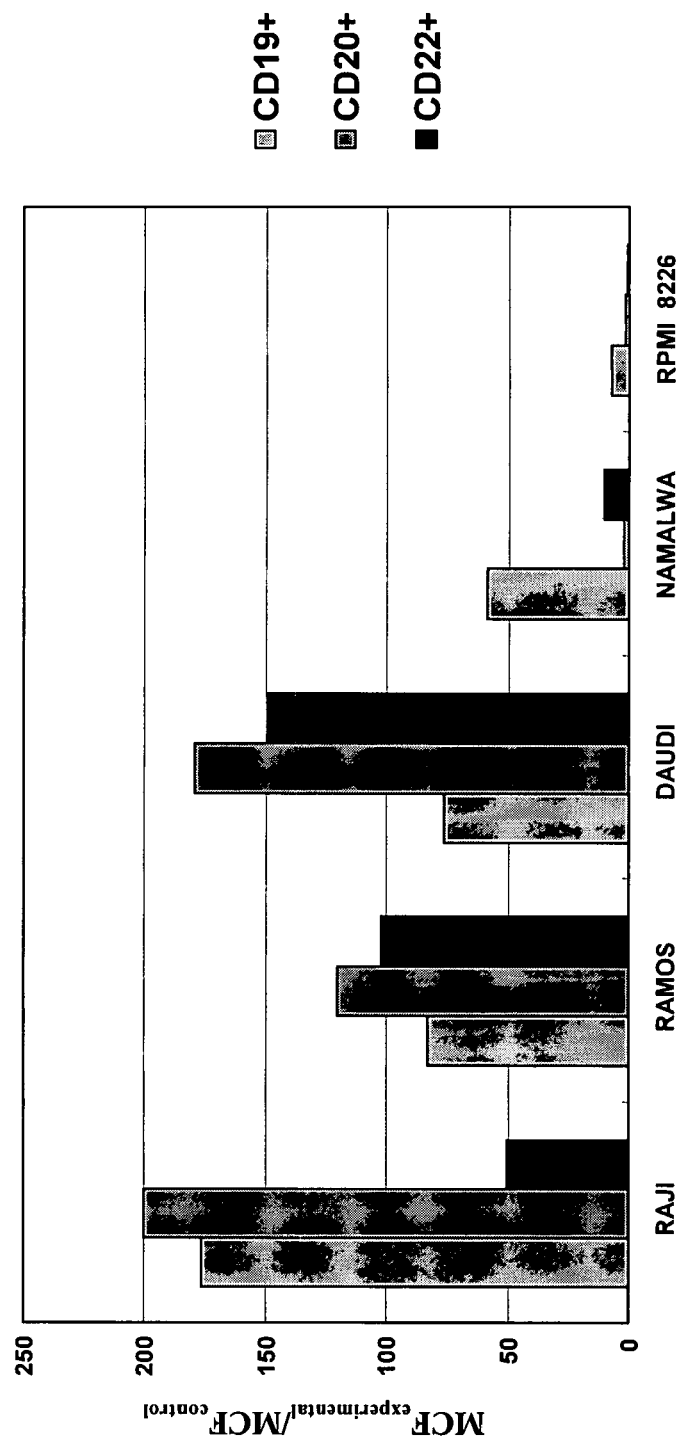

FIG. 7. CD19, CD20, and CD22 expression profile of Raji, Ramos, Daudi, and Namalwa cells. Raji, Ramos, Daudi, and Namalwa cells were immunostained with anti-CD19, anti-CD20 or anti-CD22 primary, and PE conjugated goat anti-mouse IgG secondary antibodies and subsequently analyzed on a flow cytometer. The bar graphs represent the ratio of mean channel fluorescence obtained with immunostained and secondary antibody only stained control samples. The RPMI 8226 multiple myeloma cell line that does not express either CD19, CD20 or CD22 was included as negative control. Significant surface expression of all three molecules is detected on Raji, Ramos, and Daudi cells. Namalwa cells display CD19 and CD22, but not CD20 on the cell surface.

FIG. 8. Raji (A), Daudi (B), Ramos (C), and Namalwa (D) cell susceptibility to anti-CD19 #2 mediated ADCC. ADCC assays were performed using the CytoTox 96™ kit (Promega) following the manufacturer's instructions. Antibodies used are: (i) the afucosylated anti-CD19 #2 (3649-aFuc), (ii) the 3M Fc variant of anti-CD19 #2 (3649-3M), and (iii) an anti-CD20 control. Effector to target ratio was 2.5 to 1. All four cell lines are susceptible to anti-CD19 #2 mediated ADCC. Only Raji, Daudi, and Ramos cells are susceptible to anti-CD20 mediated ADCC.

Figure 9:
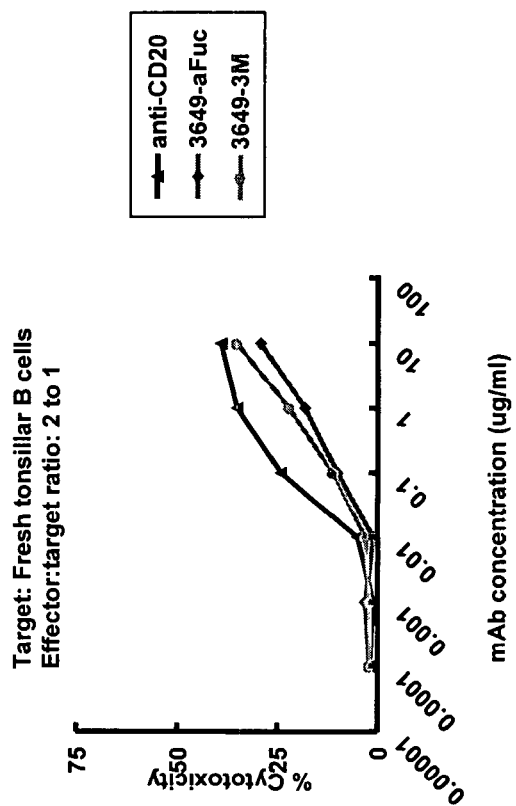

FIG. 9. Fresh tonsillar B cell susceptibility to anti-CD19 #2 mediated ADCC. ADCC assays were performed using the CytoTox 96™ kit (Promega) following the manufacturer's instructions. Antibodies used are: (i) the afucosylated anti-CD19 #2 (3649-aFuc), (ii) the 3M Fc variant of anti-CD19 #2 (3649-3M), and (iii) an anti-CD20 control. Effector to target ratio was 2 to 1. Tonsillar B cell are susceptible to ADCC mediated by all three antibodies tested.

Figure 10A:
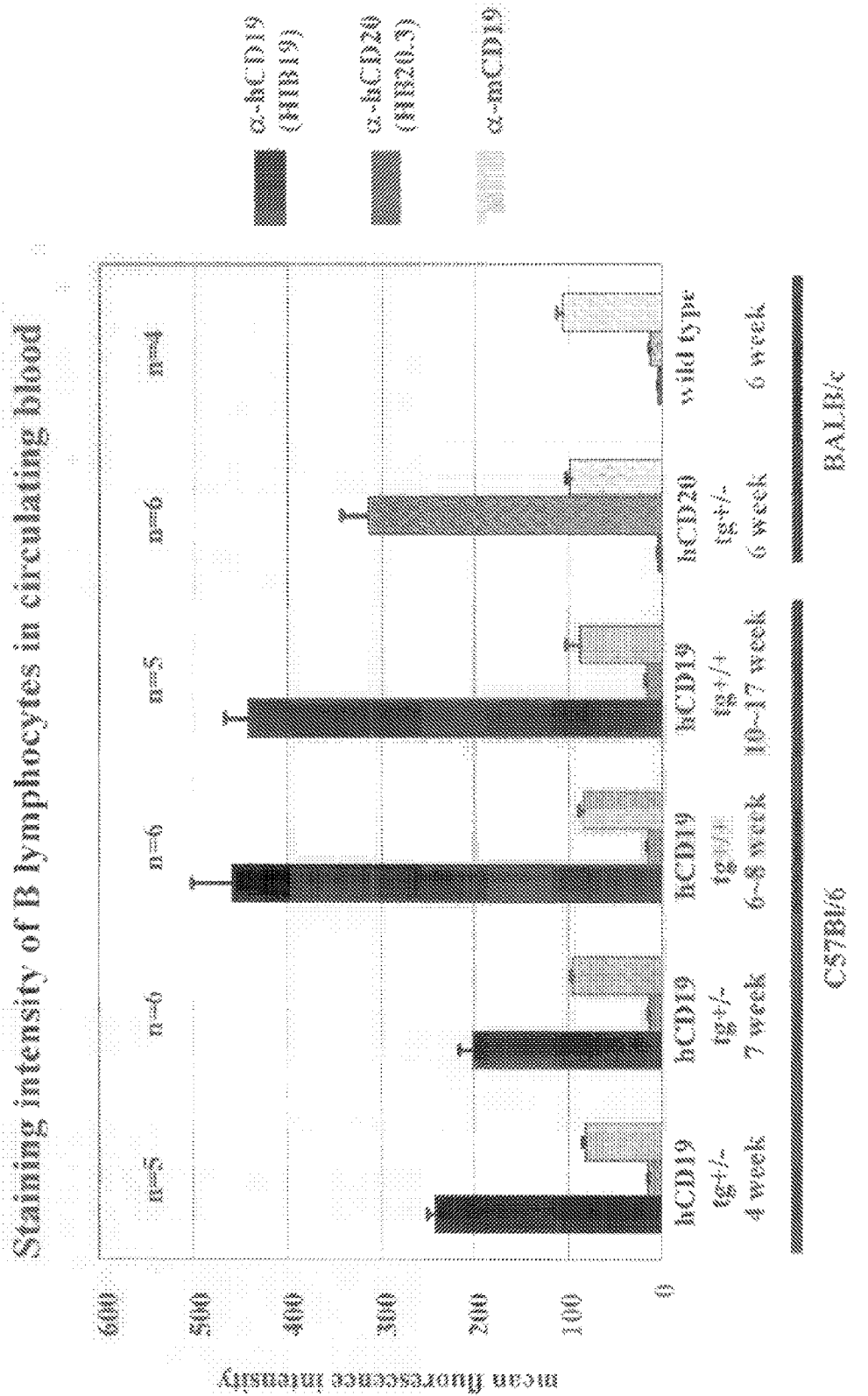

FIG. 10. Circulating lymphocytes were isolated form C57B16 hCD19 tg+/−, C57B16 hCD19 tg+/+, Balb/c hCD20 tg+/− and Balb/c mice. Isolated cells were stained with PerCP conjugated anti-mouse CD19 (α-mCD19), PE conjugated anti-CD3, Alexa488 conjugated anti-human CD19 (α-hCD19), and Alexa647 conjugated anti-human CD20 antibodies (α-hCD20). n equals the number of animals analyzed from each group. (A) The mean fluorescence intensity of CD3− cells measured in the hCD19, hCD20, and mCD19 specific channels is presented in a bar graph format. (B) Percentage of CD3− mCD19+ lymphocytes in various genetic backgrounds.

Figure 11A:
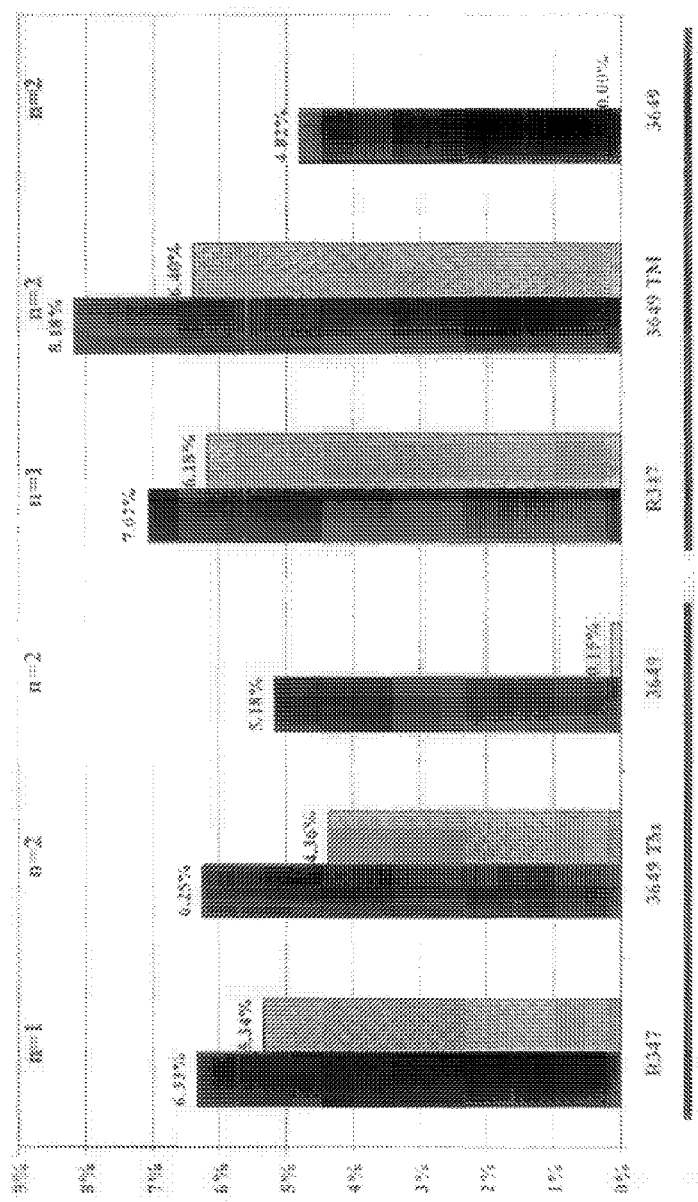

FIG. 11. In vivo B cell depletion by anti-CD19 antibody #2. (A) C57B16 hCD19 tg+/+ and (B) C57B16 hCD19 tg+/− animals were treated with a single i.v. dose of 250 or 50 μg of anti-CD19 antibody #2 (3649). Negative control antibodies used are (i) the ADCC compromised Fc variant of #2 (3649 TM) and (ii) an antibody of irrelevant specificity (R347). Circulating lymphocytes were isolated 7 days after treatment. Cells were stained with PerCP conjugated anti-mouse CD19 (α-mCD19) and PE conjugated anti-CD3 antibodies. Percentage of mCD19+ CD3− B cells is displayed. n equals the number of animals analyzed from each group. A treatment with a single dose of anti-CD19 antibody #2 resulted in a near complete depletion of B cells.

Figure 12A:
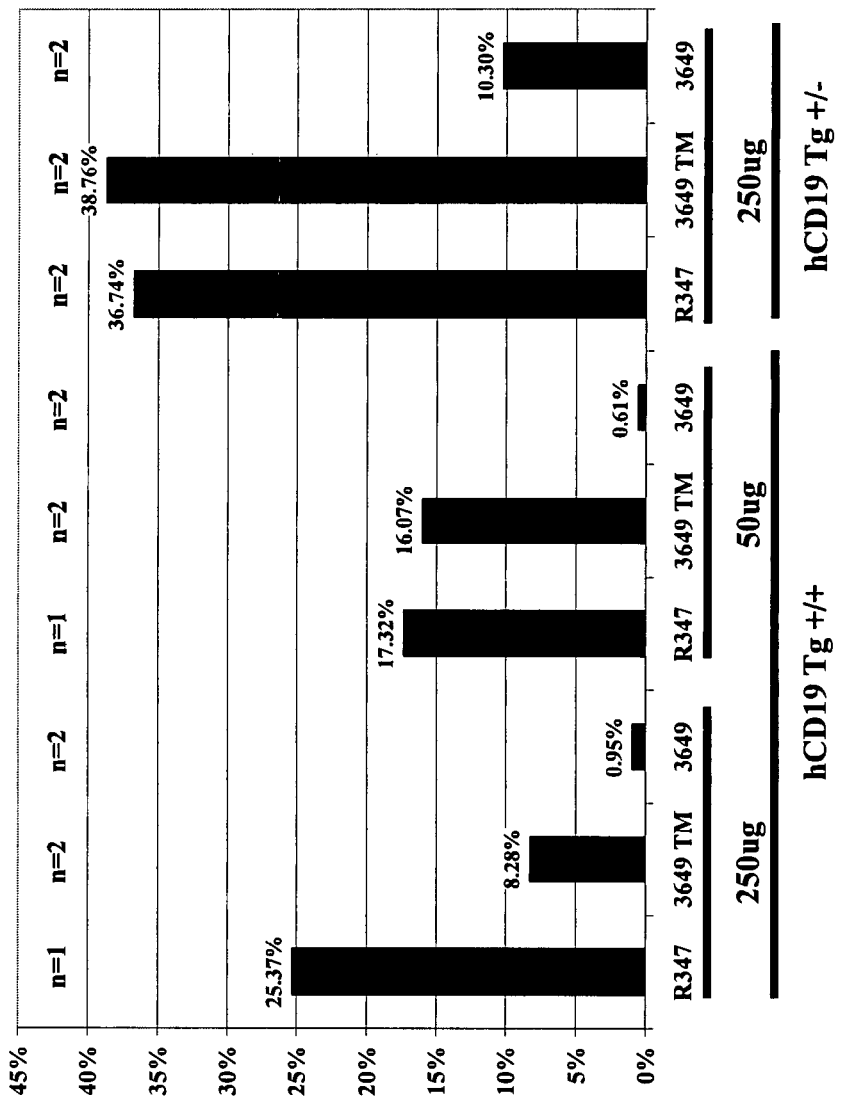
Figure 12B:
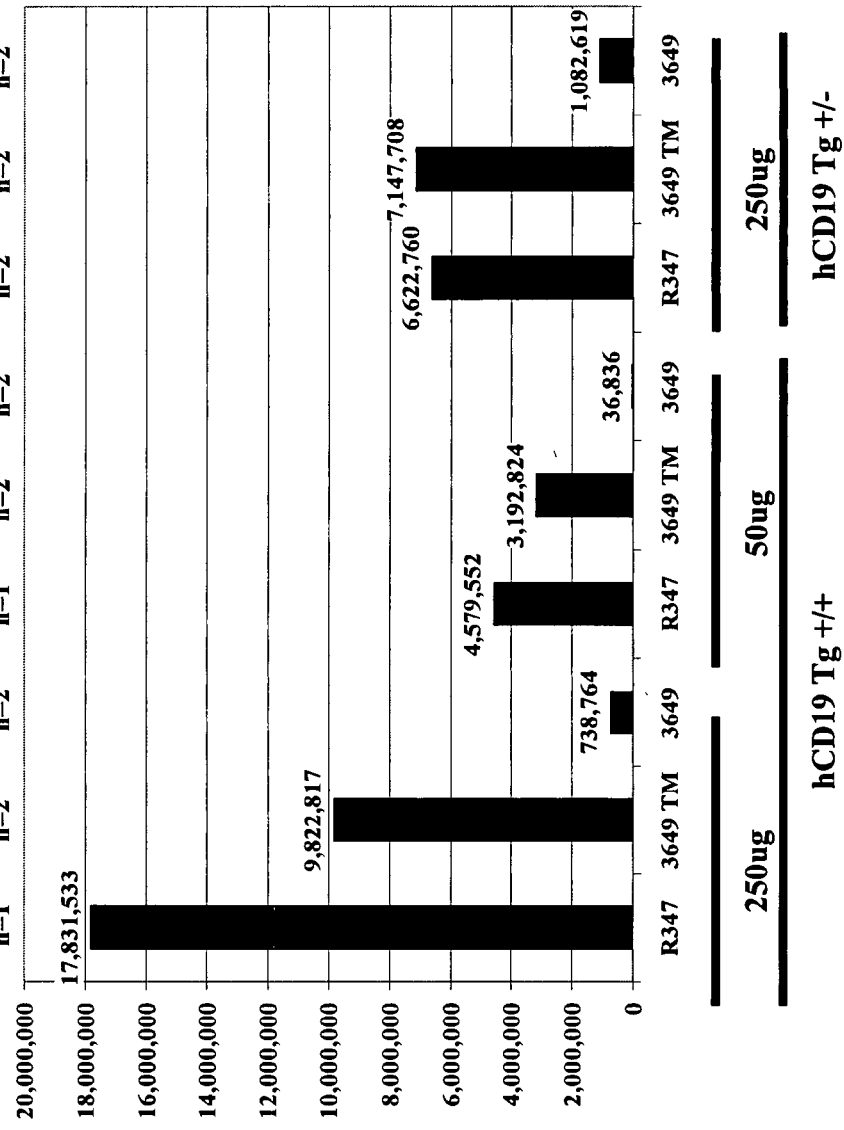

FIG. 12. In vivo B cell depletion by anti-CD19 antibody #2. C57B16 hCD19 tg+/+ and C57B16 hCD19 tg+/− animals were treated with a single i.v. dose of 250 or 50 μg of anti-CD19 antibody #2 (3649). Negative control antibodies used are (i) the ADCC compromised Fc variant of #2 (3649 TM) and (ii) an antibody of irrelevant specificity (R347). Spleen cells were isolated 7 days after treatment. Cells were stained with PerCP conjugated anti-mouse CD19 (α-mCD19) and PE conjugated anti-CD3 antibodies. Percentage of B cells (mCD19+ CD3−) among spleen lymphocytes is displayed. n equals the number of animals analyzed from each group. A treatment with a single dose of anti-CD19 antibody #2 resulted in a near complete depletion of B cells.

Figure 13:
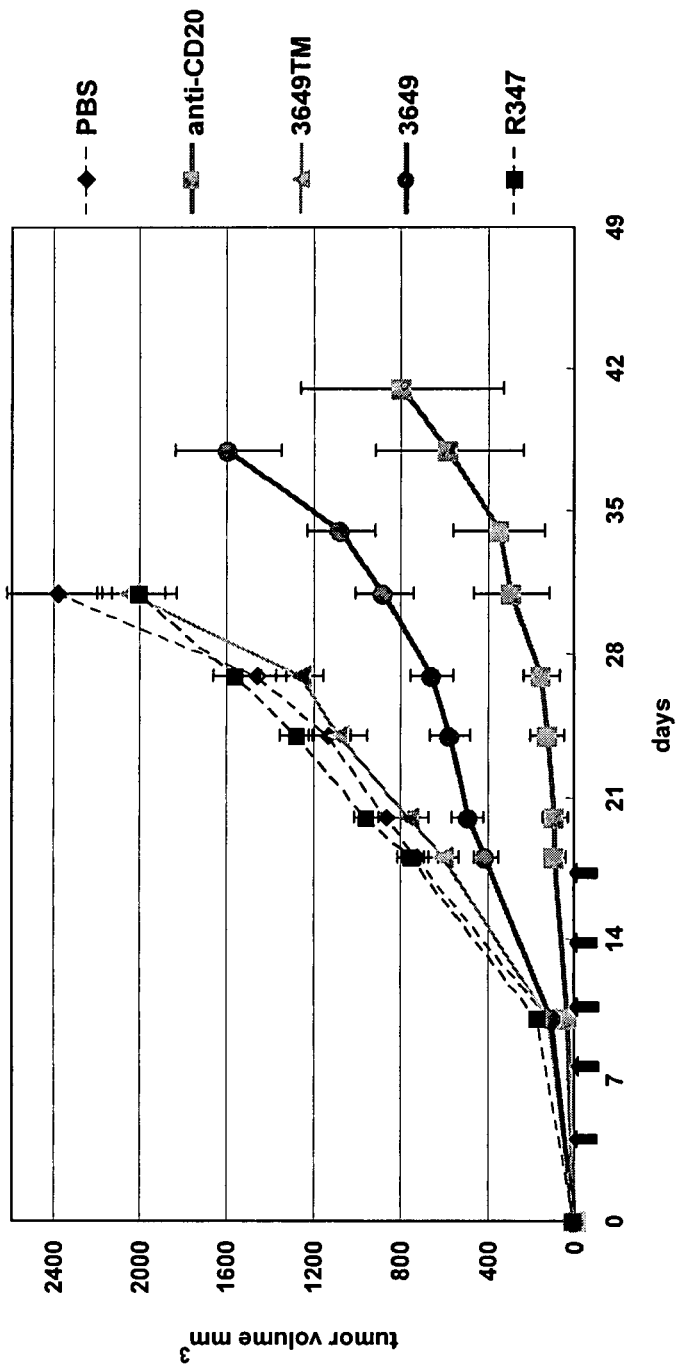

FIG. 13. Anti-CD19 antibody #2 significantly reduces tumor growth in an in vivo model system. CB17 SCID mice were injected s.c. on the hind flank with 5×106 Raji cells on day 1. Animals were treated with five biweekly doses of 10 mg/kg antibody starting on day 4. Antibodies used are: (i) anti-CD19 #2 (3649), (ii) Fc variant of anti-CD19 #2 with reduced ADCC activity (3649-TM), (iii) anti-CD20, and (iv) isotype control of irrelevant specificity (R347). A group of control animals were only given PBS. Tumor size was measured twice a week using standard procedures.

Figure 14:
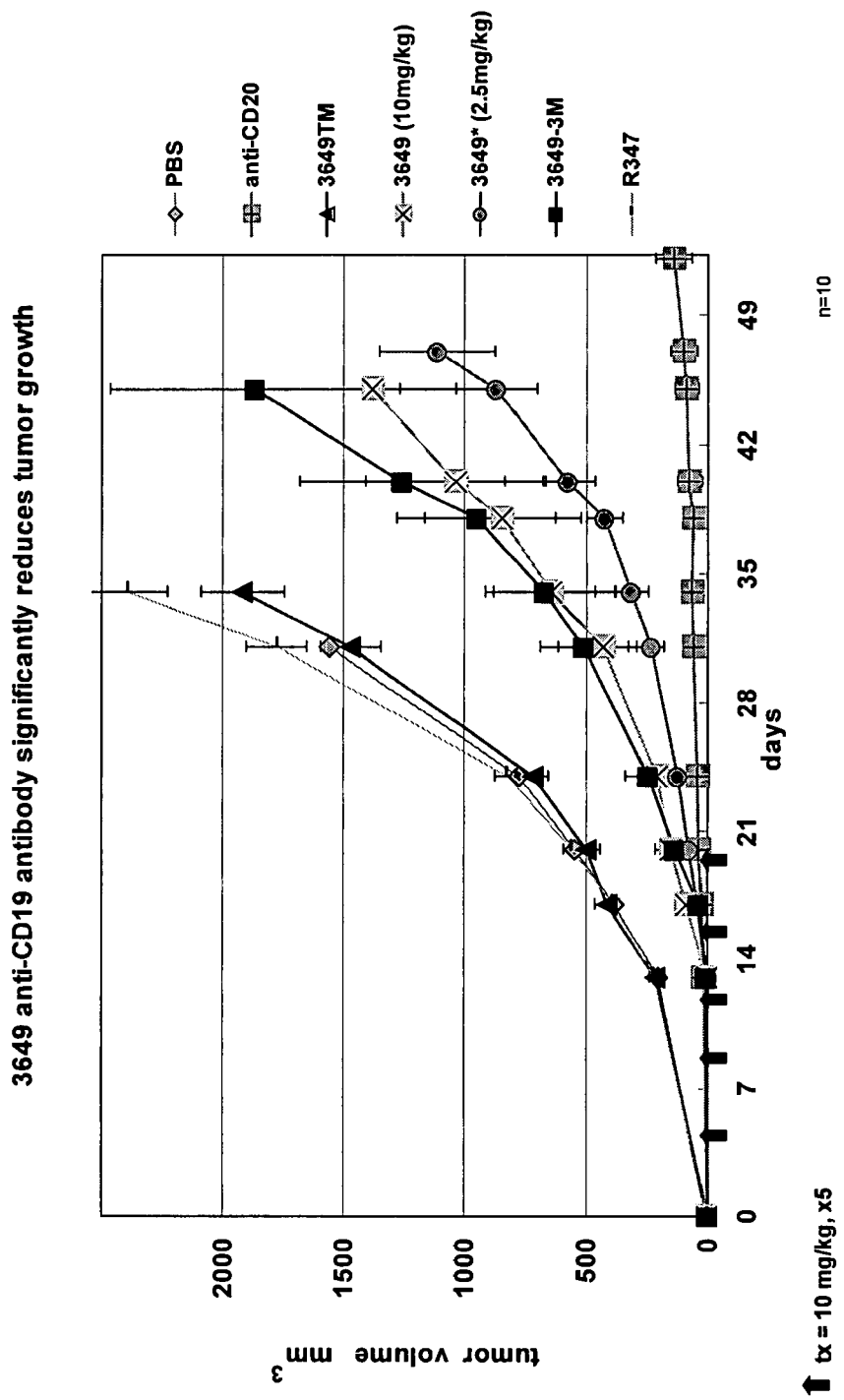

FIG. 14. Anti-CD19 antibody #2 significantly reduces tumor growth in an in vivo model system. CB17 SCID mice were injected s.c. on the hind flank with 5×106 Raji cells on day 1. Animals were treated with five biweekly doses of 10 mg/kg or 2.5 mg/kg antibody starting on day 4. Antibodies used are: (i) anti-CD19 #2 at 10 mg/kg or 2.5 mg/kg (3649 10 mg/kg and 3649*2.5 mg/kg), (ii) Fc variant of anti-CD19 #2 with reduced ADCC activity at 10 mg/kg (3649-TM), (iii) Fc variant of anti-CD19 #2 with enhanced human ADCC activity at 10 mg/kg (3649-3M), (iv) anti-CD20 at 10 mg/kg, and (v) isotype control of irrelevant specificity at 10 mg/kg (R347). A group of control animals were only given PBS. Tumor size was measured twice a week using standard procedures.

Figure 15:
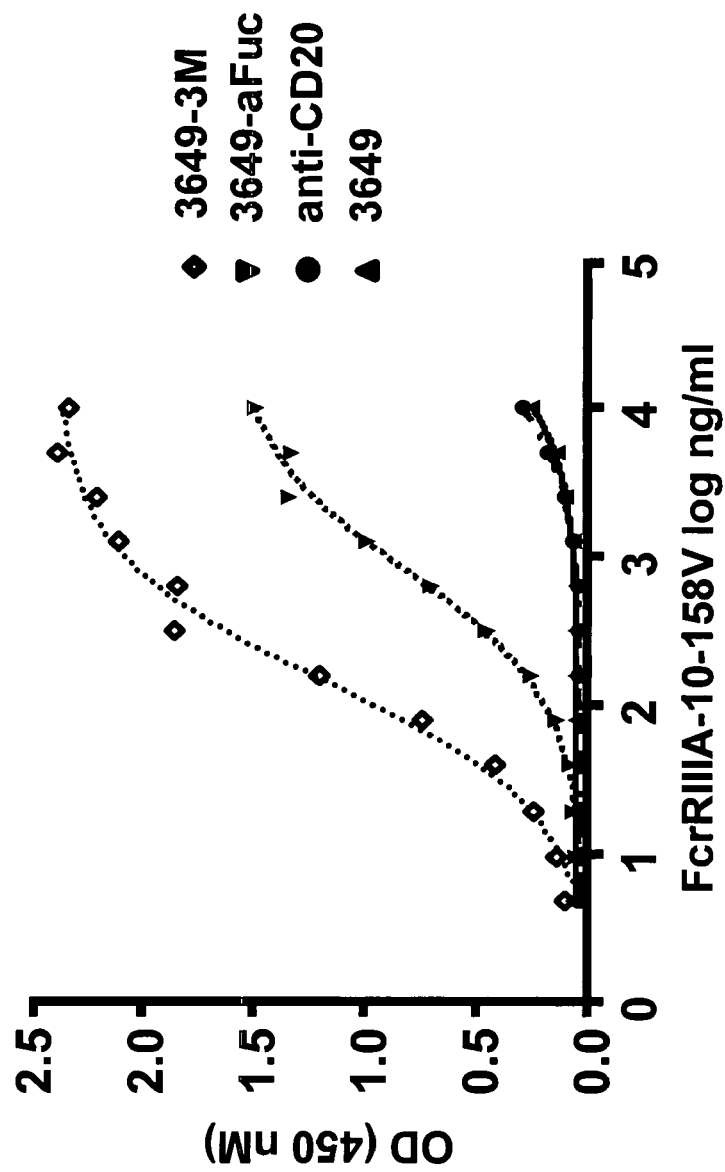

FIG. 15. Binding profile of 3649, 3649-3M, and 3649-aFuc anti-CD19 antibodies to the 158V allele of FcγRIIIA as determined by ELISA. An anti-CD20 antibody was included in the assay as a reference control. The binding affinity of the 3649-3M Fc variant antibody and the 3649-aFuc afucosylated antibody to FcγRIIIA is much higher than that of the fucosylated 3649 antibody. The 3649 and anti-CD20 antibodies have identical binding profiles.

FIG. 16. FcγRIIIA genotype of effector cells influences the in vitro ADCC activity of the anti-CD19 #2 antibody. ADCC assays were performed using the CytoTox 96™ kit (Promega) following the manufacturer's instructions. Antibodies used are: (i) the afucosylated anti-CD19 #2 (3649-aFuc), (ii) the 3M Fc variant of anti-CD19 #2 (3649-3M), and (iii) an anti-CD20 control. Daudi cells served as targets. Either an NK cell line (A) or freshly isolated NK cells (B-E) were used as effector cells. NK cell with V158/V158 (C), V158/F158 (D), and F158/F158 (E) FcγRIIIA genotype were tested. NK cells that comprise at least one copy of the high affinity isoform of FcγRIIIA receptor (V158N158 and V158/F158 genotypes) are more efficient effector cells than NK cells homozygous for the low affinity alleles (F158/F158 genotype). The observed ADCC activity of the fucosylated antibody (3649) mediated by V158/V158 or V158/F158 NK cells (C, D) is comparable to the ADCC activity of the afucosylated antibody (3649-aFuc) mediated by F158/F158 NK cells (E).

Figure 17:
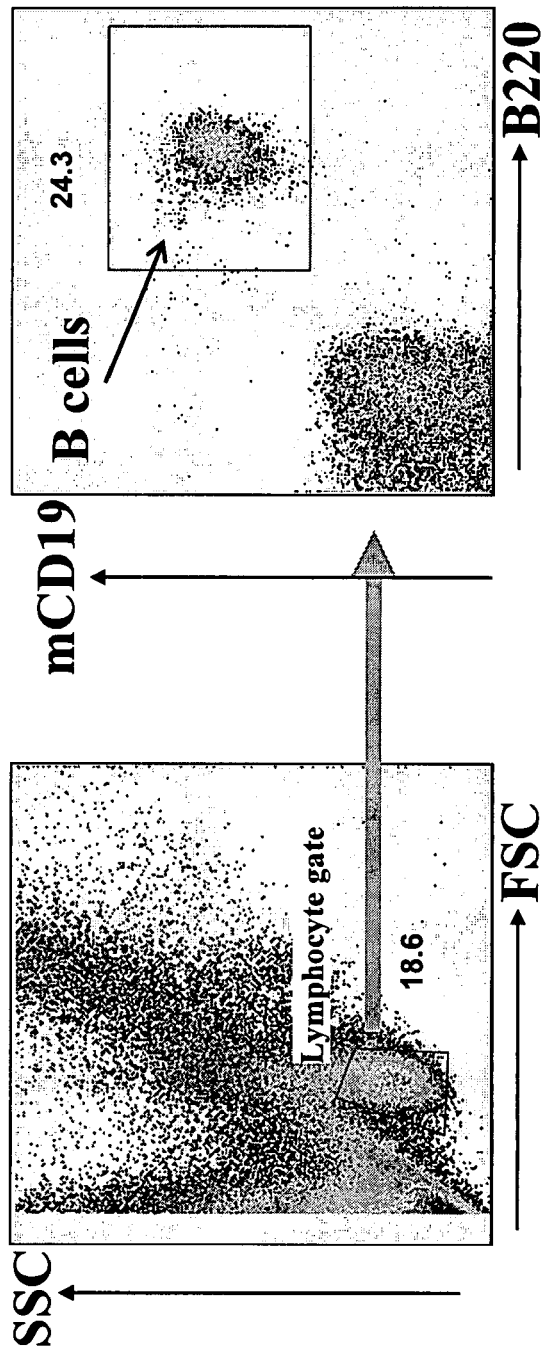
Figure 17:
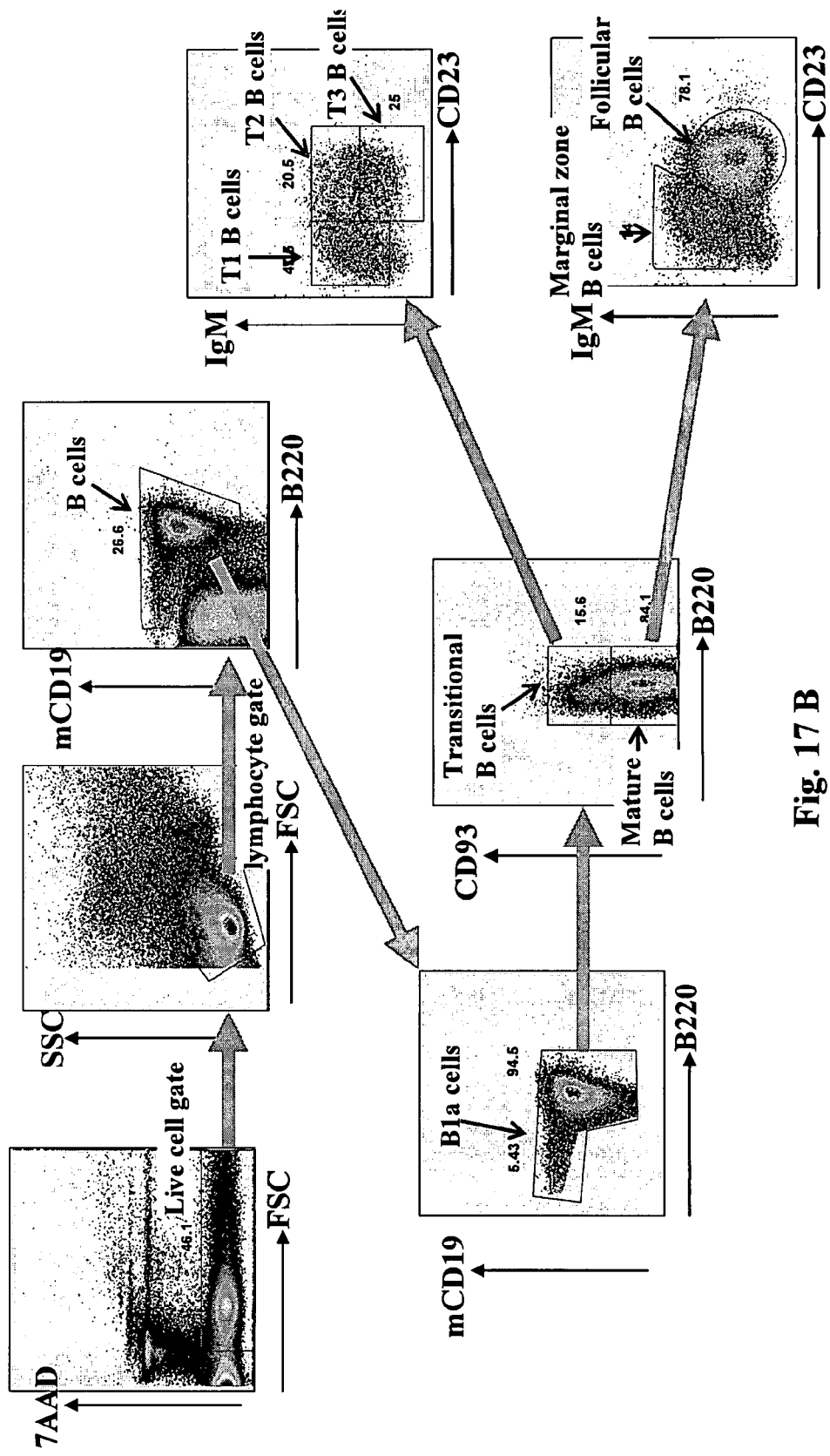
Figure 17:
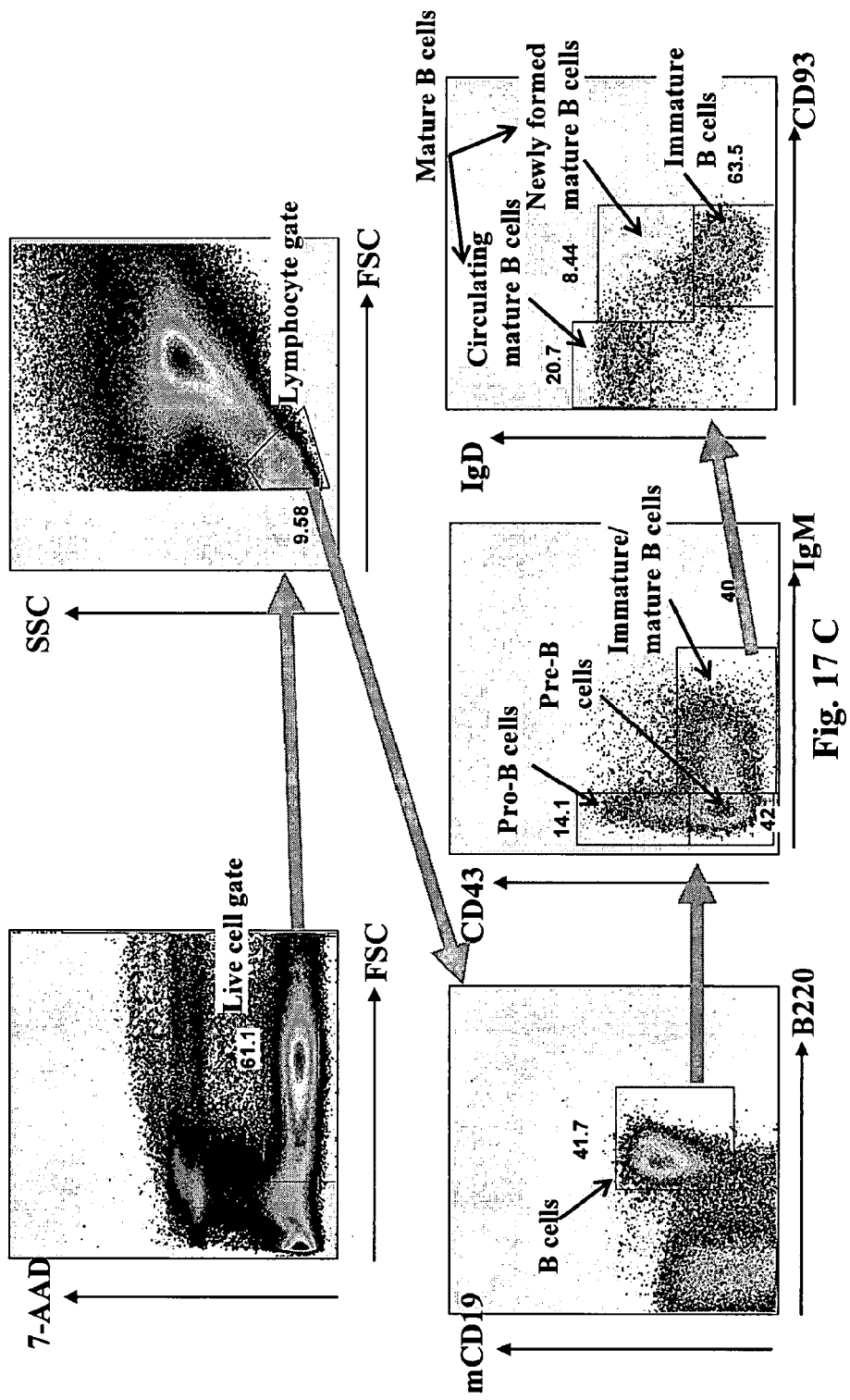
Figure 17:
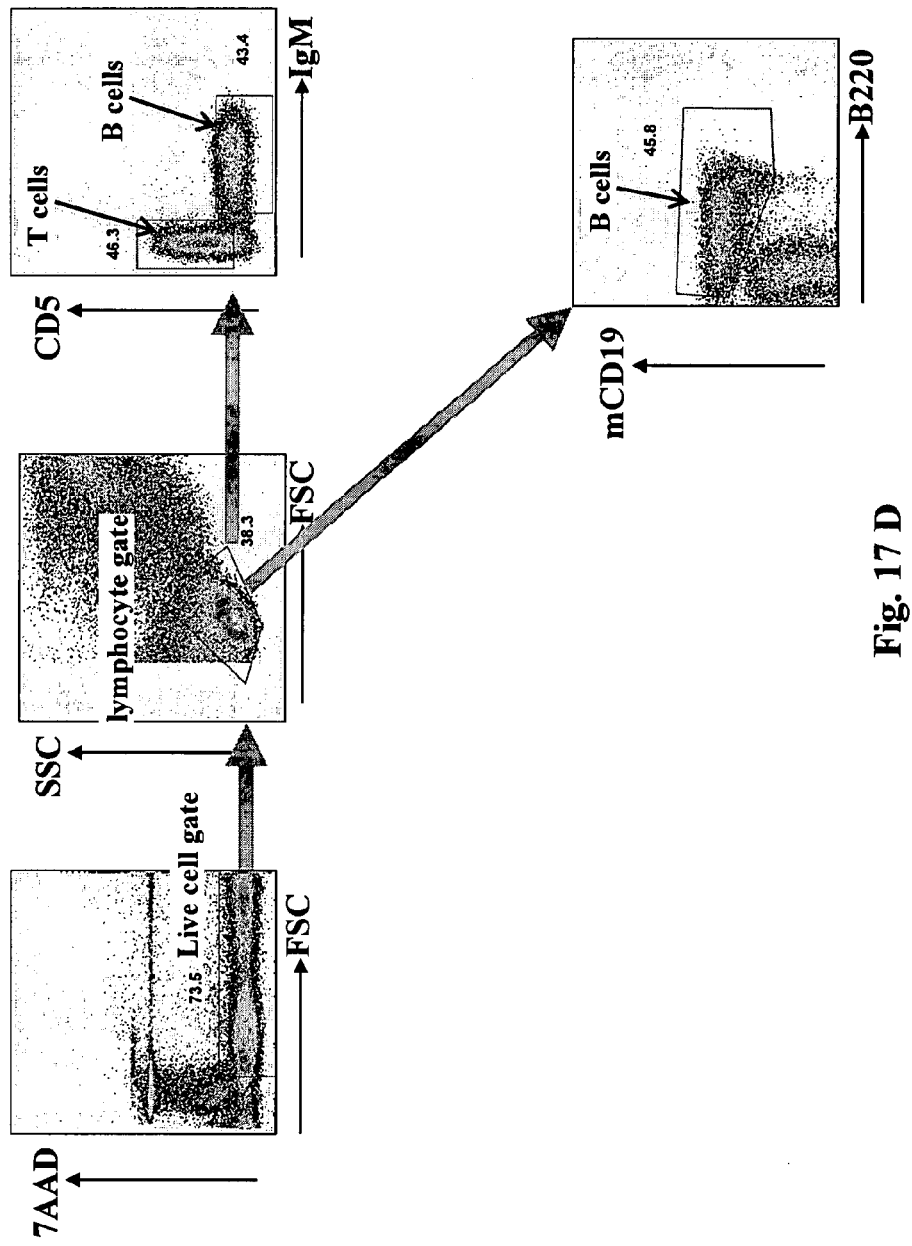

FIG. 17. Identification scheme of (A) circulating, (B) splenic, (C) bone marrow, and (D) peritoneal B cell subsets based on cell surface antigen expression phenotype. Fluorescently stained isolated cell populations were analyzed on a flow cytometer. B cell subsets were identified and measured through the sequential use of gates. The flow of the process is indicated by bold, grey arrows. For example, follicular B cells of the spleen were identified as follows: (i) live cells are gated based on low 7AAD staining, (ii) lymphocytes from the live cell fraction are identified based on their characteristic FSC and SSC phenotype, (iii) B cells among live lymphocytes are identified using anti-mCD19 and anti-B220 staining, (iv) B1a cells are separated from B cells based on differences in B220 expression, (v) mature and transitional B cell population are distinguished from each other based on differential expression of CD93, (vi) the follicular B cell subpopulation of mature B cells is separated from the marginal zone B cell fraction based on differences in CD23 expression.

Figure 18:
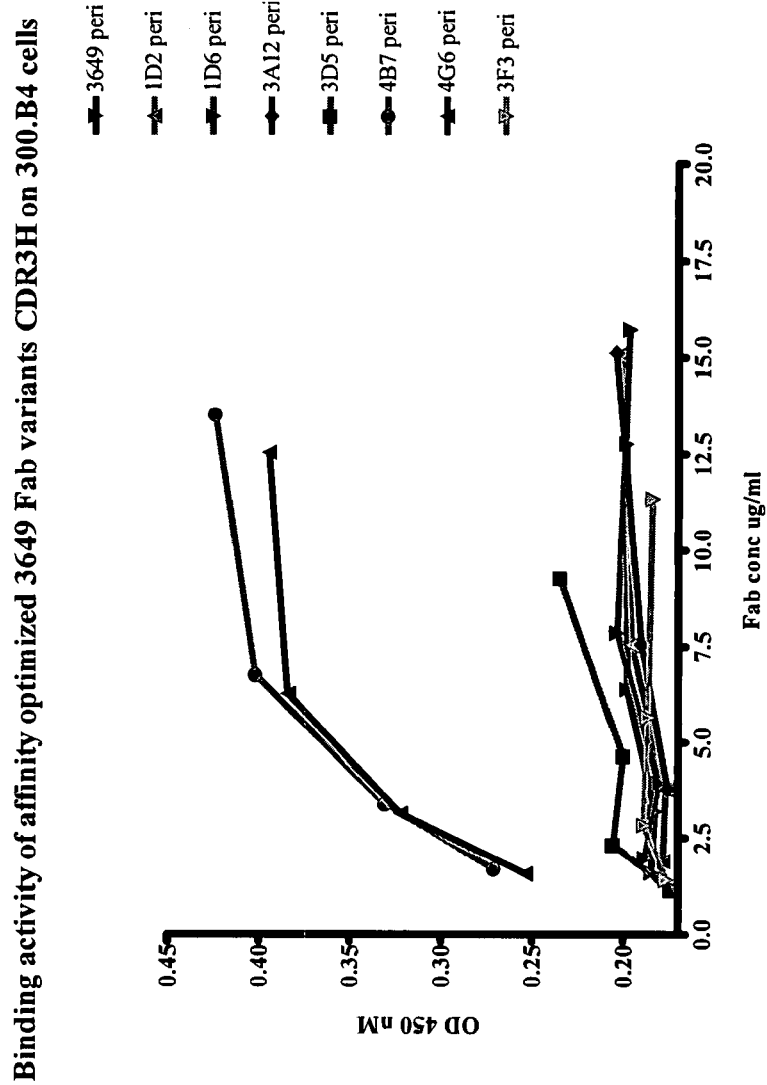

FIG. 18. Binding profile of affinity matured 3649 anti-CD19 antibody Fab fragments to recombinant human CD19 expressing 300B4 cells in a cell based ELISA assay. Results obtained with a representative sample of Fabs comprising single amino acid substitutions in the VH CDR3 is shown. The 3649 anti-CD19 Fab (3649 peri) was used as reference standard. The affinity of 4G6 and 4B7 Fabs to recombinant human CD19 expressing 300B4 cells is significantly higher than that of the control 3649 Fab. All other Fabs tested have affinities similar to that of the control 3649 Fab.

Figure 19:
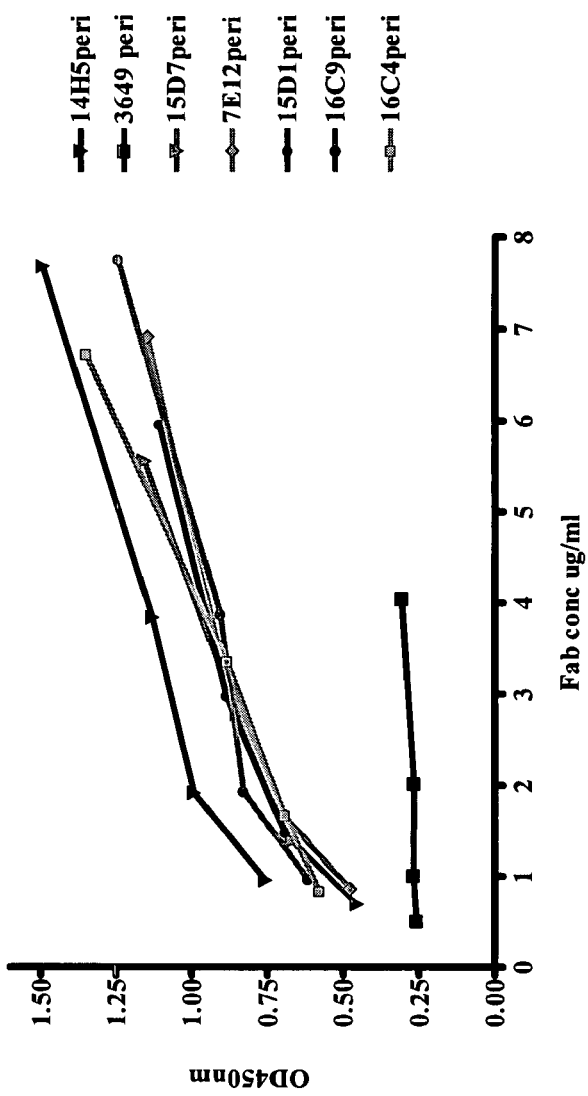

FIG. 19. Binding profile of affinity matured 3649 anti-CD19 antibody Fab fragments to recombinant human CD19 expressing 300B4 cells in a cell based ELISA assay. The Fabs characterized here were identified from a library comprising all possible combinations of the beneficial single amino acid substitutions identified in previous CDR specific screens. The binding profile of six Fabs with the highest affinity for recombinant human CD19 expressing 300B4 cells is shown. The 3649 anti-CD19 Fab (3649 peri) was used as reference standard. The affinity for recombinant human CD19 expressing 300B4 cells of all six affinity matured Fabs is higher than that of the control 3649 Fab.

Figure 20:
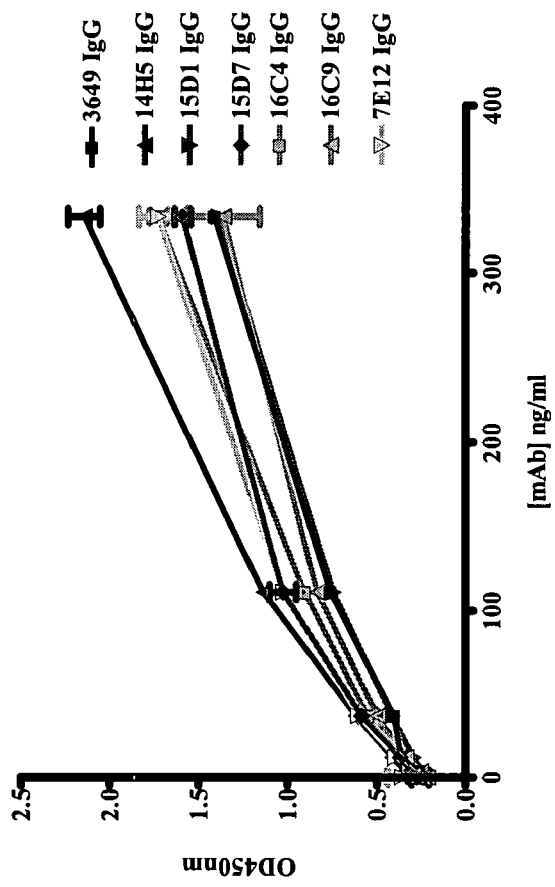

FIG. 20. Binding profile of affinity matured 3649 anti-CD19 antibodies to recombinant human CD19 expressing 300B4 cells in a cell based ELISA assay. The 3649 anti-CD19 antibody was used as reference standard. The binding profile of 16C9 IgG is similar to that of the 3649 control antibody. The binding affinity of 14H5, 15D1, 15D7, 16C4, and 7E12 affinity matured antibodies is higher than that of the control 3649 antibody.

Figure 21:
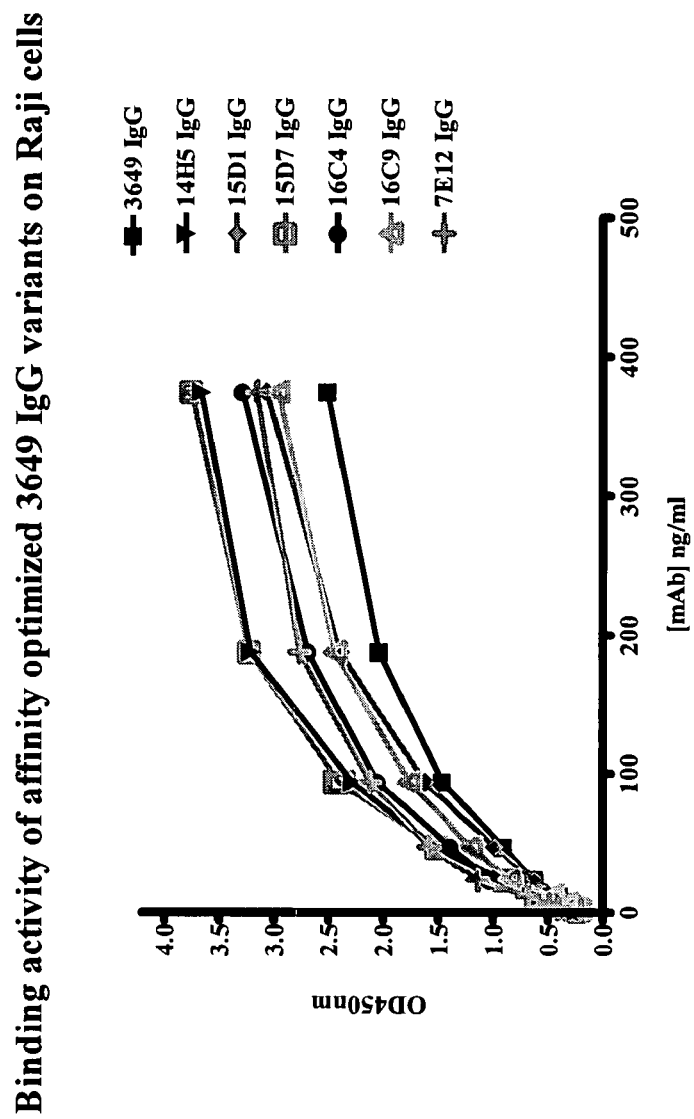

FIG. 21. Binding profile of affinity matured 3649 anti-CD19 antibodies to CD19 expressing Raji cells in a cell based ELISA assay. The 3649 anti-CD19 antibody was used as reference standard. The binding affinity of all six antibodies (14H5, 15D1, 15D7, 16C4, 16C9 and 7E12) is higher than that of the control 3649 antibody.

Figure 22:
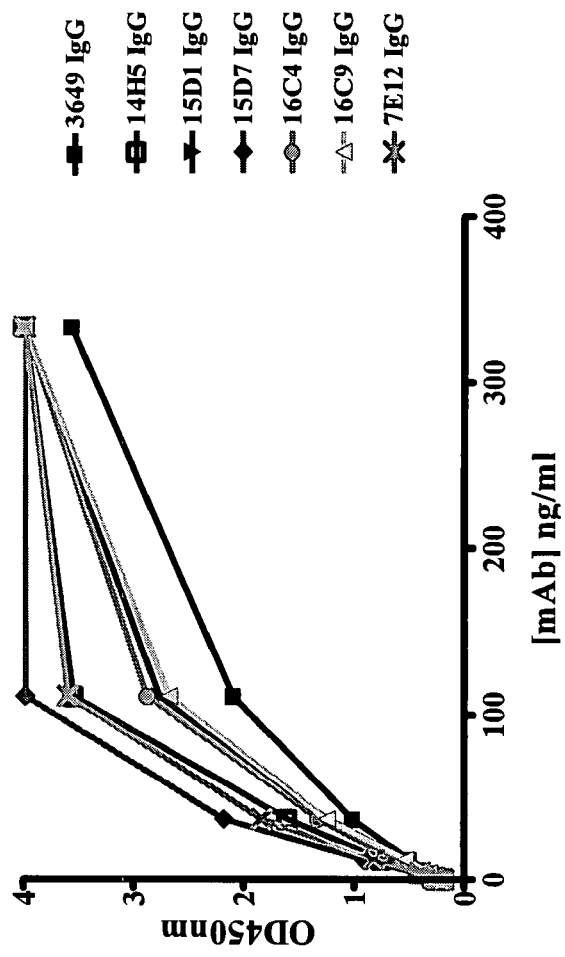

FIG. 22. Binding profile of affinity matured 3649 anti-CD19 antibodies to CD19 expressing Daudi cells in a cell based ELISA assay. The 3649 anti-CD19 antibody was used as reference standard. The binding affinity of all six antibodies (14H5, 15D1, 15D7, 16C4, 16C9 and 7E12) is higher than that of the control 3649 antibody.

Figure 23:
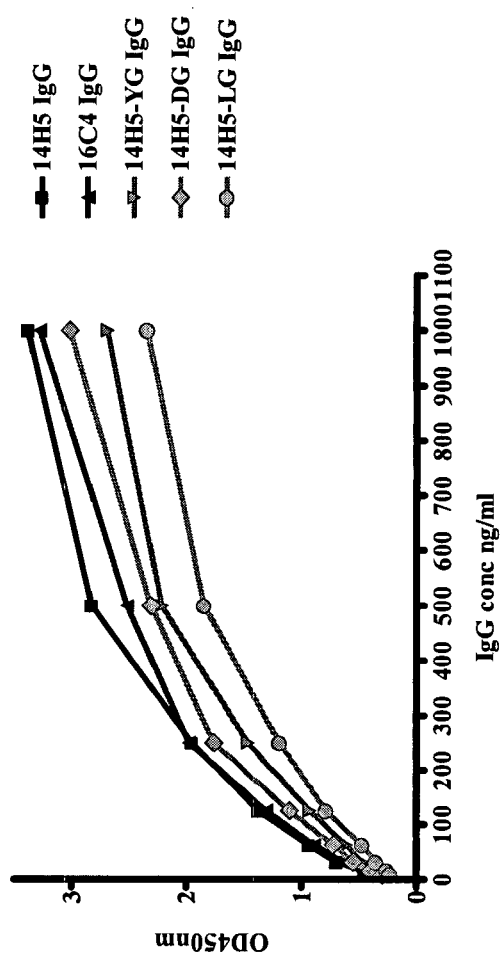

FIG. 23. Binding profile of affinity matured 3649 anti-CD19 antibodies to recombinant human CD19 expressing 300B4 cells in a cell based ELISA assay. 14H5-YG, 14H5-DG, and 14H5-LG are single amino acid substitution variants of the 14H5 affinity matured 3649 anti-CD19 antibody. 14H4 and 16C4 affinity matured 3649 anti-CD19 antibodies were used as reference standard. The binding affinity of 14H5-YG, 14H5-DG, and 14H5-LG antibodies is lower than that of the 14H5 and 16C4 control antibodies.

FIG. 24. Kinetic off rate comparison of affinity matured 3649 anti-CD19 antibodies. (A) Ramos cells were incubated with affinity matured anti-CD19 antibodies, washed and further incubated at 37° C. for 0, 30, or 60 minutes. Cells were stained with a fluorescent secondary antibody at the end of the incubation period and analyzed on a flow cytometer. Mean fluorescent intensity of cells after 0, 30, and 60 minute incubation is shown. The mean fluorescence intensity (MFI) observed at time 0 is set to 100% for each antibody studied. The 3649 anti-CD19 antibody and an anti-CD20 antibody were used as reference standards. The elimination of all six affinity matured 3649 anti-CD19 antibodies (14H5, 15D1, 15D7, 16C4, 16C9 and 7E12) from the cell surface is slower than that of the reference standards. (B) Ramos cells were stained with an Alexa 647 conjugated HB12B, 3649, or 16C4 anti-CD19 antibody, washed, and further incubated at 37° C. for 0, 30 or 60 minutes. Cells were analyzed on flow cytometer at the end of the incubation period. A directly conjugated anti-CD20 antibody was included in the experiment as a reference control. Mean fluorescence intensity (MFI) detected after various incubation periods is expressed as the ratio of MFI seen at time 0. Loss of MFI after staining with the 16C4 affinity matured anti-CD19 antibody is much slower than the loss of signal seen with the 3649 and HB12B anti-CD19 antibodies.

Figure 25:
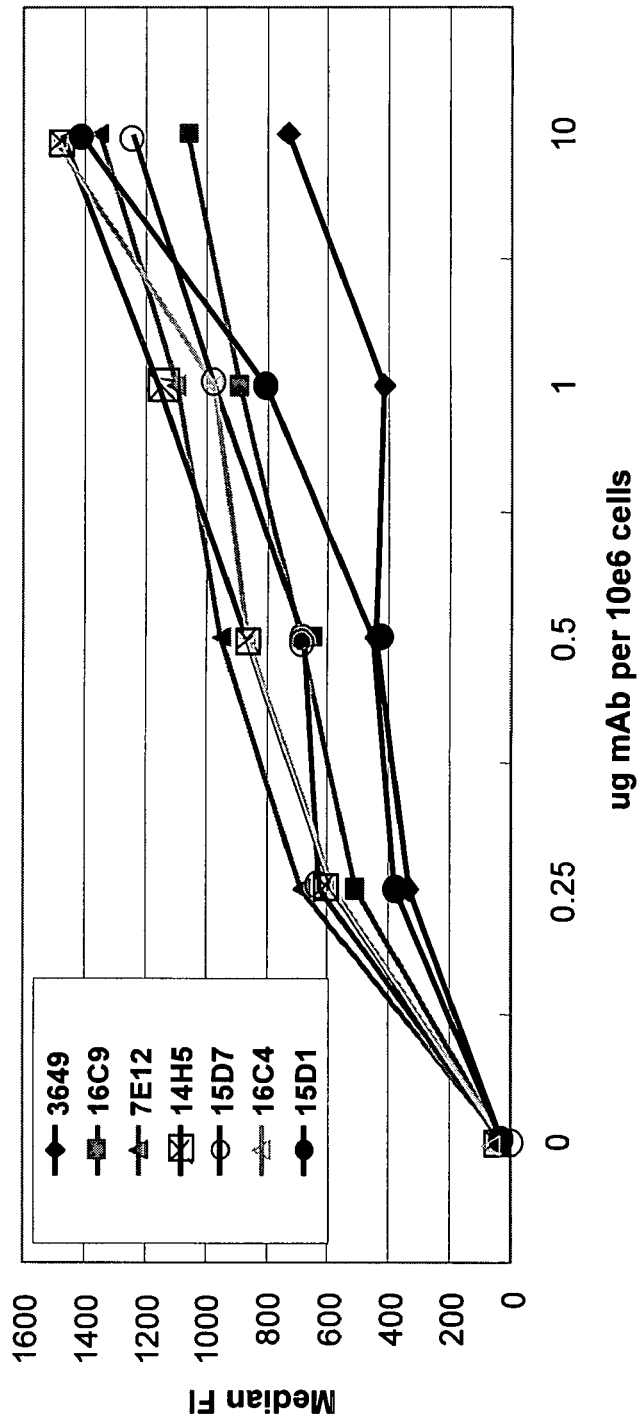

FIG. 25. Binding profile of affinity matured 3649 anti-CD19 antibodies to Daudi cells. Daudi cells were stained with the 14H5, 15D1, 15D7, 16C4, 16C9 or 7E12 affinity matured anti-CD19 antibodies and a fluorescently labeled secondary antibody. The 3649 anti-CD19 antibody was used as reference standard. Stained cells were analyzed on a flow cytometer. Median fluorescence intensity (Median FI) observed at various antibody concentrations is presented in a chart. The median FI for the affinity matured 3649 anti-CD-19 antibodies was higher than that of the reference standard.

Figure 26:
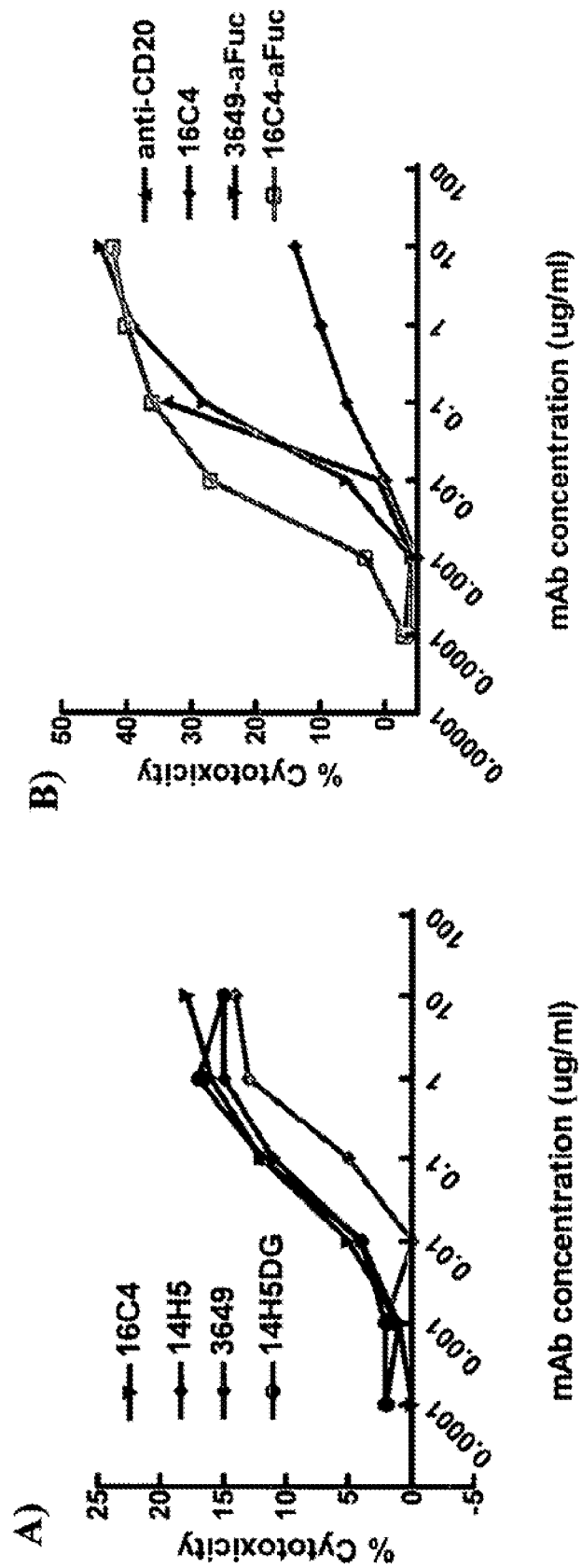

FIG. 26. In vitro ADCC activity of affinity matured 3649 anti-CD19 antibodies. (A) In vitro ADCC activity of the 14H5, 14H5-DG and 16C4 affinity matured anti-CD19 antibodies was assayed using Daudi target cells. The 3649 anti-CD-19 antibody was used as reference standard. The ADCC activity of all three affinity matured antibodies is higher than that of the reference standard at low antibody concentration (0.01 and 0.1 µg/ml antibody). The ADCC activity of all three affinity matured antibodies parallels the activity of the reference standard at high antibody concentrations (1 and 10 µg/ml antibody). (B) The ADCC activity of the afucosylated 16C4 antibody (16C4-aFuc) was determined in an in vitro assay using Daudi target cells. The ADCC activity of 16C4-aFuc is significantly higher than that of the reference control 3649-aFuc, anti-CD20 and fucosylated 16C4 reference antibodies.

Figure 27:
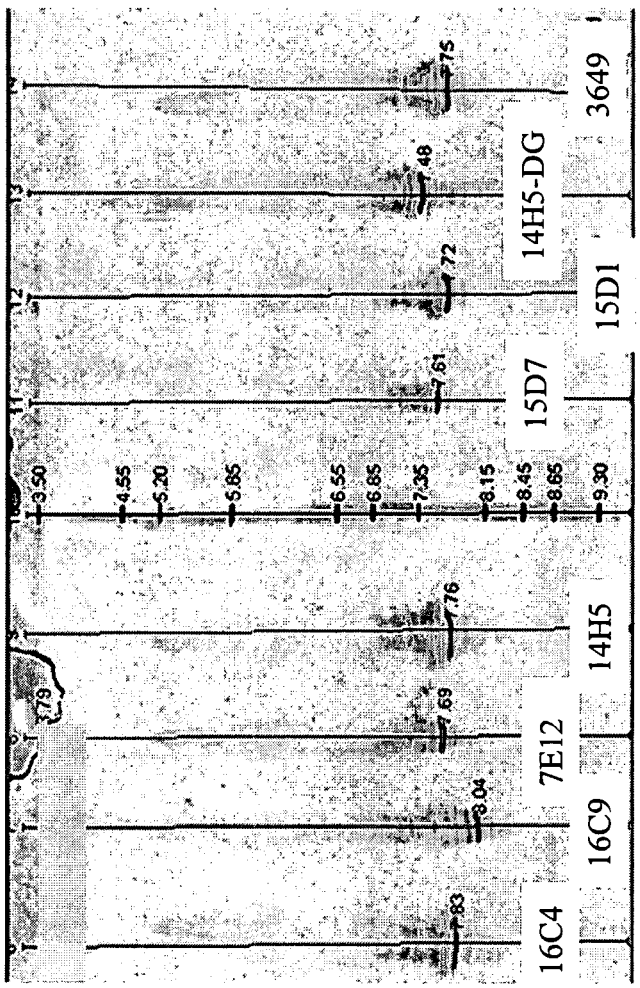

FIG. 27. Coomassic stained IEF-PAGE of affinity matured anti-CD19 antibodies. The isoelectric point of the 16C4, 16C9, 7E12, 14H5, 15D7, 15D1, 14H5-DG, and 3649 antibodies is 7.83, 8.04, 7.69, 7.76, 7.61, 7.72, 7.48, and 7.75, respectively.

FIG. 28. In vivo B cell depletion by the afucosylated 3649 anti-CD19 antibody. C57B16 hCD19 tg+/− animals were treated with a single i.v. dose of 10, 50, or 250 µg of fucosylated 3649 anti-CD19 antibody (3649) or afucosylated 3649 anti-CD19 antibody (3649-aFuc). Negative control animals were treated with (i) the ADCC compromised Fc variant of 3649 anti-CD19 antibody (3649 TM) or (ii) an antibody of irrelevant specificity (R347). Circulating lymphocytes (A) or splenic lymphocytes (B) were isolated 7 days after antibody treatment. Isolated cells were immunostained as described in Table 5 to identify various B cell populations. Percentage of B220+ CD19+ B cells is displayed. The afucosylated 3649 anti-CD19 antibody achieves a significantly higher depletion of B cells than the same amount of fucosylated anti-CD19 antibody. No depletion B cell depletion is detected in the 3649TM control antibody treated animals.

Figure 29:
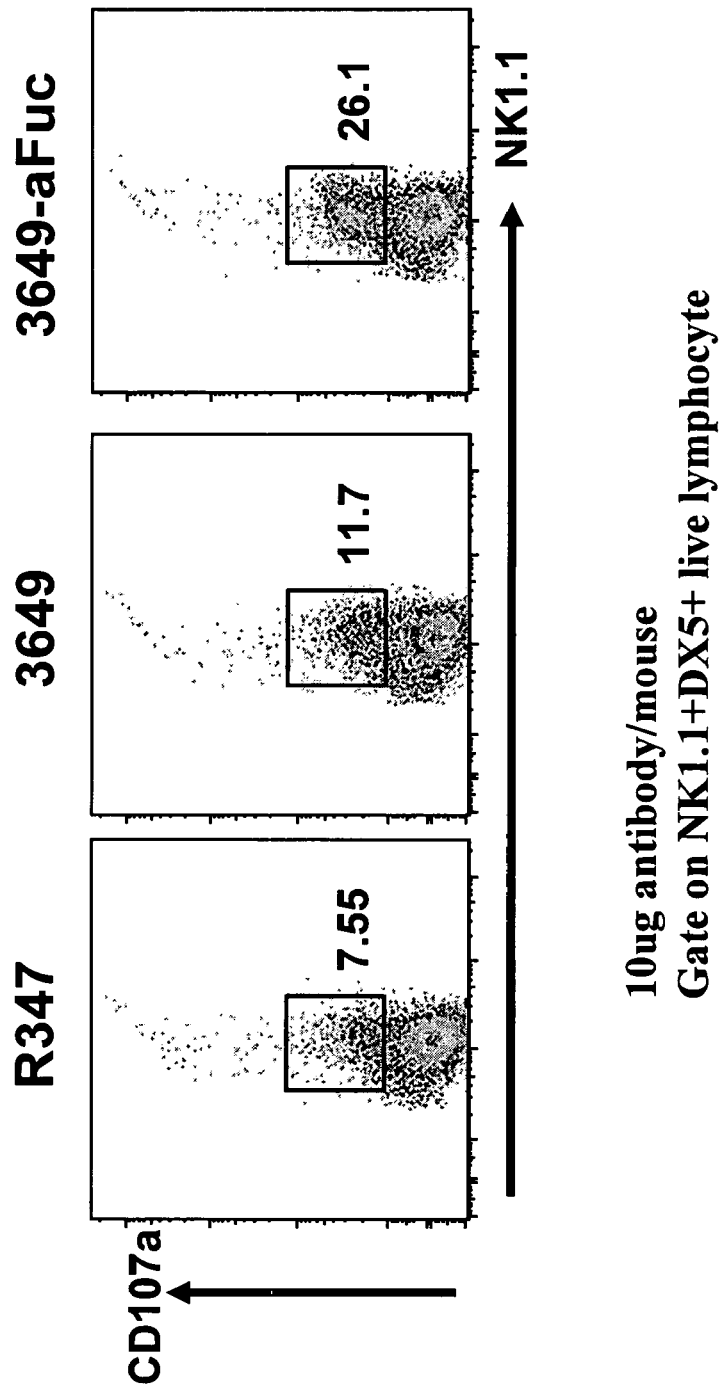

FIG. 29. Enhanced NK cell activation in afucosylated 3649 anti-CD19 antibody treated mice. C57B16 hCD19 tg+/− animals were treated with a single i.v. dose of 10 µg of fucosylated 3649 anti-CD19 antibody (3649) or afucosylated 3649 anti-CD19 antibody (3649-aFuc). Negative control animals were treated with the same amount of an isotype matched antibody of irrelevant specificity (R347). Circulating lymphocytes were isolated 7 days after antibody treatment. Isolated cells were stained with fluorescently labeled anti-NK1.1, anti-DX5, and anti-CD107a antibodies. CD107a vs. NK1.1 plot of NK1.1+, DX5+ gated live lymphocytes is displayed. A higher percentage of NK cells isolated from afucosylated 3649 anti-CD19 antibody treated animals display CD107a on their cell surface than NK cells isolated from fucosylated 3649 anti-CD19 antibody treated animals.

Figure 30:
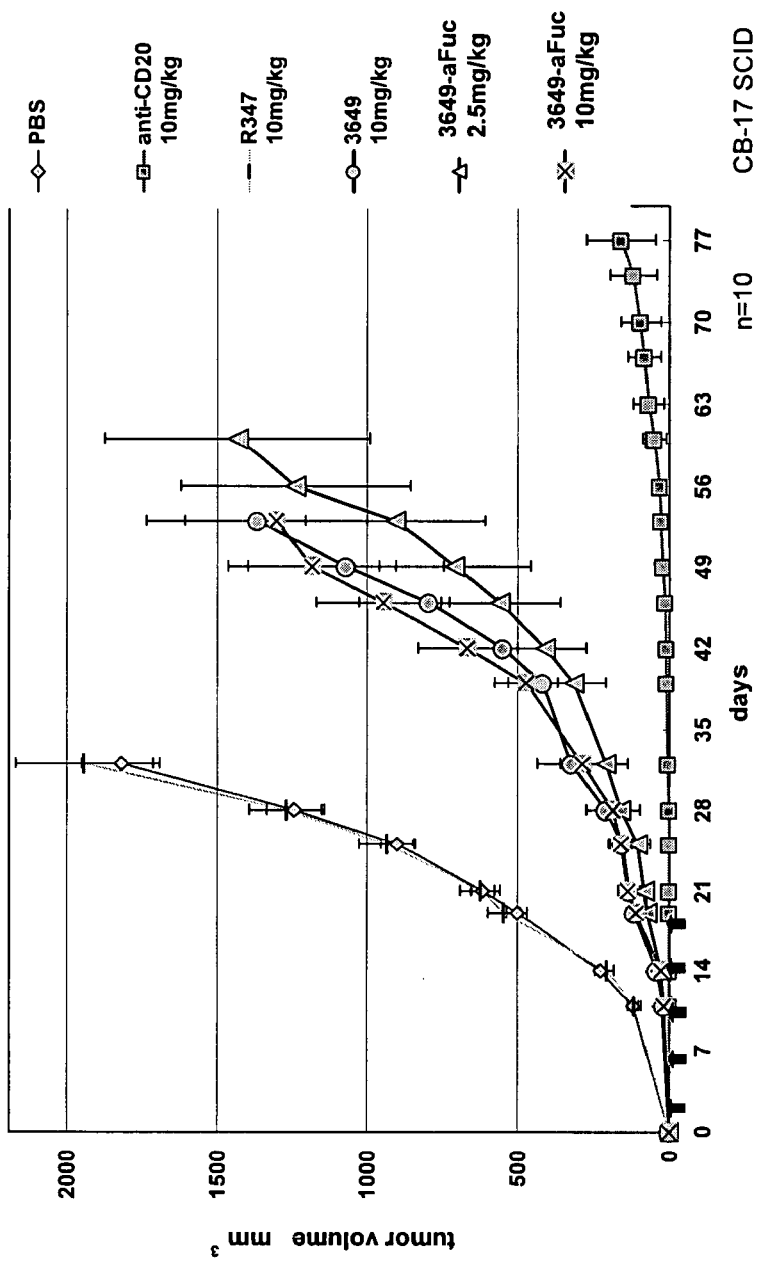

FIG. 30. Afucosylated anti-CD19 antibody #2 (3649-aFuc) significantly reduces tumor growth in an in vivo model system. CB17 SCID mice were injected s.c. on the hind flank with 5×106 Raji cells on day 1. Animals were treated with five biweekly doses of 10 mg/kg or 2.5 mg/kg antibody starting on day 4. Antibodies used are: (i) fucosylated anti-CD19 #2 at 10 mg/kg (3649), (ii) afucosylated anti-CD19 #2 at 10 mg/kg or 2.5 mg/kg (3649-aFuc), (iii) anti-CD20 at 10 mg/kg, and (iv) isotype control antibody of irrelevant specificity at 10 mg/kg (R347). A group of control animals were only given PBS. Tumor size was measured twice a week using standard procedures.

Figure 31A:
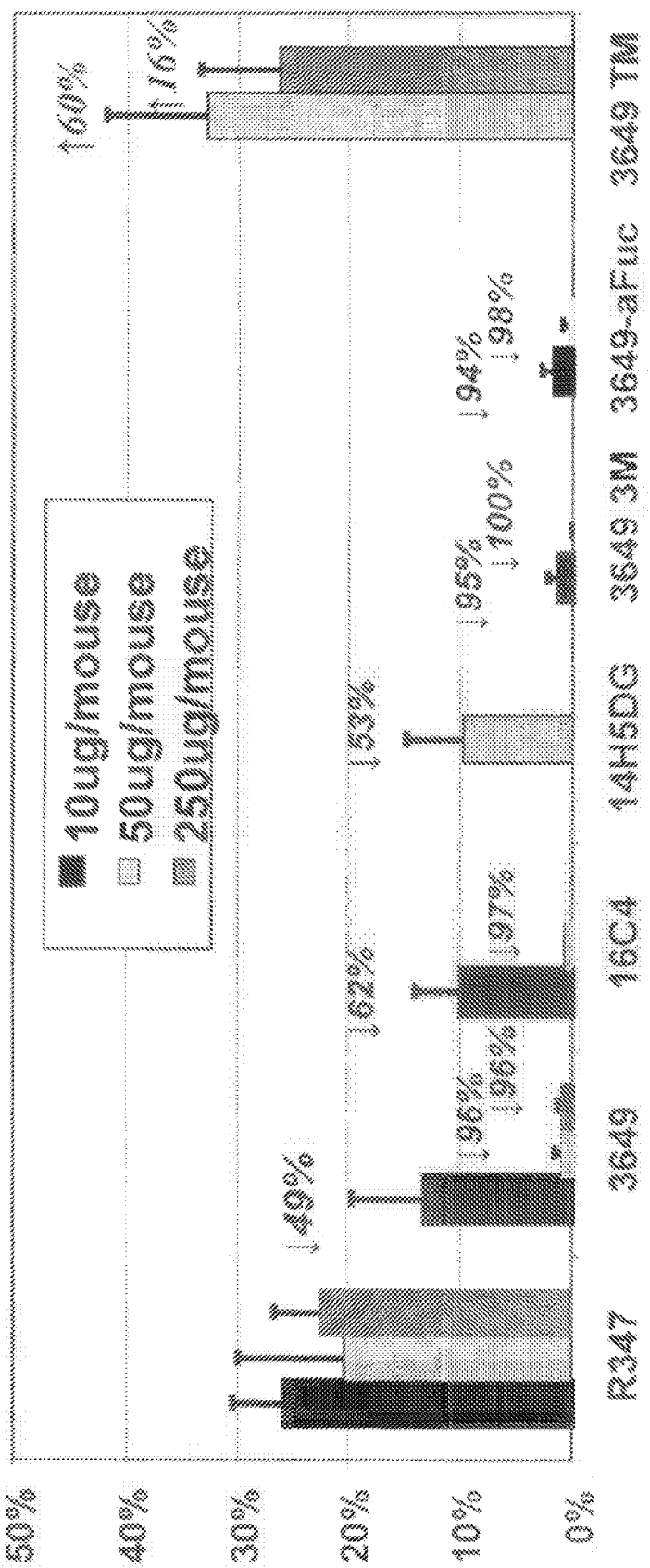
Figure 31B:
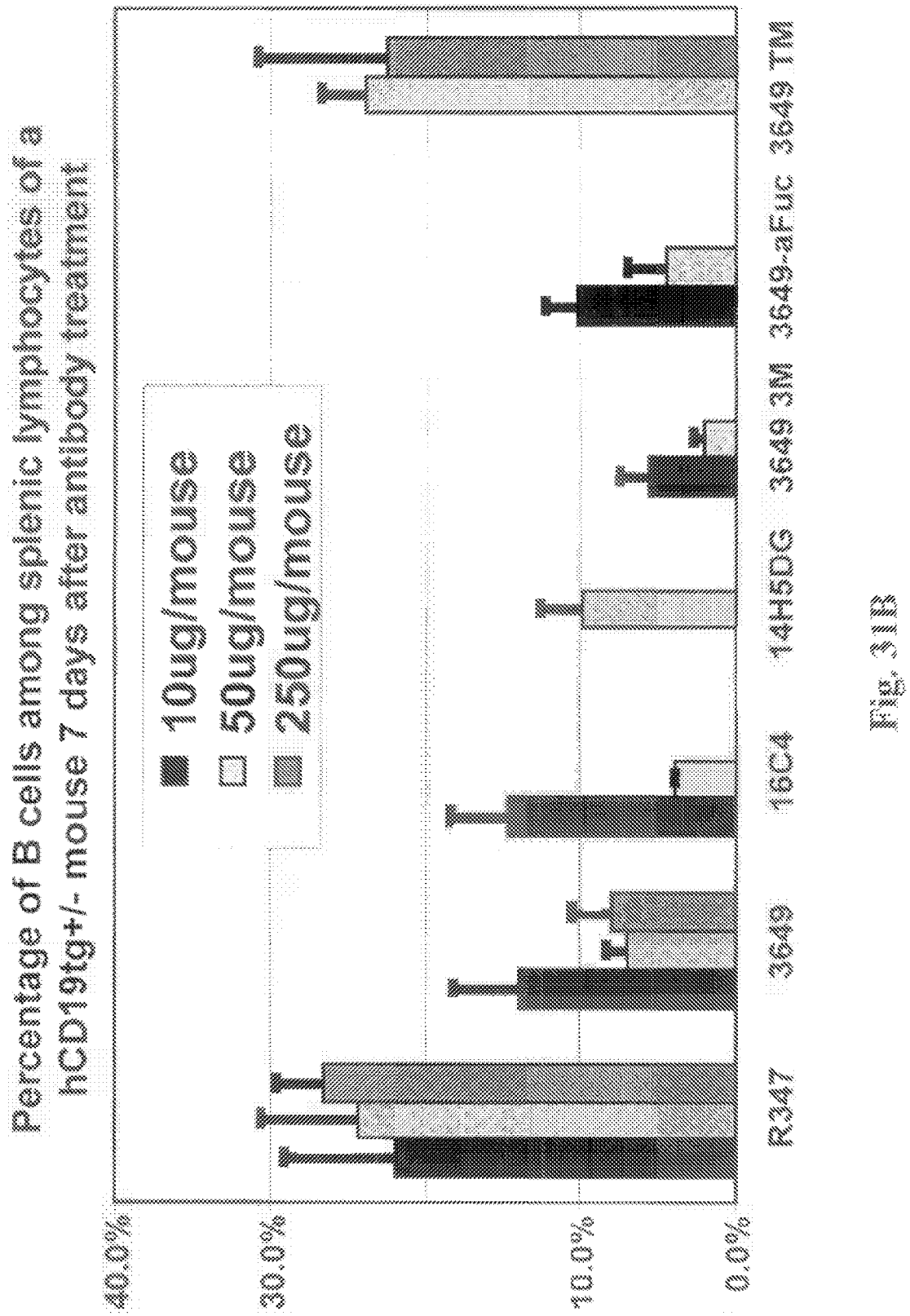

FIG. 31. In vivo B cell depletion using the 16C4 and 14H5 affinity mature anti-CD19 antibodies. C57B16 hCD19 tg+/− animals were treated with a single i.v. dose of 10, 50, or 250 µg of fucosylated 16C4 affinity matured anti-CD19 antibody (16C4) or 14H5DG affinity matured anti-CD19 antibody (14H5DG). Reference control animals were treated with (i) 3649 anti-CD19 antibody (3649), (ii) ADCC enhanced Fc variant of 3649 anti-CD19 antibody (3649 3M), and (iii) afucosylated 3649 anti-CD19 antibody (3649-aFuc). Negative control animals were treated with (i) the ADCC compromised Fc variant of 3649 anti-CD19 antibody (3649 TM) or (ii) an antibody of irrelevant specificity (R347). Circulating lymphocytes (A) or splenic lymphocytes (B) were isolated 7 days after antibody treatment. Isolated cells were immunostained as described in Table 5 to identify various B cell populations. Percentage of B220+ CD19+ B cells is displayed. The 16C4 affinity matured anti-CD19 antibody achieved a slightly higher depletion of B cells than the 3649 anti-CD19 parent antibody. The 3649-aFuc and 3649 3M antibodies achieved better depletion than the 16C4 affinity matured antibody. The 14H5DG affinity matured anti-CD19 antibody is less efficient at depleting B cells than the 3649 anti-CD19 parent antibody. Values inside panel (A) are that of the percent depletion achieved by a given antibody.

Figure 32:
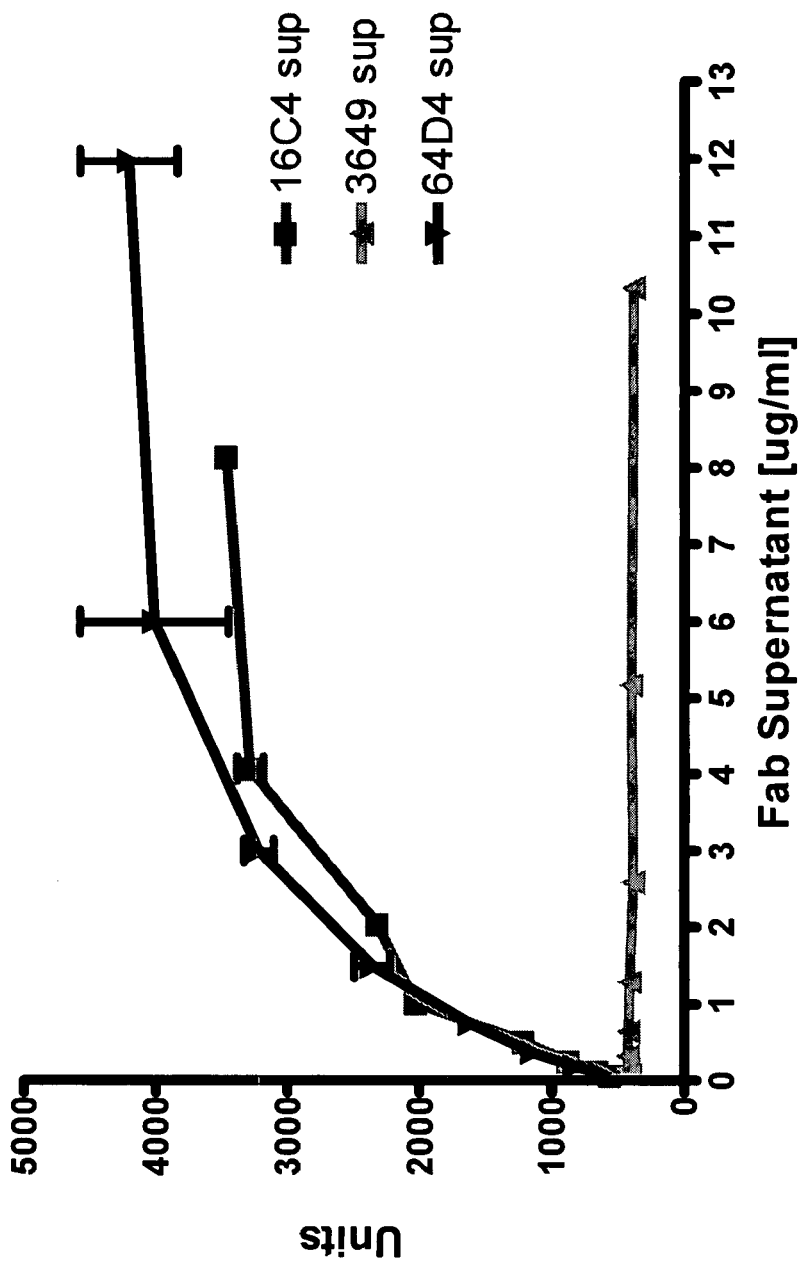

FIG. 32. Binding activity of the 64D4 affinity matured Fab to recombinant human CD19 expressing 300B4 cells in a cell based binding assay (Lu et al., *J. Immunol. Methods* 314:74-79 (2006)). 64D4 is a variant of the 16C4 anti-CD19 antibody comprising a single amino acid substitution in the VH CDR2. The 16C4 and 3649 anti-CD19 Fabs (16C4sup and 3649sup, respectively) were used as reference standards. The affinity of the 64D4 Fab to recombinant human CD19 expressing 300B4 cells is significantly higher than that of the control 16C4 and 3649 Fabs.

FIG. 33. Characterization of the affinity matured variant anti-CD19 Fabs isolated from the combinatorial phage display library. Binding profile of affinity matured variants of the 16C4 Fab to cell surface displayed human CD19 antigen was measure in a cell based binding assay using (A) 300B4 and (B) Raji cells (Lu et al., J. Immunol. Methods 314:74-79 (2006)). The 16C4 and 3649 anti-CD19 Fabs (16C4sup and 3649sup, respectively) were used as reference standards. The binding affinity of 6C11, 2B11, 3B4, 5C11, 3C3, 9G7, 1H4, and 5C4 affinity matured Fabs to 300B4 and Raji cells is higher than that of the control 3649 and 16C4 Fabs. (C) Amino acid sequence of the affinity matured Fab clones was determined using standard laboratory methods. CDR sequence of unique Fab clones is presented. Amino acid residues different from that of the parental 16C4 sequence are printed using single letter amino acid codes; residues identical to the parental sequence are marked with a "-". FIG. 33C discloses the "CDR1H"sequences as SEQ ID NOS 22, 208 208, 208, 208, 208, 208, 208, 22, 22, 208, 209, 208, 22, 22, 208, 208, 208 and 208, respectively in order of appearance, the "CDR2H" sequences as SEQ ID NOS 116, 116, 116, 116, 116, 210, 116, 116, 116, 116, 116, 116, 116, 116, 116, 210, 116, 116 and 116, respectively, in order of appearance, the "CDR3H" sequences all as SEQ ID NO: 121, the "CDR1L" sequences as SEQ ID NOS 28, 28, 211, 28, 28, 212, 28, 28, 213, 28, 28, 28, 212, 214, 28, 28, 215, 239 and 217, respectively, in order of appearance, the "CDR2L" sequences as SEQ ID NOS 125, 125, 218, 125, 125, 125, 125, 125, 218, 125, 125, 125, 219 125, 125, 220, 221, 218 and 218, respectively, in order of appearance, and the "CDR3L" sequences as SEQ ID NOS 32, 32, 222-224, 32, 225, 226, 32, 227, 228, 32, 224, 32, 226, 229, 222, 32 and 225, respectively, in order of appearance.

Figure 34:
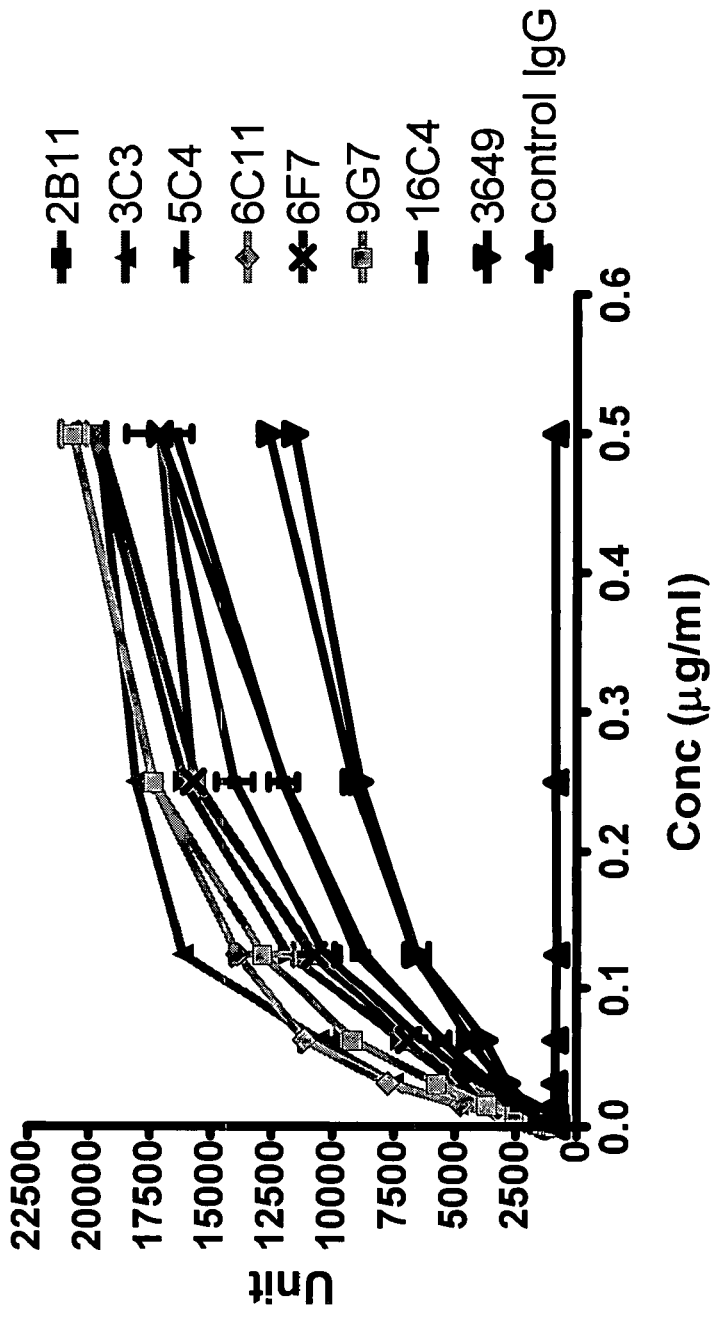

FIG. 34. Binding profile of the 2B11, 3C3, 5C4, 6C11, 6F7, and 9G7 affinity matured IgG anti-CD19 antibodies to recombinant human CD19 expressing 300B4 cells. Binding activity was measured using a cell based assay (Lu et al., *J. Immunol. Methods* 314:74-79 (2006)). The 16C4 and 3649 anti-CD19 antibodies were used as reference standards. The binding affinity of the affinity matured anti-CD19 antibodies tested to 300B4 cells is higher than that of the reference 16C4 and 3649 antibodies.

Figure 35A:
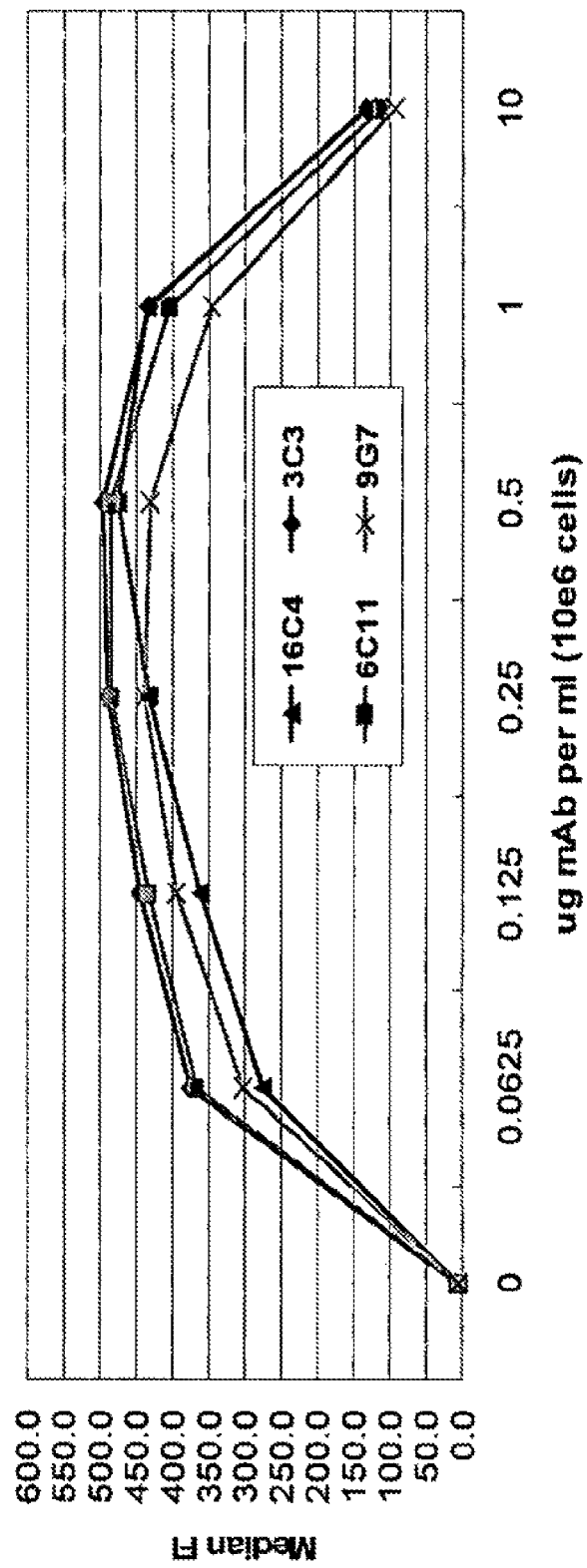
Figure 35B:
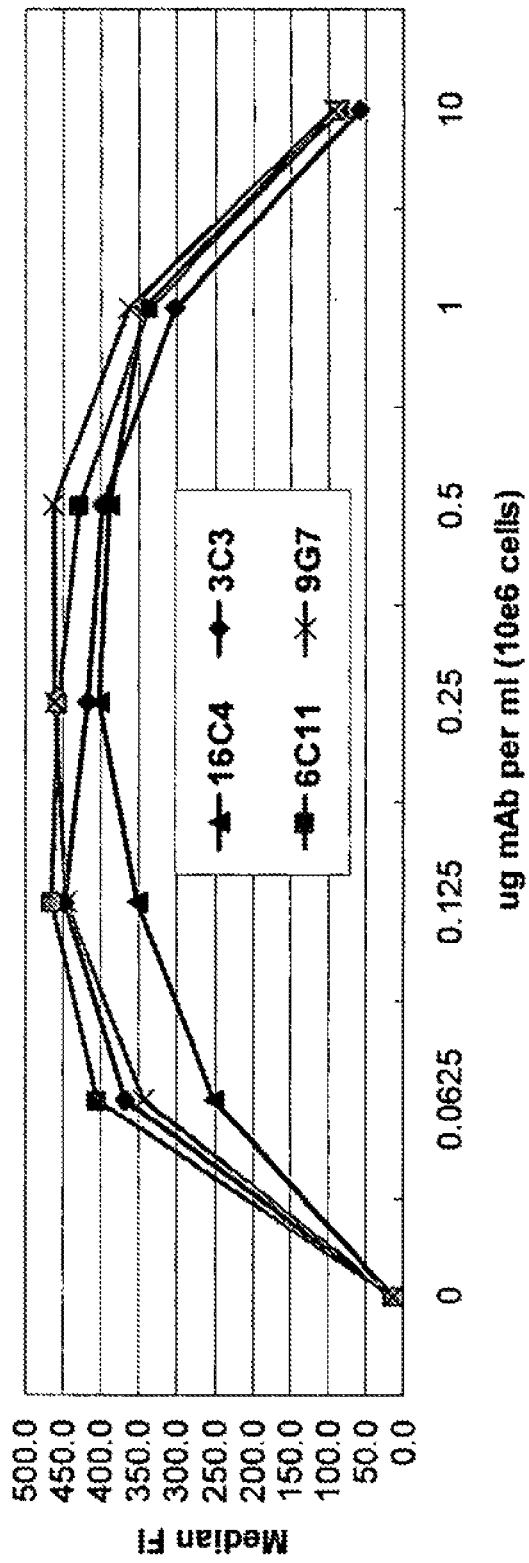

FIG. 35. Binding profile of affinity matured 16C4 anti-CD19 antibodies to (A) Raji cells and (B) Daudi cells. Cells were stained with the 3C3, 6C11, or 9G7 affinity matured anti-CD19 antibodies and a fluorescently labeled secondary antibody. The 16C4 anti-CD19 antibody was used as reference standard. Stained cells were analyzed on a flow cytometer. Median fluorescence intensity (Median FI) observed at various antibody concentrations is presented. The median FI of cells stained with the affinity matured 16C4 variant anti-CD19 antibodies was higher than that of the reference standard stained cells at 0.0625-0.125 µg/ml primary antibody concentration. Median FI obtained using affinity matured antibodies was substantially the same as that of for the reference antibody in the 0.25-10 µg/ml range.

Figure 36:
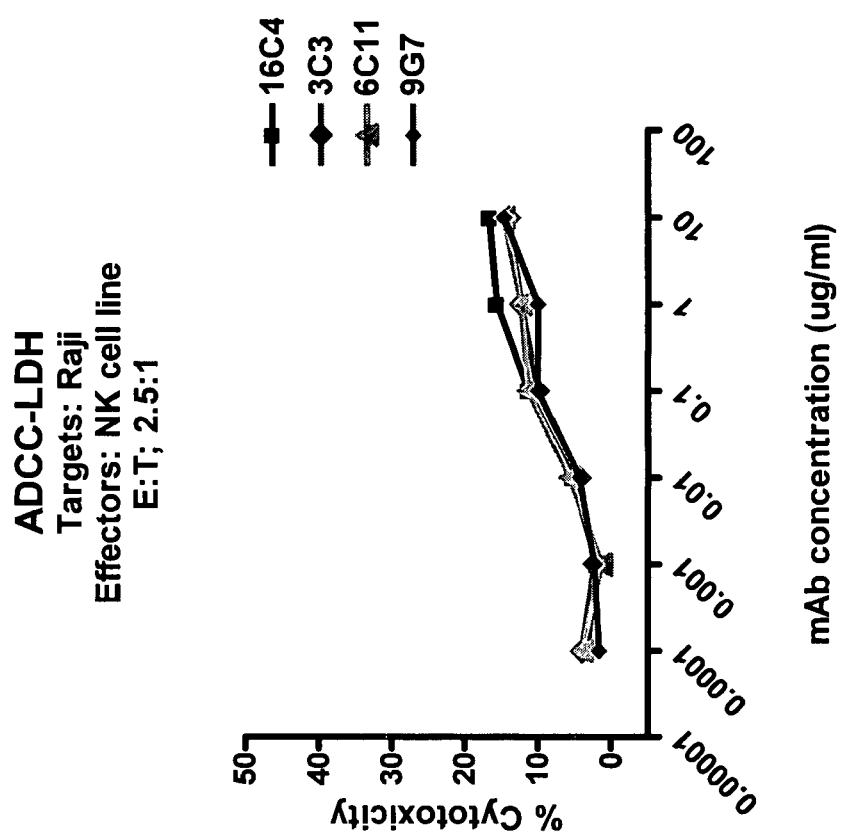

FIG. 36. In vitro ADCC activity of affinity matured 16C4 variant anti-CD19 antibodies. In vitro ADCC activity of the 3C3, 6C11, or 9G7 affinity matured anti-CD19 antibodies was assayed using Raji target cells. The 16C4 anti-CD19 antibody was used as reference standard. The ADCC activity of all three affinity matured antibodies is substantially the same as that of the reference standard at all concentrations tested (0.01-10 µg/ml).

Figure 37:
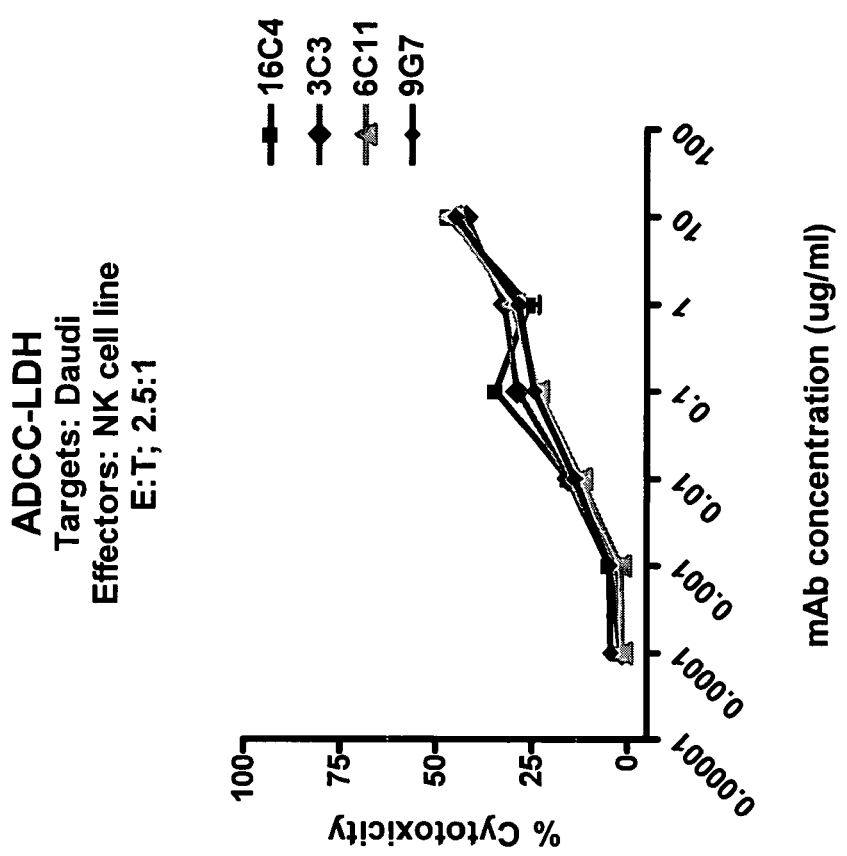

FIG. 37. In vitro ADCC activity of affinity matured 16C4 variant anti-CD19 antibodies. In vitro ADCC activity of the 3C3, 6C11, or 9G7 affinity matured anti-CD19 antibodies was assayed using Daudi target cells. The 16C4 anti-CD-19 antibody was used as reference standard. The ADCC activity of all three affinity matured antibodies is substantially the same as that of the reference standard at all concentrations tested (0.01-10 µg/ml).

FIG. 38. Long term recovery of B cells and serum immunoglobulin levels following B cell depletion with a single dose of i.v. administered afucosylated 16C4 anti-CD19 antibody. (A) Experimental protocol. Groups of four or five huCD19 tg+/− mice were administered a single i.v. dose of 250, 50, or 10 µg afucosylated 16C4 anti-CD19 antibody (16C4 aFuc). Control groups were treated with either PBS or 250 µg control antibody of irrelevant specificity (R347). Animals were bled once every two weeks; first bleed was done seven days prior to administration of the depleting antibody. Findings from the first 11 weeks are summarized in the panels. (B) The body weight of the animals in all groups remained normal. Blood B cell levels are expressed as (C) the fraction of lymphocytes or as (D) B cell number per microliter of blood. All three 16C4 aFuc antibody doses achieved complete B cell depletion. B cell recovery was complete by week 5 and week 9 in animals receiving 10 and 50 µg 16C4 aFuc antibody, respectively. B cell recovery was still incomplete 11 weeks after the administration of 250 µg 16C4 aFuc antibody. Serum (E) IgM, (F) IgG1, and (G) IgG2b was unchanged following the administration of 50 or 250 µg 16C4 aFuc. Serum immunoglobulin levels were increased following the administration of 10 µg 16C4 aFuc antibody or the control antibody R347 or PBS. The data indicates that 16C4 aFuc suppressed on-going immunoglobulin production, but had minimum impact on the pre-existing immunoglobulin in serum.

FIG. 39. Anti-CD19 antibody induced intracellular signaling. (A-B) 3649, 3649-TM, 3649-3M, 3649-aFuc, or 16C4 antibody treatment significantly increases the tyrosine phosphorylation level of CD19 in Raji cells. (C-D) Anti-CD19 antibody treatment does not inhibit anti-IgM treatment induced ERK1/2 phosphorylation.

Figure 40:
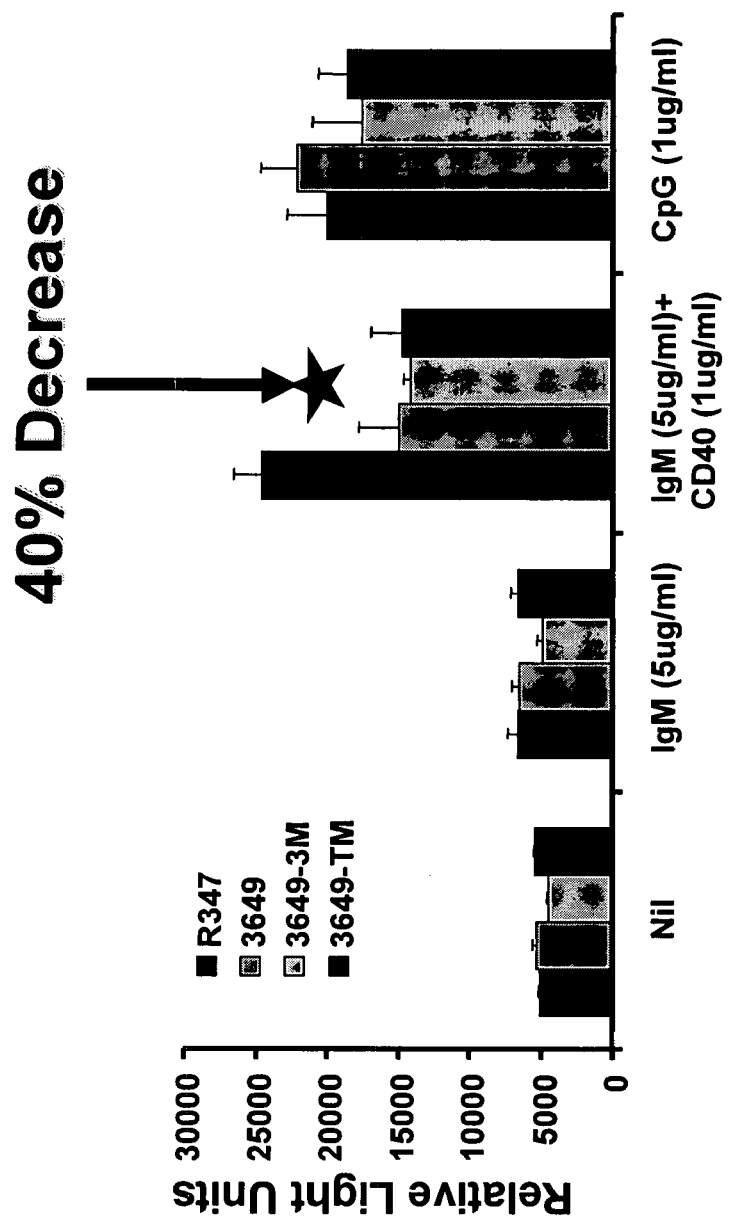

FIG. 40. Anti-CD19 antibody treatment inhibits anti-IgM/CD40 mediated B cell proliferation.

FIG. 41. Anti-CD19 antibody treatment inhibits the anti-IgM/CpG induced proliferation of purified peripheral B cells. (A) Fluorescence intensity profile of CFSE stained purified peripheral blood B cells following 4 days of incubation in the presence anti-IgM (1 µg/ml) and CpG (2 µg/ml). The CFSE profiles of an unstimulated first control cell population and a CpG only stimulated second control cell population are included as reference standards. (B) CFSE profiles of B cells following 4 days of stimulation with anti-IgM/CpG in the presence of 16C4 anti-CD19 or R347 control antibody. Anti-IgM/CpG induced B cell proliferation is significantly reduced in the presence of 16C4 antibody.

FIG. 42. The 3649-3M Fc variant anti-CD19 antibody is a more effective inhibitor of anti-IgM/CpG induced B cell proliferation than the 3649-TM Fc variant antibody. CFSE profiles of B cells following 4 days of stimulation by anti-IgM/CpG in the presence of (A) R347 control, (B) 3649-TM anti-CD19, or (C) 3649-3M anti-CD19 antibody.

FIG. 43. 3649-3M antibody induced signaling through the CD19 and FcgammaRIIB receptors synergistically inhibits anti-IgM/CpG mediated B cell proliferation.

Figure 44:
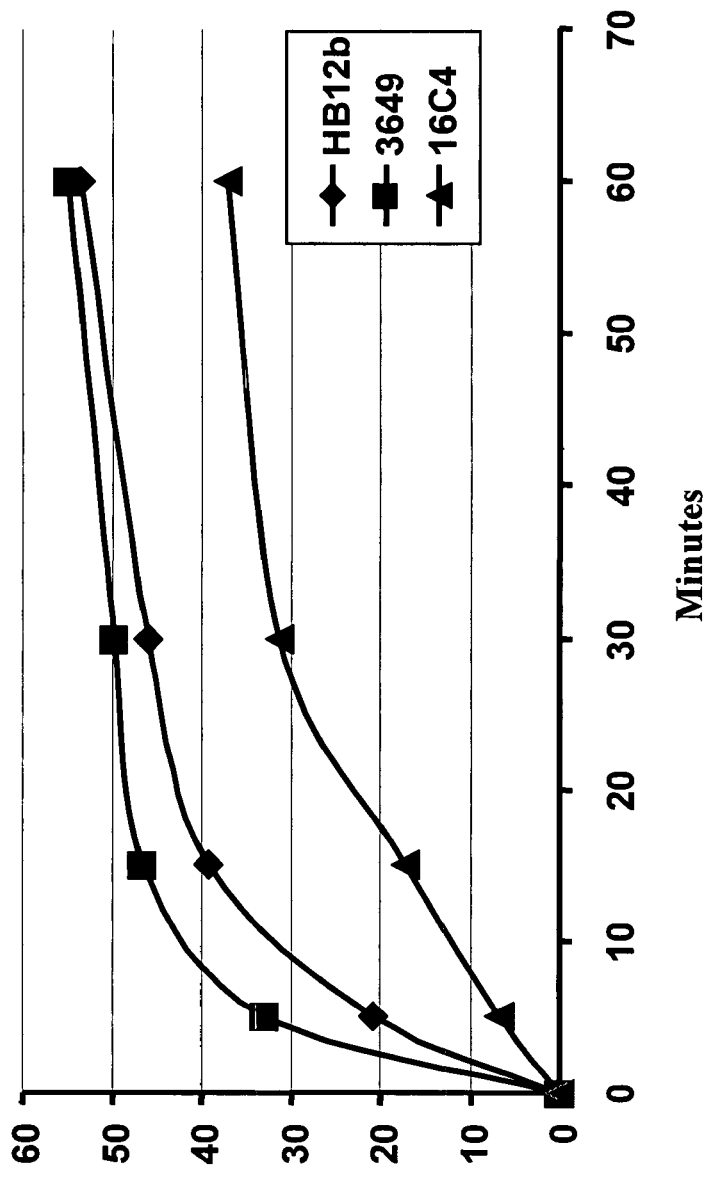

FIG. 44. Surface bound anti-CD19 antibody is efficiently internalized by Raji cells. 35% of surface bound 16C4 and 55% of surface bound HB12B and 3649 anti-CD19 antibody is internalized following 60 minutes incubation at 37° C.

Figure 45:
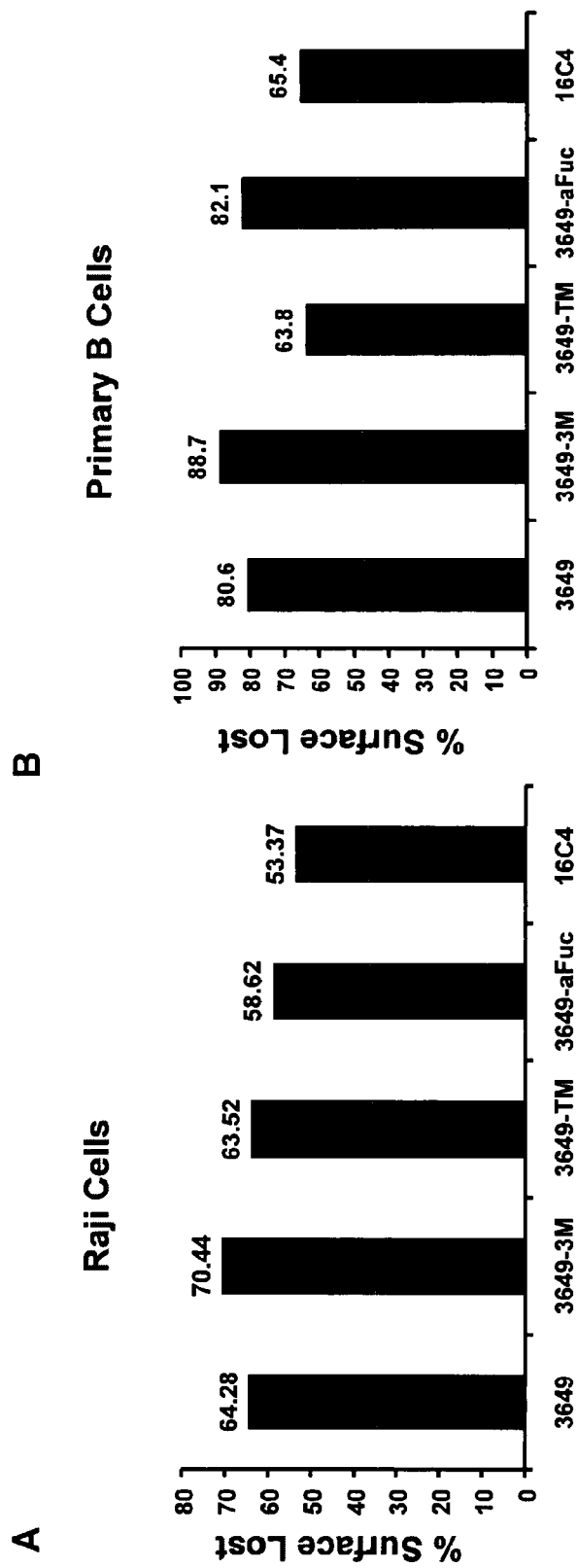

FIG. 45. Surface expression of CD19 is significantly reduced following 24 hours of anti-CD19 antibody treatment. Cell surface expression of CD19 is reduced by 55-90% in (A) Raji cells and (B) purified peripheral B cells following 24 hours incubation in the presence of 3649, 3649-TM, 3649-3M, 3649-aFuc, or 16C4 anti-CD19 antibody.

5. DETAILED DESCRIPTION

The present invention relates to human, humanized, or chimeric anti-CD19 antibodies that bind to the human CD19 antigen, as well as to compositions comprising those antibodies. In certain embodiments a human, humanized, or chimeric anti-CD19 antibody may mediate antigen-dependent-cell-mediated-cytotoxicity (ADCC). In other embodiments, the present invention is directed toward compositions comprising a human, humanized, or chimeric anti-CD19 antibody of the IgG1 and/or IgG3 human isotype, as well as to a human, humanized, or chimeric anti-CD19 antibody of the IgG2 and/or IgG4 human isotype, that may mediate human ADCC, CDC, and/or apoptosis. In further embodiments a human, humanized, or chimeric anti-CD19 antibody may inhibit anti-IgM/CpG stimulated B cell proliferation.

The present invention provides chimeric and humanized versions of the anti-CD19 mouse monoclonal antibodies HB12A and HB12B. In one embodiment, a humanized anti-CD19 antibody of the invention may bind to human CD19 with an affinity comparable to the binding affinity of HB12A or HB12B or comparable to the binding affinity of a chimeric HB12B antibody.

In one embodiment, a humanized anti-CD19 monoclonal antibody of the invention may comprise a VH and a VK, wherein the VH comprises the four framework regions, FW1, FW2, and FW3 of the human germline VH segment of V3-72 (described as DP29 in Tomlinson, I. M. et al., (1992) *J. Mol. Biol.*, 227, 776-798), and FW4 of the human germline JH4 segment (Mattila, P. S. et al., (1995) *Eur. J. Immunol.*, 25, 2578-2582); and the three VH CDR sequences of the HB12B antibody, CDR1 (SEQ ID NO:22), CDR2 (SEQ ID NO:24), and CDR3 (SEQ ID NO:26); and the VK comprises the four framework regions, FW1, FW2, FW3 of the human germline V kappa segment A10 (Straubinger, B. I et al., (1988) *Biol. Chem. Hoppe-Seyler,* 369, 601-607), and FW4 of the human germline immunoglobulin kappa J4 segment (Hieter, P. A. et al., (1982) *J. Biol. Chem.,* 257, 1516-1522); and the three VK CDR sequences of the HB12B antibody, CDR1 (SEQ ID NO:28), CDR2 (SEQ ID NO:30), and CDR3 (SEQ ID NO:32). In one embodiment, an anti-CD19 antibody of the invention may comprise a VH and a VK, wherein the VH comprises the four framework regions, FW1, FW2, and FW3 of the human germline VH segment of V3-72 (described as DP29 in Tomlinson, I. M. et al., (1992) *J. Mol. Biol.,* 227, 776-798), and FW4 of the human germline JH4 segment (Mattila, P. S. et al., (1995) *Eur. J. Immunol.,* 25, 2578-2582); and at least one CDR having the amino acid sequence of a CDR listed on Table 1 supra; and the VK comprises the four framework regions, FW1, FW2, FW3 of the human germline V kappa segment A10 (Straubinger, B. I et al., (1988) *Biol. Chem. Hoppe-Seyler,* 369, 601-607), and FW4 of the human germline immunoglobulin kappa J4 segment (Hieter, P. A. et al., (1982) *J. Biol. Chem.,* 257, 1516-1522); and at least one CDR having the amino acid sequence of a CDR listed on Table 1 supra. In one embodiment, this antibody may comprise one or more VK framework mutations selected from the group consisting of Y40F, K53H and Y91F. In one embodiment, the VK framework region may contain each of the point mutations Y40F, K53H and Y91F. In another embodiment, the VK framework region may contain only the Y40F and K53H point mutations. In another embodiment the VK framework may comprise only the Y40F point mutation.

5.1.1. CDR Regions of Anti-CD19 Antibodies

In certain embodiments, an anti-CD19 antibody of the invention may comprise a heavy chain variable region, VH, comprising at least one CDR having the amino acid sequence selected from the group consisting of SEQ ID NO:22, SEQ ID NO:24, and SEQ ID NO:26; and may further comprise at least one FW region having the amino acid sequence selected from the group consisting of SEQ ID NO:36, SEQ ID NO:38, SEQ ID NO:40, and SEQ ID NO:42. In another embodiment, an anti-CD19 antibody of the invention may comprise a heavy chain variable region, VH, comprising at least one CDR having the amino acid sequence selected from the group consisting of SEQ ID NO:22, SEQ ID NO:24, and SEQ ID NO:121 and may further comprise at least one FW region having the amino acid sequence selected from the group consisting of SEQ ID NO:36, SEQ ID NO:38, SEQ ID NO:40, and SEQ ID NO:42. In a further embodiment, an anti-CD19 antibody of the invention may comprise a heavy chain variable region, VH, comprising at least one CDR having the amino acid sequence selected from the group consisting of SEQ ID NO:22, SEQ ID NO:116, and SEQ ID NO:121 and may further comprise at least one FW region having the amino acid sequence selected from the group consisting of SEQ ID NO:36, SEQ ID NO:38, SEQ ID NO:40, and SEQ ID NO:42. In a further embodiment, an anti-CD19 antibody of the invention may comprise a heavy chain variable region, VH, comprising at least one CDR having the amino acid sequence selected from the group consisting of SEQ ID NO:208, SEQ ID NO:116, and SEQ ID NO:121 and may further comprise at least one FW region having the amino acid sequence selected from the group consisting of SEQ ID NO:36, SEQ ID NO:38, SEQ ID NO:40, and SEQ ID NO:42. In a further embodiment, an anti-CD19 antibody of the invention may comprise a heavy chain variable region, VH, comprising at least one CDR having the amino acid sequence selected from the group consisting of SEQ ID NO:208, SEQ TD NO:210, and SEQ ID NO:121 and may further comprise at least one FW region having the amino acid sequence selected from the group consisting of SEQ ID NO:36, SEQ ID NO:38, SEQ ID NO:40, and SEQ ID NO:42. In another embodiment, an anti-CD19 antibody of the invention may comprise a heavy chain variable region, VH, comprising at least one CDR having the amino acid sequence of a VH CDR1, VH CDR2, or VH CDR3 listed in Table 1 supra; and may further comprise at least one FW region having the amino acid sequence selected from the group consisting of SEQ ID NO:36, SEQ ID NO:38, SEQ ID NO:40, and SEQ ID NO:42.

In further embodiments, an anti-CD19 antibody of the invention may comprise a heavy chain variable region, VH, comprising at least one CDR sequence selected from the group consisting of SEQ ID NO:22, SEQ ID NO:24, and SEQ ID NO:26.

In additional embodiments, an anti-CD19 antibody may comprise a heavy chain variable region, VH, comprising at least one CDR sequence selected from the group consisting of SEQ ID NO:6, SEQ ID NO:8, and SEQ ID NO:10.

In one embodiment, an anti-CD19 antibody of the invention may comprise a heavy chain variable region, VH, comprising at least one CDR having the amino acid sequence selected from the group consisting of SEQ ID NO:22, SEQ ID NO:24 and SEQ ID NO:121. In another embodiment, an anti-CD19 antibody of the invention may comprise a heavy chain variable region, VH, comprising at least one CDR having the amino acid sequence selected from the group consisting of SEQ ID NO:22, SEQ ID NO:116 and SEQ ID NO:121. In another embodiment, an anti-CD19 antibody of the invention may comprise a heavy chain variable region, VH, comprising at least one CDR having the amino acid sequence selected from the group consisting of SEQ ID NO:208, SEQ ID NO:116 and SEQ ID NO:121. In another embodiment, an anti-CD19 antibody of the invention may comprise a heavy chain variable region, VH, comprising at least one CDR having the amino acid sequence selected from the group consisting of SEQ ID NO:208, SEQ ID NO:210 and SEQ ID NO:121.

In another embodiment, an anti-CD19 antibody of the invention may comprise a heavy chain variable region, VH, comprising at least one CDR having the amino acid sequence of a VH CDR1, VH CDR2, or VH CDR3 listed in Table 1 supra.

In another embodiment, an anti-CD19 antibody of the invention may comprise a heavy chain variable region, VH, comprising the amino acid sequences of a VH CDR1, VH CDR2, and VH CDR3 of any one of the antibodies listed in Table 1 supra. The anti-CD19 antibody of the invention may further comprise a light chain variable region, VL.

In another embodiment, an anti-CD19 antibody of the invention may comprise a light chain variable region, VL, comprising the amino acid sequences of a VL CDR1, VL CDR2, and VL CDR3 of any one of the antibodies listed in Table 1 supra. The anti-CD19 antibody of the invention may further comprise a heavy chain variable region, VH.

In another embodiment, an anti-CD19 antibody of the invention may comprise the amino acid sequences of a VH CDR1, VH CDR2, VH CDR3, VL CDR1, VL CDR2, and VL CDR3 of any one of the antibodies listed in Table 1 supra.

In certain embodiments, an anti-CD19 antibody may comprise the VH domain sequence of the humanized VH designated HB12B-(3-72/JH4) (SEQ ID NO:34).

In one embodiment, an anti-CD19 antibody described herein may comprise a heavy chain variable region, VH, having the amino acid sequence selected from the group consisting of SEQ ID NOs:103, 106, 191, and 192. In another embodiment, an anti-CD19 antibody described herein may comprise a heavy chain variable region, VH, having the amino acid sequence of a VH Domain listed in Table 1. supra.

In certain embodiments, an anti-CD19 antibody of the invention may comprise a light chain variable region, VK, comprising at least one CDR having an amino acid sequence selected from the group consisting of SEQ ID NO: 28, SEQ ID NO: 30, and SEQ ID NO:32 and may further comprise at least one FW region having an amino acid sequence selected from the group consisting of SEQ ID NO:54, SEQ ID NO:56, SEQ ID NO:72, SEQ ID NO:82, SEQ ID NO:64, SEQ ID NO:58, SEQ ID NO:66, and SEQ ID NO:60.

In one embodiment, an anti-CD19 antibody of the invention may comprise a light chain variable region, VK, comprising at least one CDR having an amino acid sequence selected from the group consisting of SEQ ID NO: 28, SEQ ID NO: 125, and SEQ ID NO:32 and may further comprise at least one FW region having an amino acid sequence selected from the group consisting of SEQ ID NO:54, SEQ ID NO:56, SEQ ID NO:72, SEQ ID NO:82, SEQ ID NO:64, SEQ ID NO:58, SEQ ID NO:66, and SEQ ID NO:60. In a further embodiment, an anti-CD19 antibody of the invention may comprise a light chain variable region, VK, comprising at least one CDR having an amino acid sequence selected from the group consisting of SEQ ID NO:211, SEQ ID NO:218, and SEQ ID NO:222 and may further comprise at least one FW region having an amino acid sequence selected from the group consisting of SEQ ID NO:54, SEQ ID NO:56, SEQ ID NO:72, SEQ ID NO:82, SEQ ID NO:64, SEQ ID NO:58, SEQ ID NO:66, and SEQ ID NO:60. In a further embodiment, an anti-CD19 antibody of the invention may comprise a light chain variable region, VK, comprising at least one CDR having an amino acid sequence selected from the group consisting of SEQ ID NO:28, SEQ ID NO:220, and SEQ ID NO:229 and may further comprise at least one FW region having an amino acid sequence selected from the group consisting of SEQ ID NO:54, SEQ ID NO:56, SEQ ID NO:72, SEQ ID NO:82, SEQ ID NO:64, SEQ ID NO:58, SEQ ID NO:66, and SEQ ID NO:60. In a further embodiment, an anti-CD19 antibody of the invention may comprise a light chain variable region, VK, comprising at least one CDR having an amino acid sequence selected from the group consisting of SEQ ID NO:215, SEQ ID NO:221, and SEQ ID NO:222 and may further comprise at least one FW region having an amino acid sequence selected from the group consisting of SEQ ID NO:54, SEQ ID NO:56, SEQ ID NO:72, SEQ ID NO:82, SEQ ID NO:64, SEQ ID NO:58, SEQ ID NO:66, and SEQ ID NO:60. In another embodiment, an anti-CD19 antibody of the invention may comprise a light chain variable region, VK, comprising at least one CDR having an amino acid sequence of a VK CDR1, VK CDR2, or VK CDR3 listed in Table 1 supra; and may further comprise at least one FW region having an amino acid sequence selected from the group consisting of SEQ ID NO:54, SEQ ID NO:56, SEQ ID NO:72, SEQ ID NO:82, SEQ ID NO:64, SEQ ID NO:58, SEQ ID NO:66, and SEQ ID NO:60.

In further embodiments, an anti-CD19 antibody of the invention may comprise a light chain variable region, VK, comprising at least one CDR sequence selected from the group consisting of SEQ ID NO:28, 30, and 32.

In further embodiments, an anti-CD19 antibody of the invention may comprise a light chain variable region, VK, comprising at least one CDR sequence selected from the group consisting of SEQ ID NO:12, 14, and 16.

In one embodiment, an anti-CD19 antibody of the invention may comprise a light chain variable region, VK, comprising at least one CDR having an amino acid sequence selected from the group consisting of SEQ ID NO: 28, SEQ ID NO: 125, and SEQ ID NO:32. In one embodiment, an anti-CD19 antibody of the invention may comprise a light chain variable region, VK, comprising at least one CDR having an amino acid sequence selected from the group consisting of SEQ ID NO: 211, SEQ ID NO: 218, and SEQ ID NO:222. In one embodiment, an anti-CD19 antibody of the invention may comprise a light chain variable region, VK, comprising at least one CDR having an amino acid sequence selected from the group consisting of SEQ ID NO: 28, SEQ ID NO: 220, and SEQ ID NO:229. In one embodiment, an anti-CD19 antibody of the invention may comprise a light chain variable region, VK, comprising at least one CDR having an amino acid sequence selected from the group consisting of SEQ ID NO: 215, SEQ ID NO: 221, and SEQ ID NO:222. In another embodiment of the invention may comprise a light chain variable region, VK, comprising at least one CDR having an amino acid sequence of a VK CDR1, VK CDR2, or VK CDR3 listed in Table 1 supra.

In certain embodiments, an anti-CD19 antibody may comprise the humanized VK domain sequence selected from a group consisting of HB12B-(A10-Jk4) (SEQ ID NO:52), HB12B-364987 (SEQ ID NO:62), HB12B-3649 (SEQ ID NO:68), HB12B-36 (SEQ ID NO:70), 7E12 VK (SEQ ID NO:110), 14H5 VK (SEQ ID NO:111), 16C9 VK (113), 15D1 VK (SEQ ID NO:112), 3C3 VK (SEQ ID NO:193), 6C11 VK (SEQ ID NO:204), and 9G7 VK (SEQ ID NO:205).

The present invention encompasses antibodies that bind to human CD19, comprising derivatives of the VH domains, VH CDR1s, VH CDR2s, VH CDR3s, VK domains, VK CDR1s, VK CDR2s, or VK CDR3s described herein that may bind to human CD19 (see for example the variants listed in Table 1. supra). Standard techniques known to those of skill in the art can be used to introduce mutations (e.g., additions, deletions, and/or substitutions) in the nucleotide sequence encoding an antibody, including, for example, site-directed mutagenesis and PCR-mediated mutagenesis that are routinely used to generate amino acid substitutions. In one embodiment, the VH and/or VK CDRs derivatives may include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, less than 2 amino acid substitutions, or 1 amino acid substitution relative to the original VH and/or VK CDRs of the HB12A or HB12B anti-CD19 antibody. In another embodiment, the VH and/or VK CDRs derivatives may have conservative amino acid substitutions (e.g. supra) made at one or more predicted non-essential amino acid residues (i.e., amino acid residues which are not critical for the antibody to specifically bind to human CD19). Mutations can also be introduced randomly along all or part of the VH and/or VK CDR coding sequences, such as by saturation mutagenesis, and the resultant mutants can be screened for biological activity to identify mutants that retain activity. Following mutagenesis, the encoded antibody can be expressed and the activity of the antibody can be determined. In one embodiment, antibodies of the invention disclosed herein may exclude the VH CDR1 and VH CDR2 of the hA19 antibody described in US20050070693A1.

In one embodiment, a human or humanized anti-CD19 antibody described herein may comprise a variant of any one of the VH CDRs listed in Table 1 supra wherein said variant VH CDR comprises an amino acid substitution. In a specific embodiment, an anti-CD19 antibody of the invention comprises a variant of a VH CDR listed in Table 1 wherein said variant VH CDR comprises one or more of the following natural or substituted amino acid residues: a threonine (T) at position 32 of VH CDR1, a tyrosine (Y) at position 60 of VH CDR2, an aspartic acid (D) at position 60 of VH CDR2, a leucine (L) at position 60 of VH CDR2, an alanine (A) at position 61 of VH CDR2, a valine (V) at position 61 of VH CDR2, a tyrosine (Y) at position 100B of VH CDR3, an arginine (R) at position 100B of VH CDR3, and an asparagine (N) at position 100B of VH CDR3, numbered according to Kabat.

In one embodiment, a human or humanized anti-CD19 antibody described herein may comprise a variant of a VH CDR listed in Table 1. wherein said variant VH CDR comprises one or more of the following natural or substituted amino acid residues: a glutamic acid (E) at position 33 of VH CDR1, a leucine (L) at position 33 of VHCDR1, phenylalanine (F) at position 35 of VH CDR1, a tyrosine (Y) at position 35 of VH CDR1, an aspartic acid (D) at position 35 of VH CDR1, a leucine (L) at position 35 of VH CDR1, a serine (S) at position 57 of VH CDR2, a proline (P) at position 57 of VH CDR2, an asparagine (N) at position 57 of VH CDR2, a histidine (H) at position 100B of VH CDR3, a phenylalanine (F) at position 100B of VH CDR3, and a proline (P) at position 99 of VH CDR3, numbered according to Kabat.

In one embodiment, a human or humanized anti-CD19 antibody described herein may comprise a variant of a VH CDR listed in Table 1. wherein said variant VH CDR comprises one or more of the following natural or substituted amino acid residues: a valine (V) at position 32 of VH CDR1, and a leucine (L) at position 52A of VHCDR2, numbered according to Kabat.

In another embodiment, a human or humanized anti-CD19 antibody of the invention may comprise a variant of a VK CDR listed in Table 1 wherein said VK CDR comprises one or more of the following natural or substituted amino acid residues: a histidine (H) at position 27D of VK CDR1, an isoleucine (I) at position 33 of VK CDR1, a glutamic acid (E) at position 50 of VK CDR2, a threonine (T) at position 91 in VK CDR3, and an isoleucine (I) at position 96 of VK CDR3, numbered according to Kabat.

In another embodiment, a human or humanized anti-CD19 antibody of the invention may comprise a variant of a VK CDR listed in Table 1 wherein said VK CDR comprises one or more of the following natural or substituted amino acid residues: a isoleucine (I) at position 27C of VK CDR1, a leucine (L) at position 30 of VK CDR1, an arginine (R) at position 33 of VK CDR1, a threonine (T) at position 33 of VK CDR1, a tyrosine (Y) at position 50 of VK CDR2, a threonine (T) at position 54 of VK CDR2, a proline (P) at position 54 of VK CDR2, a tyrosine (Y) at position 55 of VK CDR2, and an asparagine (N) at position 96 of VK CDR3, numbered according to Kabat.

In another embodiment, a human or humanized anti-CD19 antibody of the invention may comprise a variant of a VK CDR listed in Table 1 wherein said VK CDR comprises one or more of the following natural or substituted amino acid residues: an arginine (R) at position 54 of VK CDR2, a threonine (T) at position 54 of VK CDR2, an alanine (A) at position 54 of VK CDR2, and an alanine (A) at position 89 of VK CDR3, numbered according to Kabat.

The present invention further encompasses antibodies that bind to human CD19, said antibodies or antibody fragments comprising one or more CDRs wherein said CDRs comprise an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of one or more CDRs of the HB12A or HB12B anti-CD19 antibody. The percent identity of two amino acid sequences can be determined by any method known to one skilled in the art, including, but not limited to, BLAST protein searches.

5.1.2. Framework Regions of Anti-CD19 Antibodies

In one embodiment, the VH of a humanized anti-CD19 monoclonal antibody of the invention may comprise a framework region that has an amino acid sequence identity with the corresponding framework regions (i.e., FW1 of antibody X as compared to FW1 of antibody Y) of HB12B-(3-72/JH4) VH (SEQ ID NO:34) within the range of from about 64% to about 100%. In certain aspects of this embodiment, the human or humanized VH framework regions of antibodies described herein may have an amino acid sequence identity with the HB12B-(3-72/JH4) VH (SEQ ID NO:34) that is at least 64%, at least 70%, at least 75%, at least 80%, at least 85%, at least 90%, or at least 95%.

In particular embodiments, the human or humanized VH framework regions of anti-CD19 antibodies described herein may have an amino acid sequence identity with the corresponding framework regions of HB12B-(3-72/JH4) VH (SEQ ID NO:34) of at least 56 out of 87 amino acids (56/87) In particular embodiments, the VH framework amino acid sequence identity may be at least 56/87, 57/87, 58/87, 59/87, 60/87, 61/87, 62/87, 63/87, 64/87, 65/87, 66/87, 67/87, 68/87, 69/87, 70/87, 71,87, 72/87, 73/87 74/87, 75/87, 76/87, 77.87, 78/87, 79/87, 80/87, 81/87, 82/87, 83/87, 84/87, 85/87, 86/87, or 87/87 amino acids. VH sequences of anti-CD19 antibodies described herein may have high sequence identity to the Vernier amino acid residues of HB12B-(3-72/JH4), for example a Vernier sequence identity of at least 10 out of 16 (10/16), at least 11/16, at least 12/16, at least 13/16, at least 14/16, or at least 15/16 Vernier residues. In another embodiment, the mismatch of a Vernier amino acid residue may be a conservative amino acid substitution. A mismatch that is a conservative amino acid substitution is one in which the mismatched amino acid has physical and chemical properties similar to the Vernier amino acid, e.g., the mismatched residue has similar characteristics of polarity (polar or nonpolar), acidity (acidic or basic), side chain structure (e.g., branched or straight, or comprising a phenyl ring, a hydroxyl moiety, or a sulfur moiety) to the Vernier residue.

In other embodiments, the mismatch of a Vernier amino acid residue may be a non-conservative amino acid substitution. A mismatch that is a non-conservative amino acid substitution is one in which the mismatched amino acid does not have physical and chemical properties similar to the Vernier amino acid, e.g., the mismatched residue has a different polarity, acidity, or side chain structure (e.g., branched or straight, or comprising a phenyl ring, a hydroxyl moiety, or a sulfur moiety) as compared to the Vernier residue to be replaced.

In other embodiments, a human or humanized anti-CD19 antibody of the invention may comprise VH framework regions wherein said VH framework regions may comprise one or more of the following residues: a leucine (L) at position 20 of framework region 1, a phenylalanine (F) at position 27 of framework region 1, a threonine (T) at position 28 of framework region 1, an arginine (R) at position 38 in framework region 2, a valine (V) at position 48 of framework region 2, a phenylalanine (F) at position 67 of framework region 3, an arginine (R) at position 71 of framework region 3, a leucine (L) at position 80 of framework region 3, and a tyrosine (Y) at position 91 of framework region 3, numbered according to Kabat.

Kabat numbering is based on the seminal work of Kabat et al. (1991) *Sequences of Proteins of Immunological Interest*, Publication No. 91-3242, published as a three volume set by the National Institutes of Health, National Technical Information Service (hereinafter "Kabat"). Kabat provides multiple sequence alignments of immunoglobulin chains from numerous species antibody isotypes. The aligned sequences are numbered according to a single numbering system, the Kabat numbering system. The Kabat sequences have been updated since the 1991 publication and are available as an electronic sequence database (latest downloadable version 1997). Any immunoglobulin sequence can be numbered according to Kabat by performing an alignment with the Kabat reference sequence. Accordingly, the Kabat numbering system provides a uniform system for numbering immunoglobulin chains. Unless indicated otherwise, all immunoglobulin amino acid sequences described herein are numbered according to the Kabat numbering system. Similarly, all single amino acid positions referred to herein are numbered according to the Kabat numbering system.

In further particular embodiments, the human or humanized VH framework regions of anti-CD19 antibodies described herein may have framework regions selected for identity or conservative mismatches at one or more of the following Vernier, Interface or Canonical residue positions: 20, 22, 24, 26, 27, 28, 29, 30, 36, 37, 39, 45, 47, 48, 49, 67, 69, 71, 73, 78, 80, 90, 91, 92, 93, 94, and 103. One or more of the mismatched Vernier, Interface and Canonical residues may be changed, e.g., by mutagenesis, to match the corresponding amino acid residue of the HB12A or HB12B VH framework region.

In one embodiment of the invention, the human or humanized VK framework regions of anti-CD19 antibodies described herein may have an amino acid sequence identity with the framework regions of HB12B-(A10-Jk4) VK (SEQ ID NO:52) within the range of from about 65% to about 100%. In certain aspects of this embodiment, the human or humanized VK framework regions of antibodies described herein may have an amino acid sequence identity with the HB12B-(A10-Jk4) antibody VK that is at least 65%, at least 70%, at least 75%, at least 80%, at least 85%, at least 90%, or at least 95%.

In particular embodiments, the human or humanized VK framework regions of antibodies described herein may have an amino acid sequence identity with the corresponding framework regions (i.e., FW1 of antibody X as compared to FW1 of antibody Y) of HB12B-(A10-Jk4) VH (SEQ ID NO:52) of at least 52 out of 80 amino acids (52/80) In particular embodiments, the VH framework amino acid sequence identity may be at least 52/80, 53/80, 54/80, 55/80, 56/80, 57/80, 58/80, 59/80, 60/80, 61/80, 62/80, 63/80, 64/80, 65/80, 66/80, 67/80, 68/80, 69/80, 70/80, 71, 80, 72/80, 73/80 74/80, 75/80, 76/80, 77/80, 78/80, 79/80, or 80/80, amino acids. VK sequences of anti-CD19 antibodies described herein may have high sequence identity to the Vernier amino acid residues of HB12B (see FIG. 1), for example a Vernier sequence identity of at least 9 out of 14 (9/14), at least 10/14, at least 11/14, at least 12/14, at least 13/14 Vernier residues. In another embodiment, the mismatch of a Vernier amino acid residue may be a conservative amino acid substitution. A mismatch that is a conservative amino acid substitution is one in which the mismatched amino acid has physical and chemical properties similar to the Vernier amino acid, e.g., the mismatched residue has similar characteristics of polarity (polar or nonpolar), acidity (acidic or basic), side chain structure (e.g., branched or straight, or comprising a phenyl ring, a hydroxyl moiety, or a sulfur moiety) to the Vernier residue.

In other embodiments, the mismatch of a Vernier amino acid residue may be a non-conservative amino acid substitution. A mismatch that is a non-conservative amino acid substitution is one in which the mismatched amino acid does not have physical and chemical properties similar to the Vernier amino acid, e.g., the mismatched residue has a different polarity, acidity, or side chain structure (e.g., branched or straight, or comprising a phenyl ring, a hydroxyl moiety, or a sulfur moiety) as compared to the Vernier residue to be replaced.

In other embodiments, the human or humanized VK framework regions described herein may comprise one or more of the following residues: a phenylalanine (F) at position 36 of framework region 2, a histidine (H) at position 49 of framework region 2, and a phenylalanine (F) at position 87 of framework region 3, numbered according to Kabat.

In further particular embodiments, the human or humanized VK framework regions of antibodies described herein may have framework regions selected for identity or conservative mismatches at one or more of the following Vernier, Interface or Canonical residue positions: 2, 3, 4, 23, 35, 36, 38, 44, 56, 47, 48, 49, 64, 66, 68, 69, 71, 87, 88, and 98. One or more of the mismatched Vernier, Interface and Canonical residues may be changed, e.g., by mutagenesis, to match the corresponding amino acid residue of the HB12A or HB12B framework region.

In particular embodiments, a heavy chain comprising a humanized VH of the invention may be expressed with a light chain comprising a humanized VK of the invention to produce a humanized anti-CD19 antibody. In a specific embodiment, a humanized anti-CD19 antibody of the invention may comprise a VH sequence selected from the group consisting of the sequences designated HB12B-(3-72/JH4) (SEQ ID NO:34), 7E12 VH (SEQ ID NO:102), 14H5 VH (SEQ ID NO:103), 15D1 VH (SEQ ID NO:104), 15D7 VH (SEQ ID NO:105), 16C4 VH (SEQ ID NO:106), 14H5-YG (SEQ ID NO:107), 14H5-DG (SEQ ID NO:108), 14H5-LG (SEQ ID NO:109), 1A7 VH (SEQ ID NO:191), 3C3 VH (SEQ ID NO:191), 6C11 VH (SEQ ID NO:191), 9G7 (SEQ ID NO:191), 3B4 VH (SEQ ID NO:236), and 3F11 VH (SEQ ID NO:192); and may further comprise a VK sequence selected from the group consisting of the sequences designated HB12B-(A10/JK4) (SEQ ID NO:52); HB12B-364987 (or 364987) (SEQ ID NO:62); HB12B-3649 (or 3649) (SEQ ID NO:68); HB12B-36 (or 36) (SEQ ID NO:70), 7E12 VK (SEQ ID NO:110), 14H5 (SEQ ID NO:111), 15D1 (SEQ ID NO:112), 16C9 (SEQ ID NO:113), 3C3 VK (SEQ ID NO:193), 3E5 VK (SEQ ID NO:194), 3D4 VK (SEQ ID NO:195), 3F1 VK (SEQ ID NO:196), 5B5 VK (SEQ ID NO:197), 6F7 VK (SEQ ID NO:198), 1C11 VK (SEQ ID NO:199), 2B11 VK (SEQ ID NO:200), 2D10 VK (SEQ ID NO:201), 5C11 VK (SEQ ID NO:202), 5D4 VK (SEQ ID NO:203), 6C11 VK (SEQ ID NO:204), 9G7 VK (SEQ ID NO:205), 1H4 VK (SEQ ID NO:206), and 5C4 VK (SEQ ID NO:207). In a particular embodiment, a humanized anti-CD19 antibody comprises the VH sequence HB12B-(3-72/JH4) (SEQ ID NO:34) and the VK sequence HB12B-364987 (SEQ ID NO:62). In a particular embodiment, a humanized anti-CD19 antibody comprises the VH sequence HB12B-(3-72/JH4) (SEQ ID NO:34) and the VK sequence HB12B-3649 (SEQ ID NO:68). In yet another embodiment, a humanized anti-CD19 antibody comprises the VH sequence HB12B-(3-72/JH4) (SEQ ID NO:34) and the VK sequence HB12B-36 (SEQ ID NO:70).

In a specific embodiment, an anti-CD19 antibody of the invention comprises the VH sequence 7E12 VH (SEQ ID NO:102) and the VK sequence 7E12 VK (SEQ ID NO:110). In a specific embodiment, an anti-CD19 antibody of the invention comprises the VH sequence 14H5 VH (SEQ ID NO:103) and the VK sequence 14H5 VK (SEQ ID NO:111). In a specific embodiment, an anti-CD19 antibody of the invention comprises the VH sequence 14H5-YG VH (SEQ ID NO:107) and the VK sequence 14H5 VK (SEQ ID NO:111). In a specific embodiment, an anti-CD19 antibody of the invention comprises the VH sequence 14H5-DG VH (SEQ ID NO:108) and the VK sequence 14H5 VK (SEQ ID NO:111). In a specific embodiment, an anti-CD19 antibody of the invention comprises the VH sequence 14H5-LG VH (SEQ ID NO:109) and the VK sequence 14H5 VK (SEQ ID NO:111). In a specific embodiment, an anti-CD19 antibody of the invention comprises the VH sequence 14H5 VH (SEQ ID NO:103) and the VK sequence 16C9 VK (SEQ ID NO:113). In a specific embodiment, an anti-CD19 antibody of the invention comprises the VH sequence 15D1 VH (SEQ ID NO:104) and the VK sequence 15D1 VK (SEQ ID NO:112). In a specific embodiment, an anti-CD19 antibody of the invention comprises the VH sequence 15D7 VH (SEQ ID NO:105) and the VK sequence 14H5 VK (SEQ ID NO:111). In a specific embodiment, an anti-CD19 antibody of the invention comprises the VH sequence 16C4 VH (SEQ ID NO:106) and the VK sequence 14H5 VK (SEQ ID NO:111). In a specific embodiment, an anti-CD19 antibody of the invention comprises the VH sequence 1A7 VH (SEQ ID NO:191) and the VK sequence 14H5 VK (SEQ ID NO:111). In a specific embodiment, an anti-CD19 antibody of the invention comprises the VH sequence 1A7 VH (SEQ ID NO:191) and the VK sequence 3C3 VK (SEQ ID NO:193). In a specific embodiment, an anti-CD19 antibody of the invention comprises the VH sequence 1A7 VH (SEQ ID NO:191) and the VK sequence 3E5 VK (SEQ ID NO:194). In a specific embodiment, an anti-CD19 antibody of the invention comprises the VH sequence 1 A7 VH (SEQ ID NO:191) and the VK sequence 3D4 VK (SEQ ID NO:195). In a specific embodiment, an anti-CD19 antibody of the invention comprises the VH sequence 1A7 VH (SEQ ID NO:191) and the VK sequence 5B5 VK (SEQ ID NO:197). In a specific embodiment, an anti-CD19 antibody of the invention comprises the VH sequence 1A7 VH (SEQ ID NO:191) and the VK sequence 6F7 VK (SEQ ID NO:198). In a specific embodiment, an anti-CD19 antibody of the invention comprises the VH sequence 1 A7 VH (SEQ ID NO:191) and the VK sequence 2D10 VK (SEQ ID NO:201). In a specific embodiment, an anti-CD19 antibody of the invention comprises the VH sequence 1A7 VH (SEQ ID NO:191) and the VK sequence 5C11 VK (SEQ ID NO:202). In a specific embodiment, an anti-CD19 antibody of the invention comprises the VH sequence 1A7 VH (SEQ ID NO:191) and the VK sequence 9G7 VK (SEQ ID NO:205). In a specific embodiment, an anti-CD19 antibody of the invention comprises the VH sequence 1A7 VH (SEQ ID NO:191) and the VK sequence 1H4 VK (SEQ ID NO:206). In a specific embodiment, an anti-CD19 antibody of the invention comprises the VH sequence 1A7 VH (SEQ ID NO:191) and the VK sequence 5C4 VK (SEQ ID NO:207). In a specific embodiment, an anti-CD19 antibody of the invention comprises the VH sequence 3B4 VH (SEQ ID NO:236) and the VK sequence 14H5 VK (SEQ ID NO:111). In a specific embodiment, an anti-CD19 antibody of the invention comprises the VH sequence 3F11 VH (SEQ ID NO:192) and the VK sequence 3F11 VK (SEQ ID NO:196). In a specific embodiment, an anti-CD19 antibody of the invention comprises the VH sequence 16C4 VH (SEQ ID NO:106) and the VK sequence 1C11 VK (SEQ ID NO:199). In a specific embodiment, an anti-CD19 antibody of the invention comprises the VH sequence 16C4 VH (SEQ ID NO:106) and the VK sequence 2B11 VK (SEQ ID NO:200). In a specific embodiment, an anti-CD19 antibody of the invention comprises the VH sequence 16C4 VH (SEQ ID NO:106) and the VK sequence 5D4 VK (SEQ ID NO:203). In a specific embodiment, an anti-CD19 antibody of the invention comprises the VH sequence 16C4 VH (SEQ ID NO:106) and the VK sequence 6F7 VK (SEQ ID NO:198). In a specific embodiment, an anti-CD19 antibody of the invention comprises the VH sequence 3F11 VH (SEQ ID NO:192) and the VK sequence 6C11 VK (SEQ ID NO:204). In a specific embodiment, an anti-CD19 antibody of the invention comprises any combination of a VH and a VL listed in Table 1.

In certain embodiments, a light chain comprising a humanized VK of the invention may be expressed with a heavy chain comprising a humanized VH of the invention to produce a humanized anti-CD19 antibody. In one embodiment, a humanized anti-CD19 antibody described herein comprises a VK sequence selected from the group consisting of the sequences designated HB12B-(A10/JK4) (SEQ ID NO:52); HB12B-364987 (or 364987) (SEQ ID NO:62); HB12B-3649 (or 3649) (SEQ ID NO:68); HB12B-36 (or 36) (SEQ ID NO:70), 7E12 VK (SEQ ID NO:110), 14H5 (SEQ ID NO:111), 15D1 (SEQ ID NO:112), 16C9 (SEQ ID NO:113), 3C3 (SEQ ID NO:193), 3E5 (SEQ ID NO:194), 3D4 (SEQ ID NO:195), 3F11 (SEQ ID NO:196), 5B5 (SEQ ID NO:197), 6F7 (SEQ ID NO:198), 1C11 (SEQ ID NO:199), 2B11 (SEQ ID NO:200), 2D10 (SEQ ID NO:201), 5C11 (SEQ ID NO:202), 5D4 (SEQ ID NO:203), 6C11 (SEQ ID NO:204), 9G7 (SEQ ID NO:205), 1H4 (SEQ ID NO:206), AND 5C4 (SEQ ID NO:207). The aforementioned VK sequence may be paired with a VH sequence comprising an amino acid sequence in its framework region selected from the group consisting of SEQ ID NO:36, 38, 40, and 42.

In certain embodiments, a heavy chain comprising a humanized VH of the invention may be expressed with a light chain comprising a humanized VK of the invention to produce a humanized anti-CD19 antibody. In one embodiment, a humanized anti-CD19 antibody described herein comprises a VH sequence selected from the group consisting of the sequences designated HB12B-(3-72/JH4) (SEQ ID NO:34), 7E12 VH (SEQ ID NO:102), 14H5 VH (SEQ ID NO:103), 15D1 VH (SEQ ID NO:104), 15D7 VH (SEQ ID NO:105), 16C4 VH (SEQ ID NO:106), 14H5-YG (SEQ ID NO:107), 14H5-DG (SEQ ID NO:108), 14H5-LG (SEQ ID NO:109), 1A7 (SEQ ID NO:191), 3C3 VH (SEQ ID NO:191), 6C11 VH (SEQ ID NO:191), 9G7 (SEQ ID NO:191), 3B4 VH (SEQ ID NO:236), and 3F11 VH (SEQ ID NO:192). The aforementioned VH sequence may be paired with a VK sequence comprising an amino acid sequence in its framework region selected from the group consisting of SEQ ID NO:54, SEQ ID NO:56, SEQ ID NO:72, SEQ ID NO:82, SEQ ID NO:64, SEQ ID NO:58, SEQ ID NO:66, and SEQ ID NO:60.

In certain embodiments, a humanized VH or VK derived from the parental HB12A or HB12B hybridoma may be expressed as a chimeric immunoglobulin light chain or a chimeric immunoglobulin heavy chain to produce a chimeric anti-CD19 antibody. In a particular embodiment, a humanized VH may be expressed as a chimeric antibody comprising the HB12A VK (SEQ ID NO:4) or HB12B VK (SEQ ID NO:20). In another particular embodiment, a humanized VK may be expressed as a chimeric antibody comprising the HB12A VH (SEQ ID NO:2) or HB12B VH (SEQ ID NO:18). In another embodiment, a chimeric anti-CD19 antibody may comprise the VK sequence of HB12A VK (SEQ ID NO:4) or HB12B VK (SEQ ID NO:20) and may further comprise the VH sequence of HB12A VH (SEQ ID NO:2) or HB12B VH (SEQ ID NO:18).

In a particular embodiment, a humanized VH of the invention may further comprise a leader sequence of MGDNDIHFAFLSTGVHS (SEQ ID NO:83).

In another embodiment, a humanized VK of the invention may further comprise a leader sequence MDMRVPAQLLGLLLLWLPGAKC (SEQ ID NO:84) selected from the leader peptide of the human VKI-L12 gene.

Anti-CD19 antibodies described herein may have a high binding affinity for the human CD19 (hCD19) antigen. For example, an antibody described herein may have an association rate constant or $k_{on}$ rate (antibody (Ab)+antigen (Ag)$^{kon}$→Ab–Ag) of at least $2\times10^5$ $M^{-1}s^{-1}$, at least $5\times10^5$ $M^{-1}s^{-1}$, at least $10^6$ $M^{-1}s^{-1}$, at least $5\times10^6$ $M^{-1}s^{-1}$, at least $10^7$ $M^{-1}s^{-1}$, at least $5\times10^7$ $M^{-1}s^{-1}$, or at least $10^8$ $M^{-1}s^{-1}$.

In another embodiment, an anti-CD19 antibody of the invention may have a $k_{off}$ rate ((Ab–Ag)$^{koff}$→antibody (Ab)+antigen (Ag)) of less than $5\times10^{-1}$ $s^{-1}$, less than $10^{-1}$ $s^{-1}$, less than $5\times10^{-2}$ $s^{-1}$, less than $10^{-2}$ $s^{-1}$, less than $5\times10^{-3}$ $s^{-1}$, less than $10^{-3}$ $s^{-1}$, less than $5\times10^{-4}$ $s^{-1}$, or less than $10^{-4}$ $s^{-1}$. In a another embodiment, an antibody of the invention has a $k_{off}$ of less than $5\times10^{-5}$ $s^{-1}$, less than $10^{-5}$ $s^{-1}$, less than $5\times10^{-6}$ $s^{-1}$, less than $10^{-6}$ $s^{-1}$, less than $5\times10^{-7}$ $s^{-1}$, less than $10^{-7}$ $s^{-1}$, less than $5\times10^{-8}$ $s^{-1}$, less than $10^{-8}$ $s^{-1}$, less than $5\times10^{-9}$ $s^{-1}$, less than $10^{-9}$ $s^{-1}$, or less than $10^{-10}$ $s^{-1}$.

In another embodiment, an anti-CD19 antibody of the invention may have an affinity constant or $K_a$ ($k_{on}/k_{off}$) of at least $10^2$ $M^{-1}$, at least $5\times10^2$ $M^{-1}$, at least $10^3$ $M^{-1}$, at least $5 \times 10^3$ M$^{-1}$, at least $10^4$ M$^{-1}$, at least $5 \times 10^4$ M$^{-1}$, at least $10^5$ M$^{-1}$, at least $5 \times 10^5$ M$^{-1}$, at least $10^6$ M$^{-1}$, at least $5 \times 10^6$ M$^{-1}$, at least $10^7$ M$^{-1}$, at least $5 \times 10^7$ M$^{-1}$, at least $10^8$ M$^{-1}$, at least $5 \times 10^8$ M$^{-1}$, at least $10^9$ M$^{-1}$, at least $5 \times 10^9$ M$^{-1}$, at least $10^{10}$ M$^{-1}$, at least $5 \times 10^{10}$ M$^{-1}$, at least $10^{11}$ M$^{-1}$ at least $5 \times 10^{11}$ M$^{-1}$, at least $10^{12}$ M$^{-1}$, at least $5 \times 10^{12}$ M$^{-1}$, at least $10^{13}$ M$^{-1}$ at least $5 \times 10^{13}$ M$^{-1}$, at least $10^{14}$ M$^{-1}$, at least $5 \times 10^{14}$ M$^{-1}$, at least $10^{15}$ M$^{-1}$, or at least $5 \times 10^{15}$ M$^{-1}$. In yet another embodiment, an anti-CD19 antibody of the invention may have a dissociation constant or $K_d$ ($k_{off}/k_{on}$) of less than $5 \times 10^{-2}$ M, less than $10^{-2}$ M, less than $5 \times 10^{-3}$ M, less than $10^{-3}$ M, less than $5 \times 10^{-4}$ M, less than $10^{-4}$ M, less than $5 \times 10^{-5}$ M, less than $10^{-5}$ M, less than $5 \times 10^{-6}$ M, less than $10^{-6}$ M, less than $5 \times 10^{-7}$ M, less than $10^{-7}$ M, less than $5 \times 10^{-8}$ M, less than $10^{-8}$ M, less than $5 \times 10^{-9}$ M, less than $10^{-9}$ M, less than $5 \times 10^{-10}$ M, less than $10^{-10}$ M, less than $5 \times 10^{-11}$ M, less than $10^{-11}$ M, less than $5 \times 10^{-12}$ M, less than $10^{-12}$ M, less than $5 \times 10^{-13}$ M, less than $10^{-13}$ M, less than $5 \times 10^{-14}$ M less than $10^{-14}$ M, less than $5 \times 10^{-15}$ M, or less than $10^{-15}$ M.

In one embodiment, an antibody of the invention used in accordance with a method described herein may immunospecifically bind to human CD19 and may have a dissociation constant ($K_d$) of less than 3000 pM, less than 2500 pM, less than 2000 pM, less than 1500 pM, less than 1000 pM, less than 750 pM, less than 500 pM, less than 250 pM, less than 200 pM, less than 150 pM, less than 100 pM, less than 75 pM as assessed using a method described herein or known to one of skill in the art (e.g., a BIAcore assay, ELISA) (Biacore International AB, Uppsala, Sweden). In a specific embodiment, an antibody of the invention used in accordance with a method described herein may immunospecifically bind to a human CD19 antigen and may have a dissociation constant ($K_d$) of between 25 to 3400 pM, 25 to 3000 pM, 25 to 2500 pM, 25 to 2000 pM, 25 to 1500 pM, 25 to 1000 pM, 25 to 750 pM, 25 to 500 pM, 25 to 250 pM, 25 to 100 pM, 25 to 75 pM, 25 to 50 pM as assessed using a method described herein or known to one of skill in the art (e.g., a BIAcore assay, ELISA). In another embodiment, an anti-CD19 antibody of the invention used in accordance with a method described herein may immunospecifically bind to hCD19 and may have a dissociation constant ($K_d$) of 500 pM, 100 pM, 75 pM or 50 pM as assessed using a method described herein or known to one of skill in the art (e.g., a BIAcore assay, ELISA).

The invention further provides polynucleotides comprising a nucleotide sequence encoding a human, humanized, or chimeric anti-CD19 antibody described herein or fragments thereof. The invention also encompasses polynucleotides that hybridize under stringent or lower stringency hybridization conditions, e.g., as defined herein, to polynucleotides that encode a human, humanized, or chimeric antibody described herein that binds to hCD19.

Stringent hybridization conditions include, but are not limited to, hybridization to filter-bound DNA in 6× sodium chloride/sodium citrate (SSC) at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 60° C., or any other stringent hybridization conditions known to those skilled in the art (see, for example, Ausubel, F. M. et al., eds. 1989 Current Protocols in Molecular Biology, vol. 1, Green Publishing Associates, Inc. and John Wiley and Sons, Inc., NY at pages 6.3.1 to 6.3.6 and 2.10.3).

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

A polynucleotide encoding an antibody may also be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably polyA+RNA, isolated from, any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

The present invention also provides polynucleotide sequences encoding VH and VK framework regions and CDRs of antibodies described herein as well as expression vectors for their efficient expression in mammalian cells.

The present invention further provides for antibodies that may efficiently deplete B cells expressing a recombinant human CD19 molecule in a hCD19 transgenic mouse model system (see, Yazawa et al., Proc Natl Acad Sci USA. 102(42): 15178-83 (2005)). In a specific embodiment, an anti-CD-19 antibody of the invention may achieve B cell depletion that is at least 20%, at least 30%, at least 40%, at least 50%, at least 60%, at least 70%, at least 80%, at least 90%, at least 95%, or at least 100% of the depletion achieved by the HB12B monoclonal antibody. In a further embodiment, an anti-CD19 antibody of the invention may achieve B cell depletion that is more complete than the depletion achieved by the HB12B antibody. In one embodiment, an anti-CD19 antibody of the invention may deplete circulating B cells, blood B cells, splenic B cells, marginal zone B cells, follicular B cells, peritoneal B cells, and/or bone marrow B cells. In a one embodiment, an anti-CD19 antibody of the invention may achieve depletion of progenitor B cells, early pro-B cells, late pro-B cells, large-pre-B cells, small pre-B cells, immature B cells, mature B cells, antigen stimulated B cells, and/or plasma cells. In one embodiment, B cell depletion by an anti-CD19 antibody of the invention may persist for at least 1 day, at least 2 days, at least 3 days, at least 4 days, at least 5 days at least 6 days, at least 7 days, at least 8 days, at least 9 days, at least 10 days, at least 15 days, at least 20 days, at least 25 days, or at least 30 days. In another embodiment, B cell depletion by an anti-CD19 antibody of the invention may persist for at least 1 week, at least 2 weeks, at least 3 weeks, at least 4 weeks, at least 5 weeks, at least 6 weeks, at least 7 weeks, at least 8 weeks, at least 9 weeks, or at least 10 weeks. In a further embodiment, B cell depletion by an anti-CD19 antibody of the invention may persist for at least 1 month, at least 2 months, at least 3 months, at least 4 months, at least 5 months, at least 6 months, at least 7 months, at least 8 months, at least 9 months, at least 10 months, at least 11 months or at least 12 months.

The present invention also provides for antibodies that efficiently deplete B cells in a human subject. In a specific embodiment, an anti-CD-19 antibody of the invention may achieve at least about 20%, at least about 30%, at least about 40%, at least about 50%, at least about 60%, at least about 70%, at least about 80%, at least about 90%, at least about 95%, or about 100% B cell depletion. In another embodiment, an anti-CD19 antibody of the invention may deplete B cell subsets in a human subject. In a specific embodiment, an anti-CD19 antibody of the invention may deplete circulating B cells, blood B cells, splenic B cells, marginal zone B cells, follicular B cells, peritoneal B cells, and/or bone marrow B cells. CD19 is present on the surface of B cells at all developmental stages. An anti-CD19 antibody may therefore deplete B cells of all developmental stages. In a specific embodiment, an anti-CD19 antibody of the invention may achieve depletion of progenitor B cells, early pro-B cells, late pro-B cells, large-pre-B cells, small pre-B cells, immature B cells, mature B cells, antigen stimulated B cells, and/or plasma cells. Depletion of B cells may persist for extended periods of time. In one embodiment, B cell depletion by an anti-CD19 antibody of the invention may persist for at least 1 day, at least 2 days, at least 3 days, at least 4 days, at least 5 days at least 6 days, at least 7 days, at least 8 days, at least 9 days, at least 10 days, at least 15 days, at least 20 days, at least 25 days, or at least 30 days. In another embodiment, B cell depletion by an anti-CD19 antibody of the invention may persist for at least 1 week, at least 2 weeks, at least 3 weeks, at least 4 weeks, at least 5 weeks, at least 6 weeks, at least 7 weeks, at least 8 weeks, at least 9 weeks, or at least 10 weeks. In a further embodiment, B cell depletion by an anti-CD19 antibody of the invention may persist for at least 1 month, at least 2 months, at least 3 months, at least 4 months, at least 5 months, at least 6 months, at least 7 months, at least 8 months, at least 9 months, at least 10 months, at least 11 months or at least 12 months.

In one embodiment, an anti-CD19 antibody of the invention depletes at least about 20%, at least about 30%, at least about 40%, at least about 50%, at least about 60%, at least about 70%, at least about 80%, at least about 90%, at least about 95%, or about 100% of circulating B cells. In one embodiment, an anti-CD19 antibody of the invention depletes at least about 20%, at least about 30%, at least about 40%, at least about 50%, at least about 60%, at least about 70%, at least about 80%, at least about 90%, at least about 95%, or about 100% of blood B cells. In one embodiment, an anti-CD19 antibody of the invention depletes at least about 20%, at least about 30%, at least about 40%, at least about 50%, at least about 60%, at least about 70%, at least about 80%, at least about 90%, at least about 95%, or about 100% of splenic B cells. In one embodiment, an anti-CD19 antibody of the invention depletes at least about 20%, at least about 30%, at least about 40%, at least about 50%, at least about 60%, at least about 70%, at least about 80%, at least about 90%, at least about 95%, or about 100% of marginal zone B cells. In one embodiment, an anti-CD19 antibody of the invention depletes at least about 20%, at least about 30%, at least about 40%, at least about 50%, at least about 60%, at least about 70%, at least about 80%, at least about 90%, at least about 95%, or about 100% of follicular B cells. In one embodiment, an anti-CD19 antibody of the invention depletes at least about 20%, at least about 30%, at least about 40%, at least about 50%, at least about 60%, at least about 70%, at least about 80%, at least about 90%, at least about 95%, or about 100% of peritoneal B cells. In one embodiment, an anti-CD19 antibody of the invention depletes at least about 20%, at least about 30%, at least about 40%, at least about 50%, at least about 60%, at least about 70%, at least about 80%, at least about 90%, at least about 95%, or about 100% of bone marrow B cells. In one embodiment, an anti-CD19 antibody of the invention depletes at least about 20%, at least about 30%, at least about 40%, at least about 50%, at least about 60%, at least about 70%, at least about 80%, at least about 90%, at least about 95%, or about 100% of progenitor B cells. In one embodiment, an anti-CD19 antibody of the invention depletes at least about 20%, at least about 30%, at least about 40%, at least about 50%, at least about 60%, at least about 70%, at least about 80%, at least about 90%, at least about 95%, or about 100% of early pro-B cells. In one embodiment, an anti-CD19 antibody of the invention depletes at least about 20%, at least about 30%, at least about 40%, at least about 50%, at least about 60%, at least about 70%, at least about 80%, at least about 90%, at least about 95%, or about 100% of late pro-B cells. In one embodiment, an anti-CD19 antibody of the invention depletes at least about 20%, at least about 30%, at least about 40%, at least about 50%, at least about 60%, at least about 70%, at least about 80%, at least about 90%, at least about 95%, or about 100% of large pre-B cells. In one embodiment, an anti-CD19 antibody of the invention depletes at least about 20%, at least about 30%, at least about 40%, at least about 50%, at least about 60%, at least about 70%, at least about 80%, at least about 90%, at least about 95%, or about 100% of small pre-B cells. In one embodiment, an anti-CD19 antibody of the invention depletes at least about 20%, at least about 30%, at least about 40%, at least about 50%, at least about 60%, at least about 70%, at least about 80%, at least about 90%, at least about 95%, or about 100% of immature B cells. In one embodiment, an anti-CD19 antibody of the invention depletes at least about 20%, at least about 30%, at least about 40%, at least about 50%, at least about 60%, at least about 70%, at least about 80%, at least about 90%, at least about 95%, or about 100% of mature B cells. In one embodiment, an anti-CD19 antibody of the invention depletes at least about 20%, at least about 30%, at least about 40%, at least about 50%, at least about 60%, at least about 70%, at least about 80%, at least about 90%, at least about 95%, or about 100% of antigen stimulated B cells. In one embodiment, an anti-CD19 antibody of the invention depletes at least about 20%, at least about 30%, at least about 40%, at least about 50%, at least about 60%, at least about 70%, at least about 80%, at least about 90%, at least about 95%, or about 100% of plasma cells. Depletion of B cells may persist for extended periods of time. In one embodiment, B cell depletion by an anti-CD19 antibody of the invention may persist for at least 1 day, at least 2 days, at least 3 days, at least 4 days, at least 5 days at least 6 days, at least 7 days, at least 8 days, at least 9 days, at least 10 days, at least 15 days, at least 20 days, at least 25 days, or at least 30 days. In another embodiment, B cell depletion by an anti-CD19 antibody of the invention may persist for at least 1 week, at least 2 weeks, at least 3 weeks, at least 4 weeks, at least 5 weeks, at least 6 weeks, at least 7 weeks, at least 8 weeks, at least 9 weeks, or at least 10 weeks. In a further embodiment, B cell depletion by an anti-CD19 antibody of the invention may persist for at least 1 month, at least 2 months, at least 3 months, at least 4 months, at least 5 months, at least 6 months, at least 7 months, at least 8 months, at least 9 months, at least 10 months, at least 11 months or at least 12 months.

B cell malignancies are characterized by the pathological expansion of specific B cell subsets, for example, precursor B cell acute lymphoblastic leukemia is characterized by an abnormal expansion of B cells corresponding to pro-B cell/Pre-B cell developmental stages. The malignant B cells maintain cell surface expression of normal B cell markers such as CD19. An anti-CD19 antibody may therefore deplete malignant B cells in a human subject. In a specific embodiment, an anti-CD19 antibody of the invention may achieve at least 20%, at least 30%, at least 40%, at least 50%, at least 60%, at least 70%, at least 80%, at least 90%, at least 95%, or at least 100% depletion of malignant B cells in a human subject.

In one embodiment, a humanized anti-CD19 antibody described herein mediates antibody-dependent cellular cytotoxicity (ADCC), complement-dependent cell-mediated cytotoxicity (CDC), and/or apoptosis. In one embodiment, a humanized anti-CD19 antibody of the invention mediates antibody-dependent cellular cytotoxicity (ADCC) and/or apoptosis. In one embodiment, an anti-CD19 antibody of the invention has enhanced antibody-dependent cellular cytotoxicity (ADCC). In one embodiment, an anti-CD19 antibody of the invention comprises a variant Fc region that mediates enhanced antibody-dependent cellular cytotoxicity (ADCC). In one embodiment, an anti-CD19 antibody of the invention comprises an Fc region having complex N-glycoside-linked sugar chains linked to Asn297 in which fucose is not bound to N-acetylglucosamine in the reducing end, wherein said Fc region mediates enhanced antibody-dependent cellular cytotoxicity (ADCC).

The present invention further provides for anti-CD19 antibodies that may efficiently inhibit in vitro stimulated B cell proliferation. Proliferation of isolated peripheral B cells may be induced by various stimuli, for example, but not limited to stimulation by anti-IgM antibody, CD40 or CpG. These stimuli may be delivered in alone or in combination with each other.

In one embodiment, an anti-CD19 antibody of the invention inhibits in vitro stimulated B cell proliferation. In a another embodiment, an anti-CD19 antibody described herein inhibits in vitro B cell proliferation induced by anti-IgM/CpG or anti-IgM/CD40 stimulation. In one embodiment, an anti-CD19 antibody of the invention inhibits in vitro stimulated B cell proliferation by at least about 10%, at least about 20%, at least about 30%, at least about 40%, at least about 50% or at least about 75%.

In one embodiment, an Fc variant anti-CD19 antibody of the invention inhibits in vitro B cell proliferation induced by anti-IgM/CpG or anti-IgM/CD40 stimulation, wherein said Fc variant has altered binding affinity to one or more Fc ligand relative to a comparable non-variant molecule. In a specific embodiment, an Fc variant anti-CD19 antibody of the invention inhibits in vitro B cell proliferation induced by anti-IgM/CpG or anti-IgM/CD40 stimulation, wherein said Fc variant has enhanced binding to Fc gamma receptor IIB relative to a comparable non-variant Fc domain. In a further specific embodiment, an Fc variant anti-CD19 antibody of the invention inhibits in vitro stimulated B cell proliferation by at least about 10%, at least about 20%, at least about 30%, at least about 40%, at least about 50% or at least about 75%. In another embodiment, an Fc variant anti-CD19 antibody of the invention inhibits in vitro stimulated B cell proliferation, wherein said variant Fc domain has an affinity for Fc gamma receptor IIB that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold greater than that of a comparable non-variant Fc domain.

The present invention also relates to a method of treating a B cell malignancy in a human comprising administering to a human in need thereof, a human, humanized or chimeric anti-CD19 antibody that may mediate human antibody-dependent cellular cytotoxicity (ADCC), complement-dependent cell-mediated cytotoxicity (CDC), and/or apoptosis in an amount sufficient to deplete circulating B cells. In a particular aspect, the present invention also concerns methods of treating a B cell malignancy in a human comprising administration of a therapeutically effective regimen of a human, humanized, or chimeric anti-CD19 antibody, which is of the IgG1 or IgG3 human isotype.

The present invention further relates to a method of treating an autoimmune disease or disorder in a human comprising administering to a human in need thereof a human, humanized, or chimeric anti-CD19 antibody that may mediate human ADCC, CDC, and/or apoptosis in an amount sufficient to deplete circulating B cells. The present invention also concerns methods of treating autoimmune disorders comprising administration of a therapeutically effective regimen of a human, humanized, or chimeric anti-CD19 antibody which is of the IgG1 or IgG3 human isotype.

The present invention also provides methods for treating or preventing humoral rejection in a human transplant recipient in need thereof comprising administering to the recipient a human, humanized, or chimeric anti-CD19 antibody of the invention in an amount that may deplete circulating B cells, or circulating immunoglobulin, or both. In other embodiments, the invention provides methods for preventing graft rejection or graft versus host disease in a human transplant recipient in need thereof comprising contacting a graft prior to transplantation with an amount of a human, humanized, or chimeric anti-CD19 antibody that may deplete B cells from the graft.

5.2. Production of Humanized Anti-CD19 Antibodies

Humanized antibodies described herein can be produced using a variety of techniques known in the art, including, but not limited to, CDR-grafting (see e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, *Molecular Immunology* 28(4/5):489-498; Studnicka et al., 1994, *Protein Engineering*, 7(6):805-814; and Roguska et al., 1994, *Proc. Natl. Acad. Sci.*, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Pat. No. 6,407,213, U.S. Pat. No. 5,766,886, International Publication No. WO 9317105, Tan et al., *J. Immunol.*, 169: 1119-25 (2002), Caldas et al., *Protein Eng.*, 13(5):353-60 (2000), Morea et al., *Methods*, 20(3):267-79 (2000), Baca et al., *J. Biol. Chem.*, 272(16):10678-84 (1997), Roguska et al., *Protein Eng.*, 9(10):895-904 (1996), Couto et al., *Cancer Res.*, 55 (23 Supp):5973s-5977s (1995), Couto et al., *Cancer Res.*, 55(8):1717-22 (1995), Sandhu J S, *Gene*, 150(2):409-10 (1994), and Pedersen et al., *J. Mol. Biol.*, 235(3):959-73 (1994), each of which is incorporated herein in its entirety by reference. Often, FW residues in the FW regions will be substituted with the corresponding residue from the CDR donor antibody to alter, preferably improve, antigen binding. These FW substitutions are identified by methods well known in the art, e.g., by modeling of the interactions of the CDR and FW residues to identify FW residues important for antigen binding and sequence comparison to identify unusual FW residues at particular positions. (See, e.g., Queen et al., U.S. Pat. No. 5,585,089; and Riechmann et al., 1988, *Nature*, 332:323, which are incorporated herein by reference in their entireties.)

A humanized anti-CD19 antibody has one or more amino acid residues introduced into it from a source which is non-human. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some FW residues are substituted by residues from analogous sites in rodent antibodies. Humanization of anti-CD19 antibodies can also be achieved by veneering or resurfacing (EP 592,106; EP 519,596; Padlan, 1991, *Molecular Immunology* 28(4/5):489-498; Studnicka et al., *Protein Engineering,* 7(6): 805-814 (1994); and Roguska et al., *Proc. Natl. Acad. Sci.,* 91:969-973 (1994)) or chain shuffling (U.S. Pat. No. 5,565, 332), the contents of which are incorporated herein by reference in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequences which are most closely related to that of the rodent are then screened for the presences of specific residues that may be critical for antigen binding, appropriate structural formation and/or stability of the intended humanized mAb (Sims et al., *J. Immunol.,* 151:2296 (1993); Chothia et al., *J. Mol. Biol.,* 196:901 (1987), the contents of which are incorporated herein by reference in their entirety). The resulting FW sequences matching the desired criteria are then be used as the human donor FW regions for the humanized antibody.

Another method uses a particular FW derived from the consensus sequence of all human antibodies of a particular subgroup of light or heavy chains. The same FW may be used for several different humanized anti-CD19 antibodies (Carter et al., *Proc. Natl. Acad. Sci. USA,* 89:4285 (1992); Presta et al., *J. Immunol.,* 151:2623 (1993), the contents of which are incorporated herein by reference in their entirety).

Anti-CD19 antibodies can be humanized with retention of high affinity for CD19 and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind CD19. In this way, FW residues can be selected and combined from the recipient and import sequences so that the desired antibody characteristic, for example affinity for CD19, is achieved. In general, the CDR residues are directly and most substantially involved in influencing antigen binding.

A "humanized" antibody may retain a similar antigenic specificity as the original antibody, i.e., in the present invention, the ability to bind human CD19 antigen. However, using certain methods of humanization, the affinity and/or specificity of binding of the antibody for human CD19 antigen may be altered using methods of "directed evolution," as described by Wu et al., *J. Mol. Biol.,* 294:151 (1999), the contents of which are incorporated herein by reference herein in their entirety.

Humanized anti-CD19 antibodies described herein can be constructed by the selection of distinct human framework regions for grafting of the HB12A or HB12B complementarity determining regions, or "CDR's" as described in the sections that follow. The invention encompasses a number of humanized versions of the mouse HB12A and HB12B antibody as well as chimeric versions, designated chHB12A and chHB12B.

5.3. Monoclonal Anti-CD19 Antibodies

A monoclonal anti-CD19 antibody exhibits binding specificity to human CD19 antigen and may mediate human ADCC, CDC and/or apoptotic mechanisms. Such an antibody can be generated using a wide variety of techniques known in the art including the use of hybridoma, recombinant, and phage display technologies, or a combination thereof. Antibodies are highly specific, being directed against a single antigenic site. An engineered anti-CD19 antibody can be produced by any means known in the art, including, but not limited to, those techniques described below and improvements to those techniques. Large-scale high-yield production typically involves culturing a host cell that produces the engineered anti-CD19 antibody and recovering the anti-CD19 antibody from the host cell culture.

5.3.1. Hybridoma Technique

Monoclonal antibodies can be produced using hybridoma techniques including those known in the art and taught, for example, in Harlow et al., *Antibodies: A Laboratory Manual,* (Cold Spring Harbor Laboratory Press, 2nd ed. 1988); Hammerling et al., in *Monoclonal Antibodies and T Cell Hybridomas,* 563-681 (Elsevier, N.Y., 1981) (said references incorporated herein by reference in their entireties). For example, in the hybridoma method, a mouse or other appropriate host animal, such as a hamster or macaque monkey, is immunized to elicit lymphocytes that produce or are capable of producing antibodies that will specifically bind to the protein used for immunization. Lymphocytes may also be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59-103 (Academic Press, 1986)).

The hybridoma cells thus prepared are seeded and grown in a suitable culture medium that contains one or more substances that inhibit the growth or survival of the unfused, parental myeloma cells. For example, if the parental mycloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA.

Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the human CD19 antigen. The binding specificity of monoclonal antibodies produced by hybridoma cells can be determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

5.3.2. Recombinant DNA Techniques

DNA encoding an anti-CD19 antibody described herein is readily isolated and sequenced using conventional procedures (e.g., by using oligonucleotide probes that are capable of binding specifically to genes encoding the heavy and light chains of anti-CD19 antibodies). The hybridoma cells serve as a source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of anti-CD19 antibodies in the recombinant host cells.

In phage display methods, functional antibody domains are displayed on the surface of phage particles which carry the polynucleotide sequences encoding them. In particular, DNA sequences encoding $V_H$ and $V_L$ domains are amplified from animal cDNA libraries (e.g., human or murine cDNA libraries of affected tissues). The DNA encoding the $V_H$ and $V_L$ domains are recombined together with an scFv linker by PCR and cloned into a phagemid vector. The vector is electroporated in *E. coli* and the *E. coli* is infected with helper phage. Phage used in these methods is typically filamentous phage including fd and M13 and the $V_H$ and $V_L$ domains are usually recombinantly fused to either the phage gene III or gene VIII. Phage expressing an antigen-binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, *J. Immunol. Methods,* 182:41-50; Ames et al., 1995, *J. Immunol. Methods,* 184:177-186; Kettleborough et al., 1994, *Eur. J. Immunol.,* 24:952-958; Persic et al., 1997, *Gene,* 187:9-18; Burton et al., 1994, *Advances in Immunology,* 57:191-280; International Application No. PCT/GB91/O1 134; International Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108; each of which is incorporated herein by reference in its entirety.

As described in the above references, after phage selection, the antibody coding regions from the phage can be isolated and used to generate whole antibodies, including human antibodies, or any other desired antigen-binding fragment, and expressed in any desired host, including mammalian cells, insect cells, plant cells, yeast, and bacteria, e.g., as described below. Techniques to recombinantly produce Fab, Fab' and $F(ab')_2$ fragments can also be employed using methods known in the art such as those disclosed in PCT Publication No. WO 92/22324; Mullinax et al., 1992, *BioTechniques,* 12(6):864-869; Sawai et al., 1995, *AJRI,* 34:26-34; and Better et al., 1988, *Science,* 240:1041-1043 (said references incorporated by reference in their entireties).

Antibodies may be isolated from antibody phage libraries generated using the techniques described in McCafferty et al., *Nature,* 348:552-554 (1990). Clackson et al., *Nature,* 352:624-628 (1991). Marks et al., *J. Mol. Biol.,* 222:581-597 (1991) describe the isolation of murine and human antibodies, respectively, using phage libraries. Chain shuffling can be used in the production of high affinity (nM range) human antibodies (Marks et al., *Bio/Technology,* 10:779-783 (1992)), as well as combinatorial infection and in vivo recombination as a strategy for constructing very large phage libraries (Waterhouse et al., *Nuc. Acids. Res.,* 21:2265-2266 (1993)). Thus, these techniques are viable alternatives to traditional monoclonal antibody hybridoma techniques for isolation of anti-CD19 antibodies.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. The vectors for expressing the VH or VL domains may comprise an EF-1α promoter, a secretion signal, a cloning site for the variable domain, constant domains, and a selection marker such as neomycin. The VH and VL domains may also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also may be modified, for example, by substituting the coding sequence for human heavy and light chain constant domains in place of the homologous murine sequences (U.S. Pat. No. 4,816,567; Morrison et al., *Proc. Natl. Acad. Sci. USA,* 81:6851 (1984)), or by covalently joining to the immunoglobulin coding sequence all or part of the coding sequence for a non-immunoglobulin polypeptide.

5.4. Chimeric Antibodies

The anti-CD19 antibodies herein specifically include chimeric antibodies (immunoglobulins) in which a portion of the heavy and/or light chain is identical with or homologous to corresponding sequences in antibodies derived from a particular species or belonging to a particular antibody class or subclass, while another portion of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851-6855 (1984)). Chimeric antibodies of interest herein include "primatized" antibodies comprising variable domain antigen-binding sequences derived from a nonhuman primate (e.g., Old World Monkey, such as baboon, rhesus or cynomolgus monkey) and human constant region sequences (U.S. Pat. No. 5,693,780).

5.5. Altered/Mutant Antibodies

Anti-CD19 antibodies of compositions and methods described herein can be mutant antibodies. As used herein, "antibody mutant" or "altered antibody" refers to an amino acid sequence variant of an anti-CD19 antibody wherein one or more of the amino acid residues of an anti-CD19 antibody have been modified. The modifications to the amino acid sequence of an anti-CD19 antibody include modifications to the sequence that may improve affinity or avidity of the antibody for its antigen, and/or modifications to the Fc portion of the antibody that may improve effector function.

The present invention therefore relates to human, humanized, and chimeric anti-CD19 antibodies disclosed herein as well as altered/mutant derivatives thereof including, but not limited to ones exhibiting altered human CD19 binding characteristics; e.g. altered association constants $k_{ON}$, dissociation constants $k_{OFF}$, and/or equilibrium constant or binding affinity, $K_D$. In certain embodiments the $K_D$ of an anti-CD19 antibody described herein, or an altered/mutant derivative thereof, for human CD19 may be no more than about $10^{-6}$M, $10^{-7}$M, $10^{-8}$M, or $10^{-9}$M. Methods and reagents suitable for determination of such binding characteristics of an antibody of the present invention, or an altered/mutant derivative thereof, are known in the art and/or are commercially available (se above and, e.g., U.S. Pat. Nos. 6,849,425, 6,632,926, 6,294,391, and 6,143,574, each of which is hereby incorporated by reference in its entirety). Moreover, equipment and software designed for such kinetic analyses are commercially available (e.g. Biacore® A100, and Biacore® 2000 instruments; Biacore International AB, Uppsala, Sweden).

The modifications may be made to any known anti-CD19 antibodies or anti-CD19 antibodies identified as described herein. Such altered antibodies necessarily have less than 100% sequence identity or similarity with a known anti-CD19 antibody. By way of example, an altered antibody may have an amino acid sequence that is within the range of from about 25% to about 95% identical or similar to the amino acid sequence of either the heavy or light chain variable domain of an anti-CD19 antibody as described herein. An altered antibody may have an amino acid sequence having at least 25%, 35%, 45%, 55%, 65%, 75%, 80%, 85%, 90%, or 95% amino acid sequence identity or similarity with the amino acid sequence of either the heavy or light chain variable domain of an anti-CD19 antibody as described herein. In another embodiment, an altered antibody may have an amino acid sequence having at least 25%, 35%, 45%, 55%, 65%, 75%, 80%, 85%, 90%, or 95% amino acid sequence identity or similarity with the amino acid sequence of the heavy chain CDR1, CDR2, or CDR3 of an anti-CD19 antibody as described herein. In one embodiment, an altered antibody may maintain human CD19 binding capability. In certain embodiments, an anti-CD19 antibody as described herein may comprise a VH that is at least or about 10%, 15%, 20%, 25%, 30%, 35%, 40%, 45%, 50%, 55%, 60%, 65%, 70%, 75%, 80%, 85%, 90%, 95% or more identical to the amino acid sequence of HB12B-(3-72/JH4) (SEQ ID NO:34), HB12A VH (SEQ ID NO:2) HB12B VH (SEQ ID NO:18), 7E12 VH (SEQ ID NO:102), 14H5 VH (SEQ ID NO:103), 15D1 VH (SEQ ID NO:104), 15D7 VH (SEQ ID NO:105), 16C4 VH (SEQ ID NO:106), 14H5-YG (SEQ ID NO:107), 14H5-DG (SEQ ID NO:108), 14H5-LG (SEQ ID NO:109), 1A7 VH, 3C3 VH, 3E5 VH, 3D4 VH, 9G7 VH (SEQ ID NO:191), 3B4 VH (SEQ ID NO: 236), 3F11 VH or 6C11 VH (SEQ ID NO:192). In certain embodiments, an anti-CD19 antibody as described herein may comprise a VH that is at least or about 10%, 15%, 20%, 25%, 30%, 35%, 40%, 45%, 50%, 55%, 60%, 65%, 70%, 75%, 80%, 85%, 90%, 95% or more identical to the amino acid sequence of any of the VH domains, VL domains, or CDRs listed in Table 1.

In another embodiment, an altered antibody may have an amino acid sequence having at least 25%, 35%, 45%, 55%, 65%, 75%, 80%, 85%, 90%, or 95% amino acid sequence identity or similarity with the amino acid sequence of FW1, FW2, FW3, or FW4 regions of HB12B-(3-72/JH4) (SEQ ID NO:34), HB12A VH (SEQ ID NO:2) HB12B VH (SEQ ID NO:18), 7E12 VH (SEQ ID NO:102), 14H5 VH (SEQ ID NO:103), 15D1 VH (SEQ ID NO:104), 15D7 VH (SEQ ID NO:105), 16C4 VH (SEQ ID NO:106), 14H5-YG (SEQ ID NO:107), 14H5-DG (SEQ ID NO:108), 14H5-LG (SEQ ID NO:109), 1A7 VH, 3C3 VH, 3E5 VH, 3D4 VH, 9G7 VH (SEQ ID NO:191), 3B4 VH (SEQ ID NO: 236), 3F11 VH or 6C11 VH (SEQ ID NO:192). In another embodiment, an altered antibody may have an amino acid sequence having at least 25%, 35%, 45%, 55%, 65%, 75%, 80%, 85%, 90%, or 95% amino acid sequence identity or similarity with the amino acid sequence of FW1, FW2, FW3, or FW4 regions of any of the VH or VL domains listed in Table 1.

In another embodiment, an altered antibody may have an amino acid sequence having at least 25%, 35%, 45%, 55%, 65%, 75%, 80%, 85%, 90%, or 95% amino acid sequence identity or similarity with the amino acid sequence of the light chain CDR1, CDR2, or CDR3 of an anti-CD19 antibody as described herein. In certain embodiments, an anti-CD19 antibody of the invention may comprise a VL that is at least or about 10%, 15%, 20%, 25%, 30%, 35%, 40%, 45%, 50%, 55%, 60%, 65%, 70%, 75%, 80%, 85%, 90%, 95% or more identical to an amino acid sequence of HB12A VK (SEQ ID NO:4), HB12B VK (SEQ ID NO:20), HB12B-(A10-Jk4) (SEQ ID NO:52), HB12B-364987 (or 364987) (SEQ ID NO:62), HB12B-3649 (or 3649) (SEQ ID NO:68), HB12B-36 (or 36) (SEQ ID NO:70), 7E12 VK (SEQ ID NO:110), 14H5 (SEQ ID NO:111), 15D1 (SEQ ID NO:112), 16C9 (SEQ ID NO:113), 3C3 VK (SEQ ID NO:193), 3E5 VK (SEQ ID NO:194), 3D4 VK (SEQ ID NO:195), 3F1 VK (SEQ ID NO:196), 5B5 VK (SEQ ID NO:197), 6F7 VK (SEQ ID NO:198), 1C11 VK (SEQ ID NO:199), 2B11 VK (SEQ ID NO:200), 2D10 VK (SEQ ID NO:201), 5C11 VK (SEQ ID NO:202), 5D4 VK (SEQ ID NO:203), 6C11 VK (SEQ ID NO:204), 9G7 VK (SEQ ID NO:205), 1H4 VK (SEQ ID NO:206), or 5C4 VK (SEQ ID NO:207).

In another embodiment, an altered antibody may have an amino acid sequence having at least 25%, 35%, 45%, 55%, 65%, 75%, 80%, 85%, 90%, or 95% amino acid sequence identity or similarity with the amino acid sequence of FW1, FW2, FW3, or FW4 regions of HB12A VK (SEQ ID NO:4), HB12B VK (SEQ ID NO:20), HB12B-(A10-Jk4) (SEQ ID NO:52), HB12B-364987 (or 364987) (SEQ ID NO:62), HB12B-3649 (or 3649) (SEQ ID NO:68), HB12B-36 (or 36) (SEQ TD NO:70), 7E12 VK (SEQ ID NO:110), 14H5 (SEQ ID NO:111), 15D1 (SEQ ID NO:112), 16C9 (SEQ ID NO:113), 3C3 VK (SEQ ID NO:193), 3E5 VK (SEQ ID NO:194), 3D4 VK (SEQ ID NO:195), 3F1 VK (SEQ ID NO:196), 5B5 VK (SEQ ID NO:197), 6F7 VK (SEQ ID NO:198), 1C11 VK (SEQ ID NO:199), 2B11 VK (SEQ ID NO:200), 2D10 VK (SEQ ID NO:201), 5C11 VK (SEQ ID NO:202), 5D4 VK (SEQ ID NO:203), 6C11 VK (SEQ ID NO:204), 9G7 VK (SEQ ID NO:205), 1H4 VK (SEQ ID NO:206), or 5C4 VK (SEQ ID NO:207).

Identity or similarity with respect to a sequence is defined herein as the percentage of amino acid residues in the candidate sequence that are identical (i.e., same residue) or similar (i.e., amino acid residue from the same group based on common side-chain properties, see below) with anti-CD19 antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

"% identity," as known in the art, is a measure of the relationship between two polynucleotides or two polypeptides, as determined by comparing their sequences. In general, the two sequences to be compared are aligned to give a maximum correlation between the sequences. The alignment of the two sequences is examined and the number of positions giving an exact amino acid or nucleotide correspondence between the two sequences determined, divided by the total length of the alignment and multiplied by 100 to give a % identity figure. This % identity figure may be determined over the whole length of the sequences to be compared, which is particularly suitable for sequences of the same or very similar length and which are highly homologous, or over shorter defined lengths, which is more suitable for sequences of unequal length or which have a lower level of homology.

For example, sequences can be aligned with the software clustalw under Unix which generates a file with an ".aln" extension, this file can then be imported into the Bioedit program (Hall, T. A. 1999, *BioEdit: a user-friendly biological sequence alignment editor and analysis program for Windows 95/98/NT. Nucl. Acids. Symp. Ser.* 41:95-98) which opens the .aln file. In the Bioedit window, one can choose individual sequences (two at a time) and alignment them. This method allows for comparison of the entire sequence.

Methods for comparing the identity of two or more sequences are well known in the art. Thus for instance, programs are available in the Wisconsin Sequence Analysis Package, version 9.1 (Devereux J. et al., *Nucleic Acids Res.,* 12:387-395, 1984, available from Genetics Computer Group, Madison, Wis., USA). The determination of percent identity between two sequences can be accomplished using a mathematical algorithm. For example, the programs BESTFIT and GAP, may be used to determine the % identity between two polynucleotides and the % identity between two polypeptide sequences. BESTFIT uses the "local homology" algorithm of Smith and Waterman (*Advances in Applied Mathematics,* 2:482-489, 1981) and finds the best single region of similarity between two sequences. BESTFIT is more suited to comparing two polynucleotide or two polypeptide sequences which are dissimilar in length, the program assuming that the shorter sequence represents a portion of the longer. In comparison, GAP aligns two sequences finding a "maximum similarity" according to the algorithm of Neddleman and Wunsch (*J. Mol. Biol.,* 48:443-354, 1970). GAP is more suited to comparing sequences which are approximately the same length and an alignment is expected over the entire length. Preferably the parameters "Gap Weight" and "Length Weight" used in each program are 50 and 3 for polynucleotides and 12 and 4 for polypeptides, respectively. Preferably % identities and similarities are determined when the two sequences being compared are optimally aligned.

Other programs for determining identity and/or similarity between sequences are also known in the art, for instance the BLAST family of programs (Karlin & Altschul, 1990, Proc. Natl. Acad. Sci. USA, 87:2264-2268, modified as in Karlin & Altschul, 1993, Proc. Natl. Acad. Sci. USA, 90:5873-5877, available from the National Center for Biotechnology Information (NCB), Bethesda, Md., USA and accessible through the home page of the NCBI). These programs are non-limiting examples of a mathematical algorithm utilized for the comparison of two sequences. Such an algorithm is incorporated into the NBLAST and XBLAST programs of Altschul et al., 1990, J. Mol. Biol., 215:403-410. BLAST nucleotide searches can be performed with the NBLAST program, score=100, wordlength=12 to obtain nucleotide sequences homologous to a nucleic acid molecule encoding all or a portion if an anti-CD19 antibody of the invention. BLAST protein searches can be performed with the XBLAST program, score=50, wordlength=3 to obtain amino acid sequences homologous to a protein molecule of the invention. To obtain gapped alignments for comparison purposes, Gapped BLAST can be utilized as described in Altschul et al., 1997, Nucleic Acids Res., 25:3389-3402. PSI-Blast can also be used to perform an iterated search which detects distant relationships between molecules (Id.). When utilizing BLAST, Gapped BLAST, and PSI-Blast programs, the default parameters of the respective programs (e.g., XBLAST and NBLAST) can be used.

Another non-limiting example of a program for determining identity and/or similarity between sequences known in the art is FASTA (Pearson W. R. and Lipman D. J., *Proc. Natl. Acad. Sci. USA,* 85:2444-2448, 1988, available as part of the Wisconsin Sequence Analysis Package). Preferably the BLOSUM62 amino acid substitution matrix (Henikoff S, and Henikoff J. G., *Proc. Natl. Acad. Sci. USA,* 89:10915-10919, 1992) is used in polypeptide sequence comparisons including where nucleotide sequences are first translated into amino acid sequences before comparison.

Yet another non-limiting example of a program known in the art for determining identity and/or similarity between amino acid sequences is SeqWeb Software (a web-based interface to the GCG Wisconsin Package: Gap program) which is utilized with the default algorithm and parameter settings of the program: blosum62, gap weight 8, length weight 2.

The percent identity between two sequences can be determined using techniques similar to those described above, with or without allowing gaps. In calculating percent identity, typically exact matches are counted.

Preferably the program BESTFIT is used to determine the % identity of a query polynucleotide or a polypeptide sequence with respect to a polynucleotide or a polypeptide sequence of the present invention, the query and the reference sequence being optimally aligned and the parameters of the program set at the default value.

To generate an altered antibody, one or more amino acid alterations (e.g., substitutions) are introduced in one or more of the hypervariable regions of the species-dependent antibody. One or more alterations (e.g., substitutions) of framework region residues may also be introduced in an anti-CD19 antibody where these result in an improvement in the binding affinity of the antibody mutant for the antigen from the second mammalian species. Examples of framework region residues to modify include those which non-covalently bind antigen directly (Amit et al., *Science,* 233:747-753 (1986)); interact with/effect the conformation of a CDR (Chothia et al., *J. Mol. Biol.,* 196:901-917 (1987)); and/or participate in the $V_L$-$V_H$ interface (EP 239 400B1). In certain embodiments, modification of one or more of such framework region residues results in an enhancement of the binding affinity of the antibody for the antigen from the second mammalian species. For example, from about one to about five framework residues may be altered in this embodiment of the invention. Sometimes, this may be sufficient to yield an antibody mutant suitable for use in preclinical trials, even where none of the hypervariable region residues have been altered. Normally, however, an altered antibody will comprise additional hypervariable region alteration(s).

The hypervariable region residues which are altered may be changed randomly, especially where the starting binding affinity of an anti-CD19 antibody for the antigen from the second mammalian species is such that such randomly produced altered antibody can be readily screened.

One useful procedure for generating such an altered antibody is called "alanine scanning mutagenesis" (Cunningham and Wells, Science, 244:1081-1085 (1989)). Here, one or more of the hypervariable region residue(s) are replaced by alanine or polyalanine residue(s) to affect the interaction of the amino acids with the antigen from the second mammalian species. Those hypervariable region residue(s) demonstrating functional sensitivity to the substitutions then are refined by introducing additional or other mutations at or for the sites of substitution. Thus, while the site for introducing an amino acid sequence variation is predetermined, the nature of the mutation per se need not be predetermined. The Ala-mutants produced this way are screened for their biological activity as described herein.

Another procedure for generating such an altered antibody involves affinity maturation using phage display (Hawkins et al., *J. Mol. Biol.*, 254:889-896 (1992) and Lowman et al., *Biochemistry*, 30(45):10832-10837 (1991)). Briefly, several hypervariable region sites (e.g., 6-7 sites) are mutated to generate all possible amino acid substitutions at each site. The antibody mutants thus generated are displayed in a monovalent fashion from filamentous phage particles as fusions to the gene 111 product of M13 packaged within each particle. The phage-displayed mutants are then screened for their biological activity (e.g., binding affinity) as herein disclosed.

Mutations in antibody sequences may include substitutions, deletions, including internal deletions, additions, including additions yielding fusion proteins, or conservative substitutions of amino acid residues within and/or adjacent to the amino acid sequence, but that result in a "silent" change, in that the change produces a functionally equivalent anti-CD19 antibody. Conservative amino acid substitutions may be made on the basis of similarity in polarity, charge, solubility, hydrophobicity, hydrophilicity, and/or the amphipathic nature of the residues involved. For example, non-polar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. In addition, glycine and proline are residues that can influence chain orientation. Non-conservative substitutions will entail exchanging a member of one of these classes for a member of another class. Furthermore, if desired, non-classical amino acids or chemical amino acid analogs can be introduced as a substitution or addition into the antibody sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general.

In another embodiment, the sites selected for modification are affinity matured using phage display (see above).

Any technique for mutagenesis known in the art can be used to modify individual nucleotides in a DNA sequence, for purposes of making amino acid substitution(s) in the antibody sequence, or for creating/deleting restriction sites to facilitate further manipulations. Such techniques include, but are not limited to, chemical mutagenesis, in vitro site-directed mutagenesis (Kunkel, *Proc. Natl. Acad. Sci. USA*, 82:488 (1985); Hutchinson, C. et al., *J. Biol. Chem.*, 253:6551 (1978)), oligonucleotide-directed mutagenesis (Smith, *Ann. Rev. Genet.*, 19:423-463 (1985); Hill et al., *Methods Enzymol.*, 155:558-568 (1987)), PCR-based overlap extension (Ho et al., *Gene*, 77:51-59 (1989)), PCR-based megaprimer mutagenesis (Sarkar et al., *Biotechniques*, 8:404-407 (1990)), etc. Modifications can be confirmed by double-stranded dideoxy DNA sequencing.

In certain embodiments of the invention, an anti-CD19 antibody can be modified to produce fusion proteins; i.e., the antibody, or a fragment thereof, fused to a heterologous protein, polypeptide or peptide. In certain embodiments, the protein fused to the portion of an anti-CD19 antibody is an enzyme component of Antibody-Directed Enzyme Prodrug Therapy (ADEPT). Examples of other proteins or polypeptides that can be engineered as a fusion protein with an anti-CD19 antibody include, but are not limited to toxins such as ricin, abrin, ribonuclease, DNase I, Staphylococcal enterotoxin-A, pokeweed anti-viral protein, gelonin, diphtherin toxin, *Pseudomonas* exotoxin, and *Pseudomonas* endotoxin. See, for example, Pastan et al., *Cell*, 47:641 (1986), and Goldenberg et al., *Cancer Journal for Clinicians*, 44:43 (1994). Enzymatically active toxins and fragments thereof which can be used include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of the antiCD19 antibody or fragments thereof (e.g., an antibody or a fragment thereof with higher affinities and lower dissociation rates). See, generally, U.S. Pat. Nos. 5,605,793; 5,811,238; 5,830,721; 5,834,252; and 5,837,458, and Patten et al., 1997, *Curr. Opinion Biotechnol.*, 8:724-33; Harayama, 1998, *Trends Biotechnol.* 16(2):76-82; Hansson et al., 1999, *J. Mol. Biol.*, 287:265-76; and Lorenzo and Blasco, 1998, *Biotechniques* 24(2):308-313 (each of these patents and publications are hereby incorporated by reference in its entirety). The antibody can further be a binding-domain immunoglobulin fusion protein as described in U.S. Publication 20030118592, U.S. Publication 200330133939, and PCT Publication WO 02/056910, all to Ledbetter et al., which are incorporated herein by reference in their entireties.

5.6. Domain Antibodies

Anti-CD19 antibodies of compositions and methods of the invention can be domain antibodies, e.g., antibodies containing the small functional binding units of antibodies, corresponding to the variable regions of the heavy ($V_H$) or light ($V_L$) chains of human antibodies. Examples of domain antibodies include, but are not limited to, those available from Domantis Limited (Cambridge, UK) and Domantis Inc. (Cambridge, Mass., USA) that are specific to therapeutic targets (see, for example, WO04/058821; WO04/003019; U.S. Pat. Nos. 6,291,158; 6,582,915; 6,696,245; and 6,593,081). Commercially available libraries of domain antibodies can be used to identify anti-CD19 domain antibodies. In certain embodiments, anti-CD19 antibodies comprise a CD19 functional binding unit and a Fc gamma receptor functional binding unit.

In one embodiment, an anti-CD19 domain antibody may comprise any one of, or any combination of the CDRs of the heavy or light chains of the HB12A or HB12B monoclonal antibodies.

In another embodiment, an anti-CD19 domain antibody may comprise CDR3 of HB12A or HB12B VHs together with any combination of the CDRs comprised by the heavy or light chains variable regions of the HB12A or HB12B monoclonal antibodies. An anti-CD19 domain antibody may also comprise CDR3 of HB12A or HB12B VKs together with any combination of the CDRs comprised by the heavy or light chains variable regions of the HB12A or HB12B monoclonal antibodies.

In yet another embodiment, an anti-CD19 domain antibody may comprise CDR3 of HB12A or HB12B VHs. An anti-CD19 domain antibody may also comprise CDR3 of HB12A or HB12B VKs.

5.7. Diabodies

In certain embodiments of the invention, anti-CD19 antibodies are "diabodies". The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

5.8. Vaccibodies

In certain embodiments of the invention, anti-CD19 antibodies are Vaccibodies. Vaccibodies are dimeric polypeptides. Each monomer of a vaccibody consists of a scFv with specificity for a surface molecule on APC connected through a hinge region and a Cγ3 domain to a second scFv. In other embodiments of the invention, vaccibodies containing as one of the scFv's an anti-CD19 antibody fragment may be used to juxtapose those B cells to be destroyed and an effector cell that mediates ADCC. For example, see, Bogen et al., U.S. Patent Application Publication No. 20040253238.

5.9. Linear Antibodies

In certain embodiments of the invention, anti-CD19 antibodies are linear antibodies. Linear antibodies comprise a pair of tandem Fd segments ($V_H$-$C_{H1}$-$V_H$-$C_{H1}$) which form a pair of antigen-binding regions. Linear antibodies can be bispecific or monospecific. See, Zapata et al., *Protein Eng.*, 8(10):1057-1062 (1995).

5.10. Parent Antibody+

In certain embodiments of the invention, anti-CD19 antibody is a parent antibody. A "parent antibody" is an antibody comprising an amino acid sequence which may lack, or may be deficient in, one or more amino acid residues in or adjacent to one or more hypervariable regions thereof compared to an altered/mutant antibody as herein disclosed. Thus, the parent antibody may have a shorter hypervariable region than the corresponding hypervariable region of an antibody mutant as herein disclosed. The parent polypeptide may comprise a native antibody sequence (i.e., a naturally occurring, including a naturally occurring allelic variant) or an antibody sequence with pre-existing amino acid sequence modifications (such as other insertions, deletions and/or substitutions) of a naturally occurring sequence. The parent antibody may be a humanized antibody or a human antibody.

5.11. Antibody Fragments

"Antibody fragments" comprise a portion of a full-length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

Traditionally, these fragments were derived via proteolytic digestion of intact antibodies (see, e.g., Morimoto et al., *Journal of Biochemical and Biophysical Methods*, 24:107-117 (1992) and Brennan et al., *Science*, 229:81 (1985)). However, these fragments can now be produced directly by recombinant host cells. For example, the antibody fragments can be isolated from the antibody phage libraries discussed above. Fab'-SH fragments can also be directly recovered from *E. coli* and chemically coupled to form F(ab')$_2$ fragments (Carter et al., *Bio/Technology*, 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single-chain Fv fragment (scFv). See, for example, WO 93/16185. In certain embodiments, the antibody is not a Fab fragment.

5.12. Bispecific Antibodies

Bispecific antibodies are antibodies that have binding specificities for at least two different epitopes. Exemplary bispecific antibodies may bind to two different epitopes of the B cell surface marker. Other such antibodies may bind a first B cell marker and further bind a second B cell surface marker. An anti-B cell marker binding arm may also be combined with an arm which binds to a triggering molecule on a leukocyte such as a T cell receptor molecule (e.g., CD2 or CD3), or Fc receptors for IgG (FcγR), so as to focus cellular defense mechanisms to the B cell. Bispecific antibodies may also be used to localize cytotoxic agents to the B cell. These antibodies possess a B cell marker-binding arm and an arm which binds the cytotoxic agent (e.g., saporin, anti-interferon-α, vinca alkaloid, ricin A chain, metholaexate or radioactive isotope hapten). Bispecific antibodies can be prepared as full-length antibodies or antibody fragments (e.g., F(ab'): bispecific antibodies).

Methods for making bispecific antibodies are known in the art. (See, for example, Millstein et al., *Nature*, 305:537-539 (1983); Traunecker et al., *EMBO J.*, 10:3655-3659 (1991); Suresh et al., *Methods in Enzymology*, 121:210 (1986); Kostelny et al., *J. Immunol.*, 148(5):1547-1553 (1992); Hollinger et al., *Proc. Natl. Acad. Sci. USA*, 90:6444-6448 (1993); Gruber et al., *J. Immunol.*, 152:5368 (1994); U.S. Pat. Nos. 4,474,893; 4,714,681; 4,925,648; 5,573,920; 5,601,81; 95,731,168; 4,676,980; and 4,676,980, WO 94/04690; WO 91/00360; WO 92/200373; WO 93/17715; WO 92/08802; and EP 03089.)

In one embodiment, where an anti-CD19 antibody of compositions and methods of the invention is bispecific, the anti-CD19 antibody may be human or humanized and may have specificity for human CD19 and an epitope on a T cell or may be capable of binding to a human effector cell such as, for example, a monocyte/macrophage and/or a natural killer cell to effect cell death.

In one embodiment, an anti-CD19 antibody of the invention is a bispecific antibody capable of specifically binding to a first and second antigen, wherein said first antigen is human CD19 and said second antigen is an Fc gamma receptor selected from the group consisting of FcγRI, FcγRIIA, FcγRIIB, FcγRIIIA and/or FcγRIV. In a further embodiment, an anti-CD19 antibody of the invention is a bispecific antibody capable of specifically binding to human CD19 and FcγRIIB. In another embodiment, an anti-CD19 antibody of the invention is a bispecific antibody capable of specifically binding to human CD19 and human FcγRIIB.

5.13. Variant Fc Regions

The present invention provides formulation of proteins comprising a variant Fc region. That is, a non naturally occurring Fc region, for example an Fc region comprising one or more non naturally occurring amino acid residues. Also encompassed by the variant Fc regions of present invention are Fc regions which comprise amino acid deletions, additions and/or modifications.

It will be understood that Fc region as used herein includes the polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat et al. (1991, NIH Publication 91-3242, National Technical Information Service, Springfield, Va.). The "EU index as set forth in Kabat" refers to the residue numbering of the human IgG1 EU antibody as described in Kabat et al. supra. Fc may refer to this region in isolation, or this region in the context of an antibody, antibody fragment, or Fc fusion protein. An Fc variant protein may be an antibody, Fc fusion, or any protein or protein domain that comprises an Fc region including, but not limited to, proteins comprising variant Fc regions, which are non naturally occurring variants of an Fc. Note: Polymorphisms have been observed at a number of Fc positions, including but not limited to Kabat 270, 272, 312, 315, 356, and 358, and thus slight differences between the presented sequence and sequences in the prior art may exist.

The present invention encompasses Fc variant proteins which have altered binding properties for an Fc ligand (e.g., an Fc receptor, C1q) relative to a comparable molecule (e.g., a protein having the same amino acid sequence except having a wild type Fc region). Examples of binding properties include but are not limited to, binding specificity, equilibrium dissociation constant ($K_D$), dissociation and association rates ($k_{off}$ and $k_{on}$ respectively), binding affinity and/or avidity. It is generally understood that a binding molecule (e.g., a Fc variant protein such as an antibody) with a low $K_D$ may be preferable to a binding molecule with a high $K_D$. However, in some instances the value of the $k_{on}$ or $k_{off}$ may be more relevant than the value of the $K_D$. One skilled in the art can determine which kinetic parameter is most important for a given antibody application.

The affinities and binding properties of an Fc domain for its ligand may be determined by a variety of in vitro assay methods (biochemical or immunological based assays) known in the art for determining Fc-FcγR interactions, i.e., specific binding of an Fc region to an FcγR including but not limited to, equilibrium methods (e.g., enzyme-linked immunoabsorbent assay (ELISA), or radioimmunoassay (RIA)), or kinetics (e.g., BIACORE® analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions.

In one embodiment, the Fc variant protein has enhanced binding to one or more Fc ligand relative to a comparable molecule. In another embodiment, the Fc variant protein has an affinity for an Fc ligand that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold greater than that of a comparable molecule. In a specific embodiment, the Fc variant protein has enhanced binding to an Fc receptor. In another specific embodiment, the Fc variant protein has enhanced binding to the Fc receptor FcγRIIIA. In a further specific embodiment, the Fc variant protein has enhanced biding to the Fc receptor FcγRIIB. In still another specific embodiment, the Fc variant protein has enhanced binding to the Fc receptor FcRn. In yet another specific embodiment, the Fc variant protein has enhanced binding to C1q relative to a comparable molecule.

In one embodiment, an anti-CD19 antibody of the invention comprises a variant Fc domain wherein said variant Fc domain has enhanced binding affinity to Fc gamma receptor IIB relative to a comparable non-variant Fc domain. In a further embodiment, an anti-CD19 antibody of the invention comprises a variant Fc domain wherein said variant Fc domain has an affinity for Fc gamma receptor IIB that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold greater than that of a comparable non-variant Fc domain.

The serum half-life of proteins comprising Fc regions may be increased by increasing the binding affinity of the Fc region for FcRn. In one embodiment, the Fc variant protein has enhanced serum half life relative to comparable molecule.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the surface of target cells "arm" the cytotoxic cells and are absolutely required for such killing. Lysis of the target cell is extracellular, requires direct cell-to-cell contact, and does not involve complement. It is contemplated that, in addition to antibodies, other proteins comprising Fc regions, specifically Fc fusion proteins, having the capacity to bind specifically to an antigen-bearing target cell will be able to effect cell-mediated cytotoxicity. For simplicity, the cell-mediated cytotoxicity resulting from the activity of an Fc fusion protein is also referred to herein as ADCC activity.

The ability of any particular Fc variant protein to mediate lysis of the target cell by ADCC can be assayed. To assess ADCC activity an Fc variant protein of interest is added to target cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., 1985 79:277-282; Bruggemann et al., 1987, J Exp Med 166:1351-1361; Wilkinson et al., 2001, J Immunol Methods 258:183-191; Patel et al., 1995 J Immunol Methods 184:29-38. ADCC activity of the Fc variant protein of interest may also be assessed in vivo, e.g., in a animal model such as that disclosed in Clynes et al., 1998, *Proc. Natl. Acad. Sci. USA* 95:652-656.

In one embodiment, an Fc variant protein has enhanced ADCC activity relative to a comparable molecule. In a specific embodiment, an Fc variant protein has ADCC activity that is at least 2 fold, or at least 3 fold, or at least 5 fold or at least 10 fold or at least 50 fold or at least 100 fold greater than that of a comparable molecule. In another specific embodiment, an Fc variant protein has enhanced binding to the Fc receptor FcγRIIIA and has enhanced ADCC activity relative to a comparable molecule. In other embodiments, the Fc variant protein has both enhanced ADCC activity and enhanced serum half life relative to a comparable molecule.

In one embodiment, an Fc variant protein has reduced ADCC activity relative to a comparable molecule. In a specific embodiment, an Fc variant protein has ADCC activity that is at least 2 fold, or at least 3 fold, or at least 5 fold or at least 10 fold or at least 50 fold or at least 100 fold lower than that of a comparable molecule. In another specific embodiment, an Fc variant protein has reduced binding to the Fc receptor FcγRIIIA and has reduced ADCC activity relative to a comparable molecule. In other embodiments, the Fc variant protein has both reduced ADCC activity and enhanced serum half life relative to a comparable molecule.

"Complement dependent cytotoxicity" and "CDC" refer to the lysing of a target cell in the presence of complement. The complement activation pathway is initiated by the binding of the first component of the complement system (C1q) to a molecule, an antibody for example, complexed with a cognate antigen. To assess complement activation, a CDC assay, e.g. as described in Gazzano-Santoro et al., 1996, J. Immunol. Methods, 202:163, may be performed. In one embodiment, an Fc variant protein has enhanced CDC activity relative to a comparable molecule. In a specific embodiment, an Fc variant protein has CDC activity that is at least 2 fold, or at least 3 fold, or at least 5 fold or at least 10 fold or at least 50 fold or at least 100 fold greater than that of a comparable molecule. In other embodiments, the Fc variant protein has both enhanced CDC activity and enhanced serum half life relative to a comparable molecule.

In one embodiment, the Fc variant protein has reduced binding to one or more Fc ligand relative to a comparable molecule. In another embodiment, the Fc variant protein has an affinity for an Fc ligand that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold lower than that of a comparable molecule. In a specific embodiment, the Fc variant protein has reduced binding to an Fc receptor. In another specific embodiment, the Fc variant protein has reduced binding to the Fc receptor FcγRIIIA. In a further specific embodiment, an Fc variant described herein has an affinity for the Fc receptor FcγRIIIA that is at least about 5 fold lower than that of a comparable molecule, wherein said Fc variant has an affinity for the Fc receptor FcγRIIB that is within about 2 fold of that of a comparable molecule. In still another specific embodiment, the Fc variant protein has reduced binding to the Fc receptor FcRn. In yet another specific embodiment, the Fc variant protein has reduced binding to C1q relative to a comparable molecule.

In one embodiment, the present invention provides Fc variants, wherein the Fc region comprises a non naturally occurring amino acid residue at one or more positions selected from the group consisting of 234, 235, 236, 237, 238, 239, 240, 241, 243, 244, 245, 247, 251, 252, 254, 255, 256, 262, 263, 264, 265, 266, 267, 268, 269, 279, 280, 284, 292, 296, 297, 298, 299, 305, 313, 316, 325, 326, 327, 328, 329, 330, 331, 332, 333, 334, 339, 341, 343, 370, 373, 378, 392, 416, 419, 421, 440 and 443 as numbered by the EU index as set forth in Kabat. Optionally, the Fc region may comprise a non naturally occurring amino acid residue at additional and/or alternative positions known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752; WO 04/074455; WO 04/099249; WO 04/063351; WO 05/070963; WO 05/040217, WO 05/092925 and WO 06/020114).

In one embodiment, the present invention provides formulations, wherein the Fc region comprises a non naturally occurring amino acid residue at one or more positions selected from the group consisting of 234, 235, 236, 237, 238, 239, 240, 241, 243, 244, 245, 247, 251, 252, 254, 255, 256, 262, 263, 264, 265, 266, 267, 268, 269, 279, 280, 284, 292, 296, 297, 298, 299, 305, 313, 316, 325, 326, 327, 328, 329, 330, 331, 332, 333, 334, 339, 341, 343, 370, 373, 378, 392, 416, 419, 421, 440 and 443 as numbered by the EU index as set forth in Kabat. Optionally, the Fc region may comprise a non naturally occurring amino acid residue at additional and/or alternative positions known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752; WO 04/074455; WO 04/099249; WO 04/063351; WO 05/070963; WO 05/040217, WO 05/092925 and WO 06/020114).

In a specific embodiment, the present invention provides an Fc variant, wherein the Fc region comprises at least one non naturally occurring amino acid residue selected from the group consisting of 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235F, 236E, 239D, 239E, 239N, 239Q, 239F, 239T, 239H, 239Y, 240I, 240A, 240T, 240M, 241W, 241L, 241Y, 241E, 241R. 243W, 243L 243Y, 243R, 243Q, 244H, 245A, 247L, 247V, 247G, 251F, 252Y, 254T, 255L, 256E, 256M, 262I, 262A, 262T, 262E, 263I, 263A, 263T, 263M, 264L, 264I, 264W, 264T, 264R, 264F, 264M, 264Y, 264E, 265G, 265N, 265Q, 265Y, 265F, 265V, 265I, 265L, 265H, 265T, 266I, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 296I, 296H, 269G, 297S, 297D, 297E, 298H, 298I, 298T, 298F, 299I, 299L, 299A, 299S, 299V, 299H, 299F, 299E, 305I, 313F, 316D, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 331G, 331A, 331L, 331M, 331F, 331W, 331K, 331Q, 331E, 331S, 331V, 331I, 331C, 331Y, 331H, 331R, 331N, 331D, 331T, 332D, 332S, 332W, 332F, 332E, 332N, 332Q, 332T, 332H, 332Y, 332A, 339T, 370E, 370N, 378D, 392T, 396L, 416G, 419H, 421K, 440Y and 434W as numbered by the EU index as set forth in Kabat. Optionally, the Fc region may comprise additional and/or alternative non naturally occurring amino acid residues known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217).

In a specific embodiment, the present invention provides an Fc variant protein formulation, wherein the Fc region comprises at least one non naturally occurring amino acid residue selected from the group consisting of 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235F, 236E, 239D, 239E, 239N, 239Q, 239F, 239T, 239H, 239Y, 240I, 240A, 240T, 240M, 241W, 241 L, 241Y, 241E, 241 R, 243W, 243L 243Y, 243R, 243Q, 244H, 245A, 247L, 247V, 247G, 251F, 252Y, 254T, 255L, 256E, 256M, 262I, 262A, 262T, 262E, 263I, 263A, 263T, 263M, 264L, 264I, 264W, 264T, 264R, 264F, 264M, 264Y, 264E, 265G, 265N, 265Q, 265Y, 265F, 265V, 265I, 265L, 265H, 265T, 266I, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 296I, 296H, 269G, 297S, 297D, 297E, 298H, 298I, 298T, 298F, 299I, 299L, 299A, 299S, 299V, 299H, 299F, 299E, 305I, 313F, 316D, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 331G, 331A, 331L, 331M, 331F, 331W, 331K, 331Q, 331E, 331S, 331V, 331I, 331C, 331Y, 331H, 331R, 331N, 331D, 331I, 332D, 332S, 332W, 332F, 332E, 332N, 332Q, 332T, 332H, 332Y, 332A, 339T, 370E, 370N, 378D, 392T, 396L, 416G, 419H, 421K, 440Y and 434W as numbered by the EU index as set forth in Kabat. Optionally, the Fc region may comprise additional and/or alternative non naturally occurring amino acid residues known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217).

In another embodiment, the present invention provides an Fc variant, wherein the Fc region comprises at least one non naturally occurring amino acid at one or more positions selected from the group consisting of 239, 330 and 332, as numbered by the EU index as set forth in Kabat. In a specific embodiment, the present invention provides an Fc variant, wherein the Fc region comprises at least one non naturally occurring amino acid selected from the group consisting of 239D, 330L and 332E, as numbered by the EU index as set forth in Kabat. Optionally, the Fc region may further comprise additional non naturally occurring amino acid at one or more positions selected from the group consisting of 252, 254, and 256, as numbered by the EU index as set forth in Kabat. In a specific embodiment, the present invention provides an Fc variant, wherein the Fc region comprises at least one non naturally occurring amino acid selected from the group consisting of 239D, 330L and 332E, as numbered by the EU index as set forth in Kabat and at least one non naturally occurring amino acid at one or more positions selected from the group consisting of 252Y, 254T and 256E, as numbered by the EU index as set forth in Kabat.

In another embodiment, the present invention provides an Fc variant, wherein the Fc region comprises at least one non naturally occurring amino acid at one or more positions selected from the group consisting of 234, 235 and 331, as numbered by the EU index as set forth in Kabat. In a specific embodiment, the present invention provides an Fc variant, wherein the Fc region comprises at least one non naturally occurring amino acid selected from the group consisting of 234F, 235F, 235Y, and 331S, as numbered by the EU index as set forth in Kabat. In a further specific embodiment, an Fc variant of the invention comprises the 234F, 235F, and 331S non naturally occurring amino acid residues, as numbered by the EU index as set forth in Kabat. In another specific embodiment, an Fc variant of the invention comprises the 234F, 235Y, and 331S non naturally occurring amino acid residues, as numbered by the EU index as set forth in Kabat. Optionally, the Fc region may further comprise additional non naturally occurring amino acid at one or more positions selected from the group consisting of 252, 254, and 256, as numbered by the EU index as set forth in Kabat. In a specific embodiment, the present invention provides an Fc variant, wherein the Fc region comprises at least one non naturally occurring amino acid selected from the group consisting of 234F, 235F, 235Y, and 331S, as numbered by the EU index as set forth in Kabat; and at least one non naturally occurring amino acid at one or more positions are selected from the group consisting of 252Y, 254T and 256E, as numbered by the EU index as set forth in Kabat.

In another embodiment, the present invention provides an Fc variant protein formulation, wherein the Fc region comprises at least a non naturally occurring amino acid at one or more positions selected from the group consisting of 239, 330 and 332, as numbered by the EU index as set forth in Kabat. In a specific embodiment, the present invention provides an Fc variant protein formulation, wherein the Fc region comprises at least one non naturally occurring amino acid selected from the group consisting of 239D, 330L and 332E, as numbered by the EU index as set forth in Kabat. Optionally, the Fc region may further comprise additional non naturally occurring amino acid at one or more positions selected from the group consisting of 252, 254, and 256, as numbered by the EU index as set forth in Kabat. In a specific embodiment, the present invention provides an Fc variant protein formulation, wherein the Fc region comprises at least one non naturally occurring amino acid selected from the group consisting of 239D, 330L and 332E, as numbered by the EU index as set forth in Kabat and at least one non naturally occurring amino acid at one or more positions are selected from the group consisting of 252Y, 254T and 256E, as numbered by the EU index as set forth in Kabat.

In another embodiment, the present invention provides an Fc variant protein formulation, wherein the Fc region comprises at least one non naturally occurring amino acid at one or more positions selected from the group consisting of 234, 235 and 331, as numbered by the EU index as set forth in Kabat. In a specific embodiment, the present invention provides an Fc variant protein formulation, wherein the Fc region comprises at least one non naturally occurring amino acid selected from the group consisting of 234F, 235F, 235Y, and 331S, as numbered by the EU index as set forth in Kabat. Optionally, the Fc region may further comprise additional non naturally occurring amino acid at one or more positions selected from the group consisting of 252, 254, and 256, as numbered by the EU index as set forth in Kabat. In a specific embodiment, the present invention provides an Fc variant protein formulation, wherein the Fc region comprises at least one non naturally occurring amino acid selected from the group consisting of 234F, 235F, 235Y, and 331S, as numbered by the EU index as set forth in Kabat; and at least one non naturally occurring amino acid at one or more positions are selected from the group consisting of 252Y, 254T and 256E, as numbered by the EU index as set forth in Kabat.

In one embodiment, the Fc variants of the present invention may be combined with other known Fc variants such as those disclosed in Ghetie et al., 1997, Nat. Biotech. 15:637-40; Duncan et al, 1988, Nature 332:563-564; Lund et al., 1991, J. Immunol. 147:2657-2662; Lund et al, 1992, Mol Immunol 29:53-59; Alegre et al, 1994, Transplantation 57:1537-1543; Hutchins et al., 1995, *Proc Natl. Acad Sci USA* 92:11980-11984; Jefferis et al, 1995, Immunol Lett. 44:111-117; Lund et al., 1995, Faseb J 9:115-119; Jefferis et al, 1996, Immunol Lett 54:101-104; Lund et al, 1996, J Immunol 157:4963-4969; Armour et al., 1999, Eur J Immunol 29:2613-2624; Idusogie et al, 2000, J Immunol 164:4178-4184; Reddy et al, 2000, J Immunol 164:1925-1933; Xu et al., 2000, Cell Immunol 200:16-26; Idusogie et al, 2001, J Immunol 166:2571-2575; Shields et al., 2001, J Biol Chem 276:6591-6604; Jefferis et al, 2002, Immunol Lett 82:57-65; Presta et al., 2002, Biochem Soc Trans 30:487-490); U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 6,821,505; 6,277,375; U.S. Patent Publication Nos. 2004/0002587 and PCT Publications WO 94/29351; WO 99/58572; WO 00/42072; WO 02/060919; WO 04/029207; WO 04/099249; WO 04/063351. Also encompassed by the present invention are Fc regions which comprise deletions, additions and/or modifications. Still other modifications/substitutions/additions/deletions of the Fc domain will be readily apparent to one skilled in the art.

Methods for generating non naturally occurring Fc regions are known in the art. For example, amino acid substitutions and/or deletions can be generated by mutagenesis methods, including, but not limited to, site-directed mutagenesis (Kunkel, *Proc. Natl. Acad. Sci. USA* 82:488-492 (1985)), PCR mutagenesis (Higuchi, in "PCR Protocols: A Guide to Methods and Applications", Academic Press, San Diego, pp. 177-183 (1990)), and cassette mutagenesis (Wells et al., Gene 34:315-323 (1985)). Preferably, site-directed mutagenesis is performed by the overlap-extension PCR method (Higuchi, in "PCR Technology: Principles and Applications for DNA Amplification", Stockton Press, New York, pp. 61-70 (1989)). The technique of overlap-extension PCR (Higuchi, ibid.) can also be used to introduce any desired mutation(s) into a target sequence (the starting DNA). For example, the first round of PCR in the overlap-extension method involves amplifying the target sequence with an outside primer (primer 1) and an internal mutagenesis primer (primer 3), and separately with a second outside primer (primer 4) and an internal primer (primer 2), yielding two PCR segments (segments A and B). The internal mutagenesis primer (primer 3) is designed to contain mismatches to the target sequence specifying the desired mutation(s). In the second round of PCR, the products of the first round of PCR (segments A and B) are amplified by PCR using the two outside primers (primers 1 and 4). The resulting full-length PCR segment (segment C) is digested with restriction enzymes and the resulting restriction fragment is cloned into an appropriate vector. As the first step of mutagenesis, the starting DNA (e.g., encoding an Fc fusion protein, an antibody or simply an Fc region), is operably cloned into a mutagenesis vector. The primers are designed to reflect the desired amino acid substitution. Other methods useful for the generation of variant Fc regions are known in the art (see, e.g., U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 6,821,505; 6,277,375; U.S. Patent Publication Nos. 2004/0002587 and PCT Publications WO 94/29351; WO 99/58572; WO 00/42072; WO 02/060919; WO 04/029207; WO 04/099249; WO 04/063351).

In some embodiments, an Fc variant protein comprises one or more engineered glycoforms, i.e., a carbohydrate composition that is covalently attached to the molecule comprising an Fc region. Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, Nat. Biotechnol 17:176-180; Davies et al., 20017 Biotechnol Bioeng 74:288-294; Shields et al, 2002, J Biol Chem 277:26733-26740; Shinkawa et al., 2003, J Biol Chem 278:3466-3473) U.S. Pat. No. 6,602,684; U.S. Ser. Nos. 10/277,370; 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland). See, e.g., WO 00061739; EA01229125; US 20030115614; Okazaki et al., 2004, JMB, 336: 1239-49.

It is contemplated that an Fc variant described herein may be generated from, or a variant Fc region described herein may be introduced into any antibody described in the art including but not limited to anti-fluorescein monoclonal antibody, 4-4-20 (Kranz et al., 1982 J. Biol. Chem. 257(12): 6987-6995), a humanized anti-TAG72 antibody (CC49) (Sha et al., 1994 Cancer Biother. 9(4): 341-9), an antibody that specifically bind an Eph Receptor including, but not limited to those disclosed in PCT Publication Nos. WO 04/014292, WO 03/094859 and U.S. patent application Ser. No. 10/863,729, antibodies that specifically bind Integrin αVβ3 including, but not limited to, LM609 (Scripps), the murine monoclonal LM609 (PCT Publication WO 89/015155 and U.S. Pat. No. 5,753,230); the humanized monoclonal antibody MEDI-522 (a.k.a. VITAXIN®, MedImmune, Inc., Gaithersburg, Md.; Wu et al., 1998, PNAS USA 95(11): 6037-6042; PCT Publications WO 90/33919 and WO 00/78815), an antibody against interferon alpha as disclosed in WO/2005/05059106, an antibody against the interferon receptor 1 as disclosed in WO/2006/059106, ERBITUX™ (cetuximab) (also known as IMC-C225) (ImClone Systems Inc.), a chimerized monoclonal antibody against EGFR; HERCEPTIN® (Trastuzumab) (Genentech, CA) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection. Other examples are a humanized anti-CD18 F(ab')$_2$ (Genentech); CDP860 which is a humanized anti-CD18 F(ab')2 (Celltech, UK); PRO542 which is an anti-HIV gp120 antibody fused with CD4 (Progenics/Genzyme Transgenics); C14 which is an anti-CD14 antibody (ICOS Pharm); a humanized anti-VEGF IgG1 antibody (Genentech); OVAREX™ (Oregovomab) which is a murine anti-CA 125 antibody (Altarex); PANOREX™ (edrecolomab) which is a murine anti-17-IA cell surface antigen IgG2a antibody (Glaxo Wellcome/Centocor); IMC-C225 which is a chimeric anti-EGFR IgG antibody (ImClone System); VITAXIN™ which is a humanized anti-αVβ3 integrin antibody (Applied Molecular Evolution/MedImmune); CAMPATH™1H/LDP-03 which is a humanized anti CD52 IgG1 antibody (Leukosite); Smart M195 which is a humanized anti-CD33 IgG antibody (Protein Design Lab/Kanebo); RITUXAN™ (rituximab) which is a chimeric anti-CD20 IgG1 antibody (IDEC Pharm/Genentech, Roche/Zettyaku); LYMPHOCIDE™ (epratuzumab) which is a humanized anti-CD22 IgG antibody (Immunomedics); Smart ID10 which is a humanized anti-HLA antibody (Protein Design Lab); ONCOLYM™ (Lym-1) is a radiolabelled murine anti-HLA DR antibody (Techniclone); anti-CD11a is a humanized IgG1 antibody (Genetech/Xoma); ICM3 is a humanized anti-ICAM3 antibody (ICOS Pharm); IDEC-114 is a primatized anti-CD80 antibody (IDEC Pharm/Mitsubishi); ZEVALIN™ (ipritumomab tiuxetan) is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); Orthoclone™ OKT4A is a humanized anti-CD4 IgG antibody (Ortho Biotech); ANTOVA™ (ruplizumab) is a humanized anti-CD40L IgG antibody (Biogen); ANTEGREN™ (natalizumab) is a humanized anti-VLA-4 IgG antibody (Elan); MDX-33 is a human anti-CD64 (FcγR) antibody (Medarex/Centeon); rhuMab-E25 is a humanized anti-IgE IgG1 antibody (Genentech/Norvartis/Tanox Biosystems); IDEC-152 is a primatized anti-CD23 antibody (IDEC Pharm); ABX-CBL is a murine anti CD-147 IgM antibody (Abgenix); BTI-322 is a rat anti-CD2 IgG antibody (Medimmune/Bio Transplant); ORTHOCLONE-OKT3 ™ (muromonab-CD3) is a murine anti-CD3 IgG2a antibody (ortho Biotech); SIMULECT™ (basiliximab) is a chimeric anti-CD25 IgG1 antibody (Novartis Pharm); LDP-01 is a humanized anti-β2-integrin IgG antibody (LeukoSite); Anti-LFA-1 is a murine anti CD18 F(ab')2 (Pasteur-Mericex/Immunotech); CAT-152 is a human anti-TGF-β2 antibody (Cambridge Ab Tech); and Corsevin M is a chimeric anti-Factor VII antibody (Centocor).

Additional antibodies which may comprise an Fc variant region described herein may specifically bind a cancer or tumor antigen for example, including, but not limited to, KS 1/4 pan-carcinoma antigen (Perez and Walker, 1990, J. Immunol. 142: 3662-3667; Bumal, 1988, Hybridoma 7(4): 407-415), ovarian carcinoma antigen (CA125) (Yu et al., 1991, Cancer Res. 51(2): 468-475), prostatic acid phosphate (Tailor et al., 1990, Nucl. Acids Res. 18(16): 4928), prostate specific antigen (Henttu and Vihko, 1989, Biochem. Biophys. Res. Comm. 160(2): 903-910; Israeli et al., 1993, Cancer Res. 53: 227-230), melanoma-associated antigen p97 (Estin et al., 1989, J. Natl. Cancer Instit. 81(6): 445-446), melanoma antigen gp75 (Vijayasardahl et al., 1990, J. Exp. Med. 171(4): 1375-1380), high molecular weight melanoma antigen (HMW-MAA) (Natali et al., 1987, Cancer 59: 55-63; Mittelman et al., 1990, J. Clin. Invest. 86: 2136-2144), prostate specific membrane antigen, carcinoembryonic antigen (CEA) (Foon et al., 1994, Proc. Am. Soc. Clin. Oncol. 13: 294), polymorphic epithelial mucin antigen, human milk fat globule antigen, colorectal tumor-associated antigens such as: CEA, TAG-72 (Yokata et al., 1992, Cancer Res. 52: 3402-3408), CO17-1A (Ragnhammar et al., 1993, Int. J. Cancer 53: 751-758); GICA 19-9 (Herlyn et al., 1982, J. Clin. Immunol. 2: 135), CTA-1 and LEA, Burkitt's lymphoma antigen-38.13, CD19 (Ghetie et al., 1994, Blood 83: 1329-1336), human B-lymphoma antigen-CD20 (Reff et al., 1994, Blood 83:435-445), CD33 (Sgouros et al., 1993, J. Nucl. Med. 34:422-430), melanoma specific antigens such as ganglioside GD2 (Saleh et al., 1993, J. Immunol., 151, 3390-3398), ganglioside GD3 (Shitara et al., 1993, Cancer Immunol. Immunother. 36:373-380), ganglioside GM2 (Livingston et al., 1994, J. Clin. Oncol. 12: 1036-1044), ganglioside GM3 (Hoon et al., 1993, Cancer Res. 53: 5244-5250), tumor-specific transplantation type of cell-surface antigen (TSTA) such as virally-induced tumor antigens including T-antigen DNA tumor viruses and Envelope antigens of RNA tumor viruses, oncofetal antigen-alpha-fetoprotein such as CEA of colon, bladder tumor oncofetal antigen (Hellstrom et al., 1985, Cancer. Res. 45:2210-2188), differentiation antigen such as human lung carcinoma antigen L6, L20 (Hellstrom et al., 1986, Cancer Res. 46: 3917-3923), antigens of fibrosarcoma, human leukemia T cell antigen-Gp37 (Bhattacharya-Chatterjee et al., 1988, J. of Immun. 141:1398-1403), neoglycoprotein, sphingolipids, breast cancer antigen such as EGFR (Epidermal growth factor receptor), HER2 antigen (p185HER2), polymorphic epithelial mucin (PEM) (Hilkens et al., 1992, Trends in Bio. Chem. Sci. 17:359), malignant human lymphocyte antigen-APO-1 (Bernhard et al., 1989, Science 245: 301-304), differentiation antigen (Feizi, 1985, Nature 314: 53-57) such as T antigen found in fetal erythrocytes, primary endoderm I antigen found in adult erythrocytes, preimplantation embryos, I(Ma) found in gastric adenocarcinomas, M18, M39 found in breast epithelium, SSEA-1 found in myeloid cells, VEP8, VEP9, My1, VIM-D5, D156-22 found in colorectal cancer, TRA-1-85 (blood group H), C14 found in colonic adenocarcinoma, F3 found in lung adenocarcinoma, AH6 found in gastric cancer, Y hapten, Ley found in embryonal carcinoma cells, TL5 (blood group A), EGF receptor found in A431 cells, E1 series (blood group B) found in pancreatic cancer, FC10.2 found in embryonal carcinoma cells, gastric adenocarcinoma antigen, CO-514 (blood group Lea) found in Adenocarcinoma, NS-10 found in adenocarcinomas, CO-43 (blood group Leb), G49 found in EGF receptor of A431 cells, MH2 (blood group ALeb/Ley) found in colonic adenocarcinoma, 19.9 found in colon cancer, gastric cancer mucins, T5A7 found in myeloid cells, R24 found in melanoma, 4.2, GD3, D1.1, OFA-1, GM2, OFA-2, GD2, and M1:22:25:8 found in embryonal carcinoma cells, and SSEA-3 and SSEA-4 found in 4 to 8-cell stage embryos. In one embodiment, the antigen is a T cell receptor derived peptide from a Cutaneous Tcell Lymphoma (see, Edelson, 1998, The Cancer Journal 4:62).

An Fc variant described herein may be generated from, or a variant Fc region described herein may be introduced into any antibody. Furthermore, a variant Fc region described herein may be utilized to generate an Fc fusion protein. Accordingly, virtually any molecule may be targeted by and/or incorporated into an antibody and/or Fc fusion protein comprising an Fc variant described herein including, but not limited to, the following list of proteins, as well as subunits, domains, motifs and epitopes belonging to the following list of proteins: renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VII, factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a scrum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors such as, for example, EGFR, VEGFR; interferons such as alpha interferon (α-IFN), beta interferon (β-IFN) and gamma interferon (γ-IFN); interferon receptor components such as interferon receptor 1; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor; platelet-derived growth factor (PDGF); fibroblast growth factor such as αFGF and βFGF; epidermal growth factor (EGF); transforming growth factor (TGF) such as TGF-alpha and TGF-beta, including TGF-1, TGF-2, TGF-3, TGF-4, or TGF-5; insulin-like growth factor-I and -II (IGF-I and IGF-II); des (1-3)-IGF-I (brain IGF-I), insulin-like growth factor binding proteins; CD proteins such as CD2, CD3, CD4, CD 8, CD11a, CD14, CD18, CD19, CD20, CD22, CD23, CD25, CD33, CD34, CD40, CD40L, CD52, CD63, CD64, CD80 and CD147; erythropoietin; osteoinductive factors; immunotoxins; a bone morphogenetic protein (BMP); an interferon such as interferon-alpha, -beta, and -gamma; colony stimulating factors (CSFs), such as M-CSF, GM-CSF, and G-CSF; interleukins (ILs), e.g., IL-1 to IL-13; TNFα, HMGB1; HMGB2; superoxide dismutase; T-cell receptors; surface membrane proteins; decay accelerating factor; viral antigen such as, for example, a portion of the AIDS envelope, e.g., gp120; transport proteins; homing receptors; addressins; regulatory proteins; cell adhesion molecules such as LFA-1, Mac 1, p150.95, VLA-4, ICAM-1, ICAM-3 and VCAM, a4/p7 integrin, and (Xv/p3 integrin including either a or subunits thereof, integrin alpha subunits such as CD49a, CD49b, CD49c, CD49d, CD49e, CD49f, alpha7, alpha8, alpha9, alphaD, CD11a, CD11b, CD51, CD11c, CD41, alphaIIb, alphaIELb; integrin beta subunits such as, CD29, CD 18, CD61, CD104, beta5, beta6, beta7 and beta8; Integrin subunit combinations including but not limited to, αVβ3, αVβ5 and α4β7; a member of an apoptosis pathway; IgE; blood group antigens; flk2/flt3 receptor; obesity (OB) receptor; mp1 receptor; CTLA-4; protein C; a chitinase or chitinase-like molecule such as YKL-40 and AMCase; an Eph receptor such as EphA2, EphA4, EphB2, etc.; a Human Leukocyte Antigen (HLA) such as HLA-DR; complement proteins such as complement receptor CR1, C1Rq and other complement factors such as C3, and C5; a glycoprotein receptor such as GpIbα, GPIIb/IIIa and CD200; co-stimulatory molecules such as CD28/CTLA-4, ICOS/AILIM, PD-1.

Additional molecules which may comprise a variant Fc region described herein are those that specifically bind cancer antigens including, but not limited to, ALK receptor (pleiotrophin receptor), pleiotrophin, KS 1/4 pan-carcinoma antigen; ovarian carcinoma antigen (CA125); prostatic acid phosphate; prostate specific antigen (PSA); melanoma-associated antigen p97; melanoma antigen gp75; high molecular weight melanoma antigen (HMW-MAA); prostate specific membrane antigen; carcinoembryonic antigen (CEA); polymorphic epithelial mucin antigen; human milk fat globule antigen; colorectal tumor-associated antigens such as: CEA, TAG-72, CO17-1A, GICA 19-9, CTA-1 and LEA; Burkitt's lymphoma antigen-38.13; CD19; human B-lymphoma antigen-CD20; CD33; melanoma specific antigens such as ganglioside GD2, ganglioside GD3, ganglioside GM2 and ganglioside GM3; tumor-specific transplantation type cell-surface antigen (TSTA); virally-induced tumor antigens including T-antigen, DNA tumor viruses and Envelope antigens of RNA tumor viruses; oncofetal antigen-alpha-fetoprotein such as CEA of colon, 5T4 oncofetal trophoblast glycoprotein and bladder tumor oncofetal antigen; differentiation antigen such as human lung carcinoma antigens L6 and L20; antigens of fibrosarcoma; human leukemia T cell antigen-Gp37; neoglycoprotein; sphingolipids; breast cancer antigens such as EGFR (Epidermal growth factor receptor); NY-BR-16; NY-BR-16 and HER2 antigen (p185HER2); polymorphic epithelial mucin (PEM); malignant human lymphocyte antigen-APO-1; differentiation antigen such as I antigen found in fetal erythrocytes; primary endoderm I antigen found in adult erythrocytes; preimplantation embryos; I(Ma) found in gastric adenocarcinomas; M18, M39 found in breast epithelium; SSEA-1 found in myeloid cells; VEP8; VEP9; My1; VIM-D5; D156-22 found in colorectal cancer; TRA-1-85 (blood group H); SCP-1 found in testis and ovarian cancer; C14 found in colonic adenocarcinoma; F3 found in lung adenocarcinoma; AH6 found in gastric cancer; Y hapten; Ley found in embryonal carcinoma cells; TL5 (blood group A); EGF receptor found in A431 cells; E1 series (blood group B) found in pancreatic cancer; FC10.2 found in embryonal carcinoma cells; gastric adenocarcinoma antigen; CO-514 (blood group Lea) found in Adenocarcinoma; NS-10 found in adenocarcinomas; CO-43 (blood group Leb); G49 found in EGF receptor of A431 cells; MH2 (blood group ALeb/Ley) found in colonic adenocarcinoma; 19.9 found in colon cancer; gastric cancer mucins; T5A7 found in myeloid cells; R24 found in melanoma; 4.2, GD3, D1.1, OFA-1, GM2, OFA-2, GD2, and M1:22:25:8 found in embryonal carcinoma cells and SSEA-3 and SSEA-4 found in 4 to 8-cell stage embryos; Cutaneous Tcell Lymphoma antigen; MART-1 antigen; Sialy Tn (STn) antigen; Colon cancer antigen NY-CO-45; Lung cancer antigen NY-LU-12 variant A; Adenocarcinoma antigen ART1; Paraneoplastic associated brain-testis-cancer antigen (onconeuronal antigen MA2; paraneoplastic neuronal antigen); Neuro-oncological ventral antigen 2 (NOVA2); Hepatocellular carcinoma antigen gene 520; TUMOR-ASSOCIATED ANTIGEN CO-029; Tumor-associated antigens MAGE-C1 (cancer/testis antigen CT7), MAGE-B1 (MAGE-XP antigen), MAGE-B2 (DAM6), MAGE-2, MAGE-4a, MAGE-4b and MAGE-X2; Cancer-Testis Antigen (NY-EOS-1); YKL-40 and fragments of any of the above-listed polypeptides.

5.14. Glycosylation of Antibodies

In still another embodiment, the glycosylation of antibodies utilized in accordance with the invention is modified. For example, an aglycoslated antibody can be made (i.e., the antibody lacks glycosylation). Glycosylation can be altered to, for example, increase the affinity of the antibody for a target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861. One or more amino acid substitutions can also be made that result in elimination of a glycosylation site present in the Fc region (e.g., Asparagine 297 of IgG). Furthermore, aglycosylated antibodies may be produced in bacterial cells which lack the necessary glycosylation machinery.

An antibody can also be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) J. Biol. Chem. 277:26733-26740; Umana et al. (1999) Nat. Biotech. 17:176-1, as well as, U.S. Pat. No. 6,946,292; European Patent No: EP 1,176,195; PCT Publications WO 03/035835; WO 99/54342 each of which is incorporated herein by reference in its entirety.

5.15. Engineering Effector Function

It may be desirable to modify an anti-CD19 antibody of the invention with respect to effector function, so as to enhance the effectiveness of the antibody in treating B cell malignancies, for example. For example, cysteine residue(s) may be introduced in the Fc region, thereby allowing interchain disulfide bond formation in this region. The homodimeric antibody thus generated may have improved internalization capability and/or increased complement-mediated cell killing and/or antibody-dependent cellular cytotoxicity (ADCC). See, Caron et al., J. Exp Med., 176:1191-1195 (1992) and Shopes, B., J. Immunol., 148:2918-2922 (1992). Homodimeric antibodies with enhanced anti-tumor activity may also be prepared using heterobifunctional cross-linkers as described in Wolff et al., Cancer Research, 53:2560-2565 (1993). An antibody can also be engineered which has dual Fc regions and may thereby have enhanced complement lysis and ADCC capabilities. See, Stevenson et al., Anti-Cancer Drug Design, 3:219-230 (1989).

Other methods of engineering Fc regions of antibodies so as to alter effector functions are known in the art (e.g., U.S. Patent Publication No. 20040185045 and PCT Publication No. WO 2004/016750, both to Koenig et al., which describe altering the Fc region to enhance the binding affinity for FcγRIIB as compared with the binding affinity for FCγRIIA; see, also, PCT Publication Nos. WO 99/58572 to Armour et al., WO 99/51642 to Idusogie et al., and U.S. Pat. No. 6,395,272 to Deo et al.; the disclosures of which are incorporated herein in their entireties). Methods of modifying the Fc region to decrease binding affinity to FcγRIIB are also known in the art (e.g., U.S. Patent Publication No. 20010036459 and PCT Publication No. WO 01/79299, both to Ravetch et al., the disclosures of which are incorporated herein in their entireties). Modified antibodies having variant Fc regions with enhanced binding affinity for FcγRIIIA and/or FcγRIIA as compared with a wildtype Fc region have also been described (e.g., PCT Publication Nos. WO 2004/063351, to Stavenhagen et al., the disclosure of which is incorporated herein in its entirety).

In vitro assays known in the art can be used to determine whether anti-CD19 antibodies used in compositions and methods of the invention are capable of mediating ADCC, such as those described herein.

5.16. Manufacture/Production of Anti-CD19 Antibodies

Once a desired anti-CD19 antibody is engineered, the anti-CD19 antibody can be produced on a commercial scale using methods that are well-known in the art for large scale manufacturing of antibodies. For example, this can be accomplished using recombinant expressing systems such as, but not limited to, those described below.

5.17. Recombinant Expression Systems

Recombinant expression of an antibody or variant thereof, generally requires construction of an expression vector containing a polynucleotide that encodes the antibody. Once a polynucleotide encoding an antibody molecule or a heavy or light chain of an antibody, or portion thereof, has been obtained, the vector for the production of the antibody molecule may be produced by recombinant DNA technology using techniques well-known in the art. See, e.g., U.S. Pat. No. 6,331,415, which is incorporated herein by reference in its entirety. Thus, methods for preparing a protein by expressing a polynucleotide containing an antibody encoding nucleotide sequence are described herein. Methods which are well-known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule (see, e.g., International Publication Nos. WO 86/05807 and WO 89/01036; and U.S. Pat. No. 5,122,464) and the variable domain of the antibody may be cloned into such a vector for expression of the entire heavy, the entire light chain, or both the entire heavy and light chains.

In another embodiment, anti-CD19 antibodies can be made using targeted homologous recombination to produce all or portions of the anti-CD19 antibodies (see, U.S. Pat. Nos. 6,063,630, 6,187,305, and 6,692,737). In certain embodiments, anti-CD19 antibodies can be made using random recombination techniques to produce all or portions of the anti-CD19 antibodies (see, U.S. Pat. Nos. 6,361,972, 6,524,818, 6,541,221, and 6,623,958). Anti-CD19 antibodies can also be produced in cells expressing an antibody from a genomic sequence of the cell comprising a modified immunoglobulin locus using Cre-mediated site-specific homologous recombination (see, U.S. Pat. No. 6,091,001). The host cell line may be derived from human or nonhuman species including but not limited to mouse, and Chinese hamster. Where human or humanized antibody production is desired, the host cell line should be a human cell line. These methods may advantageously be used to engineer stable cell lines which permanently express the antibody molecule.

Once the expression vector is transferred to a host cell by conventional techniques, the transfected cells are then cultured by conventional techniques to produce an antibody. Thus, the invention includes host cells containing a polynucleotide encoding an antibody of the invention or fragments thereof, or a heavy or light chain thereof, or portion thereof, or a single-chain antibody of the invention, operably linked to a heterologous promoter. In certain embodiments for the expression of double-chained antibodies, vectors encoding both the heavy and light chains may be co-expressed in the host cell for expression of the entire immunoglobulin molecule, as detailed below.

A variety of host-expression vector systems may be utilized to express an anti-CD19 antibody or portions thereof that can be used in the engineering and generation of anti-CD19 antibodies (see, e.g., U.S. Pat. No. 5,807,715). For example, mammalian cells such as Chinese hamster ovary cells (CHO), in conjunction with a vector such as the major intermediate early gene promoter element from human cytomegalovirus is an effective expression system for antibodies (Foecking et al., *Gene,* 45:101 (1986); and Cockett et al., *Bio/Technology,* 8:2 (1990)). In addition, a host cell strain may be chosen which modulates the expression of inserted antibody sequences, or modifies and processes the antibody gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any functional immunoglobulin chains), CRL7O3O and HsS78Bst cells.

In one embodiment, human cell lines developed by immortalizing human lymphocytes can be used to recombinantly produce monoclonal human anti-CD19 antibodies.

In one embodiment, the human cell line PER.C6. (Crucell, Netherlands) can be used to recombinantly produce monoclonal human anti-CD19 antibodies.

In bacterial systems, a number of expression vectors may be advantageously selected depending upon the use intended for the antibody molecule being expressed. For example, when a large quantity of such an antibody is to be produced, for the generation of pharmaceutical compositions comprising an anti-CD19 antibody, vectors which direct the expression of high levels of fusion protein products that are readily purified may be desirable. Such vectors include, but are not limited to, the *E. coli* expression vector pUR278 (Ruther et al., *EMBO,* 12:1791 (1983)), in which the antibody coding sequence may be ligated individually into the vector in frame with the lac Z coding region so that a fusion protein is produced; pIN vectors (Inouye & Inouye, 1985, *Nucleic Acids Res.* 13:3101-3109 (1985); Van Heeke & Schuster, 1989, *J. Biol. Chem.,* 24:5503-5509 (1989)); and the like. pGEX vectors may also be used to express foreign polypeptides as fusion proteins with glutathione-S-transferase (GST). In general, such fusion proteins are soluble and can easily be purified from lysed cells by adsorption and binding to glutathione-agarose affinity matrix followed by elution in the presence of free glutathione. The pGEX vectors are designed to introduce athrombin and/or factor Xa protease cleavage sites into the expressed polypeptide so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example, the polyhedrin gene) of the virus and placed under control of an AcNPV promoter (for example, the polyhedrin promoter).

In mammalian host cells, a number of virus based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion into a non-essential region of the viral genome (e.g., region E1 or E3) will result in a recombinant virus that is viable and capable of expressing the antibody molecule in infected hosts (e.g., see, Logan & Shenk, *Proc. Natl. Acad. Sci. USA,* 81:355-359 (1984)). Specific initiation signals may also be required for efficient translation of inserted antibody coding sequences. These signals include the ATG initiation codon and adjacent sequences. Furthermore, the initiation codon should generally be in frame with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., *Methods in Enzymol.,* 153:51-544 (1987)).

Stable expression can be used for long-term, high-yield production of recombinant proteins. For example, cell lines which stably express the antibody molecule may be generated. Host cells can be transformed with an appropriately engineered vector comprising expression control elements (e.g., promoter, enhancer, transcription terminators, polyadenylation sites, etc.), and a selectable marker gene. Following the introduction of the foreign DNA, cells may be allowed to grow for 1-2 days in an enriched media, and then are switched to a selective media. The selectable marker in the recombinant plasmid confers resistance to the selection and allows cells that stably integrated the plasmid into their chromosomes to grow and form foci which in turn can be cloned and expanded into cell lines. Plasmids that encode an anti-CD19 antibody can be used to introduce the gene/cDNA into any cell line suitable for production in culture.

A number of selection systems may be used, including, but not limited to, the herpes simplex virus thymidine kinase (Wigler et al., *Cell,* 11:223 (1977)), hypoxanthineguanine phosphoribosyltransferase (Szybalska & Szybalski, *Proc. Natl. Acad. Sci. USA,* 48:202 (1992)), and adenine phosphoribosyltransferase (Lowy et al., *Cell,* 22:8-17 (1980)) genes can be employed in tk$^-$, hgprt$^-$ or aprT$^-$ cells, respectively. Also, antimetabolite resistance can be used as the basis of selection for the following genes: dhfr, which confers resistance to methotrexate (Wigler et al., *Natl. Acad. Sci. USA,* 77:357 (1980); O'Hare et al., *Proc. Natl. Acad. Sci. USA,* 78:1527 (1981)); gpt, which confers resistance to mycophenolic acid (Mulligan & Berg, *Proc. Natl. Acad. Sci. USA,* 78:2072 (1981)); neo, which confers resistance to the aminoglycoside G-418 (Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); May, TIB TECH 11(5):155-2 15 (1993)); and hygro, which confers resistance to hygromycin (Santerre et al., *Gene,* 30:147 (1984)). Methods commonly known in the art of recombinant DNA technology may be routinely applied to select the desired recombinant clone, and such methods are described, for example, in Ausubel et al. (eds.), *Current Protocols in Molecular Biology*, John Wiley & Sons, NY (1993); Kriegler, *Gene Transfer and Expression, A Laboratory Manual*, Stockton Press, NY (1990); and in Chapters 12 and 13, Dracopoli et al. (eds.), *Current Protocols in Human Genetics*, John Wiley & Sons, NY (1994); Colberre-Garapin et al., 1981, *J. Mol. Biol.*, 150:1, which are incorporated by reference herein in their entireties.

The expression levels of an antibody molecule can be increased by vector amplification (for a review, see, Bebbington and Hentschel, *The use of vectors based on gene amplification for the expression of cloned genes in mammalian cells in DNA cloning*, Vol. 3. Academic Press, New York (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.*, 3:257 (1983)). Antibody expression levels may be amplified through the use recombinant methods and tools known to those skilled in the art of recombinant protein production, including technologies that remodel surrounding chromatin and enhance transgene expression in the form of an active artificial transcriptional domain.

The host cell may be co-transfected with two expression vectors, the first vector encoding a heavy chain derived polypeptide and the second vector encoding a light chain derived polypeptide. The two vectors may contain identical or different selectable markers. A single vector which encodes, and is capable of expressing, both heavy and light chain polypeptides may also be used. In such situations, the light chain should be placed 5' to the heavy chain to avoid an excess of toxic free heavy chain (Proudfoot, *Nature* 322:562-65 (1986); and Kohler, 1980, *Proc. Natl. Acad. Sci. USA*, 77:2197 (1980)). The coding sequences for the heavy and light chains may comprise cDNA or genomic DNA.

Once an antibody molecule has been produced by recombinant expression, it may be purified by any method known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the antibodies of the present invention or fragments thereof may be fused to heterologous polypeptide sequences described herein or otherwise known in the art to facilitate purification.

5.17.1. Antibody Purification and Isolation

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology*, 10:163-167 (1992) describe a procedure for isolating antibodies which are secreted into the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody mutant is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, ion exchange chromatography, gel electrophoresis, dialysis, and/or affinity chromatography either alone or in combination with other purification steps. The suitability of protein A as an affinity ligand depends on the species and isotype of any immunoglobulin Fc domain that is present in the antibody mutant. Protein A can be used to purify antibodies that are based on human γ1, γ2, or γ4 heavy chains (Lindmark et al., *J. Immunol. Methods*, 62:1-13 (1983)). Protein G is recommended for all mouse isotypes and for human γ3 (Guss et al., *EMBO J.*, 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $CH_3$ domain, the Bakerbond ABX resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin, SEPHAROSE chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, and performed at low salt concentrations (e.g., from about 0-0.25 M salt).

5.18. Therapeutic Anti-CD19 Antibodies

An anti-CD19 antibody used in compositions and methods of the invention may be a human antibody or a humanized antibody that may mediate B cell lineage apoptosis and/or human ADCC, or can be selected from known anti-CD19 antibodies that may mediate B lineage cell apoptosis and/or human ADCC. In certain embodiments, anti-CD19 antibodies can be chimeric antibodies. In certain embodiments, an anti-CD19 antibody can be a monoclonal human, humanized, or chimeric anti-CD19 antibody. An anti-CD19 antibody used in compositions and methods of the invention may be a human antibody or a humanized antibody of the IgG1 or IgG3 human isotype or any IgG1 or IgG3 allele found in the human population. In other embodiments, an anti-CD19 antibody used in compositions and methods of the invention can be a human antibody or a humanized antibody of the IgG2 or IgG4 human isotype or any IgG2 or IgG4 allele found in the human population.

While such antibodies can be generated using the techniques described above, in other embodiments of the invention, the murine antibodies HB12A and HB12B as described herein or other commercially available anti-CD19 antibodies can be chimerized, humanized, or made into human antibodies.

For example, known anti-CD19 antibodies that can be used include, but are not limited to, HD37 (IgG1, kappa) (DAKO North America, Inc, Carpinteria, Calif.), BU12 (Callard et al., *J. Immunology*, 148(10):2983-7 (1992)), 4G7 (IgG1) (Meeker et al., *Hybridoma*, 3(4):305-20 (1984 Winter)), J4.119 (Beckman Coulter, Krefeld, Germany), B43 (PharMingen, San Diego, Calif.), SJ25C1 (BD PharMingen, San Diego, Calif.), FMC63 (IgG2a) (Zola et al., *Immunol. Cell. Biol.* 69(PT6): 411-22 (1991); Nicholson et al., *Mol. Immunol.*, 34:1157-1165 (1997); Pietersz et al., *Cancer Immunol. Immunotherapy*, 41:53-60 (1995)), 89B(B4) (IgG1) (Beckman Coulter, Miami, Fla.; Nadler et al., *J. Immunol.*, 131:244-250 (1983)), and/or HD237 (IgG2b) (Fourth International Workshop on Human Leukocyte Differentiation Antigens, Vienna, Austria, 1989; and Pezzutto et al., *J. Immunol.*, 138 (9):2793-2799 (1987)).

In certain embodiments, the antibody is an isotype switched variant of a known antibody (e.g., to an IgG1 or IgG3 human isotype) such as those described above.

An anti-CD19 antibodies used in compositions and methods of the invention can be naked antibodies, immunoconjugates or fusion proteins. Anti-CD19 antibodies described above for use in compositions and methods of the invention may be able to reduce or deplete B cells and circulating immunoglobulin in a human treated therewith. Depletion of B cells can be in circulating B cells, or in particular tissues such as, but not limited to, bone marrow, spleen, gut-associated lymphoid tissues, and/or lymph nodes. Such depletion may be achieved via various mechanisms such as antibody-dependent cell-mediated cytotoxicity (ADCC), and/or by blocking of CD19 interaction with its intended ligand, and/or complement dependent cytotoxicity (CDC), inhibition of B cell proliferation and/or induction of B cell death (e.g., via apoptosis). By "depletion" of B cells it is meant a reduction in circulating B cells and/or B cells in particular tissue(s) by at least about 25%, 40%, 50%, 65%, 75%, 80%, 85%, 90%, 95% or more. In particular embodiments, virtually all detectable B cells are depleted from the circulation and/or particular tissue(s). By "depletion" of circulating immunoglobulin (Ig) it is meant a reduction by at least about 25%, 40%, 50%, 65%, 75%, 80%, 85%, 90%, 95% or more. In particular embodiments, virtually all detectable Ig is depleted from the circulation.

5.18.1. Screening of Antibodies for Human CD19 Binding

Binding assays can be used to identify antibodies that bind the human CD19 antigen. Binding assays may be performed either as direct binding assays or as competition-binding assays. Binding can be detected using standard ELISA or standard Flow Cytometry assays. In a direct binding assay, a candidate antibody is tested for binding to human CD19 antigen. In certain embodiments, the screening assays comprise, in a second step, determining the ability to cause cell death or apoptosis of B cells expressing human CD19. Competition-binding assays, on the other hand, assess the ability of a candidate antibody to compete with a known anti-CD19 antibody or other compound that binds human CD19.

In a direct binding assay, the human CD19 antigen is contacted with a candidate antibody under conditions that allow binding of the candidate antibody to the human CD19 antigen. The binding may take place in solution or on a solid surface. The candidate antibody may have been previously labeled for detection. Any detectable compound can be used for labeling, such as, but not limited to, a luminescent, fluorescent, or radioactive isotope or group containing same, or a nonisotopic label, such as an enzyme or dye. After a period of incubation sufficient for binding to take place, the reaction is exposed to conditions and manipulations that remove excess or non-specifically bound antibody. Typically, it involves washing with an appropriate buffer. Finally, the presence of a CD19-antibody complex is detected.

In a competition-binding assay, a candidate antibody is evaluated for its ability to inhibit or displace the binding of a known anti-CD19 antibody (or other compound) to the human CD19 antigen. A labeled known binder of CD19 may be mixed with the candidate antibody, and placed under conditions in which the interaction between them would normally occur, with and without the addition of the candidate antibody. The amount of labeled known binder of CD19 that binds the human CD19 may be compared to the amount bound in the presence or absence of the candidate antibody.

In one embodiment, the binding assay is carried out with one or more components immobilized on a solid surface to facilitate antibody antigen complex formation and detection. In various embodiments, the solid support could be, but is not restricted to, polyvinylidene fluoride, polycarbonate, polystyrene, polypropylene, polyethylene, glass, nitrocellulose, dextran, nylon, polyacrylamide and agarose. The support configuration can include beads, membranes, microparticles, the interior surface of a reaction vessel such as a microtiter plate, test tube or other reaction vessel. The immobilization of human CD19, or other component, can be achieved through covalent or non-covalent attachments. In one embodiment, the attachment may be indirect, i.e., through an attached antibody. In another embodiment, the human CD19 antigen and negative controls are tagged with an epitope, such as glutathione S-transferase (GST) so that the attachment to the solid surface can be mediated by a commercially available antibody such as anti-GST (Santa Cruz Biotechnology).

For example, such an affinity binding assay may be performed using the human CD19 antigen which is immobilized to a solid support. Typically, the non-mobilized component of the binding reaction, in this case the candidate anti-CD19 antibody, is labeled to enable detection. A variety of labeling methods are available and may be used, such as luminescent, chromophore, fluorescent, or radioactive isotope or group containing same, and nonisotopic labels, such as enzymes or dyes. In one embodiment, the candidate anti-CD19 antibody is labeled with a fluorophore such as fluorescein isothiocyanate (FITC, available from Sigma Chemicals, St. Louis). Such an affinity binding assay may be performed using the human CD19 antigen immobilized on a solid surface. Anti-CD19 antibodies are then incubated with the antigen and the specific binding of antibodies is detected by methods known in the art including, but not limited to, BiaCore Analyses, ELISA, FMET and RIA methods.

Finally, the label remaining on the solid surface may be detected by any detection method known in the art. For example, if the candidate anti-CD19 antibody is labeled with a fluorophore, a fluorimeter may be used to detect complexes.

The human CD19 antigen can be added to binding assays in the form of intact cells that express human CD19 antigen, or isolated membranes containing human CD19 antigen. Thus, direct binding to human CD19 antigen may be assayed in intact cells in culture or in animal models in the presence and absence of the candidate anti-CD19 antibody. A labeled candidate anti-CD19 antibody may be mixed with cells that express human CD19 antigen, or with crude extracts obtained from such cells, and the candidate anti-CD19 antibody may be added. Isolated membranes may be used to identify candidate anti-CD19 antibodies that interact with human CD19. For example, in a typical experiment using isolated membranes, cells may be genetically engineered to express human CD19 antigen. Membranes can be harvested by standard techniques and used in an in vitro binding assay. Labeled candidate anti-CD19 antibody (e.g., fluorescent labeled antibody) is bound to the membranes and assayed for specific activity; specific binding is determined by comparison with binding assays performed in the presence of excess unlabeled (cold) candidate anti-CD19 antibody. Soluble human CD19 antigen may also be recombinantly expressed and utilized in non-cell based assays to identify antibodies that bind to human CD19 antigen. The recombinantly expressed human CD19 polypeptides can be used in the non-cell based screening assays. Peptides corresponding to one or more of the binding portions of human CD19 antigen, or fusion proteins containing one or more of the binding portions of human CD19 antigen can also be used in non-cell based assay systems to identify antibodies that bind to portions of human CD19 antigen. In non-cell based assays the recombinantly expressed human CD19 is attached to a solid substrate such as a test tube, microliter well or a column, by means well-known to those in the art (see, Ausubel et al., supra). The test antibodies are then assayed for their ability to bind to human CD19 antigen.

The binding reaction may also be carried out in solution. In this assay, the labeled component is allowed to interact with its binding partner(s) in solution. If the size differences between the labeled component and its binding partner(s) permit such a separation, the separation can be achieved by passing the products of the binding reaction through an ultrafilter whose pores allow passage of unbound labeled component but not of its binding partner(s) or of labeled component bound to its partner(s). Separation can also be achieved using any reagent capable of capturing a binding partner of the labeled component from solution, such as an antibody against the binding partner and so on.

In one embodiment, for example, a phage library can be screened by passing phage from a continuous phage display library through a column containing purified human CD19 antigen, or derivative, analog, fragment, or domain, thereof, linked to a solid phase, such as plastic beads. By altering the stringency of the washing buffer, it is possible to enrich for phage that express peptides with high affinity for human CD19 antigen. Phage isolated from the column can be cloned and affinities can be measured directly. Knowing which antibodies and their amino acid sequences confer the strongest binding to human CD19 antigen, computer models can be used to identify the molecular contacts between CD19 antigen and the candidate antibody.

In another specific embodiment, the solid support is membrane containing human CD19 antigen attached to a microtiter dish. Candidate antibodies, for example, can bind cells that express library antibodies cultivated under conditions that allow expression of the library members in the microliter dish. Library members that bind to the human CD19 are harvested. Such methods, are generally described by way of example in Parmley and Smith, 1988, *Gene*, 73:305-318; Fowlkes et al., 1992, *BioTechniques*, 13:422-427; PCT Publication No. WO94/18318; and in references cited hereinabove. Antibodies identified as binding to human CD19 antigen can be of any of the types or modifications of antibodies described above.

5.18.2. Screening of Antibodies for Human ADCC Effector Function

Antibodies of the human IgG class, which have functional characteristics such a long half-life in serum and the ability to mediate various effector functions are used in certain embodiments of the invention (*Monoclonal Antibodies: Principles and Applications*, Wiley-Liss, Inc., Chapter 1 (1995)). The human IgG class antibody is further classified into the following 4 subclasses: IgG1, IgG2, IgG3 and IgG4. A large number of studies have so far been conducted for ADCC and CDC as effector functions of the IgG class antibody, and it has been reported that among antibodies of the human IgG class, the IgG1 subclass has the highest ADCC activity and CDC activity in humans (*Chemical Immunology*, 65, 88 (1997)).

Expression of ADCC activity and CDC activity of the human IgG1 subclass antibodies generally involves binding of the Fc region of the antibody to a receptor for an antibody (hereinafter referred to as "FcγR") existing on the surface of effector cells such as killer cells, natural killer cells or activated macrophages. Various complement components can be bound. Regarding the binding, it has been suggested that several amino acid residues in the hinge region and the second domain of C region (hereinafter referred to as "Cγ2 domain") of the antibody are important (*Eur. J. Immunol.*, 23, 1098 (1993), *Immunology*, 86, 319 (1995), *Chemical Immunology*, 65, 88 (1997)) and that a sugar chain in the Cγ2 domain (*Chemical Immunology*, 65, 88 (1997)) is also important.

Anti-CD19 antibodies can be modified with respect to effector function, e.g., so as to enhance ADCC and/or complement dependent cytotoxicity (CDC) of the antibody. This may be achieved by introducing one or more amino acid substitutions in the Fc region of an antibody. Cysteine residue(s) may also be introduced in the Fc region, allowing for interchain disulfide bond formation in this region. In this way a homodimeric antibody can be generated that may have improved internalization capability and or increased complement-mediated cell killing and ADCC (Caron et al., *J. Exp. Med.*, 176:1191-1195 (1992) and Shopes, *J. Immunol.*, 148: 2918-2922 (1992)). Heterobifunctional cross-linkers can also be used to generate homodimeric antibodies with enhanced anti-tumor activity (Wolff et al., *Cancer Research*, 53:2560-2565 (1993)). Antibodies can also be engineered to have two or more Fc regions resulting in enhanced complement lysis and ADCC capabilities (Stevenson et al., *Anti-Cancer Drug Design*, (3)219-230 (1989)).

Other methods of engineering Fc regions of antibodies so as to alter effector functions are known in the art (e.g., U.S. Patent Publication No. 20040185045 and PCT Publication No. WO 2004/016750, both to Koenig et al., which describe altering the Fc region to enhance the binding affinity for FcγRIIB as compared with the binding affinity for FCγRIIA; see also PCT Publication Nos. WO 99/58572 to Armour et al., WO 99/51642 to Idusogic et al., and U.S. Pat. No. 6,395,272 to Deo et al.; the disclosures of which are incorporated herein in their entireties). Methods of modifying the Fc region to decrease binding affinity to FcγRIIB are also known in the art (e.g., U.S. Patent Publication No. 20010036459 and PCT Publication No. WO 01/79299, both to Ravetch et al., the disclosures of which are incorporated herein in their entireties). Modified antibodies having variant Fc regions with enhanced binding affinity for FcγRIIIA and/or FcγRIIA as compared with a wildtype Fc region have also been described (e.g., PCT Publication No. WO 2004/063351, to Stavenhagen et al.; the disclosure of which is incorporated herein in its entirety).

At least four different types of FcγR have been found, which are respectively called FcγRI (CD64), FcγRII (CD32), FcγRIII (CD16), and FcγRIV. In human, FcγRII and FcγRIII are further classified into FcγRIIa and FcγRIIb, and FcγRIIIa and FcγRIIIb, respectively. FcγR is a membrane protein belonging to the immunoglobulin superfamily, FcγRII, FcγRIII, and FcγRIV have an α chain having an extracellular region containing two immunoglobulin-like domains, FcγRI has an α chain having an extracellular region containing three immunoglobulin-like domains, as a constituting component, and the α chain is involved in the IgG binding activity. In addition, FcγRI and FcγRII have a γ chain or ζ chain as a constituting component which has a signal transduction function in association with the α chain (*Annu. Rev. Immunol.*, 18, 709 (2000), *Annu. Rev. Immunol.*, 19, 275 (2001)). FcγRIV has been described by Bruhns et al., *Clin. Invest. Med.*, (Canada) 27:3 D (2004).

To assess ADCC activity of an anti-CD19 antibody of interest, an in vitro ADCC assay can be used, such as that described in U.S. Pat. No. 5,500,362 or 5,821,337. The assay may also be performed using a commercially available kit, e.g. CytoTox 96® (Promega). Useful effector cells for such assays include, but are not limited to peripheral blood mononuclear cells (PBMC), Natural Killer (NK) cells, and NK cell lines. NK cell lines expressing a transgenic Fc receptor (e.g. CD16) and associated signaling polypeptide (e.g. FCεRI-γ) may also serve as effector cells (see, e.g. WO 2006/023148 A2 to Campbell). For example, the ability of any particular antibody to mediate lysis of the target cell by complement activation and/or ADCC can be assayed. The cells of interest are grown and labeled in vitro; the antibody is added to the cell culture in combination with immune cells which may be activated by the antigen antibody complexes; i.e., effector cells involved in the ADCC response. The antibody can also be tested for complement activation. In either case, cytolysis of the target cells is detected by the release of label from the lysed cells. The extent of target cell lysis may also be determined by detecting the release of cytoplasmic proteins (e.g. LDH) into the supernatant. In fact, antibodies can be screened using the patient's own serum as a source of complement and/or immune cells. The antibodies that are capable of mediating human ADCC in the in vitro test can then be used therapeutically in that particular patient. ADCC activity of the molecule of interest may also be assessed in vivo, e.g., in an animal model such as that disclosed in Clynes et al., *Proc. Natl. Acad. Sci.* (USA) 95:652-656 (1998). Moreover, techniques for modulating (i.e., increasing or decreasing) the level of ADCC, and optionally CDC activity, of an antibody are well-known in the art. See, e.g., U.S. Pat. No. 6,194,551. Antibodies of the present invention may be capable or may have been modified to have the ability of inducing ADCC and/or CDC. Assays to determine ADCC function can be practiced using human effector cells to assess human ADCC function. Such assays may also include those intended to screen for antibodies that induce, mediate, enhance, block cell death by necrotic and/or apoptotic mechanisms. Such methods including assays utilizing viable dyes, methods of detecting and analyzing caspases, and assays measuring DNA breaks can be used to assess the apoptotic activity of cells cultured in vitro with an anti-CD19 antibody of interest.

For example, Annexin V or TdT-mediated dUTP nick-end labeling (TUNEL) assays can be carried out as described in Decker et al., *Blood* (USA) 103:2718-2725 (2004) to detect apoptotic activity. The TUNEL assay involves culturing the cell of interest with fluorescein-labeled dUTP for incorporation into DNA strand breaks. The cells are then processed for analysis by flow cytometry. The Annexin V assay detects the appearance of phosphatidylserine (PS) on the outside of the plasma membrane of apoptotic cells using a fluorescein-conjugated Annexin V that specifically recognizes the exposed PS molecules. Concurrently, a viable dye such as propidium iodide can be used to exclude late apoptotic cells. The cells are stained with the labeled Annexin V and are analyzed by flow cytometry.

5.18.3. Immunoconjugates and Fusion Proteins

According to certain aspects of the invention, therapeutic agents or toxins can be conjugated to chimerized, human, or humanized anti-CD19 antibodies for use in compositions and methods of the invention. In certain embodiments, these conjugates can be generated as fusion proteins. Examples of therapeutic agents and toxins include, but are not limited to, members of the enediyne family of molecules, such as calicheamicin and esperamicin. Chemical toxins can also be taken from the group consisting of duocarmycin (see, e.g., U.S. Pat. Nos. 5,703,080 and 4,923,990), methotrexate, doxorubicin, melphalan, chlorambucil, ARA-C, vindesine, mitomycin C, cis-platinum, etoposide, bleomycin and 5-fluorouracil. Examples of chemotherapeutic agents also include Adriamycin, Doxorubicin, 5-Fluorouracil, Cytosine arabinoside (Ara-C), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Caminomycin, Aminopterin, Dactinomycin, Mitomycins, Esperamicins (see, U.S. Pat. No. 4,675,187), Melphalan, and other related nitrogen mustards.

In certain embodiments, anti-CD19 antibodies are conjugated to a cytostatic, cytotoxic or immunosuppressive agent wherein the cytotoxic agent is selected from the group consisting of an enediyne, a lexitropsin, a duocarmycin, a taxane, a puromycin, a dolastatin, a maytansinoid, and a vinca alkaloid. In certain, more specific embodiments, the cytotoxic agent is paclitaxel, docetaxel, CC-1065, SN-38, topotecan, morpholino-doxorubicin, rhizoxin, cyanomorpholino-doxorubicin, dolastatin-10, echinomycin, combretastatin, calicheamicin, maytansine, DM-1, auristatin E, AEB, AEVB, AEFP, MMAE (see, U.S. patent application Ser. No. 10/983, 340; U.S. Pat. No. 7,498,298), or netropsin.

In certain embodiments, the cytotoxic agent of an anti-CD19 antibody-cytotoxic agent conjugate of the invention is an anti-tubulin agent. In specific embodiments, the cytotoxic agent is selected from the group consisting of a vinca alkaloid, a podophyllotoxin, a taxane, a baccatin derivative, a cryptophysin, a maytansinoid, a combretastatin, and a dolastatin. In other embodiments, the cytotoxic agent is vincristine, vinblastine, vindesine, vinorelbine, VP-16, camptothecin, paclitaxel, docetaxel, epithilone A, epithilone B, nocodazole, coichicine, colcimid, estramustine, cemadotin, discodermolide, maytansine, DM-1, AEFP, auristatin E, AEB, AEVB, AEFP, MMAE or eleutherobin.

In specific embodiments, an anti-CD19 antibody is conjugated to the cytotoxic agent via a linker, wherein the linker is peptide linker. In other embodiments, an anti-CD19 antibody is conjugated to the cytotoxic agent via a linker, wherein the linker is a val-cit linker, a phe-lys linker, a hydrazone linker, or a disulfide linker.

In certain embodiments, the anti-CD19 antibody of an anti-CD19 antibody-cytotoxic agent conjugate is conjugated to the cytotoxic agent via a linker, wherein the linker is hydrolysable at a pH of less than 5.5. In a specific embodiment the linker is hydrolyzable at a pH of less than 5.0.

In certain embodiments, the anti-CD19 antibody of an anti-CD19 antibody-cytotoxic agent conjugate is conjugated to the cytotoxic agent via a linker, wherein the linker is cleavable by a protease. In a specific embodiment, the protease is a lysosomal protease. In other embodiments, the protease is, inter alia, a membrane-associated protease, an intracellular protease, or an endosomal protease.

Other toxins that can be used in immunoconjugates of the invention include poisonous lectins, plant toxins such as ricin, abrin, modeccin, botulina, and diphtheria toxins. Of course, combinations of the various toxins could also be coupled to one antibody molecule thereby accommodating variable cytotoxicity. Illustrative of toxins which are suitably employed in combination therapies of the invention are ricin, abrin, ribonuclease, DNase I, Staphylococcal enterotoxin-A, pokeweed anti-viral protein, gelonin, diphtherin toxin, *Pseudomonas* exotoxin, and *Pseudomonas* endotoxin. See, for example, Pastan et al., *Cell,* 47:641 (1986), and Goldenberg et al., *Cancer Journal for Clinicians,* 44:43 (1994).

Enzymatically active toxins and fragments thereof which can be used include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232 published Oct. 28, 1993.

Suitable toxins and chemotherapeutic agents are described in Remington's Pharmaceutical Sciences, 19th Ed. (Mack Publishing Co. 1995), and in Goodman And Gilman's The Pharmacological Basis of Therapeutics, 7th Ed. (MacMillan Publishing Co. 1985). Other suitable toxins and/or chemotherapeutic agents are known to those of skill in the art.

The present invention further encompasses antibodies (including antibody fragments or variants thereof) comprising or conjugated to a radioactive agent suitable for diagnostic purposes. Examples of suitable radioactive materials include, but are not limited to, iodine ($^{121}I$, $^{123}I$, $^{125}I$, $^{131}I$), carbon ($^{14}C$), sulfur ($^{35}S$), tritium ($^{3}H$), indium ($^{111}In$, $^{112}In$, $^{113m}In$, $^{115m}In$), technetium ($^{99}Tc$, $^{99m}Tc$), thallium ($^{201}Ti$), gallium ($^{68}Ga$, $^{67}Ga$), palladium ($^{103}Pd$), molybdenum ($^{99}Mo$), xenon ($^{135}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, and $^{97}Ru$.

Further, an anti-CD19 antibody of the invention (including an scFv or other molecule comprising, or alternatively consisting of, antibody fragments or variants thereof), may be coupled or conjugated to a radioactive metal ion utilized for therapeutic purposes. Examples of suitable radioactive ions include, but are not limited to, alpha-emitters such as $^{213}Bi$, or other radioisotopes such as $^{103}Pd$, $^{135}Xe$, $^{131}I$, $^{68}Ge$, $^{57}Co$, $^{65}Zn$, $^{85}Sr$, $^{32}P$, $^{35}S$, $^{90}Y$, $^{153}Sm$, $^{153}Gd$, $^{169}Yb$, $^{51}Cr$, $^{54}Mn$, $^{75}Se$, $^{113}Sn$, $^{90}Y$, $^{117}Tin$, $^{186}Re$, $^{188}Re$ and $^{166}Ho$. In specific embodiments, an antibody or fragment thereof is attached to macrocyclic chelators that chelate radiometal ions, including but not limited to, $^{177}Lu$, $^{90}Y$, $^{166}Ho$, and $^{153}Sm$, to polypeptides. In specific embodiments, the macrocyclic chelator is 1,4,7,10-tetraazacyclod-odecane-N,N',N'',N'''-tetraacetic acid (DOTA). In other specific embodiments, the DOTA is attached to the an antibody of the invention or fragment thereof via a linker molecule. Examples of linker molecules useful for conjugating DOTA to a polypeptide are commonly known in the art—see, for example, DeNardo et al., Clin Cancer Res 4(10):2483-90, 1998; Peterson et al., Bioconjug Chem 10(4):553-7, 1999; and Zimmerman et al., Nucl Med Biol 26(8):943-50, 1999 which are hereby incorporated by reference in their entirety.

An anti-CD19 antibody of the present invention may also be used in ADEPT by conjugating the antibody to a prodrug-activating enzyme which converts a prodrug (e.g., a peptidyl chemotherapeutic agent, see, WO81/01145) to an active anti-cancer drug. See, for example, WO 88/07378 and U.S. Pat. No. 4,975,278. The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with α-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Antibodies with enzymatic activity, also known in the art as "abzymes," can be used as well to convert the prodrugs into free active drugs (see, e.g., Massey, Nature 328:457-458 (1987)). Antibody-abzyme conjugates can be prepared as described herein for delivery of the abzyme as desired to portions of a human affected by a B cell malignancy.

Antibodies of this invention may be covalently bound to the enzymes by techniques well-known in the art such as the use of the heterobifunctional crosslinking reagents discussed above. Fusion proteins comprising at least the antigen-binding region of an anti-CD19 antibody linked to at least a functionally active portion of an enzyme may also be constructed using recombinant DNA techniques well-known in the art (see, e.g., Neuberger et al., Nature, 312:604-608 (1984)).

Covalent modifications of an anti-CD19 antibody are included within the scope of this invention. They may be made by chemical synthesis or by enzymatic or chemical cleavage of the antibody, if applicable. Other types of covalent modifications of an anti-CD19 antibody are introduced into the molecule by reacting targeted amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Similarly, iodo-reagents may also be used. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction can be performed in 0.1 M sodium cacodylate at pH 6.0.

Lysyl and amino-terminal residues are reacted with succinic or other carboxylic acid anhydrides. Derivatization with these agents has the effect of reversing the charge of the lysinyl residues. Other suitable reagents for derivatizing α-amino-containing residues and/or ε-amino-containing residues include imidoesters such as methyl picolinimidate, pyridoxal phosphate, pyridoxal, chloroborohydride, trinitrobenzenesulfonic acid, 0-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginyl residues generally requires that the reaction be performed in alkaline conditions because of the high pKa of the guanidine functional group. Furthermore, these reagents may react with the ε-amino groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay.

Carboxyl side groups (aspartyl or glutamyl) are selectively modified by reaction with carbodiimides (R—N═C═N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, CRC *Crit. Rev. Biochem.*, pp. 259-306 (1981).

5.19. Chemotherapeutic Combinations

In other embodiments, an anti-CD19 mAb can be administered in combination with one or more additional chemotherapeutic agents. For example, "CVB" (1.5 g/m$^2$ cyclophosphamide, 200-400 mg/m$^2$ etoposide, and 150-200 mg/m$^2$ carmustine) can be used in combination therapies of the invention. CVB is a regimen used to treat non-Hodgkin's lymphoma (Patti et al., *Eur. J. Haematol.*, 51:18 (1993)). Other suitable combination chemotherapeutic regimens are well-known to those of skill in the art. See, for example, Freedman et al., "*Non-Hodgkin's Lymphomas*," in Cancer Medicine, Volume 2, 3rd Edition, Holland et al. (eds.), pp. 2028-2068 (Lea & Febiger 1993). As an illustration, first generation chemotherapeutic regimens for treatment of intermediate-grade non-Hodgkin's lymphoma include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone, and leucovorin), while a suitable third generation regimen is MACOP-B (methotrexate, doxorubicin, cyclophosphamide, vincristine, prednisone, bleomycin, and leucovorin). Additional useful drugs include phenyl butyrate and brostatin-1.

According to the invention, cancer or one or more symptoms thereof may be prevented, treated, managed or ameliorated by the administration of an anti-CD19 mAb in combination with the administration of one or more therapies such as, but not limited to, chemotherapies, radiation therapies, hormonal therapies, and/or biological therapies/immunotherapies.

In a specific embodiment, methods of the invention encompass the administration of one or more angiogenesis antagonists such as but not limited to: Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combretastatin A-4; Endostatin (collagen XVIII fragment); Fibronectin fragment; Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16 kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-b); Vasculostatin; Vasostatin (calreticulin fragment); ZD6126; ZD 6474; farnesyl transferase inhibitors (FTI); and bisphosphonates (such as but are not limited to, alendronate, clodronate, etidronate, ibandronate, pamidronate, risedronate, tiludronate, and zoledronate).

In a specific embodiment, methods of the invention encompass the administration of one or more immunomodulatory agents, such as but not limited to, chemotherapeutic agents and non-chemotherapeutic immunomodulatory agents. Non-limiting examples of chemotherapeutic agents include methotrexate, cyclosporin A, leflunomide, cisplatin, ifosfamide, taxanes such as taxol and paclitaxol, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, cytochalasin B, gramicidin D, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin homologues, and cytoxan. Examples of non-chemotherapeutic immunomodulatory agents include, but are not limited to, anti-T cell receptor antibodies (e.g., anti-CD4 antibodies (e.g., cM-T412 (Boeringer), IDEC-CE9.1® (IDEC and SKB), mAB 4162W94, ORTHOCLONE® (muromonab-CD3) and OKTcdr4a (Janssen-Cilag)), anti-CD-3 antibodies (e.g., Nuvion (Product Design Labs), OKT3 (Johnson & Johnson), or RITUXAN™ (rituximab) (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH™ 1H (alemtuzumab) (Ilex)), anti-CD2 antibodies (e.g., MEDI-507

(MedImmune, Inc., International Publication Nos. WO 02/098370 and WO 02/069904), anti-CD11a antibodies (e.g., XANELIM™ (efalizumab) (Genentech)), and anti-B7 antibodies (e.g., IDEC-114) (IDEC)); anti-cytokine receptor antibodies (e.g., anti-IFN receptor antibodies, anti-IL-2 receptor antibodies (e.g., ZENAPAX™ (daclizumab) (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-1β antibodies, anti-IL-6 antibodies, anti-IL-8 antibodies (e.g., ABX-IL-8 (Abgenix)), anti-IL-12 antibodies and anti-IL-23 antibodies)); CTLA4-immunoglobulin; LFA-3TIP (Biogen, International Publication No. WO 93/08656 and U.S. Pat. No. 6,162,432); soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof); cytokines or fragments thereof (e.g., interleukin (IL)-2, IL-3, IL-4, IL-5, IL-6, IL-7, IL-8, IL-9, IL-10, IL-11, IL-12, IL-15, IL-23, TNF-α, TNF-β, interferon (IFN)-α, IFN-β, IFN-γ, and GM-CSF); and anti-cytokine antibodies (e.g., anti-IL-2 antibodies, anti-IL-4 antibodies, anti-IL-6 antibodies, anti-IL-10 antibodies, anti-IL-12 antibodies, anti-IL-15 antibodies, anti-TNF-α antibodies, and anti-IFN-γ antibodies), and antibodies that immunospecifically bind to tumor-associated antigens (e.g., HERCEPTIN™ (trastuzumab)). In certain embodiments, an immunomodulatory agent is an immunomodulatory agent other than a chemotherapeutic agent. In other embodiments an immunomodulatory agent is an immunomodulatory agent other than a cytokine or hemapoietic such as IL-1, IL-2, IL-4, IL-12, IL-15, TNF, IFN-α, IFN-β, IFN-γ, M-CSF, G-CSF, IL-3 or erythropoietin. In yet other embodiments, an immunomodulatory agent is an agent other than a chemotherapeutic agent and a cytokine or hemapoietic factor.

In a specific embodiment, methods of the invention encompass the administration of one or more anti-inflammatory agents, such as but not limited to, non-steroidal anti-inflammatory drugs (NSAIDs), steroidal anti-inflammatory drugs, beta-agonists, anticholingeric agents, and methyl xanthines. Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

In another specific embodiment, methods of the invention encompass the administration of one or more antiviral agents (e.g., amantadine, ribavirin, rimantadine, acyclovir, famciclovir, foscarnet, ganciclovir, trifluridine, vidarabine, didanosine, stavudine, zalcitabine, zidovudine, interferon), antibiotics (e.g., dactinomycin (formerly actinomycin), bleomycin, mithramycin, and anthramycin (AMC)), anti-emetics (e.g., alprazolam, dexamethasone, domperidone, dronabinol, droperidol, granisetron, haloperidol, haloperidol, iorazepam, methylprednisolone, metoclopramide, nabilone, ondansetron, prochlorperazine), anti-fungal agents (e.g., amphotericin, clotrimazole, econazole, fluconazole, flucytosine, griseofulvin, itraconazole, ketoconazole, miconazole and nystatin), anti-parasite agents (e.g., dehydroemetine, diloxanide furoate, emetine, mefloquine, melarsoprol, metronidazole, nifurtimox, paromomycin, pentabidine, pentamidine isethionate, primaquine, quinacrine, quinidine) or a combination thereof.

Specific examples of anti-cancer agents that can be used in various embodiments of the invention, including pharmaceutical compositions and dosage forms and kits, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; HMG-CoA reductase inhibitor (such as but not limited to, Lovastatin, Pravastatin, Fluvastatin, Statin, Simvastatin, and Atorvastatin); loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; Vitaxin®; vorozole; zanoterone; zeniplatin; zilascorb; and zinostatin stimalamer. Additional anti-cancer drugs are 5-fluorouracil and leucovorin. These two agents may be useful when used in methods employing thalidomide and a topoisomerase inhibitor. In specific embodiments, an anti-cancer agent is not a chemotherapeutic agent.

In more particular embodiments, the present invention also comprises the administration of an anti-CD19 mAb in combination with the administration of one or more therapies such as, but not limited to, anti-cancer agents such as those disclosed in Table 1, for the treatment of breast, ovary, melanoma, prostate, colon and lung cancers as described above. When used in a combination therapy, the dosages and/or the frequency of administration listed in Table 2 may be decreased.

TABLE 2

Anti-cancer agents

| Therapeutic Agent | Dose/Administration/Formulation | | |
|---|---|---|---|
| doxorubicin hydrochloride (Adriamycin RDF ® and Adriamycin PFS ® | Intravenous | 60-75 mg/m$^2$ on Day 1 | 21 day intervals |
| epirubicin hydrochloride (Ellence ™) | Intravenous | 100-120 mg/m$^2$ on Day 1 of each cycle or divided equally and given on Days 1-8 of the cycle | 3-4 week cycles |
| fluorousacil | Intravenous | How supplied: 5 mL and 10 mL vials (containing 250 and 500 mg flourouracil respectively) | |
| docetaxel (Taxotere ®) | Intravenous | 60-100 mg/m$^2$ over 1 hour | Once every 3 weeks |
| paclitaxel (Taxol ®) | Intravenous | 175 mg/m$^2$ over 3 hours | Every 3 weeks for 4 courses (administered sequentially to doxorubicin-containing combination chemotherapy) |
| tamoxifen citrate (Nolvadex ®) | Oral (tablet) | 20-40 mg Dosages greater than 20 mg should be given in divided doses (morning and evening) | Daily |
| leucovorin calcium for injection | intravenous or intramuscular injection | How supplied: 350 mg vial | Dosage is unclear from text. PDR 3610 |
| luprolide acetate Lupron ®) | single subcutaneous injection | 1 mg (0.2 mL or 20 unit mark) | Once a day |
| flutamide (Eulexin ®) | Oral (capsule) | 50 mg (capsules contain 125 mg flutamide each) | 3 times a day at 8 hour intervals (total daily dosage 750 mg) |
| nilutamide (Nilandron ®) | Oral (tablet) | 300 mg or 150 mg (tablets contain 50 or 150 mg nilutamide each) | 300 mg once a day for 30 days followed by 150 mg once a day |
| bicalutamide (Casodex ®) | Oral (tablet) | 50 mg (tablets contain 50 mg bicalutamide each) | Once a day |
| progesterone | Injection | USP in sesame oil 50 mg/mL | |
| ketoconazole (Nizoral ®) | Cream | 2% cream applied once or twice daily depending on symptoms | |
| prednisone | Oral (tablet) | Initial dosage may vary from 5 mg to 60 mg per day depending on the specific disease entity being treated. | |
| estramustine phosphate sodium (Emcyt ®) | Oral (capsule) | 14 mg/kg of body weight (i.e. one 140 mg capsule for each 10 kg or 22 lb of body weight) | Daily given in 3 or 4 divided doses |
| etoposide or VP-16 | Intravenous | 5 mL of 20 mg/mL solution (100 mg) | |
| dacarbazine (DTIC-Dome ®) | Intravenous | 2-4.5 mg/kg | Once a day for 10 days. May be repeated at 4 week intervals |
| polifeprosan 20 with carmustine implant (BCNU) (nitrosourea) (Gliadel ®) | wafer placed in resection cavity | 8 wafers, each containing 7.7 mg of carmustine, for a total of 61.6 mg, if size and shape of resection cavity allows | |
| cisplatin | Injection | [n/a in PDR 861] How supplied: | |

TABLE 2-continued

Anti-cancer agents

| Therapeutic Agent | | Dose/Administration/Formulation | |
|---|---|---|---|
| mitomycin | Injection | solution of 1 mg/mL in multi-dose vials of 50 mL and 100 mL supplied in 5 mg and 20 mg vials (containing 5 mg and 20 mg mitomycin) | |
| gemcitabine HCl (Gemzar ®) | Intravenous | For NSCLC-2 schedules have been investigated and the optimum schedule has not been determined 4 week schedule-administration intravenously at 1000 mg/m² over 30 minutes on 3 week schedule-Gemzar administered intravenously at 1250 mg/m² over 30 minutes | 4 week schedule-Days 1, 8 and 15 of each 28-day cycle. Cisplatin intravenously at 100 mg/m² on day 1 after the infusion of Gemzar. 3 week schedule-Days 1 and 8 of each 21 day cycle. Cisplatin at dosage of 100 mg/m² administered intravenously after administration of Gemzar on day 1. |
| carboplatin (Paraplatin ®) | Intravenous | Single agent therapy: 360 mg/m² I.V. on day 1 (infusion lasting 15 minutes or longer) Other dosage calculations: Combination therapy with cyclophosphamide, Dose adjustment recommendations, Formula dosing, etc. | Every 4 weeks |
| ifosamide (Ifex ®) | Intravenous | 1.2 g/m² daily | 5 consecutive days Repeat every 3 weeks or after recovery from hematologic toxicity |
| topotecan hydrochloride (Hycamtin ®) | Intravenous | 1.5 mg/m² by intravenous infusion over 30 minutes daily | 5 consecutive days, starting on day 1 of 21 day course |
| Bisphosphonates Pamidronate Alendronate Risedronate | Intravenous or Oral take with 6-8 oz water. | 60 mg or 90 mg single infusion over 4-24 hours to correct hypercalcemia in cancer patients 5 mg/d daily for 2 years and then 10 mg/d for 9 month to prevent or control bone resorption. 5.0 mg to prevent or control bone resorption. | |
| Lovastatin (Mevacor ™) | Oral | 10-80 mg/day in single or two divided dose. | |

The invention also encompasses administration of an anti-CD19 mAb in combination with radiation therapy comprising the use of x-rays, gamma rays and other sources of radiation to destroy the cancer cells. In particular embodiments, the radiation treatment is administered as external beam radiation or teletherapy wherein the radiation is directed from a remote source. In other embodiments, the radiation treatment is administered as internal therapy or brachytherapy wherein a radioactive source is placed inside the body close to cancer cells or a tumor mass.

Cancer therapies and their dosages, routes of administration and recommended usage are known in the art and have been described in such literature as the *Physician's Desk Reference* (56th ed., 2002).

5.20. Pharmaceutical Compositions

The invention also relates to immunotherapeutic compositions and methods for the treatment of B cell diseases and disorders in human subjects, such as, but not limited to, B cell malignancies, to immunotherapeutic compositions and methods for the treatment and prevention of GVHD, graft rejection, and post-transplant lymphocyte proliferative disorder in human transplant recipients, and to immunotherapeutic compositions and methods for the treatment of autoimmune diseases and disorders in human subjects, using therapeutic antibodies that bind to the CD19 antigen and may mediate human ADCC.

The present invention relates to pharmaceutical compositions comprising human, humanized, or chimeric anti-CD19 antibodies of the IgG1 or IgG3 human isotype. The present invention also relates to pharmaceutical compositions comprising human or humanized anti-CD19 antibodies of the IgG2 or IgG4 human isotype that may mediate human ADCC. In certain embodiments, the present invention also relates to pharmaceutical compositions comprising monoclonal human, humanized, or chimerized anti-CD19 antibodies that can be produced by means known in the art.

Therapeutic formulations and regimens are described for treating human subjects diagnosed with B cell malignancies that derive from B cells and their precursors, including but not limited to, acute lymphoblastic leukemias (ALL), Hodgkin's lymphomas, non-Hodgkin's lymphomas, B cell chronic lymphocytic leukemias (CLL), multiple myeloma, follicular lymphoma, mantle cell lymphoma, pro-lymphocytic leukemias, hairy cell leukemias, common acute lymphocytic leukemias and some Null-acute lymphoblastic leukemias.

In other particular embodiments, anti-CD19 antibodies may mediate ADCC, complement-dependent cellular cytoxicity, or apoptosis. Compositions and methods of the present invention also have the advantage of targeting a wider population of B cells than other B cell directed immunotherapies. For example, anti-CD19 antibodies of the present invention may be effective to target bone marrow cells, circulating B cells, and mature, antibody-secreting B cells. Accordingly, methods and compositions of the invention may be effective to reduce or deplete circulating B cells as well as circulating immunoglobulin.

Accordingly, in one aspect, the invention provides compositions and methods for the treatment and prevention of GVHD, graft rejection, and post-transplantation lymphoproliferative disorder, which are associated with fewer and/or less severe complications than less-targeted therapeutic agents and regimens. In one embodiment, compositions and methods of the invention are used with lower doses of traditional therapeutic agents than would be possible in the absence of the methods and compositions of the invention. In another embodiment, compositions and methods of the invention obviate the need for a more severe form of therapy, such as radiation therapy, high-dose chemotherapy, or splenectomy.

In certain embodiments, anti-CD19 antibodies and compositions may be administered to a transplant recipient patient prior to or following transplantation, alone or in combination with other therapeutic agents or regimens for the treatment or prevention of GVHD and graft rejection. For example, anti-CD19 antibodies and compositions may be used to deplete alloantibodies from a transplant recipient prior to or following transplantation of an allogeneic graft. Anti-CD19 antibodies and compositions may also be used to deplete antibody-producing cells from the graft ex vivo, prior to transplantation, or in the donor, or as prophylaxis against GVHD and graft rejection.

5.21. Pharmaceutical Formulations, Administration and Dosing

Pharmaceutical formulations of the invention contain as the active ingredient human, humanized, or chimeric anti-CD19 antibodies. The formulations contain naked antibody, immunoconjugate, or fusion protein in an amount effective for producing the desired response in a unit of weight or volume suitable for administration to a human patient, and are preferably sterile. The response can, for example, be measured by determining the physiological effects of the anti-CD19 antibody composition, such as, but not limited to, circulating B cell depletion, tissue B cell depletion, regression of a B cell malignancy, or decrease of disease symptoms. Other assays will be known to one of ordinary skill in the art and can be employed for measuring the level of the response.

5.21.1. Pharmaceutical Formulations

An anti-CD19 antibody composition may be formulated with a pharmaceutically acceptable carrier. The term "pharmaceutically acceptable" means one or more non-toxic materials that do not interfere with the effectiveness of the biological activity of the active ingredients. Such preparations may routinely contain salts, buffering agents, preservatives, compatible carriers, and optionally other therapeutic agents. Such pharmaceutically acceptable preparations may also routinely contain compatible solid or liquid fillers, diluents or encapsulating substances which are suitable for administration into a human. When used in medicine, the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, citric, boric, formic, malonic, succinic, and the like. Also, pharmaceutically acceptable salts can be prepared as alkaline metal or alkaline earth salts, such as sodium, potassium or calcium salts. The term "carrier" denotes an organic or inorganic ingredient, natural or synthetic, with which the active ingredient is combined to facilitate the application. The components of the pharmaceutical compositions also are capable of being co-mingled with the antibodies of the present invention, and with each other, in a manner such that there is no interaction which would substantially impair the desired pharmaceutical efficacy.

According to certain aspects of the invention, anti-CD19 antibody compositions can be prepared for storage by mixing the antibody or immunoconjugate having the desired degree of purity with optional physiologically acceptable carriers, excipients or stabilizers (*Remington's Pharmaceutical Sciences*, 16th edition, Osol, A. Ed. (1999)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, PLURONICS™ or polyethylene glycol (PEG).

Anti-CD19 antibody compositions also may contain, optionally, suitable preservatives, such as: benzalkonium chloride; chlorobutanol; parabens and thimerosal.

Anti-CD19 antibody compositions may conveniently be presented in unit dosage form and may be prepared by any of the methods well-known in the art of pharmacy. All methods include the step of bringing the active agent into association with a carrier which constitutes one or more accessory ingredients. In general, anti-CD19 antibody compositions are prepared by uniformly and intimately bringing the active compound into association with a liquid carrier, a finely divided solid carrier, or both, and then, if necessary, shaping the product.

Compositions suitable for parenteral administration conveniently comprise a sterile aqueous or non-aqueous preparation of anti-CD19 antibody, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administration can be found in *Remington's Pharmaceutical Sciences*, Mack Publishing Co., Easton, Pa. In certain embodiments, carrier formulation suitable for various routes of administration can be the same or similar to that described for RITUXAN™. See, *Physicians' Desk Reference (Medical Economics Company, Inc., Montvale, N.J.,* 2005), pp. 958-960 and 1354-1357, which is incorporated herein by reference in its entirety. In certain embodiments of the invention, anti-CD19 antibody compositions are formulated for intravenous administration with sodium chloride, sodium citrate dihydrate, polysorbate 80, and sterile water where the pH of the composition is adjusted to approximately 6.5. Those of skill in the art are aware that intravenous injection provides a useful mode of administration due to the thoroughness of the circulation in rapidly distributing antibodies. Intravenous administration, however, is subject to limitation by a vascular barrier comprising endothelial cells of the vasculature and the subendothelial matrix. Still, the vascular barrier is a more notable problem for the uptake of therapeutic antibodies by solid tumors. Lymphomas have relatively high blood flow rates, contributing to effective antibody delivery. Intralymphatic routes of administration, such as subcutaneous or intramuscular injection, or by catheterization of lymphatic vessels, also provide a useful means of treating B cell lymphomas. In certain embodiments, anti-CD19 antibodies of compositions and methods of the invention are self-administered subcutaneously. In such embodiments, the composition is formulated as a lyophilized drug or in a liquid buffer (e.g., PBS and/or citrate) at about 50 mg/mL.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration are typically sterile. This is readily accomplished by filtration through sterile filtration membranes.

Sustained-release preparations may be prepared. Suitable examples of sustained-release preparations include semipermeable matrices of solid hydrophobic polymers containing an anti-CD19 antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions. In certain embodiments, the pharmaceutically acceptable carriers used in compositions of the invention do not affect human ADCC or CDC.

Anti-CD19 antibody compositions disclosed herein may also be formulated as immunoliposomes. A "liposome" is a small vesicle composed of various types of lipids, phospholipids and/or surfactant which is useful for delivery of a drug (such as anti-CD19 antibodies disclosed herein) to a human. The components of the liposome are commonly arranged in a bilayer formation, similar to the lipid arrangement of biological membranes. Liposomes containing antibodies of the invention are prepared by methods known in the art, such as described in Epstein et al., *Proc. Natl. Acad. Sci. USA,* 82:3688 (1985); Hwang et al., *Proc. Natl. Acad. Sci. USA,* 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. The antibody of the present invention can be conjugated to the liposomes as described in Martin et al., *J. Biol. Chem.,* 257:286-288 (1982) via a disulfide interchange reaction. A therapeutic agent can also be contained within the liposome. See, Gabizon et al., *J. National Cancer Inst.,* (19)1484 (1989).

Some of the pharmaceutical formulations include, but are not limited to:

(a) a sterile, preservative-free liquid concentrate for intravenous (i.v.) administration of anti-CD19 antibody, supplied at a concentration of 10 mg/ml in either 100 mg (10 mL) or 500 mg (50 mL) single-use vials. The product can be formulated for i.v. administration using sodium chloride, sodium citrate dihydrate, polysorbate and sterile water for injection. For example, the product can be formulated in 9.0 mg/mL sodium chloride, 7.35 mg/mL sodium citrate dihydrate, 0.7 mg/mL polysorbate 80, and sterile water for injection. The pH is adjusted to 6.5.

(b) A sterile, lyophilized powder in single-use glass vials for subcutaneous (s.c.) injection. The product can be formulated with sucrose, L-histidine hydrochloride monohydrate, L-histidine and polysorbate 20. For example, each single-use vial can contain 150 mg anti-CD19 antibody, 123.2 mg sucrose, 6.8 mg L-histidine hydrochloride monohydrate, 4.3 mg L-histidine, and 3 mg polysorbate 20. Reconstitution of the single-use vial with 1.3 ml sterile water for injection yields approximately 1.5 ml solution to deliver 125 mg per 1.25 ml (100 mg/ml) of antibody.

(c) A sterile, preservative-free lyophilized powder for intravenous (i.v.) administration. The product can be formulated with α-trehalose dihydrate, L-histidine HCl, histidine and polysorbate 20 USP. For example, each vial can contain 440 mg anti-CD19 antibody, 400 mg α,α-trehalose dihydrate, 9.9 mg L-histidine HCl, 6.4 mg L-histidine, and 1.8 mg polysorbate 20, USP. Reconstitution with 20 ml of bacteriostatic water for injection (BWFI), USP, containing 1.1% benzyl alcohol as a preservative, yields a multi-dose solution containing 21 mg/ml antibody at a pH of approximately 6.

(d) A sterile, lyophilized powder for intravenous infusion in which an anti-CD19 antibody is formulated with sucrose, polysorbate, monobasic sodium phosphate monohydrate, and dibasic sodium phosphate dihydrate. For example, each single-use vial can contain 100 mg antibody, 500 mg sucrose, 0.5 mg polysorbate 80, 2.2 mg monobasic sodium phosphate monohydrate, and 6.1 mg dibasic sodium phosphate dihydrate. No preservatives are present. Following reconstitution with 10 ml sterile water for injection, USP, the resulting pH is approximately 7.2.

(e) A sterile, preservative-free solution for subcutaneous administration supplied in a single-use, 1 ml pre-filled syringe. The product can be formulated with sodium chloride, monobasic sodium phosphate dihydrate, dibasic sodium phosphate dihydrate, sodium citrate, citric acid monohydrate, mannitol, polysorbate 80 and water for injection, USP. Sodium hydroxide may be added to adjust pH to about 5.2.

For example, each syringe can be formulated to deliver 0.8 ml (40 mg) of drug product. Each 0.8 ml contains 40 mg anti-CD19 antibody, 4.93 mg sodium chloride, 0.69 mg monobasic sodium phosphate dihydrate, 1.22 mg dibasic sodium phosphate dihydrate, 0.24 mg sodium citrate, 1.04 mg citric acid monohydrate, 9.6 mg mannitol, 0.8 mg polysorbate 80 and water for injection, USP.

(f) A sterile, preservative-free, lyophilized powder contained in a single-use vial that is reconstituted with sterile water for injection (SWFI), USP, and administered as a subcutaneous (s.c.) injection. The product can be formulated with sucrose, histidine hydrochloride monohydrate, L-histidine, and polysorbate. For example, a 75 mg vial can contain 129.6 mg or 112.5 mg of an anti-CD19 antibody, 93.1 mg sucrose, 1.8 mg L-histidine hydrochloride monohydrate, 1.2 mg L-histidine, and 0.3 mg polysorbate 20, and is designed to deliver 75 mg of the antibody in 0.6 ml after reconstitution with 0.9 ml SWFI, USP. A 150 mg vial can contain 202.5 mg or 175 mg anti-CD19 antibody, 145.5 mg sucrose, 2.8 mg L-histidine hydrochloride monohydrate, 1.8 mg L-histidine, and 0.5 mg polysorbate 20, and is designed to deliver 150 mg of the antibody in 1.2 ml after reconstitution with 1.4 ml SWFI, USP.

(g) A sterile, lyophilized product for reconstitution with sterile water for injection. The product can be formulated as single-use vials for intramuscular (IM) injection using mannitol, histidine and glycine. For example, each single-use vial can contain 100 mg anti-CD19 antibody, 67.5 mg of mannitol, 8.7 mg histidine and 0.3 mg glycine, and is designed to deliver 100 mg antibody in 1.0 ml when reconstituted with 1.0 ml sterile water for injection. As another example, each single-use vial can contain 50 mg anti-CD19 antibody, 40.5 mg mannitol, 5.2 mg histidine and 0.2 mg glycine, and is designed to deliver 50 mg of antibody when reconstituted with 0.6 ml sterile water for injection.

(h) A sterile, preservative-free solution for intramuscular (IM) injection, supplied at a concentration of 100 mg/ml. The product can be formulated in single-use vials with histidine, glycine, and sterile water for injection. For example, each single-use vial can be formulated with 100 mg antibody, 4.7 mg histidine, and 0.1 mg glycine in a volume of 1.2 ml designed to deliver 100 mg of antibody in 1 ml. As another example, each single-use vial can be formulated with 50 mg antibody, 2.7 mg histidine and 0.08 mg glycine in a volume of 0.7 ml or 0.5 ml designed to deliver 50 mg of antibody in 0.5 ml.

In certain embodiments, a pharmaceutical composition of the invention is stable at 4° C. In certain embodiments, a pharmaceutical composition of the invention is stable at room temperature.

5.21.2. Antibody Half-Life

In certain embodiments, the half-life of an anti-CD19 antibody of compositions and methods of the invention is at least about 4 to 7 days. In certain embodiments, the mean half-life of an anti-CD19 antibody of compositions and methods of the invention is at least about 2 to 5 days, 3 to 6 days, 4 to 7 days, 5 to 8 days, 6 to 9 days, 7 to 10 days, 8 to 11 days, 8 to 12, 9 to 13, 10 to 14, 11 to 15, 12 to 16, 13 to 17, 14 to 18, 15 to 19, or 16 to 20 days. In other embodiments, the mean half-life of an anti-CD19 antibody of compositions and methods of the invention is at least about 17 to 21 days, 18 to 22 days, 19 to 23 days, 20 to 24 days, 21 to 25, days, 22 to 26 days, 23 to 27 days, 24 to 28 days, 25 to 29 days, or 26 to 30 days. In still further embodiments the half-life of an anti-CD19 antibody of compositions and methods of the invention can be up to about 50 days. In certain embodiments, the half-lives of antibodies of compositions and methods of the invention can be prolonged by methods known in the art. Such prolongation can in turn reduce the amount and/or frequency of dosing of the antibody compositions. Antibodies with improved in vivo half-lives and methods for preparing them are disclosed in U.S. Pat. No. 6,277,375; and International Publication Nos. WO 98/23289 and WO 97/3461.

The serum circulation of anti-CD19 antibodies in vivo may also be prolonged by attaching inert polymer molecules such as high molecular weight polyethyleneglycol (PEG) to the antibodies with or without a multifunctional linker either through site-specific conjugation of the PEG to the N- or C-terminus of the antibodies or via epsilon-amino groups present on lysyl residues. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods known to those of skill in the art, for example, by immunoassays described herein.

Further, the antibodies of compositions and methods of the invention can be conjugated to albumin in order to make the antibody more stable in vivo or have a longer half-life in vivo. The techniques are well known in the art, see, e.g., International Publication Nos. WO 93/15199, WO 93/15200, and WO 01/77137; and European Patent No. EP 413, 622, all of which are incorporated herein by reference.

5.21.3. Administration and Dosing

Administration of compositions of the invention to a human patient can be by any route, including but not limited to intravenous, intradermal, transdermal, subcutaneous, intramuscular, inhalation (e.g., via an aerosol), buccal (e.g., sub-lingual), topical (i.e., both skin and mucosal surfaces, including airway surfaces), intrathecal, intraarticular, intraplural, intracerebral, intra-arterial, intraperitoneal, oral, intralymphatic, intranasal, rectal or vaginal administration, by perfusion through a regional catheter, or by direct intralesional injection. In one embodiment, compositions of the invention are administered by intravenous push or intravenous infusion given over defined period (e.g., 0.5 to 2 hours). Compositions of the invention can be delivered by peristaltic means or in the form of a depot, although the most suitable route in any given case will depend, as is well known in the art, on such factors as the species, age, gender and overall condition of the subject, the nature and severity of the condition being treated and/or on the nature of the particular composition (i.e., dosage, formulation) that is being administered. In particular embodiments, the route of administration is via bolus or continuous infusion over a period of time, once or twice a week. In other particular embodiments, the route of administration is by subcutaneous injection, optionally once or twice weekly. In one embodiment, compositions, and/or methods of the invention are administered on an outpatient basis.

In certain embodiments, the dose of a composition comprising anti-CD19 antibody is measured in units of mg/kg of patient body weight. In other embodiments, the dose of a composition comprising anti-CD19 antibody is measured in units of mg/kg of patient lean body weight (i.e., body weight minus body fat content). In yet other embodiments, the dose of a composition comprising anti-CD19 antibody is measured in units of mg/m$^2$ of patient body surface area. In yet other embodiments, the dose of a composition comprising anti-CD19 antibody is measured in units of mg per dose administered to a patient. Any measurement of dose can be used in conjunction with compositions and methods of the invention and dosage units can be converted by means standard in the art.

Those skilled in the art will appreciate that dosages can be selected based on a number of factors including the age, sex, species and condition of the subject (e.g., stage of B cell malignancy), the desired degree of cellular depletion, the disease to be treated and/or the particular antibody or antigen-binding fragment being used and can be determined by one of skill in the art. For example, effective amounts of compositions of the invention may be extrapolated from dose-response curves derived in vitro test systems or from animal model (e.g., the cotton rat or monkey) test systems. Models and methods for evaluation of the effects of antibodies are known in the art (Wooldridge et al., *Blood,* 89(8): 2994-2998 (1997)), incorporated by reference herein in its entirety). In certain embodiments, for particular B cell malignancies, therapeutic regimens standard in the art for antibody therapy can be used with compositions and methods of the invention.

Examples of dosing regimens that can be used in methods of the invention include, but are not limited to, daily, three times weekly (intermittent), weekly, or every 14 days. In certain embodiments, dosing regimens include, but are not limited to, monthly dosing or dosing every 6-8 weeks.

Those skilled in the art will appreciate that dosages are generally higher and/or frequency of administration greater for initial treatment as compared with maintenance regimens.

In some embodiments of the invention, anti-CD19 antibodies bind to B cells and may result in efficient (i.e., at low dosage) depletion of B cells (as described herein). Higher degrees of binding may be achieved where the density of human CD19 on the surface of a patient's B cells is high. In certain embodiments, dosages of the antibody (optionally in a pharmaceutically acceptable carrier as part of a pharmaceutical composition) are at least about 0.0005, 0.001, 0.05, 0.075, 0.1, 0.25, 0.375, 0.5, 1, 2.5, 5, 10, 20, 37.5, or 50 mg/m$^2$ and/or less than about 500, 475, 450, 425, 400, 375, 350, 325, 300, 275, 250, 225, 200, 175, 150, 125, 100, 75, 60, 50, 37.5, 20, 15, 10, 5, 2.5, 1, 0.5, 0.375, 0.1, 0.075 or 0.01 mg/m$^2$. In certain embodiments, the dosage is between about 0.0005 to about 200 mg/m$^2$, between about 0.001 and 150 mg/m$^2$, between about 0.075 and 125 mg/m$^2$, between about 0.375 and 100 mg/m$^2$, between about 2.5 and 75 mg/m$^2$, between about 10 and 75 mg/m$^2$, and between about 20 and 50 mg/m$^2$. In related embodiments, the dosage of anti-CD19 antibody used is at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5 mg/kg of body weight of a patient. In certain embodiments, the dose of naked anti-CD19 antibody used is at least about 1 to 10, 5 to 15, 10 to 20, or 15 to 25 mg/kg of body weight of a patient. In certain embodiments, the dose of anti-CD19 antibody used is at least about 1 to 20, 3 to 15, or 5 to 10 mg/kg of body weight of a patient. In other embodiments, the dose of anti-CD19 antibody used is at least about 5, 6, 7, 8, 9, or 10 mg/kg of body weight of a patient. In certain embodiments, a single dosage unit of the antibody (optionally in a pharmaceutically acceptable carrier as part of a pharmaceutical composition) can be at least about 0.5, 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 204, 206, 208, 210, 212, 214, 216, 218, 220, 222, 224, 226, 228, 230, 232, 234, 236, 238, 240, 242, 244, 246, 248, or 250 micrograms/m$^2$. In other embodiments, dose is up to 1 g per single dosage unit.

All of the above doses are exemplary and can be used in conjunction with compositions and methods of the invention, however where an anti-CD19 antibody is used in conjunction with a toxin or radiotherapeutic agent the lower doses described above may be preferred. In certain embodiments, where the patient has low levels of CD19 density, the lower doses described above may be preferred.

In certain embodiments of the invention where chimeric anti-CD19 antibodies are used, the dose or amount of the chimeric antibody is greater than about 2, 3, 4, 5, 6, 7, 8, 9, 10, 11, 12, 13, 14, 15, or 16 mg/kg of patient body weight. In other embodiments of the invention where chimeric anti-CD19 antibodies are used, the dose or amount of the chimeric antibody is less than about 1, 0.9, 0.8, 0.7, 0.6, 0.5, 0.4, 0.3, 0.2, or 0.1 mg/kg of patient body weight.

In some embodiments of methods of this invention, antibodies and/or compositions of this invention can be administered at a dose lower than about 375 mg/m$^2$; at a dose lower than about 37.5 mg/m$^2$; at a dose lower than about 0.375 mg/m$^2$; and/or at a dose between about 0.075 mg/m$^2$ and about 125 mg/m$^2$. In certain embodiments of methods of the invention, dosage regimens comprise low doses, administered at repeated intervals. For example, in one embodiment, compositions of the invention can be administered at a dose lower than about 375 mg/m$^2$ at intervals of approximately every 1, 2, 3, 4, 5, 6, 7, 8, 9, 10, 15, 20, 25, 30, 35, 40, 45, 50, 60, 70, 80, 90, 100, 125, 150, 175, or 200 days.

The specified dosage can result in B cell depletion in the human treated using compositions and methods of the invention for a period of at least about 1, 2, 3, 5, 7, 10, 14, 20, 30, 45, 60, 75, 90, 120, 150 or 180 days or longer. In certain embodiments, pre-B cells (not expressing surface immunoglobulin) are depleted. In certain embodiments, mature B cells (expressing surface immunoglobulin) are depleted. In other embodiments, all non-malignant types of B cells can exhibit depletion. Any of these types of B cells can be used to measure B cell depletion. B cell depletion can be measured in bodily fluids such as blood serum, or in tissues such as bone marrow. In certain embodiments of methods of the invention, B cells are depleted by at least 30%, 40%, 50%, 60%, 70%, 80%, 90%, or 100% in comparison to B cell levels in the patient being treated before use of compositions and methods of the invention. In other embodiments of methods of the invention, B cells are depleted by at least 30%, 40%, 50%, 60%, 70%, 80%, 90%, or 100% in comparison to typical standard B cell levels for humans. In related embodiments, the typical standard B cell levels for humans are determined using patients comparable to the patient being treated with respect to age, sex, weight, and other factors.

In certain embodiments of the invention, a dosage of about 125 mg/m$^2$ or less of an antibody or antigen-binding fragment results in B cell depletion for a period of at least about 7, 14, 21, 30, 45, 60, 90, 120, 150, or 200 days. In another representative embodiment, a dosage of about 37.5 mg/m$^2$ or less depletes B cells for a period of at least about 7, 14, 21, 30, 45, 60, 90, 120, 150, or 200 days. In still other embodiments, a dosage of about 0.375 mg/m$^2$ or less results in depletion of B cells for at least about 7, 14, 21, 30, 45 or 60 days. In another embodiment, a dosage of about 0.075 mg/m$^2$ or less results in depletion of B cells for a period of at least about 7, 14, 21, 30, 45, 60, 90, 120, 150, or 200 days. In yet other embodiments, a dosage of about 0.01 mg/m$^2$, 0.005 mg/m$^2$ or even 0.001 mg/m$^2$ or less results in depletion of B cells for at least about 3, 5, 7, 10, 14, 21, 30, 45, 60, 90, 120, 150, or 200 days. According to these embodiments, the dosage can be administered by any suitable route, but is optionally administered by a subcutaneous route.

As another aspect, the invention provides the discovery that B cell depletion and/or treatment of B cell disorders can be achieved at lower dosages of antibody or antibody fragments than employed in currently available methods. Thus, in another embodiment, the invention provides a method of depleting B cells and/or treating a B cell disorder, comprising administering to a human, an effective amount of an antibody that specifically binds to CD19, wherein a dosage of about 500, 475, 450, 425, 400, 375, 350, 325, 300, 275, 250, 225, 200, 175, 150, 125, 100, 75, 60, 50, 37.5, 20, 10, 5, 2.5, 1, 0.5, 0.375, 0.25, 0.1, 0.075, 0.05, 0.001, 0.0005 mg/m$^2$ or less results in a depletion of B cells (circulating and/or tissue B cells) of 25%, 35%, 50%, 60%, 75%, 80%, 85%, 90%, 95%, 98% or more for a period at least about 3, 5, 7, 10, 14, 21, 30, 45, 60, 75, 90, 120, 150, 180, or 200 days or longer. In representative embodiments, a dosage of about 125 mg/m$^2$ or 75 mg/m$^2$ or less results in at least about 50%, 75%, 85% or 90% depletion of B cells for at least about 7, 14, 21, 30, 60, 75, 90, 120, 150 or 180 days. In other embodiments, a dosage of about 50, 37.5 or 10 mg/m$^2$ results in at least about a 50%, 75%, 85% or 90% depletion of B cells for at least about 7, 14, 21, 30, 60, 75, 90, 120 or 180 days. In still other embodiments, a dosage of about 0.375 or 0.1 mg/m$^2$ results in at least about a 50%, 75%, 85% or 90% depletion of B cells for at least about 7, 14, 21, 30, 60, 75 or 90 days. In further embodiments, a dosage of about 0.075, 0.01, 0.001, or 0.0005 mg/m$^2$ results in at least about a 50%, 75%, 85% or 90% depletion of B cells for at least about 7, 14, 21, 30 or 60 days.

In certain embodiments of the invention, the dose can be escalated or reduced to maintain a constant dose in the blood or in a tissue, such as, but not limited to, bone marrow. In related embodiments, the dose is escalated or reduced by about 2%, 5%, 8%, 10%, 15%, 20%, 30%, 40%, 50%, 60%, 70%, 80%, 90%, and 95% in order to maintain a desired level of an antibody of compositions and methods of the invention.

In certain embodiments, the dosage can be adjusted and/or the infusion rate can be reduced based on patient's immunogenic response to compositions and methods of the invention.

According to one aspect of methods of the invention, a loading dose of an anti-CD19 antibody and/or composition of the invention can be administered first followed by a maintenance dose until the B cell malignancy being treated progresses or followed by a defined treatment course (e.g., CAMPATH198 (alemtuzumab), MYLOTARG198 (gemtuzumab ozogamicin), or RITUXAN198 (rituximab), the latter of which allow patients to be treated for a defined number of doses that has increased as additional data have been generated).

According to another aspect of methods of the invention, a patient may be pretreated with compositions and methods of the invention to detect, minimize immunogenic response, or minimize adverse effects of compositions and methods of the invention.

5.21.4. Toxicity Testing

The tolerance, toxicity and/or efficacy of the compositions and/or treatment regimens of the present invention can be determined by standard pharmaceutical procedures in cell cultures or experimental animals, e.g., for determining the LD50 (the dose lethal to 50% of the population), the ED50 (the dose therapeutically effective in 50% of the population), and IC50 (the dose effective to achieve a 50% inhibition). In one embodiment, the dose is a dose effective to achieve at least a 60%, 70%, 80%, 90%, 95%, or 99% depletion of circulating B cells or circulating immunoglobulin, or both. The dose ratio between toxic and therapeutic effects is the therapeutic index and it can be expressed as the ratio LD50/ED50. Therapies that exhibit large therapeutic indices may be preferred. While therapies that exhibit toxic side effects may be used, care should be taken to design a delivery system that targets such agents to CD19-expressing cells in order to minimize potential damage to CD19 negative cells and, thereby, reduce side effects.

Data obtained from the cell culture assays and animal studies can be used in formulating a range of dosages of the compositions and/or treatment regimens for use in humans. The dosage of such agents may lie within a range of circulating concentrations that include the ED50 with little or no toxicity. The dosage may vary within this range depending upon the dosage form employed and the route of administration utilized. For any therapy used in methods of the invention, a therapeutically effective dose can be estimated by appropriate animal models. Depending on the species of the animal model, the dose can be scaled for human use according to art-accepted formulas, for example, as provided by Freireich et al., Quantitative comparison of toxicity of anti-cancer agents in mouse, rat, monkey, dog, and human, *Cancer Chemotherapy Reports*, NCI 1966 40:219-244. Data obtained from cell culture assays can be useful for predicting potential toxicity. Animal studies can be used to formulate a specific dose to achieve a circulating plasma concentration range that includes the IC50 (i.e., the concentration of the test compound that achieves a half-maximal inhibition of symptoms) as determined in cell culture. Such information can be used to more accurately determine useful doses in humans. Plasma drug levels may be measured, for example, by high performance liquid chromatography, ELISA, or by cell based assays.

5.22. Patient Diagnosis, Staging and Therapeutic Regimens Oncology

According to certain aspects of the invention, the treatment regimen and dose used with compositions and methods of the invention is chosen based on a number of factors including, but not limited to, the stage of the B cell disease or disorder being treated. Appropriate treatment regimens can be determined by one of skill in the art for particular stages of a B cell disease or disorder in a patient or patient population. Dose response curves can be generated using standard protocols in the art in order to determine the effective amount of compositions of the invention for treating patients having different stages of a B cell disease or disorder. In general, patients having more advanced stages of a B cell disease or disorder will require higher doses and/or more frequent doses which may be administered over longer periods of time in comparison to patients having an early stage B cell disease or disorder.

Anti-CD19 antibodies, compositions and methods of the invention may be practiced to treat B cell diseases, including B cell malignancies. The term "B cell malignancy" includes any malignancy that is derived from a cell of the B cell lineage. Exemplary B cell malignancies include, but are not limited to: B cell subtype non-Hodgkin's lymphoma (NHL) including low grade/follicular NHL, small lymphocytic (SL) NHL, intermediate grade/follicular NHL, intermediate grade diffuse NHL, high grade immunoblastic NHL, high grade lymphoblastic NHL, high grade small non-cleaved cell NHL; mantle-cell lymphoma, and bulky disease NHL; Burkitt's lymphoma; multiple myeloma; pre-B acute lymphoblastic leukemia and other malignancies that derive from early B cell precursors; common acute lymphocytic leukemia (ALL); chronic lymphocytic leukemia (CLL) including immunoglobulin-mutated CLL and immunoglobulin-unmutated CLL; hairy cell leukemia; Null-acute lymphoblastic leukemia; Waldenstrom's Macroglobulinemia; diffuse large B cell lymphoma (DLBCL) including germinal center B cell-like (GCB) DLBCL, activated B cell-like (ABC) DLBCL, and type 3 DLBCL; pro-lymphocytic leukemia; light chain disease; plasmacytoma; osteosclerotic myeloma; plasma cell leukemia; monoclonal gammopathy of undetermined significance (MGUS); smoldering multiple myeloma (SMM); indolent multiple myeloma (IMM); Hodgkin's lymphoma including classical and nodular lymphocyte pre-dominant type; lymphoplasmacytic lymphoma (LPL); and marginal-zone lymphoma including gastric mucosal-associated lymphoid tissue (MALT) lymphoma.

In a further embodiment the invention can be employed to treat mature B cell malignancies (i.e., express Ig on the cell surface) including but not limited to follicular lymphoma, mantle-cell lymphoma, Burkitt's lymphoma, multiple myeloma, diffuse large B-cell lymphoma (DLBCL) including germinal center B cell-like (GCB) DLBCL, activated B cell-like (ABC) DLBCL, and type 3 DLBCL, Hodgkin's lymphoma including classical and nodular lymphocyte pre-dominant type, lymphoplasmacytic lymphoma (LPL), marginal-zone lymphoma including gastric mucosal-associated lymphoid tissue (MALT) lymphoma, and chronic lymphocytic leukemia (CLL) including immunoglobulin-mutated CLL and immunoglobulin-unmutated CLL.

Further, CD19 is expressed earlier in B cell development than, for example, CD20, and is therefore particularly suited for treating pre-B cell and immature B cell malignancies (i.e., do not express Ig on the cell surface), for example, in the bone marrow. Illustrative pre-B cell and immature B cell malignancies include, but are not limited to, acute lymphoblastic leukemia.

In other particular embodiments, the invention can be practiced to treat extranodal tumors.

5.22.1. Diagnosis and Staging of B Cell Malignancies

The progression of cancer, such as a B cell disease or disorder capable of tumor formation (e.g., non-Hodgkin lymphoma, diffuse large B cell lymphoma, follicular lymphoma, and Burkitt lymphoma) is typically characterized by the degree to which the cancer has spread through the body and is often broken into the following four stages which are prognostic of outcome. Stage I: The cancer is localized to a particular tissue and has not spread to the lymph nodes. Stage II: The cancer has spread to the nearby lymph nodes, i.e., metastasis. Stage III: The cancer is found in the lymph nodes in regions of the body away from the tissue of origin and may comprise a mass or multiple tumors as opposed to one. Stage IV: The cancer has spread to a distant part of the body. The stage of a cancer can be determined by clinical observations and testing methods that are well known to those of skill in the art. The stages of cancer described above are traditionally used in conjunction with clinical diagnosis of cancers characterized by tumor formation, and can be used in conjunction with the compositions and methods of the present invention to treat B cell diseases and disorders. Typically early stage disease means that the disease remains localized to a portion of a patient's body or has not metastasized.

With respect to non-tumor forming B cell diseases and disorders such as, but not limited to, multiple myeloma, the criteria for determining the stage of disease differs. The Durie-Salmon Staging System has been widely used. In this staging system, clinical stage of disease (stage I, II, or III) is based on several measurements, including levels of M protein, the number of lytic bone lesions, hemoglobin values, and serum calcium levels. Stages are further divided according to renal (kidney) function (classified as A or B). According to the Durie-Salmon Staging System Stage I (low cell mass) is characterized by all of the following: Hemoglobin value >10 g/dL; Serum calcium value normal or ≤12 mg/dL; Bone x-ray, normal bone structure (scale 0) or solitary bone plasmacytoma only; and Low M-component production rate: IgG value <5 g/dL, IgA value <3 g/d, Bence Jones protein <4 g/24 h. Stage I patients typically have no related organ or tissue impairment or symptoms. Stage II (intermediate cell mass) is characterized by fitting neither stage I nor stage III. Stage III (high cell mass) is characterized by one or more of the following: Hemoglobin value <8.5 g/dL; Serum calcium value >12 mg/dL; Advanced lytic bone lesions (scale 3); High M-component production rate: IgG value >7 g/dL, IgA value >5 g/dL, Bence Jones protein >12 g/24 h Subclassification (either A or B), where A is Relatively normal renal function (serum creatinine value <2.0 mg/dL) and B is Abnormal renal function (serum creatinine value ≥2.0 mg/dL).

Another staging system for myeloma is the International Staging System (ISS) for myeloma. This system can more effectively discriminate between staging groups and is based on easily measured serum levels of beta 2-microglobulin ($\beta$2-M) and albumin. According to the ISS for myeloma, Stage I is characterized by $\beta$2-M <3.5 and Albumin ≥3.5, Stage II is characterized by $\beta$2-M <3.5 and albumin <3.5 or $\beta$2-M 3.5-5.5, and Stage III is characterized by $\beta$2-M >5.5 (Multiple Myeloma Research Foundation, New Canaan, Conn.).

The stage of a B cell malignancy in a patient is a clinical determination. As indicated above, with respect to solid tumors, the spread, location, and number of tumors are the primary factors in the clinical determination of stage. Determination of stage in patients with non-tumor forming B cell malignancies can be more complex requiring serum level measurements as described above.

The descriptions of stages of B cell diseases and disorders above are not limiting. Other characteristics known in the art for the diagnosis of B cell diseases and disorders can be used as criteria for patients to determine stages of B cell diseases or disorders.

5.22.2. Clinical Criteria for Diagnosing B Cell Malignancies

Diagnostic criteria for different B cell malignancies are known in the art. Historically, diagnosis is typically based on a combination of microscopic appearance and immunophenotype. More recently, molecular techniques such as gene-expression profiling have been applied to develop molecular definitions of B cell malignancies (see, e.g., Shaffer et al., Nature 2:920-932 (2002)). Exemplary methods for clinical diagnosis of particular B cell malignancies are provided below. Other suitable methods will be apparent to those skilled in the art.

5.22.2.1. Follicular NHL

In general, most NHL (with the exception of mantle-cell lymphoma) have highly mutated immunoglobulin genes that appear to be the result of somatic hypermutation (SHM). The most common genetic abnormalities in NHL are translocations and mutations of the BCL6 gene.

Follicular NHL is often an indolent B cell lymphoma with a follicular growth pattern. It is the second most common lymphoma in the United States and Western Europe. The median age at which this disease presents is 60 years and there is a slight female predominance. Painless lymphadenopathy is the most common symptom. Tests often indicate involvement of the blood marrow and sometimes the peripheral blood. Follicular NHL is divided into cytologic grades based on the proportion of large cells in the follicle with the grades forming a continuum from follicular small cleaved-cell to large-cell predominance. (See, S. Freedman, et al., *Follicular Lymphoma*, pp. 367-388, In *Non-Hodgkin's Lymphomas*, P. Mauch et al., eds., Lippincott Williams & Wilkins, Philadelphia, Pa. (2004); T. Lister et al., *Follicular Lymphoma*, pp. 309-324, In *Malignant Lymphoma*, B. Hancock et al., eds., Oxford University Press, New York, N.Y. (2000)).

Most follicular NHL is characterized by a translocation between chromosomes 14 and 18 resulting in overexpression of BCL2. Follicular NHL is also characterized by both SHM and ongoing SHM and a gene expression profile similar to germinal center (GC) B cells (see, e.g., Shaffer et al., *Nature* 2:920-932 (2002)), which are the putative cells of origin for this malignancy. Heavy- and light chain rearrangements are typical. The tumor cells of this disease express monoclonal surface immunoglobulin with most expressing IgM. Nearly all follicular NHL tumor cells express the antigens CD19, CD20, CD22, CD79a, CD21, CD35 and CD10 but lack expression of CD5 and CD43. Paratrabecular infiltration with small cleaved cells is observed in the bone marrow. (See, S. Freedman et al., *Follicular Lymphoma*, pp. 367-388, In *Non-Hodgkin's Lymphomas*, P. Mauch et al., eds., Lippincott Williams & Wilkins, Philadelphia, Pa. (2004); T. Lister et al., *Follicular Lymphoma*, pp. 309-324, In *Malignant Lymphoma*, B. Hancock et al., eds., Oxford University Press, New York, N.Y. (2000)).

Diagnosis of follicular NHL generally relies on biopsy of an excised node in order to evaluate tissue architecture and cytological features. Fine-needle aspirations are usually not adequate since this procedure is less likely to provide tissue that can be evaluated and it fails to provide enough tissue for additional tests. Bilateral bone marrow biopsies are also indicated since involvement can be patchy. Additional diagnostic procedures include chest x-rays, chest, abdomen, neck and pelvis computed tomography (CT) scans, complete blood count, and chemistry profile. Flow cytometry and immunohistochemistry can be used to distinguish between follicular NHL and other mature B cell lymphomas. (See, S. Freedman et al., *Follicular Lymphoma*, pp. 367-388, In *Non-Hodgkin's Lymphomas*, P. Mauch et al., eds., Lippincott Williams & Wilkins, Philadelphia, Pa. (2004); T. Lister et al., *Follicular Lymphoma*, pp. 309-324, In *Malignant Lymphoma*, B. Hancock et al., eds., Oxford University Press, New York, N.Y. (2000)).

5.22.2.2. Mantle-Cell Lymphoma

Mantle-cell lymphoma localizes to the mantle region of secondary follicles and is characterized by a nodular and/or diffuse growth pattern. Mantle-cell lymphoma patients have median age of 60-65 years with the disease affecting predominantly males. For diagnostic purposes, the usual presenting feature is a generalized lymphadenopathy. Additionally, the spleen is often enlarged. This B cell lymphoma is associated with a t(11;14) between the IgH locus and cyclin D1 gene, which results in overexpression of cyclin D1. More than 50% of cases show additional chromosomal abnormalities. Mantle-cell lymphoma is typically not characterized by SHM. (See, W. Hiddemann et al., *Mantle Cell Lymphoma*, pp. 461-476, In *Non-Hodgkin's Lymphomas*, P. Mauch et al., eds., Lippincott Williams & Wilkins, Philadelphia, Pa. (2004); D. Weisenburger et al., *Mantle Cell Lymphoma*, pp. 28-41, In *Malignant Lymphoma*, B. Hancock et al., eds., Oxford University Press, New York, N.Y. (2000)).

Immunophenotyping (flow cytometry or frozen section) immunohistochemistry of mantle cell lymphoma cells shows them to nearly always be monoclonal, bearing surface IgM. Mantle cell lymphoma cells have also been noted to bear surface IgD. The cells express the antigens CD19, CD20, CD22 and CD24, but not CD23. They also express surface antigens CD5 but not for CD10, distinguishing them from true follicle center-cell lymphomas which are almost always CD5 negative. Frequently, extranodal involvement is found including bone marrow infiltration and tumors of the liver and gastrointestinal tract. Mild anemia and leukemic expression is not uncommon with mantle-cell lymphoma. (See, A. Lal et al., *Role of Fine Needle Aspiration in Lymphoma*, pp. 181-220, In W. Finn et al., eds., *Hematopathology in Oncology*, Kluwer Academic Publishers, Norwell, Mass. (2004); W. Hiddemann et al., *Mantle Cell Lymphoma*, pp. 461-476, In *Non-Hodgkin's Lymphomas*, P. Mauch et al., eds., Lippincott Williams & Wilkins, Philadelphia, Pa. (2004)).

Diagnosis of mantle-cell lymphoma involves examination of the peripheral blood as well as bone marrow and lymph node biopsies. In addition, cytogenetic studies and immunophenotyping are useful in differential diagnosis. (See, W. Hiddemann, et al., *Mantle Cell Lymphoma* pp. 461-476, In *Non-Hodgkin's Lymphomas*, P. Mauch, et al., eds., Lippincott Williams & Wilkins, Philadelphia, Pa. (2004); D. Weisenburger, et al., *Mantle Cell Lymphoma*, pp. 28-41, In *Malignant Lymphoma*, B. Hancock, et al., eds., Oxford University Press, New York, N.Y. (2000)).

5.22.2.3. Burkitt's Lymphoma

Burkitt's lymphoma is an aggressive B cell lymphoma typically observed in children and young adults and is usually associated with bulky disease of the jaw and/or abdomen. Approximately 20% of patients have bone marrow involvement. An endemic form of Burkitt's lymphoma involves Epstein-Barr virus (EBV) infection of malignant cells; the sporadic form is independent of EBV infection. A translocation of c-myc to immunoglobulin loci, which results in deregulation of the c-myc gene, is characteristic of this disease (t(8;14)(q24;q32)). Interestingly, deletions of the c-myc sequences appear to be involved in the sporadic form of the disease, while the endemic form usually involves point mutations or insertions. (See, V. Pappa, et al., *Molecular Biology*, pp. 133-157, In *Malignant Lymphoma*, B. Hancock, et al., eds., Oxford University Press, New York, N.Y. (2000)). Burkitt's lymphoma is also characterized by SHM, and the malignant cells have a gene expression profile similar to GC B cells, suggesting that this malignancy is derived from GC B cells.

Immunophenotype of Burkett's lymphoma shows the cells of this disease express CD19, CD20, CD22, and CD79a, but not CD5, CD23, cyclin D or terminal deoxynucleotidyl transferase. Frequently, these cells are positive for CD10 and BCL6 and usually negative for BCL2. (See, I. Magrath, et al., *Burkitt's Lymphoma*, pp. 477-501, In *Non-Hodgkin's Lymphomas*, P. Mauch, et al., eds., Lippincott Williams & Wilkins, Philadelphia, Pa. (2004)).

High grade B cell Burkitt's-like lymphoma is a lymphoma borderline between Burkitt's lymphoma and large B cell lymphoma. The cells of this lymphoma express CD19, CD20, and CD22 but expression of CD10, which is nearly always present in true Burkitt's lymphoma, is frequently absent. Because of this and other characteristics, some believe this lymphoma should be classified as a diffuse large B cell lymphoma. (See, K. Maclennan, *Diffuse Aggressive B cell Lymphoma*, pp. 49-54, In *Malignant Lymphoma*, B. Hancock, et al., eds., Oxford University Press, New York, N.Y. (2000)).

Diagnosis of Burkitt's lymphoma generally relies on detection of the translocation associated with this lymphoma; thus, conventional cytogenetic analysis is usually performed. Long distance polymerase chain reaction techniques and fluorescent in situ hybridization (FISH) have been used to detect Ig-myc junctions in the translocations and other genetic alterations associated with this disease. (See, R. Siebert, et al., *Blood* 91:984-990 (1998); T. Denyssevych, et al., *Leukemia*, 16:276-283 (2002)).

5.22.2.4. Diffuse Large B-Cell Lymphoma (DLBCL)

DLBCL is the most common non-Hodgkin's lymphoma and can arise from small B cell lymphoma, follicular lymphoma or marginal zone lymphoma. Typically, patients present with lymphadenopathy; however, a large percent of patients present in extranodal sites as well, with gastrointestinal involvement being the most common. Bone marrow involvement is observed in about 15% of patients. (See, Armitage, et al., *Diffuse Large B cell Lymphoma*, pp. 427-453, In *Non-Hodgkin's Lymphomas*, P. Mauch, et al., eds., Lippincott Williams & Wilkins, Philadelphia, Pa. (2004)). Heterogeneity in clinical, biological and morphological characteristics makes this group of lymphomas difficult to subclassify. However, two distinct subgroups have been identified with one expressing genes characteristic of germinal center B cells (GC-DLBCL) and the other overexpressing genes in peripheral blood B cells. Survival rates are significantly better for patients with GC-DLBCL than those with activated B cell type (ABC)-DLBCL. (See, W. Chan, *Archives of Pathology and Laboratory Medicine* 128(12): 1379-1384 (2004)).

DLBCLs express the cell surface antigens CD19, CD20, CD22, and CD79a. CD10 is expressed in the large majority of cases and CD5 expression is observed in about 10% of cases. (See, K. Maclennan, *Diffuse Aggressive B cell Lymphoma*, pp. 49-54, In *Malignant Lymphoma*, B. Hancock, et al., eds., Oxford University Press, New York, N.Y. (2000)). DLBCL is often marked by abnormalities of BCL6 and/or translocations of BCL2 to the IgH locus. GC B cell like (GC) DLBCL is characterized by SHM with highly mutated immunoglobulin genes and ongoing SHM in malignant clones with a GC B cell-like gene expression profile. Most GC DLBCL have undergone immunoglobulin class switching. ABC-DLBCL is characterized by high level expression of NF-κB target genes including BCL2, interferon regulatory factor 4, CD44, FLIP and cyclin D. SHM, but not ongoing SHM, is present, and ABC-DLBCL does not have a GC B cell gene expression profile. Almost all ABC-DLBCL express a high level of IgM.

5.22.2.5. Extranodal Marginal-Zone Lymphoma

Extranodal marginal-zone lymphoma is an extranodal lymphoma that occurs in organs normally lacking organized lymphoid tissue (e.g., stomach, salivary glands, lungs and thyroid glands). It is largely a disease that affects older adults with a median age of over 60 years. Often, chronic inflammation or autoimmune processes precede development of the lymphoma. Gastric mucosal-associated lymphoid tissue (MALT) lymphoma, the most common type of marginal-zone lymphoma, is associated with *Helicobacter pylori* infection. Studies have shown a resolution of symptoms with eradication of the *H. pylori* infection following an antibiotic regimen. The presenting symptoms for gastric MALT lymphoma include nonspecific dyspepsia, epigastric pain, nausea, gastrointestinal bleeding and anemia. Systemic symptoms are uncommon, as are elevated levels of lactate acid dehydrogenase. (See, J. Yahalom, et al., *Extranodal Marginal Zone B cell Lymphoma of Mucosa-Associated Lymphoid Tissue*, pp. 345-360, In *Non-Hodgkin's Lymphomas*, P. Mauch, et al., eds., Lippincott Williams & Wilkins, Philadelphia, Pa. (2004); J. Radford, *Other Low-Grade Non-Hodgkin's Lymphomas*, pp. 325-330, In *Malignant Lymphoma*, B. Hancock, et al., eds., Oxford University Press, New York, N.Y. (2000). Systemic B symptoms include fevers greater than 38° C. for longer than 2 weeks without sign of infection, night sweats, extreme fatigue or unintentional weight loss of greater than or equal to 10% of body weight over the previous 6 months).

The immunophenotype of MALT lymphoma is characterized by expression of CD19, CD20, CD79a, CD21 and CD35 and lack of expression of CD5, CD23, and CD10. About half of MALT lymphomas express CD43. The immunoglobulin typically expressed in the tumor cells of this disease is IgM while IgD is not expressed. These features are critical in distinguishing this lymphoma from other small B cell lymphomas such as mantle cell lymphoma, lymphocytic lymphoma and follicular lymphoma. Trisomy 3 has been reported in 60% of MALT lymphoma cases. In 25-40% of gastric and pulmonary MALT lymphomas a t(11;18) is observed. This translocation is observed much less frequently in other MALT lymphomas. T(11;18) is associated with nuclear expression of BCLI0. (See, J. Yahalom, et al., *Extranodal Marginal Zone B cell Lymphoma of Mucosa-Associated Lymphoid Tissue*, pp. 345-360, In *Non-Hodgkin's Lymphomas*, P. Mauch, et al., eds., Lippincott Williams & Wilkins, Philadelphia, Pa. (2004)). Marginal-zone lymphomas are generally characterized by SHM and ongoing SHM.

Diagnostic procedures include immunophenotyping or flow cytometry to determine the identity of the cell surface markers. In addition, molecular genetic analysis should be done to determine the presence of t(11;18) as this is an indicator that the disease will not respond to antibiotics. Histology can be used to determine the presence of *H. pylori*. Additional tests should include a complete blood count, basic biochemical tests including that for lactate acid dehydrogenase; CT scans of the abdomen, chest and pelvis and a bone marrow biopsy. (See, J. Yahalom, et al., *Extranodal Marginal Zone B cell Lymphoma of Mucosa-Associated Lymphoid Tissue*, pp. 345-360, In *Non-Hodgkin's Lymphomas*, P. Mauch, et al., eds., Lippincott Williams & Wilkins, Philadelphia, Pa. (2004)).

5.22.2.6. Nodal Marginal Zone B Cell Lymphoma

Nodal Marginal Zone B cell Lymphoma is a relatively newly classified lymphoma thus little has been published on it. It is a primary nodal B cell lymphoma sharing genetic and morphological characteristics with extranodal and splenic marginal zone lymphomas, but does not localize to the spleen or extranodally. Hepatitis C virus has been reported to be associated with this lymphoma as has Sjögren's syndrome. (See, F. Berger, et al., *Nodal Marginal Zone B cell Lymphoma*, pp. 361-365, In *Non-Hodgkin's Lymphomas*, P. Mauch, et al., eds., Lippincott Williams & Wilkins, Philadelphia, Pa. (2004)).

Nodal marginal zone lymphoma has a heterogeneous cytology and morphology. Due to its relatively high proportion of large cells this lymphoma, unlike the other marginal lymphomas (splenic and extranodal), cannot be classified as true low grade B cell lymphoma. The genetic and immunological phenotype of nodal marginal zone lymphoma includes expression of CD19, CD20, CD22, BCL2, sIgM and cytoplasmic IgG (cIg). These cells do not express CD5, CD10, CD23, CD43 or cyclin D1. The translocation characteristic of MALT lymphoma, t(11;18), is not observed for nodal marginal zone lymphoma. These characteristics aid in the differential diagnosis of this lymphoma from other small B cell lymphomas. (See, F. Berger, et al., *Nodal Marginal Zone B cell Lymphoma*, pp. 361-365, In *Non-Hodgkin's Lymphomas*, P. Mauch, et al., eds., Lippincott Williams & Wilkins, Philadelphia, Pa. (2004)).

5.22.2.7. Splenic Marginal Zone Lymphoma

Splenic Marginal Zone Lymphoma is an indolent micronodular B cell lymphoma with a characteristic clinical presentation of prominent splenomegaly and infiltration of the peripheral blood and the bone marrow. In addition, a relatively high level of liver involvement has been reported. A role for hepatitis C virus has been postulated for this lymphoma. The immunophenotype of splenic marginal zone lymphoma is typically $CD19^+$, $CD20^+$, $IgD^+$, $BCL2^+$, $p27^+$, $CD3^-$, $CD5^-$, $CD10^-$, $CD23^-$, $CD38^-$, $CD43^-$, $BCL-6^-$, and cyclin $D1^-$. Genetic characteristics include a 7q deletion, p53 alterations and SHM. (See, M. Piris, et al., *Splenic Marginal Zone Lymphoma*, pp. 275-282, In *Non-Hodgkin's Lymphomas*, P. Mauch, et al., eds., Lippincott Williams & Wilkins, Philadelphia, Pa. (2004)).

Diagnosis generally relics on immunophenotyping to determine the identity of the cell surface markers. Genetic and biochemical analysis, in combination with data on cell surface markers, help to differentiate this lymphoma from other small B cell lymphomas. (See, M. Piris, et al., *Splenic Marginal Zone Lymphoma*, pp. 275-282, In *Non-Hodgkin's Lymphomas*, P. Mauch, et al., eds., Lippincott Williams & Wilkins, Philadelphia, Pa. (2004)).

5.22.2.8. Acute (B Cell) Lymphocytic Leukemia (ALL)

ALL is a marrow-based neoplasm largely affecting children with the highest incidence between 1-5 years. Most common symptoms at presentation include fatigue, lethargy, fever and bone and joint pain. Fatigue and lethargy correlates with the degree of anemia present. An elevated white blood cell count is common at presentment. Radiographs of the chest often show skeletal lesions. Extramedullary spread is common and involves the central nervous system, testes, lymph nodes, liver, spleen and kidney. Anterior mediastinal masses are observed in only about 5-10% of newly diagnosed cases. (See, J. Whitlock, et al., *Acute Lymphocytic Leukemia*, pp. 2241-2271, In *Wintrobe's Clinical Hematology*, Tenth Edition, G. Lee, et al., eds. Williams & Wilkins, Baltimore, Md. (1999)).

The immunophenotype of ALL is $CD10^+$, $CD19^+$, $CD20^+$, CD22, and $CD24^+$. Pre-B cell ALL cells express cytoplasmic but not surface immunoglobulin, while mature B cell ALL (which accounts for only 1-2% of ALL cases) is distinguished from other leukemias of B cell lineage by the expression of surface immunoglobulin. Cytogenetic characteristics of ALL includes t(8;14), t(2;8) and t(8;22). Although rarely detected at the cytogenetic level t(12;21) may be the most common cytogenetic abnormality associated with childhood ALL (observed in about 25% of cases). (See, M. Kinney, et al., *Classification and Differentiation of the Acute Leukemias*, pp. 2209-2240, In *Wintrobe's Clinical Hematology*, Tenth Edition, G. Lee, et al., eds. Williams & Wilkins, Baltimore, Md. (1999); J Whitlock, et al., *Acute Lymphocytic Leukemia*, pp. 2241-2271; In *Wintrobe's Clinical Hematology*, Tenth Edition, G. Lee, et al., eds. Williams & Wilkins, Baltimore, Md., (1999)).

Precise diagnosis of acute leukemia usually relies on a bone aspirate and biopsy. Aspirate smears are used for morphological, immunological and cytological assessments. The demonstration of lymphoblasts in the bone marrow is diagnostic of ALL. The presence of greater than 5% leukemic lymphoblast cells in the bone marrow confirms ALL diagnosis but most require greater than 25% for a definitive diagnosis. Lumbar punctures are used to diagnose central nervous system involvement. Serum uric acids levels and serum lactate dehydrogenase levels have been found to be elevated in ALL. (See, M. Kinney, et al., *Classification and Differentiation of the Acute Leukemias*, pp. 2209-2240, In *Wintrobe's Clinical Hematology*, Tenth Edition, G. Lee, et al., eds. Williams & Wilkins, Baltimore, Md. (1999); J. Whitlock, et al., *Acute Lymphocytic Leukemia*, pp. 2241-2271; In *Wintrobe's Clinical Hematology*, Tenth Edition, G. Lee, et al., eds. Williams & Wilkins, Baltimore, Md., (1999)).

5.22.2.9. Chronic Lymphocytic Leukemia (CLL)/Small B Cell Lymphocytic Lymphoma (SLL)

CLL/SLL is the most common type of leukemia. When the disease involves the peripheral blood and bone marrow it is referred to as CLL. However, when the lymph nodes and other tissues are infiltrated by cells that are immunologically and morphologically identical to those in CLL, but where leukemic characteristics of the disease are absent, then the disease is referred to as SLL. This disease largely afflicts the elderly with a greater incidence of the disease occurring in men than women. Painless lymphadenopathy is the most common finding at presentation. Hypogammaglobulinemia is common with most cases of CLL/SLL exhibiting reduced levels of all immunoglobulins rather than any particular subclass of immunoglobulins. Asymptomatic patients are frequently diagnosed during routine blood counts (lymphocyte count of over $5000 \times 10^9/L$). As many as 20% of CLL/SLL cases report B symptoms. An additional diagnostic feature is infiltration of the bone marrow by more than 30% by immature lymphocytes. Lymph node biopsies generally show infiltration of involved nodes with well-differentiated lymphocytes. Autoimmune phenomena are often associated with CLL/SLL including autoimmune hemolytic anemia and immune thrombocytopenia. (See, J. Gribben, et al., *Small B cell Lymphocytic Lymphoma/Chronic Lymphocytic Leukemia and Prolymphocytic Leukemia*, pp. 243-261, In *Non-Hodgkin's Lymphomas*, P. Mauch, et al., eds., Lippincott Williams & Wilkins, Philadelphia, Pa. (2004); K. Maclennan, *Diffuse Indolent B cell Neoplasms*, pp. 43-47, In *Malignant Lymphoma*, B. Hancock, et al., eds., Oxford University Press, New York, N.Y. (2000); *Clinical Oncology*, A. Neal, et al., Neal, Hoskin and Oxford University Press, co-publ., New York, N.Y. (2003)).

In contrast with many of the low-grade B cell malignancies, nonrandom reciprocal translocations are rarely found in CLL/SLL. However, other cytogenetic abnormalities have been reported including deletions at 13q14, 11q22-23 and 17q13, with the latter two involving the p53 locus. Approximately 20% of cases exhibit trisomy 12. An elevated level of 13-2 microglobulin, higher levels of CD38 expression and the production of tumor necrosis factor-alpha are all characteristic of CLL/SLL. The immunophenotype of CLL/SLL is very diagnostic and includes weak expression of surface immunoglobulin usually IgM, or IgM and IgG, as well as expression of the cell antigens CD19, CD22, CD20 and usually CD5 and CD23. (See, J. Gribben, et al., *Small B cell Lymphocytic Lymphoma/Chronic Lymphocytic Leukemia and Prolymphocytic Leukemia*, pp. 243-261, In Non-Hodgkin's Lymphomas, P. Mauch, et al., eds., Lippincott Williams & Wilkins, Philadelphia, Pa. (2004); K. Maclennan, *Diffuse Indolent B cell Neoplasms*, pp. 43-47, In Malignant Lymphoma, B. Hancock, et al., eds., Oxford University Press, New York, N.Y. (2000)).

5.22.2.10. B Cell Prolymphocytic Leukemia (PLL)

PLL, once considered a variant of CLL, is now understood to be a distinct disease. PLL is generally a disease of elderly men and is characterized by a very high white blood cell count (greater than $200 \times 10^9/L$) and splenomegaly. Additional symptoms include anemia and thrombocytopenia. Prolymphocytes in PLL comprise more than 55% of the cells in the blood and bone marrow. In contrast with CLL, autoimmune phenomena are rarely observed in PLL. (See, J. Gribben, et al., *Small B cell Lymphocytic Lymphoma/Chronic Lymphocytic Leukemia and Prolymphocytic Leukemia*, pp. 243-261, In *Non-Hodgkin's Lymphomas*, P. Mauch, et al., eds., Lippincott Williams & Wilkins, Philadelphia, Pa. (2004)).

The immunophenotype of PLL is characterized by expression of CD19, CD21, CD22, CD24 and FMC7. The cells of PLL do not express CD23 and most do not express CD5. PLL cells exhibit complex chromosomal abnormalities, with deletions at 13q14 and 11q23 being some of the most frequent. The pattern of p53 mutation in PLL cells is different from that observed for CLL. Differential diagnosis usually relies on complete blood count, histological, immunophenotypic, and genetic analyses. (See, J. Gribben, et al., *Small B cell Lymphocytic Lymphoma/Chronic Lymphocytic Leukemia and Prolymphocytic Leukemia*, pp. 243-261, In *Non-Hodgkin's Lymphomas*, P. Mauch, et al., eds., Lippincott Williams & Wilkins, Philadelphia, Pa. (2004)).

5.22.2.11. Hairy Cell Leukemia (HCL)

HCL is a rare, indolent chronic leukemia affecting more men than women and largely those of middle age. The typical symptoms include massive splenomegaly and pancytopenia. The peripheral blood and bone marrow contain the typical "hairy cells," which are B lymphocytes with cytoplasmic projections. Over 90% of HCL patients have bone marrow infiltration. (See, *Clinical Oncology*, A. Neal, et al., Neal, Hoskin and Oxford University Press, co-publ., New York, N.Y. (2003); J. Johnston, *Hairy Cell Leukemia*, pp. 2428-2446, In *Wintrobe's Clinical Hematology*, Tenth Edition, G. Lee et al., eds. Williams & Wilkins, Baltimore, Md. (1999)).

Cytogenetic analysis has shown that clonal abnormalities are present in 19% of cases and involve numerical and structural abnormalities of chromosomes 5, 7 and 14. The serum level of TNF-α is elevated in hairy cell leukemia and correlates with tumor burden. Hairy cell leukemia cells express surface immunoglobulins (IgG and IgM) and CD11c, CD19, CD20, CD22 and typically CD25. In addition, FMC7, HC-2 and CD103 are expressed. HCL cells do not express CD5 or CD10. Diagnosis generally involves the use of bone marrow aspirates, cytogenetics, blood smears and immunophenotyping. (See, *Clinical Oncology*, A. Neal, et al., Neal, Hoskin and Oxford University Press, co-publ., New York, N.Y. (2003); J. Johnston, *Hairy Cell Leukemia*, pp. 2428-2446, In *Wintrobe's Clinical Hematology*, Tenth Edition, G. Lee et al., eds. Williams & Wilkins, Baltimore, Md. (1999)).

5.22.2.12. Precursor B Cell Lymphoblastic Lymphoma/Pre-B Cell Acute Lymphoblastic Leukemia/Lymphoblastic Lymphoma Precursor B cell lymphoblastic lymphoma/pre-B cell acute lymphoblastic leukemia/Lymphoblastic lymphoma is a disease of precursor T or B cells. The T and B cell lymphoblastic lymphomas are morphologically identical, but clinical distinctions may be made based on degree of bone marrow infiltration or bone marrow involvement. 85-90% of lymphoblastic lymphomas are T-cell derived with the remainder being B cell derived. Lymphoblastic lymphoma has a median age of 20 years with a male predominance. Peripheral lymph node involvement is a common feature at presentation, occurring especially in the cervical, supraclavicular and axillary regions. This disease frequently presents with bone marrow involvement. Central nervous system is less common at presentment but often appears in cases of relapse. Other sites of involvement can include liver, spleen, bone, skin, pharynx and testes (See, J. Sweetenham, et al., *Precursor B-and T-Cell Lymphoblastic Lymphoma*, pp. 503-513, In *Non-Hodgkin's Lymphomas*, P. Mauch, et al., eds., Lippincott Williams & Wilkins, Philadelphia, Pa. (2004)).

Precursor B cell lymphoblastic lymphomas express immature markers B cell markers such as CD99, CD34 and terminal deoxynucleotidyl transferase. These cells also express CD79a, CD19, CD22 and sometimes CD20 and typically lack expression of CD45 and surface immunoglobulin. Translocations at 11q23, as well as t(9;22)(q34;q11.2) and t(12;21) (p13;q22), have been associated with poor prognosis. Good prognosis is associated with hyperdiploid karyotype, especially that associated with trisomy 4, 10, and 17 and t(12;21) (p13;q22). (See, J. Sweetenham, et al., *Precursor B-and T-Cell Lymphoblastic Lymphoma*, pp. 503-513, In *Non-Hodgkin's Lymphomas*, P. Mauch, et al., eds., Lippincott Williams & Wilkins, Philadelphia, Pa. (2004)).

Diagnostic tests include lymph node biopsies, blood tests, x-rays, CT scans, and lumbar punctures to examine the cerebralspinal fluid for malignant cells.

5.22.2.13. Primary Mediastinal Large B Cell Lymphoma

Primary mediastinal large B cell lymphoma is a diffuse large B cell lymphoma occurring predominantly in young women and characterized by a locally invasive anterior mediastinal mass originating in the thymus. Distant spread to peripheral nodes and bone marrow involvement is unusual. Systemic symptoms are common. While this disease resembles nodal large cell lymphomas, it has distinct genetic, immunological, and morphological characteristics.

The immunophenotype of tumor cells of primary mediastinal large B cell lymphoma are often surface immunoglobulin negative but do express such B cell associated antigens as CD19, CD20, CD22, and CD79a. CD10 and BCL6 are also commonly expressed. Expression of plasma cell associated markers CD15, CD30, epithelial membrane antigen (EMA) is rare. BCL6 and c-myc gene arrangements are also uncommon. The presence of clonal immunoglobulin rearrangements, immunoglobulin variable region and gene hypermutation along with BCL6 hypermutation suggest that this lymphoma derives from a mature germinal center or post-germinal center B cell. The chromosomal translocations that seem to be associated with tumors of this disease are similar to those observed in other forms of diffuse large cell lymphoma. (See, P. Zinzani, et al., *Primary Mediastinal Large B cell Lymphoma*, pp. 455-460, In *Non-Hodgkin's Lymphomas*, P. Mauch, et al., eds., Lippincott Williams & Wilkins, Philadelphia, Pa. (2004)).

The diagnostic evaluation for primary mediastinal large B cell lymphoma generally includes a complete physical examination, complete hematological and biochemical analysis, total-body computerized tomography and bone marrow biopsy. Gallium-67 scanning is a useful test for staging, response to treatment and for assessment of relapse. (See, P. Zinzani et al., *Primary Mediastinal Large B cell Lymphoma*, pp. 455-460, In *Non-Hodgkin's Lymphomas*, P. Mauch, et al., eds., Lippincott Williams & Wilkins, Philadelphia, Pa. (2004)).

5.22.2.14. Lymphoplasmacytic Lymphoma (LPL)/Lymphoplasmacytic Immunocytoma/Waldström's Macroglobulinemia LPL/Lymphoplasmacytic immunocytoma/Waldström's Macroglobulinemia is a nodal lymphoma that is usually indolent, and often involves bone marrow, lymph nodes and spleen. This is generally a disease of older adults with males slightly predominating. Most patients have monoclonal IgM paraprotein in their serum (>3 g/dL) resulting in hyperviscosity of the serum. Tumor cells have a plasmacytic morphology. A subset of LPL is characterized by recurrent translocations between chromosomes 9 and 14, which involves the PAX5 and immunoglobulin heavy-chain loci. LPL is characterized by SHM as well as ongoing SHM, and is believed to be derived from post-GC B cells. (See, A. Rohatiner, et al., *Lymphoplasmacytic Lymphoma and Waldström's Macroglobulinemia*, pp. 263-273, In *Non-Hodgkin's Lymphomas*, P. Mauch, et al., eds., Lippincott Williams & Wilkins, Philadelphia, Pa. (2004); K. Maclennan, *Diffuse Indolent B cell Neoplasms*, pp. 43-47, In *Malignant Lymphoma*, B. Hancock, et al., eds., Oxford University Press, New York, N.Y. (2000); A. Lal, et al., *Role of Fine Needle Aspiration in Lymphoma*, pp. 181-220, In W. Finn, et al., eds., *Hematopathology in Oncology*, Kluwer Academic Publishers, Norwell, Mass. (2004)).

The immunophenotype of this disease shows expression of the B cell associated antigens CD19, CD20, CD22, and CD79a and a lack of expression of CD5, CD10, and CD23. Presence of strong surface immunoglobulin and CD20, the lack of expression of CD5, and CD23 and the presence of cytoplasmic immunoglobulin are characteristics that aid in distinguishing this disease from chronic lymphocytic leukemia. Also diagnostic of this disease is t(9;14)(p13;q32). (See, A. Rohatiner, et al., *Lymphoplasmacytic Lymphoma and Waldström's Macroglobulinemia*, pp. 263-273, In *Non-Hodgkin's Lymphomas*, P. Mauch, et al., eds., Lippincott Williams & Wilkins, Philadelphia, Pa. (2004); K. Maclennan, *Diffuse Indolent B cell Neoplasms*, pp. 43-47, In *Malignant Lymphoma*, B. Hancock, et al., eds., Oxford University Press, New York, N.Y. (2000); R. Chaganti, et al., *Cytogenetics of Lymphoma*, pp. 809-824, In *Non-Hodgkin's Lymphomas*, P. Mauch, et al., eds., Lippincott Williams & Wilkins, Philadelphia, Pa. (2004)).

Diagnostic tests typically include a complete blood count, renal and liver function tests, CT scans, biopsy and aspiration of the bone marrow, protein electrophoresis to quantify and characterize the paraprotein and serum viscosity. Measurement of $\beta_2$-microglobulin is used as a prognostic test. (See, A. Rohatiner, et al., *Lymphoplasmacytic Lymphoma and Waldström's Macroglobulinemia, pp.* 263-273, In *Non-Hodgkin's Lymphomas*, P. Mauch, et al., eds., Lippincott Williams & Wilkins, Philadelphia, Pa. (2004)).

5.22.2.15. Null-Acute Lymphoblastic Leukemia

Null-acute lymphoblastic leukemia is a subset of ALL which lacks B- or T-cell characteristics. Phenotypic analysis of leukemic blasts shows a typical null ALL pattern, i.e., CD10 (common ALL antigen)-negative, strongly HLA-DR-positive, and CD19 (B4)-positive (see Katz et al. (1988) Blood 71(5):1438-47).

5.22.2.16. Hodgkin's Lymphoma

Hodgkin's lymphoma usually arises in the lymph nodes of young adults. It can be divided into classical subtype and a less common nodular lymphocytic predominant subtype. The classical type exhibits SHM, but not ongoing SHM, and does not have a GC B cell gene expression profile. The nodular lymphocyte predominant type, in contrast, is characterized by SHM and ongoing SHM and a GC B cell gene expression profile. While the two types differ clinically and biologically, they do share certain features such as a lack of neoplastic cells within a background of benign inflammatory cells. B. Schnitzer et al., *Hodgkin Lymphoma*, pp. 259-290, In W. Finn and L. Peterson, eds., *Hematopathology in Oncology*, Kluwer Academic Publishers, Norwell, Mass. (2004)).

The most common features at presentation are painless enlargement of lymph nodes, usually in the neck, but occasionally in the inguinal region. Waxing and waning of nodes is also characteristic of this disease. B symptoms are observed in about one-third of patients. Isolated extranodal involvement is rare and in cases where dissemination has occurred extranodal involvement is observed about 10-20% of the time. (See, P. Johnson et al., *Hodgkin's Disease: Clinical Features*, pp. 181-204, In *Malignant Lymphoma*, B. Hancock, et al., eds., Oxford University Press, New York, N.Y. (2000)).

Reed-Sternberg (RS) cells are the malignant cells of Hodgkin's lymphoma. RS cells and their variants express CD15, CD25, CD30 and transferrin receptor. In addition these cells express polyclonal cytoplasmic immunoglobulin. In most cases of Hodgkin's lymphoma the RS cells do not express CD45, a feature that aids in distinguishing this disease from non-Hodgkin's Lymphomas. Epstein Barr virus has been demonstrated to be present in Reed-Sternberg cells in about one-half of Hodgkin's lymphoma cases but its role is unclear.

Diagnosis is most frequently made by lymph node biopsy. Additional diagnostic tests include a full blood count (often hematological tests are normal; white blood cell counts of less than $1.0 \times 10^9$/L are seen in about 20% of cases), erythrocyte sedimentation rate (often elevated in advanced stages of the disease), biochemical tests including electrolytes, urea, creatinine, urate, calcium (hypercalcemia is rare but when present is associated with extensive bone involvement), liver blood tests, lactate dehydrogenase (elevated levels often associated with advanced disease), albumin and beta$_2$-microglobulin ($\beta$2-M). Lymphanigiograms and chest x-rays and CT scans of the chest, abdomen and pelvis are important in identifying abnormal lymph nodes and the extent of extranodal involvement. Bone marrow biopsies are typically considered optional as bone marrow involvement is unusual and the results of such biopsies appear not to affect clinical management or prognosis. Splenechtomies are not usually performed today as it rarely influences management and CT or MRI imaging provides information on splenic status. Significantly elevated levels of p55, TNF and sICAM-1 are correlated to the stage of the disease, presence of symptoms and complete response rate. (See, P. Johnson, et al., *Hodgkin's Disease: Clinical Features*, pp. 181-204, In *Malignant Lymphoma*, B. Hancock, et al., eds., Oxford University Press, New York, N.Y. (2000); Clinical Oncology, A. Neal, et al., Neal, Hoskin and Oxford University Press, co-publ., New York, N.Y. (2003); R. Stein, *Hodgkin's Disease*, pp. 2538-2571, In *Wintrobe's *Clinical Hematology*, Tenth Edition, G. Lee et al., eds. Williams & Wilkins, Baltimore, Md. (1999)).

5.22.2.17. Multiple Myeloma

Multiple myeloma is a malignancy of plasma cells. Neoplastic cells are located in the bone marrow, and osteolytic bone lesions are characteristic. Reciprocal chromosomal translocations between one of the immunoglobulin loci and a variety of other genes, e.g., cyclin D1, cyclin D3, c-MAF, MMSET (multiple myeloma SET-domain protein) or fibroblast growth factor receptor 3 are believed to be the primary oncogenic events. Multiple myeloma is characterized by SHM, and the putative cell of origin is a post-GC B cell. Multiple myeloma is typically first identified by symptoms such as recurrent infection, fatigue, pain, and kidney problems and is confirmed with clinical testing (see, for example, *Cancer: Principles and Practice of Oncology*. 6th edition. DeVita, V. T., Hellman, S, and Rosenberg, S. A. editors. 2001 Lippincott Williams and Wilkins Philadelphia, Pa. 19106 pp. 2465-2499).

In certain embodiments, patients who are candidates for treatment by compositions and methods of the invention can undergo further diagnostic tests on blood and/or urine to confirm the diagnosis or suspicion of multiple myeloma including, but not limited to, complete blood count (CBC) tests to determine if the types of cells reported in a CBC are within their normal ranges which are well known in the art, blood chemistry profile to determine whether levels of various blood components, such as albumin, blood urea nitrogen (BUN), calcium, creatinine, and lactate dehydrogenase (LDH), deviate from standard values. Serum levels of beta$_2$-microglobulin ($\beta_2$-M) can also be examined and surrogate markers for IL-6, a growth factor for myeloma cells. Urinalysis can be used to measure the levels of protein in the urine. Electrophoresis can be used to measure the levels of various proteins, including M protein in the blood (called serum protein electrophoresis, or SPEP) or urine (called urine electrophoresis, or UEP). An additional test, called immunofixation electrophoresis (IFE) or immunoelectrophoresis, may also be performed to provide more specific information about the type of abnormal antibody proteins present. Assessing changes and proportions of various proteins, particularly M protein, can be used to track the progression of myeloma disease and response to treatment regimens. Multiple myeloma is characterized by a large increase in M protein which is secreted by the myeloma tumor cells.

Diagnostic tests on bone can also be conducted to confirm the diagnosis or suspicion of multiple myeloma including, but not limited to, X-rays and other imaging tests—including a bone (skeletal) survey, magnetic resonance imaging (MRI), and computerized axial tomography (CAT), also known as computed tomography (CT)—can assess changes in the bone structure and determine the number and size of tumors in the bone. Bone marrow aspiration or bone marrow biopsy can be used to detect an increase in the number of plasma cells in the bone marrow. Aspiration requires a sample of liquid bone marrow, and biopsy requires a sample of solid bone tissue. In both tests, samples can be taken from the pelvis (hip bone). The sternum (breast bone) can also be used for aspiration of bone marrow.

Patients with multiple myeloma are typically categorized into the following three groups that help define effective treatment regimens. Monoclonal gammopathy of undetermined significance (MGUS) is typically characterized by a serum M protein level of less than 3 g/dL, bone marrow clonal plasma cells of less than 10%, no evidence of other B cell disorders, and no related organ or tissue impairment, such as hypercalcemia (increased serum calcium levels), impaired kidney function noted by increased serum creatinine, anemia, or bone lesions. Asymptomatic myelomas are typically stage I and includes smoldering multiple myeloma (SMM) and indolent multiple myeloma (IMM). SMM is characterized by serum M protein greater than or equal to 3 g/dL and IMM is characterized by bone marrow clonal plasma cells greater than or equal to 10% of the bone marrow cells. Symptomatic myeloma is characterized by M protein in serum and/or urine and includes Stage II multiple myeloma characterized by the presence of bone marrow clonal plasma cells or plasmacytoma and Stage III multiple myeloma characterized by related organ or tissue impairment.

Osteosclerotic myeloma is a component of the rare POEMS syndrome (polyneuropathy, organomegaly, endocrinopathy, monoclonal gammopathy and skin lesions). Peak incidence is at 40 to 50 years of age. Systemic features include skeletal lesions, marrow-plasma cells <5%, a normal CBC, increased platelets, and organomegaly. The CSF has a high protein with no cells present. The M-protein levels are low (<3 g/dl, median=1.1 g/dl); heavy chain class—usually α or γ; light chain class—usually λ; rare urine monoclonal and occasional cryoglobulinemia. Neuropathy occurs in 50% of the patients with weakness both proximal and distal, sensory loss is greater in larger than small fibers; and demyelination and long distal latency.

Smoldering multiple myeloma patients generally present with stable disease for months/years; no anemia, bone lesions, renal insufficiency or hypercalcemia; have >10% plasma cells in bone marrow and monoclonal serum protein. The criteria for smoldering multiple myeloma is compatible with the diagnosis of multiple myeloma; however, there is no evidence of progressive course. These are cases with a slow progression, the tumor cell mass is low at diagnosis and the percentage of bone marrow plasma cells in S phase is low (<0.5%). Characteristic clinical features include: serum M protein levels >3 g/dL and/or bone marrow plasma cells ≥10%; absence of anemia, renal failure, hypercalcemia, lytic bone lesions.

Indolent (or asymptomatic) multiple myeloma is a multiple myeloma diagnosed by chance in the absence of symptoms, usually after screening laboratory studies. Indolent multiple myeloma is similar to smoldering myeloma but with few bone lesions and mild anemia. Most cases of indolent multiple myeloma develop overt multiple myeloma within 3 years. Diagnostic criteria are the same as for multiple myeloma except: no bone lesions or one asymptomatic lytic lesion (X-ray survey); M component level <3 g/dL for IgG, 2 g/dL for IgA urine light chain <4 g/24 h; hemoglobin >10 g/dl, serum calcium normal, serum creatinine <2 mg/dL, and no infections.

5.22.2.18. Solitary Plasmacytoma

Solitary plasmacytoma is one of a spectrum of plasma cell neoplasms which range from benign monoclonal gammopathy to solitary plasmacytoma to multiple myeloma. Approximately seventy percent of all solitary plasmacytoma cases eventually result in multiple myeloma. These diseases are characterized by a proliferation of B cells which produce the characteristic paraprotein. Solitary plasmacytoma results in a proliferation of clonal plasma cells in a solitary site, usually a single bone or extramedullary tissue site. Diagnostic criteria of solitary plasmacytoma include a histologically confirmed single lesion, normal bone biopsy, negative skeletal survey, no anemia, normal calcium and renal function. Most cases exhibit minimally elevated serum M-protein (paraprotein). The median age at diagnosis is 50-55, about 5-10 years younger than the median age for multiple myeloma. (See, C. Wilson, *The Plasma Cell Dycrasias*, pp. 113-144, In W. Finn and L. Peterson, eds., *Hematopathology in Oncology*, Kluwer Academic Publishers, Norwell, Mass. (2004), S. Chaganti, et al., *Cytogenetics of Lymphoma*, pp. 809-824, In *Non-Hodgkin's Lymphomas*, P. Mauch, et al., eds., Lippincott Williams & Wilkins, Philadelphia, Pa., (2004)).

The immunophenotypic and genetic features of plasmacytoma appear to be similar to multiple myeloma.

5.22.2.19. Light Chain Disease/Light Chain Deposition Disease (LCDD)

LCDD is a plasma cell dycrasias disorder caused by the over-synthesis of immunoglobulin light chains (usually kappa light chains) that are deposited in tissues. Patients commonly present with organ dysfunction, weakness, fatigue and weight loss. In approximately 80% of cases of LCDD a monoclonal immunoglobulin is detected. Detection of monoclonal kappa light chains using immunofluorescent techniques is limited by the tendency of light chains to give excess background staining, therefore, ultrastructural immunogold labeling may be necessary. (See, C. Wilson, *The Plasma Cell Dycrasias*, pp. 113-144, In W. Finn and L. Peterson, eds., *Hematopathology in Oncology*, Kluwer Academic Publishers, Norwell, Mass. (2004)).

5.22.2.20. Plasma Cell Leukemia (PCL),

PCL, a plasma cell dycrasias, is a rare aggressive variant of multiple myeloma. The criteria for plasma cell leukemia is a peripheral blood absolute plasma cell count of greater than $2\times10^9$/L or plasma cells greater than 20% of white blood cells. Determination of the presence of a CD138$^+$ population with cytoplasmic light chain restriction by flow cytometry will distinguish PCL from lymphoid neoplasm with plasmacytic features. PCL cells are also characterized by the lack of surface light chain, CD19 and CD22 expression, and either no or weak expression of CD45. About 50% of cases of PCL express CD20 and about 50% lack expression of CD56. The genetic abnormalities observed in PCL patients are the same as those observed for multiple myeloma patients but they are found at higher frequency in PCL. (See, C. Wilson, *The Plasma Cell Dycrasias*, pp. 113-144, In W. Finn and L. Peterson, eds., *Hematopathology in Oncology*, Kluwer Academic Publishers, Norwell, Mass., (2004)).

Plasma cell leukemia has two forms: if initial diagnosis is based on leukemic phase of myeloma then the primary form is present, otherwise it is secondary. Primary plasma cell leukemia is associated with a younger age, hepatosplenomegaly, lymphadenopathy, and fewer lytic bone lesions but poorer prognosis than the secondary form. The peripheral blood of plasma cell leukemic patients has greater than 20% plasma cells with absolute count of 2000/ml or more.

5.22.2.21. Monoclonal Gammopathy of Unknown Significance (MGUS)

MGUS is a relatively common condition characterized by the presence of electrophoretically homogeneous immunoglobulins or benign M-components. The occurrence of this condition appears to increase with age. Most individuals carrying the M-components never develop malignant plasma cell dycrasias, such as multiple myeloma. However, some individuals with this condition have associated malignant conditions. When symptomatic, patients can have enlarged liver or spleen and pleuroneuropathy. (See, J. Foerster, *Plasma Cell Dycrasias General Considerations*, pp. 2612-2630, In *Wintrobe's Clinical Hematology*, Tenth Edition, G. Lee et al., eds. Williams & Wilkins, Baltimore, Md. (1999)).

MGUS can be differentiated from multiple myeloma by the presence of increased number of monoclonal plasma cells circulating in the peripheral blood. The serological characteristics of M-components are identical to other plasma cell dycrasias conditions, however, the total concentration of M-component is usually less than 30 g/L. The paraprotein is usually IgG; however multiple paraproteins may be present including IgG, IgA, IgM. The relative amount of each of the individual immunoglobulin classes is typically proportional to that found in normal serum. Proteinemia or proteinuria is rare. Serial measurements of M-protein levels in the blood and urine, and continued monitoring of the clinical and laboratory features (including protein electrophoresis) is the most reliable method of differentiating MGUS from early stage plasma cell dycrasias. In *Wintrobe's Clinical Hematology*, Tenth Edition, G. Lee et al., eds. Williams & Wilkins, Baltimore, Md. (1999)).

5.22.2.22. Mature B Cell Malignancies:

In a further embodiment the invention can be practiced to treat mature B cell malignancies including but not limited to follicular lymphoma, mantle-cell lymphoma, Burkitt's lymphoma, multiple myeloma, diffuse large B-cell lymphoma (DLBCL) including germinal center B cell-like (GCB) DLBCL, activated B cell-like (ABC) DLBCL, and type 3 DLBCL, Hodgkin's lymphoma including classical and nodular lymphocyte pre-dominant type, lymphoplasmacytic lymphoma (LPL), marginal-zone lymphoma including gastric mucosal-associated lymphoid tissue (MALT) lymphoma, and chronic lymphocytic leukemia (CLL) including immunoglobulin-mutated CLL and immunoglobulin-unmutated CLL.

5.22.2.23. Pre-B Cell Malignancies:

Further, CD19 is expressed earlier in B cell development than, for example, CD20, and is therefore particularly suited for treating pre-B cell and immature B cell malignancies, e.g., in the bone marrow. Representative pre-B cell and immature B cell malignancies include but are not limited to mantle cell lymphoma, pre-B cell acute lymphoblastic leukemia, precursor B cell lymphoblastic lymphoma, and other malignancies characterized by CD19 expression.

5.23. Patient Diagnosis and Therapeutic Regimens Transplantation

According to certain aspects of the invention, the treatment regimen and dose used with compositions and methods of the invention is chosen based on a number of factors including, for example, clinical manifestation that place a patient at risk for developing a humoral rejection, or clinical evidence that such a rejection is developing. The terms "humoral" and "antibody-mediated" are used interchangeably herein.

The criteria for assessing the risk that a patient will develop a humoral rejection are established according to the knowledge and skill in the art. In one embodiment, a positive complement dependent cytotoxicity or antiglobulin enhanced complement dependent cytotoxicity crossmatch indicates that a patient is at high risk for humoral rejection. In one embodiment, a positive crossmatch or a prior positive complement dependent cytotoxicity or anti-globulin enhanced complement dependent cytotoxicity crossmatch indicates that a patient is at an intermediate risk for humoral rejection. In one embodiment, a negative crossmatch indicates that a patient is at a low risk for humoral rejection.

In another embodiment, a transplant recipient in need of prophylaxis against graft rejection may be identified as a patient or patient population having detectable circulating anti-HLA alloantibodies prior to transplantation. In another example, the patient or patient population is identified as having panel reactive antibodies prior to transplantation. The presence of detectable circulating anti-HLA alloantibodies in a transplant recipient post-transplantation can also be used to identify the patient or patient population in need of treatment for humoral rejection according to the invention. The patient or patient population in need of treatment for humoral rejection can also be identified according to other clinical criteria that indicate that a transplant recipient is at risk for developing a humoral rejection or has already developed a humoral rejection. For example, a transplant recipient in need of treatment of humoral rejection may be identified as a patient or population in an early stage of humoral rejection, such as a latent humoral response characterized by circulating anti-donor alloantibodies. An early stage of humoral rejection may also be a silent reaction characterized by circulating anti-donor alloantibodies and C4d deposition, or a subclinical rejection characterized by circulating anti-donor alloantibodies, C4d deposition, and tissue pathology. In later stages, the recipient is identified as a patient or patient population presenting with clinical indications of humoral rejection characterized according to the knowledge and skill in the art, for example, by circulating anti-donor alloantibodies, C4d deposition, tissue pathology, and graft dysfunction.

The present invention provides compositions, therapeutic formulations, methods and regimens effective to reduce the incidence, severity, or duration of GVHD, a rejection episode, or post-transplant lymphoproliferative disorder. In certain embodiments, compositions and methods of the invention are effective to attenuate the host response to ischemic reperfusion injury of a solid tissue or organ graft. In one embodiment, compositions and methods of the invention are effective to prolong survival of a graft in a transplant recipient.

The present invention encompasses grafts that are autologous, allogeneic, or xenogeneic to the recipient. The types of grafts encompassed by the invention include tissue and organ grafts, including but not limited to, bone marrow grafts, peripheral stem cell grafts, skin grafts, arterial and venous grafts, pancreatic islet cell grafts, and transplants of the kidney, liver, pancreas, thyroid, and heart. The terms "graft" and "transplant" are used interchangeably herein. In one embodiment, the autologous graft is a bone marrow graft, an arterial graft, a venous graft or a skin graft. In one embodiment, the allograft is a bone marrow graft, a corneal graft, a kidney transplant, a pancreatic islet cell transplant, or a combined transplant of a kidney and pancreas. In one embodiment, the graft is a xenograft, wherein the possible animal donors include, but are not limited to pigs. The compositions and methods of the present invention may also be used to suppress a deleterious immune response to a non-biological graft or implant, including but not limited to an artificial joint, a stent, or a pacemaker device.

Anti-CD19 antibodies, compositions, and methods of the invention may be used to treat or prevent GVHD, humoral rejection, or post-transplant lymphoproliferative disorder without regard to the particular indications initially giving rise to the need for the transplant or the particular type of tissue transplanted.

Therapeutic formulations and regimens of the present invention are described for treating human subjects diagnosed with autoimmune diseases or disorders, including but not limited to, rheumatoid arthritis, SLE, ITP, pemphigus-related disorders, diabetes, and scleroderma.

Appropriate treatment regimens can be determined by one of skill in the art for the particular patient or patient population. In particular embodiments, the treatment regimen is a pre-transplant conditioning regimen, a post-transplant maintenance regimen, or post-transplant treatment regimen for an acute or a chronic rejection. In certain embodiments, the particular regimen is varied for a patient who is assessed as being at a high or intermediate risk of developing a humoral response, compared with the regimen for a patient who is assessed as being at a low risk of developing a humoral response.

In certain embodiments, the particular regimen is varied according to the stage of humoral rejection, with more aggressive therapy being indicated for patients at later stages of rejection. The stages of humoral rejection may be classified according to the knowledge and skill in the art. For example, the stages of humoral rejection may be classified as one of stages I to IV according to the following criteria: Stage I Latent Response, characterized by circulating anti-donor alloantibodies, especially anti-HLA antibodies; Stage II Silent Reaction, characterized by circulating anti-donor alloantibodies, especially anti-HLA antibodies, and C4d deposition, but without histologic changes or graft dysfunction; Stage III Subclinical Rejection: characterized by circulating anti-donor alloantibodies, especially anti-HLA antibodies, C4d deposition, and tissue pathology, but without graft dysfunction; Stage IV Humoral Rejection: characterized by circulating anti-donor alloantibodies, especially anti-HLA antibodies, C4d deposition, tissue pathology, and graft dysfunction.

Dose response curves can be generated using standard protocols in the art in order to determine the effective amount of compositions of the invention for use in a particular regimen, for example, in conditioning regimens prior to transplantation, and in post-transplantation regimens for prophylaxis and treatment of GVHD, humoral rejection, or post-transplantation lymphoproliferative disorders. In general, patients at high risk for developing a humoral rejection and those already exhibiting one or more clinical indicators of rejection will require higher doses and/or more frequent doses which may be administered over longer periods of time in comparison to patients who are not at high risk or who do not exhibit any indications of active rejection.

Anti-CD19 antibodies, compositions and methods of the invention may be practiced to treat or prevent GVHD, humoral rejection, or post-transplantation lymphoproliferative disorders, either alone or in combination with other therapeutic agents or treatment regimens. Other therapeutic regimens for the treatment or prevention of GVHD, humoral rejection, or post-transplantation lymphoproliferative disorders may comprise, for example, one or more of anti-lymphocyte therapy, steroid therapy, antibody depletion therapy, immunosuppression therapy, and plasmapheresis.

Anti-lymphocyte therapy may comprise the administration to the transplant recipient of anti-thymocyte globulins, also referred to as thymoglobulin. Anti-lymphocyte therapy may also comprise the administration of one or more monoclonal antibodies directed against T cell surface antigens. Examples of such antibodies include, without limitation, OKT3™ (muromonab-CD3), CAMPATH™-1H (alemtuzumab), CAMPATH™-1G, CAMPATH™-1M, SIMULECT™ (basiliximab), and ZENAPAX™ (daclizumab). In a specific embodiment, the anti-lymphocyte therapy comprises one or more additional antibodies directed against B cells, including, without limitation, RITUXAN™ (rituximab).

Steroid therapy may comprise administration to the transplant recipient of one or more steroids selected from the group consisting of cortisol, prednisone, methyl prednisolone, dexamethazone, and indomethacin. One or more of the steroids may be corticosteroids, including without limitation, cortisol, prednisone, and methylprednisolone.

Antibody depletion therapy may include, for example, administration to the transplant recipient of intravenous immunoglobulin. Antibody depletion therapy may also comprise immunoadsorption therapy applied to the graft ex vivo, prior to transplantation. Immunoadsorption may be accomplished using any suitable technique, for example, protein A affinity, or antibody based affinity techniques using antibodies directed against T cell or B cell surface markers such as anti-CD3 antibodies, anti-CD19 antibodies, anti-CD20 antibodies, and anti-CD19 antibodies.

Immunosuppression therapy may comprise the administration of one or more immunosuppressive agents such as inhibitors of cytokine transcription (e.g., cyclosporin A, tacrolimus), nucleotide synthesis (e.g., azathiopurine, mycophenolate mofetil), growth factor signal transduction (e.g., sirolimus, rapamycin), and the T cell interleukin 2 receptor (e.g., daclizumab, basiliximab). In a particular embodiment, an immunosuppressant agent used in combination with compositions and methods of the invention includes one or more of the following: adriamycin, azathiopurine, busulfan, cyclophosphamide, cyclosporin A ("CyA"), cytoxin, fludarabine, 5-fluorouracil, methotrexate, mycophenolate mofetil (MOFETIL), nonsteroidal anti-inflammatories (NSAIDs), rapamycin, and tacrolimus (FK506). Immunosuppressive agents may also comprise inhibitors of complement, for example, soluble complement receptor-1, anti-05 antibody, or a small molecule inhibitor of C1s, for example as described in Buerke et al. (*J. Immunol.*, 167:5375-80 (2001).

In one embodiment, compositions and methods of the invention are used in combination with one or more therapeutic regimens for suppressing humoral rejection, including, without limitation, tacrolimus and mycophenolate mofetil therapy, immunoadsorption, intravenous immunoglobulin therapy, and plasmapheresis.

5.23.1. Diagnosis and Clinical Criteria

The present invention provides antibodies, compositions and methods for treating and preventing GVHD, humoral rejection, and post-transplant lymphoproliferative disorder in human transplant recipients. Compositions and methods of the invention can be used regardless of the particular indications which gave rise to the need for a transplant. Similarly, the use of compositions and methods of the invention for the treatment and prevention of GVHD, humoral rejection, and post-transplant lymphoproliferative disorders is not limited by the particular type of tissue which is intended for transplantation or which has been transplanted.

In one embodiment, the invention provides compositions and methods for the prevention of humoral rejection in a human transplant recipient wherein the transplant recipient is identified as a patient or patient population at increased risk for developing a humoral rejection. Such patients may also be referred to as "sensitized." The criteria for the identification of sensitized patients is known to the skilled practitioner. Such criteria may include, for example, patients having detectable levels of circulating antibodies against HLA antigens, e.g., anti-HLA alloantibodies. Such criteria may also include patients who have undergone previous transplantations, a pregnancy, or multiple blood transfusions. Patients who are at an increased risk for humoral rejection also include those having imperfect donor-recipient HLA matching, and those transplantations which are ABO-incompatible. Sensitized individuals are candidates for pretreatment or conditioning prior to transplantation. Sensitized individuals are also candidates for post-transplantation maintenance regimens for the prevention of humoral rejection.

In one embodiment, antibodies, compositions, and methods of the invention comprise or are used in combination with a therapeutic regimen for the treatment of an acute or chronic rejection. In particular embodiments, the rejection is characterized as a Stage I, a Stage II, a Stage III, or a Stage IV humoral rejection.

In one embodiment, antibodies, compositions, and methods of the invention comprise or are used in combination with a therapeutic regimen for the treatment of an early stage humoral rejection. In particular embodiments, the early stage humoral rejection is a Stage I, II, or III rejection. Clinical indications of an early stage humoral rejection are determined according to the knowledge and skill in the art and may include, for example, the development in the patient of circulating donor-specific anti-HLA antibodies, the presence of complement markers of antibody activity such as C4d and C3d deposits in graft biopsies, and the presence of anti-HLA antibodies in graft biopsies. Other indicators of an early stage humoral rejection are known to the skilled practitioner and may include, for example, the development of antiendothelial antibodies, especially antivimentin antibodies, and the development of nonclassical MHC class I-related chain A (MICA) alloantibodies.

In one embodiment, compositions and methods of the invention comprise or are used in combination with a therapeutic regimen for the treatment of humoral rejection characterized in part by graft dysfunction. In particular embodiments, the patient or patient population in need of treatment for humoral rejection is identified according to criteria known in the art for graft dysfunction. Examples of such criteria for particular types of grafts are provided in the sections that follow. In other embodiments, the patient or patient population in need of treatment for humoral rejection is identified according to other criteria that are particular to the type of tissue graft, such as histological criteria. Examples of such criteria are also provided in the sections that follow.

5.23.2. Bone Marrow Transplants

Compositions and methods of the invention are useful for treating or preventing GVHD, humoral rejection, and post-transplant lymphoproliferative disorder in a bone marrow transplant recipient. In one embodiment, compositions and methods of the invention comprise or are used in combination with a pre-transplant conditioning regimen.

In one embodiment, compositions and methods of the invention are used to deplete B cells from a bone marrow graft prior to transplantation. The graft may be from any suitable source, for example, cord blood stem cells, peripheral blood stem cells, or a bone marrow tap. Peripheral blood stem cells may be harvested from donor blood following a suitable conditioning regimen. Suitable regimens are known in the art and may include, for example, administration of one or more of the following to the donor prior to harvesting the donor blood: NEUPOGEN, cytokines such as GM-CSF, low dose chemotherapeutic regimens, and chemokine therapy. The graft may be either allogeneic or autologous to the transplant recipient. The graft may also be a xenograft.

Compositions and methods may be useful in a number of contexts in which there is a hematopoietic indication for bone marrow transplantation. In one embodiment, an autologous bone marrow graft is indicated for a B cell leukemia or lymphoma, including, but not limited to acute lymphoblastic leukemia ("ALL") or non-Hodgkins lymphoma, and compositions and methods of the invention may be used for the depletion of residual malignant cells contaminating the graft. In one embodiment, an autologous bone marrow transplant is indicated for patients unable to clear a viral infection, for example a viral infection associated with Epstein Barr virus (EBV), human immunodeficiency virus (HIV), or cytomegalovirus (CMV), and compositions and methods of the invention may be used to deplete the graft of B cells which may harbor the virus. In another embodiment, the graft is an allogeneic graft and compositions and methods of the invention may be used for depleting donor B cells from the graft as prophylaxis against GVHD.

In one embodiment, the indication is a B cell associated autoimmune condition and compositions and methods of the invention may be used to deplete the deleterious B cells from the patient without the need for chemotherapy or radiation therapy conditioning regimens. In one embodiment, compositions of the invention are administered in combination with a chemotherapy or radiation therapy regimen, which regimen comprises a lower dose of one or more chemotherapeutic agents, or a lower dose of radiation, than the dose that is administered in the absence of compositions of the invention. In one embodiment, the patient receives an autologous bone marrow graft subsequent to chemotherapy or radiation therapy, wherein the graft is depleted of deleterious B cells prior to transplantation using the compositions and methods described herein.

A patient or patient population in need of, or likely to benefit from, a bone marrow transplant is identified according to the knowledge and skill in the art. Examples of patients that may be candidates for bone marrow transplantation include patients who have undergone chemotherapy or radiation therapy for the treatment of a cancer or an autoimmune disease or disorder, and patients who are unable to clear a viral infection residing in cells of the immune system.

5.23.3. Liver Transplants

Compositions and methods of the invention are useful for treating or preventing GVHD, humoral rejection, and post-transplant lymphoproliferative disorder in a liver transplant recipient. In particular embodiments, the rejection is an acute or a chronic rejection. In one embodiment, compositions and methods of the invention are used for the prevention of GVHD, humoral rejection, and post-transplant lymphoproliferative disorder in a liver transplant recipient. In one embodiment, compositions and methods of the invention comprise or are used in combination with a pre-transplant conditioning regimen. In one embodiment, compositions of the invention are administered to the transplant recipient. In one embodiment, compositions of the invention are contacted with the graft, ex vivo, prior to transplantation.

The liver transplant may be from any suitable source as determined according to the knowledge and skill in the art. In one embodiment, the liver is an HLA-matched allogeneic graft. In another embodiment, the liver is a xenograft from a pig donor. In one embodiment, the liver is used ex vivo to filter the patient's blood, e.g., extracorporeal perfusion. Extracorporeal perfusion is a form of liver dialysis in which the patient is surgically connected to a liver maintained outside the body. This procedure is sometimes referred to as "bioartificial liver." In accordance with this embodiment, compositions and methods of the invention are used to prevent the development of antibodies against liver antigens which may contaminate the patient's blood.

In one embodiment, compositions and methods of the invention comprise an improved therapeutic regimen for the treatment and prevention of GVHD, humoral rejection, and post-transplant lymphoproliferative disorder. In a particular embodiment, compositions and methods of the invention comprise an improved therapeutic regimen, wherein the improvement lies in a decreased incidence and/or severity of complications associated with traditional immunosuppressive agents. In one embodiment, the incidence and/or severity of nephrotoxicity, hepatotoxicity, and hirsutism is reduced compared with traditional regimens relying on cyclosporin A or other calcineurin inhibitors. In one embodiment, the incidence and/or severity of obesity, osteodystrophy, diabetes mellitus and susceptibility to bacterial and viral infections is reduced compared with traditional regimens relying on corticosteroids.

In one embodiment, compositions and methods of the invention are used in combination with lower doses of one or more traditional immunosuppressive agents than the doses that are used in the absence of anti-lymphocyte antibody therapy. The lower doses may result in a decreased incidence and/or severity of one or more complications associated with the one or more traditional immunosuppressive agents.

A patient or patient population in need of, or likely to benefit from, a liver transplant is identified according to the knowledge and skill in the art. Examples of patients that may be candidates for liver transplantation include persons having one or more of the following conditions, diseases, or disorders: acute liver failure, amyloidosis, bilirubin excretion disorders, biliary atresia, Budd-Chiari syndrome, chronic active autoimmune hepatitis, cirrhosis (either associated with viral hepatitis including hepatitis B and hepatitis C, alcoholic cirrhosis, or primary biliary cirrhosis), cholangitis, congenital factor VIII or IX disorder, copper metabolism disorders, cystic fibrosis, glycogenesis, hypercholesterolemia, lipidoses, mucopolysaccharidosis, primary sclerosing cholangitis, porphyrin metabolism disorders, purine and pyrimidine metabolism disorders, and primary benign and malignant neoplasms, especially of the liver and intrahepatic bile ducts, biliary system, biliary passages, or digestive system.

The clinical criteria for the identification of a patient or patient population in need of, or likely to benefit from, a liver transplant can be determined according to the knowledge and skill in the art. Such criteria may include, for example, one or more of the following symptoms: fatigue, weight loss, upper abdominal pain, purities, jaundice, liver enlargement, discolored urine, elevated alkaline phosphatase, and gamma glutamylpeptidase activity, elevated bilirubin levels, decreased serum albumin, elevated liver-specific enzymes, low bile production, increased blood urea nitrogen, increased creatinine and/or presence of anti-neutrophil cytoplasmic antibodies (ANCA) titers, recurrent variceal hemorrhage, intractable ascites, spontaneous bacterial peritonitis, refractory encephalopathy, severe jaundice, exacerbated synthetic dysfunction, sudden physiologic deterioration, and fulminant hepatic failure.

5.23.4. Kidney (Renal) Transplants

Compositions and methods of the invention are useful for treating or preventing GVHD, humoral rejection, and post-transplant lymphoproliferative disorder in a renal transplant recipient. As used herein, the term "renal transplant" encompasses the transplant of a kidney and the combined transplant of a kidney and a pancreas. In particular embodiments, the rejection is characterized as an acute rejection or a chronic rejection.

In one embodiment, compositions and methods of the invention comprise or are used in combination with a pre-transplant conditioning regimen. In one embodiment, a single dose of one or more of the compositions of the present invention is effective to reduce panel reactive antibodies and deplete B cells in the patient or patient population. In another embodiment, multiple doses of one or more of the compositions of the invention are effective to reduce panel reactive antibodies and deplete B cells in the patient or patient population. In one embodiment, a single dose of one or more of the compositions of the present invention is administered in combination with one or more immunosuppressive agents and is effective to reduce panel reactive antibodies and deplete B cells in the patient or patient population.

In certain embodiments, compositions and methods of the invention are for treating or preventing GVHD and graft rejection in a patient having received a renal transplant. In one embodiment, the patient has not yet exhibited clinical signs of rejection. In a related embodiment, compositions and methods of the invention comprise or are used in combination with a maintenance regimen for the prevention of graft rejection in the transplant recipient. In one embodiment, compositions and methods of the invention are for the treatment of a sub-clinical humoral rejection. In a related embodiment, the patient or patient population in need of treatment for a sub-clinical humoral rejection is indicated by the detection of Cd4 deposition in a biopsy from the graft or by the detection of circulating anti-HLA antibodies.

In one embodiment, compositions and methods of the invention comprise or are used in combination with a therapeutic regimen for the treatment of an acute or chronic rejection episode in a transplant recipient. In one embodiment, the patient or patient population in need of treatment for an acute or chronic rejection episode is identified by the detection of one or more clinical indicators of rejection. In specific embodiments, the one or more clinical indicators of rejection are detected one to six weeks post-transplantation. In one embodiment, the one or more clinical indicators of rejection are detected 6, 12, 18, 24, 36, 48, or 60 months post-transplantation. In one embodiment, the acute rejection is biopsy-confirmed acute humoral rejection.

In one embodiment, one or more of the compositions of the invention comprise a therapeutic regimen for the treatment of acute rejection. In a particular embodiment, the therapeutic regimen further comprises one or more of the following: plasmapheresis, tacrolimus/mycophenolate, intravenous immunoglobulin, immunoadsorption with protein A, and anti-CD20 antibody. In one embodiment, the patient has been on an immunosuppressive protocol prior to the development of the rejection. In a particular embodiment, the immunosuppressive protocol includes one or more of cyclosporine, azathioprine, and steroid therapy.

Clinical indicators of acute humoral rejection are known in the art and include, for example, a sudden severe deterioration of renal function, the development of oliguria, and compromised renal perfusion. Additional indicators include, for example, inflammatory cells in peritubular capillaries on biopsy and circulating donor-specific alloantibodies. In one embodiment, the patient presents with one or more of the following diagnostic criteria for a humoral rejection of a renal allograft: (1) morphological evidence of acute tissue injury; (2) evidence of antibody action, such as C4d deposits or immunoglobulin and complement in arterial fibrinoid necrosis; and (3) detectable circulating antibodies against donor HLA antigens or donor endothelial antigens. In one embodiment, the patient presents with all three of the above diagnostic criteria.

In one embodiment, the patient presents with one or more of the foregoing diagnostic criteria of acute humoral rejection and compositions of the present invention are used in combination with one or more of the following immunosuppressive agents to treat the acute humoral rejection: intravenous immunoglobulin, anti-thymocyte globulins, anti-CD20 antibody, mycophenolate mofetil, or tacrolimus. In another embodiment, compositions of the invention are used in combination with one or more immunosuppressive agents and a procedure for the removal of alloantibodies from the patient, such as plasmapheresis or immunoadsorption.

In one embodiment, compositions and methods of the invention comprise or are used in combination with a therapeutic regimen for the treatment of a chronic renal allograft rejection. In one embodiment, one or more of the compositions of the invention are used alone or in combination with one or more immunosuppressive agents, including for example, anti-CD154 (CD40L), tacrolimus, sirolimus, and mizoribin. In one embodiment, one or more of the anti-CD19 antibodies are used in combination with tacrolimus and mycophenolate.

Clinical indicators of chronic rejection in the kidneys are known in the art and may include, for example, arterial intimal fibrosis with intimal mononuclear cells (chronic allograft vasculopathy), duplication of the glomerular basement membranes (chronic allograft glomerulopathy), lamination of the peritubular basement membrane, C4d in peritubular capillaries, and detectable circulating donor HLA-reactive antibodies. In one embodiment, compositions and methods of the invention comprise or are used in combination with a therapeutic regimen to treat chronic rejection before graft lesions develop.

In another embodiment, the patient or patient population in need of treatment is identified as having one or more clinical indicators of transplant glomerulopathy. In a related embodiment, compositions of the invention comprise or are used in combination with a therapeutic regimen comprising one or more therapeutic agents. In certain embodiments, the therapeutic regimen is effective to stabilize renal function and inhibit graft rejection. In a particular embodiment, the one or more therapeutic agents include angiotensin converting enzyme (ACE) inhibitors and/or receptor antagonists, intravenous immunoglobulin, anti-thymocyte globulins, anti-CD20 antibody, mycophenolate mofetil, or tacrolimus. Anti-CD19 antibodies may be used in combination with mycophenolate mofetil and tacrolimus, with or without other therapeutic agents. Plasmapheresis may also be used as part of the therapeutic regimen.

A patient or patient population in need of, or likely to benefit from, a renal transplant is identified according to the knowledge and skill in the art. Examples of patients that may be candidates for renal transplantation include patients diagnosed with amyloidosis, diabetes (type I or type II), glomerular disease (e.g., glomerulonephritis), gout, hemolytic uremic syndrome, HIV, hereditary kidney disease (e.g., polycystic kidney disease, congenital obstructive uropathy, cystinosis, or prune bell syndrome), other kidney disease (e.g., acquired obstructive nephropathy, acute tubular necrosis, acute intersititial nephritis), rheumatoid arthritis, systemic lupus erythematosus, or sickle cell anemia. Other candidates for renal transplant include patients having insulin deficiency, high blood pressure, severe injury or burns, major surgery, heart disease or heart attack, liver disease or liver failure, vascular disease (e.g., progressive systemic sclerosis, renal artery thrombosis, scleroderma), vesicoureteral reflux, and certain cancers (e.g., incidental carcinoma, lymphoma, multiple myeloma, renal cell carcinoma, Wilms tumor). Other candidates for renal transplant may include, for example, heroin users, persons who have rejected a previous kidney or pancreas graft, and persons undergoing a therapeutic regimen comprising antibiotics, cyclosporin, or chemotherapy.

The clinical criteria for the identification of a patient or patient population in need of, or likely to benefit from, a kidney transplant can be determined according to the knowledge and skill in the art. Such criteria may include, for example, one or more of the following: urinary problems, bleeding, easy bruising, fatigue, confusion, nausea and vomiting, loss of appetite, pale skin (from anemia), pain in the muscles, joints, flanks, and chest, bone pain or fractures, and itching 5.23.5. Cardiac Transplants Compositions and methods of the invention are useful for treating or preventing GVHD, humoral rejection, and post-transplant lymphoproliferative disorder in a cardiac transplant recipient. In particular embodiments, the rejection is an acute or a chronic rejection. In one embodiment, compositions and methods of the invention comprise or are used in combination with a pre-transplant conditioning regimen.

In certain embodiments, compositions and methods of the invention comprise or are used in combination with a therapeutic regimen for the treatment of acute humoral rejection in a cardiac transplant recipient. In a particular embodiment, the therapeutic regimen further comprises one or more of the following: plasmapheresis, intravenous immunoglobulin, and anti-CD20 antibody therapy. The patient or patient population in need of treatment for an acute humoral rejection is identified by the detection of one or more of the clinical indications of acute humoral rejection. Examples of clinical indicators of acute humoral rejection may include one or more of the following: hemodynamic dysfunction, defined by shock, hypotension, decreased cardiac output, and a rise in capillary wedge or pulmonary artery pressure. In a particular embodiment, the acute humoral rejection is diagnosed within 6, 12, 18, 24, 36, 48, or 60 months post-transplantation.

In one embodiment, compositions and methods of the invention comprise or are used in combination with a therapeutic regimen for the prevention of rejection in a cardiac transplant recipient. In one embodiment, the transplant recipient in need of prophylaxis against rejection is identified as a patient or patient population having one or more of the following risk factors: female sex, cytomegalovirus seropositivity, elevated response to panel reactive antibodies, positive pre- and/or post-transplant crossmatch, and presensitization with immunosuppressive agents.

In one embodiment, compositions and methods of the invention are for the treatment or prevention of graft deterioration in a heart transplant recipient. In one embodiment, the transplant recipient in need of treatment for, or prophylaxis against, graft deterioration is identified as a patient or patient population having one or more of the following clinical indications of humoral rejection: deposition of immunoglobulin, C1q, C3, and/or C4d in capillaries, evidence of CD68-positive cells within capillaries, and evidence of infiltration of the graft by inflammatory cells upon biopsy. In one embodiment, compositions of the present invention are used in combination with one or more of the following immunosuppressive agents to treat graft deterioration in a heart transplant recipient: intravenous immunoglobulin, anti-thymocyte globulins, anti-CD20 antibody, mycophenolate mofetil, or tacrolimus. In another embodiment, anti-CD19 antibody compositions may be used in combination with one or more immunosuppressive agents and a procedure for the removal of alloantibodies from the patient, such as plasmapheresis or immunoadsorption.

In one embodiment, compositions and methods of the invention comprise or are used in combination with a therapeutic regimen for the treatment of chronic cardiac rejection, for example chronic allograft vasculopathy, also referred to as transplant coronary artery disease. In another embodiment, compositions and methods of the invention comprise or are used in combination with a therapeutic regimen for the prevention of transplant coronary artery disease in a patient or patient population at risk. The criteria for identifying a patient or patient population at risk of developing transplant coronary artery disease are known in the art and may include, for example, patients having poorly matched transplants, patients who develop circulating anti-HLA antibodies, and patients who develop one or more clinical indications of humoral rejection early after cardiac transplant.

A patient or patient population in need of, or likely to benefit from, a heart transplant is identified according to the knowledge and skill in the art. Examples of patients that may be candidates for heart transplantation include those who have been diagnosed with any of the following diseases and disorders: coronary artery disease, cardiomyopathy (noninflammatory disease of the heart), heart valve disease with congestive heart failure, life-threatening abnormal heart rhythms that do not respond to other therapy, idiopathic cardiomyopathy, ischemic cardiomyopathy, dilated cardiomyopathy, ischemic cardiomyopathy, and congenital heart disease for which no conventional therapy exists or for which conventional therapy has failed.

The clinical criteria for the identification of a patient or patient population in need of, or likely to benefit from, a heart transplant can be determined according to the knowledge and skill in the art. Such criteria may include, for example, one or more of the following: ejection fraction less than 25%, intractable angina or malignant cardiac arrhythmias unresponsive to conventional therapy, and pulmonary vascular resistance of less than 2 Wood units. In addition, the patient or patient population in need of a heart transplant may be identified by performing a series of tests according to the knowledge and skill in the art. Such tests include, for example, resting and stress echocardiograms, EKG, assay of blood creatinine levels, coronary arteriography, and cardiopulmonary evaluation including right- and left-heart catheterization.

5.23.6. Lung Transplant

Compositions and methods of the invention are useful for treating or preventing GVHD, humoral rejection, and post-transplant lymphoproliferative disorder in a lung transplant recipient. In particular embodiments, the rejection is characterized as an acute or a chronic rejection. In one embodiment, compositions and methods of the invention comprise or are used in combination with a pre-transplant conditioning regimen.

A patient or patient population in need of, or likely to benefit from, a lung transplant is identified according to the knowledge and skill in the art. Examples of patients that may be candidates for lung transplantation include patients having one of the following diseases or conditions: bronchiectasis, chronic obstructive pulmonary disease, cystic fibrosis, Eisenmenger syndrome or congenital heart disease with Eisenmenger syndrome. emphysema, eosinophilic granuloma of the lung, or histiocytosis X, inhalation/burn trauma, lymphangioleiomyomatosis (LAM), primary pulmonary hypertension, pulmonary fibrosis (scarring of the lung), or sarcoidosis.

The clinical criteria for the identification of a patient or patient population in need of, or likely to benefit from, a lung transplant can be determined according to the knowledge and skill in the art. Such criteria may include, for example, one or more of the following: Chronic obstructive pulmonary disease (COPD) and alpha1-antitrypsin deficiency emphysema characterized by one or more of the following indicators: postbronchodilator FEV1 of less than 25% predicted, resting hypoxemia, i.e., $PaO_2$ of less than 55-60 mm Hg, hypercapnia. secondary pulmonary hypertension, a rapid rate of decline in FEV1, or life-threatening exacerbations; cystic fibrosis characterized by one or more of the following indicators: postbronchodilator FEV1 of less than 30% predicted, resting hypoxemia, hypercapnia, or increasing frequency and severity of exacerbations; idiopathic pulmonary fibrosis characterized by one or more of the following indicators: vital capacity (VC) and TLC of less than 60-65% predicted, and resting hypoxemia; secondary pulmonary hypertension characterized by clinical, radiographic, or physiologic progression while on medical therapy; primary pulmonary hypertension characterized by one or more of the following indicators: NYHA functional class III or IV, mean right atrial pressure of greater than 10 mm Hg, mean pulmonary arterial pressure of greater than 50 mm Hg, cardiac index of less than 2.5 L/min/m$^2$, and failure of therapy with long-term prostacyclin infusion.

5.23.7. Post-Transplant Lymphoproliferative Disorder

The immunosuppression necessary for successful transplantation can give rise to a post-transplant lymphoproliferative disorder of B cell origin. Generally, a post-transplant lymphoproliferative disorder is associated with Epstein-Barr virus infected cells. Post-transplant lymphoproliferative disorder (PTLD) can range in severity from a benign self-limiting mononucleosis-like syndrome to an aggressive non-Hodgkins lymphoma. Compositions and methods of the present invention may be used to treat PTLD arising from any transplant. The transplant may be a solid organ transplant, for example a heart transplant, a liver transplant, a kidney transplant, or a combined kidney-pancreas transplant. In one embodiment, compositions and methods of the invention are used to treat PTLD as part of a therapeutic regimen that includes a temporary cessation or reduction of other immunosuppressive therapy.

In one embodiment, anti-CD19 antibody compositions are administered as part of a therapeutic regimen including one or more of the following: high dose intravenous gamma globulin, a cytokine, an anti-viral agent, and an anti-CD20 monoclonal antibody. The therapeutic regimen may include a temporary cessation or reduction of immunosuppression therapy. In one embodiment, intravenous gamma globulin is administered at a daily dose of 0.4 g/kg for 1 to 5 days, preferably for 3 days, and the cytokine is interferon alpha administered for at least 7 days. In one embodiment, one or more cytokines is used in the regimen. In one embodiment, one or more anti-viral agents is used in the regimen. The anti-viral agent may be selected from any suitable anti-viral agent known to those of skill in the art. In one embodiment, the anti-viral agent is aciclovir or ganciclovir. The anti-viral agent may be administered for at least one or two weeks. The anti-viral agent may also be administered for longer periods, for example, 1 month, 2 months, 3 months, 4 months, or 5 months.

5.24. Patient Diagnosis and Therapeutic Regimens: Autoimmune Disease

According to certain aspects of the invention, the treatment regimen and dose used with compositions and methods of the invention is chosen based on a number of factors including, but not limited to, the stage of the autoimmune disease or disorder being treated. Appropriate treatment regimens can be determined by one of skill in the art for particular stages of an autoimmune disease or disorder in a patient or patient population. Dose response curves can be generated using standard protocols in the art in order to determine the effective amount of compositions of the invention for treating patients having different stages of a autoimmune disease or disorder. In general, patients having more activity of a autoimmune disease or disorder will require higher doses and/or more frequent doses which may be administered over longer periods of time in comparison to patients having less activity of an autoimmune disease or disorder.

Anti-CD19 antibodies, compositions and methods described herein may be practiced to treat an autoimmune disease or disorder. The term "autoimmune disease or disorder" refers to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, including, but not limited to chronic inflammation. Autoimmune disorders may or may not be associated with inflammation. Moreover, inflammation may or may not be caused by an autoimmune disorder. Thus, certain disorders may be characterized as both autoimmune and inflammatory disorders. Exemplary autoimmune diseases or disorders include, but are not limited to: alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, diabetes, eosinophilic fascites, fibromyalgia-fibromyositis, glomerulonephritis, Graves' disease, Guillain-Barre, Hashimoto's thyroiditis, Henoch-Schönlein purpura, idiopathic pulmonary fibrosis, idiopathic/autoimmune thrombocytopenia purpura (ITP), IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus-related disorders (e.g., pemphigus vulgaris), pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosis (SLE), Sweet's syndrome, Still's disease, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, graft versus host disease, urticaria, Vogt-Koyanagi-Hareda syndrome and chronic inflammation resulting from chronic viral or bacteria infections.

Anti-CD19 immunotherapy encompasses the administration of an anti-CD19 antibody as a single agent therapeutic for the treatment of an autoimmune disease or disorder. In one embodiment, an anti-CD19 immunotherapy of the invention encompasses the administration of an anti-CD19 antibody capable of inhibiting in vitro stimulated B cell proliferation. In another embodiment, an anti-CD19 immunotherapy of the invention encompasses the administration of an Fc variant anti-CD19 antibody wherein said Fc variant has altered binding affinity to one or more Fc ligand relative to a comparable non-variant molecule. In a specific embodiment, an anti-CD19 immunotherapy of the invention encompasses the administration of an Fc variant anti-CD19 antibody wherein said Fc variant has enhanced binding to Fc gamma receptor IIB relative to a comparable non-variant Fc domain.

Anti-CD19 immunotherapy further encompasses the administration of an anti-CD19 bispecific antibody as a single agent therapeutic for the treatment of an autoimmune disease or disorder. In one embodiment, an anti-CD19 immunotherapy of the invention encompasses the administration of an anti-CD19 bispecific antibody capable to specifically bind to a first and second antigen, wherein said first antigen is human CD19 and said second antigen is an Fc gamma receptor selected from the group consisting of FcγRI, FcγRIIA, FcγRIIB, FcγRIIIA and/or FcγRIV. In a further embodiment, an anti-CD19 immunotherapy of the invention encompasses the administration of an anti-CD19 bispecific antibody capable of specifically binding to human CD19 and FcγRIIB.

CD19 is expressed on immature B cells, therefore an anti-CD19 mAb may be particularly suited for depleting pre-B cells and immature B cells, e.g, in the bone marrow.

5.24.1. Diagnosis of Autoimmune Diseases or Disorders

The diagnosis of an autoimmune disease or disorder is complicated in that each type of autoimmune disease or disorder manifests differently among patients. This heterogeneity of symptoms means that multiple factors are typically used to arrive at a clinical diagnosis. Generally, clinicians use factors, such as, but not limited to, the presence of autoantibodies, elevated cytokine levels, specific organ dysfunction, skin rashes, joint swelling, pain, bone remodeling, and/or loss of movement as primarily indicators of an autoimmune disease or disorder. For certain autoimmune diseases or disorders, such as RA and SLE, standards for diagnosis are known in the art. For certain autoimmune diseases or disorders, stages of disease have been characterized and are well known in the art. These art recognized methods for diagnosing autoimmune diseases and disorders as well as stages of disease and scales of activity and/or severity of disease that are well known in the art can be used to identify patients and patient populations in need of treatment for an autoimmune disease or disorder using compositions and methods of the invention.

5.24.2. Clinical Criteria for Diagnosing Autoimmune Diseases or Disorders

Diagnostic criteria for different autoimmune diseases or disorders are known in the art. Historically, diagnosis is typically based on a combination of physical symptoms. More recently, molecular techniques such as gene-expression profiling have been applied to develop molecular definitions of autoimmune diseases or disorders. Exemplary methods for clinical diagnosis of particular autoimmune diseases or disorders are provided below. Other suitable methods will be apparent to those skilled in the art.

In certain embodiments, patients with low levels of autoimmune disease activity or patients with an early stage of an autoimmune disease (for diseases where stages are recognized) can be identified for treatment using anti-CD19 antibody compositions and methods. The early diagnosis of autoimmune disease is difficult due to the general symptoms and overlap of symptoms among diseases. In such embodiments, a patient treated at an early stage or with low levels of an autoimmune disease activity has symptoms comprising at least one symptom of an autoimmune disease or disorder. In related embodiments, a patient treated at an early stage or with low levels of an autoimmune disease has symptoms comprising at least 1, 2, 3, 4, 5, 6, 7, 8, 9, 10, 11, 12, 13, 14, or 15 symptoms of an autoimmune disease or disorder. The symptoms may be of any autoimmune diseases and disorders or a combination thereof. Examples of autoimmune disease and disorder symptoms are described below.

5.24.3. Rheumatoid Arthritis

Rheumatoid arthritis is a chronic disease, mainly characterized by inflammation of the lining, or synovium, of the joints. It can lead to long-term joint damage, resulting in chronic pain, loss of function and disability. Identifying patients or patient populations in need of treatment for rheumatoid arthritis is a process. There is no definitive test that provides a positive or negative diagnosis of rheumatoid arthritis. Clinicians rely on a number of tools including, medical histories, physical exams, lab tests, and X-rays.

Physical symptoms vary widely among patients and commonly include, but are not limited to, joint swelling, joint tenderness, loss of motion in joints, joint malalignment, bone remodeling, fatigue, stiffness (particularly in the morning and when sitting for long periods of time), weakness, flu-like symptoms (including a low-grade fever), pain associated with prolonged sitting, the occurrence of flares of disease activity followed by remission or disease inactivity, rheumatoid nodules or lumps of tissue under the skin (typically found on the elbows, they can indicate more severe disease activity), muscle pain, loss of appetite, depression, weight loss, anemia, cold and/or sweaty hands and feet, and involvement of the glands around the eyes and mouth, causing decreased production of tears and saliva (Sjögren's syndrome). For Sjögren's specifically, the following references may be used, Fox et al. Arthritis Rheum. (1986) 29:577-586, and Vitali et al. Ann. Rheum. Dis. (2002). 61:554-558.

Apart form physical symptoms, clinicians commonly use tests, such as, but not limited to, complete blood count, erythrocyte sedimentation rate (ESR or sed rate), C-reactive protein, rheumatoid factor, anti-DNA antibodies, antinuclear antibodies (ANA), anti-cardiolipin antibodies, imaging studies, radiographs (X-rays), magnetic resonance imaging (MRI) of joints or organs, joint ultrasound, bone scans, and bone densitometry (DEXA). These tests are examples of tests that can be used in conjunction with compositions and methods of the invention to check for abnormalities that might exist (i.e., identify patients or patient populations in need of treatment) or to monitor side effects of drugs and check progress.

Early symptoms of rheumatoid arthritis commonly are found in the smaller joints of the fingers, hands and wrists. Joint involvement is usually symmetrical, meaning that if a joint hurts on the left hand, the same joint will hurt on the right hand. In general, more joint erosion indicates more severe disease activity.

Symptoms of more advanced disease activity include damage to cartilage, tendons, ligaments and bone, which causes deformity and instability in the joints. The damage can lead to limited range of motion, resulting in daily tasks (grasping a fork, combing hair, buttoning a shirt) becoming more difficult. Skin ulcers, greater susceptibility to infection, and a general decline in health are also indicators of more advanced disease activity.

Progression of rheumatoid arthritis is commonly divided into three stages. The first stage is the swelling of the synovial lining, causing pain, warmth, stiffness, redness and swelling around the joint. Second is the rapid division and growth of cells, or pannus, which causes the synovium to thicken. In the third stage, the inflamed cells release enzymes that may digest bone and cartilage, often causing the involved joint to lose its shape and alignment, more pain, and loss of movement.

Molecular techniques can also be used to to identify patients or patient populations in need of treatment. For example, rheumatoid arthritis has been shown to be associated with allelic polymorphisms of the human leukocyte antigen (HLA)-DR4 and HLA-DRB1 genes (Ollier and Winchester, 1999, Genes and Genetics of Autoimmunity. Basel, Switzerland; Stastny, 1978, N. Engl J Med 298:869-871; and Gregersen et al., 1987, Arthritis Rheum 30:1205-1213). Rheumatoid arthritis patients frequently express two disease-associated HLA-DRB1*04 alleles (Weyand et al., 1992 Ann Intern Med 117:801-806). Patients can be tested for allelic polymorphisms using methods standard in the art. MHC genes are not the only germline-encoded genes influencing susceptibility to RA that can be used to diagnose or identify patients or patient populations in need of treatment. Female sex clearly increases the risk, and female patients develop a different phenotype of the disease than do male patients. Any molecular indicators of rheumatoid arthritis can be used to identify patients or patient populations in need of treatment with an anti-CD19 antibody composition or method.

Methods for determining activity of rheumatoid arthritis in a patient in relation to a scale of activity are well known in the art and can be used in connection with pharmaceutical compositions and methods of the invention. For example, the American College of Rheumatologists Score (ACR score) can be used to determine the activity of rheumatoid arthritis of a patient or a patient population. According to this method, patients are given a score that correlates to improvement. For example, patients with a 20% improvement in factors defined by the ACR would be given an ACR20 score.

Initially, a patient exhibiting the symptoms of rheumatoid arthritis may be treated with an analgesic. In other embodiments, a patient diagnosed with or exhibiting the symptoms of rheumatoid arthritis is initially treated with nonsteroidal anti-inflammatory (NSAID) compounds. As the disease progresses and/or the symptoms increase in severity, rheumatoid arthritis may be treated by the administration of steroids such as but not limited to dexamethasone and prednisone. In more severe cases, a chemotherapeutic agent, such as but not limited to methotrexate or cytoxin may be administered to relieve the symptoms of rheumatoid arthritis.

In certain instances, rheumatoid arthritis may be treated by administration of gold, while in other instances a biologic, such as an antibody or a receptor (or receptor analog) may be administered. Examples of such therapeutic antibodies are RITUXAN™ (rituximab) and REMICADE® (infliximab). An illustrative example of a soluble receptor that can be administered to treat rheumatoid arthritis is ENBREL® (etanercept).

In extremely severe cases of rheumatoid arthritis, surgery may be indicated. Surgical approaches may include, but not be limited to: synovectomy to reduce the amount of inflammatory tissue by removing the diseased synovium or lining of the joint; arthroscopic surgery to take tissue samples, remove loose cartilage, repair tears, smooth a rough surface or remove diseased synovial tissue; osteotomy, meaning "to cut bone," this procedure is used to increase stability by redistributing the weight on the joint; joint replacement surgery or arthroplasty for the surgical reconstruction or replacement of a joint; or arthrodesis or fusion to fuse two bones together.

In certain embodiments of the methods of invention, a patient can be treated with an anti-CD19 antibody prior, concurrent, or subsequent to any of the therapies disclosed above. Moreover, anti-CD19 antibodies of the present invention may be administered in combination with any of the analgesic, NSAID, steroid, or chemotherapeutic agents noted above, as well as in combination with a biologic administered for the treatment of rheumatoid arthritis.

5.24.4. Systemic Lupus Erythematosis (SLE)

Systemic lupus erythematosis (SLE) is a chronic (long-lasting) rheumatic disease which affects joints, muscles and other parts of the body. Patients or patient populations in need of treatment for SLE can be identified by examining physical symptoms and/or laboratory test results. Physical symptoms vary widely among patients. For example, in SLE, typically 4 of the following 11 symptoms exist before a patient is diagnosed with SLE: 1) malar rash: rash over the cheeks; 2) discoid rash: red raised patches; 3) photosensitivity: reaction to sunlight, resulting in the development of or increase in skin rash; 4) oral ulcers: ulcers in the nose or mouth, usually painless; 5) arthritis: nonerosive arthritis involving two or more peripheral joints (arthritis in which the bones around the joints do not become destroyed); 6) serositis pleuritis or pericarditis: (inflammation of the lining of the lung or heart); 7) renal disorder: excessive protein in the urine (greater than 0.5 gm/day or 3+ on test sticks) and/or cellular casts (abnormal elements the urine, derived from red and/or white cells and/or kidney tubule cells); 8) neurologic disorder: seizures (convulsions) and/or psychosis in the absence of drugs or metabolic disturbances which are known to cause such effects; 9) hematologic disorder: hemolytic anemia or leukopenia (white blood count below 4,000 cells per cubic millimeter) or lymphopenia (less than 1,500 lymphocytes per cubic millimeter) or thrombocytopenia (less than 100,000 platelets per cubic millimeter) (The leukopenia and lymphopenia must be detected on two or more occasions. The thrombocytopenia must be detected in the absence of drugs known to induce it); 10) antinuclear antibody: positive test for antinuclear antibodies (ana) in the absence of drugs known to induce it; and/or 11) immunologic disorder: positive anti-double stranded anti-DNA test, positive anti-sm test, positive antiphospholipid antibody such as anticardiolipin, or false positive syphilis test (vdrl).

Other physical symptoms that may be indicative of SLE include, but are not limited to, anemia, fatigue, fever, skin rash, muscle aches, nausea, vomiting and diarrhea, swollen glands, lack of appetite, sensitivity to cold (Raynaud's phenomenon), and weight loss.

Laboratory tests can also be used to identify patients or patient populations in need of treatment. For example, a blood test can be used to detect a autoantibodies found in the blood of almost all people with SLE. Such tests may include but are not limited to tests for antinuclear antibodies (ANA) in the absence of drugs known to induce it (Rahman, A. and Hiepe, F. *Lupus*. (2002). 11(12):770-773), anti-double stranded anti-DNA (Keren, D. F. *Clin. Lab. Med*. (2002) 22(2):447-474), anti-Sm, antiphospholipid antibody such as anticardiolipin (Gezer, S. *Dis. Mon*. 2003. 49(12):696-741), or false positive syphilis tests (VDRL).

Other tests may include a complement test (C3, C4, CH50, CH100) can be used to measure the amount of complement proteins circulating in the blood (Manzi et al. *Lupus* 2004. 13(5):298-303), a sedimentation rate (ESR) or C-reactive protein (CRP) may be used to measure inflammation levels, a urine analysis can be used to detect kidney problems, chest X-rays may be taken to detect lung damage, and an EKG can be used to detect heart problems.

Chronic SLE is associated with accumulating collateral damage to involved organ, particularly the kidney. Accordingly, early therapeutic intervention is desirable, i.e. prior to, for example, kidney failure. Available treatments for SLE are similar to those available for rheumatoid arthritis. These include initial treatments, either with an analgesic or a nonsteroidal anti-inflammatory (NSAID) compound. As the disease progresses and/or the symptoms increase in severity, SLE may be treated by the administration of steroids such as but not limited to dexamethasone and prednisone.

In more severe cases, a chemotherapeutic agent, such as but not limited to methotrexate or cytoxin may be administered to relieve the symptoms of SLE. However, this approach is not preferred where the patient is a female of child-bearing age. In such instances, those therapeutic approaches that do not interfere with the reproductive capacity of the patient are preferred.

In certain instances, SLE may be treated by administration of a biologic, such as an antibody or a receptor (or receptor analog). Examples of such therapeutic antibodies are RITUXAN™ (rituximab) and REMICADE® (infliximab). An illustrative example of a soluble receptor for an inflammatory cytokine that can be administered to treat SLE is ENBREL® (etanercept).

In certain embodiments of the methods of invention, a patient can be treated with an anti-CD19 antibody prior, concurrent, or subsequent to any of the therapies disclosed above that are used for the treatment of SLE. Moreover, anti-CD19 antibodies of the present invention may be administered in combination with any of the analgesic, NSAID, steroid, or chemotherapeutic agents noted above, as well as in combination with a biologic administered for the treatment of SLE.

5.24.5. Idiopathic/Autoimmune Thrombocytopenia Purpura (ITP)

Idiopathic/autoimmune thrombocytopenia purpura (ITP) is a disorder of the blood characterized by immunoglobulin G (IgG) autoantibodies that interact with platelet cells and result in the destruction of those platelet cells. Typically, the antibodies are specific to platelet membrane glycoproteins. The disorder may be acute (temporary, lasting less than 2 months) or chronic (persisting for longer than 6 months). Patients or patient populations in need of treatment for ITP can be identified by examining a patient's medical history, physical symptoms, and/or laboratory test results. (Provan, D., and Newland, A., *Br. J. Haematol.* (2002) 118(4):933-944; George, J. N. *Curr. Hematol.* (2003) 2(5):381-387; Karptkin, S. *Autoimmunity*. (2004) 37(4):363-368; Cines, D. B., and Blanchette, V. S., *N. Engl. J. Med.* (2002) 346(13)995-1008).

Physical symptoms include purplish-looking areas of the skin and mucous membranes (such as the lining of the mouth) where bleeding has occurred as a result of a decrease in the number of platelet cells. The main symptom is bleeding, which can include bruising ("ecchymosis") and tiny red dots on the skin or mucous membranes ("petechiae"). In some instances bleeding from the nose, gums, digestive or urinary tracts may also occur. Rarely, bleeding within the brain occurs. Common signs, symptoms, and precipitating factors also include, but are not limited to, abrupt onset (childhood ITP), gradual onset (adult ITP), nonpalpable petechiae, purpura, menorrhagia, epistaxis, gingival bleeding, hemorrhagic bullae on mucous membranes, signs of GI bleeding, menometrorrhagia, evidence of intracranial hemorrhage, nonpalpable spleen, retinal hemorrhages, recent live virus immunization (childhood ITP), recent viral illness (childhood ITP), spontaneous bleeding when platelet count is less than 20,000/mm$^3$, and bruising tendency.

Laboratory test that can be used to diagnose ITP include, but are not limited to, a complete blood count test, or a bone marrow examination to verify that there are adequate plateletforming cells (megakaryocyte) in the marrow and to rule out other diseases such as metastatic cancer and leukemia. Isolated thrombocytopenia is the key finding regarding laboratory evaluation. Giant platelets on peripheral smear are indicative of congenital thrombocytopenia. A CT scan of the head may be warranted if concern exists regarding intracranial hemorrhage.

The current treatments for ITP include, platelet transfusions and splenectomy. Other treatments include, the administration of glucocorticoids, administration of immunosuppressive agents, administration of agents that enhance platelet production, such as IL-11, and agents that activate megakaryocytes to produce platelets, such as thrombopoietin (TPO).

In more severe cases, a chemotherapeutic agent, such as but not limited to vincristine and vinblastine may be administered to relieve the symptoms of ITP. However, this approach is not preferred where the patient is a female of child-bearing age. In such instances, those therapeutic approaches that do not interfere with the reproductive capacity of the patient are preferred.

In certain instances, ITP may be treated by administration of a biologic, such as an antibody or a receptor (or receptor analog). Examples of such therapeutic antibodies are anti-CD20 antibodies, such as, Rituximab.

In certain embodiments of the methods of invention, a patient can be treated with an anti-CD19 antibody prior, concurrent, or subsequent to any of the therapies disclosed above that are used for the treatment of ITP. Moreover, anti-CD19 antibodies of the present invention may be administered in combination with any of the agents noted above, as well as in combination with a biologic administered for the treatment of ITP.

5.24.6. Pemphigus and Pemphigoid-Related Disorders

Both pemphigus- and pemphigoid-related disorders are a heterogenous group of autoimmune diseases characterized by a blistering condition of the skin and/or mucosal surfaces. In both diseases, the blistering is caused by autoimmune antibodies that recognize various proteins expressed on the surface of epithelial cells in the dermis and/or epidermis.

In patients with pemphigus-related disease, the blistering occurs within the epidermis and is due to the binding of autoantibodies specific for desmoglein 1 (Dsg1) and/or desmoglein 3 (Dsg3). The classic subtypes of pemphigus can be distinguished according to anti-desmoglein antibody specificities. Patients with pemphigus foliaceus (PF) produce anti-Dsg1 antibodies only. Patients with pemphigus vulgaris (PV) and paraneoplastic pemphigus (PNP) produce anti-Dsg3 antibodies if their lesions are restricted to mucosal tissues. In contrast, PV and PNP patients with lesions of the skin and mucosa produce both anti-Dsg1 and -Dsg3 autoantibodies. (Nagasaka, T., et al. *J. Clin. Invest.* 2004. 114:1484-1492; Seishema, M., et al. *Arch Dermatol.* 2004. 140(12):1500-1503; Amagai, M., *J. Dermatol. Sci.* 1999. 20(2):92-102)

In patients with pemphigoid-related disease including but not limited to, bulous phemphigoid, urticarial bulous pemphigoid, cicatricial pemphigoid, epidermolysis bullosa acquisita, and Linear IgA bullous dermatosis, the blistering occurs at the interface of the dermis with the epidermis. The most common form of pemphigoid disease is bulous pemphigoid (BP) which is characterized by the presence of autoantibodies that bind the bullous pemphigoid antigen 180 (BP180), bullous pemphigoid antigen 230 (BP230), laminin 5, and/or beta 4 integrin. (Fontao, L., et al. *Mol. Biol. Cell.* 2003) 14(5):1978-1992; Challacombe, S. J., et al *Acta Odontol. Scand*. (2001). 59(4):226-234.)

Patients or patient populations in need of treatment for pemphigus- or pemphigoid-related disorders can be identified by examining a patient's medical history, physical symptoms, and/or laboratory test results (reviewed in: Mutasim, D. F. *Drugs Aging*. (2003).20(9):663-681; Yeh, S. W. et al. *Dermatol. Ther*. (2003). 16(3):214-223; Rosenkrantz, W. S. *Vet. Dermatol*. 15(2):90-98).

Typically, diagnosis of these pemphigus- or pemphigoid-related disorders is made by skin biopsy. The biopsy skin sample is examined microscopically to determine the anatomical site of the blister (e.g. epidermis or between dermis and epidermis). These findings are correlated with direct or indirect immunohistochemical analyses to detect the presence of autoantibodies at the site of the lesion. Serum samples from patients may also be examined for the presence of circulating autoantibodies using an ELISA-based test for specific proteins. Several ELISA-based assays have been described for detection of desmoglein antibodies in human samples (Hashimoto, T. *Arch. Dermatol. Res.* (2003) 295

Suppl. 1:S2-11). The presence of these desmoglein autoantibodies in biopsy samples is diagnostic of pemphigus.

Clinically, pemphigus vulgaris can be diagnosed by the presence of blisters in the mouth. Inflammation or erosions may also be present in the lining of the eye and eyelids, and the membranes of the nose or genital tract. Half of the patients also develop blisters or erosions of the skin, often in the groin, underarm, face, scalp and chest areas. Pemphigus foliaccus is a superficial, relatively mild form of pemphigus. It usually manifests on the face and scalp, but also involves the back and chest. Lesions do not occur in the mouth. The blisters are more confined to the outermost surface and often itch. Paraneoplastic pemphigus is very rare and generally occurs in people who have cancer. The lesions are painful and affect the mouth, lips and esophagus (swallowing tube) as well as the skin. Due to involvement of the airways, signs of respiratory disease may occur and can be life-threatening The current treatments for pemphigus or pemphigoid-related disease includes the topical administration of creams and ointments to alleviate the discomfort associated with the skin condition, the administration of anti-inflammatory agents or the administration of immunosuppressive agents.

In certain embodiments of the methods of invention, a patient can be treated with an anti-CD19 antibody prior, concurrent, or subsequent to any of the therapies disclosed above that are used for the treatment of pemphigoid or pemphigoid related disease. Moreover, anti-CD19 antibodies of the present invention may be administered in combination with any of the agents noted above.

5.24.7. Autoimmune Diabetes

According to certain aspects of the invention, a patient in need of treatment for autoimmune diabetes, also known as type 1A diabetes, can be treated with anti-CD19 antibody compositions and methods. Type 1A diabetes is an autoimmune disease caused by the synergistic effects of genetic, environmental, and immunologic factors that ultimately destroy the pancreatic beta cells. The consequences of pancreatic beta cell destruction are a decrease in beta cell mass, a reduced insulin production/secretion and a gradual rise in blood glucose levels.

Patients or patient populations in need of treatment for type 1A diabetes can be identified by examining a patient's medical history, physical symptoms, and/or laboratory test results. Symptoms often come on suddenly and include, but are not limited to, low or non-existent blood insulin levels, increased thirst, increased urination, constant hunger, weight loss, blurred vision, and/or fatigue. Overt diabetes does not usually become evident until a majority of beta cells are destroyed (>80%). Typically, diabetes is clinically diagnosed if a patient has a random (without regard to time since last meal) blood glucose concentration ≥11.1 mmol/L (200 mg/dL) and/or a fasting (no caloric intake for at least 8 hours) plasma Glucose ≥7.0 mmol/L (126 mg/dI) and/or a two-hour plasma glucose ≥11.1 mmol/L (200 mg/dL). Ideally, these tests should be repeated on different days with comparable results before diagnosis is confirmed. (Harrison's Principles of Internal Medicine, 16$^{th}$ ed./editors, Dennis L. Kasper, et al. The McGraw-Hill Companies, Inc. 2005 New York, N.Y.).

Although the precise etiology of type 1A diabetes is unknown, there exists clear genetic linkage to specific HLA serotypes. In particular, autoimmune diabetes is associated with HLA DR3 and DR4 serotypes. The presence of both DR3 and DR4 confers the highest known genetic risk. Susceptibility to autoimmune diabetes is also linked to HLA class II (HLA-DQB1*0302. In contrast, HLA haplotypes with DRB1-1501 and DQA1-0102-DQB1-0602 are associated with protection from type 1A diabetes (Redondo, M. J., et al. *J. Clin. Endocrinol. Metabolism* (2000) 10:3793-3797.)

The destruction of the insulin producing beta islet cells can be accompanied by islet cell autoantibodies, activated lymphocytic infiltrates in the pancreas and draining lymph nodes, T lymphocytes responsive to islet cell proteins, and release of inflammatory cytokines within the islets (Harrison's Principles of Internal Medicine, 16$^{th}$ ed./editors, Dennis L. Kasper, et al. The McGraw-Hill Companies, Inc. 2005 New York, N.Y.).

Autoantibodies associated with type 1A diabetes include but are not limited to antibodies that bind insulin, glutamic acid decarboxylase (GAD), ICA-512/IA-2, phogrin, islet ganglioside and carboxypeptidase H (Gianani, R. and Eisenbarth, G. S. *Immunol. Rev.* (2005) 204:232-249; Kelemen, K. et al, *J. Immunol.* (2004) 172(6):3955-3962); Falorni, A. and Borozzetti, A. *Best Pract. Res. Clin. Endocrinol. Metab.* 2005. 19(1):119-133.)

The current treatments for autoimmune diabetes include the administration of vitamin D, corticosteroids, agents which control blood pressure and agents that control glycemia (blood sugar levels).

In certain embodiments of the methods of invention, a patient can be treated with an anti-CD19 antibody prior, concurrent, or subsequent to any of the therapies disclosed above that are used for the treatment of autoimmune diabetes. Moreover, anti-CD19 antibodies of the present invention may be administered in combination with any of the agents noted above.

5.24.8. Systemic Sclerosis (Scleroderma) and Related Disorders

Systemic sclerosis also known as Scleroderma encompasses a heterogeneous group of diseases including but not limited to, Limited cutaneous disease, Diffuse cutaneous disease, Sine scleroderma, Undifferentiated connective tissue disease, Overlap syndromes, Localized scleroderma, Morphea, Linear scleroderma, En coup de saber, Scleredema adultorum of Buschke, Scleromyxedema, Chronic graft-vs.-host disease, Eosinophilic fasciitis, Digital sclerosis in diabetes, and Primary anylooidosisand anyloidosis associated with multiple myeloma. (Reviewed in: Harrison's Principles of Internal Medicine, 16$^{th}$ ed./editors, Dennis L. Kasper, et al. The McGraw-Hill Companies, Inc. 2005 New York, N.Y.).

Clinical features associated with scleroderma can include Raynaud's phenomenon, skin thickening, subcutaneous calcinosis, telangiectasia, arthralgias/arthritis, myopathy, esophageal dysmotility. pulmonary fibrosis, isolated pulmonary arterial hypertension, congestive heart failure and renal crisis. The extent to which an patient displays one or more of these disease manifestations can influence the diagnosis and potential treatment plan.

Autoantibodies include: Anti-topioisomerase 1, anticentromere, anti-RNA polymerase I, II, and/or III, anti-Th RNP, anti-U, RNP (anti-fibrillarin), anti-PM/Sci, anti-nuclear antibodies (ANA).

Identification of patients and patient populations in need of treatment of scleroderma can be based on clinical history and physical findings. Patients or patient populations in need of treatment for scleroderma can be identified by examining a patient's medical history, physical symptoms, and/or laboratory test results. Diagnosis may be delayed in patients without significant skin thickening Laboratory, X-ray, pulmonary function tests, and skin or renal (kidney) biopsies can be used to determine the extent and severity of internal organ involvement.

In the early months or years of disease onset, scleroderma may resemble many other connective tissue diseases, such as, but not limited to, Systemic Lupus Erythematosus, Polymyositis, and Rheumatoid Arthritis.

The most classic symptom of systemic sclerosis (scleroderma) is sclerodactyl). Initial symptoms include swollen hands, which sometimes progress to this tapering and claw-like deformity. Not everyone with scleroderma develops this degree of skin hardening Other symptoms can include morphea, linear sclerodactyly (hardened fingers), Raynaud's syndrome, calcinosis, and telangiectasia.

Blood tests such as antinuclear antibody (ANA) tests can be used in the diagnosis of both localized and systemic scleroderma. For example, anti-centromere antibodies (ACA) and anti-Scl-70 antibodies are indicative of patients in need of treatment for systemic sclerosis (Ho et al., 2003, Arthritis Res Ther. 5:80-93); anti-topo II alpha antibody are indicative of patients in need of treatment for local scleroderma; and anti-topo I alpha antibody are indicative of patients in need of treatment for systemic scleroderma. Several types of scleroderma and methods for diagnosing these types are recognized and well known in the art, including, but not limited to, juvenile scleroderma (Foeldvari, Curr Opin Rheumatol 14:699-703 (2002); Cefle et al., Int J Clin Pract. 58:635-638 (2004)); localized scleroderma; Nodular Scleroderma (Cannick, J Rheumatol. 30:2500-2502 (2003)); and Systemic scleroderma, including, but not limited to, Calcinosis, Raynaud's, Esophagus, Sclerodactyl), and Telangiectasia (CREST), limited systemic scleroderma, and diffuse systemic scleroderma. Systemic scleroderma is also known as systemic sclerosis (SSc). It may also be referred to as Progressive Systemic Sclerosis (PSSc), or Familial Progressive Systemic Sclerosis (FPSSc) (Nadashkevich et al., Med Sci Monit. 10:CR615-621 (2004); Frances et al., Rev Prat. 52:1884-90 (2002)). Systemic sclerosis is a multisystem disorder characterized by the presence of connective tissue sclerosis, vascular abnormalities concerning small-sized arteries and the microcirculation, and autoimmune changes.

The type of systemic scleroderma known as CREST is not characterized by any skin tightening CREST is characterized by Calcinosis (calcium deposits), usually in the fingers; Raynaud's; loss of muscle control of the Esophagus, which can cause difficulty swallowing; Sclerodactyl), a tapering deformity of the bones of the fingers; and Telangiectasia, small red spots on the skin of the fingers, face, or inside of the mouth. Typically two of these symptoms is sufficient for diagnosis of CREST. CREST may occur alone, or in combination with any other form of Scleroderma or with other autoimmune diseases.

Limited Scleroderma is characterized by tight skin limited to the fingers, along with either pitting digital ulcers (secondary to Raynaud's) and/or lung fibrosis. The skin of the face and neck may also be involved in limited scleroderma.

Diffuse Scleroderma is diagnosed whenever there is proximal tight skin Proximal means located closest to the reference point. Proximal tight skin can be skin tightness above the wrists or above the elbows. Typically, a patient with skin tightness only between their elbows and their wrists will receive a diagnosis of either diffuse or limited systemic Scleroderma, depending on which meaning of proximal the diagnosing clinician uses.

The current therapies for scleroderma include extracorporeal photophoresis following 6-methoxypsoralen, and autologous stem cell transplant, The current treatments for scleroderma include the administration of the following agents, penicillamine, cholchicine, interferon alpha, interferon gamma, chlorambucil, cyclosporine, 5-fluorouracil, cyclophosphamide, minocycline, thalidomide, etanercept, or methotrexate.

In certain embodiments of the methods of invention, a patient can be treated with an anti-CD19 antibody prior, concurrent, or subsequent to any of the therapies disclosed above that are used for the treatment of autoimmune diabetes. Moreover, anti-CD19 antibodies of the present invention may be administered in combination with any of the agents noted above.

5.25. Determining CD19 Density in a Sample or Subject

While not required, assays for CD19 density can be employed to further characterize the patient's diagnosis. Methods of determining the density of antibody binding to cells are known to those skilled in the art (See, e.g., Sato et al., *J. Immunology* 165:6635-6643 (2000); which discloses a method of assessing cell surface density of specific CD antigens). Other standard methods include Scatchard analysis. For example, the antibody or fragment can be isolated, radiolabeled, and the specific activity of the radiolabeled antibody determined. The antibody is then contacted with a target cell expressing CD19. The radioactivity associated with the cell can be measured and, based on the specific activity, the amount of antibody or antibody fragment bound to the cell determined.

Fluorescence activated flow cytometry can also be employed. Generally, the antibody or antibody fragment is bound to a target cell expressing CD19. A second reagent that binds to the antibody is then added, for example, a fluorochrome labeled anti-immunoglobulin antibody. Fluorochrome staining can then be measured and used to determine the density of antibody or antibody fragment binding to the cell.

As another suitable method, the antibody or antibody fragment can be directly labeled with a detectable label, such as a fluorophore, and bound to a target cell. The ratio of label to protein is determined and compared with standard beads with known amounts of label bound thereto. Comparison of the amount of label bound to the cell with the known standards can be used to calculate the amount of antibody bound to the cell.

In yet another aspect, the present invention provides a method for detecting in vitro or in vivo the presence and/or density of CD19 in a sample or individual. This can also be useful for monitoring disease and effect of treatment and for determining and adjusting the dose of the antibody to be administered. The in vivo method can be performed using imaging techniques such as PET (positron emission tomography) or SPECT (single photon emission computed tomography). One could also label an anti-CD19 antibody with Indium using a covalently attached chelator. The resulting antibody can be imaged using standard gamma cameras the same way as ZEVALIN™ (ipritumomab tiuxetan) (Indium labeled anti-CD20 mAb) (Biogen Idec, Cambridge Mass.) is used to image CD20 antigen.

In one embodiment, the in vivo method can be performed by contacting a sample to be tested, optionally along with a control sample, with a human anti-CD19 antibody under conditions that allow for formation of a complex between an antibody of the invention and the human CD19 antigen. Complex formation is then detected (e.g., using fluorescent activated flow cytometry or Western blotting). When using a control sample along with the test sample, a complex is detected in both samples and any statistically significant difference in the formation of complexes between the samples is indicative of the presence of human CD19 in the test sample.

In other embodiments, mean florescence intensity can be used as a measure of CD19 density. In such embodiments, B cells are removed from a patient and stained with CD19 antibodies that have been labeled with a florescent label and the fluorescence intensity is measured using flow cytometry. Fluorescence intensities can be measured and expressed as an average of intensity per B cell. Using such methods, mean florescence intensities that are representative of CD19 density can be compared for a patient before and after treatment using methods and compositions of the invention, or between patients and normal levels of hCD19 on B cells.

In patients where the density of CD19 expression on B cells has been determined, the density of CD19 may influence the determination and/or adjustment of the dosage and/or treatment regimen used with an anti-CD19 antibody of compositions and methods of the invention. For example, where density of CD19 is high, it may be possible to use anti-CD19 antibodies that less efficiently mediate ADCC in humans. In certain embodiments, where the patient treated using compositions and methods of the invention has a low CD19 density, a higher dosage of an anti-CD19 antibody of compositions and methods of the invention may be used. In other embodiments, where the patient treated using compositions and methods of the invention has a low CD19 density, a low dosage of an anti-CD19 antibody of compositions and methods of the invention may be used. In certain embodiments, where the patient treated using compositions and methods of the invention has a high CD19 density, a lower dosage of an anti-CD19 antibody of compositions and methods of the invention may be used. In certain embodiments, CD19 density can be compared to CD20 density in a patient, CD19 density can be compared to an average CD19 density for humans or for a particular patient population, or CD19 density can be compared to CD19 levels in the patient prior to therapy or prior to onset of a B cell disease or disorder. In certain embodiments, the patient treated using compositions and methods of the invention has a B cell malignancy where CD19 is present on the surface of B cells.

5.26. Immunotherapeutic Protocols

Anti-CD19 antibody compositions used in the therapeutic regimen/protocols, referred to herein as "anti-CD19 immunotherapy" can be naked antibodies, immunoconjugates and/or fusion proteins. Compositions of the invention can be used as a single agent therapy or in combination with other therapeutic agents or regimens. Anti-CD19 antibodies or immunoconjugates can be administered prior to, concurrently with, or following the administration of one or more therapeutic agents. Therapeutic agents that can be used in combination therapeutic regimens with compositions of the invention include any substance that inhibits or prevents the function of cells and/or causes destruction of cells. Examples include, but are not limited to, radioactive isotopes, chemotherapeutic agents, and toxins such as enzymatically active toxins of bacterial, fungal, plant or animal origin, or fragments thereof.

The therapeutic regimens described herein, or any desired treatment regimen can be tested for efficacy using a transgenic animal model which expresses human CD19 antigen in place of native CD19 antigen. Thus, an anti-CD19 antibody treatment regimen can be tested in an animal model to determine efficacy before administration to a human.

Anti-CD19 antibodies, compositions and methods may be practiced to treat B cell diseases, including B cell malignancies. The term "B cell malignancy" includes any malignancy that is derived from a cell of the B cell lineage. Exemplary B cell malignancies include, but are not limited to: B cell sub-type non-Hodgkin's lymphoma (NHL) including low grade/follicular, NHL, small lymphocytic (SL) NHL, intermediate grade/follicular NHL, intermediate grade diffuse NHL, high grade immunoblastic NHL, high grade lymphoblastic NHL, high grade small non-cleaved cell NHL; mantle-cell lymphoma, and bulky disease NHL; Burkitt's lymphoma; multiple myeloma; pre-B acute lymphoblastic leukemia and other malignancies that derive from early B cell precursors; common acute lymphocytic leukemia (ALL); chronic lymphocytic leukemia (CLL) including immunoglobulin-mutated CLL and immunoglobulin-unmutated CLL; hairy cell leukemia; Null-acute lymphoblastic leukemia; Waldenstrom's Macroglobulinemia; diffuse large B cell lymphoma (DLBCL) including germinal center B cell-like (GCB) DLBCL, activated B cell-like (ABC) DLBCL, and type 3 DLBCL; pro-lymphocytic leukemia; light chain disease; plasmacytoma; osteosclerotic myeloma; plasma cell leukemia; monoclonal gammopathy of undetermined significance (MGUS); smoldering multiple myeloma (SMM); indolent multiple myeloma (IMM); Hodgkin's lymphoma including classical and nodular lymphocyte pre-dominant type; lymphoplasmacytic lymphoma (LPL); and marginal-zone lymphoma including gastric mucosal-associated lymphoid tissue (MALT) lymphoma.

In a further embodiment the invention can be employed to treat mature B cell malignancies (i.e., express Ig on the cell surface) including but not limited to follicular lymphoma, mantle-cell lymphoma, Burkitt's lymphoma, multiple myeloma, diffuse large B-cell lymphoma (DLBCL) including germinal center B cell-like (GCB) DLBCL, activated B cell-like (ABC) DLBCL, and type 3 DLBCL, Hodgkin's lymphoma including classical and nodular lymphocyte predominant type, lymphoplasmacytic lymphoma (LPL), marginal-zone lymphoma including gastric mucosal-associated lymphoid tissue (MALT) lymphoma, and chronic lymphocytic leukemia (CLL) including immunoglobulin-mutated CLL and immunoglobulin-unmutated CLL.

Further, CD19 is expressed earlier in B cell development than, for example, CD20, and is therefore particularly suited for treating pre-B cell and immature B cell malignancies (i.e., do not express Ig on the cell surface), for example, in the bone marrow. Illustrative pre-B cell and immature B cell malignancies include but are not limited to acute lymphoblastic leukemia In other particular embodiments, the invention can be practiced to treat extranodal tumors.

5.27. Anti-CD19 Immunotherapy

In accordance with the present invention "anti-CD19 immunotherapy" encompasses the administration of any of the anti-CD19 antibodies of the invention in accordance with any therapeutic regimen described herein. Anti-CD19 antibodies can be administered as naked antibodies, or immunoconjugates or fusion proteins.

Anti-CD19 immunotherapy encompasses the administration of an anti-CD19 antibody as a single agent therapeutic for the treatment of a B cell malignancy. Anti-CD19 immunotherapy encompasses methods of treating an early stage disease resulting from a B cell malignancy. Anti-CD19 immunotherapy encompasses methods of treating a B cell malignancy wherein an anti-CD19 antibody mediates ADCC. Anti-CD19 immunotherapy encompasses methods of treating a B cell malignancy wherein an anti-CD19 antibody is administered before the patient has received any treatment for the malignancy, whether that therapy is chemotherapy, radio chemical based therapy or surgical therapy.

In one embodiment, a human subject having a B cell malignancy can be treated by administering a human or humanized antibody that may be able to mediate human ADCC. In cases of early stage disease, or single agent therapies, any anti-CD19 antibody that may mediate ADCC can be used in the human subjects (including murine and chimeric antibodies); however, human and humanized antibodies may be preferred.

Antibodies of IgG1 or IgG3 human isotypes are in some cases preferred for therapy. However, the IgG2 or IgG4 human isotypes can be used as well, provided they have the relevant effector function, for example human ADCC. Such effector function can be assessed by measuring the ability of the antibody in question to mediate target cell lysis by effector cells in vitro or in vivo.

In one embodiment, the dose of antibody used should be sufficient to deplete circulating B cells. Progress of the therapy can be monitored in the patient by analyzing blood samples. Other signs of clinical improvement can be used to monitor therapy.

Methods for measuring depletion of B cells that can be used in connection with compositions and methods of the invention are well known in the art and include, but are not limited to the following embodiments. In one embodiment, circulating B cells depletion can be measured with flow cytometry using a reagent other than an anti-CD19 antibody that binds to B cells to define the amount of B cells. In other embodiments, B cell levels in the blood can be monitored using standard serum analysis. In such embodiments, B cell depletion is indirectly measured by defining the amount to an antibody known to be produced by B cells. The level of that antibody is then monitored to determine the depletion and/or functional depletion of B cells. In another embodiment, B cell depletion can be measured by immunochemical staining to identify B cells. In such embodiments, B cells or tissues or serum comprising B cells extracted from a patient can be placed on microscope slides, labeled and examined for presence or absence. In related embodiments, a comparison is made between B cells extracted prior to therapy and after therapy to determine differences in the presence of B cells.

Tumor burden can be measured and used in connection with compositions and methods of the invention. Methods for measuring tumor burden are well known in the art and include, but are not limited to the following embodiments. In certain embodiments, PET scans can be used to measure metabolic activity and identify areas of higher activity which are indicative of tumors. CT scans and MRI can also be used to examine soft tissue for the presence and size of tumors. In other embodiments, bone scan can be used to measure tumor volume and location. In yet other embodiments, tumor burden can be measured by examining the blood flow into and out of a tumor using doppler technology (e.g., ultrasound). In such embodiments, changes in blood flow over time or deviations from normal blood flow in the appropriate tissue of a patient can be used to calculate an estimate to tumor burden. Such methods for measuring tumor burden can be used prior to and following methods of treatment of the invention.

In certain embodiments of methods of the invention B cells are depleted and/or tumor burden is decreased while ADCC function is maintained.

In embodiments of the invention where an anti-CD19 antibody is administered as a single agent therapy, the invention contemplates use of different treatment regimens.

According to certain aspects of the invention, an anti-CD19 antibody used in compositions and methods of the invention, is a naked antibody. In related embodiments, the dose of naked anti-CD19 antibody used is at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5 mg/kg of body weight of a patient. In certain embodiments, the dose of naked anti-CD19 antibody used is at least about 1 to 10, 5 to 15, 10 to 20, or 15 to 25 mg/kg of body weight of a patient. In certain embodiments, the dose of naked anti-CD19 antibody used is at least about 1 to 20, 3 to 15, or 5 to 10 mg/kg of body weight of a patient. In other embodiments, the dose of naked anti-CD19 antibody used is at least about 5, 6, 7, 8, 9, or 10 mg/kg of body weight of a patient.

In certain embodiments, the dose comprises about 375 mg/m$^2$ of anti-CD19 antibody administered weekly for 4 to 8 consecutive weeks. In certain embodiments, the dose is at least about 1, 2, 3, 4, 5, 6, 7, 8, 9, 10, 11, 12, 13, 14, or 15 mg/kg of body weight of the patient administered weekly for 4 to 8 consecutive weeks.

The exemplary doses of anti-CD19 antibody described above can be administered as described in Section 5.21.3. In one embodiment, the above doses are single dose injections. In other embodiments, the doses are administered over a period of time. In other embodiments, the doses are administered multiple times over a period of time. The period of time may be measured in days, weeks, or months. Multiple doses of an anti-CD19 antibody can be administered at intervals suitable to achieve a therapeutic benefit while balancing toxic side effects. For example, where multiple doses are used, it may be preferred to time the intervals to allow for recovery of the patient's monocyte count prior to the repeat treatment with antibody. This dosing regimen will optimize the efficiency of treatment, since the monocyte population reflects ADCC function in the patient.

In certain embodiments, compositions of the invention are administered to a human patient as long as the patient is responsive to therapy. In other embodiments, compositions of the invention are administered to a human patient as long as the patient's disease does not progress. In related embodiments, compositions of the invention are administered to a human patient until a patient's disease does not progress or has not progressed for a period of time, then the patient is not administered compositions of the invention unless the disease reoccurs or begins to progress again. For example, a patient can be treated with any of the above doses for about 4 to 8 weeks, during which time the patient is monitored for disease progression. If disease progression stops or reverses, then the patient will not be administered compositions of the invention until that patient relapses, i.e., the disease being treated reoccurs or progresses. Upon this reoccurrence or progression, the patient can be treated again with the same dosing regimen initially used or using other doses described above.

In certain embodiments, compositions of the invention can be administered as a loading dose followed by multiple lower doses (maintenance doses) over a period of time. In such embodiments, the doses may be timed and the amount adjusted to maintain effective B cell depletion. In certain embodiments, the loading dose is about 10, 11, 12, 13, 14, 15, 16, 17, or 18 mg/kg of patient body weight and the maintenance dose is at least about 5 to 10 mg/kg of patient body weight. In other embodiments, the maintenance dose is administered at intervals of every 7, 10, 14 or 21 days. The maintenance doses can be continued indefinitely, until toxicity is present, until platelet count decreases, until there is no disease progression, until the patient exhibits immunogenicity, or until disease progresses to a terminal state. In yet other embodiments, compositions of the invention are administered to a human patient until the disease progresses to a terminal stage.

In embodiments of the invention where circulating monocyte levels of a patient are monitored as part of a treatment regimen, doses of anti-CD19 antibody administered may be spaced to allow for recovery of monocyte count. For example, a composition of the invention may be administered at intervals of every 8, 9, 10, 11, 12, 13, 14, 15, 16, 17, 18, 19, 20, 21, 22, 23, 24, 25, 26, 27, 28, 29, or 30 days.

In embodiments of the invention where an anti-CD19 antibody is conjugated to or administered in conjunction with a toxin, one skilled in the art will appreciate that the dose of anti-CD19 antibody can be adjusted based on the toxin dose and that the toxin dose will depend on the specific type of toxin being used. Typically, where a toxin is used, the dose of anti-CD19 antibody will be less than the dose used with a naked anti-CD19 antibody. The appropriate dose can be determined for a particular toxin using techniques well known in the art. For example, a dose range study can be conducted to determine the maximum tolerated dose of anti-CD19 antibody when administered with or conjugated to a toxin.

In embodiments of the invention where an anti-CD19 antibody is conjugated to or administered in conjunction with a radiotherapeutic agent, the dose of the anti-CD19 antibody will vary depending on the radiotherapeutic used. In certain embodiments, a two step process is used. First, the human patient is administered a composition comprising a naked anti-CD19 antibody and about 6, 7, 8, 9, or 10 days later a small amount of the radiotherapeutic is administered. Second, once the tolerance, distribution, and clearance of the low dose therapy has been determined, the patient is administered a dose of the naked anti-CD19 antibody followed by a therapeutic amount of the radiotherapeutic is administered. Such treatment regimens are similar to those approved for treatment of Non-Hodgkin's lymphoma using ZEVALIN™ (impritumomab tiuxetan) (Indium labeled anti-CD20 mAb) (Biogen Idec) or BEXXAR™ (tositumomab) (GSK, Coulter Pharmaceutical).

5.28. Combination with Chemotherapeutic Agents

Anti-CD19 immunotherapy (using naked antibody, immunoconjugates, or fusion proteins) can be used in conjunction with other therapies including but not limited to, chemotherapy, radioimmunotherapy (RIT), chemotherapy and external beam radiation (combined modality therapy, CMT), or combined modality radioimmunotherapy (CMRIT) alone or in combination, etc. In certain embodiments, an anti-CD19 antibody therapy of the present invention can be administered in conjunction with CHOP (Cyclophosphamide-Hydroxy-doxorubicin-Oncovin (vincristine)-Prednisolone), the most common chemotherapy regimen for treating non-Hodgkin's lymphoma. As used herein, the term "administered in conjunction with" means that an anti-CD19 immunotherapy can be administered before, during, or subsequent to the other therapy employed.

In certain embodiments, an anti-CD19 immunotherapy is in conjunction with a cytotoxic radionuclide or radiotherapeutic isotope. For example, an alpha-emitting isotope such as $^{225}$Ac, $^{224}$Ac, $^{211}$At, $^{212}$Bi, $^{213}$Bi, $^{212}$Pb, $^{224}$Ra, or $^{223}$Ra. The cytotoxic radionuclide may also be a beta-emitting isotope such as $^{186}$Rc, $^{188}$Rc, $^{90}$Y, $^{131}$I, $^{67}$Cu, $^{177}$Lu, $^{153}$Sm, $^{166}$Ho, or $^{64}$Cu. Further, the cytotoxic radionuclide may emit Auger and low energy electrons and include the isotopes $^{125}$I, $^{123}$I or $^{77}$Br. In other embodiments the isotope may be $^{198}$Au, $^{32}$P, and the like. In certain embodiments, the amount of the radionuclide administered to the subject is between about 0.001 mCi/kg and about 10 mCi/kg.

In some embodiments, the amount of the radionuclide administered to the subject is between about 0.1 mCi/kg and about 1.0 mCi/kg. In other embodiments, the amount of the radionuclide administered to the subject is between about 0.005 mCi/kg and 0.1 mCi/kg.

In certain embodiments, an anti-CD19 immunotherapy is in conjunction with a chemical toxin or chemotherapeutic agent. The chemical toxin or chemotherapeutic agent may be selected from the group consisting of an enediyne such as calicheamicin and esperamicin; duocarmycin, methotrexate, doxorubicin, melphalan, chlorambucil, ARA-C, vindesine, mitomycin C, cis-platinum, etoposide, bleomycin and 5-fluorouracil.

Suitable chemical toxins or chemotherapeutic agents that can be used in combination therapies with an anti-CD19 immunotherapy include members of the enediyne family of molecules, such as calicheamicin and esperamicin. Chemical toxins can also be taken from the group consisting of duocarmycin (see, e.g. U.S. Pat. Nos. 5,703,080 and 4,923,990), methotrexate, doxorubicin, melphalan, chlorambucil, ARA-C, vindesine, mitomycin C, cis-platinum, etoposide, bleomycin and 5-fluorouracil. Examples of chemotherapeutic agents also include Adriamycin, Doxorubicin, 5-Fluorouracil, Cytosine arabinoside ("Ara-C"), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Caminomycin, Aminopterin, Dactinomycin, Mitomycins, Esperamicins (see, U.S. Pat. No. 4,675,187), Melphalan and other related nitrogen mustards.

In other embodiments, for example, "CVB" (1.5 g/m$^2$ cyclophosphamide, 200-400 mg/m$^2$ etoposide, and 150-200 mg/m$^2$ carmustine) can be used in combination therapies of the invention. CVB is a regimen used to treat non-Hodgkin's lymphoma. Patti et al., *Eur. J. Haematol.* 51:18 (1993). Other suitable combination chemotherapeutic regimens are well-known to those of skill in the art. See, for example, Freedman et al., "*Non-Hodgkin's Lymphomas*," in CANCER MEDICINE, VOLUME 2, 3rd Edition, Holland et al. (eds.), pp. 2028-2068 (Lea & Febiger 1993). As an illustration, first generation chemotherapeutic regimens for treatment of intermediate-grade non-Hodgkin's lymphoma include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate and brostatin-1. In a multimodal therapy, both chemotherapeutic drugs and cytokines are co-administered with an antibody, immunoconjugate or fusion protein according to the present invention. The cytokines, chemotherapeutic drugs and antibody, immunoconjugate or fusion protein can be administered in any order, or together.

Other toxins that may be used in compositions and methods of the invention include poisonous lectins, plant toxins such as ricin, abrin, modeccin, botulina and diphtheria toxins. Of course, combinations of the various toxins could also be coupled to one antibody molecule thereby accommodating variable cytotoxicity. Illustrative of toxins which are suitably employed in combination therapies of the invention are ricin, abrin, ribonuclease, DNase I, Staphylococcal enterotoxin-A, pokeweed antiviral protein, gelonin, diphtherin toxin, *Pseudomonas exotoxin*, and *Pseudomonas endotoxin*. See, for example, Pastan et al., *Cell* 47:641 (1986), and Goldenberg et al., *Cancer Journal for Clinicians* 44:43 (1994). Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S),

*momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

Suitable toxins and chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985). Other suitable toxins and/or chemotherapeutic agents are known to those of skill in the art.

An anti-CD19 immunotherapy of the present invention may also be in conjunction with a prodrug-activating enzyme which converts a prodrug (e.g., a peptidyl chemotherapeutic agent, see, WO81/01145) to an active anti-cancer drug. See, for example, WO 88/07378 and U.S. Pat. No. 4,975,278. The enzyme component of such combinations includes any enzyme capable of acting on a prodrug in such a way so as to covert it into its more active, cytotoxic form. The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "*Prodrugs in Cancer Chemotherapy*" Biochemical Society Transactions, 14, pp. 375-382, 615th Meeting Belfast (1986) and Stella et al., "*Prodrugs: A Chemical Approach to Targeted Drug Delivery,*" Directed Drug Delivery, Borchardt et al. (ed.), pp. 247-267, Humana Press (1985). Prodrugs that can be used in combination with anti-CD19 antibodies include, but are not limited to, phosphate-containing prodrugs, thiophosphate-containing prodrugs, sulfate-containing prodrugs, peptide-containing prodrugs, D-amino acid-modified prodrugs, glycosylated prodrugs, α-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

In certain embodiments, administration of compositions and methods of the invention may enable the postponement of toxic therapy and may help avoid unnecessary side effects and the risks of complications associated with chemotherapy and delay development of resistance to chemotherapy. In certain embodiments, toxic therapies and/or resistance to toxic therapies is delayed in patients administered compositions and methods of the invention delay for up to about 6 months, 1, 2, 3, 4, 5, 6, 7, 8, 9, or 10 years.

5.29. Combination with Therapeutic Antibodies

An anti-CD19 immunotherapy described herein may be administered in combination with other antibodies, including, but not limited to, anti-CD20 mAb, anti-CD52 mAb, anti-CD22 antibody, and anti-CD20 antibodies, such as RITUXAN™ (C2B8; RITUXIMAB™; IDEC Pharmaceuticals). Other examples of therapeutic antibodies that can be used in combination with antibodies of the invention or used in compositions of the invention include, but are not limited to, HERCEPTIN™ (Trastuzumab; Genentech), MYLOTARG™ (Gemtuzumab ozogamicin; Wyeth Pharmaceuticals), CAMPATH™ (Alemtuzumab; Berlex), ZEVALIN™ (Ipritumomab tiuxetan; Biogen Idec), BEXXAR™ (Tositumomab; GlaxoSmithKline Corixa), ERBITUX™ (Cetuximab; Imclone), and AVASTIN™ (Bevacizumab; Genentech).

An anti-CD19 immunotherapy described herein may be administered in combination with an antibody specific for an Fc receptor selected from the group consisting of FcγRI, FcγRIIA, FcγRIIB, FcγRIII and/or FcγRIV. In a specific embodiment, an anti-CD19 immunotherapy described herein may be administered in combination with an antibody specific for FcγRIIB. Anti-FcγRIIB antibodies suitable for this purpose have been described in US Patent Application Publication No. 2004185045 (U.S. Pat. No. 7,425,620), PCT Publication Nos. WO05051999A, WO05018669 and WO04016750.

In certain embodiments, an anti-CD19 and an anti-CD20 and/or an anti-CD22 mAb and/or an anti-CD52 mAb can be administered, optionally in the same pharmaceutical composition, in any suitable ratio. To illustrate, the ratio of the anti-CD19 and anti-CD20 antibody can be a ratio of about 1000:1, 500:1, 250:1, 100:1, 90:1, 80:1, 70:1, 60;1, 50:1, 40:1, 30:1. 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90. 1:100, 1:250, 1:500 or 1:1000 or more. Likewise, the ratio of the anti-CD19 and anti-CD22 antibody can be a ratio of about 1000:1, 500:1, 250:1, 100:1, 90:1, 80:1, 70:1, 60;1, 50:1, 40:1, 30:1. 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90. 1:100, 1:250, 1:500 or 1:1000 or more. Similarly, the ratio of the anti-CD19 and anti-CD52 antibody can be a ratio of about 1000:1, 500:1, 250:1, 100:1, 90:1, 80:1, 70:1, 60;1, 50:1, 40:1, 30:1. 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90. 1:100, 1:250, 1:500 or 1:1000 or more.

5.30. Combination Compounds that Enhance Monocyte or Macrophage Function

In certain embodiments of methods of the invention, a compound that enhances monocyte or macrophage function (e.g., at least about 25%, 50%, 75%, 85%, 90%, 95% or more) can be used in conjunction with an anti-CD19 immunotherapy. Such compounds are known in the art and include, without limitation, cytokines such as interleukins (e.g., IL-12), and interferons (e.g., alpha or gamma interferon).

The compound that enhances monocyte or macrophage function or enhancement can be formulated in the same pharmaceutical composition as the antibody, immunoconjugate or antigen-binding fragment. When administered separately, the antibody/fragment and the compound can be administered concurrently (within a period of hours of each other), can be administered during the same course of therapy, or can be administered sequentially (i.e., the patient first receives a course of the antibody/fragment treatment and then a course of the compound that enhances macrophage/monocyte function or vice versa). In such embodiments, the compound that enhances monocyte or macrophage function is administered to the human subject prior to, concurrently with, or following treatment with other therapeutic regimens and/or compositions of the invention. In one embodiment, the human subject has a blood leukocyte, monocyte, neutrophil, lymphocyte, and/or basophil count that is within the normal range for humans. Normal ranges for human blood leukocytes (total) is about 3.5- about 10.5 ($10^9$/L). Normal ranges for human blood neutrophils is about 1.7- about 7.0 ($10^9$/L), monocytes is about 0.3- about 0.9 ($10^9$/L), lymphocytes is about 0.9- about 2.9 ($10^9$/L), basophils is about 0- about 0.3 ($10^9$/L), and eosinophils is about 0.05- about 0.5 ($10^9$/L). In other embodiments, the human subject has a blood leukocyte count that is less than the normal range for humans, for example at least about 0.01, 0.05, 0.1, 0.2, 0.3, 0.4, 0.5, 0.6, 0.7, or 0.8 ($10^9$/L) leukocytes.

This embodiment of the invention can be practiced with the antibodies, immunoconjugates or antibody fragments of the invention or with other antibodies known in the art and is particularly suitable for subjects that are resistant to anti-CD22, anti-CD52 and/or anti-CD20 antibody therapy (for example, therapy with existing antibodies such as C2B8), subjects that are currently being or have previously been treated with chemotherapy, subjects that have had a relapse in a B cell disorder, subjects that are immunocompromised, or subjects that otherwise have an impairment in macrophage or monocyte function. The prevalence of patients that are resistant to therapy or have a relapse in a B cell disorder may be attributable, at least in part, to an impairment in macrophage or monocyte function. Thus, the invention provides methods of enhancing ADCC and/or macrophage and/or monocyte function to be used in conjunction with the methods of administering anti-CD19 antibodies and antigen-binding fragments.

5.31. Combination with Immunoregulatory Agents

An anti-CD19 immunotherapy of the invention may also be in conjunction with an immunoregulatory agent. In this approach, a chimeric, human or humanized anti-CD19 antibody can be used. The term "immunoregulatory agent" as used herein for combination therapy refers to substances that act to suppress, mask, or enhance the immune system of the host. This would include substances that suppress cytokine production, downregulate or suppress self-antigen expression, or mask the MHC antigens. Examples of such agents include 2-amino-6-aryl-5-substituted pyrimidines (see, U.S. Pat. No. 4,665,077), azathioprine (or cyclophosphamide, if there is an adverse reaction to azathioprine); bromocryptine; glutaraldehyde (which masks the MHC antigens, as described in U.S. Pat. No. 4,120,649); anti-idiotypic antibodies for MHC antigens and MHC fragments; cyclosporin A; steroids such as glucocorticosteroids, e.g., prednisone, methylprednisolone, and dexamethasone; cytokine or cytokine receptor antagonists including anti-interferon-γ, -β, or -α antibodies; anti-tumor necrosis factor-α antibodies; anti-tumor necrosis factor-β antibodies; anti-interleukin-2 antibodies and anti-IL-2 receptor antibodies; anti-L3T4 antibodies; heterologous anti-lymphocyte globulin; pan-T antibodies, for example anti-CD3 or anti-CD4/CD4a antibodies; soluble peptide containing a LFA-3 binding domain (WO 90/08187 published Jul. 26, 1990); streptokinase; TGF-β; streptodornase; RNA or DNA from the host; FK506; RS-61443; deoxyspergualin; rapamycin; T-cell receptor (U.S. Pat. No. 5,114, 721); T-cell receptor fragments (Offner et al., Science 251: 430-432 (1991); WO 90/11294; and WO 91/01133); and T-cell receptor antibodies (EP 340,109) such as T10B9. Examples of cytokines include, but are not limited to lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α; mullerian-inhibiting substance; mouse gonadotropin-associated peptide; inhibin; activin; vascular endothelial growth factor; integrin; thrombopoietin (TPO); nerve growth factors such as NGF-α; platelet-growth factor; transforming growth factors (TGFs) such as TGF-α and TGF-α; insulin-like growth factor-I and -II; erythropoietin (EPO); osteoinductive factors; interferons; colony stimulating factors (CSFs) such as macrophage-CSF (M-CSF); granulocyte-macrophage-CgP (GM-CSP); and granulocyte-CSF (G-CSF); interleukins (ILs) such as IL-1, IL-1a, IL-2, IL-3, IL-4, IL-5, IL-6, IL-7, IL-8, IL-9, IL-1 I, IL-12, IL-15; a tumor necrosis factor such as TNF-α or TNF-13; and other polypeptide factors including LIF and kit ligand (KL). As used herein, the term cytokine includes proteins from natural sources or from recombinant cell culture and biologically active equivalents of the native sequence cytokines. In certain embodiments, the methods further include administering to the subject one or more immunomodulatory agents, for example a cytokine Suitable cytokines may be selected from the group consisting of interleukin-1 (IL-1), IL-2, IL-3, IL-12, IL-15, IL-18, G-CSF, GM-CSF, thrombopoietin, and γ interferon.

These immunoregulatory agents are administered at the same time or at separate times from anti-CD19 antibodies. The preferred immunoregulatory agent will depend on many factors, including the type of disorder being treated, as well as the patient's history, but the agent frequently may be selected from cyclosporin A, a glucocorticosteroid (for example prednisone or methylprednisolone), OKT-3 monoclonal antibody, azathioprine, bromocryptine, heterologous anti-lymphocyte globulin, or a mixture thereof.

5.32. Combination with Other Therapeutic Agents

Agents that act on the tumor neovasculature can also be used in conjunction with anti-CD19 immunotherapy and include tubulin-binding agents such as combrestatin A4 (Griggs et al., Lancet Oncol. 2:82, (2001)) and angiostatin and endostatin (reviewed in Rosen, Oncologist 5:20 (2000), incorporated by reference herein). Immunomodulators suitable for use in combination with anti-CD19 antibodies include, but are not limited to, of α-interferon, γ-interferon, and tumor necrosis factor alpha (TNFα). In certain embodiments, the therapeutic agents used in combination therapies using compositions and methods of the invention are peptides.

In certain embodiments, an anti-CD19 immunotherapy is in conjunction with one or more calicheamicin molecules. The calicheamicin family of antibiotics are capable of producing double-stranded DNA breaks at sub-picomolar concentrations. Structural analogues of calicheamicin which may be used include, but are not limited to, $\gamma 1^I$, $\gamma 2^I$, $\gamma 3^I$, N-acetyl-$\gamma 1^I$, PSAG and 011 Hinman et al., Cancer Research 53:3336-3342 (1993) and Lode et al., Cancer Research 58: 2925-2928 (1998)).

A fusion protein comprising an anti-CD19 antibody and a cytotoxic agent may also be made, e.g., by recombinant techniques or peptide synthesis.

In yet another embodiment, an anti-CD19 antibody may be conjugated to a "receptor" (such as streptavidin) for utilization in tumor pretargeting wherein the antagonist-receptor conjugate is administered to the patient, followed by removal of unbound conjugate from the circulation using a clearing agent and then administration of a "ligand" (e.g., avidin) which is conjugated to a therapeutic agent (e.g., a radionucleotide).

In certain embodiments, a treatment regimen includes compounds that mitigate the cytotoxic effects of an anti-CD19 antibody composition. Such compounds include analgesics (e.g., acetaminophen), bisphosphonates, antihistamines (e.g., chlorpheniramine maleate), and steroids (e.g., dexamethasone, retinoids, deltoids, betamethasone, cortisol, cortisone, prednisone, dehydrotestosterone, glucocorticoids, mineralocorticoids, estrogen, testosterone, progestins).

In certain embodiments, the therapeutic agent used in combination with an anti-CD19 immunotherapy is a small molecule (i.e., inorganic or organic compounds having a molecular weight of less than about 2500 daltons). For example, libraries of small molecules may be commercially obtained from Specs and BioSpecs B. V. (Rijswijk, The Netherlands), Chembridge Corporation (San Diego, Calif.), Comgenex USA Inc. (Princeton, N.J.), and Maybridge Chemicals Ltd. (Cornwall PL34 OHW, United Kingdom).

In certain embodiments an anti-CD19 immunotherapy can be administered in combination with an anti-bacterial agent. Non-limiting examples of anti-bacterial agents include proteins, polypeptides, peptides, fusion proteins, antibodies, nucleic acid molecules, organic molecules, inorganic molecules, and small molecules that inhibit and/or reduce a bacterial infection, inhibit and/or reduce the replication of bacteria, or inhibit and/or reduce the spread of bacteria to other cells or subjects. Specific examples of anti-bacterial agents include, but are not limited to, antibiotics such as penicillin, cephalosporin, imipenem, axtreonam, vancomycin, cycloserine, bacitracin, chloramphenicol, erythromycin, clindamycin, tetracycline, streptomycin, tobramycin, gentamicin, amikacin, kanamycin, neomycin, spectinomycin, trimethoprim, norfloxacin, rifampin, polymyxin, amphotericin B, nystatin, ketocanazole, isoniazid, metronidazole, and pentamidine.

In certain embodiments an anti-CD19 immunotherapy can be administered in combination with an anti-fungal agent. Specific examples of anti-fungal agents include, but are not limited to, azole drugs (e.g., miconazole, ketoconazole (NIZORAL®), caspofungin acetate (CANCIDAS®), imidazole, triazoles (e.g., fluconazole (DIFLUCAN®)), and itraconazole))(SPORANOX®)), polyene (e.g., nystatin, amphotericin B)(FUNGIZONE®), amphotericin B lipid complex ("ABLC"))(ABELCET®), amphotericin B colloidal dispersion ("ABCD"))(AMPHOTEC®), liposomal amphotericin B (AMBISONE®), potassium iodide (KI), pyrimidine (e.g., flucytosine)(ANCOBON®), and voriconazole))(VFEND®). Administration of anti bacterial and anti-fungal agents can mitigate the effects or escalation of infectious disease that may occur in methods of the invention where a patient's B cells are significantly depleted.

In certain embodiments of the invention, an anti-CD19 immunotherapy can be administered in combination with one or more of the agents described above to mitigate the toxic side effects that may accompany administration of compositions of the invention. In other embodiments, an anti-CD19 immunotherapy can be administered in combination with one or more agents that are well known in the art for use in mitigating the side effects of antibody administration, chemotherapy, toxins, or drugs.

In certain embodiments of the invention where an anti-CD19 immunotherapy is administered to treat multiple myeloma, compositions of the invention may be administered in combination with or in treatment regimens with high-dose chemotherapy (melphalan, melphalan/prednisone (MP), vincristine/doxorubicin/dexamethasone (VAD), liposomal doxorubicin/vincristine, dexamethasone (DVd), cyclophosphamide, etoposide/dexamethasone/cytarabine, cisplatin (EDAP)), stem cell transplants (e.g., autologous stem cell transplantation or allogeneic stem cell transplantation, and/or mini-allogeneic (non-myeloablative) stem cell transplantation), radiation therapy, steroids (e.g., corticosteroids, dexamethasone, thalidomide/dexamethasone, prednisone, melphalan/prednisone), supportive therapy (e.g., bisphosphonates, growth factors, antibiotics, intravenous immunoglobulin, low-dose radiotherapy, and/or orthopedic interventions), THALOMID™ (thalidomide, Celgene), and/or VELCADE™ (bortezomib, Millennium).

In embodiments of the invention where an anti-CD19 immunotherapy is administered in combination with another antibody or antibodies and/or agent, the additional antibody or antibodies and/or agents can be administered in any sequence relative to the administration of the antibody of this invention. For example, the additional antibody or antibodies can be administered before, concurrently with, and/or subsequent to administration of an anti-CD19 antibody or immunoconjugate to the human subject. The additional antibody or antibodies can be present in the same pharmaceutical composition as an antibody of the invention, and/or present in a different pharmaceutical composition. The dose and mode of administration of an antibody of this invention and the dose of the additional antibody or antibodies can be the same or different, in accordance with any of the teachings of dosage amounts and modes of administration as provided in this application and as are well known in the art.

5.33. Use of Anti-CD19 Antibodies in Diagnosing B Cell Malignancies

The present invention also encompasses anti-CD19 antibodies, and compositions thereof, that immunospecifically bind to the human CD19 antigen, which anti-CD19 antibodies are conjugated to a diagnostic or detectable agent. In certain embodiments, the antibodies are human or humanized anti-CD19 antibodies. Such anti-CD19 antibodies can be useful for monitoring or prognosing the development or progression of a B cell malignancy as part of a clinical testing procedure, such as determining the efficacy of a particular therapy. Such diagnosis and detection can be accomplished by coupling an anti-CD19 antibody that immunospecifically binds to the human CD19 antigen to a detectable substance including, but not limited to, various enzymes, such as but not limited to, horseradish peroxidase, alkaline phosphatase, beta-galactosidase, or acetylcholinesterase; prosthetic groups, such as but not limited to, streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I, carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, noradioactive paramagnetic metal ions, and molecules that are radiolabelled or conjugated to specific radioisotopes. Any detectable label that can be readily measured can be conjugated to an anti-CD19 antibody and used in diagnosing B cell malignancies. The detectable substance may be coupled or conjugated either directly to an antibody or indirectly, through an intermediate (such as, for example, a linker known in the art) using techniques known in the art. See, e.g., U.S. Pat. No. 4,741,900 for metal ions which can be conjugated to antibodies for use as a diagnostics according to the present invention. In certain embodiments, the invention provides for diagnostic kits comprising an anti-CD19 antibody conjugated to a diagnostic or detectable agent.

5.34. Use of Anti-CD19 Antibodies in Monitoring Immune Reconstitution

The present invention also encompasses anti-CD19 antibodies, and compositions thereof, that immunospecifically bind to the human CD19 antigen, which anti-CD19 antibodies are conjugated to a diagnostic or detectable agent. In certain embodiments, the antibodies are human or humanized anti-CD19 antibodies. Such anti-CD19antibodies can be useful for monitoring immune system reconstitution following immunosuppressive therapy or bone marrow transplantation. Such monitoring can be accomplished by coupling an anti-CD19 antibody that immunospecifically binds to the human CD19 antigen to a detectable substance including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as, but not limited to, luciferase, luciferin, and aequorin; radioactive materials, such as, but not limited to, iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, 149Pm, $^{140}$La, $^{175}$Yb, $^{166}$Ho, $^{90}$Y, $^{47}$Sc $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron-emitting metals using various positron-emission tomographies, noradioactive paramagnetic metal ions, and molecules that are radiolabelled or conjugated to specific radioisotopes. Any detectable label that can be readily measured can be conjugated to an anti-CD19 antibody and used in diagnosing an autoimmune disease or disorder. The detectable substance may be coupled or conjugated either directly to an antibody or indirectly, through an intermediate (such as, for example, a linker known in the art) using techniques known in the art. See, e.g., U.S. Pat. No. 4,741,900 for metal ions which can be conjugated to antibodies for use as a diagnostics according to the present invention. In certain embodiments, the invention provides for diagnostic kits comprising an anti-CD19 antibody conjugated to a diagnostic or detectable agent.

5.35. Use of Anti-CD19 Antibodies in Diagnosing Autoimmune Diseases or Disorders The present invention also encompasses anti-CD19 antibodies, and compositions thereof, that immunospecifically bind to the human CD19 antigen, which anti-CD19 antibodies are conjugated to a diagnostic or detectable agent. In certain embodiments, the antibodies are human or humanized anti-CD19 antibodies. Such anti-CD19 antibodies can be useful for monitoring or prognosing the development or progression of an autoimmune disease or disorder as part of a clinical testing procedure, such as determining the efficacy of a particular therapy. Such diagnosis and detection can be accomplished by coupling an anti-CD19 antibody that immunospecifically binds to the human CD19 antigen to a detectable substance including, but not limited to, various enzymes, such as but not limited to, horseradish peroxidase, alkaline phosphatase, beta-galactosidase, or acetylcholinesterase; prosthetic groups, such as but not limited to, streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, noradioactive paramagnetic metal ions, and molecules that are radiolabelled or conjugated to specific radioisotopes. Any detectable label that can be readily measured can be conjugated to an anti-CD19 antibody and used in diagnosing an autoimmune disease or disorder. The detectable substance may be coupled or conjugated either directly to an antibody or indirectly, through an intermediate (such as, for example, a linker known in the art) using techniques known in the art. See, e.g., U.S. Pat. No. 4,741,900 for metal ions which can be conjugated to antibodies for use as a diagnostics according to the present invention. In certain embodiments, the invention provides for diagnostic kits comprising an anti-CD19 antibody conjugated to a diagnostic or detectable agent.

5.36. Kits

The invention provides a pharmaceutical pack or kit comprising one or more containers filled with a composition of the invention for the prevention, treatment, management or amelioration of a B cell malignancy, or one or more symptoms thereof, potentiated by or potentiating a B cell malignancy.

The present invention provides kits that can be used in the above-described methods. In one embodiment, a kit comprises a composition of the invention, in one or more containers. In another embodiment, a kit comprises a composition of the invention, in one or more containers, and one or more other prophylactic or therapeutic agents useful for the prevention, management or treatment of a B cell malignancy, or one or more symptoms thereof, potentiated by or potentiating a B cell malignancy in one or more other containers. The kit may further comprise instructions for preventing, treating, managing or ameliorating a B cell malignancy, as well as side effects and dosage information for method of administration. Optionally associated with such container(s) can be a notice in the form prescribed by a governmental agency regulating the manufacture, use or sale of pharmaceuticals or biological products, which notice reflects approval by the agency of manufacture, use or sale for human administration.

6. SPECIFIC EMBODIMENTS

1. A chimeric, humanized, or human monoclonal antibody or fragment thereof that binds a human CD19 antigen.

2. The antibody of embodiment 1 comprising at least one CDR comprising an amino acid sequence selected from the group consisting of: SEQ ID NO: 6, 8, 10, 12, 14, 16, 22, 24, 26, 28, 30, 32, 114, 115, 116, 117, 118, 119, 120, 121, 122, 123, 124, 125, 126, and 127.

3. The antibody of embodiment 1 comprising at least one framework region of the HB12B-(A10-Jk4), HB12B-3649, or HB12B-364987 light chain variable regions.

4. The antibody of embodiment 1 comprising at least one framework region of the HB12B-(3-72\JH4) or HB12B-9m heavy chain variable regions.

5. The antibody of embodiment 1 comprising at least one heavy chain polypeptide comprising the amino acid sequence selected from the group consisting of: SEQ ID NO: 2, 18, 34, 44, 102, 103, 104, 105, 106, 107, 108, and 109.

6. The antibody of embodiment 1 comprising at least one light chain polypeptide comprising an amino acid sequence selected from the group consisting of: SEQ ID NO: 4, 20, 52, 62, 68, 70, 110, 111, 112, and 113.

7. The antibody of embodiment 5 further comprising at least one light chain CDR comprising the amino acid sequence selected from the group consisting of: SEQ ID NO: 12, 14, 16, 28, 30, 32, 123, 124, 125, 126, and 127.

8. The antibody of embodiment 3 further comprising at least one heavy chain CDR comprising the amino acid sequence selected from the group consisting of: SEQ ID NO: 6, 8, 10, 22, 24, 26, 114, 115, 116, 117, 118, 119, 120, 121, and 122.

9. The antibody of embodiment 1 comprising at least one heavy chain polypeptide comprising the amino acid sequence selected from the group consisting of: SEQ ID NO: 2, 18, 34, 44, 102, 103, 104, 105, 106, 107, 108, and 109, and at least one light chain polypeptide comprising an amino acid sequence selected from the group consisting of: SEQ ID NO: 4, 20, 52, 62, 68, 70, 110, 111, 112, and 113.

10. The antibody of embodiment 1 comprising at least one light chain polypeptide and at least one heavy chain polypeptide wherein said light chain polypeptide comprises an amino acid sequence selected from the group consisting of: HB12A VK (SEQ ID NO: 4); and HB12B VK (SEQ ID NO:20), and wherein said heavy chain polypeptide comprises an amino acid sequence selected from the group consisting of: HB12A VH (SEQ ID NO: 2); and HB12B VH (SEQ ID NO:18).

11. The antibody of embodiment 1 comprising the HB12B-(3-72\JH4) heavy chain variable region and the HB12B-3649 light chain variable region.

12. The antibody of embodiment 1 comprising a VH and a VK, wherein said VH comprises the amino acid sequence of SEQ ID NO: 106, and wherein said VK comprises the amino acid sequence of SEQ ID NO: 111.

13. A nucleic acid encoding a polypeptide comprising an amino acid sequence selected from the group consisting of: SEQ ID NO: 2, 18, 34, 36, 38, 40, 42, 44, 102, 103, 104, 105, 106, 107, 108, and 109.

14. A nucleic acid encoding a polypeptide comprising an amino acid sequence selected from the group consisting of: SEQ ID NO: 4, 20, 52, 62, 64, 66, 68, 70, 110, 111, 112, and 113.

15. A vector comprising the nucleic acid of embodiment 13 and/or 14.

16. An isolated cell comprising the vector of embodiment 15.

17. An isolated cell expressing the antibody as in any of embodiments 1-12.

18. A method of producing an antibody comprising culturing the isolated cell of embodiment 17 under conditions sufficient for the production of the antibody and recovering the antibody from the culture.

19. A pharmaceutical composition comprising the antibody as in any of embodiments 1-12 in a pharmaceutically-acceptable carrier.

20. The pharmaceutical composition of embodiment 19, wherein the antibody is of the IgG1, IgG2, IgG3, or IgG4 human isotype.

21. A method of treating a B cell malignancy in a human comprising administering to a human in need thereof a therapeutically-effective amount of the antibody as in any of embodiments 1-12.

22. A method of treating an autoimmune disease or disorder in a human, comprising administering to a human in need thereof a therapeutically-effective amount of the antibody as in any of embodiments 1-12.

23. A method of treating or preventing humoral rejection in a human transplant patient, comprising administering to a human in need thereof a therapeutically-effective amount of the antibody as in any of embodiments 1-12.

24. The antibody as in any of embodiments 1-12, wherein said antibody depletes B cells with the same efficiency as that of the murine monoclonal HB12B antibody.

25. The antibody as in any of embodiments 1-12, wherein said antibody induces B cell apoptosis.

26. The antibody as in any of embodiments 1-12, wherein said antibody has complex N-glycoside-linked sugar chains bound to the Fc region in which fucose is not bound to N-acetylglucosamine in the reducing end in the sugar chain.

27. The antibody as in any of embodiments 1-12, wherein said antibody is an Fc variant antibody wherein said Fc variant comprises mutations that result in enhanced ADCC activity.

28. A method of depleting B cells in a human patient comprising administering to a human in need thereof a therapeutically-effective amount of the antibody as in any of embodiments 24-27.

29. The antibody as in any of embodiments 1-12, wherein said antibody is an Fc variant antibody wherein said Fc variant has an affinity for the Fc receptor FcγRIIIA that is at least about 5 fold lower than that of a comparable molecule, wherein said Fc variant has an affinity for the Fc receptor FcγRIIB that is within about 2 fold of that of a comparable molecule.

30. A method of depleting B cells in a human patient comprising administering to a human in need thereof a therapeutically-effective amount of the antibody of embodiment 29.

7. EXAMPLES

7.1. Construction, Expression and Binding Characteristics of Humanized Anti-CDK19 Antibodies The following sections describe the design and construction of a chimeric variant of the parental HB12B antibody (chHB12B) in which the mouse heavy chain and light chain constant regions have been replaced with human IgHγ1 and human IgLκ regions, respectively. These sections also describe strategies for generation of humanized variants of HB12B heavy and light chain variable regions.

The CD19-binding activity of antibodies produced from various combinations of (chimeric or humanized) heavy and light chain variable regions is also described. For example, humanized forms of HB12B which exhibit a CD19 binding profile comparable to that of chHB12B are described.

The sections below also describe several mutations in the human framework regions that, when introduced into certain humanized anti-CD19 antibodies, result in human CD19 binding comparable to that of the reference antibody, chHB12B comprising HB12B VH and HB12B VK. In the VK these residues comprise, for example, the Vernier residues F36 and H49 and Interchain residue F87.

7.1.1. Gene Assembly and Expression Cloning

Constructs were generated by a PCR-based gene assembly method first described by Stemmer (Stemmer, W. P. et al. 1995 *Gene,* 164:49-53). This method consists of four steps: oligonucleotide synthesis; gene assembly; gene amplification and cloning Eight gene specific primers were synthesized for each VH and VK segments. Representative primer sets for the assembly of the HB12B-(3-72/JH4) VH region and the HB12B-(A10-Jk4) VK are shown in Table 3; primer sets for variant VH and VK regions comprising specific amino acid substitutions were generated by modifying the nucleic acid sequence of the primer encoding the given amino acid residue. Primers were designed to overlap by 15-20 nucleotides and were ligated into a complete variable region during thermal cycling. In case of VH, an additional vector specific primer (Universal VH FW in Table 3.) was included in the PCR mediated gene assembly process. The external 5' and 3' primers for VH region incorporated a unique recognition site for the XbaI and ApaI restriction endonuclease, respectively, to help with the subsequent cloning steps. The external 5' and 3' primers for VK incorporated a unique recognition site for the XmaI and BsiWI restriction endonuclease, respectively, to help with the subsequent cloning steps. PCR products of the correct size were restriction digested and ligated in frame into an expression vector wherein VH regions were digested with XbaI and ApaI, and VK regions were digested with XmaI and BsiWI according to the manufacturer's instructions. The vector used for heavy chain assembly comprises eukaryotic transcription control elements operably linked to a polynucleotide encoding the MGDNDIHFAFLSTGVHS VH leader (SEQ ID NO:83) and a human IgHγ1 constant region wherein said transcription control elements comprise a CMV immediate early promoter and a SV40 poly A addition signal. The use of appropriately designed primers for VH assembly ensured that the polynucleotide sequences encoding the VH leader, VH region and IgHγ1 constant region were joined in frame within the final heavy chain expression vector. The vector for light chain assembly comprises eukaryotic transcription control elements operably linked to a polynucleotide encoding the human VKI-L12 leader (amino acid sequence MDMRVPAQLLGLLLLWLPGAKC (SEQ ID NO:84); Bentley, D. L. & Rabbitts, T. H., Nature 288, 730-733 (1980)) and a human IgLκ constant region wherein said transcription control elements comprise a CMV immediate early promoter and a SV40 poly A addition signal. The use of appropriately designed primers for VK assembly ensured that the polynucleotide sequences encoding the VKI-L12 leader, VK region and IgLκ constant region were joined in frame within the final light chain expression vector. The ligation product was used to transform DH10B competent E. coli cells according to the manufacturer's protocols. Colonies containing the plasmid and a correct sized insert can be identified using various methods known in the art (e.g. restriction digest of vector DNA preparation, PCR amplification of vector sequences). Plasmid clones with correct sized insert were sequenced using dideoxy sequencing reaction (e.g., Big-Dye® Terminator v3.0 Cycle Sequencing Ready Reaction Kit, ABI). Plasmid DNA was prepared from selected clones using the QIAGEN Mini and Maxi Plasmid Kit according to the manufacturer's protocols.

Pairs of DNA plasmid expression vector preparations encoding a humanized or chimeric immunoglobulin heavy chain and a humanized or chimeric immunoglobulin light chain were used to co-transfect HEK293 cells. These co-transfected HEK293 cells were cultured for three days to yield antibody-containing conditioned medium suitable for determining total IgG concentrations and CD19 binding activity.

Total Ig concentrations in the HEK293 cell supernatant were quantified using a capture ELISA assay. IgG molecules were captured on a 96-well plate via an immobilized goat anti-human IgG H+L specific antibody, and detected with an HRP conjugated anti-human kappa light chain antibody. The assay was calibrated using a reference IgG1 mAb of irrelevant specificity.

TABLE 3

Representative primer sets for HB12B-(3-72/JH4) VH region and the HB12B-(A10-Jk4) VK region assembly. Gene specific nucleotides are printed in upper case, vector specific nucleotides are printed in lower case. Recognition sites for restriction endonucleases used for VH and VK fragment cloning are underlined.

| | |
|---|---|
| Universal VH FW | tatatatatctagacatatatatgggtgacaatgacatccactttgcctttctctcc (SEQ ID NO: 85) |
| HB12B-(3-72/JH4) FW1 | tccactttgcctttctctccacaggtgtccactccGAGGTGCAGCTGGTGGAGTCTGGGG GAGGCTTGGTCCAGCCTGGAGGGTCCCTG (SEQ ID NO: 86) |
| HB12B-(3-72/JH4) RE2 | GTTCATCCAAGAGCTACTGAAGGTGAATCCAGAGGCTGCACAGGA GAGTCTCAGGGACCCTCCAGGC (SEQ ID NO: 87) |
| HB12B-(3-72/JH4) FW3 | AGCTCTTGGATGAACTGGGTCCGCCAGGCTCCAGGGAAGGGGCTG GAGTGGGTTGGCCGGATTTATCCTGGAG (SEQ ID NO: 88) |
| HB12B-(3-72/JH4) RE4 | GCCCTTGAACTTCCCATTGTAGTTAGTATCTCCATCTCCAGGATAA ATCCGGCCAACCCACTCCA (SEQ ID NO: 89) |
| HB12B-(3-72/JH4) FW5 | GGAAGTTCAAGGGCAGATTCACCATCTCAAGAGATGATTCAAAGA ACTCACTGTATCTGCAAATGAACAG (SEQ ID NO: 90) |
| HB12B-(3-72/JH4) RE6 | AATCCTGATCTAGCACAGTAATACACGGCCGTGTCCTCGGTTTTCA GGCTGTTCATTTGCAGATACAG (SEQ ID NO: 91) |
| HB12B-(3-72/JH4) FW7 | GTGTATTACTGTGCTAGATCAGGATTTATTACTACGGTTTTAGACT TTGACTACTGGG (SEQ ID NO: 92) |
| HB12B-(3-72/JH4) RE8 | tatatagggcccttggtggaggcTGAGGAGACGGTGACCAGGGTTCCTTGGCC CCAGTAGTCAAAGTCTAAA (SEQ ID NO: 93) |
| HB12B-(A10-Jk4) FW1 | tatatacccgggggccaaatgtGAAATTGTGCTGACTCAGTCTCCAGACTTC AGTCTGTG (SEQ ID NO: 94) |
| HB12B-(A10-Jk4) RE2 | CAACACTTTCGCTGGCTCTGCAGGTGATGGTGACTTTCTCCTTTGG AGTCACAGACTGAAAGTCTGG (SEQ ID NO: 95) |

TABLE 3-continued

Representative primer sets for HB12B-(3-72/JH4) VH region and
the HB12B-(A10-Jk4) VK region assembly. Gene specific nucleotides
are printed in upper case, vector specific nucleotides are printed
in lower case. Recognition sites for restriction endonucleases
used for VH and VK fragment cloning are underlined.

| | |
|---|---|
| HB12B-(A10-Jk4) FW3 | GCCAGCGAAAGTGTTGATACTTTTGGCATTAGTTTTATGAACTGGT ACCAGCAGAAACCAGATCAGTC (SEQ ID NO: 96) |
| HB12B-(A10-Jk4) RE4 | CGAGGGGACCCCGGATCCTTGATTGGATGCAGCCTTGATGAGGAG CTTTGGAGACTGATCTGGTTTC (SEQ ID NO: 97) |
| HB12B-(A10-Jk4) FW5 | GATCCGGGGTCCCCTCGAGGTTCAGTGGCAGTGGATCTGGGACAG ATTTCACCCTCACCATCAATAGC (SEQ ID NO: 98) |
| HB12B-(A10-Jk4) RE6 | GAACCTCCTTACTTTGCTGACAGTAATACGTTGCAGCATCTTCAGC TTCCAGGCTATTGATGGTGAGG (SEQ ID NO: 99) |
| HB12B-(A10-Jk4) FW7 | GCAAAGTAAGGAGGTTCCATTCACGTTCGGCGGAGGGACCAAGGT GGAGATCAAA (SEQ ID NO: 100) |
| HB12B-(A10-Jk4) RE8 | tatatatacgtacgTTTGATCTCCACCTTGGTCCCTCCGCCGA (SEQ ID NO: 101) |

7.1.2. The 300B4-CD19 Binding Assay

CD19 binding activity was assessed using a cell-based recombinant human CD19 ELISA assay wherein said assay was performed using equivalent concentrations of each humanized or chimeric antibody, thereby facilitating direct comparisons between alternative humanized versions of the HB12B antibody and chHB12B.

The ability of chHB12B and its humanized variants to bind hCD19 was assessed in a cell based CD19 binding assay utilizing 300B4 cells expressing recombinant cell-surface human CD19 as a capture agent. 300B4 cells were cultured according to standard protocols in RPMI 1640 medium containing L-glutamine and supplemented with 10% Fetal Calf Serum, β-mercaptoethanol in the presence of 1 mg/ml G418. A standard ELISA protocol can be used for the cell based CD19 binding assay. For example, individual wells of a 96 well U bottom plate are seeded with 1×10e5 300B4 cells and incubated overnight. Cells are washed once with ELISA buffer prior to incubation on ice with human, humanized, or chimeric HB12B antibodies. Binding reactions are performed in triplicates for each antibody concentration tested. Negative control wells using an isotype matched antibody of irrelevant specificity should be included in the assay. Following incubation with the antibody 300B4 cells are washed three times with 200 micro liter of ELISA buffer. The amount of chimeric, humanized, or human anti-CD19 antibodies bound to 300B4 cells can be detected using a goat anti-human kappa antibody conjugated with horseradish peroxidase according to standard protocols.

7.1.3. Construction, Expression and Binding Characteristics of chHB12B

An expression vector encoding the chHB12B heavy chain comprising the murine HB12B VH and the human IgHγ1 constant regions was constructed according to the methods described in Section 6.1. An expression vector encoding the chHB12B light chain comprising the murine HB12B VK and the human IgLκ constant regions was constructed according to the methods described in Section 6.1.

HEK293 cells were co-transfected simultaneously with the expression vectors encoding chHB12B heavy and light chains. These transfected cells were cultured for three days to allow for antibody production. The culture medium containing soluble, secreted chHB12b antibody was harvested, and the concentration of chHB12B antibody was determined according to the method described in Section 6.1.

chHB12B binding to human CD19 was assessed using the 300B4 cell based ELISA assay described in Section 6.2. An isotype matched human antibody of irrelevant specificity was included in the assay as a negative control. Results obtained using the cell based ELISA assay showed that for concentrations of antibody above 100 ng/ml, there was a significant binding of chimeric antibody to recombinant human CD19 expressed on the surface of 300B4 cells, indicating that the chHB12B has retained hCD19 binding activity (FIG. 2).

7.1.4. Construction of Humanized HB12B VH Encoding Expression Vectors

The following sections describe the design of humanized variants of the HB12B VH region comprising the murine HB12B CDR regions and a suitable human, or substantially human framework regions. These sections also describe strategies for generation of variants of humanized HB12B Ig heavy chains.

7.1.4.1. Identification of Human Heavy Chain Acceptor Framework Regions

An amino acid sequence database containing the framework residues of all human germline immunoglobulin heavy chain V, D, and J regions were compiled. The necessary information can be obtained from a variety of sources, e.g. V Base: the database of human antibody genes (http://vbase.mrc-cpe.cam.ac.uk/). The database was queried for human germline V and J segments that display sequence similarity with the corresponding framework regions of the murine HB12b VH at key residues, e.g. canonical, interchain and Vernier residues.

The human germline V3-72 (Tomlinson, I. M. et al., *J. Mol. Biol.*, 227:776-798 (1992)) and JH4 (Ravetch, J. V. et al., *Cell* 27: 583-591 (1981)) segments were selected to serve as the acceptor framework for the humanization of the HB12B murine anti-CD19 antibody.

7.1.4.2. Generation of Humanized HB12B Heavy Chains

HB12B-(3-72/JH4) VH (SEQ ID NO:34) was designed by combining the CDRs of HB12B VH with the framework residues of human germline V3-72/JH4 regions. An expression vector comprising HB12B-(3-72/JH4) VH was generated according to the methods described in Section 6.1.

HB12B-9m VH (SEQ ID NO:44) is a variant of HB12B-(3-72/JH4) VH comprising the following nine amino acid substitutions: L20I, F27Y, T28A, R38I, V49I, F67A, R71A, L80M, I91Y (residues numbered according to Kabat). Gene specific primers for HB12B-9m were designed as described in Section 6.1. An expression vector comprising HB12B-9m VH was generated according to the methods described in Section 6.1.

7.1.5. Construction of Humanized HB12B Ig Light Chain Encoding Expression Vectors The following sections describe the design of humanized variants of the HB12B VK region comprising murine HB12B CDR regions and suitable human, or substantially human framework regions. These sections also describe strategies for generation of variants of humanized HB12B Ig light chain.

7.1.5.1. Identification of Human Light Chain Acceptor Framework Regions

An amino acid sequence database containing the framework residues of all human germline immunoglobulin light chain V and J regions were compiled. The necessary information can be obtained from a variety of sources, e.g. V Base: the database of human antibody genes (http://vbase.mrc-cpe.cam.ac.uk/). The database was queried for human germline V and J segments that display sequence similarity with the corresponding framework regions of the murine HB12B VK at key residues, e.g. canonical, interchain and Vernier residues.

The human germline Vk A10 (Straubinger, B. et al., *Biol. Chem. Hoppe-Seyler* 369:601-607 (1988)) and Jk4 (Hieter, P. A. et al., *J. Biol. Chem.* 257:1516-1522 (1982)) segments were selected to serve as the acceptor framework for the humanization of the HB12B murine anti-CD19 antibody.

7.1.5.2. Generation of Humanized HB12B Light Chains

HB12B-(A10-Jk4) VK (SEQ ID NO:52) was designed by combining the HB12B VK CDRs with the framework residues of human germline A-10/Jk4 regions. An expression vector comprising HB12B-(A10-Jk4) VK was generated according to the methods described in Section 6.1.

HB12B-364987 VK (SEQ ID NO:62) is a variant of HB12B-(A10-Jk4) VK comprising the following three amino acid substitutions: Y40F, K53H, Y91F (residues numbered according to Kabat). Gene specific primers for HB12B-364987 were designed as described in Section 6.1. An expression vector comprising HB12B-364987 VK was generated according to the methods described in Section 6.1.

7.1.6. Binding Characteristics of Humanized HB12B Antibodies

Pairs of DNA plasmid expression vector preparations encoding (humanized or chimeric) heavy and light immunoglobulin chains were used to transfect HEK293 cells. These transfected HEK293 cells were cultured for three days to yield antibody-containing conditioned medium suitable for determining total IgG concentrations and CD19 binding activity.

Human CD19 binding activity of chimeric and humanized HB12B antibodies was assessed using a 300B4 cell based ELISA assay described in Section 6.2. An isotype matched human antibody of irrelevant specificity was included in the assay as a negative control. As shown in FIG. 2, the binding of a chimeric antibody comprising chHB12B heavy and chHB12B light chains and the novel humanized antibody #1 comprising HB12B-(3-72/JH4) VH and HB12B-364987 VK regions were found to be comparable. For concentrations of antibody above 100 ng/ml, there was a significant specific binding of both antibodies to CD19, indicating that humanized anti-CD19 antibody #1 comprising HB12B-(3-72/JH4) VH and HB12B-364987 VK regions has retained CD19 binding activity. Surprisingly, humanized antibodies comprising the HB12B-9m VH region displayed a significant loss in CD19 compared to chHB12B control.

Pairs of chimeric or humanized HB12B heavy and light chains were tested and their human CD19 binding activity is summarized in Table 4.

TABLE 4

CD19 binding of chimeric and humanized HB12B antibodies. CD19 binding activity of various chimeric and humanized HB12B antibodies was assessed using a cell based ELISA assay. VH-VK combinations displaying significant binding activity are marked with "++". VH-VK combinations with no significant binding to human CD19 are marked with "−".

|  | chHB12B VH | HB12B-(3-72/ JH4) VH | HB12B-9m VH |
|---|---|---|---|
| chHB12B VK | ++ | ++ | − |
| HB12B-(A10-Jk4) VK | − | − | − |
| HB12B-364987 VK | ++ | ++ | − |

7.1.7. Construction, Expression and Binding Characteristics of Humanized HB12B Light Chains Antibody humanization protocols generally try to limit the number of non-human framework residues in order to minimize the HAMA response. Accordingly, additional variants of humanized HB12B VK were generated and their hCD19 binding activity was assessed.

HB12B-3649 VK (SEQ ID NO:68) is a variant of HB12B-(A10-Jk4) VK comprising the following two amino acid substitutions: Y40F, K53H (numbering according to Kabat). An expression vector comprising HB12B-3649 VK was generated via site directed mutagenesis using the QuickChange kit (Stratagene, La Jolla, Calif.) on a DNA preparation of an expression vector comprising HB12B-364987 VK according to the manufacturer's instruction.

HB12B-3687 VK (SEQ ID NO:74) is a variant of HB12B-(A10-Jk4) VK comprising the following two amino acid substitutions: Y40F, and Y91F (numbering according to Kabat). An expression vector comprising HB12B-3687 VK was generated via site directed mutagenesis using the QuickChange kit (Stratagene, La Jolla, Calif.) on a DNA preparation of an expression vector comprising HB12B-364987 VK according to the manufacturer's instruction.

HB12B-4987 VK (SEQ ID NO:76) is a variant of HB12B-(A10-Jk4) VK comprising the following two amino acid substitutions: K53H, and Y91F (numbering according to Kabat). An expression vector comprising HB12B-4987 VK was generated via site directed mutagenesis using the QuickChange kit (Stratagene, La Jolla, Calif.) on a DNA preparation of an expression vector comprising HB12B-364987 VK according to the manufacturer's instruction.

HB12B-36 VK (SEQ ID NO:70) is a variant of HB12B-(A10-Jk4) VK comprising the following acid substitution: Y40F (numbering according to Kabat). An expression vector comprising HB12B-36 VK was generated via site directed mutagenesis using the QuickChange kit (Stratagene, La Jolla, Calif.) on a DNA preparation of an expression vector comprising HB12B-(A10-Jk4) VK according to the manufacturer's instruction.

HB12B-49 VK (SEQ ID NO:80) is a variant of HB12B-(A10-Jk4) VK comprising the following amino acid substitution: K53H (numbering according to Kabat). An expression vector comprising HB12B-49 VK was generated via site directed mutagenesis using the QuickChange kit (Stratagene, La Jolla, Calif.) on a DNA preparation of an expression vector comprising HB12B-(A10-Jk4) VK according to the manufacturer's instruction.

HB12B-87 VK (SEQ ID NO:78) is a variant of HB12B-(A10-Jk4) VK comprising the following amino acid substitution: Y91F (numbering according to Kabat). An expression vector comprising HB12B-87 VK was generated via site directed mutagenesis using the QuickChange kit (Stratagene, La Jolla, Calif.) on a DNA preparation of an expression vector comprising HB12B-(A10-Jk4) VK according to the manufacturer's instruction.

Pairs of DNA plasmid expression vector preparations encoding a heavy chain comprising HB12B-(3-72/JH4) VH and each of the VK variants described in Section 6.1.7. were used to co-transfect HEK293 cells. These co-transfected HEK293 cells were cultured for three days to yield humanized antibody-containing conditioned medium suitable for determining total IgG concentrations and hCD19 binding activity.

Human CD19 binding activity of humanized HB12B antibodies was assessed using a 300B4 cell based ELISA assay described in Section 6.1.2. chHB12B was included in the assay as a positive control. As shown in FIG. 3, the binding of chHB12B antibody comprising chHB12B VH and chHB12B VK and the novel humanized HB12B antibody #2 comprising HB12B-(3-72/JH4) VH and HB12B-3649 VK were found to be comparable. For concentrations of antibody above 100 ng/ml, there was a significant specific binding of both antibodies to hCD19, indicating that the humanized antibody comprising HB12B-(3-72/JH4) VH and HB12B-3649 VK retained hCD19 binding activity. Humanized HB12B antibody #1 comprising HB12B-364987VK also displayed binding of human CD19. Humanized HB12B antibody #3 comprising HB12B-36 VK exhibited significantly reduced binding to hCD19 compared to the binding of the chHB12B control antibody.

Taken together, these data indicate that a number of humanized versions of the HB12B VH and VK chains were created that retains the binding properties of the parental mouse antibody derived from the HB12B hybridoma.

7.2. In Vitro ADCC Activity of Humanized Anti-CD19 Antibodies.

The following sections describe the characterization of the in vitro ADCC activity of humanized anti-CD19 antibodies.

7.2.1. Humanized Anti-CD19 Antibody Preparations.

Purified humanized anti-CD19 antibody #2 comprising HB12B-(3-72/JH4) VH, HB12B-3649 VK, and IgG1 heavy chain constant region (hereinafter referred to as "3649 antibody" or "3649") is prepared using standard techniques. Briefly, a DNA plasmid expression vector preparation encoding the heavy and light chains of 3649 is used to transfect HEK293F cells. Transfected cells are fed at day 3 and 6 and the antibody-containing conditioned medium is harvested at day 9. Antibody is purified from the conditioned medium using a pre-cast protein A column (GE Healthcare). Antibody is eluted from the column with low pH buffer, neutralized, and dialyzed against PBS. The concentration of the purified antibody is calculated from the solution's optical density at 280 nm.

An antibody expression vector encoding a 3649 Fc variant comprising S239D, A330L, and I332E amino acid substitutions (hereinafter referred to as "3649-3M") is generated using methods described in US 2004/0132101 and US 2005/0054832, both to Lazar et al. Briefly, the antibody expression vector encoding 3649 is modified using a site directed mutagenesis kit (e.g., QuickChange (Promega)) by introducing the necessary nucleotide residue substitutions into the polynucleotide sequence encoding the heavy chain constant region to generate the 3649-3M antibody expression vector. Purified 3649-3M antibody is generated by transfecting HEK239F cells with the 3649-3M antibody expression vector. Transfected cells are fed at day 3 and 6 and the antibody-containing conditioned medium is harvested at day 9. Antibody is purified from the conditioned medium using a pre-cast protein A column (GE Healthcare). Antibody is eluted from the column with low pH buffer, neutralized, and dialyzed against PBS. The concentration of the purified antibody is calculated from the solution's optical density at 280 nm.

An antibody expression vector encoding a 3649 Fc variant comprising the L234F, L235E, and P331S amino acid substitutions (hereinafter referred to as "3649-TM") is generated using methods described in US 2004/0132101 and US 2005/0054832, both to Lazar et al., each of which is incorporated herein by reference in their entirety. Briefly, the antibody expression vector encoding 3649 is modified using a site directed mutagenesis kit (e.g., QuickChange (Promega)) by introducing the necessary nucleotide residue substitutions into the polynucleotide sequence encoding the heavy chain constant region to generate the 3649-TM antibody expression vector. Purified 3649-TM antibody is generated by transfecting HEK239F cells with the 3649-TM antibody expression vector. Transfected cells are fed at day 3 and 6 and the antibody-containing conditioned medium is harvested at day 9. Antibody is purified from the conditioned medium using a pre-cast protein A column (GE Healthcare). Antibody is eluted from the column with low pH buffer, neutralized, and dialyzed against PBS. The concentration of the purified antibody is calculated from the solution's optical density at 280 nm.

A 3649 antibody composition (hereinafter referred to as 3649-aFuc) comprising a plurality of antibodies having complex N-glycoside-linked sugar chains linked to Asn297 of the Fc region in which fucose is not bound to N-acetylglucosamine in the reducing end was prepared according to the methods set forth in U.S. Pat. No. 6,946,292 to Kanda et al., which is incorporated herein by reference in its entirety. Briefly, fucosyltransferase knock-out CHO cells are transfected with a DNA plasmid expression vector preparation encoding the heavy and light chains of 3649. Transfected cells are fed at day 3 and 6 and the antibody-containing conditioned medium is harvested at day 9. Antibody is purified from the conditioned medium using a pre-cast protein A column (GE Healthcare). Antibody is eluted from the column with low pH buffer, neutralized, and dialyzed against PBS. The concentration of the purified antibody is calculated from the solution's optical density at 280 nm.

Antibody preparations were substantially pure from contaminating proteins as demonstrated in FIG. 4. Antigen binding affinity of 3649-aFuc is comparable to that of 3649 as shown in FIG. 5.

7.2.2. In vitro ADCC Assay

The CytoTox 96® Non-Radioactive Cytotoxicity Assay (Promega) is a colorimetric alternative to $^{51}$Cr release cytotoxicity assays. The CytoTox 96® Assay quantitatively measures lactate dehydrogenase (LDH), a stable cytosolic enzyme that is released upon cell lysis. Released LDH in culture supernatants is measured with a 30-minute coupled enzymatic assay, which results in the conversion of a tetrazolium salt (INT) into a red formazan product. The amount of color formed is proportional to the number of lysed cells.

The assays are performed according to the manufacturer's directions. Briefly, target cells are washed with PBS, resuspended in RPMI-5 Phenol Free media at a cell density of $0.4 \times 10^6$/ml. NK effector cells are washed once in PBS and resuspended in RPMI-5 Phenol Free media at a cell density $1 \times 10^6$/ml. Assays are performed in U bottom 96 well plates. Each assay plate includes a combination of experimental and control wells. Experimental wells are set up by combining 50 µl of the appropriate antibody dilution, 50 ul of target cell suspension and 50 ul of effector cell suspension. The cell densities described above result in a 1:2.5 target to effector cell ratio; effector cell stock may be further diluted or concentrated if a different target to effector ratio is desired. Several different types of control wells are used to account for (i) the spontaneous LDH release form target cells (Target Spontaneous), (ii) the spontaneous LDH release from effector cells (Effector Spontaneous), (iii) the maximum LDH release from the target cells (Target Maximum), and (iv) the presence of contaminants in the culture medium (Background). All wells in use on a 96 well plate contain the same final volume. Reactions are set up in triplicates. Following set up, plates are spun at 120×g for 3 minutes to pellet the cells. Incubate plate at 37° C./5% $CO_2$ for 4 hours. Forty five minutes prior to the end of incubation 15 µl of manufacturer provided Lysis Buffer is added to the Target Cell Maximum Release Control well. After incubation the plate is centrifuged at 120×g for 4 minutes. 50 µl of the supernatant from each well is transferred to a new flat bottom 96 well plate. 50 µl of reconstituted substrate mix (assembled from manufacturer provided components) is added and the plate is incubated at room temperature 10-20 minutes protected from light. 50 µl of manufacturer provided stop buffer is added and absorbance at 490 or 492 nm is measured in a plate reader. % cytotoxicity equals (Experimental-Effector spontaneous−Target Spontaneous)/(Target Maximum−Target Spontaneous). Prior to calculating the % cytotoxicity all other values are reduced by the Background.

3649 efficiently recruits effector cells to human CD20 expressing target cells in an ADCC assay. The ADCC activity of the afucosylated form (3649-aFuc) is even more robust. Fc variants with increased (3649-3M) or decreased (3649-TM) affinity for Fcγ receptors display increased or decreased, respectively, ADCC activity as expected. ADCC activity was observed with both immortalized and freshly isolated human target cells. A representative sample of the experimental data supporting these assertions is presented in FIGS. 5 to 9.

7.2.3. In vitro Anti-CD19 Antibody Mediated ADCC is Influenced by Fc Region Affinity to FcγRIIIA Receptor.

Relative binding affinity of various humanized anti-CD19 antibody preparations to human FcγRIIIA receptor (CD16) may be ascertained using an ELISA assay. Microtiter plates are coated with 50 µl antibody preparation (50 µg/ml) at 4° C. overnight. Any remaining binding sites are blocked with 4% skimmed milk in PBS buffer (blocking buffer) for 1 h at 37° C. After washing the wells, 50 µl of serially diluted monomeric FcγRIIIA-flag protein is added to each well and incubated for 60 min at 37° C. 50 µl of 2.5 µg/ml anti-flag-ME-biotin (Sigma) is added to each well and incubated for 30 min at 37° C. Wells are washed between incubation with each of the following reagents. 50 µl of 0.1 µg/ml avidin-conjugated HRP (PIERCE) is added to each well and incubated for 30 min at 37° C. Detection is carried out by adding 30 µl of tetramethylbenzidine (TMB) substrate (Pierce) followed by neutralization with 30 µl of 0.2 M $H_2SO_4$. The absorbance was read at 450 nm.

As shown in FIG. 15, the binding affinity of the enhanced ADCC Fc variant 3649 antibody (3649-3M) and afucosylated 3649 antibody (3649-aFuc) for FcgRIIIA is higher than that of the fucosylated wild type 3649 antibody. The experiment was performed using an FcγRIIIA-flag protein comprising the extracellular domain of the V158 high affinity isoform of human FcγRIIIA.

The Fc receptor-Fc region interaction, and thus the effector function of an antibody, are also influenced by allelic variations in the Fc receptor. The effect of high affinity and low affinity FcgRIIIA receptors on ADCC may be studied by performing ADCC reactions with freshly isolated NK effector cells comprising different allelic variant receptors. FIG. 16 summarizes the results of such an experiment. ADCC reactions are performed as described above using Daudi target cells. Both fucosylated (3649) and afucosylated (3649-aFuc) anti-CD19 antibody #2 is tested. Control reactions are done using an anti-CD20 antibody. NK effector cells are isolated from healthy donors following standard protocols. NK cell genotype may be determined utilizing allele specific PCR reactions (see, Leppers-van de Straat et al., *J Immunol Methods*. 242(1-2):127-32 (2000)). FIGS. 16 A and B show that all three antibodies tested display ADCC activity under the reaction conditions used. The ADCC activity is detectable using either an NK cell line (A) or freshly isolated NK cells (B) as effectors. NK cells that comprise at least one copy of the high affinity isoform of FcγRIIIA receptor (V158/V158 and V158/F158 genotypes) are more efficient effector cells than NK cells homozygous for the low affinity receptor alleles (F158/F158 genotype) (FIG. 16C-E). Lack of fucosylation increases the ADCC activity of an antibody regardless of the FcγRIIIA genotype of the effector cells. The observed ADCC activity of the fucosylated antibody (3649) mediated by V158/V158 or V158/F158 NK cells (C, D) is comparable to the ADCC activity of the afucosylated antibody (3649-aFuc) mediated by F158/F158 NK cells (E).

7.3. Antibodies and Immunofluorescence Analysis

Anti-CD19 antibodies described above, which bind to the human CD19 antigen, can be used in the approaches disclosed below. Other antibodies, which could be employed in the experiments described below include monoclonal mouse anti-CD22 antibodies that bind to mouse CD22, e.g. HIB22 (Abcam; Dorken B et al., *J Immunol* 136:4470-9 (1986)); monoclonal mouse CD20-specific antibodies (Uchida et al., *Intl. Immunol.*, 16:119-129 (2004)); B220 antibody RA3-6B2 (DNAX Corp., Palo Alto, Calif.); and CD5, CD43 and CD25 antibodies (BD PHARMINGEN™, Franklin Lakes, N.J.). Isotype-specific and anti-mouse Ig or IgM antibodies can be obtained from Southern Biotechnology Associates, Inc. (Birmingham, Ala.).

Either mouse pre-B cell lines, transfected with hCD19 cDNA, which can be developed using methods and materials known in the art (see e.g. Alt et al., *Cell*, 27:381-388 (1981) and Tedder and Isaacs, *J. Immunol.*, 143:712-717 (1989)), or single-cell leukocyte suspension, are stained on ice using predetermined, optimal concentrations of each fluorescently-labeled antibody for 20-30 minutes according to established methods (Zhou et al., *Mol. Cell. Biol.*, 14:3884-3894 (1994)). Cells with the forward and side light scatter properties of lymphocytes can then be analyzed on FACSCAN® or FAC-SCALIBUR® flow cytometers (Becton Dickinson, San Jose, Calif.). Background staining would be determined using unreactive control antibodies (CALTAG™ Laboratories, Burlingame, Calif.) with gates positioned to exclude nonviable cells. For each sample examined, ten thousand cells with the forward and side light scatter properties of mononuclear cells are analyzed whenever possible, with fluorescence intensities shown on a four-decade log scale.

Mice. Transgenic mice expressing hCD19 and their wild-type (WT) littermates can be produced as described in the art (Zhou et al., *Mol. Cell. Biol.*, 14:3884-3894 (1994)). For example, hCD19tg mice can be generated from original hCD19 founders (e.g. C57BL/6×B6/SJL), and then crossed onto a C57BL/6 background for at least 7 generations. After multiple generations of backcrossing, mice would be obtained in which their B cells would express cell surface density of human CD19 at about the same density found on human B cells.

Mice bred with FcR (Fc receptor) common γ chain (FcRγ)-deficient mice (FcRγ$^{-/-}$, B6.129P2-Fcerg1$^{tm1}$) are available from Taconic Farms (Germantown, N.Y.) and could be used to generate hCD19$^{+/-}$ FcRγ$^{-/-}$ and WT littermates. Mice hemizygous for a c-Myc transgene (Eµ-cMycTG, C57B1/6J-TgN(IghMyc); The Jackson Laboratory, Bar Harbor, Me.) are described in the art (Harris et al., *J. Exp. Med.*, 167:353 (1988) and Adams et al., *Nature*, 318:533 (1985)). c-MycTG mice (B6/129 background) could be crossed with hCD19tg mice to generate hemizygous hCD19tg cMycTG$^{+/-}$ offspring that could be identified by PCR screening. Rag1$^{-/-}$ (B6.129S7-Rag1$^{tm1Mom}$/J) mice are available from The Jackson Laboratory. Macrophage-deficient mice can be generated by tail vein injections of clodronate-encapsulated liposomes (0.1 mL/10 gram body weight; Sigma Chemical Co., St. Louis, Mo.) into C57BL/6 mice on day −2, 1 and 4 in accordance with standard methods (Van Rooijen and Sanders, *J. Immunol. Methods*, 174:83-93 (1994)). All mice should be housed in a specific pathogen-free barrier facility and first used at 6-9 weeks of age.

ELISAs. Serum Ig concentrations are determined by ELISA using affinity-purified mouse IgM, IgG1, IgG2a, IgG2b, IgG3, and IgA (Southern Biotechnology Associates, Inc., Birmingham, Ala.) to generate standard curves as described (Engel et al., *Immunity*, 3:39 (1995)). Serum IgM and IgG autoantibody levels against dsDNA, ssDNA and histone are determined by ELISA using calf thymus double-stranded (ds) DNA (Sigma-Aldrich, St. Louis, Mo.), boiled calf thymus DNA (which contains single-stranded (ss) DNA) or histone (Sigma-Aldrich) coated microtiter plates as described (Sato et al., *J. Immunol.*, 157:4371 (1996)).

Immunotherapy.

Sterile anti-CD19 and unreactive, isotype control antibodies (0.5-250 µg) in 200 µL phosphate-buffered saline (PBS) are injected through lateral tail veins. For example, experiments would use a fixed amount (e.g. 250 µg) of antibody. Blood leukocyte numbers are quantified by hemocytometer following red cell lysis, B220$^+$ B cell frequencies are determined by immunofluorescence staining with flow cytometry analysis. Antibody doses in humans and mice would be compared using the Oncology Tool Dose Calculator.

Immunizations. Two-month old WT mice are immunized i.p. with 50 µg of 2,4,6-trinitrophenyl (TNP)-conjugated lipopolysaccharide (LPS) (Sigma, St. Louis, Mo.) or 25 µg 2,4-dinitrophenol-conjugated (DNP)—FICOLL® (Biosearch Technologies, San Rafael, Calif.) in saline. Mice are also immunized i.p. with 100 µg of DNP-conjugated keyhole limpet hemocyanin (DNP-KLH, CALBIOCHEM®-NOVABIOCHEM® Corp., La Jolla, Calif.) in complete Freund's adjuvant and are boosted 21 days later with DNP-KLH in incomplete Freund's adjuvant. Mice are bled before and after immunizations as indicated. DNP- or TNP-specific antibody titers in individual serum samples are measured in duplicate using ELISA plates coated with DNP-BSA (CALBIOCHEM®-NOVABIOCHEM® Corp., La Jolla, Calif.) or TNP-BSA (Biosearch Technologies, San Rafael, Calif.) according to standard methods (Engel et al., *Immunity*, 3:39-50 (1995)). Sera from TNP-LPS immunized mice are diluted 1:400, with sera from DNP-FICOLL® and DNP-BSA immunized mice diluted 1:1000 for ELISA analysis.

Statistical Analysis. All data would be shown as means±SEM with Student's t-test used to determine the significance of differences between sample means 7.4. Human CD19 Expression in Transgenic Mice Transgenic hCD19tg mice, which can be developed as described herein, or other transgenic animals expressing human CD19 can be used to assess different therapeutic regimens comprising anti-CD19 antibodies, such as variations in dosing concentration, amount, and timing. The efficacy in human patients of different therapeutic regimens can be predicted using the two indicators described below, i.e., B cell depletion in certain bodily fluids and/or tissues and the ability of a monoclonal human or humanized anti-CD19 antibody to bind B cells. In particular embodiments, treatment regimens that are effective in human CD19 transgenic mice could be used with compositions and methods of the invention to treat human B cell disorders and disease including, but not limited to, B cell malignancies and autoimmune diseases or disorders.

In order to determine whether human CD19 is expressed on B cells from transgenic mice (hCD19tg) expressing the human CD19 transgene, B cells would be extracted from the bone marrow, blood, spleen and peritoneal lavage of these mice. Human CD19 and mouse CD19 expression would be assessed in these cells by contacting the cells with anti-CD19 antibodies that specifically bind human CD19 or mouse CD19 (mCD19). Binding of the antibody to the B lineage cells would be detected using two-color immunofluorescence staining with flow cytometry analysis. The relative expression levels of mCD19 and hCD19, would be assessed by measuring mean fluorescence intensity (anti-hCD19 for hCD19 and anti-mCD19 for mCD19) respectively.

Expression level of a human CD19 and human CD20 transgenes was determined essentially as described above. Circulating lymphocytes are isolated form C57B16 hCD19 tg+/−, C57B16 hCD19 tg+/+, Balb/c hCD20 tg+/− and Balb/c wild type mice using standard procedures. Animals were housed in a pathogen free facility. The age and number of animals used from each genotype is listed in FIG. 10. Isolated cells are stained with PerCP Cy5.5 conjugated anti-mouse CD19 (clone 1D3, BD Biosciences), PE conjugated anti-CD3 (e.g., clone 17A2, BD Biosciences), Alexa Fluor® 488 conjugated anti-human CD19 (clone HIB19, BD Biosciences), and Alexa Fluor® 647 conjugated anti-human CD20 antibodies (e.g., clone 2H7, AbD serotec). Immunostained cells are analyzed on a flow cytometer. B cell population is defined as anti-mouse CD19 +, anti-CD3− cells. Mean fluorescence intensity of anti-mouse CD19 +, anti-CD3− cells detected in the hCD19 and hCD20 channels is described in FIG. 10A. Human CD19 expression is detected only on hCD19 transgenic cells as expected. hCD19 expression is dose dependent; staining levels in tg+/+ is approximately twice that of seen on tg+/− B cells. hCD19 expression level was stable in all age groups examined.

Percentage of B cells among circulating lymphocytes was calculated for all samples. B cells were defined as anti-mouse CD19 +, anti-CD3− cells for the purpose of the calculation. Results are displayed in FIG. 10B. Animals with a hCD19 transgene have reduced B cell numbers among circulating lymphocytes. Reduction in B cell numbers are more pronounced in hCD19 tg+/+ animals. These results are in agreement with previously published observations (Zhou et al., *Mol. Cell. Biol.*, 14:3884-3894 (1994)).

7.5. Anti-CD19 Antibody Mediated Depletion of B Cells In Vivo

Anti-CD19 antibodies of the invention, which bind to human CD19, can be assessed for their ability to deplete hCD19tg blood, spleen, and lymph node B cells in vivo. For example, each antibody would be given to mice at either 250 or 50 µg/mouse, a single dose about 10 to 50-fold lower than the 375 mg/m$^2$ dose primarily given four times for anti-CD20 therapy in humans (Maloney et al., *J. Clin. Oncol.*, 15:3266-74 (1997) and McLaughlin et al., *Clinical status and optimal use of rituximab for B cell lymphomas, Oncology* (Williston Park), 12:1763-9 (1998)). B cell depletion from blood, spleen and lymph nodes of hCD19tg mice would be determined by immunofluorescence staining with flow cytometry analysis. The results using anti-CD19 antibodies identified as capable of depleting B cells can be correlated to use in humans and antibodies with properties of the identified antibodies can be used in the compositions and methods of the invention for the treatment of human B cell disorders and disease including, but not limited to, B cell malignancies and autoimmune diseases or disorders.

3649 humanized anti-CD19 antibody was tested in a B cell depletion assay essentially as described above. C57B16 hCD19 tg +/− and C57B16 hCD19 tg +/+ mice are given a single i.v. dose of 50 or 250 μg 3649 antibody. Two control groups are used. Members of the first group receive 50 or 250 μg of R347 antibody of irrelevant specificity; members of the second group receive 50 or 250 μg of the 3649-TM Fc variant with diminished ADCC activity (see FIG. 6). Number of animals in each group are described in FIGS. 11 and 12. Animals are housed in a pathogen free facility. 7 days post treatment mononuclear cells are isolated from circulating blood and spleens. Isolated cells are stained with PerCP Cy5.5 conjugated anti-mouse CD19 (clone 1D3, BD Biosciences) and Apc-Cy5.5 conjugated anti-mouse B220 (cloneRA3-6B2, Invitrogen) antibodies. Immunostained samples are analyzed on a flow cytometer. B cells are defined as anti-mouse CD19 +, anti-mouse B220+ cells for the purposes of the experiment. The percentage of B cells among circulating lymphocytes is presented in FIG. 11. The percentage and absolute number of B cells among spleen cells is described in FIG. 12. A single dose of 50 mg 3649 anti-CD19 antibody is sufficient to achieve significant depletion of circulating and splenic B cells. Level of depletion is influenced by antibody dose and hCD19 surface density. Depletion is most complete in hCD19 tg+/+ animals receiving 250 μg antibody. Depletion is more extensive among circulating lymphocytes than in spleen in all animals tested.

A separate study was also performed to measure the ability of various 3649 anti-CD19 antibody preparations to deplete circulating, splenic, peritoneal and bone marrow B cell subpopulations in a hCD19 tg+/− animal. The experiment was performed as follows: Three to four-month old sex matched C57B16 hCD19 tg+/− mice were injected through the lateral tail veins with sterile endotoxin-free anti-CD19 antibody preparations diluted in PBS at 10, 50 or 250 ug per mouse doses. The following anti-CD19 antibodies were tested: fucosylated anti-CD19 antibody #2 (3649), afucosylated anti-CD19 antibody #2 (3649-aFuc), ADCC enhanced Fc variant anti-CD19 antibody #2 (3649-3M), and reduced ADCC Fc variant anti-CD19 antibody #2 (3649-TM). A group of control animals were injected with an isotype matched control antibody of irrelevant specificity (R347). Seven days post injection, mice were scarified and cells from blood, spleen, bona marrow and peritoneal cavity were collected. Red cells were lysed following standard protocols and total viable cell count was determined using a Via-Cell automated cell counting machine. Isolated single cell suspensions were immunostained and analyzed on a flow cytometer following standard protocols. Antibodies used for immunostaining are listed in Table 5. Depletion results are summarized in Tables 6-21. Depletion results obtained using the afucosylated anti-CD19 antibody #2 (3649-aFuc) is presented in FIG. 28. NK cell activation phenotype of animals treated with the afucosylated or fucosylated anti-CD19 antibody #2 (3649-aFuc or 3649, respectively) is presented in FIG. 29. B cell subset definitions used during the analysis are as follows:

Blood: B cells: B220+, mouse CD19+

Spleen: B cells: B220+, mouse CD19+

Transitional B cells: after gating on B cells, CD93+

Transitional 1 B cells (T1): IgM+CD23−

Transitional 1 B cells (T2): IgM+CD23+

Transitional 1 B cells (T3): IgMlowCD23+

Mature B cells: after gating on B cells, CD93−

Follicular B cells: IgM+CD23+

Marginal Zone B cells: IgMhighCD23−

Bone Marrow: B cells: B220+, mouse CD19+

Pro-B cells: after gating on B cells, CD43+IgM−

Pre-B cells: after gating on B cells, CD43−IgM−

Immature and Mature B cells: after gating on B cells, CD43−IgM+

Immature B cells: CD43−IgM+CD93+

Mature B cells: CD43−IgM+CD93+low/−

Peritoneal Cavity: B cells: IgM+

TABLE 5

Antibodies used for B cell identification in in vivo depletion experiments. Dead cells were detected by 7-AAD staining.

| | Antigen | Dye | Clone Number | Source |
|---|---|---|---|---|
| Spleen | B220 | FITC | RA3-6B2 | BD Bioscience |
| | CD19 | PerCP-Cy5.5 | 1D3 | BD Bioscience |
| | CD23 | PE | B3B4 | Biolegend |
| | hCD19 | PE-Alexa 610 | SJ25-C1 | Invitrogen |
| | IgM | PE-Cy7 | II/41 | eBioscience |
| | C1qRp | Apc | AA4.1 | eBioscience |
| Bone Marrow | B220 | FITC | RA3-6B2 | BD Bioscience |
| | CD19 | PerCP-Cy5.5 | 1D3 | BD Bioscience |
| | CD43 | PE | S7 | BD Bioscience |
| | hCD19 | PE-Alexa 610 | SJ25-C1 | Invitrogen |
| | IgM | PE-Cy7 | II/41 | eBioscience |
| | C1qRp | Apc | AA4.1 | eBioscience |
| Peritoneal Cavity | B220 | FITC | RA3-6B2 | BD Bioscience |
| | CD19 | PerCP-Cy5.5 | 1D3 | BD Bioscience |
| | CD43 | PE | S7 | BD Bioscience |
| | hCD19 | PE-Alexa 610 | SJ25-C1 | Invitrogen |
| | IgM | PE-Cy7 | II/41 | eBioscience |
| | CD5 | Apc | 53-7.3 | eBioscience |
| Blood | hCD19 | Alexa 488 | SJC25 | Invitrogen |
| | CD3 | PE | | |
| | mCD19 | PerCP Cy5.5 | 1D3 | BD Bioscience |
| | B220 | Alexa 647 | RA3-6B2 | BD Bioscience |

TABLE 6

Summary of circulating B cell depletion results. 3649, 3649-3M, 3649-TM or control R347 antibody was administered to hCD19tg+/− mice following the protocol described above. % B cell is defined as the B220+, mouse CD19+ fraction of blood lymphocytes; lymphocyte population is detected based on characteristic forward and side scatter profile (see FIG. 17A for details). % depletion was calculated as 100 × (% B cell (control antibody) − % B cell(experimental antibody))/% B cell (control antibody). Negative depletion numbers are used when the size of a cell population in the treated animal was larger than the corresponding size in the control animal.

| Antibody | Dose (μg/mouse) | % B cell | % Depletion |
|---|---|---|---|
| R347 | 10 | 26.8% | N/A |
| R347 | 50 | 37.9% | N/A |
| R347 | 250 | 22.2% | N/A |
| 3649 | 10 | 16.9% | 36.94% |
| 3649 | 50 | 1.5% | 96.12% |
| 3649 | 250 | 1.0% | 95.64% |
| 3649-3M | 10 | 1.1% | 95.82% |
| 3649-3M | 50 | 0.1% | 99.84% |
| 3649-TM | 50 | 32.8% | 13.47% |
| 3649-TM | 250 | 26.4% | (−18.7%) |

TABLE 7

Summary of splenic B cell depletion results. 3649, 3649-3M, 3649-TM, or control R347 antibody was administered to hCD19tg+/− mice following the protocol described above. % B cell is defined as the B220+, mouse CD19+ fraction of lymphocytes (see FIG. 17B for details). % depletion was calculated as 100 × (cell number (control antibody) − cell number (experimental antibody))/cell number (control antibody). Negative depletion numbers are used when the size of a cell population in the treated animal was larger than the corresponding size in the control animal.

| Antibody | Dose (μg/mouse) | % B cell | Cell number/animal | % Depletion |
|---|---|---|---|---|
| R347 | 10 | 17.2% | 5,991,451 | N/A |
| R347 | 50 | 22.5% | 4,620,997 | N/A |
| R347 | 250 | 25.7% | 5,317,874 | N/A |
| 3649 | 10 | 13.4% | 3,267,904 | 45.5% |
| 3649 | 50 | 6.8% | 773,147 | 83.3% |
| 3649 | 250 | 7.8% | 947,293 | 82.2% |
| 3649-3M | 10 | 4.1% | 532,244 | 91.1% |
| 3649-3M | 50 | 1.6% | 102,285 | 97.8% |
| 3649-TM | 50 | 28.5% | 6,199,144 | (−34.1%) |
| 3649-TM | 250 | 21.8% | 4,182,489 | 21.4% |

TABLE 8

Summary of splenic transitional B cell depletion results. 3649, 3649-3M, 3649-TM, or control R347 antibody was administered to hCD19tg+/- mice following the protocol described above. % transitional B cells are defined as the CD93+ fraction of B cells (see FIG. 17B for details). % depletion was calculated as 100 × (cell number (control antibody) − cell number (experimental antibody))/cell number (control antibody).

| Antibody | Dose (μg/mouse) | % transitional B cells | Cell number/animal | % Depletion |
|---|---|---|---|---|
| R347 | 10 | 17.4% | 1,131,356 | N/A |
| R347 | 50 | 18.4% | 937,239 | N/A |
| R347 | 250 | 17.0% | 975,450 | N/A |
| 3649 | 10 | 11.1% | 402,770 | 64.4% |
| 3649 | 50 | 3.0% | 24,173 | 97.4% |
| 3649 | 250 | 4.0% | 39,299 | 96.0% |
| 3649-3M | 10 | 7.2% | 43,106 | 96.2% |
| 3649-3M | 50 | 5.2% | 5,272 | 99.4% |
| 3649-TM | 50 | 12.4% | 840,608 | 10.3% |
| 3649-TM | 250 | 10.2% | 455,248 | 53.3% |

TABLE 9

Summary of splenic T1 B cell depletion results. 3649, 3649-3M, 3649-TM, or control R347 antibody was administered to hCD19tg+/− mice following the protocol described above. T1 B cells are defined as the IgM+, CD23− fraction of transitional B cells (see FIG. 17B for details). % depletion was calculated as 100 × (cell number (control antibody) − cell number (experimental antibody))/cell number (control antibody).

| Antibody | Dose (μg/mouse) | % T1 B cells | Cell number/animal | % Depletion |
|---|---|---|---|---|
| R347 | 10 | 28.8% | 335,185 | N/A |
| R347 | 50 | 36.0% | 332,727 | N/A |
| R347 | 250 | 34.6% | 367,735 | N/A |
| 3649 | 10 | 27.2% | 107,298 | 68.0% |
| 3649 | 50 | 23.3% | 5,845 | 98.2% |
| 3649 | 250 | 30.4% | 12,678 | 96.6% |
| 3649-3M | 10 | 24.2% | 10,438 | 96.9% |
| 3649-3M | 50 | 20.4% | 1,168 | 99.6% |
| 3649-TM | 50 | 29.4% | 253,730 | 23.7% |
| 3649-TM | 250 | 27.3% | 125,491 | 65.9% |

TABLE 10

Summary of splenic T2 B cell depletion results. 3649, 3649-3M, 3649-TM, or control R347 antibody was administered to hCD19tg+/− mice following the protocol described above. T2 B cells are defined as the IgM+, CD23+ fraction of transitional B cells (see FIG. 17B for details). % depletion was calculated as 100 × (cell number (control antibody) − cell number (experimental antibody))/cell number (control antibody).

| Antibody | Dose (μg/mouse) | % T2 B cells | Cell number/animal | % Depletion |
|---|---|---|---|---|
| R347 | 10 | 21.3% | 242,018 | N/A |
| R347 | 50 | 17.3% | 166,575 | N/A |
| R347 | 250 | 23.0% | 212,106 | N/A |
| 3649 | 10 | 23.4% | 95,554 | 60.5% |
| 3649 | 50 | 18.9% | 4,322 | 97.4% |
| 3649 | 250 | 16.6% | 6,945 | 96.7% |
| 3649-3M | 10 | 26.4% | 11,368 | 95.3% |
| 3649-3M | 50 | 10.9% | 607 | 99.6% |
| 3649-TM | 50 | 16.7% | 135,944 | 18.4% |
| 3649-TM | 250 | 21.6% | 93,662 | 55.8% |

TABLE 11

Summary of splenic T3 B cell depletion results. 3649, 3649-3M, 3649-TM, or control R347 antibody was administered to hCD19tg+/− mice following the protocol described above. T3 B cells are defined as the CD93+, IgM low, CD23+ fraction of transitional B cells (see FIG. 17B for details). % depletion was calculated as 100 × (cell number (control antibody) − cell number (experimental antibody))/cell number (control antibody). Negative depletion numbers are used when the size of a cell population in the treated animal was larger than the corresponding size in the control animal.

| Antibody | Dose (μg/mouse) | % T3 B cells | Cell number/animal | % Depletion |
|---|---|---|---|---|
| R347 | 10 | 34.3% | 378,181 | N/A |
| R347 | 50 | 25.2% | 242,767 | N/A |
| R347 | 250 | 30.7% | 306,514 | N/A |
| 3649 | 10 | 33.1% | 135,097 | 64.3% |
| 3649 | 50 | 25.4% | 5,652 | 97.7% |
| 3649 | 250 | 21.1% | 8,062 | 97.4% |
| 3649-3M | 10 | 26.2% | 11,148 | 97.1% |
| 3649-3M | 50 | 9.4% | 518 | 99.8% |
| 3649-TM | 50 | 47.8% | 399,685 | (−64.6%) |
| 3649-TM | 250 | 37.9% | 172,129 | 43.8% |

TABLE 12

Summary of splenic mature B cell depletion results. 3649, 3649-3M, 3649-TM, or control R347 antibody was administered to hCD19tg+/− mice following the protocol described above. Mature B cells are defined as the CD93− fraction of B cells (see FIG. 17B for details). % depletion was calculated as 100 × (cell number (control antibody) − cell number (experimental antibody))/cell number (control antibody). Negative depletion numbers are used when the size of a cell population in the treated animal was larger than the corresponding size in the control animal.

| Antibody | Dose (μg/mouse) | % mature B cells | Cell number/ animal | % Depletion |
|---|---|---|---|---|
| R347 | 10 | 80.0% | 5,175,585 | N/A |
| R347 | 50 | 80.7% | 3,883,914 | N/A |
| R347 | 250 | 82.1% | 4,454,167 | N/A |
| 3649 | 10 | 86.3% | 3,042,745 | 41.2% |
| 3649 | 50 | 96.2% | 794,477 | 79.5% |
| 3649 | 250 | 94.3% | 933,936 | 79.0% |
| 3649-3M | 10 | 88.7% | 532,482 | 89.7% |
| 3649-3M | 50 | 93.5% | 108,806 | 97.2% |
| 3649-TM | 50 | 87.5% | 5,724,882 | (−47.4%) |
| 3649-TM | 250 | 87.5% | 3,792,089 | 14.9% |

TABLE 13

Summary of splenic follicular B cell depletion results. 3649, 3649-3M, 3649-TM, or control R347 antibody was administered to hCD19tg+/− mice following the protocol described above. Follicular B cells are defined as the IgM+, CD23+ fraction of mature B cells (see FIG. 17B for details). % depletion was calculated as 100 × (cell number (control antibody) − cell number (experimental antibody))/cell number (control antibody). Negative depletion numbers are used when the size of a cell population in the treated animal was larger than the corresponding size in the control animal.

| Antibody | Dose (μg/mouse) | % follicular B cells | Cell number/ animal | % Depletion |
|---|---|---|---|---|
| R347 | 10 | 78.2% | 4,053,717 | N/A |
| R347 | 50 | 69.3% | 2,731,740 | N/A |
| R347 | 250 | 74.4% | 3,298,335 | N/A |
| 3649 | 10 | 76.9% | 2,345,011 | 42.2% |
| 3649 | 50 | 38.8% | 310,160 | 88.6% |
| 3649 | 250 | 45.6% | 427,691 | 87.0% |
| 3649-3M | 10 | 58.2% | 306,833 | 92.4% |
| 3649-3M | 50 | 40.6% | 40,611 | 98.5% |
| 3649-TM | 50 | 79.9% | 4,573,294 | (−67.4%) |
| 3649-TM | 250 | 81.6% | 3,091,310 | 6.3% |

TABLE 14

Summary of splenic marginal zone B cell depletion results. 3649, 3649-3M, 3649-TM, or control R347 antibody was administered to hCD19tg+/− mice following the protocol described above. Marginal zone B cells are defined as the IgM high, CD23− fraction of mature B cells (see FIG. 17B for details). % depletion was calculated as 100 × (cell number (control antibody) − cell number (experimental antibody))/cell number (control antibody). Negative depletion numbers are used when the size of a cell population in the treated animal was larger than the corresponding size in the control animal.

| Antibody | Dose (μg/mouse) | % marginal zone B cells | Cell number/ animal | % Depletion |
|---|---|---|---|---|
| R347 | 10 | 10.6% | 546,769 | N/A |
| R347 | 50 | 14.3% | 526,975 | N/A |
| R347 | 250 | 19.0% | 861,171 | N/A |
| 3649 | 10 | 10.8% | 326,581 | 40.3% |
| 3649 | 50 | 36.9% | 291,707 | 44.6% |
| 3649 | 250 | 40.1% | 375,834 | 56.4% |
| 3649-3M | 10 | 20.6% | 110,411 | 79.8% |
| 3649-3M | 50 | 22.0% | 26,845 | 94.9% |
| 3649-TM | 50 | 14.6% | 835,215 | (−58.54%) |
| 3649-TM | 250 | 7.9% | 297,329 | 65.5% |

TABLE 15

Summary of bone marrow B cell depletion results. 3649, 3649-3M, 3649-TM, or control R347 antibody was administered to hCD19tg+/− mice following the protocol described above. B cells are defined as the B220+, mouse CD19+ fraction of lymphocytes (see FIG. 17C for details). % depletion was calculated as 100 × (cell number (control antibody) − cell number (experimental antibody))/cell number (control antibody).

| Antibody | Dose (μg/mouse) | % B cells | Cell number/ animal | % Depletion |
|---|---|---|---|---|
| R347 | 10 | 36.5% | 1,423,555 | N/A |
| R347 | 50 | 23.0% | 1,253,562 | N/A |
| R347 | 250 | 49.0% | 1,638,383 | N/A |
| 3649 | 10 | 23.9% | 828,302 | 41.8% |
| 3649 | 50 | 5.3% | 192,629 | 84.6% |
| 3649 | 250 | 15.1% | 325,810 | 80.1% |
| 3649-3M | 10 | 12.2% | 380,642 | 73.3% |
| 3649-3M | 50 | 3.6% | 100,271 | 92.0% |
| 3649-TM | 50 | 28.6% | 1,192,432 | 4.9% |
| 3649-TM | 250 | 59.2% | 1,551,662 | 5.3% |

TABLE 16

Summary of bone marrow pro-B cell depletion results. 3649, 3649-3M, 3649-TM, or control R347 antibody was administered to hCD19tg+/− mice following the protocol described above. Pro-B cells are defined as the CD43+, IgM− fraction of B cells (see FIG. 17C for details). % depletion was calculated as 100 × (cell number (control antibody) − cell number (experimental antibody))/cell number (control antibody). Negative depletion numbers are used when the size of a cell population in the treated animal was larger than the corresponding size in the control animal.

| Antibody | Dose (μg/mouse) | % pro-B cells | Cell number/ animal | % Depletion |
|---|---|---|---|---|
| R347 | 10 | 8.0% | 106,735 | N/A |
| R347 | 50 | 10.8% | 135,709 | N/A |
| R347 | 250 | 12.9% | 298,552 | N/A |
| 3649 | 10 | 17.6% | 143,882 | (−34.8%) |
| 3649 | 50 | 44.6% | 87,312 | 35.7% |
| 3649 | 250 | 59.7% | 233,214 | 21.9% |
| 3649-3M | 10 | 42.2% | 160,572 | (−50.4%) |
| 3649-3M | 50 | 49.5% | 50,159 | 63.0% |
| 3649-TM | 50 | 9.1% | 110,932 | 18.3% |
| 3649-TM | 250 | 18.9% | 298,063 | 0.2% |

TABLE 17

Summary of bone marrow pre-B cell depletion results. 3649, 3649-3M, 3649-TM, or control R347 antibody was administered to hCD19tg+/− mice following the protocol described above. Pre-B cells are defined as the CD43−, IgM− fraction of B cells (see FIG. 17C for details). % depletion was calculated as 100 × (cell number (control antibody) − cell number (experimental antibody))/cell number (control antibody).

| Antibody | Dose (μg/mouse) | % pre-B cells | Cell number/ animal | % Depletion |
| --- | --- | --- | --- | --- |
| R347 | 10 | 54.2% | 786,256 | N/A |
| R347 | 50 | 53.4% | 665,597 | N/A |
| R347 | 250 | 44.9% | 1,037,445 | N/A |
| 3649 | 10 | 44.3% | 368,091 | 53.2% |
| 3649 | 50 | 44.3% | 82,854 | 87.6% |
| 3649 | 250 | 28.7% | 112,154 | 89.2% |
| 3649-3M | 10 | 44.0% | 166,139 | 78.9% |
| 3649-3M | 50 | 43.4% | 42,831 | 93.6% |
| 3649-TM | 50 | 52.5% | 618,151 | 7.1% |
| 3649-TM | 250 | 40.8% | 631,574 | 39.1% |

TABLE 18

Summary of bone marrow immature/mature-B cell depletion results. 3649, 3649-3M, 3649-TM, or control R347 antibody was administered to hCD19tg+/− mice following the protocol described above. Immature/mature B cells are defined as the CD43−, IgM+ fraction of B cells (see FIG. 17C for details). % depletion was calculated as 100 × (cell number (control antibody) − cell number (experimental antibody))/cell number (control antibody). Negative depletion numbers are used when the size of a cell population in the treated animal was larger than the corresponding size in the control animal.

| Antibody | Dose (μg/mouse) | % immature/mature B cells | Cell number/ animal | % Depletion |
| --- | --- | --- | --- | --- |
| R347 | 10 | 34.7% | 488,578 | N/A |
| R347 | 50 | 30.3% | 382,746 | N/A |
| R347 | 250 | 36.1% | 835,327 | N/A |
| 3649 | 10 | 32.5% | 267,869 | 45.2% |
| 3649 | 50 | 7.8% | 16,149 | 95.8% |
| 3649 | 250 | 7.4% | 27,688 | 96.7% |
| 3649-3M | 10 | 9.9% | 38,723 | 92.1% |
| 3649-3M | 50 | 4.3% | 4,340 | 98.9% |
| 3649-TM | 50 | 35.0% | 421,214 | (−10.1%) |
| 3649-TM | 250 | 34.6% | 532,935 | 36.2% |

TABLE 19

Summary of bone marrow immature B cell depletion results. 3649, 3649-3M, 3649-TM, or control R347 antibody was administered to hCD19tg+/− mice following the protocol described above. Immature B cells are defined as the CD93+ fraction of immature/mature B cells (see FIG. 17C for details). % depletion was calculated as 100 × (cell number (control antibody) − cell number (experimental antibody))/cell number (control antibody). Negative depletion numbers are used when the size of a cell population in the treated animal was larger than the corresponding size in the control animal.

| Antibody | Dose (μg/mouse) | % B cells | Cell number/ animal | % Depletion |
| --- | --- | --- | --- | --- |
| R347 | 10 | 46.4% | 230,643 | N/A |
| R347 | 50 | 47.6% | 181,178 | N/A |
| R347 | 250 | 43.9% | 183,209 | N/A |
| 3649 | 10 | 33.2% | 89,491 | 61.2% |
| 3649 | 50 | 43.6% | 7,542 | 95.8% |
| 3649 | 250 | 18.2% | 2,515 | 98.6% |
| 3649-3M | 10 | 65.6% | 24,592 | 89.3% |
| 3649-3M | 50 | 41.9% | 1,780 | 99.0% |
| 3649-TM | 50 | 39.4% | 161,537 | 10.8% |
| 3649-TM | 250 | 37.1% | 204,694 | (−11.7%) |

TABLE 30

Summary of bone marrow mature B cell depletion results. 3649, 3649-3M, 3649-TM, or control R347 antibody was administered to hCD19tg+/− mice following the protocol described above. Mature B cells are defined as the CD93 low/− fraction of immature/mature B cells (see FIG. 17C for details). % depletion was calculated as 100 × (cell number (control antibody) − cell number (experimental antibody))/cell number (control antibody). Negative depletion numbers are used when the size of a cell population in the treated animal was larger than the corresponding size in the control animal.

| Antibody | Dose (μg/mouse) | % mature B cells | Cell number/ animal | % Depletion |
| --- | --- | --- | --- | --- |
| R347 | 10 | 52.0% | 249,983 | N/A |
| R347 | 50 | 41.3% | 159,933 | N/A |
| R347 | 250 | 49.2% | 205,556 | N/A |
| 3649 | 10 | 63.6% | 169,712 | 32.1% |
| 3649 | 50 | 22.6% | 3,904 | 97.6% |
| 3649 | 250 | 39.2% | 5,435 | 97.4% |
| 3649-3M | 10 | 31.4% | 13,102 | 94.8% |
| 3649-3M | 50 | 18.7% | 802 | 99.5% |
| 3649-TM | 50 | 58.9% | 252,755 | (−58.0%) |
| 3649-TM | 250 | 55.8% | 290,984 | (−41.6%) |

TABLE 31

Summary of peritoneal cavity B cell depletion results. 3649, 3649-3M, 3649-TM, HB12B or control R347 antibody was administered to hCD19tg+/− mice following the protocol described above. Peritoneal cavity B cells are defined as the IgM+ fraction of peritoneal lymphocytes (see FIG. 17D for details). % depletion was calculated as 100 × (% B cell (control antibody) − % B cell(experimental antibody))/% B cell (control antibody). Negative depletion numbers are used when the size of a cell population in the treated animal was larger than the corresponding size in the control animal.

| Antibody | Dose (μg/mouse) | % B cell | % Depletion |
| --- | --- | --- | --- |
| R347 | 10 | 25.9% | N/A |
| R347 | 50 | 30.3% | N/A |
| R347 | 250 | 55.6% | N/A |
| 3649 | 10 | 16.8% | 35.3% |
| 3649 | 50 | 20.1% | 33.6% |
| 3649 | 250 | 35.8% | 35.6% |
| 3649-3M | 10 | 15.3% | 41.1% |
| 3649-3M | 50 | 13.1% | 56.9% |
| 3649-TM | 50 | 26.7% | 11.9% |
| 3649-TM | 250 | 56.5% | (−1.65%) |
| HB12B | 50 | 23.6% | 22.0% |
| HB12B | 250 | 23.3% | 58.2% |

7.5.1. CD19 Density Influences the Effectiveness of CD19 Antibody-Induced B cell Depletion To determine whether an anti-CD19 antibody's ability to deplete B cells is dependent on CD19 density, anti-CD19 antibodies of the invention can be administered to mice having varying levels of hCD19 expression. The results obtained will demonstrate whether human CD19 density on B cells and antibody isotype can influence the depletion of B cells in the presence of an anti-CD19 antibody. The same assay can be used to determine whether other anti-CD19 antibodies can effectively deplete B cells. The results can be correlated to treatment of human patients with varying levels of CD19 expression. Thus, the methods for examining CD19 presence and density, described herein, can be used in human subjects to identify patients or patient populations for which certain anti-CD19 antibodies can deplete B cells and/or to determine suitable dosages.

To determine whether CD19 density influences the effectiveness of anti-CD19 antibody-induced B cell depletion representative blood and spleen B cell depletion can be examined in hCD19tg mice after treatment with the anti-CD19 antibodies of the invention (7 days, 250 µg/mouse). The results are expected to demonstrate that CD19 density influences the efficiency of B cell depletion by anti-CD19 antibodies in vivo. For example, low-level CD19 expression in hCD19tg mice would be expected to have a marked influence on circulating or tissue B cell depletion by the administered antibody. B cell clearance can be assessed 24 hours after anti-CD19 or control mAb treatment of individual mice.

7.5.2. Determination Whether Tissue B Cell Depletion is FcγR-Dependent

Should administration of an anti-CD19 mAb of the invention result in tissue B cell depletion, the following assays can be used to demonstrate dependence upon FcγR expression. Through a process of interbreeding hCD19tg mice with mice lacking expression of certain FcγR, mice can be generated that express hCD19 and lack expression of certain FcγR. Such mice can be used in assays to assess the ability of anti-CD19 antibodies to deplete B cells through pathways that involve FcγR expression, e.g., ADCC. Thus, anti-CD19 antibodies identified in these assays can be used to engineer chimeric, human or humanized anti-CD19 antibodies using the techniques described above. Such antibodies can in turn be used in the compositions and methods of the invention for the treatment of human B cell disorders and diseases including, but not limited to, autoimmune diseases and disorders.

The innate immune system mediates B cell depletion following anti-CD20 antibody treatment through FcγR-dependent processes. Mouse effector cells express four different FcγR classes for IgG, the high-affinity FcγRI (CD64), and the low-affinity FcγRII (CD32), FcγRIII (CD16), and FcγRIV molecules. FcγRI, FcγRIII and FcγRIV are hetero-oligomeric complexes in which the respective ligand-binding α chains associate with a common γ chain (FcRγ). FcRγ chain expression is required for FcγR assembly and for FcγR triggering of effector functions, including phagocytosis by macrophages. Since FcRγ$^{-/-}$ mice lack high-affinity FcγRI (CD64) and low-affinity FcγRIII (CD16) and FcγRIV molecules, FcRγ$^{-/-}$ mice expressing hCD19 can be used to assess the role of FcγR in tissue B cell depletion following anti-CD19 antibody treatment.

7.5.3. Durability of Anti-CD19 Antibody-Induced B Cell Depletion

To assess the efficacy and duration of B cell depletion, hCD19tg mice can be administered a single low dose (e.g. 250 µg) injection of anti-CD19 antibody and the duration and dose response of B cell depletion followed as a function of time. The results are expected to demonstrate that circulating B cells are depleted for a substantial amount of time (e.g. one week to six months), followed by a gradual recovery of blood-borne B cells.

7.6. Persistence of CD19 on the Surface of B Cells after Administration of Anti-CD19 Antibody Whether CD19 internalization will influence B cell depletion in vivo can be assessed by comparing cell-surface CD19 expression following administration of the anti-CD19 antibodies of the present invention. For example, cell surface CD19 expression and B cell clearance in hCD19tg mice treated with an anti-CD19 antibody of the present invention or isotype-matched control antibody (250 µg) in vivo can be studied as a function of time. Thus, spleen B cells can be harvested and assayed for CD19 at time zero (prior to anti-CD19 administration), and at 1, 4, and 24 hours post-antibody administration. Isolated B cells may also be treated in vitro with saturating concentrations of each anti-CD19 antibody plus isotype-specific secondary antibody in vitro with flow cytometry analysis to visualize total cell surface CD19 expression. Where CD19 on the surface of B cells is maintained, it will indicate continued susceptibility to ADCC, CDC, and apoptosis. If CD19 persists on the cell surface following binding of an anti-CD19 antibody, the B cell will remain accessible to the ADCC, CDC, or apoptotic activity. Such results would demonstrate, in part, why the anti-CD19 antibodies and treatment regimens of the invention will be efficacious in providing therapy for human B cell disorders and diseases including, but not limited to, transplant rejection and autoimmune diseases and disorders.

7.7. Anti-CD19 Antibody Treatment May Abrogate Humoral Immunity and Autoimmunity In the event CD19 therapy decreases B cell representation, then the assays described in this example can be used to demonstrate that the anti-CD19 antibodies of the invention are capable of eliminating or attenuating immune responses. These assays can also be used to identify other anti-CD19 antibodies that can be used to engineer chimeric, human or humanized anti-CD19 antibodies using the techniques described above. Such antibodies can in turn be used in the compositions and methods of the invention for the treatment of autoimmune diseases and disorders in humans, as well as for transplantation therapy.

The effect of anti-CD19 antibody-induced B cell depletion on serum antibody levels can be assessed by giving hCD19tg mice a single injection of anti-CD19 antibody and then assessing the reduction in immunoglobulin levels in those mice. For example, two-month-old littermates can be treated with a single injection of an anti-CD19 antibody of the present invention or a control antibody (e.g. 250 µg) on day 0. Antibody levels are then determined by ELISA. It is expected that the results will show that after 1 to 2 weeks, serum IgM, IgG2b, IgG3, and IgA antibody levels are significantly reduced, and remain reduced for at least 10 weeks.

The influence of B cell depletion on T cell-independent type 1 (TI-1) and type 2 (TI-2) antibody responses may also be assessed by immunizing hCD19tg mice with TNP-LPS or DNP-Ficoll (at day zero), 7 days after anti-CD19 antibody or control antibody treatment. Significant hapten-specific IgM, IgG, and IgA antibody responses are expected not to be observed in anti-CD19 antibody-treated mice immunized with either antigen. Antibody responses to the T cell-dependent (TD) Ag, DNP-KLH, may also be assessed using mice treated with anti-CD19 antibody 7 days before immunization, where it is expected that DNP-KLH immunized mice treated with anti-CD19 antibody will show reduced humoral immunity.

7.8. Anti-CD19 Antibody Treatment in Conjunction with Anti-CD22 Antibody Treatment The assay described herein can be used to determine whether combination therapies, e.g., anti-CD19 antibodies in combination with chemotherapy, toxin therapy or radiotherapy, have beneficial effects, such as an additive or more that additive depletion in B cells. The results of combination therapies tested in animal models can be correlated to humans by means well-known in the art.

Anti-CD20 antibodies are effective in depleting human and mouse B cells in vivo. Therefore, the benefit of simultaneous treatment with an anti-CD19 antibody of the present invention and anti-CD20 (e.g., MB20-11; see, Yazawa et al., *Proc Natl Acad Sci USA*. 102(42):15178-83 (2005)) antibodies can be assessed to determine whether this will enhance B cell depletion. Mice can be treated with suboptimal doses (e.g. 2 µg, 5 µg, 10 µg, 20 µg, or 50 µg) of each antibody either individually, or as a combination of both antibodies. It is expected that the results will demonstrate that simultaneous anti-CD19 and anti-CD20 antibody treatments are beneficial. In a similar manner, the efficacy may be determine for treatment with a combination of an anti-CD19 antibody of the present invention with an anti-CD22 antibody, or a combination of an anti-CD19 antibody of the present invention, an anti-CD20 antibody, and an anti-CD22 antibody.

7.9. Therapeutic Efficacy of Subcutaneous (S.C.) Administration of an Anti-CD19 Antibody of the Invention The assay described herein can be used to determine whether a subcutaneous route of administration of an anti-CD19 antibody of the invention can effectively deplete B cells. The results of the efficacy of different delivery routes tested in animal models can be correlated to humans by means well-known in the art.

For example, hCD19tg mice can be treated with an anti-CD19 antibody of the invention at 250 µg either by subcutaneous (s.c.), intraperitoneal (i.p.) or intravenous (i.v.) administration. Values are determined for the mean (±SEM) blood (per mL), bone marrow, spleen, lymph node, and peritoneal cavity B220$^+$ B cell numbers on day seven as assessed using flow cytometry. Results are expected to demonstrate that subcutaneous (s.c.), intraperitoneal (i.p.) and intravenous (i.v.) administration of an anti-CD19 antibody of the invention will effectively deplete circulating and tissue B cells in vivo.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

7.10. Anti-CD19 Antibodies Reduce Tumor Growth in an in vivo Lymphoma Model

Anti-CD19 antibodies of the invention, which bind to human CD19, may be assessed for their ability to reduce tumor growth in in vivo animal models. For example, SCID mice would be injected with human lymphoma cell lines to establish a tumor xenograft (e.g., s.c. injection of Raji cells). Subsequently, the mice would be given several doses of an anti-CD19 antibody of the invention (e.g., 100 µg antibody/mouse 5 times). Tumor growth would be followed using standard methods (e.g., tumor volume, animal weight, paralysis) The effect of anti-CD19 treatment on tumor growth may be determined by comparing animals receiving anti-CD19 or control antibody treatment. The results obtained using anti-CD19 antibodies identified as capable of reducing tumor growth can be correlated to use in humans, and antibodies capable of reducing tumor growth can be used in the compositions and methods of the invention for the treatment of human B cell disorders and disease including, but not limited to, B cell malignancies.

To determine whether an anti-CD19 antibody's ability to reduce tumor growth is dependent on CD19 density, tumor cell lines with different CD19 expression profiles may be tested in the above described in vivo tumor growth assay. For example, Daudi, Raji, Namalwa, and Ramos cells all have significant levels of CD19 on their cell surface; RPMI 8226 multiple myeloma cell line on the other hand does not express CD19. The results obtained may demonstrate whether human CD19 density on the tumor cell surface can influence the tumor growth reducing activity of an anti-CD19 antibody. The results can be correlated to treatment of human patients with varying levels of CD19 expression. Thus, the methods for examining CD19 presence and density, described herein, can be used in human subjects to identify patients or patient populations for which certain anti-CD19 antibodies can reduce the growth of malignant B cells and/or to determine suitable dosages.

To determine whether an anti-CD19 antibody's ability to reduce tumor growth is dependent FcγR, the above described in vivo tumor growth assay would be performed using SCID mice with compromised Fcγ receptor activity (e.g., FcRγ$^{-/-}$). Through a process of interbreeding SOD mice with mice lacking expression of certain FcγR, SCID mice can be generated that also lack expression of certain FcγR (e.g., SCID, FcRγ$^{-/-}$ mice). Such mice can be used in assays to assess the ability of anti-CD19 antibodies to reduce tumor growth through pathways that involve FcγR expression, e.g., ADCC. Based on the results, anti-CD19 antibodies with increased ADCC can be engineered using the techniques described above. Such antibodies can in turn be used in the compositions and methods of the invention for the treatment of human B cell disorders and diseases including, but not limited to, B cell malignancies.

Following are the details of experiments demonstrating the ability of 3649 humanized anti-CD19 antibody to reduce tumor growth in an in vivo animal model. On day 1 of the experiment, 4-6 weeks old female CB-17 SCID mice are injected s.c. with 5×10$^6$Raji human lymphoma cells in their hind flank. Raji cells express significant levels of CD19 on their surface and are sensitive to 3649 directed ADCC (see, FIGS. 7 and 8). Groups of 10 Raji cells injected animals are treated with a humanized anti-CD19 antibody, control anti-CD20 antibody, isotype control antibody of irrelevant specificity. Multiple different doses of an antibody may be tested side by side. A non-limiting example for treatment schedule is 5 bi-weekly i.p. doses of 10 mg/kg antibody starting on day 4. An additional control group of animals receiving PBS only is included as well. Tumor volume is measured using standard methods. Animals with tumor volume greater than 2000 mm$^3$ or with significant signs of morbidity are humanely euthanized. Tumor growth is plotted over time.

In the experiment summarized in FIG. 13, ten Raji cell injected animals each were treated with 5 bi-weekly i.p. doses of 10 mg/kg (i) anti-CD20 antibody, (ii) 3649-TM Fc variant with reduced ADCC, (iii) 3649 antibody, or (iv) R347 control antibody starting on day 4. An additional control group of 10 animals received PBS only. Treatment with 3649 anti-CD19 antibody and positive control anti-CD20 antibody significantly reduced tumor growth. The standard deviation in tumor size for the groups receiving 3649 or anti-CD20 antibody increased with time because of the presence of completely tumor free individuals in both treatment groups. The 3649-TM Fc variant did not have a significant effect on tumor growth, suggesting that the tumor growth reducing effect of 3649 humanized anti-CD19 antibody is mediated through ADCC.

In the experiment summarized in FIG. 14, ten Raji cell injected animals each were treated with 5 bi-weekly i.p. doses of (i) anti-CD20 antibody at 10 mg/kg (anti-CD20), (ii) 3649-TM Fc variant with reduced ADCC at 10 mg/kg (3649TM), (iii) 3649 antibody at 10 mg/kg (3649), (iv) 3649 antibody at 2.5 mg/kg (3649*) or (v) R347 control antibody at 10 mg/kg starting on day 4. Treatment with 3649 anti-CD19 antibody, 3649-3M human ADCC enhanced anti-CD-19 antibody and positive control anti-CD20 antibody significantly reduced tumor growth. The 3649-TM Fc variant anti-CD19 antibody did not have a significant effect on tumor growth, suggesting that the tumor growth reducing effect of 3649 is mediated through ADCC.

In the experiment summarized in FIG. 30, ten Raji cell injected animals each were treated with 5 bi-weekly i.p. doses of (i) anti-CD20 antibody at 10 mg/kg (anti-CD20), (ii) 3649 antibody at 10 mg/kg (3649), (iii) afucosylated 3649 antibody at 2.5 or 10 mg/kg (3649-aFuc) or (iv) R347 control antibody at 10 mg/kg starting on day 4. Treatment with 3649 anti-CD19 antibody, 3649-aFuc anti-CD-19 antibody and positive control anti-CD20 antibody significantly reduced tumor growth.

7.11. Affinity Matured 3649 Anti-CD19 Antibodies

The following sections describe the identification of affinity matured CDR variants of the 3649 anti-CD19 antibody that display an increased binding affinity towards cell surface displayed human CD19 antigen compared to the parental 3649 anti-CD19 antibody. The section also describes the in vitro characterization of the affinity matured anti-CD19 antibodies.

7.11.1. Identification Of 3649 Variant Antibodies with Increased Affinity.

3649 variant anti-CD19 antibodies were identified by screening Fab fragment libraries comprising variant CDR sequences (see, US Patent Application Publication No. US2006/0121042; Wu, H., *Methods Mol Biol.*, 207:197-212 (2003); Wu & An, *Methods Mol Biol.*, 207:213-33 (2003); Wu et al., *J. Mol. Biol.*, 350:126-144 (2005); Wu et al., *Proc. Natl. Acad. Sci. USA* 95:6037-6042 (1998)).

Reagents: All chemicals were of analytical grade. Restriction enzymes, DNA-modifying enzymes, T4 ligase and T7 DNA polymerase were purchased from New England Biolabs, Inc. (Beverly, Mass.). Custom oligonucleotides were synthesized by Operon (Huntsville, Ala.). Streptavidin magnetic beads were purchased from Dynal (Lake Success, N.Y.).

Construction of 3649 Fab phage expression vector: Polynucleotides encoding the VH and VK domains of 3649 anti-CD19 antibody were cloned into an M13-based phage expression vector that facilitates the expression of Fab fragments under the control of the lacZ promoter (Dall'Acqua et al., *Methods* 36:43-60 (2005)). The vector comprises the first constant region of the human γ1 heavy chain, the constant domain of a human kappa (K) light chain and two annealing sites for the cloning of VH and VK genes. Cloning was carried out by hybridization mutagenesis (Kunkel et al., *Proc. Natl. Acad. Sci. USA* 82: 4778-82 (1985)) as described in Wu & An, *Methods Mol Biol.*, 207:213-33 (2003). Briefly, polynucleotides encoding the VH and VK region of 3649 were amplified using approximately 0.5 pmol of each of the following gene-specific oligonucleotide primers: 3649 VH Fab Fw (SEQ ID NO:128), 3649 VH Fab Rev (SEQ ID NO:129), 3649 VK Fab Fw (SEQ ID NO:130), and 3649 VK Fab Rev (SEQ ID NO:131) (see Table 32). The 5' nucleotide sequence of each primer comprises M13 vector specific sequences to allow for annealing between the PCR products and the single stranded vector. The nucleotide sequence of 3649 VH Fab Fw (SEQ ID NO:128) and 3649 VK Fab Fw (SEQ ID NO:130) primers comprises a 28/25 nucleotide sequence, respectively, corresponding to the M13 gene 3 leader sequence. The 5' nucleotide sequence of 3649 VH Fab Rev (SEQ ID NO:129) and 3649 VK Fab Rev (SEQ ID NO:131) primers comprises a 28/30 nucleotide sequence corresponding to the first constant region of the human γ1 heavy chain and the constant domain of a human kappa (κ) light chain, respectively. Forward primers 3649 VH Fab Fw (SEQ ID NO:128) and 3649 VK Fab Fw (SEQ ID NO:130) were biotinylated to aid the isolation of the minus strand of the PCR fragments. Polynucleotides encoding the 3649 VH and VK genes were PCR amplified from the corresponding 3649 IgG expression constructs described above using the 3649 VH Fab Fw (SEQ ID NO:128)/3649 VH Fab Rev (SEQ ID NO:129) and 3649 VK Fab Fw (SEQ ID NO:130)/3649 VK Fab Rev (SEQ ID NO:131) primer combinations, respectively. PCR products were purified by agarose gel electrophoresis/electroelution, and subsequently phosphorylated using T4 polynucleotide kinase (Roche). The minus strand of the PCR fragments was isolated by dissociating the double-stranded PCR product with sodium hydroxide, depleting the plus biotinylated strand using streptavidin-coated magnetic beads, and recovering the minus strands by ethanol precipitation. Equimolar amounts of the isolated minus strand of VH and VK PCR fragments were annealed to the uridinylated single strand M13 MD 101-5A template, and treated with T4 DNA polymerase (Roche), T4 DNA ligase (Roche) following the manufacturer's instructions. The M13 specific nucleotide sequences incorporated into the isolated VH and VK minus strand polynucleotides specifically anneal them to two separate regions of the M13 vector DNA, each of which contain a palindromic loop comprising a recognition site for the Xba I restriction endonuclease. Because the palindromic loops self anneal even in the presence of annealed VH or VK sequences, XbaI digestion of the annealed, T4 DNA polymerase/T4 DNA ligase treated DNA complexes allows for the selection of newly synthesized minus vector strands comprising both VH and VK domains fused in frame with the human kappa K constant and first human γ1 constant regions, respectively, at the expense of the digested parental template plus strand. The reaction product was digested with XbaI, heat inactivated and electroporated into DH10B cells. Transformed DH10B cells were titered on bacterial plates with an *Escherichia coli* XL-1 Blue lawn. Phage DNA isolated from several independent plaques was sequenced to aid the identification of a clone encoding the 3649 Fab fragment.

TABLE 32

PCR primers used to generate 3649 VH and VK encoding polynucleotides used for hybridization mutagenesis. 3649 specific residues are underlined.

| Name | | SEQ ID NO |
|---|---|---|
| 3649 VH M13 Fw | GCTGGTGGTGCCGTTCTATAGCCATAGC<u>GAG GTGCAGCTGGTGGAGTCTGG</u> | 128 |
| 3649 VH M13 Rev | GGAAGACCGATGGGCCCTTGGTGGAGGC<u>TGA GGAGACGGTGACCAGGGTTCCTTG</u> | 129 |
| 3649 VK M13 Fw | GGTCGTTCCATTTTACTCCCACTCC<u>GAAATTG TGCTGACTCAGTCTCCAGACTTTCAG</u> | 130 |
| 3649 VK M13 Rev | GATGAAGACAGATGGTGCAGCCACAGTAC<u>GT TTGATCTCCACCTTGGTCCCTCCGCCGAACG</u> | 131 |

Generation of single CDR focused Fab libraries: Two separate single amino acid substitution libraries were prepared for each of the six CDR regions of the 3649 antibody. The "NSS" libraries comprised all possible single amino acid substituted variants of a given CDR wherein the substitute amino acid is any one of eight amino acids encoded by the NSS degenerate codon. The "NWS" libraries comprise all possible single amino acid substituted variants of a given CDR wherein the substitute amino acid is any one of twelve amino acids encoded by the NWS degenerate codon. Individual libraries were prepared by hybridization mutagenesis of the 3649 Fab encoding phage vector described above (Kunkel et al., *Proc. Natl. Acad. Sci. USA* 82: 4778-82 (1985); Wu & An, *Methods Mol Biol.*, 207:213-33 (2003)). Briefly, two sets of degenerate minus strand oligonucleotides were prepared for each of the six CDRs. The "NSS" and "NWS" sets comprised all possible single codon substitutions of a CDR region with the NSS and NWS, respectively, degenerate codon. The oligonucleotide sets used for the preparation of the heavy chain CDR1 focused libraries are listed in Table 33 as an example. Each degenerate minus strand oligonucleotide was phosphorylated prior to annealing at a 10:1 molar ratio to a uridinylated single stranded 3649 Fab phage template DNA. The temperature of the annealing reaction was lowered from 95° C. to 55° C. over 1 hour. T4 ligase and T7 DNA polymerase was added to the annealed material and incubated for 1.5 hours at 37° C. The final negative strand synthesis products obtained using different oligonucleotides from a single CDR specific set were pooled; the NSS and NWS pools, however, were maintained separately and screened independently. Typically, one µl of the pooled negative strand synthesis reaction was electroporated into XL1-Blue for plaque formation on XL1-Blue bacterial lawn. Individual phage clones are eluted 200 µl of 10 mM Tris (pH 7.4), 100 mM NaCl buffer and stored at 4° C. The library may be characterized by sequencing 24 randomly selected phage clones to determine the distribution of mutations within the CDR as well as to calculate the mutagenesis rate.

achieved by screening 5×8×2=80 randomly selected individual clones. In the experiment described herein ~400 clones were screened, however, for each library regardless of the CDR length, or synthesis efficiency. Supernatant of small scale phage cultures were isolated as described in Wu & An, *Methods Mol Biol.*, 207:213-33 (2003). Briefly, 0.75 mL of exponentially growing TG1 cells are inoculated with 75 µl of eluted phage stock in the presence of 0.5 mM IPTG and incubated at 37° C. for 1 hr in 96-well plates. The plate cultures are moved to room temperature and grown overnight on an orbital shaker. Bacteria from 0.36 ml of the overnight cultures is collected by filtration through a low protein binding nylon membrane (e.g., Silent screen plate from Nalgene) and treated on the filter with 200 µl of TES buffer (30 mM Tris pH 8.0, 2 mM EDTA, 20% sucrose) with 2 mg/ml lysozyme for 10 minutes at room temperature to release the secreted Fab from the periplasmic space. Fab fragment containing extracts are collected by filtration. Fab fragment concentration in the extract is determined using standard assays. 300B4 cell based ELISA was performed as described supra. The parental 3649 Fab expressing phage clone was included in the cell based ELISA assays as a positive control. Relative binding affinity of variant Fab fragments was compared by plotting the ELISA signal against Fab concentration. For example, FIG. 18 shows the results obtained with 3649 variant Fabs comprising a random single amino acid substitution within VH

TABLE 33

Oligonucleotides used for the generation of 3649 heavy chain CDR1 focused libraries. The NSS and NWS codon comprising oligonucleotides were used for the generation of the separate "NSS" and "NWS" libraries. Nucleotides encoding CDR residues are underlined.

| Name | | SEQ ID NO |
|---|---|---|
| HCDR1/NSS1 | GCCTGGCGGACCCASSNCATCCAAGAGCTACTGAAGGTGAATCCAG | 132 |
| HCDR1/NSS2 | GCCTGGCGGACCCAGTTSSNCCAAGAGCTACTGAAGGTGAATCCAG | 133 |
| HCDR1/NSS3 | GCCTGGCGGACCCAGTTCATSSNAGAGCTACTGAAGGTGAATCCAG | 134 |
| HCDR1/NSS4 | GCCTGGCGGACCCAGTTCATCCASSNGCTACTGAAGGTGAATCCAG | 135 |
| HCDR1/NSS5 | GCCTGGCGGACCCAGTTCATCCAAGASSNACTGAAGGTGAATCCAG | 136 |
| HCDR1/NWS1 | GCCTGGCGGACCCAWSNCATCCAAGAGCTACTGAAGGTGAATCCAG | 137 |
| HCDR1/NWS2 | GCCTGGCGGACCCAGTTWSNCCAAGAGCTACTGAAGGTGAATCCAG | 138 |
| HCDR1/NWS3 | GCCTGGCGGACCCAGTTCATWSNAGAGCTACTGAAGGTGAATCCAG | 139 |
| HCDR1/NWS4 | GCCTGGCGGACCCAGTTCATCCAWSNGCTACTGAAGGTGAATCCAG | 140 |
| HCDR1/NWS5 | GCCTGGCGGACCCAGTTCATCCAAGAWSNACTGAAGGTGAATCCAG | 141 |

Primary screen of the single CDR focused Fab libraries: The primary screen consisted of a single point ELISA (SPE) performed using the secreted Fab containing supernatant of 1 ml phage cultures and recombinant human CD19 expressing 300B4 cells as a capture agent. An exhaustive screen of a library can usually be achieved by testing a number of individual clones that equals three times the size of the library taking into account the rate of mutagenesis. For example, exhaustion of a VH CDR1 (5 amino acid residues) "NSS" substitution library (8 possible amino acids encoded by the degenerate NSS codon) with a 50% mutagenesis rate may be CDR3. Fabs 4B7 and 4G6 display significantly increased binding affinity to human CD19 expressing 300B4 cells compared to that of the parental 3649 Fab.

Secondary screen of the single CDR focused Fab libraries: CDR variant Fab clones with a primary screen ELISA signal of at least 10% higher than that of the 3649 parental Fab were re-grown at a 15 ml scale, and re-assayed by the same 300B4 cell based ELISA in duplicate wells to confirm the positive result. 15 ml scale Fab extract were prepared following the protocol described in Wu, H., *Methods Mol Biol.*, 207:197-212 (2003). Fab concentration was determined using standard assays. 300B4 cell based ELISA was performed as described supra. The 3649 parental Fab was included in the assay as a positive control. Clones with a secondary screen signal of at least 10% higher than that of the 3649 control Fab were sequenced to determine the identity of single amino acid substitutions leading to increased human CD19 antigen binding. Amino acid substitutions identified by sequencing the isolated affinity improved anti-CD19 Fab clones are listed in Table 34.

TABLE 34

List of beneficial single amino acid substitutions isolated from the single CDR focused Fab libraries. Amino acid positions are numbered according to Kabat.

|  | Clone | Substitution | Position |
|---|---|---|---|
| VH CDR1 | 2A11 | Ser > Thr | 32 |
|  | 1H1 | Trp > Glu | 33 |
|  | 5H12 | Trp > Leu | 33 |
|  | 1A8 | Asn > Phe | 35 |
|  | 1C5 | Asn > Tyr | 35 |
|  | 3C3 | Asn > Asp | 35 |
|  | 6H6 | Asn > Leu | 35 |
| VH CDR2 | 3A11 | Thr > Ser | 57 |
|  | 4G8 | Thr > Pro | 57 |
|  | 3E9 | Thr > Asn | 57 |
|  | 4D4 | Asn > Leu | 60 |
|  | 5A11 | Asn > Tyr | 60 |
|  | 2H11 | Gly > Ala | 61 |
| VH CDR3 | 4B7 | Leu > Arg | 100B |
|  | 7E3 | Leu > His | 100B |
|  | 12E3 | Leu > Phe | 100B |
|  | 7H11 | Leu > Tyr | 100B |
|  | 11G12 | Thr > Pro | 99 |
| VL CDR1 | 8A10 | Asp > Ile | 27C |
|  | 9D11 | Thr > His | 27D |
|  | 2B8 | Ile > Leu | 30 |
|  | 1C10 | Met > Arg | 33 |
|  | 1H10 | Met > Thr | 33 |
|  | 12E3 | Met > Ile | 33 |
| VL CDR2 | 10D3 | Ala > Tyr | 50 |
|  | 10G4 | Ala > Glu | 50 |
|  | 2C12 | Gln > Thr | 54 |
|  | 4F10 | Gln > Pro | 54 |
|  | 9B10 | Gly > Tyr | 55 |

TABLE 34-continued

List of beneficial single amino acid substitutions isolated from the single CDR focused Fab libraries. Amino acid positions are numbered according to Kabat.

|  | Clone | Substitution | Position |
|---|---|---|---|
| VL CDR3 | 2F7 | Ser > Thr | 91 |
|  | 6E10 | Phe > Ile | 96 |
|  | 2C12 | Phe > Asn | 96 |

Generation of combinatorial Fab library: Two combinatorial libraries comprising all possible combinations of beneficial single amino acid substitutions identified from the CDR focused libraries were generated by hybridization mutagenesis. The first combinatorial library was generated using a set of degenerate oligonucleotides that encoded both the parental 3649 residues as well as the identified beneficial single amino acid substitutions (Table 35). A second combinatorial library was generated using a separate set of degenerate oligonucleotides that encodes only the most beneficial single amino acid substitution residues but not the 3649 parental residues (Table 36). The two libraries were generated and screened separately. Library generation was done as described in Wu, H., Methods Mol Biol., 207:197-212 (2003); Wu & An, Methods Mol Biol., 207:213-33 (2003). Briefly, degenerate primer sets were synthesized and phosphorylated. Hybridization mutagenesis was performed by using all primers in a single annealing and synthesis reaction. Library generation, testing and screening was performed as described supra. The ELISA profile of the six combinatorial Fab clones with the highest binding affinity for human recombinant CD19 expressing 300B4 cells is shown in FIG. 19. Clone 7E12 was recovered from the first combinatorial library generated with degenerate oligonucleotides encoding both the parental and beneficial CDR substitution residues. Clones 14H5, 15D7, 15D1, 16C9, and 16C4 were recovered from the second combinatorial library generated with degenerate oligonucleotides encoding only the most beneficial CDR substitution residues. All phage clones listed in FIG. 19 were sequenced to determine the amino acid sequence of the variant CDR regions with increased human CD19 binding affinity.

TABLE 35

Degenerate oligonucleotides for combinatorial phage library generation. The oligonucleotide set listed herein encodes both the parental residues and the beneficial substitution residues identified from the CDR focused single substitution libraries.

| Name | | SEQ ID NO. |
|---|---|---|
| H1CDR1H | CTGGCGGACCCAGTHCATCMAAGWGCTACTGA AGGTGAATCC | 142 |
| H2CDR1HP3E | CTGGCGGACCCAGTHCATCTCAGWGCTACTGA AGGTGAATCC | 143 |
| H3CDR1HP3WP4L | CTGGCGGACCCAGAGCATCMAAGWGCTACTGA AGGTGAATCC | 144 |
| H4CDR1HP3EP4L | CTGGCGGACCCAGAGCATCTCAGWGCTACTGA AGGTGAATCC | 145 |
| H5CDR2H | CTGCCCTTGAACTTCSCATWGTAGTTAGDATCT CCATCTCCAG | 146 |
| H6CDR2HP9N | CTGCCCTTGAACTTCSCATWGTAGTTATTATCTC CATCTCCAG | 147 |
| H7CDR2HP12L | CTGCCCTTGAACTTCSCAAGGTAGTTAGDATCT CCATCTCCAG | 148 |

TABLE 35-continued

Degenerate oligonucleotides for combinatorial phage library generation. The oligonucleotide set listed herein encodes both the parental residues and the beneficial substitution residues identified from the CDR focused single substitution libraries.

| Name | | SEQ ID NO. |
|---|---|---|
| H8CHR2HP9N,P12L | CTGCCCTTGAACTTCSCAAGGTAGTTATTATCTC CATCTCCAG | 149 |
| H9CDR3HP8H/Y | CCCAGTAGTCAAAGTCGTRAACCGTAGKAATA AATCCTGATCTAGC | 150 |
| H10CDR3HP8F | CCCAGTAGTCAAAGTCSAAAACCGTAGKAATA AATCCTGATCTAGC | 151 |
| H11CDR3HP8R | CCCAGTAGTCAAAGTCTCGAACCGTAGKAATA AATCCTGATCTAGC | 152 |
| L12aCDR1Lp7Ip8H | CTGCTGGAACCAGTTYVTAAAACTAAKGCCAA AATGAATAACACTTTCGCTGGC | 153 |
| L13aCDR1Lp8H | CTGCTGGAACCAGTTYVTAAAACTAAKGCCAA AATGATCAACACTTTCGCTGGC | 154 |
| L14aCDR1Lp7I | CTGCTGGAACCAGTTYVTAAAACTAAKGCCAA AAGTAATAACACTTTCGCTGGC | 155 |
| L15aCDR1Lp11p14 | CTGCTGGAACCAGTTYVTAAAACTAAKGCCAA AAGTATCAACACTTTCGCTGGC | 156 |
| L16CDR2Lp1Y | GGGGACCCCGGATCCTTGATTGGATGCATAATG GATGAGGAGCTTTGG | 157 |
| L17CDR2Lp1Yp6Y | GGGGACCCCGGAGTATTGATTGGATGCATAATG GATGAGGAGCTTTGG | 158 |
| L18CDR2Lp1Yp5T/P | GGGGACCCCGGATCCTGKATTGGATGCATAATG GATGAGGAGCTTTGG | 159 |
| L19CDR2Lp1E/A | GGGGACCCCGGATCCTTGATTGGATGCCKCATG GATGAGGAGCTTTGG | 160 |
| L20CDR2Lp1E/Ap6Y | GGGGACCCCGGAGTATTGATTGGATGCCKCATG GATGAGGAGCTTTGG | 161 |
| L21CDR2Lp1E/Ap5T/P | GGGGACCCCGGATCCTGKATTGGATGCCKCATG GATGAGGAGCTTTGG | 162 |
| L22CDR3Lp3T/Sp8F/T | CTCCGCCGAACGTGAWTGGAACCTCCTTAGWT TGCTGACAGTAATACG | 163 |
| L23CDR3Lp3T/Sp8N | CTCCGCCGAACGTGTTTGGAACCTCCTTAGWTT GCTGACAGTAATACG | 164 |

TABLE 36

Degenerate oligonucleotides for combinatorial phage library generation. The oligonucleotide set listed herein encodes only the most beneficial substitution residues identified from the CDR focused single substitution libraries.

| Name | | SEQ ID NO. |
|---|---|---|
| L24CDR1Lp7Ionly | AACTAATGCCAAAaGTAatAACACTTTCGCTGG CTCTG | 165 |
| L25CDR1Lp7Ip9Honly | CATAAAACTAATGCCAAAatgAatAACACTTTC GCTGGCTCTGCAGG | 166 |
| L26CDR1Lp8Honly | CCAGTTCATAAAACTAATGCCAAAatgATCAA CACTTTCGCTGGCTC | 167 |

TABLE 36-continued

Degenerate oligonucleotides for combinatorial phage library generation. The oligonucleotide set listed herein encodes only the most beneficial substitution residues identified from the CDR focused single substitution libraries.

| Name | | SEQ ID NO. |
|---|---|---|
| L27CDR2Lp1Eonly | GGATCCTTGATTGGATGCctCATGGATGAGGAGCTTTGG | 168 |
| L28CDR3Lp8I/Nonly | GTCCCTCCGCCGAACGTGwtTGGAACCTCCTTACTTTGC | 169 |
| H29CDR1Hp3Eonly | CCTGGCGGACCCAGTTCATCtcAGAGCTACTGAAGGTGAATCC | 170 |
| H30CDR1Hp3Ep5Yonly | CCTGGCGGACCCAGTaCATCtcAGAGCTACTGAAGGTGAATCC | 171 |
| H31CDR1Hp5Yonly | CCTGGCGGACCCAGTaCATCCAAGAGCTACTGAAGGTGAATCC | 172 |
| H32CDR2Hp13Aonly | GAATCTGCCCTTGAACTTCgCATTGTAGTTAGTATCTCCATC | 173 |
| H33CDR3Hp8Ronly | CTTGGCCCCAGTAGTCAAAGTCTcgAACCGTAGTAATAAATCCTG | 174 |
| H34CDR3Hp8R/Honly | CTTGGCCCCAGTAGTCAAAGTCgygAACCGTAGTAATAAATCCTG | 175 |

7.11.2. Characterization of Increased Affinity Variant Anti-CD19 Antibodies

Polynucleotides encoding the variable regions of 7E12, 14H5, 15D7, 15D1, 16C9, and 16C4 Fab variants with improved anti-CD19 binding activity were PCR-amplified from the corresponding V region-encoding M13 phage vectors using pfu DNA polymerase (see, Dall'Acqua et al., *Methods* 36:43-60 (2005)). The polynucleotides were then individually cloned into mammalian expression vectors encoding a human cytomegalovirus major immediate early (hCMVie) enhancer, promoter and 5'-untranslated region (M. Boshart, et al., *Cell* 41:521-530 (1985)). In this system, a human γ1 chain is secreted along with a human κ chain (S. Johnson, et al., *Infect. Dis.* 176:1215-1224 (1997)). The different constructs were expressed transiently in HEK-293 cells and harvested 72 and 144 hours post-transfection. The secreted, soluble human IgG1s were purified from the conditioned media directly using 1 ml HiTrap protein A columns according to the manufacturer's instructions (APBiotech, Inc., Piscataway, N.J.). Purified human IgG1s (typically >95% homogeneity, as judged by SDS-PAGE) were dialyzed against phosphate buffered saline (PBS), flash frozen and stored at −70° C.

7.11.2.1. Cell Based ELISA Assays

The ability of 7E12, 14H5, 15D7, 15D1, 16C9, and 16C4 IgG antibodies to bind human CD19 was assessed in a cell based CD19 binding assays. Three different cell lines were used as capture reagents: (i) human recombinant CD19 expressing 300B4 cells (FIG. 20), (ii) Raji cells (FIG. 21), and (iii) Daudi cells (FIG. 22). All three cell lines were cultured according to standard protocols. A standard ELISA procedure can be used for the cell based CD19 binding assay. For example, individual wells of a 96-well U bottom plate are seeded with 1×10e5 300B4 cells and incubated overnight. Cells are washed once with ELISA buffer prior to incubation on ice with various amounts of anti-CD19 antibodies. Binding reactions are performed in triplicates for each antibody concentration tested. Positive control wells using 3649 anti-CD19 antibody are included in the assay. Following incubation with the antibody, 300B4 cells are washed three times with 200 micro liter of ELISA buffer. Cell surface bound anti-CD19 antibodies are detected using a goat anti-human kappa antibody conjugated with horseradish peroxidase according to standard protocols.

ELISA binding curves of 3649, 7E12, 14H5, 15D7, 15D1, 16C9, and 16C4 anti-CD19 IgG antibodies using 300B4 cells, Raji cells, or Daudi cells as capture reagents are shown in FIGS. 20-22. All of the tested antibodies except for 16C9 and 15D1 display significantly higher binding affinity for cell surface displayed human CD19 than the control 3649 antibodies. The binding affinity of 16C9 and 15D1 matches that of the 3649 antibody when 300B4 cells are used as capture reagent. The binding affinity of 16C9 and 15D1 antibodies to human CD19 is higher than that of the control 3649 antibody when Raji cells or Daudi cells are used as capture reagents.

7.11.2.2. 14H5 Anti-CD19 Antibody Variants with Modified Deamidation Site.

The primary amino acid sequence of the 3649, 7E12, 14H5, 15D7, and 16C9 antibodies comprises an NG (residues 60-61 of VH CDR2) deamidation motif. Three deamidation minus variants of 14H5 were generated by changing the asparagine (N) residue at Kabat position 60 to tyrosine (Y), aspartic acid (D), or leucine (L). The Y60, D60, and L60 comprising 14H5 variant VH regions are designated as 14H5-YG (SEQ ID NO:107), 14H5-DG (SEQ ID NO:108), and 14H5-LG (SEQ ID NO:109), respectively. Antibody expression vectors comprising polynucleotides encoding the deamidation minus 14H5 variants were generated using standard molecular cloning techniques. Transiently expressed 14H5-

YG, 14H5-DG, and 14H5-LG anti-CD19 IgG was purified as described above. The binding affinity of 14H5-YG, 14H5-DG, and 14H5-LG antibodies was ascertained using a cell based ELISA assay utilizing the human recombinant CD10 expressing 300B4 cells as a capture reagent. The 14H5 and 16C4 anti-CD10 antibodies were employed as positive controls. Results obtained are presented in FIG. 23. The binding affinity of 14H5-YG, 14H5-DG, and 14H5-LG antibodies to recombinant human CD19 expressing 300B4 cells is lower than that of either the 14H5 or 16C4 antibodies.

7.11.2.3. Kinetic Off Rate of Affinity Matured Anti-CD19 Antibodies.

The kinetic off rate of 7E12, 14H5, 15D7, 15D1, 16C9, and 16C4 anti-CD19 IgG antibodies was ascertained by following over time the elimination of cell surface bound anti-CD19 antibodies. Briefly, Ramos cells were incubated with the 7E12, 14H5, 15D7, 15D1, 16C9, or 16C4 affinity matured anti-CD19 antibody following standard staining protocols. Cells were washed following the incubation to eliminate any unbound primary antibody and further incubated at 37° C. for 0, 30, or 60 minutes. At the end of the incubation period, cells were stained with an RPE conjugated mouse anti-human IgG Fc fragment secondary reagent following standard protocols and analyzed on a flow cytometer. Control batches of cells were incubated with the 3649 anti-CD19 antibody or a reference control anti-CD20 antibody prior to incubation at 37° C. Mean fluorescence intensity measured at various time points using the different antibodies is displayed in FIG. 24A. 100% mean fluorescence intensity corresponds to the staining intensity seen at time 0 with a given antibody.

Figure 24A:
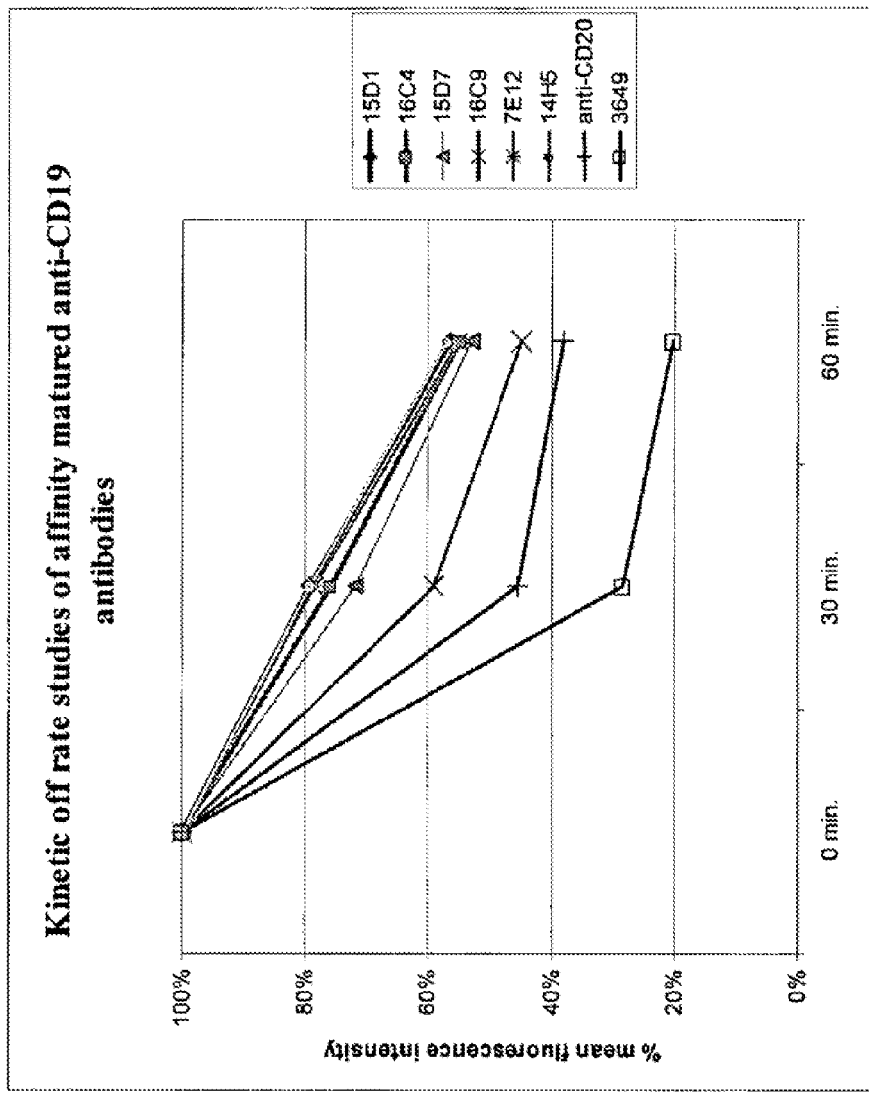

The loss of mean fluorescence intensity observed with the affinity matured 7E12, 14H5, 15D7, 15D1, 16C9, and 16C4 anti-CD19 antibodies is lower than that of observed with the anti-CD20 reference control antibody. In contrast, the 3649 anti-CD19 antibody stained Ramos cells display a faster loss of mean fluorescence intensity that cells stained with the reference control anti-CD20 antibody (FIG. 24A).

Figure 24B:
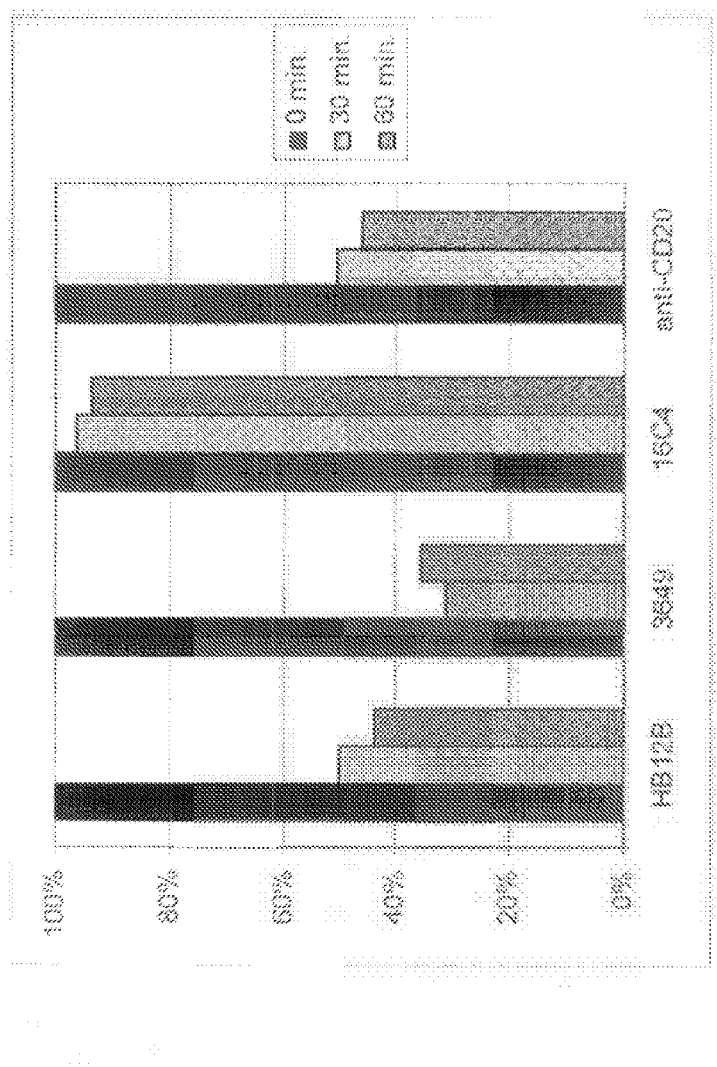

In a separate experiment, Ramos cells were stained with an Alexa 647 conjugated 16C4, 3649, or HB12B anti-CD19 antibody following standard protocols. Following the staining, cells were washed to remove unbound antibody and further incubated at 37° C. for 0, 30, or 60 minutes. Cells were subsequently analyzed on a flow cytometer. A fluorescently conjugated anti-CD20 antibody was included in the experiment as a reference control. Mean fluorescence intensity (MFI) seen at various time points is shown in FIG. 24B. MFI is expressed as a fraction of the MFI value seen at time 0. Loss of MFI detected with the 16C4 affinity matured anti-CD19 antibody is significantly slower than the loss of MFI seen with the 3649 or HB12B anti-CD19 antibodies. The anti-CD20 reference control antibody displays the same off rate as the 3649 and HB12B anti-CD19 antibodies.

7.11.2.4. Cell Surface Staining by Affinity Matured Anti-CD19 Antibodies

Daudi cells were immunostained with 7E12, 14H5, 15D7, 15D1, 16C9, and 16C4 anti-CD19 antibodies and a RPE conjugated goat anti-human IgG (Fab')2 fragment secondary reagent according to standard protocols. Immunostained cells were analyzed on a flow cytometer. Median fluorescence intensity (MFI) of stained cells at various primary antibody concentrations is plotted in FIG. 25. Cells stained with the 3649 anti-CD19 antibody were included as a reference control. Staining intensity detected with 7E12, 14H5, 15D7, 16C9, and 16C4 anti-CD19 antibodies was higher than that of the 3649 antibody stained cells at all concentrations tested. Staining intensity detected with 15D1 was similar to the staining intensity detected with the 3649 antibody at low antibody concentrations (0.5 mg/ml or lower). MFI of 15D1 stained cells was higher, however, than that of the 3649 antibody stained cells at elevated antibody concentrations (1 mg/ml or higher).

7.11.2.5. In vitro ADCC Activity of Affinity Matured Anti-CD19 Antibodies.

In vitro ADCC activity of affinity matured anti-CD19 antibodies was measured using assays described herein. For example, results obtained with 16C4, 14H5, and 14H5-DG antibodies using Daudi target cells are presented in FIG. 26. The 3549 anti-CD19 antibody was used as a reference control. All three affinity matured antibody displayed increased ADCC activity at antibody concentrations of 0.1 mg/ml or less compared to the 3649 reference control antibody. The ADCC activity of 16C4, 14H5, and 14H5-DG antibodies matched the activity of the 3649 antibody at 1 mg/ml or higher antibody concentrations.

In vitro ADCC activity of affinity matured afucosylated anti-CD19 antibodies was also measured using assays described herein. For example, afucosylated 16C4 antibody (16C4-aFuc) mediated ADCC was measured using Daudi target cells (FIG. 26). The experiments also included 16C4, 3649-aFuc, and anti-CD20 antibodies as reference controls. ADCC of 16C4-aFuc is significantly higher than that of the 3649-aFuc, anti-CD20, or fucosylated 16C4 reference antibodies. ADCC mediated by 16C4-aFuc is comparable to that of the antibodies.

In vitro ADCC activity of 16C4, 16C4-aFuc, and 3649-aFuc anti-CD19 antibodies were further characterized in a standardized in vitro ADCC assay using a variety of target cells. An anti-CD20 antibody was included in the assay as a control. Target cells used represent a variety of B cell malignancies as well as different CD19 cell surface densities (Table 37). Relative surface expression of CD19 and CD20 of the target cells was determined by flow cytometry following standard protocols. Table 37 lists the mean fluorescence intensity (MFI) of target cells stained with fluorescently labeled anti-CD20 or 16C4 anti-CD19 antibodies. ADCC reactions were performed following the protocols described above. Reactions were set up in triplicates using 50,000 effector cells and 20,000 target cells to achieve an E:T ratio of 2.5:1. Transgenic NK cells expressing CD16 and associated signaling polypeptide FCεRI-γ served as effector cells. ADCC reactions were allowed to proceed for 4 hours at 37° C. ADCC activity was determined at various antibody concentrations. Data was plotted as % cytotoxicity as a function of antibody concentration. Maximum cell killing and EC50 values (antibody concentrations required for half-maximum cytotoxicity under the conditions used) were established for target cell/antibody combinations using standard methods. Table 37 presents the final results. Oci-LY19, KArpas-422, Nalm-6, and Namalwa cells representing DLCL, NHL, ALL, and Burkitt's lymphoma, respectively, were sensitive to 16C4-aFuc antibody mediated cytotoxicity but largely not sensitive to anti-CD20 mediated ADCC. Daudi, Toledo, RL and Raji cells were significantly more sensitive to 16C4-aFuc antibody mediated cytotoxicity than to anti-CD20 mediated ADCC.

TABLE 37

Quantitative assessment of 16C4, 16C4-aFuc, and 3649-aFuc anti-CD19 antibody mediated ADCC. MFI@1 µg/ml:
mean fluorescence intensity of cells stained with 1 µg/ml fluorescently labeled antibody; ADCC EC50:
antibody concentration yielding half maximum killing under the conditions used; % max, cell kill at 10 µg/ml:
maximum target cell killing achived with 10 ug/ml antibody in the ADCC assay under the conditions used

| | | anti-CD20 MFI @ 1 ug/ml | 16C4 MFI @ 1 ug/ml | anti-CD20 | | 16C4-aFuc | | 3649-aFuc | | 16C4 | |
|---|---|---|---|---|---|---|---|---|---|---|---|
| | | | | ADCC EC50 [ng/ml] | % max. cell kill at 10 ug/ml | ADCC EC50 [ng/ml] | % max. cell kill at 10 ug/ml | ADCC EC50 [ng/ml] | % max. cell kill at 10 ug/ml | ADCC EC50 [ng/ml] | % max. cell kill at 10 ug/ml |
| Target cell lines | Daudi (Burkitt) | 253 | 161 | 0.041 | 51 | 0.0031 | 50 | 0.0576 | 51 | 0.0576 | 16 |
| | Granta-519 (NHL/MCL) | 403 | 75 | 0.0663 | 34 | n.d. | 6 | n.d. | 9 | n.d. | 0 |
| | Toledo (DLCL) | 312 | 472 | 0.0319 | 55 | 0.0075 | 48 | 0.0155 | 53 | 0.0545 | 12 |
| | Oci-LY19 (DLCL) | 12 | 258 | n.d. | 4 | 0.0163 | 47 | 0.0518 | 54 | n.d. | 6 |
| | Karpas-422 (NHL) | 45 | 53 | n.d. | 5 | 0.0181 | 62 | 0.0442 | 64 | n.d. | 6 |
| | Farage (DLCL) | 581 | 226 | 0.0113 | 54 | 0.0141 | 48 | 0.0536 | 48 | 0.0927 | 13 |
| | Nalm-6 (ALL) | 26 | 448 | n.d. | 14 | 0.0199 | 35 | 0.0605 | 39 | n.d. | 17 |
| | Karpas-1106P | 102 | 66 | 0.0137 | 71 | 0.009 | 59 | 0.0142 | 59 | 0.533 | 16 |
| | DB (DLCL) | 70 | 61 | 0.2399 | 46 | n.d. | 34 | n.d. | 42 | n.d. | 6 |
| | RL (NHL) | 261 | 344 | 0.0296 | 56 | 0.0073 | 45 | 0.0194 | 46 | 0.0393 | 15 |
| | Raji (Burkitt) | 422 | 823 | 0.008 | 40 | 0.003 | 43 | 0.009 | 44 | 0.012 | 26 |
| | Namalwa (Burkitt) | 664 | 298 | n.d. | 7 | 0.012 | 23 | 0.04 | 25 | n.d. | 4 |

7.11.2.6. In Vivo B Cell Depletion by Affinity Matured Anti-CD19 Antibodies

Affinity matured anti-CD19 antibodies were tested in a B cell depletion assay essentially as described above. C57B16 hCD19 tg +/− animals were treated with a single i.v. dose of 10, 50, or 250 µg of 16C4 affinity matured anti-CD19 antibody (16C4) or 14H5DG affinity matured anti-CD19 antibody (14H5DG). Reference control animals were treated with (i) 3649 anti-CD19 antibody (3649), (ii) ADCC enhanced Fc variant of 3649 anti-CD19 antibody (3649 3M), and (iii) afucosylated 3649 anti-CD19 antibody (3649-aFuc). Negative control animals were treated with (i) the ADCC compromised Fc variant of 3649 anti-CD19 antibody (3649 TM) or (ii) an antibody of irrelevant specificity (R347). Circulating lymphocytes and splenic lymphocytes were isolated 7 days after antibody treatment. Isolated cells were immunostained as described in Table 5 to identify various B cell populations. Samples were analysed on a flow cytometer following standard protocols.

The 16C4 affinity matured anti-CD19 antibody achieved a slightly higher depletion of B cells than the 3649 anti-CD19 parent antibody. The 3649-aFuc and 3649 3M antibodies achieved better depletion than the 16C4 affinity matured antibody. The 14H5DG affinity matured anti-CD19 antibody is less efficient at depleting B cells than the 3649 anti-CD19 parent antibody.

7.11.2.7. Long Term Recovery of B Lymphocytes Following Administration of a Single Depleting Dose of Affinity Matured Anti-CD19 Antibodies.

Long term recovery of the B cell compartment was studied following the administration of a single depleting dose of 16C4-aFuc anti-CD19 monoclonal antibody. Twenty five C57B16 hCD19 tg +/− mice (13 males, 12 females, 2.5-3 months of age) were divided into 5 groups. A week before administering the experimental antibodies (week −1) the animals were examined for overall health, weighed and a small aliquot of blood was collected for each one of them for analysis. On day 0 of the experiment 250 µg of 16C4-aFuc mAb, 50 µg of 16C4-aFuc mAb, 10 µg of 16C4-aFuc mAb, 250 mg of R347 control antibody of irrelevant specificity, or PBS were administered intravenously to animals in groups 1, 2, 3, 4, and 5, respectively. On day 7 (week 1), and at weekly intervals afterwards, mice in each group were examined and bled. Blood samples were subjected to flow cytometry to determine B cell, T cell, NK T cell, neutrophil, monocyte and dendritic cell numbers. The blood samples were further analysed to determine the serum concentration of IgM, IgG1, IgG2b, IgG2c, IgG3, IgA, anti-dsDNA IgM, anti-dsDNA IgG, anti-ssDNA IgM, anti-ssDNA IgG as well as the serum levels of IL-7, CXCL12, CXCL13 and BAFF. Measurements were performed following standard procedures. The outline of the experiment and results obtained are presented in FIG. 38.

Figure 38A:
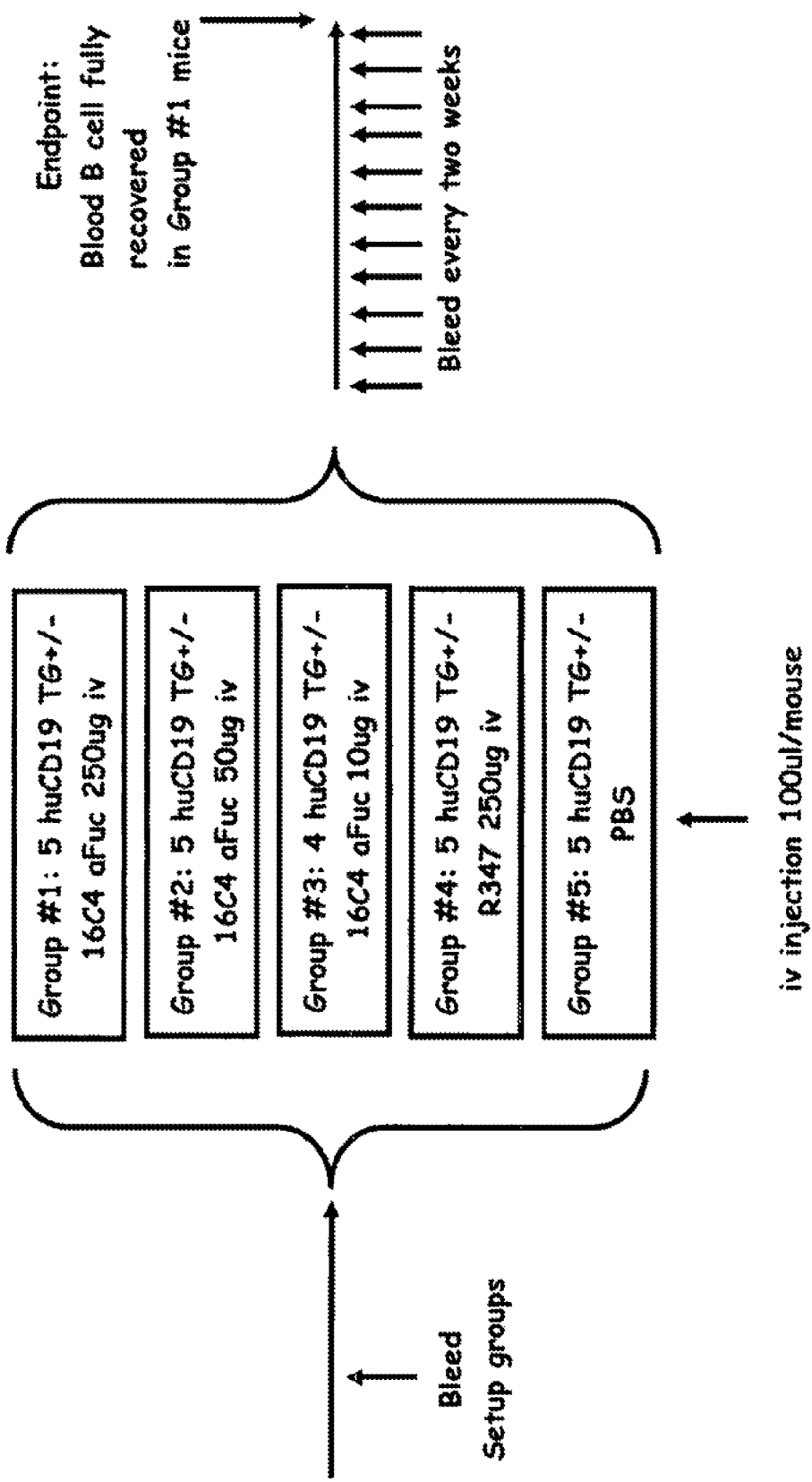
Figure 38B:
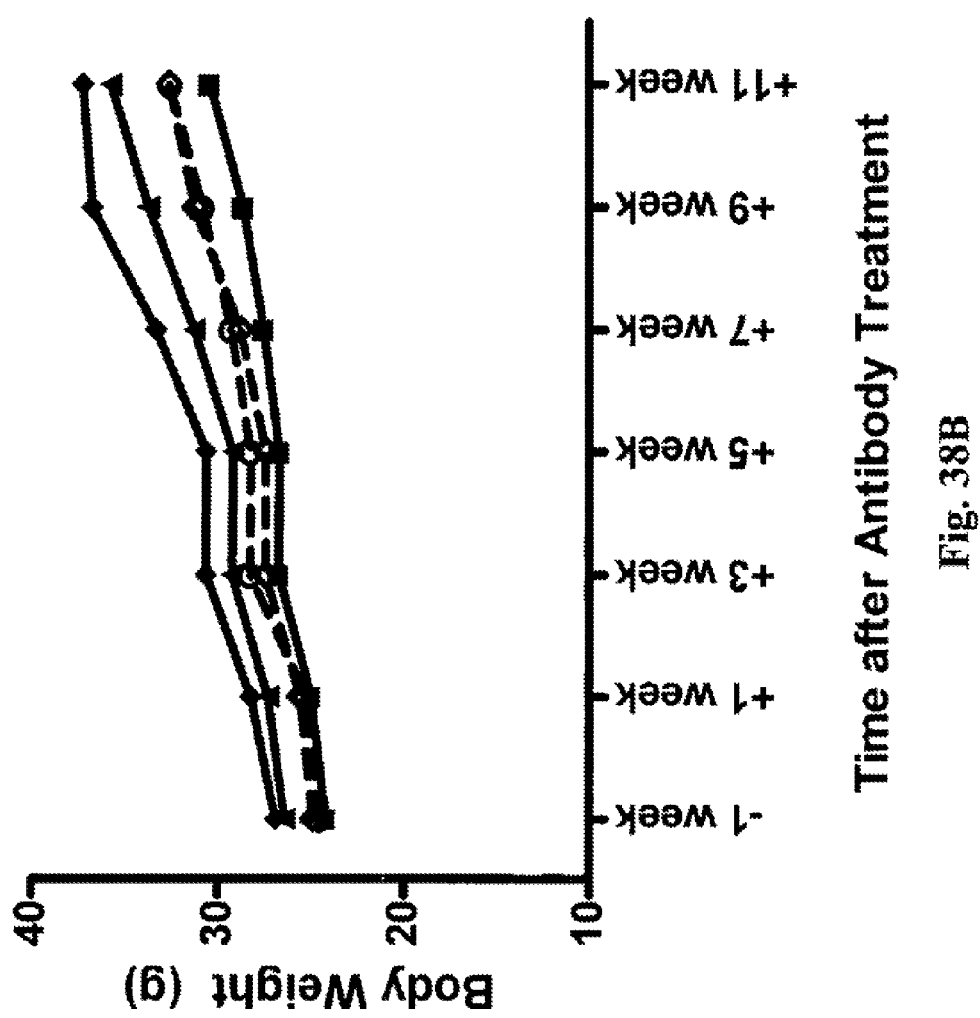
Figure 38C:
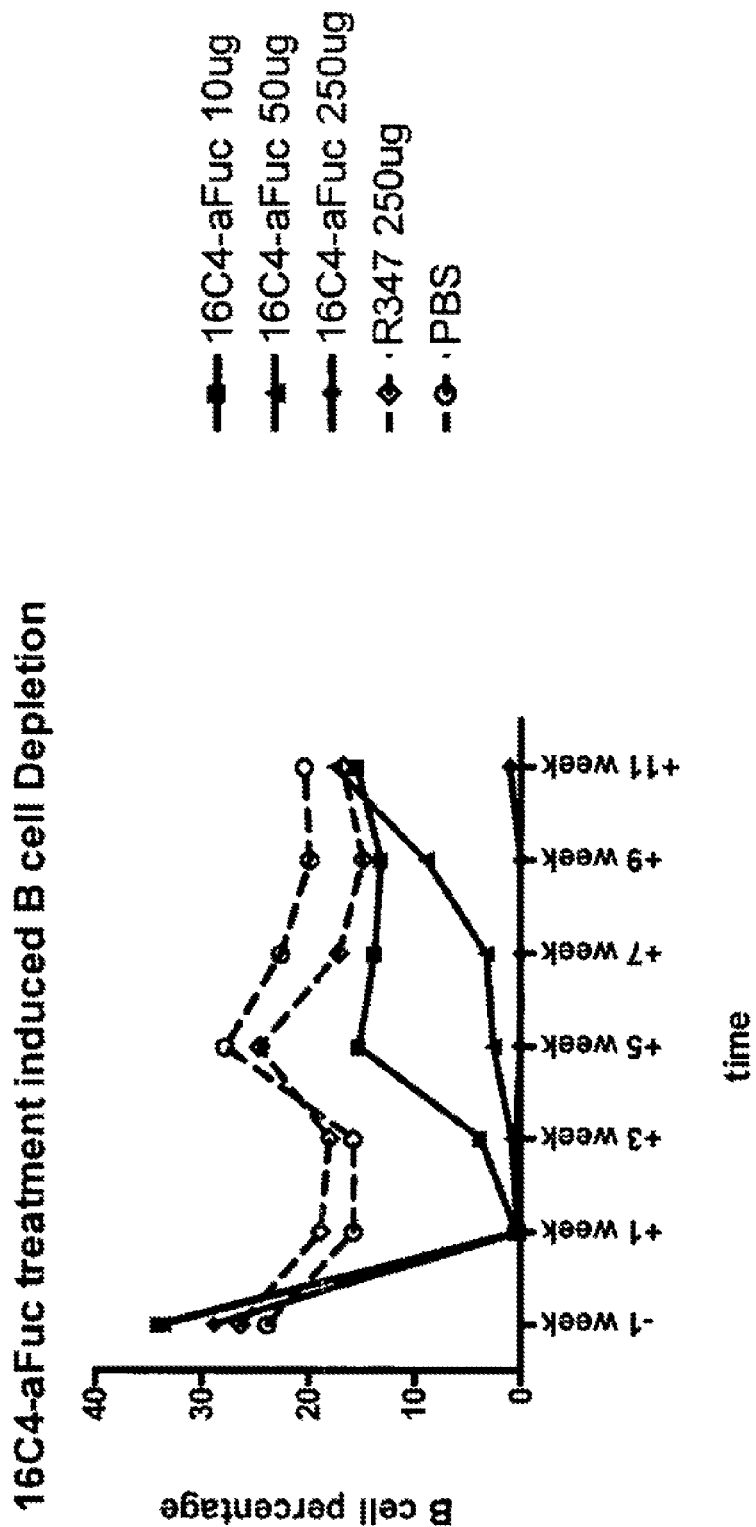
Figure 38D:
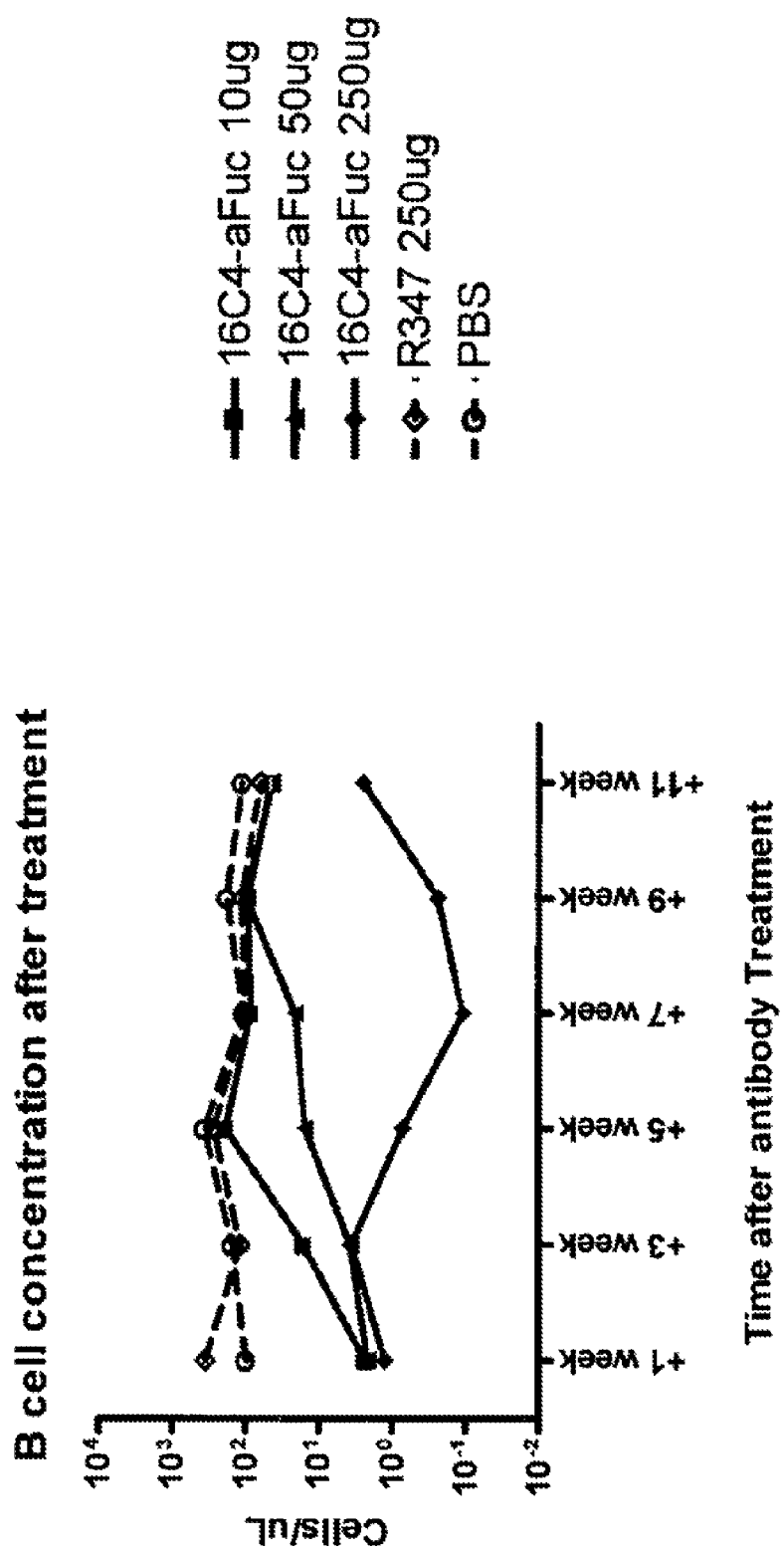
Figure 38E:
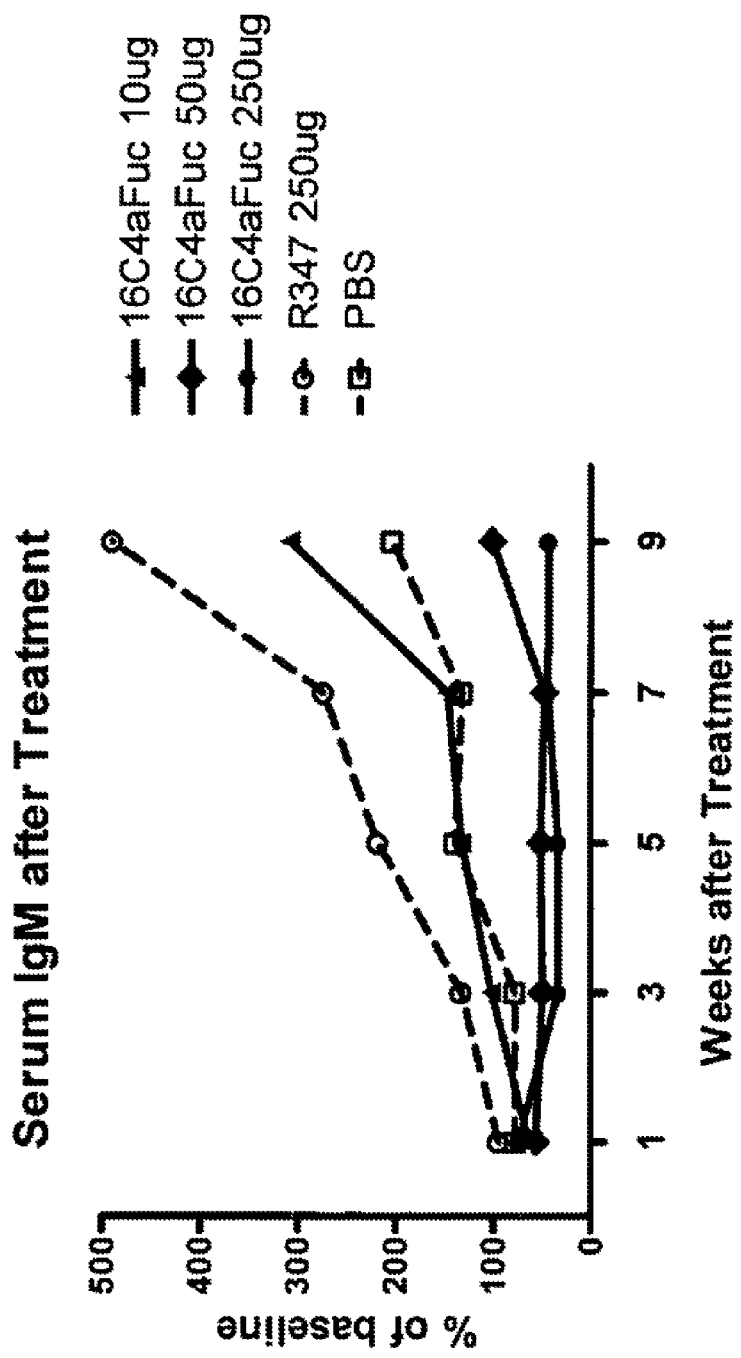
Figure 38F:
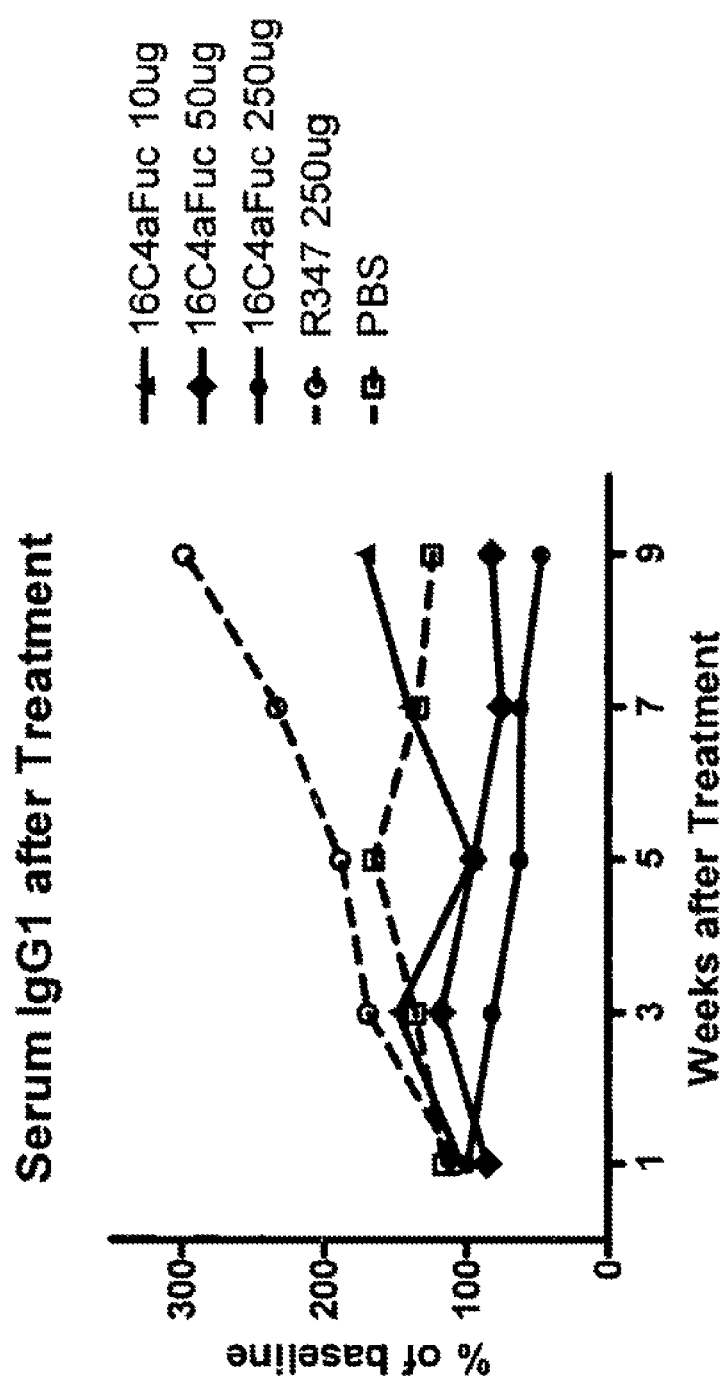
Figure 38G:
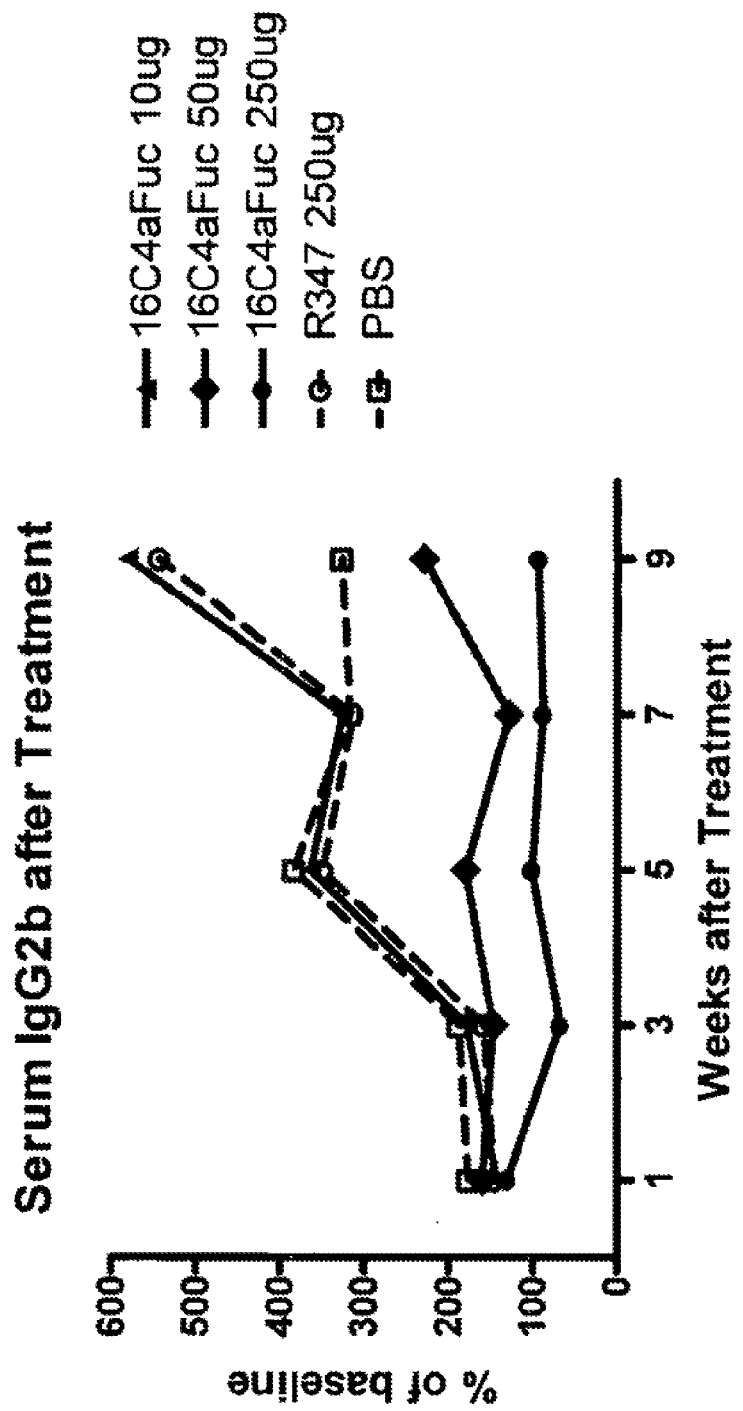

No obvious adverse effect was observed following drug treatment. Animals in all experimental groups maintained normal activity levels and weight (FIG. 38B). B cell levels of animals receiving 16C4-aFuc anti-CD19 antibody was significantly lower than that of the control animals (FIGS. 38C and D). B cell depletion was complete even in animals receiving 10 mg of 16C4-aFuc. The duration of B cell depletion was dose dependent; the duration of depletion increased with higher dose of 16C4-aFuc antibody. B cells on animals receiving 16C4-aFuc started to recover by week 3 and reached normal levels by week 5. Recovery of the animals receiving 50 µg of 16C4-aFuc took 9 weeks. Animals receiving 250 mg of 16C4-aFuc were still almost completely without B cells at week 11 of the experiment. Blood concentration of T cells, NK-T cells, NK cells, dendritic cells, neutrophils, and monocytes were not affected by the 16C4-aFuc antibody (data not shown). Serum levels of IgM, IgG1 and IgG2b were also reduced by 16C4-aFuc antibody treatment (FIGS. 38E-G). Reduction in immunoglobulin levels was dose sensitive; significant reduction in levels was only seen in animals treated with 50 or 250 µg 16C4-aFuc antibody. Recovery in immunoglobulin levels largely track recovery of the B cell compartment.

7.11.2.8. IEF-PAGE Analysis of Anti-CD19 Antibodies.

Native Isoelectric Focusing Polyacrylamide Gel Electrophoresis (IEF-PAGE) analysis was performed on 16C4, 16C9, 7E12, 14H5, 15D7, 15D1, 14H5-DG, and 3649 anti-CD19 antibodies following standard protocols. Pre-cast ampholine gels (Amersham Biosciences, pI range 3.5-9.5) were loaded with 8 µg of purified protein. Protein samples were dialyzed in 10 mM Histidine pH 6.0 buffer before loading on the gel. Broad range pI marker standards (Amersham, pI range 3-10, 8 μL) were used to determine relative pI values. Electrophoresis was performed at 1500 V, 50 mA for 105 minutes. The gel was fixed for 45 minutes and stained overnight at room temperature using Simply Blue stain (Invitrogen). Destaining was carried out with a 25% ethanol, 8% acetic acid solution. Isoelectric points were determined using a Bio-Rad GS-800 Densitometer with Quantity One Imaging Software. The Coomassie stained gel is shown in FIG. 27. The isoelectric point of the 16C4, 16C9, 7E12, 14H5, 15D7, 15D1, 14H5-DG, and 3649 antibodies is 7.83, 8.04, 7.69, 7.76, 7.61, 7.72, 7.48, and 7.75, respectively.

7.11.3. Fc Variant Affinity Matured Anti-CD19 Antibodies

Antibody expression vectors encoding a 16C4 Fc variant antibody comprising the L234F/L235F/P331S or L234F/L235Y/P331S amino acid substitutions (hereinafter referred to as "16C4-235F" or "16C4-235Y") is generated using methods described in US 2004/0132101 and US 2005/0054832, both to Lazar et al. Briefly, the antibody expression vector encoding 16C4 is modified using a site directed mutagenesis kit (e.g., QuickChange (Promega)) by introducing the necessary nucleotide residue substitutions into the polynucleotide sequence encoding the heavy chain constant region to generate the 16C4-235F or 16C4-235Y antibody expression vector. Purified 16C4 Fc variant antibody is generated by transfecting HEK239F cells with the appropriate antibody expression vector. Transfected cells are fed at day 3 and 6 and the antibody-containing conditioned medium is harvested at day 9. Antibody is purified from the conditioned medium using a pre-cast protein A column (GE Healthcare). Antibody is eluted from the column with low pH buffer, neutralized, and dialyzed against PBS. The concentration of the purified antibody is calculated from the solution's optical density at 280 nm.

Measurement of Equilibrium Binding Constants ($K_D$): The equilibrium binding constants of all Fcγ receptors (human FcγRI, FcγRIIA, FcγRIIB, FcγRIIIA-V158, as well as murine FcγRIIB, FcγRIII and FcγRIV) to 16C4 and its Fc variants was measured on a BIAcore 3000 instrument (Uppsala, Sweden). Briefly, all IgGs were immobilized onto separate flow cells of two CM5 sensor chips using standard amino coupling chemistry as recommended by the manufacturer. Immobilized IgG levels ranged from 8194 to 8725 RUs. Stock solutions of the recombinantly expressed extracellular domains of all FcγRs at either 4000 or 16000 nM were prepared and then serially diluted down to the desired concentrations using the instrument buffer (50 mM HBS buffer containing 0.01 M HEPES, pH 7.4, 0.15 M NaCl, 3 mM EDTA and 0.005% P-20). Duplicate injections of each concentration of FcγR were then injected over all of the IgG surfaces at a flow rate of 5 μL/min. Binding data were collected for approximately 50 min, followed by a 30 sec. pulse of 5 mM HCl between injections to regenerate the IgG surfaces. Several buffer injections were also interspersed throughout the injection series. One of these buffer injections was used along with the reference cell data to correct the raw data sets. After all binding data was collected, individual data sets were averaged for each γ concentration, then fit to a 1:1 binding isotherm from which the equilibrium binding constants, $K_D$, were derived. This was carried out using the BIAevaluation software, v. 4.1. $K_D$ values (nM) are presented in Table 38.

TABLE 38

Binding affinities ($K_D$, nM) of various human IgG1s to human and mouse FcγR.

| | 16C4 | 16C4-235F | 16C4-235Y |
|---|---|---|---|
| Human FcγRI | 19 | 1530 | 8650 |
| Human FcγRIIA | 1280 | 6360 | 6980 |
| Human FcγRIIB | 14500 | 6810 | 17100 |
| Human FcγRIIIA (V158) | 574 | 4610 | 5140 |
| Mouse FcγRIIB | 1470 | 2820 | 2670 |
| Mouse FcγRIV | 329 | 11100 | N/A |
| Mouse FcγRIII | 6360 | 10900 | 9240 |

7.12. Isolation of Affinity Matured Variants of the 16C4 Anti-CD19 Antibody

Affinity matured variants of the 16C4 antibody were identified using the protocols described herein. The screen consisted of two stages. The first stage focused on the identification of 16C4 variant Fabs comprising single amino acid substitution that resulted in increased binding activity to cell surface displayed human CD19 antibodies. 16C4 variant Fabs comprising a beneficial single amino acid substitution were identified via screening single CDR focused phage display libraries. The second stage of the screen consisted of screening a combinatorial library of Fab clones representing all possible combinations of beneficial single amino acid substitutions identified either (i) in the first stage of the 16C4 affinity maturation process or (ii) during the affinity maturation process of the 3649 anti-CD19 antibody.

CDR specific phage display libraries were generated as described above. Libraries were screened by testing a large number of phage clones (approximately 400 clones per library) in single point cell based binding assay (Lu et al., J. Immunol. Methods 314:74-79 (2006)). Reagents and disposables were purchased from Meso Scale Discovery; assays were performed following the manufacturer's instructions. Briefly, 5,000 Raji or 300B4 cells/well were plated and incubated for 1 hr at RT in 25 μl 1×PBS; wells were blocked with 25 μl 30% FBS for 20 min RT; supernatant is discarded; 25 μl of anti-CD19 Ab added into each well and incubated for 1 hr at RT; wells are washed 3× with 1×PBS; add 25 μl 0.25 μg/ml goat-anti-human Fab'$_2$-MSDTag to each well and incubate for 1 hr at RT; wash wells 3× with 1×PBS; signal is read with 150 μl of 1×T Read Buffer. The binding curve of a representative clone comprising a beneficial amino acid substitution in VH CDR2 is shown in FIG. 32. Beneficial single amino acid substitutions identified from the 16C4 CDR specific libraries are listed in Table 39.

TABLE 39

Beneficial single amino acid substitutions identified from the 16C4 antibody based CDR specific phage display libraries.

| | Clone | Substitution | Position |
|---|---|---|---|
| VH CDR1 | 17B7 | Ser > Val | 32 |
| VH CDR2 | 64D4 | Pro > Leu | 52A |
| VL CDR2 | 40A5 | Gln > Arg | 54 |
| | 40C10 | Gln > Thr | 54 |
| | 43A10 | Gln > Ala | 54 |
| VL CDR3 | 2F7 | Gln > Ala | 89 |

Combinatorial phage display libraries were prepared as described above. 16C4 Fab specific oligonucleotides used for library generation are listed in Table 40. Individual Fab clones from the combinatorial library were tested for binding to 300B4 and Raji cells (Lu et al., J. Immunol. Methods 314:74-

Figure 33A:
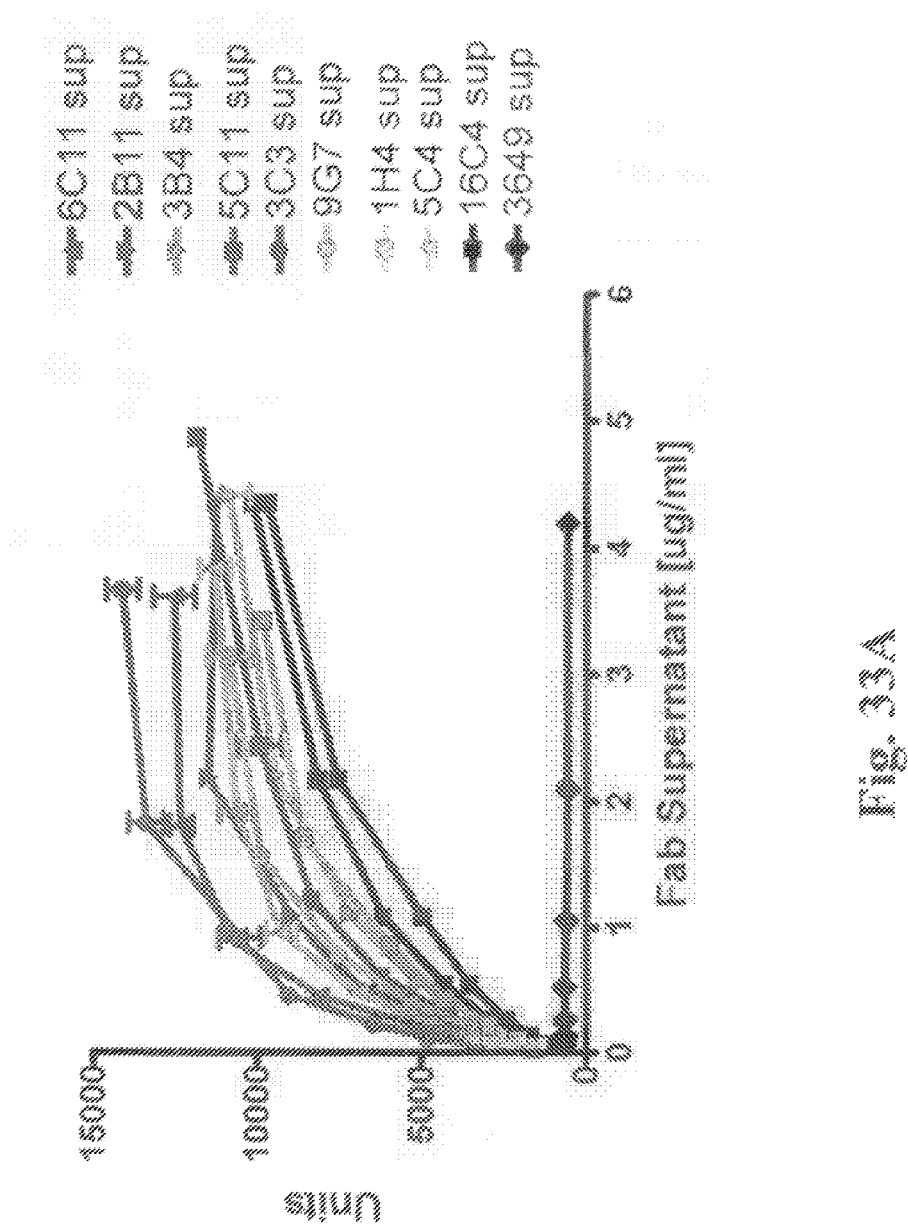
Figure 33B:
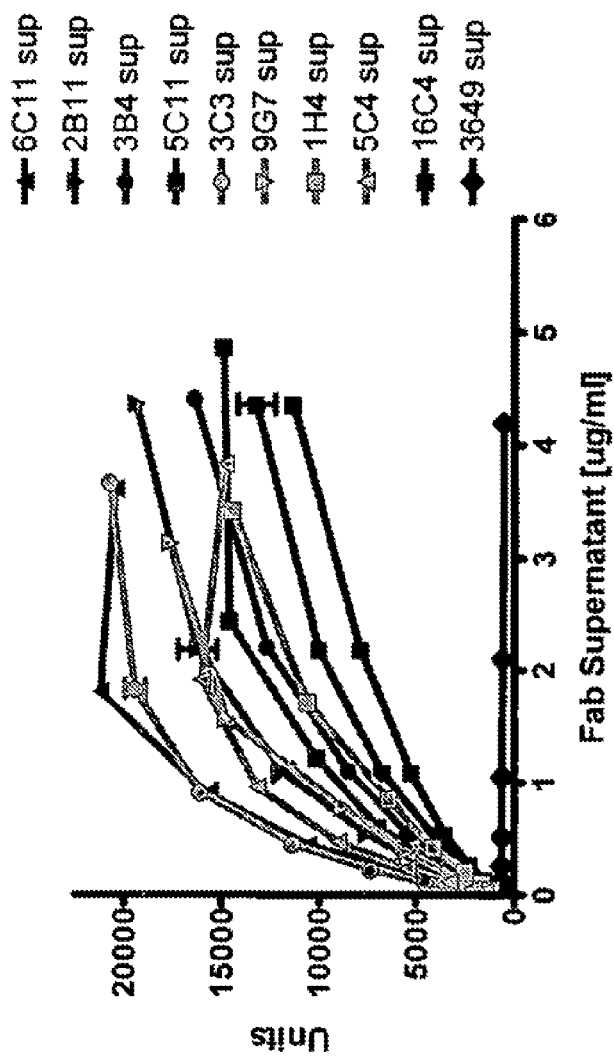

79 (2006)). Binding curves of representative Fab clones are shown in FIG. 33A-B. Fab clones with increased binding activity to 300B4 cells, Raji cells, or both were sequenced using standard methods. A summary of amino acid changes found in the CDR sequences of unique Fab clones is presented in FIG. 33C.

TABLE 40

Degenerate oligonucleotides for combinatorial phage library generation.

| Name | | SEQ ID NO. |
|---|---|---|
| L35 CDR2L p5T/R | GGACCCCGGATCCTSTATTGGATGCCTCATGG | 176 |
| L36 CDR2L p5T/R, p6Y | CCTCGAGGGGACCCCGGAGTATSTATTGGAT GCCTCATGGATG | 177 |
| L37 CDR2L p5A/P | GGACCCCGGATCCTGSATTGGATGCCTCATGG | 178 |
| L38 CDR2L p5A/P, p6Y | CCTCGAGGGGACCCCGGAGTATGSATTGGAT GCCTCATGGATG | 179 |
| L39 CDR3L p3S/T, p8N/I | CTCCGCCGAACGTGWTTGGAACCTCCTTAGW TTGCTGACAGTAATACG | 180 |
| L40 CDR3L p1A/P, p3S/T, 5R | CGCCGAACGTGAATGGAACCCGCTTAGWTTG CGCACAGTAATACGTTGCAGC | 181 |
| L41 CDR3L p3S/T, p5R | CGCCGAACGTGAATGGAACCCGCTTAGWTTG CTGACAGTAATACGTTG | 182 |
| L42 CDR3L p1A/P, p3S/T, p8N/I | CTCCGCCGAACGTGWTTGGAACCTCCTTAGW TTGCGCACAGTAATACGTTGC | 183 |
| H43 CDR1H p2V | CCTGGCGGACCCAGTTCATCCAAACGCTACT GAAGGTGAATCC | 184 |
| H44 CDR1H p2V, p3W/L, p5N/Y | GCCTGGCGGACCCAGTWCATCMAAACGCTA CTGAAGGTGAATC | 185 |
| H45 CDR1H p2V, p3W/L, p5L | GAGCCTGGCGGACCCAGAGCATCMAAACGCT ACTGAAGGTGAATC | 186 |
| H46 CDR2H p4L/P, p9T/N, p12N/Y | CTTGAACTTCACATWGTAGTTAKTATCTCCAT CTCCARGATAAATCCGGCCA | 187 |
| H47 CDR2H p4L/P, p9T/N | CTTGAACTTCACATTGTAGTTAKTATCTCCAT CTCCARGATAAATCCGGCCA | 188 |
| H48 CDR2H p4L/P, p12N/Y | CTTGAACTTCACATWGTAGTTAGTATCTCCAT CTCCARGATAAATCCGGCCA | 189 |
| H49 CDR3H p5P/T | GTCAAAGTCGCGAACCGTAGKAATAAATCCT GATCTAGC | 190 |

Six affinity matured 16C4 variant Fab clones with improved binding activity to cell surface displayed human CD19 antigen were transformed into full IgG1 antibodies using methods described herein. The binding activity of 3C3, 6F7, 2B11, 6C11, 9G7, and 5C4 affinity matured anti-CD19 antibodies were characterized in various cell based assays. FIG. 34 presents the results obtained using 300.B4 cells in a cell based ECL assay (Lu et al., J. Immunol. Methods 314: 74-79 (2006)). The CD19 binding activity of affinity matured 16C4 variant antibodies is higher than that of the control 16C4 or 3649 antibodies.

Cell surface staining by affinity matured anti-CD19 antibodies. Daudi and Raji cells were immunostained with 3C3, 6C11, and 9G7 anti-CD19 antibodies and a RPE conjugated goat anti-human IgG (Fab')2 fragment secondary reagent according to standard protocols. Immunostained cells were analyzed on a flow cytometer. Median fluorescence intensity (MFI) of stained cells at various primary antibody concentrations is plotted in FIG. 35. Cells stained with the 16C4 anti-CD19 antibody were included as a reference control. Staining intensity detected with the 3C3 and 6C11 affinity matured antibodies on Raji cells at 0.0625-0.25 µg/ml antibody concentration is higher than that of detected with the 16C4 control. Raji cell staining intensity of the affinity matured and control antibodies is the same at 0.5-10 µg/ml antibody concentration. Raji cell staining by the 9G7 antibody is similar to the control antibody at lower (0.0625-0.25 µg/ml) antibody concentrations and weaker than the control at higher (0.5-10 µg/ml) antibody concentrations. Median FI of 9G7 and 6C11 stained Daudi cells is higher than that of the 16C4 stained cells. Median FI of 3C3 stained Daudi cells is higher than the control cells at 0.0625 and 0.125 µg/ml antibody concentration; and substantially the same as that of the control cells at 0.25-10 µg/ml antibody concentration.

In vitro ADCC activity of affinity matured 16C4 variant anti-CD19 antibodies. In vitro ADCC activity of affinity matured anti-CD19 antibodies was measured using assays described herein. For example, results obtained with 3C3, 6C11, and 9G7 antibodies using Raji and Daudi target cells are presented in FIGS. 36 and 37, respectively. The 16C4 anti-CD19 antibody was used as a reference control. All three affinity matured antibody displayed substantially the same ADCC activity as the control over the concentration range tested 90.0001-10 µg/ml).

It is understood by persons of skill in the art that the affinity matured variants of the 16C4 anti-CD19 antibody may be further modified according to the protocols described herein. Specifically, the 3C3, 6C11, and 9G7 antibodies may be modified to comprise any one of the variant Fc regions described herein. An afucosylated version of the antibodies may also be prepared. The affinity matured antibodies may also be characterized using the assays described herein. Specifically, the ability of the 3C3, 6C11, and 9G7 antibodies to mediate ADCC, to in vivo deplete B cells, to reduce the size of tumor xenografts, to inhibit anti-IgM/CpG stimulated B cell proliferation may be tested following the protocols described herein.

7.13. Anti-CD19 Antibody Mediated Inhibition of B Cell Proliferation 7.13.1. Anti-CD19 Antibody Treatment Induced CD19 Phosphorylation Ten million cells were incubated for 15 minutes in the presence of 5 µg/ml 3649, 3649-3M, 3649-aFuc, 3649-TM or 16C4 anti-CD19 antibody. Control cells treated with the R347 antibody of irrelevant specificity as well as control cells without antibody treatment were included in the experiment as negative controls. Following incubation, cell lysates were prepared and subjected to immunoprecipitation according to standard protocols. Immunoprecipitated material and input cell lysate were separated on a Laemmli SDS-PAGE, transferred to solid support (Nitrocellulose Invitrogen Cat#LC2001) and subjected to Western blotting. Immunoprecipitation was performed with 2 µg HB12B anti-CD19 antibody following standard protocols. Total CD19 protein and phosphorylated CD19 levels were detected in the immunoprecipitated material by Western blotting using the (1:1000) anti-CD19 (Cell Signaling Technology #3574) or (1:250) anti-phospho tyrosine (PY20) (Santa Cruz Biotechnology #sc-508 HRP) antibody, respectively. Phosphorylated Erk1/2 protein and total Erk1/2 protein levels in the input cell lysate were detected by Western blotting using the (1:2000) anti-phospho Erk1/2 (Cell Signaling Technology #9106S) and (1:1000) anti-Erk1/2 (Cell Signaling Technology #9102) antibody, respectively.

FIG. 39A shows the results of HB12B immunoprecipitation followed by Western blotting. In addition to the immunoprecipitated samples from the various experimental ("3649", "3649-3M", "3649-aFuc", "3649-TM" or "16C4") and control cell lysates ("nil" and "R347"), the membrane also contained an HB12B antibody only control lane ("Ab alone"). Total CD19 protein levels were substantially identical in all immunoprecipitated samples. Phosphorylated CD19 levels were significantly higher in the samples immunoprecipitated from cell lysates prepared from the anti-CD19 treated cells than in the control samples. FIG. 39B shows the Western blot results on total cell lysates. Total Erk1/2 protein levels were substantially identical in all cell lysates. Phosphorylated Erk1/2 levels were significantly higher in the cell lysates prepared from the anti-CD19 treated cells than in the control samples.

7.13.2. Anti-CD19 Treatment does not Inhibit Anti-IgM Mediated Erk1/2 Activation.

One million cells were stimulated with 5 µg/ml anti-IgM antibody or PMA (50 ng/ml)/ionomycin (1 µM) for five or ten minutes in the presence of either 10 µg/ml 3648-3M anti-CD19 antibody or 10 µg/m R347 control antibody. Cells with only 3649 or R347 treatment were included as controls. Cells were harvested and lysed at the end of the incubation period. Total cell lysate was separated on a Laemmli SDS-PAGE, transferred to a nitrocellulose support membrane and subjected to Western blotting following standard protocols. Western blotting using anti-phospho Erk1/2 antibody and anti-Erk1/2 antibody was performed to detect phosphorylated Erk1/2 and total Erk1/2 levels, respectively, in the cell lysate. Results are shown in FIG. 39C-D.

Total Erk1/2 levels were substantially identical in all cell lysates. Baseline phosphorylated Erk1/2 level in 3649 antibody only treated cells was higher than that of R347 only treated cells. Anti-IgM or PMA/ionomycin stimulation increased phosphorylated Erk1/2 levels above the baseline in both 3649 or R347 treated cells. Erk1/2 phosphorylation level was significantly higher following PMA/ionomycin stimulation than after stimulation with anti-IgM antibody.

7.13.3. Anti-CD19 Antibody Treatment Inhibits Anti-IgM/CD40 Induced B Cell Proliferation.

Peripheral B cells are purified from 200 mls of blood using a B cell isolation kit (Miltenyi Biotec #130-091-151). 100,000 cells are seeded in a 96-well U-bottomed plate (100 ul of $1 \times 10^6$ cell/ml). Next, the appropriate concentration of antibody is added to the cells in a 50 ul volume. The plate is returned to the incubator for 15 minutes. Then, the stimulus is added to the cells in a 50 ul volume. The final volume of cell/antibody/stimulus mixture is 200 ul. Cells are incubated for three days. Cell numbers are read on day three using the CellTiter-Glo® Luminescent Cell Viability Assay (Promega). Experiments on immortalized cell lines were seeded with 10,000 cells per well.

The effect of anti-CD19 antibody treatment on anti-IgM/CD40 induced B cell proliferation is shown in FIG. 40. B cells were plated in the presence of 10 µg/ml 3649, 3649-TM, and 3649-3M anti-CD19 antibody. 15 minutes later cells B cells were stimulated with anti-IgM (5 µg/ml) alone, anti-IgM (5 µg/ml)/CD40 (1 µg/ml), or CpG (1 µg/ml) alone. B cell stimulation was allowed to proceed for three days. Viable cell numbers were measured at the end of the experiment using the CellTiter-Glo® Luminescent Cell Viability Assay (Promega). Cells treated with the R347 antibody of irrelevant specificity were included as control. Viable cell numbers were increased by anti-IgM/CD40 or CpG stimulation, but not by IgM alone stimulation. Anti-IgM/CD40 induced cell proliferation was significantly inhibited by anti-CD19 antibody treatment. Level of inhibition (40%) was identical for all anti-CD19 antibodies tested. CpG induced cell proliferation was unaffected by anti-CD19 antibody treatment.

7.13.4. Anti-CD19 Antibody Treatment Inhibits Anti-IgM/CpG Induced B Cell Proliferation.

Cell proliferation in response to various stimuli was assessed using the CFSE assay. Briefly, purified B cells are re-suspended in phosphate buffered saline (PBS) at approximately 10 million cells per milliliter. To that an equal volume of 1 uM CFSE in PBS is added. The final concentration of CFSE is 0.5 uM and the cells are at 5 million per milliliter. The suspension is kept in the dark for 10 minutes. An equal volume of Fetal Calf Serum (FCS) is added to the mixture to quench extracellular CFSE. Cells are washed and diluted in media. 100,000 CFSE labeled cells are seeded in a 96-well U-bottomed plate (100 ul of $1 \times 10^6$ cell/ml). Next, the appropriate concentration of antibody is added to the cells in a 50 ul volume. The plate is returned to the incubator for 15 minutes. Next, the stimulus is added to the cells in a 50 ul volume. The final volume of cell/antibody/stimulus mixture is 200 ul. Cells are incubated for four days. At the end of incubation, cells are washed, stained with 7-amino actinomycin D (7-AAD) (BD Bioscience), and analyzed on a flow cytometer. CFSE signal of live cells is detected. CFSE signal decrease in the CFSE profile of a cell population is indicative of cell division. The extent of CFSE signal decrease correlates with cell proliferation levels.

Figure 41A:
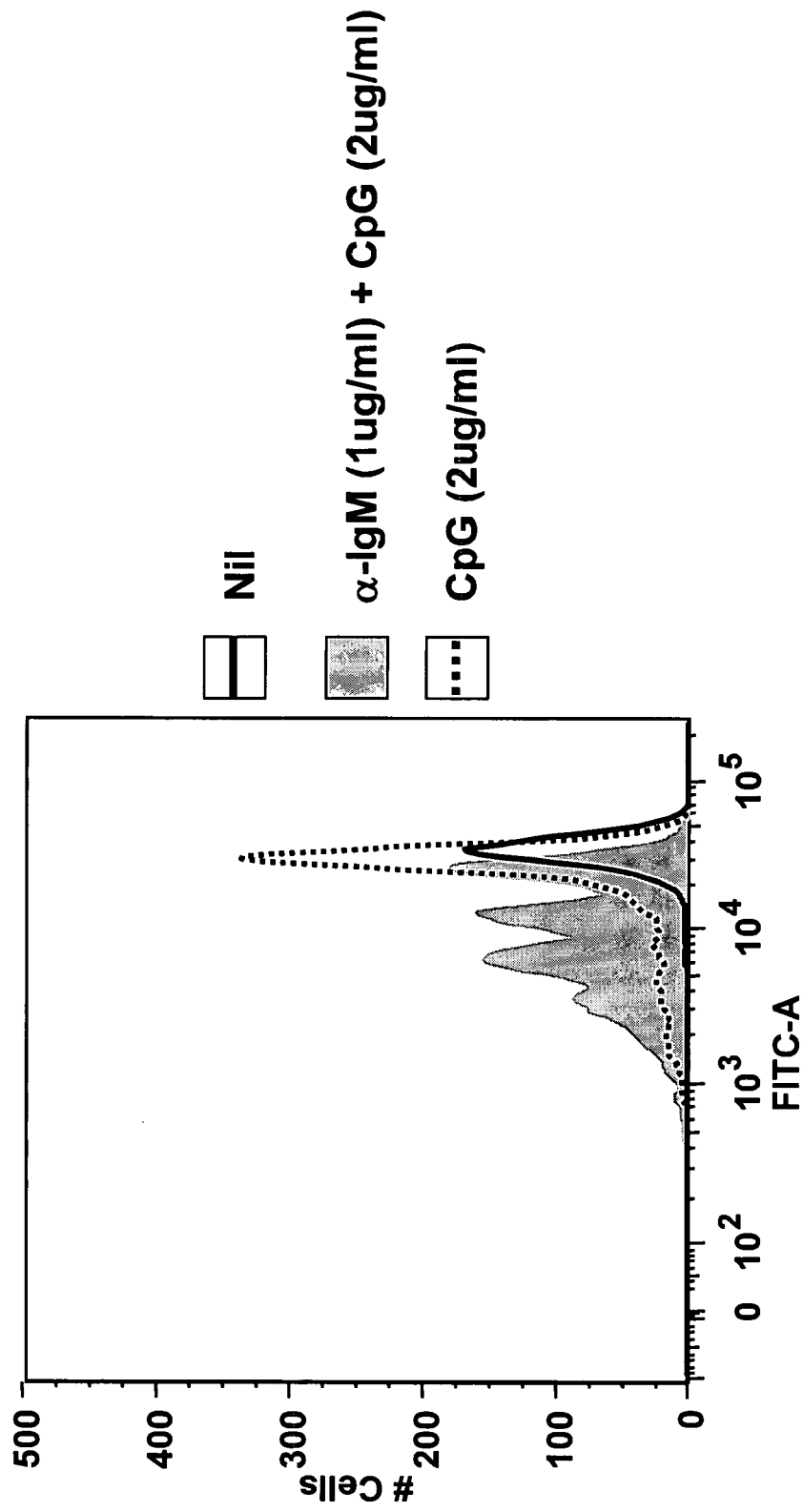

Purified peripheral B cell were stimulated with anti-IgM (1 µg/ml)/CpG (2 µg/ml) or CpG (2 µg/ml) alone for four days. Cell proliferation is assessed using the CFSE assay. FIG. 41A shows the CFSE profile of stimulated and unstimulated control cells. The CFSE signal of IgM (1 µg/ml)/CpG (2 µg/ml) stimulated cells is significantly lower than that of the control cells indicating that IgM (1 µg/ml)/CpG (2 µg/ml) stimulation resulted in extensive cell proliferation. The CFSE profile of CpG only stimulated cells indicates only limited cell proliferation.

Figure 41B:
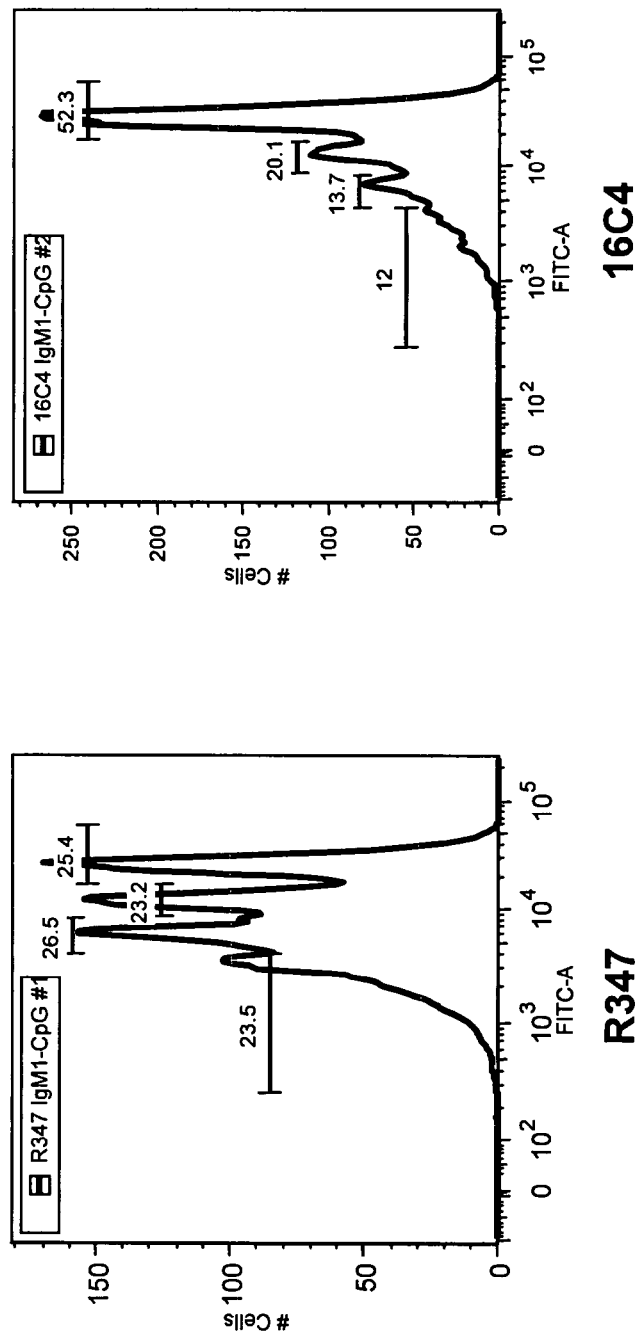

16C4 anti-CD19 antibody inhibits anti-IgM/CpG induced B cell proliferation. Purified peripheral B cells were stimulated with anti-IgM (1 µg/ml)/CpG (2 µg/ml) in the presence of 5 µg/ml of R347 control antibody or 5 µg/ml 16C4 anti-CD19 antibody for four days. Cell proliferation is assessed using the CFSE assay. FIG. 41B shows the CFSE profile of B cells stimulated with IgM (1 µg/ml)/CpG (2 µg/ml) in the presence of R347 or 16C4 antibody. The CFSE profile of B cells stimulated with anti-IgM (1 µg/ml)/CpG (2 µg/ml) in the presence of R347 antibody is indicative of extensive cell proliferation. The CFSE profile of B cells stimulated with anti-IgM (1 µg/ml)/CpG (2 µg/ml) in the presence of 16C4 anti-CD19 antibody is indicative of less extensive cell proliferation than that of seen in the control cells.

7.13.5. Fc Variant Anti-CD19 Antibodies Display Altered Inhibitory Properties.

Purified peripheral B cells were stimulated for four days with anti-IgM (1 µg/ml)/CpG (2 µg/ml) in the presence of 5 µg/ml of R347 control antibody, 3649-3M Fc variant anti-CD19 antibody or 3649-TM Fc variant anti-CD19 antibody. Cell proliferation is assessed using the CFSE assay. FIG. 42A shows the CFSE profile of B cells stimulated with anti-IgM (1 µg/ml)/CpG (2 µg/ml) in the presence of R347 control antibody. The CFSE profile shows that 23.5+26.5+23.2=73.2% of the B cells underwent at least one round of cell division. FIGS. 42B and C shows the CFSE profile of B cells stimulated with anti-IgM (1 µg/ml)/CpG (2 µg/ml) in the presence of 3649-TM and 3649-3M Fc variant anti-CD19 antibody, respectively. The CFSE profiles show that 44.8% and 30.3% of B cells stimulated in the presence of 3649-TM and 3649-3M Fc variant anti-CD19 antibody, respectively, underwent at least one round of cell division during the four day long incubation period. Closer inspection of all three CFSE profiles reveals that not only the number of cells undergoing at least one division, but also the number of cells undergoing more than one divisions drops with highest and lowest cell proliferation seen in the presence of R347 and 3649-3M, respectively. Treatment with 3649-TM inhibits cell proliferation less effectively than treatment with 3649-3M.

Purified B cells were stimulated for four days with anti-IgM (5 µg/ml)/CpG (1 µg/ml) in the presence of 5 µg/ml R347, R347-3M F c variant, 3649, 3649-3M Fc variant, or 3649-TM Fc variant antibodies. Cell proliferation is assessed using the CFSE assay. CFSE profile of B cells stimulated in the presence of R347 is included in all panels as a reference standard. CFSE profiles of B cells stimulated in the presence of R347-3M F c variant, 3649, 3649-3M Fc variant, and 3649-TM Fc variant antibodies is shown in panels A-D. Cell proliferation in the presence of R347-3M Fc variant is same as the one seen in the presence of the R347 reference standard. Cell proliferation is inhibited by all three anti-CD19 antibodies. The wild type 3649 and 3649-TM Fc variant antibodies inhibited cell proliferation to the same extent. 3649-3M was more effective at inhibiting B cell proliferation than either the 3649 or 3649-TM antibodies.

Inhibitory synergism of anti-CD19 and anti-Fcgamma receptor IIB (FcγRIIb or CD32b) antibodies: The following experimental design will further test whether there is a synergistic interaction between the anti-CD32b and anti-CD19 antibody mediated inhibitions of B cell proliferation. Purified B cells will be stimulated for four days with anti-IgM (2 µg/ml)/CpG (2 µg/ml) in the presence of (i) an anti-CD32b antibody (e.g., AT10), (ii) an anti-CD19 antibody or (iii) both anti-CD32b and CD19 antibodies. Cell proliferation will be assessed using the CFSE assay. Synergism between anti-CD32b and anti-CD19 antibody mediated inhibition of B cell proliferation is expected to lead to lower B cell proliferation in the presence of both antibodies than the cell proliferation seen in the presence of either antibody alone.

7.13.6. Anti-CD19 Antibodies are Efficiently Internalized.

Antibody internalization assay: Cells are incubated with 5 µg/ml Alexa Flour 488-labeled antibodies at 37° C. for up to 60 minutes. An aliquot of cells are removed at 10 minute intervals, washed, divided into two parts, and placed on ice. One half aliquot is left untreated on ice. The second half aliquot is treated on ice for 45 seconds with a low pH (2.0) PBS solution containing 0.03M sucrose and 10% FCS to strip all cell surface bound antibody molecules. Both acid treated and untreated samples are washed, fixed with 4% paraformaldehyde, and analyzed on a flow cytometer. % internalized antibody is calculated as the ratio of the fluorescence signal of acid washed cells (internal signal only) and that of untreated cells (total signal from cell surface and internal compartments).

FIG. 44 shows the internalization of HB12B, 3649, and 16C4 antibodies by Raji cells over a 60 minute time period. Internalization curves show that anti-CD19 uptake reaches a maximum around 20-30 minutes. Maximum internalization is about 50% for the HB12B and 3649 antibodies and ~30% for the 16C4 antibody.

7.13.7. Loss of CD19 from the Cell Surface Following 24 Hrs of Anti-CD19 Antibody Treatment.

Cells are incubated in the presence of an anti-CD19 antibody for 24 hours. A control cell population is incubated in the presence of the R347 antibody of irrelevant specificity. Following incubation, cells are harvested, washed and incubated on ice for 10 minutes in a staining solution comprising 5 µg/ml anti-CD19 antibody for 10 minutes. Surface bound anti-CD19 antibody is detected by staining the cells for 10 minutes with a PE conjugated goat anti-human IgG secondary antibody. Immunostained cells are fixed in 4% paraformaldehyde and analyzed on a flow cytometer. CD19 surface loss is calculated by comparing the mean fluorescence intensity (MFI) of anti-CD19 antibody treated cells to the MFI of immunostained R347 treated cells (0% surface loss) and secondary antibody only stained R347 treated cells (100% surface loss).

FIG. 45 displays the CD19 surface loss on Raji cells and primary B cells following incubation for 24 hours in the presence of 5 µg/ml of 3649, 3649-3M, 3649-TM, 3648-aFuc, and 16C4 anti-CD19 antibodies. A 55-70% and 65-90% loss of CD19 surface expression is detected in Raji cells and primary B cells, respectively, following treatment with anti-CD19 antibodies.

Those skilled in the art will recognize, or be able to ascertain using no more than routine experimentation, many equivalents to the specific embodiments of the invention described herein. Such equivalents are intended to be encompassed by the following claims.

Various publications are cited herein, the disclosures of which are incorporated by reference in their entireties for all purposes. The disclosure of U.S. Provisional Application Nos. 60/842,935 filed Sep. 8, 2006, 60/866,917, filed Nov. 22, 2006, 60/911,397, filed Apr. 12, 2007, 60/915,309, filed May 1, 2007, and 60/939,429, filed May 22, 2007 are incorporated by reference herein in their entirety for all purposes.

Although the foregoing invention has been described in some detail by way of illustration and example for purposes of clarity of understanding, it will be obvious that certain changes and modifications may be practiced within the scope of the appended claims.

What is claimed is:

1. An isolated nucleic acid encoding a polypeptide comprising an amino acid sequence comprising SEQ ID NO: 106.

2. An isolated nucleic acid encoding a polypeptide comprising an amino acid sequence comprising SEQ ID NO: 111.

3. An expression vector comprising the nucleic acid of claim 1.

4. An expression vector comprising the nucleic acid of claim 2.

5. An expression vector comprising an isolated nucleic acid encoding an antibody comprising the amino acid sequence of SEQ ID NO: 106 and 111, wherein the antibody binds a CD19 antigen.

6. A host cell transfected with the vector of claim 1.

7. A host cell transfected with the vector of claim 2.

8. A host cell transfected with the vector of claim 5.

9. A method of producing an antibody comprising culturing host cells according to claim 8 under conditions for production of the antibody.

* * * * *